US011866430B2

(12) United States Patent
Chupak et al.

(10) Patent No.: US 11,866,430 B2
(45) Date of Patent: Jan. 9, 2024

(54) NAPHTHYRIDINONE COMPOUNDS USEFUL AS T CELL ACTIVATORS

(71) Applicant: BRISTOL-MYERS SQUIBB COMPANY, Princeton, NJ (US)

(72) Inventors: Louis S. Chupak, Old Saybrook, CT (US); Min Ding, Stow, MA (US); Robert G. Gentles, Killingworth, CT (US); Yazhong Huang, Wallingford, CT (US); Scott W. Martin, Middletown, CT (US); Ivar M. Mcdonald, Woodstock, CT (US); Stephen E. Mercer, Wakefield, MA (US); Richard E. Olson, Cambridge, MA (US); Upender Velaparthi, Princeton Junction, NJ (US); Michael Wichroski, Yardley, PA (US); Xiaofan Zheng, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 545 days.

(21) Appl. No.: 17/254,914

(22) PCT Filed: Jun. 26, 2019

(86) PCT No.: PCT/US2019/039131
§ 371 (c)(1),
(2) Date: Dec. 22, 2020

(87) PCT Pub. No.: WO2020/006016
PCT Pub. Date: Jan. 2, 2020

(65) Prior Publication Data
US 2021/0277004 A1    Sep. 9, 2021

Related U.S. Application Data

(60) Provisional application No. 62/690,444, filed on Jun. 27, 2018.

(51) Int. Cl.
C07D 471/04    (2006.01)
A61K 31/4375    (2006.01)
A61P 35/00    (2006.01)

(52) U.S. Cl.
CPC ........ C07D 471/04 (2013.01); A61K 31/4375 (2013.01); A61P 35/00 (2018.01)

(58) Field of Classification Search
CPC .......................... C07D 471/04; A61K 31/4375
See application file for complete search history.

(56) References Cited

U.S. PATENT DOCUMENTS

| 4,324,893 | A  | 4/1982  | Scotese et al. |
| 7,084,141 | B2 | 8/2006  | Gaeta et al. |
| 7,173,036 | B2 | 2/2007  | Sircar et al. |
| 7,220,856 | B2 | 5/2007  | Dunning et al. |
| 7,279,481 | B2 | 10/2007 | Falchi et al. |
| 7,381,401 | B2 | 6/2008  | Gajewski |
| 9,050,334 | B2 | 6/2015  | Gaweco et al. |
| 9,133,164 | B2 | 9/2015  | Gaweco et al. |
| 2005/0124604 | A1 | 6/2005 | Sircar et al. |
| 2005/0266510 | A1 | 12/2005 | Gajewski |
| 2008/0139551 | A1 | 6/2008 | Sircar et al. |
| 2011/0281908 | A1 | 11/2011 | Sun et al. |
| 2015/0224142 | A1 | 8/2015 | Albelda et al. |
| 2018/0334454 | A1 | 11/2018 | Lanman et al. |

FOREIGN PATENT DOCUMENTS

| WO | 2004056824 A2 | 7/2004 |
| WO | 2004074218 A2 | 9/2004 |
| WO | 2004087880 A2 | 10/2004 |

(Continued)

OTHER PUBLICATIONS

Avila-Flores, A. et al., "Predominant Contribution of DGKζ over DGKα in the Control of PKC/PDK-1-Regulated Functions in T Cells", Immunology and Cell Biology (2017) 95: 549-563.

(Continued)

Primary Examiner — Samantha L Shterengarts
Assistant Examiner — Karen Cheng
(74) Attorney, Agent, or Firm — Gary Greenblatt

(57) ABSTRACT

Disclosed are compounds of Formula (I): or a salt thereof, wherein: $R_1$, $R_2$, $R_3$, and $R_4$ are defined herein. Also disclosed are methods of using such compounds to inhibit the activity of one or both of diacylglycerol kinase alpha (DGK α) and diacylglycerol kinase zeta (DGKζ), and pharmaceutical compositions comprising such compounds. These compounds are useful in the treatment of viral infections and proliferative disorders, such as cancer.

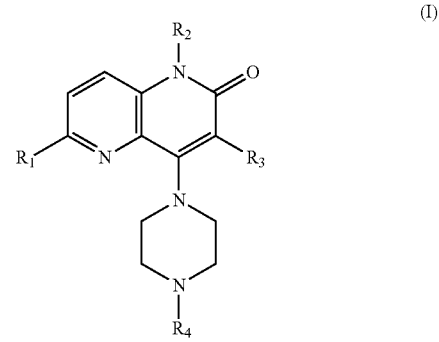

(I)

11 Claims, No Drawings

Specification includes a Sequence Listing.

(56) References Cited

FOREIGN PATENT DOCUMENTS

| | | |
|---|---|---|
| WO | 2005009967 A2 | 2/2005 |
| WO | 2005021546 A1 | 3/2005 |
| WO | 2007109251 A2 | 9/2007 |
| WO | 2007132948 A1 | 11/2007 |
| WO | 2007136125 A1 | 11/2007 |
| WO | 2010042489 A2 | 4/2010 |
| WO | 2010088408 A2 | 8/2010 |
| WO | 2012009649 A1 | 1/2012 |
| WO | 2012142498 A2 | 10/2012 |
| WO | 2013118071 A1 | 8/2013 |
| WO | 14078637 A1 | 5/2014 |
| WO | 2016164675 A1 | 10/2016 |
| WO | 2017106607 A1 | 6/2017 |
| WO | 2017177037 A1 | 10/2017 |
| WO | 18073788 A1 | 4/2018 |
| WO | 2018119183 A2 | 6/2018 |
| WO | 2018134685 A2 | 7/2018 |
| WO | 2019005883 A1 | 1/2019 |

OTHER PUBLICATIONS

Barraza et al., "Discovery of Anthranilamides as a Novel Class of Inhyibitors of Neurotropic Alphavirus Replication", Bioorg. Med. Chem 23 (2015) 1569-1587.

Boroda et al., "Dual Activites of Ritanserin and R59022 as DGKα inhibitors and Serotonin Receptor Antagonists" Biochemical Pharmacology 123 (2017) 29-39.

Chen et al., "Diacylglycerol Kinases in T Cell Tolerance and Effector Function", Frontiers in Cell and Development Biology 2016 4, 130.

Dagia et al., "A fluorinated Analog of ISO-1 blocks the Recognition and Biological Function of MIF and is Orally Efficacious in a Murine Model of Colitis" Eur. J. Pharmacology 607 (2009) 201-212.

Database Registry Chemical Abstracts Service: Database RN 2249638-34-2 (Entered STN Nov. 19, 2018).

Facciabene, et al. "T-Regulartory Cells: Key Players in Tumor Immune Escape and Angiogenesis" Cancer Res. 72(9) 2162-2171 (2012).

Franks et al., "The Ligand Binding Landscape of Diacylglycerol Kinases" Cell Chem Bio 24, 879-880 (2017).

Ganesan et al., "Comprehensive in vitro Characterization of PD-L1 Small Molecule Inhibitors", Scientific Reports 9, Article No. 12392 (2019).

International Preliminary Report on Patentability for PCT Application PCT/US2019/039131, dated Dec. 29, 2020 for 13176-WO-PCT.

International Search Report for PCT Application PCT/US2019/039131, dated Sep. 2, 2019 for 13176-WO-PCT.

Jing et al., "T Cells Deficient In Diacylglycerol Kinase ζ are Resistance to PD-1 Inhibition and Help Create Persistent Host Immunity to Leukemia" Cancer Res 77(20) 5676-5686 (2017).

Krishna et al., "Regulation of Lipid Signaling by Diacylglycerol Kinases During T Cell Development and Function" Front Immunolog. (2013) 4: Article 178.

Liu et al., "A Novel Diacylglycerol Kinase α-Selective Inhibitor CU-3, Induces Cancer Cell Apoptosis and Enhances Immune Response" J. Lipid Res. 57, 368-379 (2016).

McCloud et al., "Deconstructing Lipid Kinase Inhibitors By Chemical Proteomics" Biochem. 2018, 57, 231-236.

McLean et al., "Fragment Screening of Inhibitors for MIF Tautomerase Reveals a Cryptic Surface Binding Site" Bio. Med. Chem. Lett. 20 (2010) 1821-1824.

Mellman et al. "Cancer Immunotherapy Comes of Age" Nature 480 480-489 (2011).

Merida et al., "Redundant and Specialized Roles for Diacylglycerol Kinases α and ζ in the Control of T cell Functions" Science Signaling 8 (374), re6 (2015).

Merida I., Arranz-Nicolás J., et al., "Diacylglycerol Kinase Malfunction in Human Disease and the Search for Specific Inhibitors", Handbook of Experimental Pharmacology. Springer, Berlin, Heidelberg (2019). First Online: Jun. 22, 2019.

Mizoguchi et al., "Alterations in Signal Transduction Molecules in T Lymphocytes from Tumor-Bearing Mice" (1992) Science 258:1795-98.

Noessner, "DGK-α: A Checkpoint in Cancer-Mediated Immuno-Inhibition and Target for Immunotherapy" Front Cell Dev Bio 2017 5, Article 16.

Olenchock et al., "Disruption of the Diacylglycerol Metabolism Impairs the Induction of T cell Anergy", Nature Immunology 7(11) 1174-1181 (2006).

Prinz et al., "High DGK-α and Disabled MAPK Pathways Cause Dysfunction of Human Tumor-Infiltrating CD8+ T Cells that Is Reversible by Pharmacologic Intervention", J Immunology 188(12) 5990-6000 (2012).

Purow, B. "Molecular Pathways: Targeting Diacylglycerol Kinase Aplha in Cancer" Clin. Cancer Res. 21(22) 5008-5012 (2015).

Riese et al., "Decreased Diacylglycerol Metabolism Enhances ERK Activation and Augments DC8+ T Cell Functional Responses", J Bio Chem 286(7) 5254-5265 (2011).

Riese et al., "Diacylglycerol Kinases (DGKs): Novel Targets for Improving T Cell Activity in Cancer" Frontiers Cell Dev Bio (2016) 4, Article 108.

Santilli et al., "2-Oxo-1,8-naphthyridine-3-carboxylic Acid Derivaties with Potent Gastric Antisecretory Properties" J. Med. Chem. 1987, 30, 2270-2277.

Sjoblom et al. "The Consensus Coding Sequences of Human Breast and Colorectal Cancers" Science 314 268-274 (2006).

Topalian et al., "Targetomg the PD-1/B7-H1(PD-L1) Pathway to Activate Anti-tumor Immunity", Curr. Opin. Immunol. 2012, 24:207-212.

Velnati et al., "Identification of a Novel DGKα Inhibitor for XLP-1 Therapy by Virtual Screening", Eur J Med Chem 164 (2019) 378-390.

Wesley et al., "Diacylglycerol Kinase ζ (DGKζ) and Casitas b-Lineage Proto-Oncogene b-Deficient Mice Have Similar Functional Outcomes in T Cells but DGK ζ-Deficient Mice have Increased T Cell Activatin and Tumor Clearance" ImmunoHorizons 2018 2 94) 107-118.

Zha Y et al., "T Cell Anergy is Reversed by Active Ras and is Regulated by Diacylglycerol Kinase-α" Nature Immunology, (2006) 7(11) 1166-1173; Erratum 7(12) 1343.

SEQUENCE LISTING

<160> NUMBER OF SEQ IDS: 4

<210> SEQ ID NO 1
<211> LENGTH: 2256
<212> TYPE: DNA
<213> ORGANISM: Homo sapiens

<400> SEQUENCE: 1

```
atggccaagg agaggggcct aataagcccc agtgattttg cccagctgca aaatacatg      60 gaatactcca ccaaaaaggt cagtgatgtc ctaaagctct tcgaggatgg cgagatggct    120
aaatatgtcc aaggagatgc cattgggtac gagggattcc agcaattcct gaaaatctat    180
ctcgaagtgg ataatgttcc cagacaccta agcctggcac tgtttcaatc ctttgagact    240
ggtcactgct taaatgagac aaatgtgaca aaagatgtgg tgtgtctcaa tgatgtttcc    300
tgctactttt cccttctgga gggtggtcgg ccagaagaca agttagaatt caccttcaag    360
ctgtacgaca cggacagaaa tgggatcctg gacagctcag aagtggacaa aattatccta    420
cagatgatgc gagtggctga atacctggat tgggatgtgt ctgagctgag gccgattctt    480
caggagatga tgaaagagat tgactatgat ggcagtggct ctgtctctca agctgagtgg    540
gtccgggctg ggccaccac cgtgccactg ctagtgctgc tgggtctgga gatgactctg    600
aaggacgacg gacagcacat gtggaggccc aagaggttcc ccagaccagt ctactgcaat    660
ctgtgcgagt caagcattgg tcttggcaaa cagggactga gctgtaacct tgtaagtac    720
```

```
actgttcacg accagtgtgc catgaaagcc ctgccttgtg aagtcagcac ctatgccaag    780
tctcggaagg acattggtgt ccaatcacat gtgtgggtgc gaggaggctg tgagtccggg    840
cgctgcgacc gctgtcagaa aaagatccgg atctaccaca gtctgaccgg gctgcattgt    900
gtatggtgcc acctagagat ccacgatgac tgcctgcaag cggtgggcca tgagtgtgac    960
tgtgggctgc tccgggatca catcctgcct ccatcttcca tctatcccag tgtcctggcc   1020
tctggaccgg atcgtaaaaa tagcaaaaca agcagaaga ccatggatga tttaaatttg    1080
agcacctctg aggctctgcg gattgaccct gttcctaaca cccacccact ctcgtctttt   1140
gtcaatccta agagtggcgg gaagcagggg cagagggtgc tctggaagtt ccagtatata   1200
ttaaaccctc gacaggtgtt caacctccta aaggatggtc ctgagatagg gctccgatta   1260
ttcaaggatg ttcctgatag ccggattttg gtgtgtggtg gagacggcac agtaggctgg   1320
attctagaga ccattgacaa agctaacttg ccagttttgc ctcctgttgc tgtgttgccc   1380
ctgggtactg gaaatgatct ggctcgatgc ctaagatggg gaggaggtta tgaaggacag   1440
aatctggcaa agatcctcaa ggatttagag atgagtaaag tggtacatat ggatcgatgg   1500
tctgtggagg tgatacctca acaaactgaa gaaaaagtg acccagtccc ctttcaaatc    1560
atcaataact acttctctat ggcgtggat gcctctattg ctcatcgatt ccacatcatg     1620
cgagagaaat atccggagaa gttcaacagc agaatgaaga acaagctatg gtacttcgaa    1680
tttgccacat ctgaatccat cttctcaaca tgcaaaaagc tggaggagtc tttgacagtt    1740
gagatctgtg ggaaaccgct ggatctgagc aacctgtccc tagaaggcat cgcagtgcta    1800
aacatcccta gcatgcatgg tggctccaac ctctggggtg ataccaggag accccatggg    1860
gatatctatg ggatcaacca ggccttaggt gctacagcta agagtcatca cgaccctgat    1920
atcctgaaaa cctgtgtacc agacctaagt gacaagagac tggaagtggt tgggctggag    1980
ggtgcaattg agatgggcca aatctatacc aagctcaaga tgctggacg tcggctggcc    2040 aagtgctctg agatcacctt ccacaccaca aaaacccttc ccatgcaaat tgacggagaa    2100
ccctggatgc agacgccctg tacaatcaag atcacccaca gaaccagat gcccatgctc     2160 atgggcccac cccccgctc caccaatttc tttggcttct tgagcggatc ctcggagaca    2220
gtgcggtttc agggacacca ccaccatcac cactga                            2256
```

<210> SEQ ID NO 2
<211> LENGTH: 751
<212> TYPE: PRT
<213> ORGANISM: Homo sapiens

<400> SEQUENCE: 2

Met Ala Lys Glu Arg Gly Leu Ile Ser Pro Ser Asp Phe Ala Gln Leu
1               5                   10                  15

Gln Lys Tyr Met Glu Tyr Ser Thr Lys Lys Val Ser Asp Val Leu Lys
            20                  25                  30

Leu Phe Glu Asp Gly Glu Met Ala Lys Tyr Val Gln Gly Asp Ala Ile
        35                  40                  45

Gly Tyr Glu Gly Phe Gln Gln Phe Leu Lys Ile Tyr Leu Glu Val Asp
    50                  55                  60

Asn Val Pro Arg His Leu Ser Leu Ala Leu Phe Gln Ser Phe Glu Thr
65                  70                  75                  80

Gly His Cys Leu Asn Glu Thr Asn Val Thr Lys Asp Val Val Cys Leu
                85                  90                  95

Asn Asp Val Ser Cys Tyr Phe Ser Leu Leu Glu Gly Gly Arg Pro Glu

```
            100                 105                 110
Asp Lys Leu Glu Phe Thr Phe Lys Leu Tyr Asp Thr Asp Arg Asn Gly
            115                 120                 125

Ile Leu Asp Ser Ser Glu Val Asp Lys Ile Ile Leu Gln Met Met Arg
            130                 135                 140

Val Ala Glu Tyr Leu Asp Trp Asp Val Ser Glu Leu Arg Pro Ile Leu
145                 150                 155                 160

Gln Glu Met Met Lys Glu Ile Asp Tyr Asp Gly Ser Gly Ser Val Ser
                    165                 170                 175

Gln Ala Glu Trp Val Arg Ala Gly Ala Thr Thr Val Pro Leu Leu Val
            180                 185                 190

Leu Leu Gly Leu Glu Met Thr Leu Lys Asp Asp Gly Gln His Met Trp
            195                 200                 205

Arg Pro Lys Arg Phe Pro Arg Pro Val Tyr Cys Asn Leu Cys Glu Ser
            210                 215                 220

Ser Ile Gly Leu Gly Lys Gln Gly Leu Ser Cys Asn Leu Cys Lys Tyr
225                 230                 235                 240

Thr Val His Asp Gln Cys Ala Met Lys Ala Leu Pro Cys Glu Val Ser
                    245                 250                 255

Thr Tyr Ala Lys Ser Arg Lys Asp Ile Gly Val Gln Ser His Val Trp
                    260                 265                 270

Val Arg Gly Gly Cys Glu Ser Gly Arg Cys Asp Arg Cys Gln Lys Lys
            275                 280                 285

Ile Arg Ile Tyr His Ser Leu Thr Gly Leu His Cys Val Trp Cys His
            290                 295                 300

Leu Glu Ile His Asp Asp Cys Leu Gln Ala Val Gly His Glu Cys Asp
305                 310                 315                 320

Cys Gly Leu Leu Arg Asp His Ile Leu Pro Pro Ser Ser Ile Tyr Pro
                    325                 330                 335

Ser Val Leu Ala Ser Gly Pro Asp Arg Lys Asn Ser Lys Thr Ser Gln
                    340                 345                 350

Lys Thr Met Asp Asp Leu Asn Leu Ser Thr Ser Glu Ala Leu Arg Ile
            355                 360                 365

Asp Pro Val Pro Asn Thr His Pro Leu Leu Val Phe Val Asn Pro Lys
            370                 375                 380

Ser Gly Gly Lys Gln Gly Gln Arg Val Leu Trp Lys Phe Gln Tyr Ile
385                 390                 395                 400

Leu Asn Pro Arg Gln Val Phe Asn Leu Lys Asp Gly Pro Glu Ile
                    405                 410                 415

Gly Leu Arg Leu Phe Lys Asp Val Pro Asp Ser Arg Ile Leu Val Cys
            420                 425                 430

Gly Gly Asp Gly Thr Val Gly Trp Ile Leu Glu Thr Ile Asp Lys Ala
            435                 440                 445

Asn Leu Pro Val Leu Pro Pro Val Ala Val Leu Pro Leu Gly Thr Gly
            450                 455                 460

Asn Asp Leu Ala Arg Cys Leu Arg Trp Gly Gly Gly Tyr Glu Gly Gln
465                 470                 475                 480

Asn Leu Ala Lys Ile Leu Lys Asp Leu Glu Met Ser Lys Val Val His
                    485                 490                 495

Met Asp Arg Trp Ser Val Glu Val Ile Pro Gln Gln Thr Glu Glu Lys
            500                 505                 510

Ser Asp Pro Val Pro Phe Gln Ile Ile Asn Asn Tyr Phe Ser Ile Gly
            515                 520                 525
```

| | | | | | | | | | | | | |
|---|---|---|---|---|---|---|---|---|---|---|---|---|
|Val|Asp|Ala|Ser|Ile|Ala|His|Arg|Phe|His|Ile|Met|Arg|Glu|Lys|Tyr|
| |530| | | |535| | | |540| | | | | | |

Val Asp Ala Ser Ile Ala His Arg Phe His Ile Met Arg Glu Lys Tyr
    530                 535                 540

Pro Glu Lys Phe Asn Ser Arg Met Lys Asn Lys Leu Trp Tyr Phe Glu
545                 550                 555                 560

Phe Ala Thr Ser Glu Ser Ile Phe Ser Thr Cys Lys Lys Leu Glu Glu
                565                 570                 575

Ser Leu Thr Val Glu Ile Cys Gly Lys Pro Leu Asp Leu Ser Asn Leu
            580                 585                 590

Ser Leu Glu Gly Ile Ala Val Leu Asn Ile Pro Ser Met His Gly Gly
        595                 600                 605

Ser Asn Leu Trp Gly Asp Thr Arg Arg Pro His Gly Asp Ile Tyr Gly
    610                 615                 620

Ile Asn Gln Ala Leu Gly Ala Thr Ala Lys Val Ile Thr Asp Pro Asp
625                 630                 635                 640

Ile Leu Lys Thr Cys Val Pro Asp Leu Ser Asp Lys Arg Leu Glu Val
                645                 650                 655

Val Gly Leu Glu Gly Ala Ile Glu Met Gly Gln Ile Tyr Thr Lys Leu
            660                 665                 670

Lys Asn Ala Gly Arg Arg Leu Ala Lys Cys Ser Glu Ile Thr Phe His
        675                 680                 685

Thr Thr Lys Thr Leu Pro Met Gln Ile Asp Gly Glu Pro Trp Met Gln
    690                 695                 700

Thr Pro Cys Thr Ile Lys Ile Thr His Lys Asn Gln Met Pro Met Leu
705                 710                 715                 720

Met Gly Pro Pro Pro Arg Ser Thr Asn Phe Phe Gly Phe Leu Ser Gly
                725                 730                 735

Ser Ser Glu Thr Val Arg Phe Gln Gly His His His His His His
            740                 745                 750

<210> SEQ ID NO 3
<211> LENGTH: 2838
<212> TYPE: DNA
<213> ORGANISM: Homo sapiens

<400> SEQUENCE: 3

```
atggagccgc gggacggtag ccccgaggcc cggagcagcg actccgagtc ggcttccgcc    60
tcgtccagcg gctccgagcg cgacgccggt cccgagccgg acaaggcgcc gcggcgactc   120
aacaagcggc gcttcccggg gctgcggctc ttcgggcaca ggaaagccat cacgaagtcg   180
ggcctccagc acctggcccc ccctccgccc acccctgggg ccccgtgcag cgagtcagag   240
cggcagatcc ggagtacagt ggactggagc gagtcagcga catatgggga gcacatctgg   300
ttcgagacca acgtgtccgg ggacttctgc tacgttgggg agcagtactg tgtagccagg   360
atgctgcaga agtcagtgtc tcgaagaaag tgcgcagcct gcaagattgt ggtgcacacg   420
ccctgcatcg agcagctgga gaagataaat ttccgctgta gccgtccctt ccgtgaatca   480
ggctccagga atgtccgcga gccaaccttt gtacggcacc actgggtaca gacgacgc    540
caggacggca agtgtcggca ctgtgggaag ggattccagc agaagttcac cttccacagc   600
aaggagattg tggccatcag ctgctcgtgg tgcaagcagg cataccacag caaggtgtcc   660
tgcttcatgc tgcagcagat cgaggagccg tgctcgctgg gggtccacgc agccgtggtc   720
atcccgccca cctggatcct ccgcgcccgg aggcccagca atactctgaa agcaagcaag   780
aagaagaaga gggcatcctt caagaggaag tccagcaaga agggcctga ggagggccgc   840
```

| | |
|---|---|
| tggagaccct tcatcatcag gcccaccccc tccccgctca tgaagcccct gctggtgttt | 900 |
| gtgaaccca agagtggggg caaccagggt gcaaagatca tccagtcttt cctctggtat | 960 |
| ctcaatcccc gacaagtctt cgacctgagc cagggagggc caaggaggc gctggagatg | 1020 |
| taccgcaaag tgcacaacct gcggatcctg gcgtgcgggg gcgacggcac ggtgggctgg | 1080 |
| atcctctcca ccctggacca gctacgcctg aagccgccac ccctgttgc catcctgccc | 1140 |
| ctgggtactg gcaacgactt ggcccgaacc ctcaactggg gtgggggcta cacagatgag | 1200 |
| cctgtgtcca agatcctctc ccacgtggag gaggggaacg tggtacagct ggaccgctgg | 1260 |
| gacctccacg ctgagcccaa ccccgaggca gggcctgagg accgagatga aggcgccacc | 1320 |
| gaccggttgc ccctggatgt cttcaacaac tacttcagcc tgggctttga cgcccacgtc | 1380 |
| accctggagt tccacgagtc tcgagaggcc aacccagaga aattcaacag ccgctttcgg | 1440 |
| aataagatgt tctacgccgg gacagctttc tctgacttcc tgatgggcag ctccaaggac | 1500 |
| ctggccaagc acatccgagt ggtgtgtgat ggaatggact tgactcccaa gatccaggac | 1560 |
| ctgaaaccc agtgtgttgt tttcctgaac atccccaggt actgtgcggg caccatgccc | 1620 |
| tggggccacc ctggggagca ccacgacttt gagcccagc ggcatgacga cggctacctc | 1680 |
| gaggtcattg gcttcaccat gacgtcgttg gccgcgctgc aggtgggcgg acacggcgag | 1740 |
| cggctgacgc agtgtcgcga ggtggtgctc accacatcca aggccatccc ggtgcaggtg | 1800 |
| gatggcgagc cctgcaagct tgcagcctca cgcatccgca tcgccctgcg caaccaggcc | 1860 |
| accatggtgc agaaggccaa gcggcggagc gccgcccccc tgcacagcga ccagcagccg | 1920 |
| gtgccagagc agttgcgcat ccaggtgagt cgcgtcagca tgcacgacta tgaggccctg | 1980 |
| cactacgaca aggagcagct caaggaggcc tctgtgccgc tgggcactgt ggtggtccca | 2040 |
| ggagacagtg acctagagct ctgccgtgcc cacattgaga gactccagca ggagcccgat | 2100 |
| ggtgctggag ccaagtcccc gacatgccag aaactgtccc caagtggtg cttcctggac | 2160 |
| gccaccactg ccagccgctt ctacaggatc gaccgagccc aggagcacct caactatgtg | 2220 |
| actgagatcg cacaggatga gatttatatc ctggaccctg agctgctggg gcatcggcc | 2280 |
| cggcctgacc tcccaacccc cacttcccct ctccccacct caccctgctc acccacgccc | 2340 |
| cggtcactgc aagggatgc tgcacccct caaggtgaag agctgattga ggctgccaag | 2400 |
| aggaacgact tctgtaagct ccaggagctg caccgagctg ggggcgacct catgcaccga | 2460 |
| gacgagcaga gtcgcacgct cctgcaccac gcagtcagca ctggcagcaa ggatgtggtc | 2520 |
| cgctacctgc tggaccacgc cccccccagag atccttgatg cggtggagga aaacggggag | 2580 |
| acctgtttgc accaagcagc ggccctgggc cagcgcacca tctgccacta catcgtggag | 2640 |
| gccggggcct cgctcatgaa gacagaccag caggcgaca ctccccggca gcgggctgag | 2700 |
| aaggctcagg acaccgagct ggccgcctac ctggagaacc ggcagcacta ccagatgatc | 2760 |
| cagcgggagg accaggagac ggctgtggga tcctcggaga cagtgcggtt tcagggacac | 2820 |
| caccaccatc accactga | 2838 |

<210> SEQ ID NO 4
<211> LENGTH: 945
<212> TYPE: PRT
<213> ORGANISM: Homo sapiens

<400> SEQUENCE: 4

Met Glu Pro Arg Asp Gly Ser Pro Glu Ala Arg Ser Ser Asp Ser Glu
1               5                   10                  15

```
Ser Ala Ser Ala Ser Ser Ser Gly Ser Glu Arg Asp Ala Gly Pro Glu
            20                  25                  30

Pro Asp Lys Ala Pro Arg Arg Leu Asn Lys Arg Phe Pro Gly Leu
        35                  40                  45

Arg Leu Phe Gly His Arg Lys Ala Ile Thr Lys Ser Gly Leu Gln His
    50                  55                  60

Leu Ala Pro Pro Pro Thr Pro Gly Ala Pro Cys Ser Glu Ser Glu
65                  70                  75                  80

Arg Gln Ile Arg Ser Thr Val Asp Trp Ser Glu Ser Ala Thr Tyr Gly
                85                  90                  95

Glu His Ile Trp Phe Glu Thr Asn Val Ser Gly Asp Phe Cys Tyr Val
            100                 105                 110

Gly Glu Gln Tyr Cys Val Ala Arg Met Leu Gln Lys Ser Val Ser Arg
            115                 120                 125

Arg Lys Cys Ala Ala Cys Lys Ile Val Val His Thr Pro Cys Ile Glu
        130                 135                 140

Gln Leu Glu Lys Ile Asn Phe Arg Cys Lys Pro Ser Phe Arg Glu Ser
145                 150                 155                 160

Gly Ser Arg Asn Val Arg Glu Pro Thr Phe Val Arg His His Trp Val
                165                 170                 175

His Arg Arg Arg Gln Asp Gly Lys Cys Arg His Cys Gly Lys Gly Phe
            180                 185                 190

Gln Gln Lys Phe Thr Phe His Ser Lys Glu Ile Val Ala Ile Ser Cys
        195                 200                 205

Ser Trp Cys Lys Gln Ala Tyr His Ser Lys Val Ser Cys Phe Met Leu
    210                 215                 220

Gln Gln Ile Glu Glu Pro Cys Ser Leu Gly Val His Ala Ala Val Val
225                 230                 235                 240

Ile Pro Pro Thr Trp Ile Leu Arg Ala Arg Arg Pro Gln Asn Thr Leu
                245                 250                 255

Lys Ala Ser Lys Lys Lys Arg Ala Ser Phe Lys Arg Lys Ser Ser
            260                 265                 270

Lys Lys Gly Pro Glu Glu Gly Arg Trp Arg Pro Phe Ile Ile Arg Pro
        275                 280                 285

Thr Pro Ser Pro Leu Met Lys Pro Leu Leu Val Phe Val Asn Pro Lys
290                 295                 300

Ser Gly Gly Asn Gln Gly Ala Lys Ile Ile Gln Ser Phe Leu Trp Tyr
305                 310                 315                 320

Leu Asn Pro Arg Gln Val Phe Asp Leu Ser Gln Gly Gly Pro Lys Glu
                325                 330                 335

Ala Leu Glu Met Tyr Arg Lys Val His Asn Leu Arg Ile Leu Ala Cys
            340                 345                 350

Gly Gly Asp Gly Thr Val Gly Trp Ile Leu Ser Thr Leu Asp Gln Leu
        355                 360                 365

Arg Leu Lys Pro Pro Pro Val Ala Ile Leu Pro Leu Gly Thr Gly
370                 375                 380

Asn Asp Leu Ala Arg Thr Leu Asn Trp Gly Gly Gly Tyr Thr Asp Glu
385                 390                 395                 400

Pro Val Ser Lys Ile Leu Ser His Val Glu Glu Gly Asn Val Val Gln
                405                 410                 415

Leu Asp Arg Trp Asp Leu His Ala Glu Pro Asn Pro Glu Ala Gly Pro
            420                 425                 430

Glu Asp Arg Asp Glu Gly Ala Thr Asp Arg Leu Pro Leu Asp Val Phe
```

```
                435                 440                 445
Asn Asn Tyr Phe Ser Leu Gly Phe Asp Ala His Val Thr Leu Glu Phe
    450                 455                 460
His Glu Ser Arg Glu Ala Asn Pro Glu Lys Phe Asn Ser Arg Phe Arg
465                 470                 475                 480
Asn Lys Met Phe Tyr Ala Gly Thr Ala Phe Ser Asp Phe Leu Met Gly
                485                 490                 495
Ser Ser Lys Asp Leu Ala Lys His Ile Arg Val Val Cys Asp Gly Met
            500                 505                 510
Asp Leu Thr Pro Lys Ile Gln Asp Leu Lys Pro Gln Cys Val Val Phe
        515                 520                 525
Leu Asn Ile Pro Arg Tyr Cys Ala Gly Thr Met Pro Trp Gly His Pro
    530                 535                 540
Gly Glu His His Asp Phe Glu Pro Gln Arg His Asp Asp Gly Tyr Leu
545                 550                 555                 560
Glu Val Ile Gly Phe Thr Met Thr Ser Leu Ala Ala Leu Gln Val Gly
                565                 570                 575
Gly His Gly Glu Arg Leu Thr Gln Cys Arg Glu Val Val Leu Thr Thr
            580                 585                 590
Ser Lys Ala Ile Pro Val Gln Val Asp Gly Glu Pro Cys Lys Leu Ala
        595                 600                 605
Ala Ser Arg Ile Arg Ile Ala Leu Arg Asn Gln Ala Thr Met Val Gln
    610                 615                 620
Lys Ala Lys Arg Arg Ser Ala Ala Pro Leu His Ser Asp Gln Gln Pro
625                 630                 635                 640
Val Pro Glu Gln Leu Arg Ile Gln Val Ser Arg Val Ser Met His Asp
                645                 650                 655
Tyr Glu Ala Leu His Tyr Asp Lys Glu Gln Leu Lys Glu Ala Ser Val
            660                 665                 670
Pro Leu Gly Thr Val Val Pro Gly Asp Ser Asp Leu Glu Leu Cys
        675                 680                 685
Arg Ala His Ile Glu Arg Leu Gln Gln Glu Pro Asp Gly Ala Gly Ala
    690                 695                 700
Lys Ser Pro Thr Cys Gln Lys Leu Ser Pro Lys Trp Cys Phe Leu Asp
705                 710                 715                 720
Ala Thr Thr Ala Ser Arg Phe Tyr Arg Ile Asp Arg Ala Gln Glu His
                725                 730                 735
Leu Asn Tyr Val Thr Glu Ile Ala Gln Asp Glu Ile Tyr Ile Leu Asp
            740                 745                 750
Pro Glu Leu Leu Gly Ala Ser Ala Arg Pro Asp Leu Pro Thr Pro Thr
        755                 760                 765
Ser Pro Leu Pro Thr Ser Pro Cys Ser Pro Thr Pro Arg Ser Leu Gln
    770                 775                 780
Gly Asp Ala Ala Pro Gln Gly Glu Glu Leu Ile Glu Ala Ala Lys
785                 790                 795                 800
Arg Asn Asp Phe Cys Lys Leu Gln Glu Leu His Arg Ala Gly Gly Asp
                805                 810                 815
Leu Met His Arg Asp Glu Gln Ser Arg Thr Leu Leu His Ala Val
            820                 825                 830
Ser Thr Gly Ser Lys Asp Val Val Arg Tyr Leu Leu Asp His Ala Pro
        835                 840                 845
Pro Glu Ile Leu Asp Ala Val Glu Glu Asn Gly Glu Thr Cys Leu His
    850                 855                 860
```

```
Gln Ala Ala Ala Leu Gly Gln Arg Thr Ile Cys His Tyr Ile Val Glu
865                 870                 875                 880

Ala Gly Ala Ser Leu Met Lys Thr Asp Gln Gln Gly Asp Thr Pro Arg
                885                 890                 895

Gln Arg Ala Glu Lys Ala Gln Asp Thr Glu Leu Ala Ala Tyr Leu Glu
                900                 905                 910

Asn Arg Gln His Tyr Gln Met Ile Gln Arg Glu Asp Gln Glu Thr Ala
                915                 920                 925

Val Gly Ser Ser Glu Thr Val Arg Phe Gln Gly His His His His
    930                 935                 940

His
945
```

NAPHTHYRIDINONE COMPOUNDS USEFUL AS T CELL ACTIVATORS

CROSS REFERENCE

This application claims the benefit of U.S. Provisional Application Ser. No. 62/690,444, filed Jun. 27, 2018, which is incorporated herein in its entirety.

DESCRIPTION

The present invention generally relates to naphthyridinone compounds that activate T cells, promote T cell proliferation, and/or exhibit antitumor activity. Provided herein are naphthyridinone compounds, compositions comprising such compounds, and methods of their use. The invention further pertains to pharmaceutical compositions comprising at least one compound according to the invention that are useful for the treatment of proliferative disorders, such as cancer, and viral infections.

BACKGROUND OF THE INVENTION

Human cancers harbor numerous genetic and epigenetic alterations, generating neoantigens potentially recognizable by the immune system (Sjoblom et al. (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities. However, although an endogenous immune response to cancer is observed in preclinical models and patients, this response is ineffective, and established cancers are viewed as "self" and tolerated by the immune system. Contributing to this state of tolerance, tumors may exploit several distinct mechanisms to actively subvert anti-tumor immunity. These mechanisms include dysfunctional T-cell signaling (Mizoguchi et al., (1992) *Science* 258:1795-98), suppressive regulatory cells (Facciabene et al., (2012) *Cancer Res.* 72:2162-71), and the co-opting of endogenous "immune checkpoints", which serve to down-modulate the intensity of adaptive immune responses and protect normal tissues from collateral damage, by tumors to evade immune destruction (Topalian et al., (2012) *Curr. Opin. Immunol.* 24:1-6; Mellman et al. (2011) *Nature* 480:480-489).

Diacylglycerol kinases (DGKs) are lipid kinases that mediate the conversion of diacylglycerol to phosphatidic acid thereby terminating T cell functions propagated through the TCR signaling pathway. Thus, DGKs serve as intracellular checkpoints and inhibition of DGKs are expected to enhance T cell signaling pathways and T cell activation. Supporting evidence include knock-out mouse models of either DGKα or DGKζ which show a hyper-responsive T cell phenotype and improved anti-tumor immune activity (Riese M. J. et al., *Journal of Biological Chemistry*, (2011) 7: 5254-5265; Zha Y et al., *Nature Immunology*, (2006) 111343; Olenchock B. A. et al., (2006) 11: 1174-81). Furthermore tumor infiltrating lymphocytes isolated from human renal cell carcinoma patients were observed to over-express DGKα which resulted in inhibited T cell function (Prinz, P. U. et al., *J. Immunology* (2012) 12:5990-6000). Thus, DGKα and DGKζ are viewed as targets for cancer immunotherapy (Riese M. J. et al., *Front Cell Dev Biol.* (2016) 4: 108: Chen, S. S. et al., *Front Cell Dev Biol.* (2016) 4: 130; Avila-Flores, A. et al., *Immunology and Cell Biology* (2017) 95: 549-563; Noessner, E., *Front Cell Dev Biol.* (2017) 5: 16; Krishna, S., et al., *Front Immunology* (2013) 4:178; Jing, W. et al., *Cancer Research* (2017) 77: 5676-5686.

There remains a need for compounds useful as inhibitors of one or both of DGKα and DGKζ. Additionally, there remains a need for compounds useful as inhibitors of one of both of DGKα and DGKζ that have selectivity over other diacylglycerol kinases, protein kinases, and/or other lipid kinases.

Accordingly, an agent that is safe and effective in restoring T cell activation, lowering antigen threshold, enhancing antitumor functionality, and/or overcoming the suppressive effects of one or more endogenous immune checkpoints, such as PD-1, LAG-3 and TGFβ, would be an important addition for the treatment of patients with proliferative disorders, such as cancer, as well as viral infections.

Applicants have found compounds that have activity as inhibitors of one or both of DGKα and DGKζ. Further, applicants have found compounds that have activity as inhibitors of one or both of DGKα and DGKζ and have selectivity over other diacylglycerol kinases, protein kinases, and/or other lipid kinases. These compounds are provided to be useful as pharmaceuticals with desirable stability, bioavailability, therapeutic index, and toxicity values that are important to their drugability.

SUMMARY OF THE INVENTION

The present invention provides naphthyridinone compounds of Formula (I), which are useful as inhibitors of DGKα, DGKζ, or both DGKα and DGKζ, including salts and prodrugs thereof.

The present invention also provides pharmaceutical compositions comprising a compound of Formula (I) and/or a pharmaceutically acceptable salt thereof; and a pharmaceutically acceptable carrier.

The present invention also provides a method of treating a disease or disorder associated with the activity of DGKα, DGKζ, or both DGKα and DGKζ, the method comprising administering to a mammalian patient a compound of Formula (I) and/or a pharmaceutically acceptable salt thereof.

The present invention also provides processes and intermediates for making the compounds of Formula (I) and/or salts thereof.

The present invention also provides a compound of Formula (I) and/or a pharmaceutically acceptable salt thereof, for use in therapy.

The present invention also provides the use of the compounds of Formula (I) and/or pharmaceutically acceptable salts thereof, for the manufacture of a medicament for the treatment of proliferative disorders, such as cancer and viral infections.

The compounds of Formula (I) and compositions comprising the compounds of Formula (I) may be used in treating, preventing, or curing viral infections and various proliferative disorders, such as cancer. Pharmaceutical compositions comprising these compounds are useful in treating, preventing, or slowing the progression of diseases or disorders in a variety of therapeutic areas, such as viral infections and cancer.

These and other features of the invention will be set forth in expanded form as the disclosure continues.

DETAILED DESCRIPTION

The first aspect of the present invention provides at least one compound of Formula (I):

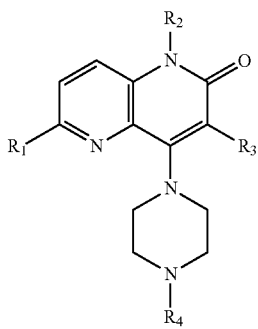

or a salt thereof, wherein:

$R_1$ is H, Cl, Br, —CN, $C_{1-4}$ alkyl, $C_{2-3}$ alkenyl, $C_{1-3}$ alkoxy, —C(O)OH, —C(O)O($C_{1-3}$ alkyl), —C(O)NR$_a$R$_a$, —NR$_a$R$_a$, —NR$_a$C(O)O($C_{1-4}$ alkyl), or —NR$_a$C(O)NR$_a$ ($C_{1-4}$ alkyl);

each $R_a$ is independently H or $C_{1-2}$ alkyl;

$C_2$ is $C_{1-6}$ alkyl, $C_{1-4}$ cyanoalkyl, $C_{1-4}$ fluoroalkyl, $C_{2-4}$ alkenyl, —(CH$_2$)$_{1-3}$CH=CF$_2$, $C_{3-5}$ alkynyl, —(CH$_2$)$_{1-4}$O ($C_{1-3}$ alkyl), —(CH$_2$)$_{1-4}$O(CH$_2$)$_{1-3}$O($C_{1-3}$ alkyl), —(CH$_2$)$_{1-3}$C(O)($C_{1-3}$ alkyl), —(CH$_2$)$_{1-3}$C(O)O($C_{1-3}$ alkyl), —(CH$_2$)$_{1-3}$R$_b$, —(CH$_2$)$_{1-3}$OR$_b$, or —(CH$_2$)$_{1-3}$OCH$_2$R$_b$;

$R_b$ is $C_{3-6}$ cycloalkyl or dioxanyl, each substituted with zero to 2 substituents independently selected from F, —CN, —CH$_3$, and —OCH$_3$;

$R_3$ is H, F, Cl, Br, —CN, $C_{1-3}$ alkyl, $C_{1-3}$ fluoroalkyl, —NO$_2$, —C(O)($C_{1-3}$ alkyl), —C(O)O($C_{1-3}$ alkyl), or —C(O)($C_{1-3}$ fluoroalkyl);

$R_4$ is:
(a) 2,3-dihydro-1H-indenyl substituted with zero to 2 substituents independently selected from F, Cl, —OH, $C_{1-2}$ alkyl, $C_{1-2}$ fluoroalkyl, $C_{1-2}$ alkoxy, and —OCH$_2$CH=CH$_2$; or
(b) —CH$_2$R$_y$, —C(CH$_3$)$_2$R$_y$, —CHR$_x$R$_y$, —CH$_2$CH(OH)R$_x$, —CH(CH$_3$)(CH$_3$CH$_2$OCH$_3$), or $C_{3-6}$ coalkyl substituted with fluorophenyl;

$R_x$ is $C_{1-6}$ alkyl, $C_{1-3}$ hydroxyalkyl, $C_{1-2}$ aminoalkyl, $C_{3-6}$ cycloalkyl, or phenyl substituted with zero to 2 substituents independently selected from F, Cl, —OH, $C_{1-3}$ alkyl, $C_{1-2}$ fluoroalkyl, $C_{1-2}$ alkoxy, —OCH$_2$CH=CH$_2$, and —OCH$_2$C≡CH;

$R_y$ is 1,3-benzodiazolyl, indazolyl, indolyl, indolinyl, naphthalenyl, oxoindolinyl, pyridinyl, pyrimidinyl, or phenyl, each substituted with zero to 3 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, —OCH$_2$CH=CH$_2$, —OCH$_2$C≡CH, —OCH$_2$(cyanopyridinyl), —NR$_c$R$_c$, —NR$_a$S(O)$_2$($C_{1-3}$ alkyl), —NR$_a$C (O)($C_{1-3}$ alkyl), —NR$_a$C(O)O($C_{1-4}$ alkyl), —NR$_a$C(O) R$_d$, —NR$_a$C(O)NR$_a$R$_d$, and R$_d$;

each $R_c$ is independently H or $C_{1-2}$ alkyl; and $R_d$ is phenyl substituted with zero to 1 substituent selected from Cl, —CH$_3$, and —OCH$_3$.

In one embodiment, a compound of Formula (I) or a salt thereof is provided wherein $R_1$ is H, Cl, Br, —CN, $C_{1-3}$ alkyl, $C_{2-3}$ alkenyl, $C_{1-2}$ alkoxy, —C(O)OH, —C(O)O($C_{1-2}$ alkyl), —C(O)NR$_a$R$_a$, —NR$_a$R$_a$, or —NR$_a$C(O)O($C_{1-4}$ alkyl); $R_2$ is $C_{1-4}$ alkyl, $C_{1-3}$ cyanoalkyl, $C_{1-3}$ fluoroalkyl, $C_{2-3}$ alkenyl, —CH$_2$CH$_2$CH=CF$_2$, $C_{3-4}$ alkynyl, —(CH$_2$)$_{1-3}$OCH$_3$, —(CH$_2$)$_{1-3}$O(CH$_2$)$_{1-2}$OCH$_3$, —(CH$_2$)$_{1-3}$C(O)CH$_3$, —(CH$_2$)$_{1-3}$C(O)O($C_{1-2}$ alkyl), —(CH$_2$)$_{1-2}$R$_b$, —(CH$_2$)$_{1-3}$OR$_b$, or —(CH$_2$)$_{1-3}$OCH$_2$R$_b$; $R_b$ is $C_{3-6}$ cycloalkyl or dioxanyl, each substituted with zero to 1 substituent selected from F, —CN, —CH$_3$, and —OCH$_3$; $R_3$ is H, F, Cl, Br, —CN, $C_{1-2}$ alkyl, $C_{1-2}$ fluoroalkyl, —NO$_2$, —C(O)O($C_{1-2}$ alkyl), or —C(O)($C_{1-2}$ fluoroalkyl); $R_4$ is: (a) 2,3-dihydro-H-indenyl substituted with zero to 2 substituents independently selected from F, Cl, —OH, —CH$_3$, —CF$_3$, —OCH$_3$, and —OCH$_2$CH=CH$_2$; or (b) —CH$_2$R$_y$, —C(CH$_3$)$_2$R$_y$, —CHR$_x$R$_y$, —CH$_2$CH(OH)R$_x$, —CH(CH$_3$) (CH$_2$CH$_2$OCH$_3$), or cyclopropyl substituted with fluorophenyl; $R_x$ is $C_{1-5}$ alkyl, $C_{1-2}$ hydroxyalkl, $C_{1-2}$ aminoalkyl, $C_{3-6}$ cycloalkyl, or phenyl substituted with zero to 2 substituents independently selected from F, Cl, —OH, $C_{1-2}$ alkyl, —CHF$_2$, —OCH$_3$, —OCH$_2$CH=CH$_2$, and —OCH$_2$C≡CH; and $R_y$ is 1,3-benzodiazolyl, indazolyl, indolyl, indolinyl, naphthalenyl, oxoindolinyl, pyridinyl, pyrimidinyl, or phenyl, each substituted with zero to 3 substituents independently selected from F, Cl, Br, —OH, —CN, $C_{1-4}$ alkyl, $C_{1-2}$ fluoroalkyl, $C_{1-2}$ alkoxy, $C_{1-2}$ fluoroalkoxy, —OCH$_2$CH=CH$_2$, —OCH$_2$C≡CH, —OCH$_2$(cyanopyridinyl), —NR$_c$R$_c$, —NHS(O)$_2$CH$_3$, —NHC(O)($C_{1-2}$ alkyl), —NHC(O)O($C_{1-4}$ alkyl), —NHC(O)(phenyl), —NHC(O) NH(phenyl), and phenyl; and R$_a$, R$_c$, and R$_d$ are defined in the first aspect.

In one embodiment, a compound of Formula (I) or a salt thereof is provided wherein $R_1$ is H, Cl, Br, —CN, $C_{1-2}$ alkyl, —CH=CH$_2$, —OCH$_3$, —C(O)OH, —C(O)OCH$_3$, —C(O)N(CH$_3$)$_2$, —NH$_2$, or —NHC(O)OC(CH$_3$)$_3$; $R_2$ is —CH$_3$, —CH$_2$CH$_3$, —CH$_2$CH$_2$CH$_3$, —CH$_2$CH$_2$CH$_2$CH$_3$, —CH$_2$CN, —CH$_2$CH$_2$CH$_2$CN, —CH$_2$CH$_2$CF$_3$, —CH$_2$CH=CH$_2$, —CH$_2$CH$_2$CH=CF$_2$, —CH$_2$C≡CH, —CH$_2$CH$_2$OCH$_3$, —CH$_2$CH$_2$CH$_2$OCH$_3$, —CH$_2$CH$_2$CH$_2$OCH$_2$CH$_2$OCH$_3$, —CH$_2$CH$_2$CH$_2$C(O)CH$_3$, —CH$_2$C(O)OCH$_2$CH$_3$, —CH$_2$(cyclopropyl), —CH$_2$ (methyl isoxazolyl), —CH$_2$(methylphenyl), —CH$_2$(cyanophenyl), —CH$_2$(fluorophenyl), —CH$_2$(methoxyphenyl), —CH$_2$CH$_2$(dioxanyl), —CH$_2$(phenyl), —CH$_2$CH$_2$(phenyl), —CH$_2$CH$_2$(methoxyphenyl), —CH$_2$CH$_2$CH$_2$O(phenyl), —CH$_2$CH$_2$CH$_2$OCH$_2$(phenyl), or phenyl; $R_3$ is H, F, Cl, Br, —CN, —CH$_3$, —CF$_3$, —NO$_2$, —C(O)OCH$_2$CH$_3$, or —C(O)CF$_3$; $R_4$ is: (a) 2,3-dihydro-1H-indenyl substituted with 1 to 2 substituents independently selected from F, —OH, —OCH$_3$, and —OCH$_2$CH=CH$_2$; or (b) —CH$_2$R$_y$, —C(CH$_3$)$_2$R$_y$, —CHR$_x$R$_y$, —CH$_2$CH(OH)R$_x$, —CH(CH$_3$) (CH$_2$CH$_2$OCH$_3$), or cyclopropyl substituted with fluorophenyl; $R_x$ is $C_{1-2}$ alkyl, —CH(CH$_3$)$_2$, —C(CH$_3$)$_3$, —CH$_2$C (CH$_3$)$_3$, —CH$_2$OH, —CH$_2$NH$_2$, cyclopropyl, cyclobutyl, cyclohexyl, or phenyl substituted with zero to 2 substituents independently selected from F, Cl, —OH, and —OCH$_3$; and $R_y$ is 1,3-benzodiazolyl, indazolyl, indolyl, ethyl indolyl, indolinyl, naphthalenyl, hydroxynaphthalenyl, oxoindolinyl, pyridinyl, methoxypyridinyl, pyrimidinyl, or phenyl substituted with zero to 3 substituents independently selected from F, Cl, Br, —OH, —CN, —CH$_3$, —C(CH$_3$)$_3$, —CHF$_2$, —CF$_3$, —OCH$_3$, —OCF$_3$, —OCH$_2$CH=CH$_2$, —OCH$_2$C≡CH, —OCH$_2$(cyanopyridinyl), —NH$_2$, —NHS (O)$_2$CH$_3$, —N(CH$_3$)(CH$_2$CH$_3$), —NHC(O)CH$_3$, —NHC (O)O(C(CH$_3$)$_3$), —NHC(O)(phenyl), —NHC(O)NH(phenyl), and phenyl.

In one embodiment, a compound of Formula (I) or a salt thereof is provided wherein $R_1$ is H, Cl, Br, —CN, $C_{1-4}$ alkyl, $C_{2-3}$ alkenyl, $C_{1-3}$ alkoxy, —C(O)OH, —C(O)O($C_{1-3}$ alkyl), —C(O)NR$_a$R$_a$, —NR$_a$R$_a$, or —NR$_a$C(O)O($C_{1-4}$ alkyl); and $R_2$, $R_3$, $R_4$, and $R_a$ are defined in the first aspect. Included in this embodiment are compounds in which $R_1$ is H, Cl, Br, —CN, $C_{1-3}$ alkyl, $C_{2-3}$ alkenyl, $C_{1-2}$ alkoxy, —C(O)OH, —C(O)O($C_{1-2}$ alkyl), —C(O)NR$_a$R$_a$, —NR$_a$R$_a$, or —NR$_a$C(O)O($C_{1-4}$ alkyl). Also included in this embodiment are compounds in which $R_1$ is H, Cl, Br, —CN, $C_{1-2}$ alkyl, —CH═CH$_2$, —OCH$_3$, —C(O)OH, —C(O)OCH$_3$, —C(O)N(CH$_3$)$_2$, —NH$_2$, or —NHC(O)OC(CH$_3$)$_3$.

In one embodiment, a compound of Formula (I) or a salt thereof is provided wherein $R_1$ is H, Cl, Br, —CN, $C_{1-4}$ alkyl, $C_{2-3}$ alkenyl, $C_{1-3}$ alkoxy, —C(O)OH, —C(O)O($C_{1-3}$ alkyl), —C(O)NR$_a$R$_a$, —NR$_a$R$_a$, or —NR$_a$C(O)O($C_{1-4}$ alkyl); each $R_a$ is independently H or $C_{1-2}$ alkyl; and $R_2$, $R_3$, and $R_4$ are defined in the first aspect. Included in this embodiment are compounds in which $R_1$ is H, Cl, Br, —CN, $C_{1-3}$ alkyl, $C_{2-3}$ alkenyl, $C_{1-2}$ alkoxy, —C(O)OH, —C(O)O($C_{1-2}$ alkyl), —C(O)NR$_a$R$_a$, —NR$_a$R$_a$, or —NR$_a$C(O)O($C_{1-4}$ alkyl).

In one embodiment, a compound of Formula (I) or a salt thereof is provided wherein $R_2$ is $C_{1-5}$ alkyl, $C_{1-4}$ cyanoalkyl, $C_{1-3}$ fluoroalkyl, $C_{2-4}$ alkenyl, —(CH$_2$)$_{2-3}$CH═CF$_2$, $C_{3-5}$ alkynyl, —(CH$_2$)$_{1-4}$O($C_{1-2}$ alkyl), —(CH$_2$)$_{1-4}$O(CH$_2$)$_{1-3}$O($C_{1-2}$ alkyl), —(CH$_2$)$_{1-3}$C(O)($C_{1-2}$ alkyl), —(CH$_2$)$_{1-3}$C(O)O($C_{1-3}$ alkyl), —(CH$_2$)$_{1-3}$R$_b$, —(CH$_2$)$_{1-3}$OR$_b$, or —(CH$_2$)$_{1-3}$OCH$_2$R$_b$; and $R_1$, $R_3$, $R_4$, and $R_b$ are defined in the first aspect. Included in this embodiment are compounds in which $R_2$ is $C_{1-4}$ alkyl, $C_{1-3}$ cyanoalkyl, $C_{1-3}$ fluoroalkyl, $C_{2-3}$ alkenyl, —CH$_2$CH$_2$CH═CF$_2$, $C_{3-4}$ alkynyl, —(CH$_2$)$_{1-3}$OCH$_3$, —(CH$_2$)$_{1-3}$O(CH$_2$)$_{1-2}$OCH$_3$, —(CH$_2$)$_{1-3}$C(O)CH$_3$, —(CH$_2$)$_{1-3}$C(O)O($C_{1-2}$ alkyl), —(CH$_2$)$_{1-2}$R$_b$, —(CH$_2$)$_{1-3}$OR$_b$, or —(CH$_2$)$_{1-3}$OCH$_2$R$_b$. Also included in this embodiment are compounds in which $R_2$ is —CH$_3$, —CH$_2$CH$_3$, —CH$_2$CH$_2$CH$_3$, —CH$_2$CH$_2$CH$_2$CH$_3$, —CH$_2$CN, —CH$_2$CH$_2$CN, —CH$_2$CH$_2$CF$_3$, —CH$_2$CH═CH$_2$, —CH$_2$CH$_2$CH═CF$_2$, —CH$_2$C≡CH, —CH$_2$CH$_2$OCH$_3$, —CH$_2$CH$_2$CH$_2$OCH$_3$, —CH$_2$CH$_2$CH$_2$OCH$_2$CH$_2$OCH$_3$, —CH$_2$CH$_2$CH$_2$C(O)CH$_3$, —CH$_2$C(O)OCH$_2$CH$_3$, —CH$_2$(cyclopropyl), or —CH$_2$CH$_2$(dioxanyl).

In one embodiment, a compound of Formula (I) or a salt thereof is provided wherein $R_2$ is $C_{1-5}$ alkyl, $C_{1-4}$ cyanoalkyl, $C_{1-3}$ fluoroalkyl, $C_{2-4}$ alkenyl, —(CH$_2$)$_{2-3}$CH═CF$_2$, $C_{3-5}$ alkynyl, —(CH$_2$)$_{1-4}$O($C_{1-2}$ alkyl), —(CH$_2$)$_{1-4}$O(CH$_2$)$_{1-3}$O($C_{1-2}$ alkyl), —(CH$_2$)$_{1-3}$C(O)($C_{1-2}$ alkyl), or —(CH$_2$)$_{1-3}$C(O)O($C_{1-3}$ alkyl); and $R_1$, $R_3$, and $R_4$ are defined in the first aspect. Included in this embodiment are compounds in which $R_2$ is $C_{1-4}$ alkyl, $C_{1-3}$ cyanoalkyl, $C_{1-3}$ fluoroalkyl, $C_{2-3}$ alkenyl, —CH$_2$CH$_2$CH═CF$_2$, $C_{3-4}$ alkynyl, —(CH$_2$)$_{1-3}$OCH$_3$, —(CH$_2$)$_{1-3}$O(CH$_2$)$_{1-2}$OCH$_3$, —(CH$_2$)$_{1-3}$C(O)CH$_3$, or —(CH$_2$)$_{1-3}$C(O)O($C_{1-2}$ alkyl). Also included in this embodiment are compounds in which $R_2$ is —CH$_3$, —CH$_2$CH$_3$, —CH$_2$CH$_2$CH$_3$, —CH$_2$CH$_2$CH$_2$CH$_3$, —CH$_2$CN, —CH$_2$CH$_2$CH$_2$CN, —CH$_2$CH$_2$CF$_3$, —CH$_2$CH═CH$_2$, —CH$_2$CH$_2$CH═CF$_2$, —CH$_2$C≡CH, —CH$_2$CH$_2$OCH$_3$, —CH$_2$CH$_2$CH$_2$OCH$_3$, —CH$_2$CH$_2$CH$_2$OCH$_2$CH$_2$OCH$_3$, —CH$_2$CH$_2$CH$_2$C(O)CH$_3$, or —CH$_2$C(O)OCH$_2$CH$_3$.

In one embodiment, a compound of Formula (I) or a salt thereof is provided wherein $R_2$ is —(CH$_2$)$_{1-3}$R$_b$, —(CH$_2$)$_{1-3}$OR$_b$, or —(CH$_2$)$_{1-3}$OCH$_2$R$_b$; and $R_1$, $R_3$, $R_4$, and $R_b$ are defined in the first aspect. Included in this embodiment are compounds in which $R_2$ is —(CH$_2$)$_{1-2}$R$_b$, —(CH$_2$)$_{1-3}$OR$_b$, or —(CH$_2$)$_{1-3}$OCH$_2$R$_b$; and $R_b$ is $C_{3-6}$ cycloalkyl or dioxanyl, each substituted with zero to 1 substituent selected from F, —CN, —CH$_3$, and —OCH$_3$. Also included in this embodiment are compounds in which $R_2$ is —CH$_2$(cyclopropyl) or —CH$_2$CH$_2$(dioxanyl).

In one embodiment, a compound of Formula (I) or a salt thereof is provided wherein $R_3$ is H, F, Cl, Br, —CN, $C_{1-3}$ alkyl, $C_{1-3}$ fluoroalkyl, —NO$_2$, —C(O)O($C_{1-3}$ alkyl), —C(O)($C_{1-2}$ alkyl), or —C(O)($C_{1-3}$ fluoroalkyl); and $R_1$, $R_2$, and $R_4$ are defined in the first aspect. Included in this embodiment are compounds in which $R_3$ is H, F, Cl, Br, —CN, $C_{1-2}$ alkyl, $C_{1-2}$ fluoroalkyl, —NO$_2$, —C(O)O($C_{1-2}$ alkyl), or —C(O)($C_{1-2}$ fluoroalkyl). Also included in this embodiment are compounds in which $R_3$ is H, F, Cl, Br, —CN, —CH$_3$, —CF$_3$, —NO$_2$, —C(O)OCH$_2$CH$_3$, or —C(O)CF$_3$.

In one embodiment, a compound of Formula (I) or a salt thereof is provided wherein $R_4$ is 2,3-dihydro-1H-indenyl substituted with zero to 2 substituents independently selected from F, Cl, —OH, $C_{1-2}$ alkyl, $C_{1-2}$ fluoroalkyl, $C_{1-2}$ alkoxy, and —OCH$_2$CH═CH$_2$; and $R_1$, $R_2$, and $R_3$ are defined in the first aspect. Included in this embodiment are compounds in which $R_4$ is 2,3-dihydro-1H-indenyl substituted with zero to 2 substituents independently selected from F, Cl, —OH, —CH$_3$, —CF$_3$, —OCH$_3$, and —OCH$_2$CH═CH$_2$. Also included in this embodiment are compounds in which $R_4$ is 2,3-dihydro-1H-indenyl substituted with 1 to 2 substituents independently selected from F, —OH, —OCH$_3$, and —OCH$_2$CH═CH$_2$.

In one embodiment, a compound of Formula (I) or a salt thereof is provided wherein $R_4$ is —CH$_2$R$_y$, —C(CH$_3$)$_2$R$_y$, —CHR$_x$R$_y$, —CH$_2$CH(OH)R$_x$, —CH(CH$_3$)(CH$_2$CH$_2$OCH$_3$), or $C_{3-6}$ cycloalkyl substituted with fluorophenyl; and $R_1$, $R_2$, $R_3$, $R_x$, and $R_y$ are defined in the first aspect. Included in this embodiment are compounds in which $R_x$ is $C_{1-4}$ alkyl, $C_{1-3}$ hydroxyalkyl, $C_{1-2}$ aminoalkyl, $C_{3-6}$ cycloalkyl, or phenyl substituted with zero to 2 substituents independently selected from F, Cl, —OH, $C_{1-3}$ alkyl, $C_{1-2}$ fluoroalkyl, $C_{1-2}$ alkoxy, —OCH$_2$CH═CH$_2$, and —OCH$_2$C≡CH; $R_y$ is 1,3-benzodiazolyl, indazolyl, indolyl, indolinyl, naphthalenyl, oxoindolinyl, pyridinyl, pyrimidinyl, or phenyl, each substituted with zero to 3 substituents independently selected from F, Cl, Br, —OH, —CN, $C_{1-4}$ alkyl, $C_{1-3}$ fluoroalkyl, $C_{1-3}$ alkoxy, $C_{1-3}$ fluoroalkoxy, —OCH$_2$CH═CH$_2$, —OCH$_2$C≡CH, —OCH$_2$(cyanopyridinyl), —NR$_c$R$_c$, —NR$_a$S(O)$_2$($C_{1-3}$ alkyl), —NR$_a$C(O)($C_{1-2}$ alkyl), —NR$_a$C(O)O($C_{1-2}$ alkyl), —NR$_a$C(O)R$_d$, —NR$_a$C(O)NR$_a$R$_a$, and R$_d$; and R$_a$, R$_c$, and R$_d$ are defined in the first aspect. Also included in this embodiment are compounds in which $R_x$ is $C_{1-5}$ alkyl, $C_{1-2}$ hydroxyalkyl, $C_{1-2}$ aminoalkyl, $C_{3-6}$ cycloalkyl, or phenyl substituted with zero to 2 substituents independently selected from F, Cl, —OH, $C_{1-2}$ alkyl, —CHF$_2$, —OCH$_3$, —OCH$_2$CH═CH$_2$, and —OCH$_2$C≡CH; and $R_y$ is 1,3-benzodiazolyl, indazolyl, indolyl, indolinyl, naphthalenyl, oxoindolinyl, pyridinyl, pyrimidinyl, or phenyl, each substituted with zero to 3 substituents independently selected from F, Cl, Br, —OH, —CN, $C_{1-4}$ alkyl, $C_{1-2}$ fluoroalkyl, $C_{1-2}$ alkoxy, $C_{1-2}$ fluoroalkoxy, —OCH$_2$CH═CH$_2$, —OCH$_2$C≡CH, —OCH$_2$(cyanopyridinyl), —NR$_c$R$_c$, —NHS(O)$_2$CH$_3$, —NHC(O)($C_{1-2}$ alkyl), —NHC(O)O($C_{1-4}$ alkyl), —NHC(O)(phenyl), —NHC(O)NH(phenyl), and phenyl.

In one embodiment, a compound of Formula (I) or a salt thereof is provided wherein $R_4$ is —CH$_2$R$_y$, —C(CH$_3$)$_2$R$_y$, —CH$_2$R$_x$R$_y$, or —CH$_2$CH(O)R$_x$; $R_x$ is $C_{1-2}$ alkyl, —CH(CH$_3$)$_2$, —C(CH$_3$)$_3$, —CH$_2$C(CH$_3$)$_3$, —CH$_2$OH, —CH$_2$NH, cyclopropyl, cyclobutyl, cyclohexyl, or phenyl substituted with zero to 2 substituents independently selected from F, Cl, —OH, and —OCH$_3$; and $R_y$ is 1,3-benzodiazolyl, indazolyl, indolyl, ethyl indolyl, indolinyl, naphthalenyl, hydroxynaphthalenyl, oxoindolinyl, pyridinyl, methoxypyridinyl, pyrimidinyl, or phenyl substituted with zero to 3 substituents independently selected from F, Cl, Br, —OH, —CN, —C$_3$, —C(CH$_3$)$_3$, —CHF$_2$, —CF$_3$, —OCH$_3$, —OCF$_3$, —OCH$_2$CH═CH$_2$, —OCH$_2$C≡CH, —OCH$_2$(cyanopyridinyl), —NH$_2$, —NHS(O)$_2$CH$_3$, —N(CH$_3$)(CH$_2$CH$_3$), —NHC(O)CH$_3$, —NHC(O)O(C(CH$_3$)$_3$), —NHC(O)(phenyl), —NHC(O)NH(phenyl), and phenyl; and R$_1$, R$_2$, and R$_3$ are defined in the first aspect.

In one embodiment, a compound of Formula (I) or a salt thereof is provided wherein R$_4$ is —CHR$_x$R$_y$; and R$_1$, R$_2$, R$_3$, R$_x$, and R$_y$ are defined in the first aspect. Included in this embodiment are compounds in which R$_x$ is phenyl substituted with zero to 2 substituents independently selected from F, Cl, —OH, C$_{1-2}$ alkyl, C$_{1-2}$ fluoroalkyl, C$_{1-2}$ alkoxy, —OCH$_2$CH═CH$_2$, and —OCH$_2$C≡CH. Also included in this embodiment are compounds in which R$_x$ is phenyl substituted with zero to 2 substituents independently selected from F, Cl, —OH, C$_{1-2}$ alkyl, —CHF$_2$, —OCH$_3$, —OCH$_2$CH═CH$_2$, and —OCH$_2$C≡CH; and R$_y$ is phenyl substituted with zero to 3 substituents independently selected from F, Cl, Br, —OH, —CN, C$_{1-4}$ alkyl, C$_{1-2}$ fluoroalkyl, C$_{1-2}$ alkoxy, C$_{1-2}$ fluoroalkoxy, —OCH$_2$CH═CH$_2$, —OCH$_2$C≡CH, —OCH$_2$(cyanopyridinyl), —NR$_c$R$_c$, —NHS(O)$_2$CH$_3$, —NHC(O)(C$_{1-2}$ alkyl), —NHC(O)O(C$_{1-4}$ alkyl), —NHC(O)(phenyl), —NHC(O)NH(phenyl), and phenyl. This embodiment also includes compounds in which R$_x$ is phenyl substituted with zero to 2 substituents independently selected from F, Cl, —OH, and —OCH$_3$; and R$_y$ is phenyl substituted with zero to 3 substituents independently selected from F, Cl, Br, —OH, —CN, —CH$_3$, —C(CH$_3$)$_3$, —CHF$_2$, —CF$_3$, —OCH$_3$, —OCF$_3$, —OCH$_2$CH═CH$_2$, —OCH$_2$C≡CH, —OCH$_2$(cyanopyridinyl), —NH$_2$, —NHS(O)$_2$CH$_3$, —N(CH$_3$)(CH$_2$CH$_3$), —NHC(O)CH, —NHC(O)O(C(CH$_3$)$_3$), —NHC(O)(phenyl), —NHC(O)NH(phenyl), and phenyl.

In one embodiment, a compound of Formula (I) or a salt thereof is provided wherein R$_4$ is —CHR$_x$R$_y$; R$_x$ is phenyl substituted with zero to 1 substituent selected from F and —OH; R$_y$ is phenyl substituted with zero to 3 substituents independently selected from F, Cl, Br, —OH, —CN, —CH$_3$, —C(CH$_3$)$_3$, —CHF$_2$, —CF$_3$, —OCH$_3$, —OCF$_3$, —OCH$_2$CH═CH$_2$, —OCH$_2$C≡CH, —OCH$_2$(cyanopyridinyl), —NH$_2$, —NHS(O)$_2$CH$_3$, —N(CH$_3$)(CH$_2$CH$_3$), —NHC(O)CH$_3$, —NHC(O)O(C(CH$_3$)$_3$), —NHC(O)(phenyl), —NHC(O)NH(phenyl), and phenyl; and R$_1$, R$_2$, R$_3$ are defined in the first aspect. Included in this embodiment are compounds in which R$_y$ is phenyl substituted with zero to 2 substituents independently selected from F, —OH, —CH$_3$, and —OCH$_3$.

In one embodiment, a compound of Formula (I) or a salt thereof is provided wherein R$_4$ is —CHR$_x$R$_y$ or —CH$_2$CH(OH)R$_x$; and R$_1$, R$_2$, R$_3$, R$_x$, and R$_y$ are defined in the first aspect. Included in this embodiment are compounds in which R$_x$ is C$_{1-5}$ alkyl, C$_{1-3}$ hydroxyalkyl, C$_{1-2}$ aminoalkyl, C$_{3-6}$ cycloalkyl, or phenyl substituted with zero to 2 substituents independently selected from F, Cl, —OH, C$_{1-3}$ alkyl, C$_{1-2}$ fluoroalkyl, C$_{1-2}$ alkoxy, —OCH$_2$CH═CH$_2$, and —OCH$_2$C≡CH; R$_y$ is 1,3-benzodiazolyl indazolyl, indolyl, indolinyl, naphthalenyl, oxoindolinyl, pyridinyl, pyrimidinyl, or phenyl, each substituted with zero to 3 substituents independently selected from F, Cl, Br, —OH, —CN, C$_{1-3}$ alkyl, C$_{1-3}$ fluoroalkyl, C$_{1-3}$ alkoxy, —OCH$_2$CH═CH$_2$, —OCH$_2$C≡CH, —OCH$_2$(cyanopyridinyl), —NR$_c$R$_c$, —NR$_a$S(O)$_2$(C$_{1-3}$ alkyl), —NR$_a$C(O)(C$_{1-2}$ alkyl), —NR$_a$C(O)O(C$_{1-3}$ alkyl), —NR$_a$C(O)R$_d$, —NR$_a$C(O)NR$_a$R$_d$, and R$_d$; and R$_a$, R$_c$, and R$_d$ are defined in the first aspect. Also included in this embodiment are compounds in which R$_x$ is C$_{1-5}$ alkyl, C$_{1-2}$ hydroxyalkyl, C$_{1-2}$ aminoalkyl, C$_{3-6}$ cycloalkyl, or phenyl substituted with zero to 2 substituents independently selected from F, —OH, C$_{1-2}$ alkyl, —CHF$_2$, —OCH$_3$, —OCH$_2$CH═CH$_2$, and —OCH$_2$C≡CH; and R$_y$ is F, Cl, Br, —OH, —CN, C$_{1-4}$ alkyl, C$_{1-2}$ fluoroalkyl, C$_{1-2}$ alkoxy, C$_{1-2}$ fluoroalkoxy, —OCH$_2$CH═CH$_2$, —OCH$_2$C≡CH, —OCH$_2$(cyanopyridinyl), —NR$_c$R$_c$, —NHS(O)$_2$CH$_3$, —NHC(O)(C$_{1-2}$ alkyl), —NHC(O)O(C$_{1-4}$ alkyl), —NHC(O)(phenyl), —NHC(O)NH(phenyl), or phenyl. Additionally, included in this embodiment are compounds in which R$_x$ is C$_{1-2}$ alkyl, —CH(CH)$_2$, —C(CH$_3$)$_3$, —CH$_2$C(CH$_3$)$_3$, —CH$_2$OH, —CH$_2$NH$_2$, cyclopropyl, cyclobutyl, cyclohexyl, or phenyl substituted with zero to 2 substituents independently selected from F, Cl, —OH, and —OCH$_3$; and R$_y$ is phenyl substituted with zero to 3 substituents independently selected from F, Cl, Br, —OH, —CN, —CH$_3$, —C(CH$_3$), —CHF$_2$, —CF$_3$, —OCH$_3$, —OCF$_3$, —OCH$_2$CH═CH, —OCH$_2$C≡CH, —OCH$_2$(cyanopyridinyl), —NH$_2$, —NHS(O)$_2$CH$_3$, —N(CH$_3$)(CH$_2$CH$_3$), —NHC(O)CH$_3$, —NHC(O)O(C(CH$_3$)$_3$), —NHC(O)(phenyl), —NHC(O)NH(phenyl), and phenyl.

In one embodiment, a compound of Formula (I) or a salt thereof is provided wherein R$_4$ is —CH$_2$R$_y$ or —C(CH$_3$)$_2$R$_y$; and R$_1$, R$_2$, R$_3$, and R$_y$ are defined in the first aspect. Included in this embodiment are compounds in which R$_y$ is 1,3-benzodiazolyl, indazolyl, indolyl, indolinyl, naphthalenyl, oxoindolinyl, pyridinyl, pyrimidinyl, or phenyl, each substituted with zero to 3 substituents independently selected from F, Cl, Br, —OH, —CN, C$_{1-4}$ alkyl, C$_{1-2}$ fluoroalkyl, C$_{1-2}$ alkoxy, C$_{1-2}$ fluoroalkoxy, —OCH$_2$CH═CH$_2$, —OCH$_2$C≡CH, —OCH$_2$(cyanopyridinyl), —NR$_c$R$_c$, —NHS(O)$_2$CH$_3$, —NHC(O)(C$_{1-2}$ alkyl), —NHC(O)O(C$_{1-4}$ alkyl), —NHC(O)(phenyl), —NHC(O)NH(phenyl), and phenyl; and R$_4$ is defined in the first aspect. Also included are compounds in which R$_y$ is 1,3-benzodiazolyl, indazolyl, indolyl, ethyl indolyl, indolinyl, naphthalenyl, hydroxynaphthalenyl, oxoindolinyl, pyridinyl, methoxypyridinyl, pyrimidinyl, or phenyl substituted with zero to 3 substituents independently selected from F, Cl, Br, —OH, —CN, —CH$_3$, —C(CH$_3$)$_3$, —CHF$_2$, —CF$_3$, —OCH$_3$, —OCF$_3$, —OCH$_2$CH═CH$_2$, —OCH$_2$C≡CH, —OCH$_2$(cyanopyridinyl), —NH$_2$, —NHS(O)$_2$CH$_3$, —N(CH$_3$)(CH$_2$CH$_3$), —NHC(O)CH$_3$, —NHC(O)O(C(CH$_3$)$_3$), —NHC(O)(phenyl), —NHC(O)NH(phenyl), and phenyl.

In one embodiment, a compound of Formula (I) or a salt thereof is provided wherein said compound is: ethyl 4-(4-(bis(4-fluorophenyl)methyl)piperazin-1-yl)-6-bromo-1-methyl-2-oxo-1,2-dihydro-1,5-naphthyridine-3-carboxylate (1); 6-bromo-4-(4-(2-hydroxybenzyl)piperazin-1-yl)-1-methyl-2-oxo-1,2-dihydro-1,5-naphthyridine-3-carbonitrile (2); 4-(4-(bis(4-fluorophenyl)methyl)piperazin-1-yl)-1-methyl-3-nitro-1,5-naphthyridin-2(1H)-one (3); 6-bromo-4-{4-[(4-fluorophenyl)[2-(prop-2-yn-1-yloxy) phenyl]methyl]piperazin-1-yl}-1-methyl-2-oxo-1,2-dihydro-1,5-naphthyridine-3-carbonitrile (5); 6-bromo-4-{4-[(4-fluorophenyl)[2-(prop-2-yn-1-yloxy)phenyl]methyl]piperazin-1-yl}-1-methyl-2-ox-1,2-dihydro-1,5-naphthyridine-3-carbonitrile (5-7); 6-bromo-4-{4-[(4-fluorophenyl)(2-hydroxyphenyl)methyl]piperazin-1-yl}-1-methyl-2-oxo-1,2-dihydro-1,5-naphthyridine-3-carbonitrile (8-10); 8-{4-[(4-fluorophenyl)(2-hydroxyphenyl)methyl]piperazin-1-yl}-5-methyl-6-oxo-5,6-dihydro-1,5-naphthyridine-2,7-dicarbonitrile (11); 6-bromo-4-{4-[(4-fluorophenyl)(2-methoxyphenyl)methyl]piperazin-1-yl}-1-methyl-2-oxo-1,2-dihydro-1,5-naphthyridine-3-carbonitrile (12-14); 6-bromo-4-{4-[(4-fluoro-2-methoxyphenyl)(4-fluorophenyl)methyl]piperazin-1-yl}-1-methyl-2-oxo-1,2-dihydro-1, 5-naphthyridine-3-carbonitrile (15-17); 8-{4-[(4-fluorophenyl)(2-methoxyphenyl)methyl]piperazin-1-yl}-5-methyl-7-nitro-6-oxo-5,6-dihydro-1,5-naphthyridine-2-carbonitrile (18-20); 6-bromo-4-[4-(6-methoxy-2,3-dihydro-1H-inden-1-yl)piperazin-1-yl]-1-methyl-2-oxo-1,2-dihydro-1,5-naphthyridine-3-carbonitrile (21); 6-bromo-4-{4-[1-(4-fluorophenyl)ethyl]piperazin-1-yl}-1-methyl-2-oxo-1,2-dihydro-1,5-naphthyridine-3-carbonitrile (22-24); 6-bromo-4-{4-[i-(4-fluorophenyl)propyl]piperazin-1-yl}-1-methyl-2-oxo-1,2-dihydro-1,5-naphthyridine-3-carbonitrile (25-27); 6-bromo-4-{4-[2-(4-fluorophenyl)-2-hydroxyethyl]piperazin-1-yl}-1-methyl-2-oxo-1,2-dihydro-1,5-naphthyridine-3-carbonitrile (28-30); 6-bromo-4-{4-[1-(4-fluorophenyl)-2-hydroxyethyl]piperazin-1-yl}-1-methyl-2-oxo-1,2-dihydro-1,5-naphthyridine-3-carbonitrile (31); 8-{4-[1-(4-fluorophenyl)propyl]piperazin-1-yl}-5-methyl-7-nitro-6-oxo-5,6-dihydro-1,5-naphthyridine-2-carbonitrile (32-34); 6-bromo-4-{4-[cyclopropyl(4-fluorophenyl)methyl]piperazin-1-yl}-1-methyl-2-oxo-1,2-dihydro-1,5-naphthyridine-3-carbonitrile (35); 8-{4-[2-(4-fluorophenyl)-2-hydroxyethyl]piperazin-1-yl}-5-methyl-7-nitro-6-oxo-5,6-dihydro-1,5-naphthyridine-2-carbonitrile (36); 8-{4-[1-(4-fluorophenyl)-2-hydroxyethyl]piperazin-1-yl}-5-methyl-7-nitro-6-oxo-5,6-dihydro-1,5-naphthyridine-2-carbonitrile (37); 1-methyl-4-{4-[(naphthalen-1-yl)methyl]piperazin-1-yl}-3-nitro-1,2-dihydro-1,5-naphthyridin-2-one (38); 6-chloro-4-{4-[(4-fluorophenyl)[2-(prop-2-yn-1-yloxy)phenyl]methyl]piperazin-1-yl}-1-methyl-2-oxo-1,2-dihydro-1,5-naphthyridine-3-carbonitrile (39); 8-(4-(bis(4-fluorophenyl)methyl) piperazin-1-yl)-5-methyl-7-nitro-6-oxo-5,6-dihydro-1,5-naphthyridine-2-carbonitrile (40); 8-(4-benzhydrylpiperazin-1-yl)-5-methyl-7-nitro-6-oxo-5,6-dihydro-1,5-naphthyridine-2-carbonitrile (41); 8-(4-((2-hydroxyphenyl)(phenyl)methyl)piperazin-1-yl)-5-methyl-7-nitro-6-oxo-5,6-dihydro-1,5-naphthyridine-2-carbonitrile (42); 8-(4-(1-(4-fluorophenyl)ethyl)piperazin-1-yl)-5-methyl-7-nitro-6-oxo-5,6-dihydro-1,5-naphthyridine-2-carbonitrile (43-45); 8-(4-(6-methoxy-2,3-dihydro-1H-inden-1-yl) piperazin-1-yl)-5-methyl-7-nitro-6-oxo-5,6-dihydro-1,5-naphthyridine-2-carbonitrile (46); 8-(4-(2-hydroxy-1-phenylethyl)piperazin-1-yl)-5-methyl-7-nitro-6-oxo-5,6-dihydro-1,5-naphthyridine-2-carbonitrile (47); 8-(4-(2-hydroxy-2-phenylethyl)piperazin-1-yl)-5-methyl-7-nitro-6-oxo-5,6-dihydro-1,5-naphthyridine-2-carbonitrile (48); 8-(4-(cyclopropyl(4-fluorophenyl)methyl)piperazin-1-yl)-5-methyl-7-nitro-6-oxo-5,6-dihydro-1,5-naphthyridine-2-carbonitrile (49-51); 4-(4-benzhydrylpiperazin-1-yl)-6-bromo-1-methyl-3-nitro-1,5-naphthyridin-2(1H)-one (52); 4-(4-(bis(4-fluorophenyl)methyl) piperazin-1-yl)-6-bromo-1-methyl-3-nitro-1,5-naphthyridin-2(1H)-one (53); 6-bromo-4-(4-((1-ethyl-1H-indol-4-yl)methyl)piperazin-1-yl)-1-methyl-3-nitro-1,5-naphthyridin-2(1H)-one (54); 6-bromo-1-methyl-4-(4-(naphthalen-1-ylmethyl)piperazin-1-yl)-3-nitro-1,5-naphthyridin-2(1H)-one (55); 6-bromo-4-(4-((4-fluoro-2-methoxyphenyl)(4-fluorophenyl)methyl) piperazin-1-yl)-1-methyl-3-nitro-1,5-naphthyridin-2(1H)-one (56-58); 6-bromo-4-(4-((4-fluorophenyl)(2-methoxy-6-methylphenyl)methyl)piperazin-1-yl)-1-methyl-3-nitro-1,5-naphthyridin-2(1H)-one (59-61); tert-butyl (8-(4-(bis(4-fluorophenyl)methyl)piperazin-1-yl)-5-methyl-7-nitro-6-oxo-5,6-dihydro-1,5-naphthyridin-2-yl)carbamate (62); 6-amino-4-(4-(bis(4-fluorophenyl)methyl)piperazin-1-yl)-1-methyl-3-nitro-1,5-naphthyridin-2(1H)-one (63); 6-bromo-4-(4-(2-(difluoromethyl) benzyl)piperazin-1-yl)-2-oxo-1-(prop-2-yn-1-yl)-1,2-dihydro-1,5-naphthyridine-3-carbonitrile (64); 6-bromo-4-(2-hydroxybenzyl)piperazin-1-yl)-2-oxo-1-(prop-2-yn-1-yl)-1,2-dihydro-1,5-naphthyridine-3-carbonitrile (65); 6-bromo-4-(4-(2-hydroxy-4-methylbenzyl)piperazin-1-yl)-2-oxo-1-(prop-2-yn-1-yl)-1,2-dihydro-1,5-naphthyridine-3-carbonitrile (66); 6-bromo-4-(4-(4-fluoro-2-hydroxybenzyl)piperazin-1-yl)-2-oxo-1-(prop-2-yn-1-yl)-1,2-dihydro-1,5-naphthyridine-3-carbonitrile (67); 6-bromo-4-(4-(4-fluoro-2-methoxybenzyl)piperazin-1-yl)-2-oxo-1-(prop-2-yn-1-yl)-1,2-dihydro-1,5-naphthyridine-3-carbonitrile (68); 6-bromo-4-(4-(2-hydroxy-4,6-dimethylbenzyl) piperazin-1-yl)-2-oxo-1-(prop-2-yn-1-yl)-1,2-dihydro-1,5-napthyridine-3-carbonitrile (69); 6-bromo-4-(4-((4-fluorophenyl)(2-hydroxyphenyl)methyl)piperazin-1-yl)-1-methyl-3-nitro-1,5-naphthyridin-2(1H)-one (70); 6-bromo-4-(4-((2-fluoro-4-methylphenyl)(2-hydroxyphenyl)methyl)piperazin-1-yl)-1-methyl-3-nitro-1,5-naphthyridin-2(1H)-one (71); 6-bromo-4-(4-((2,4-dimethylphenyl)(2-hydroxyphenyl)methyl) piperazin-1-yl)-1-methyl-3-nitro-1,5-naphthyridin-2(1H)-one (72); 6-bromo-4-(4-((2-hydroxyphenyl)(o-tolyl)methyl) piperazin-1-yl)-1-methyl-3-nitro-1,5-naphthyridin-2(1H)-one (73); 6-bromo-4-(4-((3-fluoro-2-hydroxyphenyl)(4-fluorophenyl)methyl)piperazin-1-yl)-1-methyl-3-nitro-1,5-naphthyridin-2(1H)-one (74-76); 6-bromo-4-(4-((2-hydroxyphenyl) (phenyl)methyl)piperazin-1-yl)-1-methyl-3-nitro-1,5-naphthyridin-2(1H)-one (77-79); 6-bromo-4-(4-((4-fluoro-2-hydroxyphenyl)(4-fluorophenyl)methyl) piperazin-1-yl)-1-methyl-3-nitro-1,5-naphthyridin-2(1H)-one (80-82); 6-bromo-4-(4-((4-fluorophenyl)(2-hydroxy-3-methylphenyl)methyl)piperazin-1-yl)-1-methyl-3-nitro-1,5-naphthyridin-2(1H)-one (83-85); 6-bromo-4-(4-((4-fluorophenyl)(2-hydroxy-5-methylphenyl)methy) piperazin-1-yl)-1-methyl-3-nitro-1,5-naphthyridin-2(1H)-one (86); 6-bromo-4-(4-((4-fluorophenyl)(2-hydroxy-6-methylphenyl)methyl)piperazin-1-yl)-1-methyl-3-nitro-1,5-naphthyridin-2(1H)-one (87); 5-((2-((4-(6-bromo-1-methyl-3-nitro-2-oxo-1,2-dihydro-1,5-naphthyridin-4-yl)piperazin-1-yl)(4-fluorophenyl)methyl)-3-methylphenoxy)methyl) nicotinonitrile (88-90); 5-((2-((4-(6-bromo-1-methyl-3-nitro-2-oxo-1,2-dihydro-1,5-naphthyridin-4-yl)piperazin-1-yl)(4-fluorophenyl)methyl)-5-fluorophenoxy)methyl) nicotinonitrile (91-93); 4-(4-((2-(allyloxy)-6-methylphenyl)(4-fluorophenyl)methyl) piperazin-1-yl)-6-bromo-1-methyl-3-nitro-1,5-naphthyridin-2(1H)-one (94-96); 8-(4-((4-fluorophenyl)(2-hydroxyphenyl)methyl)piperazin-1-yl)-5-methyl-7-nitro-6-oxo-5,6-dihydro-1,5-naphthyridine-2-carbonitrile (97-99); 8-(4-((4-fluorophenyl)(2-(prop-2-yn-1-yloxy)phenyl)methyl)piperazin-1-yl)-5-methyl-7-nitro-6-oxo-5,6-dihydro-1,5-naphthyridine-2-carbonitrile (100-102); 4-(4-(bis(4-fluorophenyl)methyl)piperazin-1-yl)-6-methoxy-1-methyl-2-oxo-1,2-dihydro-1,5-naphthyridine-3-carbonitrile (103); 4-(4-((4-fluorophenyl)(2-hydroxyphenyl) methyl)piperazin-1-yl)-6-methoxy-1-methyl-2-oxo-1,2-dihydro-1,5-naphthyridine-3-carbonitrile (104); 6-bromo-4-(4-((4-fluorophenyl)(2-hydroxyphenyl)methyl)piperazin-1-yl)-2-oxo-1-(prop-2-yn-1-yl)-1,2-dihydro-1,5-naphthyridine-3-carbonitrile (105-10$^7$); 4-(4-(bis(4-fluorophenyl)methyl)piperazin-1-yl)-6-bromo-1-(2-methoxyethyl)-2-oxo-1,2-dihydro-1,5-naphthyridine-3-carbonitrile (113); 6-bromo-4-(4-((4-fluoro-2-methoxyphenyl)(4-fluorophenyl)methyl)piperazin-1-yl)-1-(2-methoxyethyl)-2-oxo-1,2-dihydro-1,5-naphthyridine-3-carbonitrile (114-116); 6-bromo-4-(4-((4-fluorophenyl)(2-hydroxyphenyl)methyl)piperazin-1-yl)-1-(2-methoxyethyl)-2-oxo-1,2-dihydro-1,5-naphthyridine-3-carbonitrile (117); 8-(4-(bis(4-fluorophenyl)methyl) piperazin-1-yl)-7-nitro-6-oxo-5-(prop-2-yn-1-yl)-5,6-dihydro-1,5-naphthyridine-2-carbonitrile (118); 8-(4-((4-fluoro-2-hydroxyphenyl)(4-fluorophenyl)methyl)piperazin-1-yl)-7-nitro-6-oxo-5-(prop- 2-yn-1-yl)-5,6-dihydro-1,5-naphthyridine-2-carbonitrile (119-121); 8-(4-((4-fluoro-2-hydroxyphenyl)(4-fluorophenyl)methyl)piperazin-1-yl)-5-methyl-7-nitro-6-oxo-5,6-dihydro-1,5-naphthyridine-2-carbonitrile (122); 8-(4-((4-fluoro-2-methoxyphenyl)(4-fluorophenyl)methyl)piperazin-1-yl)-5-methy-7-nitro-6-oxo-5,6-dihydro-1,5-naphthyridine-2-carbonitrile (123-125); 8-(4-((4-fluoro-2-methoxyphenyl)(4-fluorophenyl)methyl)piperazin-1-yl)-7-nitro-6-oxo-5-(prop-2-yn-1-yl)-5,6-dihydro-1,5-naphthyridine-2-carbonitrile (126-128); 8-(4-((4-fluorophenyl)(2-methoxyphenyl)methyl) piperazin-1-yl)-7-nitro-6-oxo-5-(prop-2-yn-1-yl)-5,6-dihydro-1,5-naphthyridine-2-carbonitrile (129-131); 8-(4-((4-fluorophenyl)(2-hydroxyphenyl)methyl)piperazin-1-yl)-7-nitro-6-oxo-5-(prop-2-yn-1-yl)-5,6-dihydro-1,5-naphthyridine-2-carbonitrile (132-134); 8-(4-(1-(4-fluorophenyl)ethyl)piperazin-1-yl)-7-nitro-6-oxo-5-(prop-2-yn-1-yl)-5,6-dihydro-1,5-naphthyridine-2-carbonitrile (135-137); 8-(4-(6-methoxy-2,3-dihydro-1H-inden-1-yl)piperazin-1-yl)-7-nitro-6-oxo-5-(prop-2-yn-1-yl)-5,6-dihydro-1,5-naphthyridine-2-carbonitrile (138); 8-{4-[1-(4-fluorophenyl)propyl]piperazin-1-yl}-7-nitro-6-oxo-5-(prop-2-yn-1-yl)-5,6-dihydro-1,5-naphthyridine-2-carbonitrile (139-141); 8-(4-(cyclopropyl(4-fluorophenyl)methyl)piperazin-1-yl)-7-nitro-6-oxo-5-(prop-2-yn-1-yl)-5,6-dihydro-1, 5-naphthyridine-2-carbonitrile (142-144); 8-(4-((4-fluorophenyl)(2-hydroxyphenyl)methyl)piperazin-1-yl)-5-(2-methoxyethyl)-7-nitro-6-oxo-5,6-dihydro-1,5-naphthyridine-2-carbonitrile (145); 8-(4-(6-methoxy-2,3-dihydro-1H-inden-1-yl) piperazin-1-yl)-5-(2-methoxyethyl)-7-nitro-6-oxo-5,6-dihydro-1,5-naphthyridine-2-carbonitrile (146); 8-(4-(bis(4-fluorophenyl)methyl)piperazin-1-yl)-5-(2-methoxyethyl)-7-nitro-6-oxo-5,6-dihydro-1,5-naphthyridine-2-carbonitrile (147); 8-(4-(1-(4-fluorophenyl)ethyl)piperazin-1-yl)-5-(2-methoxyethyl)-7-nitro-6-oxo-5,6-dihydro-1,5-naphthyridine-2-carbonitrile (148-150); 5-(cyanomethyl)-S-(4-(1-(4-fluorophenyl)ethyl) piperazin-1-yl)-7-nitro-6-oxo-5,6-dihydro-1,5-naphthyridine-2-carbonitrile (151); 8-(4-(bis(4-fluorophenyl)methyl)piperazin-1-yl)-5-(cyanomethyl)-7-nitro-6-oxo-5,6-dihydro-1,5-naphthyridine-2-carbonitrile (152); 4-(4-(bis(4-fluorophenyl)methyl)piperazin-1-yl)-6-bromo-1-(cyanomethyl)-2-oxo-1,2-dihydro-1,5-naphthyridine-3-carbonitrile (153); 6-bromo-1-(cyanomethyl)-4-(4-(1-(4-fluorophenyl)ethyl)piperazin-1-yl)-2-oxo-1,2-dihydro-1,5-naphthyridine-3-carbonitrile (154); 6-bromo-1-(cyanomethyl)-4-(4-(1-(4-fluorophenyl)propyl)piperazin-1-yl)-2-oxo-1,2-dihydro-1,5-naphthyridine-3-carbonitrile (155); 6-bromo-1-(cyanomethyl)-4-(4-(6-methoxy-2,3-dihydro-1H-inden-1-yl)piperazin-1-yl)-2-oxo-1,2-dihydro-1, 5-naphthyridine-3-carbonitrile (156); 6-bromo-1-(cyanomethyl)-4-(4-((4-fluorophenyl)(2-hydroxyphenyl)methyl)piperazin-1-lv)-2-oxo-1,2-dihydro-1,5-naphthyridine-3-carbonitrile (157); 6-bromo-1-(cyclopropylmethyl)-4-(4-((4-fluorophenyl)(2-methoxyphenyl)methyl)piperazin-1-yl)-2-oxo-1,2-dihydro-1,5-naphthyridine-3-carbonitrile (158-160); 4-(4-(bis(4-fluorophenyl)methyl)piperazin-1-yl)-6-bromo-1-(cyclopropylmethyl)-2-oxo-1,2-dihydro-1,5-naphthyridine-3-carbonitrile (161); 6-bromo-1-(cyclopropylmethyl)-4-(4-(1-(4-fluorophenyl)ethyl)piperazin-1-yl)-2-oxo-1,2-dihydro-1,5-naphthyridine-3-carbonitrile (162-164); 4-(4-benzhydrylpiperazin-1-yl)-3-nitro-1-(prop-2-yn-1-yl)-1,5-naphthyridin-2(1H)-one (165); 1-(2-(1,3-dioxan-2-yl) ethyl)-4-(4-benzhydrylpiperazin-1-yl)-3-nitro-1,5-naphthyridin-2(1H)-one (166); 1-allyl-4-(4-benzhydrylpiperazin-1-yl)-3-nitro-1,5-naphthyridin-2(1H)-one (176); 4-(4-benzhydrylpiperazin-1-yl)-1-butyl-3-nitro-1,5-naphthyridin-2(1H)-one (177); 4-(4-(4-benzhydrylpiperazin-1-yl)-3-nitro-2-oxo-1,5-naphthyridin-(2H)-yl)butanenitrile (183); 4-(4-benzhydrylpiperazin-1-yl)-3-nitro-1-(3,3,3-trifluoropropyl)-1,5-naphthyridin-2 (1H)-one (185); 4-(4-benzhydrylpiperazin-1-yl)-1-(4,4-difluorobut-3-en-1-yl)-3-nitro-1,5-naphthyridin-2(1H)-one (186); 4-(4-benzhydrylpiperazin-1-yl)-3-nitro-1-(4-oxopentyl)-1,5-naphthyridin-2(1H)-one (187); 4-(4-benzhydrylpiperazin-1-yl)-1-(3-(2-methoxyethoxy)propyl)-3-nitro-1,5-naphthyridin-2(1H)-one (189); 4-(4-benzhydrylpiperazin-1-yl)-1-(3-methoxypropyl)-3-nitro-1,5-naphthyridin-2(1H)-one (190); 4-(4-benzhydrylpiperazin-1-yl)-6-bromo-1-methyl-2-oxo-1,2-dihydro-1,5-naphthyridine-3-carbonitrile (191); 6-bromo-4-(4-(4-fluoro-2-hydroxybenzyl)piperazin-1-yl)-1-methyl-2-oxo-1,2-dihydro-1,5-naphthyridine-3-carbonitrile (192); 6-chloro-4-(4-(4-fluoro-2-hydroxybenzyl)piperazin-1-yl)-1-methyl-2-oxo-1,2-dihydro-1,5-naphthyridine-3-carbonitrile (193); 4-(4-(4-fluoro-2-hydroxybenzyl)piperazin-1-yl)-1,6-dimethyl-2-oxo-1,2-dihydro-1,5-naphthyridine-3-carbonitrile (194); 4-(4-(1-(2-(allyloxy)-4-fluorophenyl)ethyl)piperazin-1-yl)-6-chloro-1-methyl-2-oxo-1,2-dihydro-1,5-naphthyridine-3-carbonitrile (195); 4-(4-benzhydrylpiperazin-1-yl)-1-methyl-2-oxo-1,2-dihydro-1,5-naphthyridine-3-carbonitrile (196); 6-chloro-4-(4-(2-hydroxybenzyl) piperazin-1-yl)-1-methyl-2-oxo-1,2-dihydro-1,5-naphthyridine-3-carbonitrile (198); 6-chloro-4-(4-(3-(ethyl(methyl)amino)benzyl)piperazin-1-yl)-1-methyl-2-oxo-1,2-dihydro-1,5-naphthyridine-3-carbonitrile (199); 4-(4-(7-(allyloxy)-5-fluoro-2,3-dihydro-1H-inden-1-yl)piperazin-1-yl)-6-chloro-1-methyl-2-oxo-1,2-dihydro-1, 5-naphthyridine-3-carbonitrile (200); 6-chloro-4-(4-(5-fluoro-7-hydroxy-2,3-dihydro-1H-inden-1-yl) piperazin-1-yl)-1-methyl-2-oxo-1,2-dihydro-1,5-naphthyridine-3-carbonitrile (201); 4-(4-benzhydrylpiperazin-1-yl)-6-ethyl-1-methyl-2-oxo-1,2-dihydro-1,5-naphthyridine-3-carbonitrile (202); 4-(4-benzhydrylpiperazin-1-yl)-1,6-dimethyl-2-oxo-1,2-dihydro-1,5-naphthyridine-3-carbonitrile (204); 4-(4-benzhydrylpiperazin-1-yl)-1-methyl-2-oxo-6-vinyl-1,2-dihydro-1,5-naphthyridine-3-carbonitrile (208); 6-chloro-4-(4-(cyclohexyl (phenyl)methyl)piperazin-1-yl)-1-methyl-2-oxo-1,2-dihydro-1,5-naphthyridine-3-carbonitrile (209); 4-(4-(2-aminobenzyl) piperazin-1-yl)-6-bromo-1-methyl-2-oxo-1,2-dihydro-1,5-naphthyridine-3-carbonitrile (211); N-(2-((4-(6-bromo-3-cyano-1-methyl-2-oxo-1,2-dihydro-1,5-naphthyridin-4-yl) piperazin-1-yl)methyl)phenyl) methanesulfonamide (212); N-(2-((4-(6-bromo-3-cyano-1-methyl-2-oxo-1,2-dihydro-1, 5-naphthyridin-4-yl)piperazin-1-yl)methyl)phenyl)benzamide (213); 1-(2-((4-(6-bromo-3-cyano-1-methyl-2-oxo-1, 2-dihydro-1,5-naphthyridin-4-yl)piperazin-1-yl)methyl) phenyl)-3-phenylurea (214); N-(2-((4-(6-bromo-3-cyano-1-methyl-2-oxo-1,2-dihydro-1,5-naphthyridin-4-yl)piperazin-1-yl)methyl)phenyl)acetamide (215); 6-chloro-4-(4-(indolin-7-ylmethyl)piperazin-1-yl)-1-methyl-2-oxo-1,2-dihydro-1,5-naphthyridine-3-carbonitrile (216); 8-(4-(bis(4-fluorophenyl)methyl)piperazin-1-yl)-5-methyl-6-oxo-5,6-dihydro-1,5-naphthyridine-2,7-dicarbonitrile (217); 4-(4-(bis(4-fluorophenyl)methyl)piperazin-1-yl)-6-chloro-1-methyl-2-oxo-1,2-dihydro-1,5-naphthyridine-3-carbonitrile (218); 6-chloro-4-(4-((2-hydroxyphenyl)(phenyl)methyl)piperazin-1-yl)-1-methyl-2-oxo-1,2-dihydro-1,5-naphthyridine-3-carbonitrile (219); 6-chloro-4-(4-((i-ethyl-1H-indol-4-yl)methyl) piperazin-1-yl)-1-methyl-2-oxo-1,2-dihydro-1, 5-naphthyridine-3-carbonitrile (220); 6-chloro-1-methyl-4-(4-(naphthalen-1-ylmethyl)piperazin-1-yl)-2-oxo-1,2-dihydro-1,5-naphthyridine-3-carbonitrile (221); 6-chloro-4-(4-((4-fluoro-2-hydroxyphenyl)(4-fluorophenyl)methyl)

piperazin-1-yl)-1-methyl-2-oxo-1,2-dihydro-1,5-naphthyridine-3-carbonitrile (222); 8-(4-benzhydrylpiperazin-1-yl)-5-methyl-7-nitro-6-oxo-5,6-dihydro-1,5-naphthyridine-2-carbonitrile (223) 3-bromo-4-(4-(1-(4-fluorophenyl)ethyl)piperazin-1-yl)-1,6-dimethyl-1,5-naphthyridin-2(1H)-one (224); 6-bromo-4-(4-((1-ethyl-1H-indol-4-yl)methyl)piperazin-1-yl)-1-methyl-2-oxo-1,2-dihydro-1,5-naphthyridine-3-carbonitrile (225); 4-(4-(bis(4-fluorophenyl)methyl)piperazin-1-yl)-1,6-dimethyl-2-oxo-1,2-dihydro-1,5-naphthyridine-3-carbonitrile (226); 4-(4-(bis(4-fluorophenyl)methyl)piperazin-1-yl)-1-methy-3-(2,2,2-trifluoroacetyl)-1,5-naphthyridin-2(1H)-one (227); 4-(4-(bis(4-fluorophenyl)methyl)piperazin-1-yl)-1,6-dimethyl-3-(2,2,2-trifluoroacetyl)-1,5-naphthyridin-2(1H)-one (228); 4-(4-(bis(4-fluorophenyl)methyl)piperazin-1-yl)-6-bromo-2-oxo-1-(prop-2-yn-1-yl)-1,2-dihydro-1,5-naphthyridine-3-carbonitrile (229); 4-(4-(bis(4-fluorophenyl)methyl)piperazin-1-yl)-3-bromo-1-methyl-1,5-naphthyridin-2(1H)-one (230); 8-(4-(bis(4-fluorophenyl)methyl)piperazin-1-yl)-7-cyano-N,N,5-trimethyl-6-oxo-5,6-dihydro-1,5-naphthyridine-2-carboxamide (231); 4-(4-(bis(4-fluorophenyl)methyl) piperazin-1-yl)-1,6-dimethyl-3-(trifluoromethyl)-1,5-naphthyridin-2(1H)-one (232); 4-(4-(bis(4-fluorophenyl)methyl)piperazin-1-yl)-3-chloro-1,6-dimethyl-1,5-naphthyridin-2(1H)-one (233); 4-(4-(bis(4-fluorophenyl)methyl)piperazin-1-yl)-3-fluoro-1,6-dimethyl-1,5-naphthyridin-2(1H)-one (234); 4-(4-(bis(4-fluorophenyl)methyl)piperazin-1-yl)-6-bromo-1-methyl-2-oxo-1,2-dihydro-1,5-naphthyridine-3-carbonitrile, TFA (235); 3-bromo-4-(4-((1-ethyl-1H-indol-4-yl)methyl)piperazin-1-yl)-1-methyl-1,5-naphthyridin-2(1H)-one (236); 6-bromo-1-methyl-4-(4-(naphthalen-1-ylmethyl)piperazin-1-yl)-2-oxo-1,2-dihydro-1,5-naphthyridine-3-carbonitrile (237); 4-(4-(([1,1'-biphenyl]-2-ylmethyl) piperazin-1-yl)-6-bromo-1-methyl-2-oxo-1,2-dihydro-1,5-naphthyridine-3-carbonitrile, TFA (238); 4-(4-(bis(4-fluorophenyl)methyl)piperazin-1-yl)-3-bromo-1,6-dimethyl-1,5-naphthyridin-2(1H)-one (239); methyl 8-(4-(bis(4-fluorophenyl)methyl)piperazin-1-yl)-7-cyano-5-methyl-6-oxo-5,6-dihydro-1,5-naphthyridine-2-carboxylate (240); 8-(4-(bis(4-fluorophenyl)methyl)piperazin-1-yl)-7-cyano-5-methyl-6-oxo-5,6-dihydro-1,5-naphthyridine-2-carboxylic acid (241); 4-[4-(diphenylmethyl)piperazin-1-yl]-1-methyl-3-nitro-1,2-dihydro-1,5-naphthyridin-2-one (242); 4-[4-(diphenylmethyl)piperazin-1-yl]-1-ethyl-3-nitro-1,2-dihydro-1,5-naphthyridin-2-one (243); 4-[4-(diphenylmethyl)piperazin-1-yl]-1-(2-methoxyethyl)-3-nitro-1,2-dihydro-1,5-naphthridine-2-one (244); 2-{4-[4-(diphenylmethyl)piperazin-1-yl]-3-nitro-2-oxo-1,2-dihydro-1,5-naphthyridin-1-yl}acetonitrile (245); ethyl 2-{4-[4-(diphenylmethyl)piperazin-1-yl]-3-nitro-2-oxo-1,2-dihydro-1,5-naphthyridin-1-yl}acetate (246); 4-[4-(diphenylmethyl)piperazin-1-yl]-3-nitro-1-propyl-1,2-dihydro-1,5-naphthyridin-2-one (248); 4-{4-[cyclopropyl(4-fluorophenyl)methyl]piperazinyl-yl}-1,6-dimethyl-2-oxo-1,2-dihydro-1,5-naphthyridine-3-carbonitrile (250); 4-{4-[bis(4-fluoro-2-methoxyphenyl)methyl]piperazin-1-yl}-1,6-dimethyl-2-oxo-1,2-dihydro-1,5-naphthyridine-3-carbonitrile (251); 4-[4-(4-methoxybutan-2-yl)piperazin-1-yl]-1,6-dimethyl-2-oxo-1,2-dihydro-1,5-naphthyridine-3-carbonitrile (252); 4-[4-(3,4-dihydro-2H-1-benzopyran-4-yl)piperazin-1-yl]-1,6-dimethyl-2-oxo-1,2-dihydro-1,5-naphthyridine-3-carbonitrile (253); 4-{4-[4-fluorophenyl)(2-methoxypyridin-3-yl)methyl]piperazin-1-yl}-1,6-dimethyl-2-oxo-1,2-dihydro-1,5-naphthyridine-3-carbonitrile (254); 4-{4-[(4-fluorophenyl)(3-methoxypyridin-2-yl)methyl]piperazin-1-yl}-1,6-dimethyl-2-oxo-1,2-dihydro-1,5-naphthyridine-3-carbonitrile (255); 4-{4-[(4-fluorophenyl)(pyridin-2-yl)methyl]piperazin-1-yl}-1,6-dimethyl-2-oxo-1,2-dihydro-1,5-naphthyridine-3-carbonitrile (256); 4-{4-[(2-bromo-6-hydroxyphenyl)methyl]piperazin-1-yl}-6-chloro-1-methyl-2-oxo-1,2-dihydro-1,5-naphthyridine-3-carbonitrile (258); 6-bromo-4-{4-[(2-hydroxy-6-methylphenyl)methyl]piperazin-1-yl}-1-methyl-2-oxo-1,2-dihydro-1,5-naphthyridine-3-carbonitrile (259); 8-{4-[2-(4-fluorophenyl)propan-2-yl]piperazin-1-yl}-5-methyl-7-nitro-6-oxo-5,6-dihydro-1,5-naphthyridine-2-carbonitrile (260): 4-{4-[(4-tert-butyl-2-hydroxyphenyl)methyl]piperazin-1-yl}-6-chloro-1-methyl-2-oxo-1,2-dihydro-1,5-naphthyridine-3-carbonitrile (261); 4-(4-{[2-hydroxy-5-(trifluoromethoxy)phenyl]methyl}piperazin-1-yl)-1,6-dimethyl-2-oxo-1,2-dihydro-1,5-naphthyridine-3-carbonitrile (262); 8-{4-[(4-bromo-2-hydroxyphenyl)methyl]piperazin-1-yl}-5-methyl-6-oxo-5,6-dihydro-1,5-naphthyridine-2,7-dicarbonitrile (263); 6-chloro-4-{4-[(2-hydroxy-6-methoxyphenyl)methyl]piperazin-1-yl}-1-methyl-2-oxo-1,2-dihydro-1,5-naphthyridine-3-carbonitrile (264); 8-(4-{[2-hydroxy-4-(trifluoromethoxy)phenyl]methyl}piperazin-1-yl)-5-methyl-6-oxo-5,6-dihydro-1,5-naphthyridine-2,7-dicarbonitrile (265); 6-bromo-4-{4-[(4-chloro-2-hydroxyphenyl)methyl]piperazin-1-yl}-1-methyl-2-oxo-1,2-dihydro-1,5-naphthyridine-3-carbonitrile (266); 6-chloro-4-{4-[(2-chloro-6-hydroxyphenyl)methyl]piperazin-1-yl}-1-methyl-2-oxo-1,2-dihydro-1,5-naphthyridine-3-carbonitrile (267); 4-{4-[(3-bromo-2-hydroxyphenyl)methyl]piperazin-1-yl}-6-chloro-1-methyl-2-oxo-1,2-dihydro-1,5-naphthyridine-3-carbonitrile (268); 8-{4-[(4-chloro-2-hydroxyphenyl)methyl]piperazin-1-yl}-5-methyl-6-oxo-5,6-dihydro-1,5-naphthyridine-2,7-dicarbonitrile (269); 6-bromo-4-(4-{[2-hydroxy-5-(trifluoromethoxy)phenyl]methyl}piperazin-1-yl)-1-methyl-2-oxo-1,2-dihydro-1,5-naphthyridine-3-carbonitrile (270); 6-bromo-4-{4-[(2-bromo-6-hydroxyphenyl)methyl]piperazin-1-yl}-1-methyl-2-oxo-1,2-dihydro-1,5-naphthyridine-3-carbonitrile (271): 6-chloro-4-{4-[(2-chlorophenyl)methyl]piperazin-1-yl}-1-methyl-2-oxo-1,2-dihydro-1,5-naphthyridine-3-carbonitrile (272); 6-chloro-4-{4-[(2-hydroxy-4-methylphenyl)methyl]piperazin-1-yl}-1-methyl-2-oxo-1,2-dihydro-1,5-naphthyridine-3-carbonitrile (273); 6-chloro-4-{4-[(3-fluoro-2-methoxyphenyl)methyl]piperazin-1-yl}-1-methyl-2-oxo-1,2-dihydro-1,5-naphthyridine-3-carbonitrile (274); 4-{4-[(5-bromo-2-hydroxyphenyl)methyl]piperazin-1-yl}-6-chloro-1-methyl-2-oxo-1,2-dihydro-1,5-naphthyridine-3-carbonitrile (275); 4-{4-[(4-bromo-2-hydroxyphenyl)methyl]piperazin-1-yl}-6-chloro-1-methyl-2-oxo-1,2-dihydro-1,5-naphthyridine-3-carbonitrile (276); 4-{4-[(5-bromo-2-hydroxyphenyl)methyl]piperazin-1-yl}-1,6-dimethyl-2-oxo-1,2-dihydro-1,5-naphthyridine-3-carbonitrile (277); 6-bromo-4-{4-[(3-chloro-2-hydroxyphenyl)methyl]piperazin-1-yl}-1-methyl-2-oxo-1,2-dihydro-1,5-naphthyridine-3-carbonitrile (278); 6-chloro-4-{4-[(3-fluoro-4-methoxyphenyl) methyl]piperazin-1-yl}-1-methyl-2-oxo-1,2-dihydro-1,5-naphthyridine-3-carbonitrile (279); 6-chloro-4-{4-[(2-fluoro-6-hydroxyphenyl)methyl]piperazin-1-yl}-1-methyl-2-oxo-1,2-dihydro-1,5-naphthyridine-3-carbonitrile (280); 6-chloro-4-{4-[(2-fluoro-3-methylphenyl)methyl]piperazin-1-yl}-1-methyl-2-oxo-1,2-dihydro-1,5-naphthyridine-3-carbonitrile (281); 6-bromo-4-{4-[(5-bromo-2-hydroxyphenyl)methyl]piperazin-1-yl}-1-methyl-2-oxo-1,2-dihydro-1,5-naphthyridine-3-carbonitrile (282); 6-chloro-4-{4-[(2-hydroxy-5-methylphenyl)methyl]piperazin-1-yl}-1-methyl-2-oxo-1,2-dihydro-1,5-naphthyridine-3-carbonitrile (283); tert-butyl N-(2-{[4-(6-bromo-3-cyano-1-methyl-2-oxo-1,2-dihydro-1,5-naphthyridin-4-yl)piperazin-1-yl]methyl}phenyl)carbamate (284); 6-chloro-1- methyl-2-oxo-4-(4-{[2-(trifluoromethoxy)phenyl]methyl}piperazin-1-yl)-1,2-dihydro-1,5-naphthyridine-3-carbonitrile (285); 4-{4-[(3-bromo-2-hydroxyphenyl)methyl]piperazin-1-yl}-1,6-dimethyl-2-oxo-1,2-dihydro-1,5-naphthyridine-3-carbonitrile (286); 6-chloro-4-{4-[(2-chloro-4-fluorophenyl)methyl]piperazin-1-lv}-1-methyl-2-oxo-1,2-dihydro-1,5-naphthyridine-3-carbonitrile (287); 6-chloro-4-{4-[(4-chloro-2-hydroxyphenyl)methyl]piperazin-1-yl}-1-methyl-2-oxo-1,2-dihydro-1,5-naphthylidine-3-carbonitrile (288); 6-chloro-4-{4-[(3-fluoro-4-methylphenyl)methyl]piperazin-1-yl}-1-methyl-2-oxo-1,2-dihydro-1,5-naphthyridine-3-carbonitrile (289); 6-chloro-4-{4-[(3-fluoro-5-methylphenyl)methyl]piperazin-1-yl}-1-methyl-2-oxo-1,2-dihydro-1,5-naphthyridine-3-carbonitrile (290); 6-chloro-4-{4-[(3,5-difluorophenyl)methyl]piperazin-1-yl}-1-methyl-2-oxo-1,2-dihydro-1,5-naphthyridine-3-carbonitrile (291); 6-chloro-4-{4-[(2-hydroxy-6-methylphenyl)methyl]piperazin-1-yl}-1-methyl-2-oxo-1,2-dihydro-1,5-naphthyridine-3-carbonitrile (292); 6-chloro-4-{4-[(3-chloro-2-hydroxyphenyl)methyl]piperazin-1-yl}-1-methyl-2-oxo-1,2-dihydro-1,5-naphthyridine-3-carbonitrile (293); 6-bromo-4-{4-[(2-fluoro-6-hydroxyphenyl)methyl]piperazin-1-yl}-1-methyl-2-oxo-1,2-dihydro-1,5-naphthyridine-3-carbonitrile (294); 6-bromo-4-{4-[(2-hydroxy-4-methoxyphenyl)methyl]piperazin-1-yl}-1-methyl-2-oxo-1,2-dihydro-1,5-naphthyridine-3-carbonitrile (295); 4-{4-[(5-chloro-2-hydroxyphenyl)methyl]piperazin-1-yl}-1,6-dimethyl-2-oxo-1,2-dihydro-1,5-naphthyridine-3-carbonitrile (296); 6-bromo-4-{4-[(2-methoxyphenyl)methyl]piperazin-1-yl}-1-methyl-2-oxo-1,2-dihydro-1,5-naphthyridine-3-carbonitrile (297); 6-chloro-4-{4-[(3,5-difluoro-2-hydroxyphenyl)methyl]piperazin-1-yl}-1-methyl-2-oxo-1,2-dihydro-1,5-naphthyridine-3-carbonitrile (298); 6-bromo-4-{4-[(2,3-dihydro-1H-indol-7-yl)methyl]piperazin-1-yl}-1-methyl-2-oxo-1,2-dihydro-1,5-naphthyridine-3-carbonitrile (299); 6-bromo-4-{4-[(2-chlorophenyl)methyl]piperazin-1-yl}-1-methyl-2-oxo-1,2-dihydro-1,5-naphthyridine-3-carbonitrile (300); 6-chloro-4-{4-[(2-hydroxy-4-methoxyphenyl)methyl]piperazin-1-yl}-1-methyl-2-oxo-1,2-dihydro-1,5-naphthyridine-3-carbonitrile (301); 6-chloro-4-{4-[(3-chlorophenyl)methyl]piperazin-1-yl}-1-methyl-2-oxo-1,2-dihydro-1,5-naphthyridine-3-carbonitrile (302); 6-chloro-4-{4-[(1H-indol-7-yl)methyl]piperazin-1-yl}-1-methyl-2-oxo-1,2-dihydro-1,5-naphthyridine-3-carbonitrile (303); 6-bromo-4-{4-[(3-fluoro-2-hydroxyphenyl)methyl]piperazin-1-yl}-1-methyl-2-oxo-1,2-dihydro-1,5-naphthyridine-3-carbonitrile (304); 6-chloro-4-{4-[(2-hydroxy-5-methoxyphenyl)methyl]piperazin-1-yl}-1-methyl-2-oxo-1,2-dihydro-1,5-naphthyridine-3-carbonitrile (305): 6-chloro-4-{4-[(3-fluoro-2-hydroxyphenyl)methy]piperazin-1-yl}-1-methyl-2-oxo-1,2-dihydro-1,5-naphthyridine-3-carbonitrile (306); 6-chloro-4-{4[(3,5-dichloro-2-hydroxyphenyl)methyl]piperazin-1-yl}-1-methyl-2-oxo-1,2-dihydro-1,5-naphthyridine-3-carbonitrile (307); 6-chloro-4-{4-[(4-fluorophenyl)methyl]piperazin-1-yl}-1-methyl-2-oxo-1,2-dihydro-1,5-naphthyridine-3-carbonitrile (308); 6-bromo-4-{4-[(3-ter-butyl-2-hydroxyphenyl)methyl]piperazin-1-yl}-1-methyl-2-oxo-1,2-dihydro-1,5-naphthyridine-3-carbonitrile (309); 6-chloro-4-{4-[(2,4-dichlorophenyl) methyl]piperazin-1-yl}-1-methyl-2-oxo-1,2-dihydro-1,5-naphthyridine-3-carbonitrile (310); 6-chloro-4-(4-{[2-hydroxy-4-(trifluoromethyl)phenyl]methyl}piperazin-1-yl)-1-methyl-2-oxo-1,2-dihydro-1,5-naphthyridine-3-carbonitrile (311); 6-chloro-4-{4-[(5-fluoro-2-hydroxyphenyl)methyl]piperazin-1-yl}-1-methyl-2-oxo-1,2-dihydro-1,5-naphthyridine-3-carbonitrile (312); 6-chloro-4-(4-{[3-fluoro-5-(trifluoromethyl)phenyl]methyl}piperazin-1-yl)-1-methyl-2-oxo-1,2-dihydro-1,5-naphthyridine-3-carbonitrile (313); 6-bromo-4-{4-[(2-hydroxy-6-methoxyphenyl)methyl]piperazin-1-yl}-1-methyl-2-oxo-1,2-dihydro-1,5-naphthyridine-3-carbonitrile (314); 6-chloro-4-{4-[1-(4-fluorophenyl)-2-methylpropyl]piperazin-1-yl}-1-methyl-2-oxo-1,2-dihydro-1,5-naphthridine-3-carbonitrile (315-316); 8-{4-[(2-hydroxyphenyl)methyl]piperazin-1-yl}-5-methyl-6-oxo-5,6-dihydro-1,5-naphthyridine-2,7-dicarbonitrile (317); 6-chloro-4-{4-[(2,5-difluorophenyl)methyl]piperazin-1-yl}-1-methyl-2-oxo-1,2-dihydro-1,5-naphthyridine-3-carbonitrile (318); 6-chloro-4-{4-[(3,4-difluorophenyl)methyl]piperazin-1-yl}-1-methyl-2-oxo-1,2-dihydro-1,5-naphthyridine-3-carbonitrile (319); 6-bromo-4-{4-[(3,5-difluoro-2-hydroxyphenyl)methyl]piperazin-1-yl}-1-methyl-2-oxo-1,2-dihydro-1,5-naphthyridine-3-carbonitrile (320); 6-chloro-4-{4-[(3-fluorophenyl)methyl]piperazin-1-yl}-1-methyl-2-oxo-1,2-dihydro-1,5-naphthyridine-3-carbonitrile (321); 6-chloro-4-{4-[(1H-indazol-7-yl)methyl]piperazin-1-yl}-1-methyl-2-oxo-1,2-dihydro-1,5-naphthyridine-3-carbonitrile (322); 6-chloro-4-{4-[(4-chloro-3-hydroxyphenyl)methyl]piperazin-1-yl}-1-methyl-2-oxo-1,2-dihydro-1,5-naphthyridine-3-carbonitrile (323); 6-chloro-4-{4-[(3-chloro-5-fluorophenyl)methyl]piperazin-1-yl}-1-methyl-2-oxo-1,2-dihydro-1,5-naphthyridine-3-carbonitrile (324); 8-[4-(diphenylmethyl)piperazin-1-yl]-5-methyl-6-oxo-5,6-dihydro-1,5-naphthyridine-2,7-dicarbonitrile (325); 6-chloro-4-{4-[(4-chloro-3-fluorophenyl)methyl]piperazin-1-yl}-1-methyl-2-oxo-1,2-dihydro-1,5-naphthyridine-3-carbonitrile (326); 6-chloro-4-{4-[(3-methoxyphenyl)methyl]piperazin-1-yl}-1-methyl-2-oxo-1,2-dihydro-1,5-naphthyridine-3-carbonitrile (327); 6-chloro-4-{4-[(3-hydroxy-4-methylphenyl)methyl]piperazin-1-yl}-1-methyl-2-oxo-1,2-dihydro-1,5-naphthyridine-3-carbonitrile (328); 4-{4-[(3-fluoro-2-hydroxyphenyl)methyl]piperazin-1-yl}-1,6-dimethyl-2-oxo-1,2-dihydro-1,5-naphthyridine-3-carbonitrile (329); 6-chloro-4-{4-[(2,3-difluorophenyl)methyl]piperazin-1-yl}-1-methyl-2-oxo-1,2-dihydro-1.5-naphthyridine-3-carbonitrile (330); 6-chloro-4-{4-[(2-methoxyphenyl)methyl]piperazin-1-yl}-1-methyl-2-oxo-1,2-dihydro-1,5-naphthyridine-3-carbonitrile (331); 8-{4-[(4-chloro-3-hydroxyphenyl)methyl]piperazin-1-yl}-5-methyl-6-oxo-5,6-dihydro-1,5-naphthyridine-2,7-dicarbonitrile (332); 6-bromo-4-{4-[(1H-indazol-7-yl)methyl]piperazin-1-yl}-1-methyl-2-oxo-1,2-dihydro-1,5-naphthyridine-3-carbonitrile (333); 4-{4-[(1-ethyl-1H-indol-4-yl)methyl]piperazin-1-yl}-1-methyl-2-oxo-1,2-dihydro-1,5-naphthyridine-3-carbonitrile (334): 6-chloro-4-{4-[(2-fluoro-6-methoxyphenyl)methyl]piperazin-1-yl}-1-methyl-2-oxo-1,2-dihydro-1,5-naphthyridine-3-carbonitrile (335); 6-chloro-4-{4-[(2-hydroxynaphthalen-1-yl)methyl]piperazin-1-yl}-1-methyl-2-oxo-1,2-dihydro-1,5-naphthyridine-3-carbonitrile (336); 4-{4-[(2-hydroxyphenyl)methyl]piperazin-1-yl}-1,6-dimethyl-2-oxo-1,2-dihydro-1,5-naphthyridine-3-carbonitrile (337); 6-chloro-4-{4-[(3-fluoro-5-hydroxyphenyl)methyl]piperazin-1-yl}-1-methyl-2-oxo-1,2-dihydro-1,5-naphthyridine-3-carbonitrile (338); 6-chloro-4-{4-[(2-fluorophenyl)methyl]piperazin-1-yl}-1-methyl-2-oxo-1,2-dihydro-1,5-naphthyridine-3-carbonitrile (339); 6-chloro-4-{4-[(5-cyano-2-fluorophenyl)methyl]piperazin-1-yl}-1-methyl-2-oxo-1,2-dihydro-1,5-naphthyridine-3-carbonitrile (340); 6-chloro-4-{4-[(4-methoxyphenyl) methyl]piperazin-1-yl}-1-methyl-2-oxo-1,2-dihydro-1,5-naphthyridine-3-carbonitrile (341); 8-{4-[1-(4-fluorophenyl)cyclopropyl]piperazin-1-yl}-5-methyl-7-nitro-6-oxo-5,6-dihydro-1,5-naphthyridine-2-carbonitrile (342); 4-(4-benzylpiperazin-1-yl)-6-chloro-1-methyl-2-oxo-1,2-dihydro-1,5- naphthyridine-3-carbonitrile (343); 6-bromo-4-{4-[2-fluorophenyl)methyl]piperazin-1-yl}-1-methyl-2-oxo-1,2-dihydro-1,5-naphthyridine-3-carbonitrile (344); 6-chloro-4-{4-[(3-chloro-5-hydroxyphenyl)methyl]piperazin-1-yl}-1-methyl-2-oxo-1,2-dihydro-1,5-naphthyridine-3-carbonitrile (345); 6-chloro-1-methyl-4-{4-[(2-methylphenyl)methyl]piperazin-1-yl}-2-oxo-1,2-dihydro-1,5-naphthyridine-3-carbonitrile (346); 4-{4-[bis(4-fluorophenyl)methyl]piperazin-1-yl}-1-methyl-2-oxo-1,2-dihydro-1,5-naphthyridine-3-carbonitrile (347); 6-chloro-4-{4-[(4-fluoro-3-hydroxyphenyl)methyl]piperazin-1-yl}-1-methyl-2-oxo-1,2-dihydro-1,5-naphthyridine-3-carbonitrile (348); 4-{4-[(2-hydroxyphenyl)(phenyl)methyl]piperazin-1-yl}-1-methyl-2-oxo-1,2-dihydro-1,5-naphthyridine-3-carbonitrile (349); 6-chloro-4-{4-[(2,4-difluorophenyl)methyl]piperazin-1-yl}-1-methyl-2-oxo-1,2-dihydro-1,5-naphthyridine-3-carbonitrile (350); 6-chloro-4-{4-[(3-hydroxyphenyl)methyl]piperazin-1-yl}-1-methyl-2-oxo-1,2-dihydro-1,5-naphthyridine-3-carbonitrile (351); 4-{4-[(2-hydroxy-3-methoxyphenyl)methyl]piperazin-1-yl}-1,6-dimethyl-2-oxo-1,2-dihydro-1,5-naphthyridine-3-carbonitrile (352); 6-chloro-4-{4-[(3-hydroxy-4-methoxyphenyl)methyl]piperazin-1-yl}-1-methyl-2-oxo-1,2-dihydro-1,5-naphthyridine-3-carbonitrile (353); 6-chloro-4-{4-[(3-chloro-4-hydroxyphenyl)methyl]piperazin-1-yl}-1-methyl-2-oxo-1,2-dihydro-1,5-naphthyridine-3-carbonitrile (354); 6-chloro-4-(4-{[4-hydroxy-3-(trifluoromethyl)phenyl]methyl}piperazin-1-yl)-1-methyl-2-oxo-1,2-dihydro-1,5-naphthyridine-3-carbonitrile (355); 6-chloro-4-{4-[(4-hydroxy-3-methylphenyl)methyl]piperazin-1-yl}-1-methyl-2-oxo-1,2-dihydro-1,5-naphthyridine-3-carbonitrile (356); 6-chloro-4-{4-[(3-fluoro-4-hydroxyphenyl)methyl]piperazin-1-yl}-1-methyl-2-oxo-1,2-dihydro-1,5-naphthyridine-3-carbonitrile (357); 6-chloro-4-[4-(diphenylmethyl) piperazin-1-yl]-1-methyl-2-oxo-1,2-dihydro-1,5-naphthyridine-3-carbonitrile (358); 4-{4-[(1H-1,3-benzodiazol-7-yl)methyl]piperazin-1-yl}-6-chloro-1-methyl-2-oxo-1,2-dihydro-1,5-naphthyridine-3-carbonitrile (359); 4-{4-[(1H-1,3-benzodiazol-7-yl)methyl]piperazin-1-yl}-6-bromo-1-methyl-2-oxo-1,2-dihydro-1,5-naphthyridine-3-carbonitrile (360); 6-chloro-4-{4-[(4-hydroxyphenyl)methyl]piperazin-1-yl}-1-methyl-2-oxo-1,2-dihydro-1,5-naphthyridine-3-carbonitrile (362); 8-{4-[(3-fluoro-4-hydroxyphenyl) methyl]piperazin-1-yl}-5-methyl-6-oxo-5,6-dihydro-1,5-naphthyridine-2,7-dicarbonitrile (363); 6-chloro-4-{4-[(2-fluoro-5-methylphenyl)methyl]piperazin-1-yl}-1-methyl-2-oxo-1,2-dihydro-1,5-naphthyridine-3-carbonitrile (364); 6-chloro-4-{4-[(2-chloro-6-methoxyphenyl)methyl]piperazin-1-yl}-1-methyl-2-oxo-1,2-dihydro-1,5-naphthyridine-3-carbonitrile (365); 6-bromo-4-{4-[(3,5-dichloro-2-hydroxyphenyl)methyl]piperazin-1-yl}-1-methyl-2-oxo-1,2-dihydro-1,5-naphthyridine-3-carbonitrile (366); 6-bromo-4-{4-[(5-chloro-2-hydroxyphenyl)methyl]piperazin-1-yl}-1-methyl-2-oxo-1,2-dihydro-1,5-naphthyridine-3-carbonitrile (367); 6-bromo-4-{4-[(2-hydroxy-3-methoxyphenyl) methyl]piperazin-1-yl}-1-methyl-2-oxo-1,2-dihydro-1,5-naphthyridine-3-carbonitrile (368); 6-chloro-4-(4-{[2-hydroxy-5-(trifluoromethoxy)phenyl]methyl}piperazin-1-yl)-1-methyl-2-oxo-1,2-dihydro-1,5-naphthyridine-3-carbonitrile (369); 6-chloro-4-{4-[(5-chloro-2-hydroxyphenyl)methyl]piperazin-1-yl}-1-methyl-2-oxo-1,2-dihydro-1,5-naphthyridine-3-carbonitrile (370); 6-chloro-4-{4-[(2-hydroxy-3-methoxyphenyl)methyl]piperazin-1-yl}-1-methyl-2-oxo-1,2-dihydro-1,5-naphthyridine-3-carbonitrile (371); 6-bromo-4-{4-[(2-hydroxy-4-methylphenyl)methyl]piperazin-1-yl}-1-methyl-2-oxo-1,2-dihydro-1,5-naphthyridine-3-carbonitrile (372); 6-bromo-4-{4-[(1H-indol-7-yl)methyl]piperazin-1-yl}-1-methyl-2-oxo-1,2-dihydro-1,5-naphthyridine-3-carbonitrile (373); 6-bromo-1-methyl-2-oxo-4-{4-[(2-oxo-2,3-dihydro-1H-indol-7-yl)methyl]piperazin-1-yl}1,2-dihydro-1,5-naphthyridine-3-carbonitrile (374); 6-chloro-4-(4-{[3-fluoro-4-(trifluoromethyl)phenyl]methyl}piperazin-1-yl)-1-methyl-2-oxo-1,2-dihydro-1,5-naphthyridine-3-carbonitrile (375); 6-chloro-1-methyl-2-oxo-4-{4-[(2-oxo-2,3-dihydro-1H-indol-7-yl)methyl]piperazin-1-yl}-1,2-dihydro-1,5-naphthyridine-3-carbonitrile (376); 6-chloro-4-{4-[1-(4-fluorophenyl)-3,3-dimethylbutyl]piperazin-1-yl}-1-methyl-2-oxo-1,2-dihydro-1,5-naphthyridine-3-carbonitrile (377-378); 6-chloro-4-{4-[(4-cyano-2-fluorophenyl)methyl]piperazin-1-yl}-1-methyl-2-oxo-1,2-dihydro-1,5-naphthyridine-3-carbonitrile (379): 6-bromo-4-{4-[(3-bromo-2-hydroxyphenyl)methyl]piperazin-1-yl}-1-methyl-2-oxo-1,2-dihydro-1,5-naphthyridine-3-carbonitrile (380); 6-chloro-4-(4-{[2-hydroxy-4-(trifluoromethoxy)phenyl]methyl}piperazin-1-yl)-1-methyl-2-oxo-1,2-dihydro-1,5-naphthyridine-3-carbonitrile (381); 6-chloro-4-{4-[cyclobutyl(4-fluorophenyl)methyl]piperazin-1-yl}-1-methyl-2-oxo-1,2-dihydro-1,5-naphthyridine-3-carbonitrile (382-383); 4-{4-[(3-tert-butyl-2-hydroxyphenyl)methyl]piperazin-1-yl}-6-chloro-1-methyl-2-oxo-1,2-dihydro-1,5-naphthyridine-3-carbonitrile (384); 6-chloro-1-methyl-4-{4-[(3-methylphenyl)methyl]piperazin-1-yl}-2-oxo-1,2-dihydro-1,5-naphthyridine-3-carbonitrile (385); 6-chloro-1-methyl-4-{4-[(4-methylphenyl)methyl]piperazin-1-yl}-2-oxo-1,2-dihydro-1,5-naphthyridine-3-carbonitrile (386); 6-chloro-4-{4-[1-(4-fluorophenyl)ethyl]piperazin-1-yl}-1-methyl-2-oxo-1,2-dihydro-1,5-naphthyridine-3-carbonitrile (387-388); 4-{4-[(3-chloro-2-hydroxyphenyl)methyl]piperazin-1-yl}-1,6-dimethyl-2-oxo-1,2-dihydro-1,5-naphthyridine-3-carbonitrile (389); 6-bromo-4-{4-[(2-chloro-6-hydroxyphenyl)methyl]piperazin-1-yl}-1-methyl-2-oxo-1,2-dihydro-1,5-naphthyridine-3-carbonitrile (390); 6-chloro-4-{4-[(2-hydroxy-3-methylphenyl)methyl]piperazin-1-yl}-1-methyl-2-oxo-1,2-dihydro-1,5-naphthyridine-3-carbonitrile (391); 8-{4-[(4-fluoro-2-methoxyphenyl)(4-fluorophenyl)methyl]piperazin-1-yl}-5-methyl-6-oxo-5,6-dihydro-1,5-naphthyridine-2-carbonitrile (392); 4-{4-[bis(4-chlorophenyl)methyl]piperazin-1-yl}-6-bromo-1-methyl-2-oxo-1,2-dihydro-1,5-naphthyridine-3-carbonitrile (393); 8-{4-[bis(4-chlorophenyl)methyl]piperazin-1-yl}-5-methyl-6-oxo-5,6-dihydro-1,5-naphthyridine-2,7-dicarbonitrile (394); 4-{4-[bis(4-chlorophenyl)methyl]piperazin-1-yl}-6-methoxy-1-methyl-2-oxo-1,2-dihydro-1,5-naphthyridine-3-carbonitrile (395); 4-{4-[(4-fluorophenyl)(2-methoxypyridin-3-yl)methyl]piperazin-1-yl}-6-methoxy-1-methyl-2-oxo-1,2-dihydro-1,5-naphthyridine-3-carbonitrile (396); 4-{4-[4-fluorophenyl)(3-methoxypyridin-2-yl)methyl]piperazin-1-yl}-6-methoxy-1-methyl-2-oxo-1,2-dihydro-1,5-naphthyridine-3-carbonitrile (397); 4-{4-[1-(4-fluorophenyl)propyl]piperazin-1-yl}-1,6-dimethyl-2-oxo-1,2-dihydro-1,5-naphthyridine-3-carbonitrile (398); 8-{4-[(S)-(4-chlorophenyl)(phenyl)methyl]piperazin-1-yl}-5-methyl-7-nitro-6-oxo-5,6-dihydro-1,5-naphthyridine-2-carbonitrile (399); 8-{4-[4-fluorophenyl)(pyridin-2-yl)methyl]piperazin-1-yl}-5-methyl-6-oxo-5,6-dihydro-1,5-naphthyridine-2,7-dicarbonitrile (400); 4-{4-[(4-fluoro-2-methoxyphenyl)(pyrimidin-2-yl)methyl]piperazin-1-yl}-6-methoxy-1-methyl-2-oxo-1,2-dihydro-1,5-naphthyridine-3-carbonitrile (401); 4-{4-[bis(4-fluoro-2-methoxyphenyl)methy]piperazin-1-yl}-6-methoxy-1-methyl-2-oxo-1,2-dihydro-1,5-naphthyridine-3-carbonitrile (402); 4-{4-[(4-fluorophenyl)(pyridin-2-v)methyl]piperazin-1-yl}-6-methoxy-1-methyl-2-oxo-1,2-dihydro-1,5-naphthyridine-3-carbonitrile (403); 5-methyl-8-{4-[(naphthalen-1-yl)methyl]piperazin-1-yl}-6-oxo-5,6-dihydro-1,5-naphthyridine-2,7-dicarbonitrile (404); 8-{4-[(4-fluoro-2-methoxyphenyl)(4-fluorophenyl)methyl]piperazin-1-yl}-5-methyl-6-oxo-5,6-dihydro-1,5-naphthyridine-2,7-dicarbonitrile (405-407); 5-methyl-8-{4-[(4-methylphenyl)(phenyl)methyl]piperazin-1-yl}-6-oxo-5,6-dihydro-1,5-naphthyridine-2,7-dicarbonitrile (408); 8-{4-[bis(4-fluoro-2-methoxyphenyl)methyl]piperazin-1-yl}-5-methyl-6-oxo-5,6-dihydro-1,5-naphthyridine-2,7-dicarbonitrile (409); 8-{4-[(4-fluorophenyl)(3-methoxypyridin-2-yl)methyl]piperazin-1-yl}-5-methyl-6-oxo-5,6-dihydro-1,5-naphthyridine-2,7-dicarbonitrile (410); 8-{4-[(4-fluorophenyl)(phenyl)methyl]piperazin-1-yl}-5-methyl-6-oxo-5,6-dihydro-1,5-naphthyridine-2,7-dicarbonitrile (411); 4-{4-[(4-fluoro-2-methoxyphenyl)(4-fluorophenyl)methyl]piperazin-1-yl}-6-methoxy-1-methyl-2-oxo-1,2-dihydro-1,5-naphthyridine-3-carbonitrile (412); 4-{4-[(4-fluoro-2-methoxyphenyl)(4-fluorophenyl) methyl]piperazin-1-yl}-6-methoxy-1-methyl-2-oxo-1,2-dihydro-1,5-naphthyridine-3-carbonitrile (413); 8-{4-[(S)-(4-chlorophenyl)(phenyl)methyl]piperazin-1-yl}-5-methyl-6-oxo-5,6-dihydro-1,5-naphthyridine-2,7-dicarbonitrile (414); 5-methyl-8-{4-[(naphthalen-1-yl)methyl]piperazin-1-yl}-7-nitro-6-oxo-5,6-dihydro-1,5-naphthyridine-2-carbonitrile (415); 8-{4-[(4-fluorophenyl)(2-methoxy-4-methylphenyl)methyl]piperazin-1-yl}-5-methyl-7-nitro-6-oxo-5,6-dihydro-1,5-naphthyridine-2-carbonitrile (416); 6-chloro-4-{4-[(4-chlorophenyl)methyl]piperazin-1-yl}-1-methyl-2-oxo-1,2-dihydro-1,5-naphthyridine-3-carbonitrile (417); 8-{4-[(2-hydroxyphenyl)(phenyl)methyl]piperazin-1-yl}-5-methyl-6-oxo-5,6-dihydro-1,5-naphthylidine-2,7-dicarbonitrile (418); 6-chloro-4-{4-[(2-chloro-6-methylphenyl)methyl]piperazin-1-yl}-1-methyl-2-oxo-1,2-dihydro-1,5-naphthyridine-3-carbonitrile (419); 6-chloro-4-{4-[(2-chloro-6-fluorophenyl)methyl]piperazin-1-yl}-1-methyl-2-oxo-1,2-dihydro-1,5-naphthyridine-3-carbonitrile (420); 6-chloro-4-{4-[1-(4-fluorophenyl)cyclopropyl]piperazin-1-yl}-1-methyl-2-oxo-1,2-dihydro-1,5-naphthyridine-3-carbonitrile (421); 6-chloro-4-{4-[(2,6-difluorophenyl) methyl]piperazin-1-yl}-1-methyl-2-oxo-1,2-dihydro-1,5-naphthyridine-3-carbonitrile (422); 6-chloro-4-{4-[(2-fluoro-4-methylphenyl)methyl]piperazin-1-yl}-1-methyl-2-oxo-1,2-dihydro-1,5-naphthyridine-3-carbonitrile (423); 6-chloro-4-{4-[(4-cyano-2-methoxyphenyl)methyl]piperazin-1-yl}-1-methyl-2-oxo-1,2-dihydro-1,5-naphthyridine-3-carbonitrile (424); 6-chloro-4-{4-[2-(4-fluorophenyl)propan-2-yl]piperazin-1-yl}-1-methyl-2-oxo-1,2-dihydro-1,5-naphthyridine-3-carbonitrile (425); 4-(4-(bis(4-fluorophenyl)methyl)piperazin-1-yl)-1-methyl-1,5-naphthyridin-2(1H)-one (426); 4-{4-[bis(4-fluorophenyl)methyl]piperazin-1-yl}-1,6-dimethyl-1,2-dihydro-1,5-naphthyridin-2-one (427); 6-bromo-4-{4-[(S)-(4-chlorophenyl)(phenyl)methyl]piperazin-1-yl}-1-methyl-2-oxo-1,2-dihydro-1,5-naphthyridine-3-carbonitrile (428); 6-bromo-4-{4-[(4-chlorophenyl)(phenyl)methyl]piperazin-1-yl}-1-methyl-2-oxo-1,2-dihydro-1,5-naphthyridine-3-carbonitrile (429); 6-bromo-4-{4-[(4-fluorophenyl)(phenyl)methyl]piperazin-1-yl}-1-methyl-2-oxo-1,2-dihydro-1,5-naphthyridine-3-carbonitrile (430); 6-bromo-1-methyl-4-{4-[(4-methylphenyl)(phenyl)methyl]piperazin-1-yl}-2-oxo-1,2-dihydro-1,5-naphthyridine-3-carbonitrile (431); or 8-{4-[bis(4-fluorophenyl)methyl]piperazin-1-yl}-5-methyl-6-oxo-5,6-dihydro-1,5-naphthyridine-2-carbonitrile (432).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "amino" refers to the group —NH$_2$.
The term "oxo" refers to the group =O.
The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "cyanoalkyl" includes both branched and straight-chain saturated alkyl groups substituted with one or more cyano groups. For example, "cyanoalkyl" includes —$CH_2CN$, —$CH_2CH_2CN$, and $C_{1-4}$ cyanoalkyl.

The term "aminoalkyl" includes both branched and straight-chain saturated alkyl groups substituted with one or more amine groups. For example, "aminoalkyl" includes —$CH_2NH_2$, —$CH_2CH_2NH_2$, and $C_{1-4}$ aminoalkyl.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "alkylenyl" refers to a saturated carbon chain with two attachment points to the core or backbone structure. The alkalenyl group has the structure —$(CH_2)_n$— in which n is an integer of 1 or greater. Examples of alkylenyl linkages include —$CH_2CH_2$—, —$CH_2CH_2CH_2$—, and —$(CH_2)_{2-4}$—.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulflates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-epheniamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in.

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor of DGKα and/or DGKζ or effective to treat or prevent viral infections and proliferative disorders, such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) and/or pharmaceutically acceptable salts thereof can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents.

The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions nay be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one pharmaceutically acceptable salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Utility

The compounds of Formula (I) are useful for the treatment of cancer.

In another embodiment, the present invention provides a combined preparation of a compound of Formula (I), and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with DGK target inhibition in T cells.

In another aspect, the invention provides a method of treating a patient suffering from or susceptible to a medical condition that is associated with DGK target inhibition in T cells. A number of medical conditions can be treated. The method comprises administering to the patient a therapeutically effective amount of a composition comprising a compound of Formula (I) and/or a pharmaceutically acceptable salt thereof, a stereoisomer thereof or a tautomer thereof. For example, the compounds described herein may be used to treat or prevent viral infections and proliferative diseases such as cancer.

The compounds for Formula (I) and pharmaceutical compositions comprising at least one compound of Formula (I)

are useful in treating or preventing any disease or conditions that are associated with DGK target inhibition in T cells. These include viral and other infections (e.g., skin infections, GI infection, urinary tract infections, genito-urinary infections, systemic infections), and proliferative diseases (e.g., cancer). The compounds of Formula (I) and pharmaceutical compositions comprising in at least one compound of Formula (I) may be administered to animals, preferably mammals (e.g., domesticated animals, cats, dogs, mice, rats), and more preferably humans. Any method of administration may be used to deliver the compound or pharmaceutical composition to the patient. In certain embodiments, the compound of Formula (I) or pharmaceutical composition comprising at least compound of Formula (I) is administered orally. In other embodiments, the Formula (I) or pharmaceutical composition comprising at least compound of Formula (I) is administered parenterally.

The compounds of Formula (I) can inhibit activity of the diacylglycerol kinase alpha and zeta (DGKα/ζ). For example, the compounds of Formula (I) can be used to inhibit activity of DGKα and DGKζ in a cell or in an individual in need of modulation of DGKα and DGKζ by administering an inhibiting amount of a compound of Formula (I) or a salt thereof.

The present invention further provides methods of treating diseases associated with activity or expression, including abnormal activity and/or overexpression, of DGKα and DGKζ in an individual (e.g., patient) by administering to the individual in need of such treatment a therapeutically effective amount or dose of a compound of Formula (I) or a pharmaceutical composition thereof. Example diseases can include any disease, disorder or condition that is directly or indirectly linked to expression or activity of DGKα and DGKζ enzyme, such as over expression or abnormal activity. A DGKα and DGKζ-associated disease can also include any disease, disorder or condition that can be prevented, ameliorated, or cured by modulating DGKα and DGKζ enzyme activity. Examples of DGKα and DGKζ associated diseases include cancer and viral infections such as HIV infection, hepatitis B, and hepatitis C.

In one aspect, the compound(s) of Formula (I) are sequentially administered prior to administration of the immuno-oncology agent. In another aspect, compound(s) of Formula (I) are administered concurrently with the immuno-oncology agent. In yet another aspect, compound(s) of Formula (I) are sequentially administered after administration of the immuno-oncology agent.

In another aspect, compounds of Formula (I) may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In one aspect, T cell responses can be stimulated by a combination of a compound of Formula (I) and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of Formula (I) for the treatment of cancer include antagonists of inhibitory receptors on NK cells or agonists of activating receptors on NK cells. For example, compounds of Formula (I) can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 WO11/140249; WO13169264; WO14/036357).

In another aspect, compounds of Formula (I) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MED14736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, BMS-986205, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7113) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the DGKα and DGKζ enzyme with a compound of Formula (I) includes the administration of a compound of the present invention to an individual or patient, such as a human, having DGKα and DGKζ, as well as, for example, introducing a compound of Formula (I) into a sample containing a cellular or purified preparation containing DGKα and DGKζ-enzyme.

The term "DGKα and DGKζ inhibitor" refers to an agent capable of inhibiting the activity of diacylglycerol kinase alpha and/or diacylglycerol kinase zeta (DGKα and DGKζ in T cells resulting in T cell stimulation. The DGKα and DGKζ inhibitor may be a reversible or irreversible DGKα and DGKζ inhibitor. "A reversible DGKα and DGKζ inhibitor" is a compound that reversibly inhibits DGKα and DGKζ enzyme activity either at the catalytic site or at a non-catalytic site and "an irreversible DGKα and DGKζ inhibitor" is a compound that irreversibly destroys DGKα and DGKζ enzyme activity by forming a covalent bond with the enzyme.

Types of cancers that may be treated with the compound of Formula (I) include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of Formula (I) for treatment of DGKα and DGKζ associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of Formula (I) include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds of Formula (I) may also be combined with immunotherapy drugs, including cytokines such as interferon alpha, interleukin 2, and tumor necrosis factor (TNF) in the treatment of melanoma.

Compounds of Formula (I) may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of Formula (I), using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 38.9° C. to 40° C. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®) (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, Flavopiridol and UCN-01 (see, for example, Sausville, *Curr. Med. Chem. Anti-Canc. Agents*, 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one compound of Formula (I) may be in separate pharmaceutical compositions. In a specific embodiment of the present invention, at least one compound of Formula (I) and at least one STI may be administered to the patient concurrently or sequentially. In other words, at least one compound of Formula (I) may be administered first, at least one STI may be administered first, or at least one compound of Formula (I) and at least one STI may be administered at the same time. Additionally, when more than one compound of Formula (I) and/or STI is used, the compounds may be administered in any order.

The present invention further provides a pharmaceutical composition for the treatment of a chronic viral infection in a patient comprising at least one compound of Formula (I), optionally, at least one chemotherapeutic drug, and, optionally, at least one antiviral agent, in a pharmaceutically acceptable carrier.

Also provided is a method for treating a chronic viral infection in a patient by administering an effective amount of the above pharmaceutical composition.

In a specific embodiment of the present invention, at least one compound of Formula (I) and at least one chemotherapeutic agent are administered to the patient concurrently or sequentially. In other words, at least one compound of Formula (I) may be administered first, at least one chemotherapeutic agent may be administered first, or at least one compound of Formula (I) and the at least one STI may be administered at the same time. Additionally, when more than one compound of Formula (I) and/or chemotherapeutic agent is used, the compounds may be administered in any order. Similarly, any antiviral agent or STI may also be administered at any point in comparison to the administration of the compound of Formula (I).

Chronic viral infections that may be treated using the present combinatorial treatment include, but are not limited to, diseases caused by: hepatitis C virus (HC V), human papilloma virus (HPV), cytomegalovirus (CMV), herpes simplex virus (ISV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

Suitable antiviral agents contemplated for use in combination with the compound of Formula (I) can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94) lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

The present invention also includes pharmaceutical kits useful, for example, in the treatment or prevention of DGKα and DGKζ-associated diseases or disorders, and other diseases referred to herein which include one or more containers containing a pharmaceutical composition comprising a therapeutically effective amount of a compound of Formula (I). Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The invention also provides pharmaceutically acceptable compositions which comprise a therapeutically effective amount of one or more of the compounds of Formula (I) formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms; and not injurious to the patient.

The term "pharmaceutical composition" means a composition comprising a compound of the invention in combination with at least one additional pharmaceutically acceptable carrier.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 ng), lactose (75 mg), and magnesium stearate (15 mg). The mixture is passed through a 60 mesh sieve and packed into a No. L gelatin capsule.

A typical injectable preparation is produced by aseptically placing at least one of the compounds of the present invention (250 mg) into a vial, aseptically freeze-drying and sealing. For use, the contents of the vial are mixed with 2 nL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a desired compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, Greene's Protective Groups in Organic Synthesis, Fourth Edition, Wiley and Sons (2007).

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1 or I1, Int. 2 or I2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety. $^1$H NMR data collected in deuterated dimethyl sulfoxide used water suppression in the data processing. The reported spectra are uncorrected for the effects of water suppression. Protons adjacent to the water suppression frequency of 3.35 ppm exhibit diminished signal intensity.

Abbreviations

Ac acetyl
anhyd. anhydrous
aq. aqueous
aza-HOBt 7-aza-1-hydroxybenzotriazole
Bn benzyl
1-BOC-piperazine tert-butyl piperazine-1-carboxylate
Bu butyl
CV Column Volumes
DCE dichloroethane
DCM dichloromethane
DEA diethylamine
DIEA diisopropyl ethyl amine (Hunig's base)
DIPEA diisopropyl ethyl amine
DMA N,N-dimethylacetamide
DMF dimethylformamide
DMSO dimethyl sulfoxide
EA ethyl acetate
EDC 1-(3-dimethylaminopropyl)-3-ethylcarbodiimide hydrochloride
Et ethyl
h, hours or hrs hour(s)
HATU (1-[bis(dimethylamino)methylene]-1H-1,2,3-triazolo[4,5-b]pyridinium 3-oxid hexafluorophosphate)
HCl hydrochloric acid
HPLC high pressure liquid chromatography
K-MDS potassium bis(trimethylsilyl)amide
LC liquid chromatography
LCMS liquid chromatography-mass spectrometry
M molar
mM millimolar
Me methyl
MHz megahertz
mins minute(s)
M$^{+1}$ (M+H)$^+$
MS mass spectrometry
n or N normal NaHMDS sodium bis(trimethylsilyl)amide
NBS N-bromosuccinimide
nM nanomolar
NMP N-methylpyrrolidinone
Ph phenyl
PYBROP bromotripyrrolidinophosphonium hexafluorophosphate
RuPhos precatalyst chloro(2-dicyclohexylphosphino-2',6'-diisopropoxy-1,1'-biphenyl)[2-(2'-amino-1,1'-biphenyl)]palladium(II)
RT or Ret time retention time
sat. saturated
t-BuOH tertiary butanol
TEA triethylamine
TFA trifluoroacetic acid
THF tetrahydrofuran
TLC thin layer chromatography
POCl$_3$ phosphorous oxychloride
2$^{nd}$ Gen Xphos CAS number 1310584-14-5

Intermediate 1

2-(Methylthio)-3-nitro-1,5-naphthyridin-4-ol

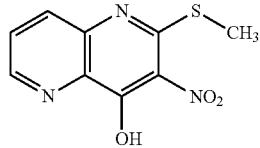

(I-1)

Ethyl 3-aminopicolinate (1.71 g, 10.29 mmol) and (2-nitroethene-1,1-diyl) bis(methylsulfane) (1.75 g, 10.59 mmol) were combined without solvent and melted together at 130° C. After 44 hours, the reaction mixture was cooled to room temperature and stirred with excess diethyl ether. The orange solids were collected on a paper filter (1.7 g, 68%). $^1$H NMR (400 MHz, DMSO-d$_6$) δ 8.75 (d, J=4.6 Hz, 1H), 8.53 (d, J=8.6 Hz, 1H), 799 (dd, J=8.4, 5.0 Hz, 1H), 2.59 (s, 3H).

Intermediate 2

4-chloro-2-(methylthio)-3-nitro-1,5-naphthyridine

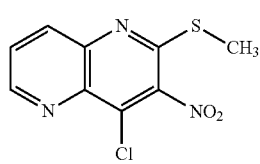

(I-2)

At room temperature, 2-(methylthio)-3-nitro-1,5-naphthyridin-4-ol (1.5 g, 6.32 mmol) and phosphorus oxychloride (8.84 mL, 95 mmol) were combined and then heated with stirring at 50° C. overnight. The reaction mixture was cooled to room temperature and water was added slowly. Orange solids were collected on filter paper and dried under vacuum to afford Intermediate 2 (1 g, 62%). $^1$H NMR (400 MHz, chloroform-d) δ 9.06 (d, J=3.9 Hz, 1H), 8.35 (d, J=8.3 Hz, 1H), 7.79 (dd, J=8.6, 4.2 Hz, 1H), 2.77 (s, 3H). Analytical LC/MS conditions: column: Phenomenex Luna C18, 2.0×50 mm, 3.0 μm particles; Mobile Phase A: 5:95 methanol:water with 0.1% trifluoroacetic acid; Mobile Phase B: 95:5 methanol:water with 0.1% trifluoroacetic acid; Gradient: 0-100% B over 4 minutes, then a 0.75 minute hold at 100% B; Flow: 0.8 mL/min; Detection: UV at 220 nm. LC/MS results: 3.7 minutes, 256, 258 (M+H).

Intermediate 3

4-(4-(bis(4-fluorophenyl)methyl)piperazin-1-yl)-2-(methylthio)-3-nitro-1,5-naphthyridine

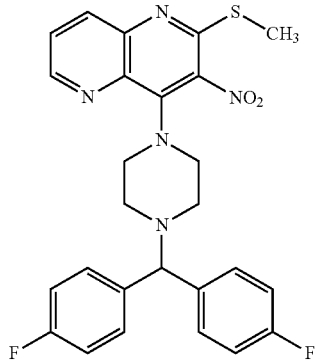

(I-3)

To a solution of 4-chloro-2-(methylthio)-3-nitro-1,5-naphthyridine (0.8 g, 3.13 mmol) in dichloromethane (15.64 mL) were added 1-(bis(4-fluorophenyl)methyl) piperazine (0.992 g, 3.44 mmol) and triethylamine (0.436 mL, 3.13 mmol). The reaction mixture was stirred at room temperature for 1 hour. The reaction was determined to be complete by LC/MS analysis. The solvent was removed by rotary evaporation. The residue was purified by silica gel chromatography with ethyl acetate and hexanes to afford (0.7 g, 44%) as a yellow solid. $^1$H NMR (400 MHz, chloroform-d) δ 8.71 (dd, J=4.2, 1.7 Hz, 1H), 8.15 (dd, J=8.6, 1.7 Hz, 1H), 7.56 (dd, J=8.6, 4.2 Hz, 1H), 7.47-7.37 (m, 4H), 7.07-6.96 (m, 4H), 5.32 (s, 1H), 4.34 (s, 1H), 3.73-3.60 (m, 4H), 2.69-2.63 (m, 7H). LC/MS Analytical LC/MS conditions: column: Phenomenex Luna C18, 2.0×50 mm, 3.0 μm particles; Mobile Phase A: 5:95 methanol:water with 0.1% trifluoroacetic acid; Mobile Phase B: 95:5 methanol:water with 0.1% trifluoroacetic acid; Gradient: 0-100% B over 4 minutes, then a 0.75 minute hold at 100% B; Flow: 0.8 mL/min; Detection: UV at 220 nm. LC/MS results: 4.1 minutes, 508 (M+H).

Intermediate 4

4-(4-(bis(4-fluorophenyl)methyl)piperazin-1-yl)-3-nitro-1,5-naphthyridin-2(1H)-one

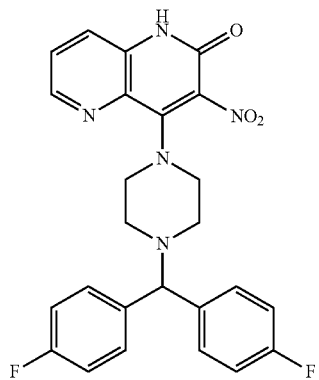

(I-4)

4-(4-(bis(4-fluorophenyl)methyl)piperazin-1-yl)-2-(methylthio)-3-nitro-1,5-naphthyridine (0.69 g, 1.359 mmol) was dissolved in acetic acid (13.59 mL) to give a yellow suspension. Hydrogen peroxide (0.166 mL, 1.631 mmol) and sodium tungstate dihydrate (0.067 g, 0.204 mmol) were added sequentially and the mixture was stirred at room temperature overnight. The acetic acid was removed by rotary evaporation and the residue was chromatographed on silica gel with 0-80% ethyl acetate in hexanes. A white solid (400 mg, 62%0) was isolated. $^1$H NMR (400 MHz, chloroform-d) δ 8.54-8.48 (m, 1H), 7.70-7.60 (m, 1H), 7.50-7.45 (m, 1H), 7.41 (dd, J=8.8, 5.4 Hz, 4H), 7.02 (t, J=8.7 Hz, 4H), 4.34 (s, 1H), 3.72 (br. s., 4H), 2.65 (d, J=4.4 Hz, 4H). Analytical LC/MS conditions: Column: Phenomenex Luna C18, 2.0×50 mm, 3.0 µm particles; Mobile Phase A: 5:95 methanol:water with 0.1% trifluoroacetic acid; Mobile Phase B: 95:5 methanol:water with 0.100 trifluoroacetic acid; Gradient: 0-100% B over 4 minutes, then a 0.75 minute hold at 1000% B; Flow: 0.8 mL/min; Detection: UV at 220 nm. LC/MS results: 3.3 minutes, 478 (M+H).

Intermediate 5

4-(4-benzhydrylpiperazin-1-yl)-2-(methylthio)-3-intro-1,5-naphthyridine

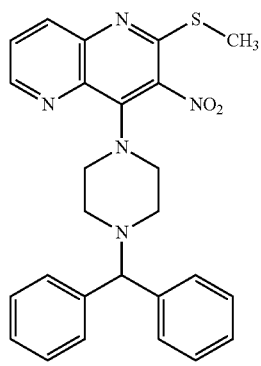

(I-5)

In a round bottom flask, 4-chloro-2-(methylthio)-3-nitro-1,5-naphthyridine (1 g, 3.91 mmol) and 1-benzhydrylpiperazine (0.987 g, 3.91 mmol) were dissolved in dichloromethane (19.56 mL). Triethylamine (0.545 mL, 3.91 mmol) was added and the reaction mixture was stirred at room temperature for 1 hour. LC/MS analysis showed the reaction was complete. The solvent was removed by rotary evaporation. The residue was purified by silica gel chromatography with ethyl acetate and hexanes to give the title compound (1.5 g, 3.2 mmol, 81% yield) as a yellow solid. $^1$H NMR (400 MHz, chloroform-d) δ 8.66 (dd, J=4.1, 1.6 Hz, 1H), 8.10 (dd, J=8.4, 16 Hz, 1H), 7.52 (dd, J=8.5, 4.0 Hz, 1H), 7.48-7.40 (m, 4H), 7.30-7.25 (m, 4H), 7.20-7.15 (m, 2H), 4.30 (s, 1H), 3.69-3.60 (m, 4H), 2.67-2.61 (m, 4H), 2.59 (s, 3H). Analytical LC/MS conditions: column: Phenomenex Luna C18, 2.0×50 mm, 3.0 µm particles; Mobile Phase A: 5:95 methanol:water with 0.1% trifluoroacetic acid; Mobile Phase B: 95:5 methanol:water with 0.1% trifluoroacetic acid; Gradient: 0-100% B over 4 minutes, then a 0.75 minute hold at 100% B; Flow: 0.8 mL/min; Detection: UV at 220 nm. LC/MS results: 3.6 minutes, 472 (M+H).

Intermediate 6

4-(4-benzhydrylpiperazin-1-yl)-3-nitro-1,5-naphthyridin-2(1H)-one

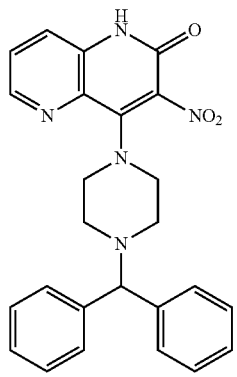

(I-6)

In a round bottom flask, 4-(4-benzhydrylpiperazin-1-yl)-2-(methylthio)-3-nitro-1,5-naphthyridine (1.5 g, 3.18 mmol) was dissolved in acetic acid (31.8 mL) to give a yellow suspension. Hydrogen peroxide (0.389 mL, 3.82 mmol) was added followed by sodium tungstate dihydrate (0.157 g, 0.477 mmol). The resulting suspension was stirred at room temperature overnight and then heated at 30° C. for 72 hours. LC/MS showed a single peak consistent with the desired product. The volatile components were removed under high vacuum to afford the title compound (1.4 g, 3.2 mmol, 78% yield). $^1$H NMR (400 MHz, DMSO-d$_6$) δ 8.51 (d, J=4.2 Hz, 1H), 7.71-7.66 (m, 1H), 7.60 (dd, J=7.9, 4.3 Hz, 1H), 7.48 (d, J=7.6 Hz, 4H), 7.32 (t, J=7.3 Hz, 4H), 7.25-7.17 (m, 2H), 4.42 (s, 1H), 3.51 (d, J=4.2 Hz, 4H), 2.58-2.52 (m, 4H hidden by residual DMSO). Analytical LC/MS conditions: Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5 minute hold at 100% B; Flow: 1

Intermediate 7

6-bromo-4-chloro-1-methyl-2-oxo-1,2-dihydro-1,5-naphthyridine-3-carbonitrile

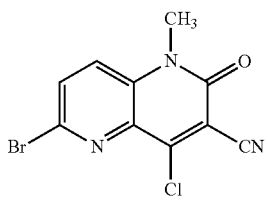

(I-7)

In a 500 mL round bottom flask charged with 6-bromo-1-methyl-2,4-dioxo-1,2,3,4-tetrahydro-1,5-naphthyridine-3-carbonitrile (2.50 g, 8.93 mmol) in acetonitrile (89 mL) was added DIEA (9.4 mL, 53.8 mmol). The reaction mixture was stirred for a couple of minutes. The reaction mixture became a homogeneous solution after the addition of DIEA. Phosphorous oxychloride (3.3 mL, 35.4 mmol) was added to the reaction mixture followed by the addition of benzyltriethylammonium chloride (2.68 g, 11.77 mmol). The reaction mixture was stirred under nitrogen at room temperature overnight to give a dark brownish and heterogeneous mixture. Volatiles were removed in vacuo using a rotary evaporator/vacuum pump combination. To the reaction residue, ice and 1.5 M dibasic potassium phosphate solution were added and the mixture was partitioned into dichloromethane and chloroform. The aqueous portion was extracted with chloroform. The combined organic extracts were washed with dibasic potassium phosphate, 1 N HCl, and then a mixture of dibasic potassium phosphate and brine. The organic portions were dried over sodium sulfate, filtered and the solvent removed in vacuo using a rotary evaporator to give a brown solid (~3.1 g). The solid was redissolved in chloroform/dichloromethane and adsorbed onto 9.8 g of silica gel. The material was purified by chromatography on 83 g of silica gel slurry loaded in 2% ethyl acetate in dichloromethane and eluted with 2% ethyl acetate in dichloromethane. Fractions containing the product were combined and the solvent removed under vacuum to provide 1.922 g (72%) of the title compound. $^1$H NMR (chloroform-d) δ 7.81 (d, J=8.8 Hz, 1H), 7.66 (d, J=9.0 Hz, 1H), 3.75 (s, 3H). Analytical LC/MS conditions: Waters Acquity UPLC BEH C18, 2.1×50 nm, 1.7 μm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 nm. Analytical LC/MS results were consistent with the title compound: 1.3 minutes, 298, 300 (M+H).

Intermediate 8 tert-butyl 4-([1,1'-biphenyl]-2-ylmethyl)piperazine-1-carboxylate

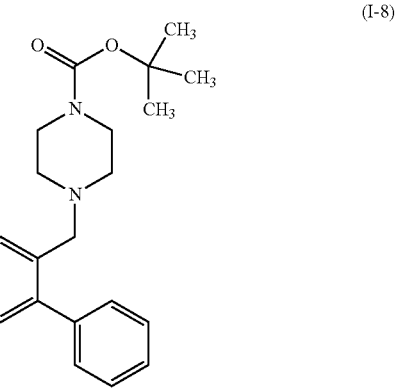

(I-8)

2-Phenylbenzyl bromide (2.264 g, 9.16 mmol) was dissolved in DMF (70 mL). Next, 1-BOC-piperazine (1.717 g, 9.22 mmol) was added followed by the addition of potassium carbonate (1.272 g, 9.20 mmol). The reaction vessel was capped. The reaction mixture was stirred at room temperature overnight (21 hours). Volatiles were removed from the reaction mixture in vacuo using a rotary evaporator. The reaction mixture was partitioned between ethyl acetate and water. The aqueous phase was extracted with ethyl acetate (1×). The organic extracts were combined and washed with brine and dried over magnesium sulfate. The drying agent was filtered off and the solvent was removed from the filtrate in vacuo using a rotary evaporator to afford Intermediate 8 as a clear oil. LCMS: Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 μL. Retention Time=1.24 min.; Obs. Adducts: [M+H]; Obs. Masses: 353.3. $^1$H NMR (Acetonitrile-d$_3$) δ 7.51 (dd, J=7.1, 1.6 Hz, 1H), 7.28-7.45 (m, 7H), 7.21-7.28 (m, 1H), 3.37 (s, 2H), 3.24-3.32 (m, 4H), 2.18-2.26 (m, 4H), 1.39 (s, 9H).

Intermediate 9

1-([1,1'-biphenyl]-2-ylmethyl)piperazine, TFA

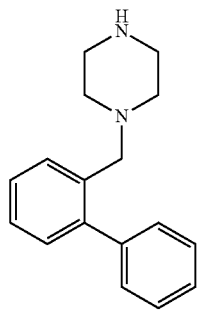

(I-9)

tert-Butyl 4-([1,1'-biphenyl]-2-ylmethyl)piperazine-1-carboxylate (3.219 g, 9.13 mmol) was dissolved in dichloromethane (25 mL) then TFA (50.0 mL) was added. The reaction mixture was placed under a nitrogen atmosphere and stirred at room temperature for 2 hours. Volatiles were removed from the reaction mixture in vacuo using a rotary evaporator. Toluene was added to the reaction product and volatiles were removed in vacuo to assist removing excess TFA. The dissolution in toluene and removal of volatiles was repeated. To convert the oil product into a solid, ethyl acetate, hexanes, and diethyl ether were added, affording a semi-solid colorless precipitate. Removal of solvents and drying of the product in vacuo at room temperature yielded Intermediate 9 as a colorless solid. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 μL. Retention Time=0.92 min.; Obs. Adducts: [M+H]; Obs. Masses: 253.2. $^1$H NMR (DMSO-d$_6$) δ 8.65 (br. s., 2H), 7.52-7.62 (m, 1H), 7.34-7.51 (m, 7H), 7.20-7.32 (m, 1H), 3.67 (br. s., 2H), 3.08 (br. s., 4H), 2.52-2.71 (m, 4H).

Intermediate 10 tert-butyl 4-(naphthalen-1-ylmethyl)piperazine-1-carboxylate

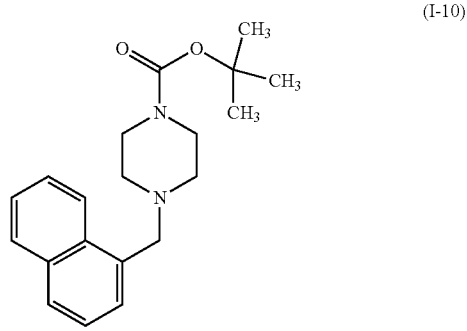 [SMILES: CC(C)(C)OC(=O)N1CCN(Cc2cccc3ccccc23)CC1]

(I-10)

Intermediate I-10A: 1-(iodomethyl)naphthalene

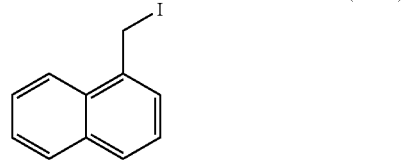

(I-10A)

1-(chloromethyl)naphthalene (1.5 g, 8.49 mmol) was dissolved in acetone (54 mL). Sodium iodide (1.52 g, 10.14 mmol) was added to the reaction mixture. The reaction mixture was heated to reflux for 1.25 hrs. The reaction mixture was cooled and filtered through a celite plug. Solvent was removed from the filtrate using a rotary evaporator. The reaction product was dissolved in diethyl ether and filtered through another celite plug to remove remaining salts. Solvent was again removed in vacuo using a rotary evaporator to yield 2.25 g of 1-(iodomethyl)naphthalene as an amber solid. Estimated purity from NMR was 80-85%. $^1$H NMR (500 MHz, DMSO-d$_6$) δ 8.16-8.13 (m, 1.0H), 7.99 (d, J=8.2 Hz, 1.0H), 7.91 (d, J=8.4 Hz, 1.0H), 7.74-7.71 (m, 1.2H), 7.70-7.66 (m, 1.2H), 7.56 (ddd, J=8.1, 6.9, 1.1 Hz, 1.1H), 7.42 (dd, J=8.1, 7.2 Hz, 1.0H), 5.13 (s, 2.0H).

Intermediate 10

1-(iodomethyl)naphthalene (2.248 g, 8.39 mmol) was dissolved in DMF (70 mL) and 1-BOC-piperazine (1.586 g 8.52 mmol). Potassium carbonate (1.164 g, 8.42 mmol) were added. The reaction vessel was capped. The reaction mixture was stirred at room temperature for 2 hours. Solvent was removed in vacuo using a rotary evaporator and the reaction residue was partitioned between ethyl acetate and saturated aqueous sodium bicarbonate. The organic extract was washed sequentially with a mixture of water and brine, and then brine only. The organic extract was dried over magnesium sulfate. The drying agent was filtered off and the solvent removed in vacuo to afford an orange oil. The orange oil was purified using a silica gel chromatography column eluting with a 0% to 10% gradient of ethyl acetate in dichloromethane. The purified product fractions were combined to yield 2.46 g of tert-butyl 4-(naphthalen-1-ylmethyl)piperazine-1-carboxylate as a colorless oil. LCMS; Column: Waters Acquity BEH C18 2.1 mm×50 mm, 1.7 μm particles; Mobile Phase A: 100% water with 0.05% TFA; Mobile Phase B: 100% acetonitrile with 0.05% TFA; Temperature: 40° C.; Gradient 2% B to 98% B over 1.5 minutes, then 0.5 min hold at 98% B; Flow: 0.8 mL/min; Detection: MS and UV (220 nm). Injection volume: 3 μL. Retention Time=0.88 min.; Obs. adducts: [M+H]; Obs. Masses: 327.2. $^1$H NMR (Acetonitrile-d$_3$) δ 8.28-8.35 (m, 1H), 7.87-7.92 (m, 1H), 7.80-7.85 (m, 1H), 7.48-7.57 (m, 2H) 7.41-7.47 (m, 2H), 3.90 (s, 2H), 3.25-3.40 (m, 4H), 2.34-2.48 (m, 4H), 1.42 (s, 9H).

Intermediate 11

1-(naphthalen-1-ylmethyl)piperazine

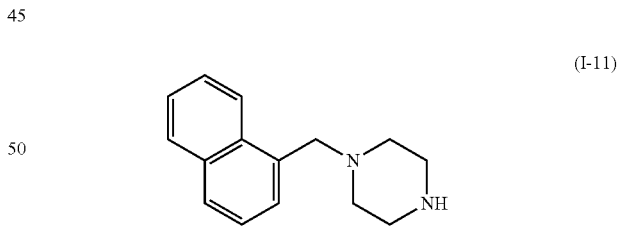

(I-11)

tert-Butyl 4-(naphthalen-1-ylmethyl)piperazine-1-carboxylate (2.41 g, 7.38 mmol) was dissolved in dichloromethane (37 mL). Next, TFA (37.0 mL) was added. The reaction vessel was capped under a nitrogen atmosphere. The reaction mixture was stirred at room temperature for 1.5 hours. Toluene (70 mL) was added to the reaction mixture and volatiles were removed in vacuo. Dichloromethane and toluene were added to the mixture. Volatiles were removed in vacuo to aid in removal of excess TFA. The product was obtained as a cream-beige colored solid. LCMS: Column: Waters Acquity BEH C18 2.1 mm×50 mm, 1.7 μm particles; Mobile Phase A: 100% water with 0.05% TFA; Mobile Phase B: 100% acetonitrile with 0.05% TFA; Temperature:

40° C.; Gradient 2% B to 98% B over 1.5 minutes, then 0.5 min hold at 98% B; Flow: 0.8 mL/min; Detection: MS and UV (220 nm). Injection volume: 3 μL. Retention Time=0.68 min.; Obs. Adducts: [M+H]; Obs. Masses: 227.1. $^1$H NMR (DMSO-d$_6$) δ 8.73 (br. s., 2H), 8.28 (d, J=8.2 Hz, 1H), 7.87-8.06 (m, 2H), 7.39-7.69 (m, 4H), 4.26 (br. s., 2H), 3.17 (br. s., 4H), 2.91 (br. s., 3H).

Intermediate 12

Ethyl 3-amino-6-bromopicolinate

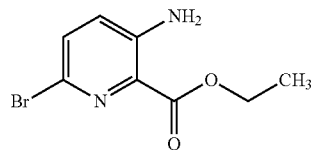

(I-12)

Ethyl 3-aminopicolinate (8.0 g, 48.1 mmol) was suspended in water (66 mL) in a 250 mL three neck round bottom flask equipped with a mechanical stirrer, addition funnel and thermocouple temperature probe. Sulfuric acid (1.7 mL, 31.9 mmol) and acetic acid (3.31 mL, 57.8 mmol) were added slowly while the flask was immersed in a room temperature water bath to control temperature. To the reaction mixture, a solution of bromine (2.5 mL, 48.5 mmol) in acetic acid (17.5 mL, 306 mmol) was added over 15 minutes at ambient temperature with vigorous stirring while maintaining the internal temperature of the reaction mixture below 23° C. The water bath removed and the reaction mixture was stirred at ambient temperature for 2 hours. The reaction suspension was filtered and rinsed with a small amount of water, and then dried in vacuo at room temperature to yield 9.305 g of Intermediate 12 as a yellow solid. LCMS: Column: Waters Acquity UPLC BEH C18, 2.1×50 mm, 1.7 μm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 nm. Retention Time=0.94 min.; Obs. Adducts: [M+H]; Obs. Masses: 245.0. $^1$H NMR (DMSO-d$_6$) δ 7.44 (d, J=8.8 Hz, 1H), 7.21 (d, J=8.7 Hz, 1H), 6.88 (br. s., 2H), 4.29 (q, J=7.1 Hz, 2H), 1.31 (t, J=7.1 Hz, 3H).

Intermediate 13

Ethyl 3-acetamido-6-bromopicolinate

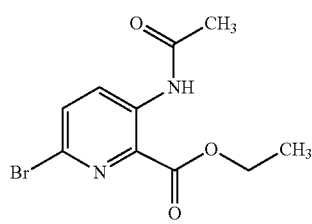

(I-13)

Ethyl 3-amino-6-bromopicolinate (1.31 g, 5.35 mmol) was dissolved in THF (6 mL) followed by the addition of acetic anhydride (1.6 mL, 16.96 mmol). The reaction mixture was a suspension/partial solution. The reaction mixture was placed under a nitrogen atmosphere and heated to reflux. The reaction mixture became homogeneous within 15 minutes. The reaction mixture was refluxed for 4 hrs. The reaction volatiles were removed in vacuo using a rotary evaporator. A small amount of ethyl acetate was added to the reaction residue and a nearly colorless solid was filtered off and dried in vacuo to yield 787 mg of Intermediate 13. LCMS: Column: Waters Acquity UPLC BEH C18, 2.1×50 mm, 1.7 μm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 nm. Retention Time=0.98 min.; Obs. Adducts: [M+H]; Obs. Masses: 287.0. $^1$H NMR (DMSO-d$_6$) δ 10.40 (s, 1H), 8.32 (d, J=8.7 Hz, 1H), 7.83 (d, J=8.8 Hz, 1H), 4.33 (q, J=7.1 Hz, 2H), 2.12 (s, 3H), 1.32 (t, J=7.2 Hz, 3H). Removal of solvent from the filtrate provided an additional 695 mg of product (87% pure).

Intermediate 14

Ethyl 3-acetamido-6-cyanopicolinate

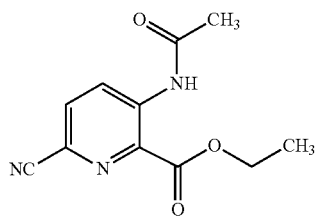

(I-14)

To a 2.5 mL Biotage microwave vial charged with copper (I) cyanide (86 mg, 0.960 mmol) and ethyl 3-acetamido-6-bromopicolinate (200 mg, 0.697 mmol), N,N-dimethylformamide (3.5 mL). A magnetic stir bar were added and the vial was capped under nitrogen. The reaction mixture was heated to 200° C. for 8 minutes in a Biotage Initiator microwave set to normal adsorption. The reaction mixture was transferred to a round bottom flask and solvent was removed in vacuo using a vacuum pump/rotary evaporator combination. The brown residue was triturated with ethyl acetate (25 mL) containing DCM and the resultant suspension filtered through a plug of celite. Solvent was removed from the filtrate to afford the crude product as 102 mg of yellow solid. The crude product was purified on a Biotage Isolera One system employing a 4 g Isco RediSep silica gel cartridge using a gradient of 1% ethyl acetate to 10% ethyl acetate in dichloromethane. Pure fractions were combined and solvent removed in vacuo to give 84 mg of pure product as a colorless solid. LCMS: Column: Waters Acquity UPLC BEH C18, 2.1×50 mm, 1.7 μm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 n/min; Detection: UV at 220 nm. Retention Time=0.92 min.; Obs. Adducts: [M+H]; Obs. Masses: 234.1. RH NMR (DMSO-d$_6$) δ 10.67 (s, 1H), 8.58 (d, J=8.7 Hz, 1H), 8.19 (d, J=8.7 Hz, 1H), 4.36 (q, J=7.1 Hz, 2H), 2.17 (s, 3H), 1.33 (t, J=7.1 Hz, 3H).

Intermediate 15

Ethyl 6-cyano-3-(N-methylacetamido)picolinate

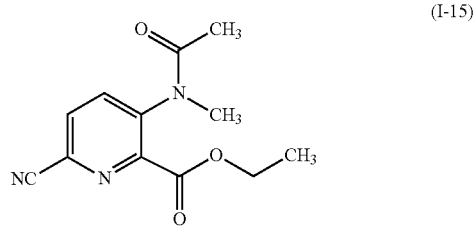 [SMILES: CCOC(=O)c1nc(C#N)ccc1N(C)C(C)=O]

(I-15)

Ethyl 3-acetamido-6-cyanopicolinate (20 mg, 0.086 mmol) was dissolved in DMF (0.85 mL). Next, cesium carbonate (39.1 mg, 0.120 mmol) was added followed by the addition of methyl iodide (9 μL, 0.144 mmol). The reaction vessel was capped and the reaction mixture was stirred at room temperature overnight. The reaction mixture was diluted with 2.8 mL of acetonitrile, and filtered through a 0.45 μm syringe filter. Volatiles were removed from the filtrate, then triturated with DCM/ethyl acetate and filtered again through a 0.45 μm syringe filter to remove salts. The volatiles were removed in vacuo using a rotary evaporator to afford the crude product as an amber oil. The oil was dissolved in deuterated chloroform for proton NMR. The proton NMR exhibited characteristics of restricted rotation (rotamers): $^1$H NMR (CHLOROFORM-d) δ 7.65-8.01 (m, 2H), 4.32-4.56 (m, 2H), 3.43 (br. s., 1H), 3.22 (s, 2H), 2.26 (br. s., 1H), 1.82 (s, 2H), 1.34-1.50 (m, 3H). The $^{13}$C DEPT spectra was consistent with N-methylation with signal at 37 ppm.

The NMR sample was recovered by removing volatiles in vacuo using a rotary evaporator and the sample dissolved in a 1 mL, 1:1 mixture of DMF/acetonitrile. The crude material was purified via preparative LC/MS with the following conditions: Column: XBridge C18, 19×200 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-30% B over 20 minutes, then a 5 minute hold at 100% B; Flow: 20 mL/min. Fractions containing the product were combined and dried via centrifugal evaporation. The yield of the product was 17.9 mg, and its estimated purity by LCMS analysis was 99%. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Results: Retention Time=1.11 min.; Obs. Adducts: [M+H]; Obs. Masses: 248.0. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 urn. Retention Time=1.01 min.; Obs. Adducts: [M+H]; Obs. Masses: 248.0

Intermediate 16

8-Hydroxy-5-methyl-6-oxo-5,6-dihydro-1,5-naphthyridine-2-carbonitrile

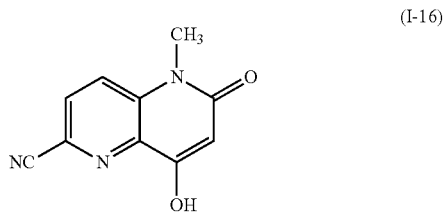

(I-16)

To a 25 mL round bottom flask, potassium bis(trimethylsilyl)amide (KHMDS) (3.0 mL, 1.500 mmol) in 0.5 M in toluene was added. The flask was placed under nitrogen and cooled to −78° C. To the solution of KHMDS was added a solution of ethyl 6-cyano-3-(N-methylacetamido)picolinate (333 mg, 1.347 mmol) in THF (13.5 mL) via cannula over approximately 23 minutes. After 20 minutes at −78° C., the dry ice bath was removed and the reaction mixture was warmed to room temperature over 1.25 hours. Ethyl acetate and water were added to the reaction mixture. The reaction mixture was transferred to a separatory funnel and additional ethyl acetate was added. The reaction mixture was gently shaken and then partitioned collecting the aqueous phase in a small Erlenmeyer flask. The aqueous phase (~20 mL) was acidified with 1.6 mL of 1N hydrochloric acid. A fine yellow precipitate was filtered off and rinsed with ~2 mL of deionized water and dried in vacuo at room temperature yielding 229 mg of Intermediate 16 as a yellow solid. LCMS: Column: Waters Acquity UPLC BEH C18, 2.1×50 mm, 1.7 μm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 mu. Retention Time=068 min. Obs. Adducts: [M+H]; Obs. Masses: 202.1. $^1$H NMR (DMSO-d$_6$) δ 11.51 (br. s., 1H), 8.21 (d, J=8.8 Hz, 1H), 8.11 (d, J=8.8 Hz, 1H), 6.16 (s, 1H), 3.54 (s, 3H).

Intermediate 17

8-Hydroxy-5-methyl-7-nitro-6-oxo-5,6-dihydro-1,5-naphthyridine-2-carbonitrile

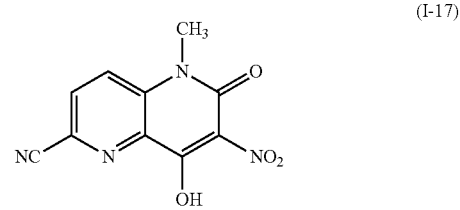 [SMILES: Cn1c(=O)c([N+](=O)[O-])c(O)c2nc(C#N)ccc21]

(I-17)

In a 2 dram vial containing 8-hydroxy-5-methyl-6-oxo-5,6-dihydro-1,5-naphthyridine-2-carbonitrile (227 mg, 1.128 mmol), add acetic acid (2.8 mL), stir and slowly add nitric acid (0.151 mL, 3.39 mmol). The mixture was allowed to stir approximately one minute then capped and heated to 100° C. for 18 minutes. The reaction mixture became homogeneous after approximately 3 minutes at 100° C. The mixture was cooled then placed in an ice bath and subsequently the yellow precipitate filtered and rinsed with 2×0.5 mL of cold ethanol. The product was dried in vacuo at room temperature to yield 202 mg of the title compound as a yellow solid. LCMS: Column: Waters Acquity UPLC BEH CIS, 2.1×50 mm, 1.7 µm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 nm. Retention Time=0.67 min.; Obs. Adducts: [M+H]; Obs. Masses: 247.1. $^1$H NMR (DMSO-d$_6$) δ 8.30-8.38 (m, 1H), 8.19-8.28 (m, 1H), 3.59 (s, 3H).

Intermediate 18

8-Chloro-5-methyl-7-nitro-6-oxo-5,6-dihydro-1,5-naphthyridine-2-carbonitrile

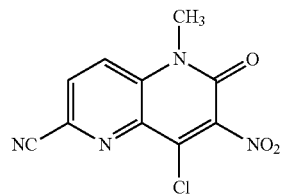

(I-18)

In a 2 dram vial containing 8-hydroxy-5-methyl-7-nitro-6-oxo-5,6-dihydro-1,5-naphthyridine-2-carbonitrile (192 mg, 0.780 mmol) a magnetic stir bar and acetonitrile (3.1 mL) were added. Next, DIEA (0.272 mL, 1.560 mmol) was added to the suspension. The reaction mixture was stirred for 1-2 minutes until the reaction mixture became a homogeneous yellow solution. To the reaction mixture was added phosphorous oxychloride (0.131 mL, 1.404 mmol). The vial was capped under nitrogen with vent to an oil bubbler. The reaction mixture was stirred at room temperature for 1.5 hours then benzyltriethylammonium chloride (200 mg, 0.878 mmol) was added to the reaction mixture. The vial was capped under a nitrogen atmosphere and immersed in an oil bath (65° C.) and heated for 1 hour. The reaction mixture was cooled and the reaction volatiles were remove in vacuo using a rotary evaporator. The reaction residue was dissolved in ethyl acetate, poured into a beaker containing ice (~10 mL), and then transferred to a separatory funnel. The aqueous phase was extracted with ethyl acetate. The organic extracts combined and washed sequentially with 1.5 M K$_2$HPO$_4$, saturated aqueous sodium bicarbonate, and brine. The organic extract was dried over magnesium sulfate, filtered, and solvent removed in vacuo to give a 204 mg of a brownish crystalline solid. LCMS: Column: Waters Acquity UPLC BEH C18, 2.1×50 mm, 1.7 µm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% 1B; Flow: 0.8 mL/min; Detection: UV at 220 nm. Retention Time=1.01 min.; Obs. Adducts: [M+H]; Obs. Masses: 265.0 (weak ionization). $^1$H NMR (CHLOROFORM-d) δ 8.03 (d, J=8.8 Hz, 1H), 7.89-7.97 (m, 1H), 3.82 (s, 3H).

Intermediate 19

6-bromo-4-chloro-1-methyl-2-oxo-1,2-dihydro-1,5-naphthyridine-3-carbonitrile

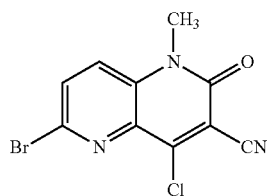

(I-19)

6-Bromo-1-methyl-2,4-dioxo-1,2,3,4-tetrahydro-1,5-naphthyridine-3-carbonitrile (2.50 g, 8.93 mmol) was suspended in acetonitrile (89 mL). Next, DIEA (9.4 mL, 53.8 mmol) was added and the mixture was stirred for a couple of minutes. Phosphorous oxychloride (POCl$_3$) (3.3 mL, 35.4 mmol) was added to the reaction mixture followed by the addition of benzyltriethylammonium chloride (2.68 g, 11.77 mmol). The reaction mixture was placed under a nitrogen atmosphere and stirred at room temperature for 18 hours. The volatile components of the reaction mixture were removed in vacuo using a rotary evaporator and vacuum pump combination. Ice was added to the reaction residue then a 1.5 M solution of dipotassium phosphate was added. Next, dichloromethane and chloroform were added. The mixture was transferred to a separatory funnel for mixing and the separation of the aqueous and organic phases. The aqueous phase was extracted with chloroform. The organic extracts were combined and sequentially washed with 1.5 M dipotassium phosphate, 1 N hydrochloric acid and a mixture of dipotassium phosphate and brine. The organic extract was dried over sodium sulfate, then filtered and the solvents from the filtrate removed in vacuo to afford a brown solid. The product was purified using silica gel column chromatography eluting with 2% ethyl acetate in dichloromethane. Pure fractions by TLC analysis were combined and the solvent removed in vacuo to give 1.684 g of the title compound as a yellow solid. LCMS; Column: Waters Acquity BEH 2.1 mm×50 mm, 1.7 µm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 µL. Retention Time=1.29 min.; Obs. Adducts: [M+H]; Obs. Masses: 298.1. $^1$H NMR (CHLOROFORM-d) δ 7.81 (d, J=8.8 Hz, 1H), 7.66 (d, J=9.0 Hz, 1H), 3.75 (s, 3H).

Intermediate 20 tert-butyl 4-(6-bromo-3-cyano-1-methyl-2-oxo-1,2-dihydro-1,5-naphthyridin-4-yl) piperazine-1-carboxylate

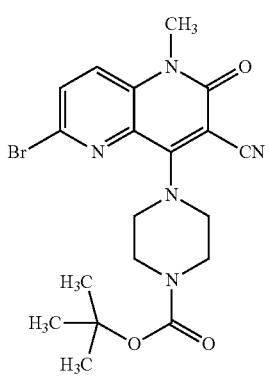

(I-20)

6-Bromo-4-chloro-1-methyl-2-oxo-1,2-dihydro-1,5-naphthyridine-3-carbonitrile (545 mg, 1.826 mmol) was dissolved in DMF (18 mL). Next, 1-BOC-piperazine (354 mg, 1.901 mmol) and potassium carbonate (381 mg, 2.76 mmol) were added. The reaction mixture was stirred at room temperature under nitrogen. After approximately 1 hr, the reaction mixture was heterogeneous and became a slurry. The slurry was stirred for 5.5 hours. HPLC analysis indicated that the reaction was 99% complete. DMF (9 ml) was added to the reaction mixture and the mixture was stirred overnight. Next, ethyl acetate and 1.0M of dipotassium phosphate (pH~4.5) were added. TI-IF was added. The mixture was placed in a separatory funnel and some of the aqueous phase drained away, the remaining mixture was filtered through a Buchner funnel and the resulting filter cake washed with deionized water. The product was dried in vacuo at room temperature to afford 307 mg of the title compound as a yellow solid. Additional product was recovered from the filtrate. Ethyl acetate and THF were added to the filtrate to redissolve material which precipitated out from solvent reduction in vacuo. The organic phase was washed with brine and dried over magnesium sulfate. The drying agent was filtered off and the solvents removed in vacuo using a rotary evaporator to give an additional 492 mg of product. $^1$H NMR (DMSO-$d_6$) δ 7.94-8.00 (m, 1H), 7.89-7.94 (m, 1H), 3.74-3.84 (m, J=4.4 Hz, 4H), 3.54-3.62 (m, J=4.3 Hz, 4H), 3.52 (s, 3H), 1.44 (s, 9H).

Intermediate 21 methyl 8-(4-(tert-butoxycarbonyl)piperazin-1-yl)-7-cyano-5-methyl-6-oxo-5,6-dihydro-1,5-naphthyridine-2-carboxylate

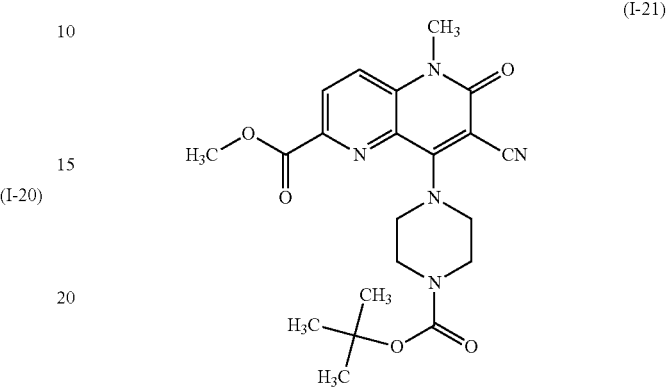

(I-21)

A two dram vial fitted with a septa cap was charged with palladium(II) acetate (1.502 mg, 6.69 μmol), 1,1'-bis(diphenylphosphino)ferrocene (7.42 mg, 0.013 mmol) and tert-butyl 4-(6-bromo-3-cyano-1-methyl-2-oxo-1,2-dihydro-1,5-naphthyridin-4-yl) piperazine-1-carboxylate (30 mg, 0.067 mmol). To the vial was add DMF (1.1 mL) (sparged with nitrogen for 30 min). The vial was evacuated and back filled with carbon monoxide from a balloon (10×) through a needle and 3-way valve, then methanol (0.46 mL) was added. The reaction mixture was heated at 60° C. for 1 hour. Next, triethylamine (0.020 mL, 0.143 mmol) was added. The heating of the reaction mixture at 60° C. under carbon monoxide (1 atm) continued overnight. The reaction mixture was cooled and filtered through a syringe filter. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 20-60% B over 25 minutes, then a 5 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.9%; Observed Mass: 428.11; Retention Time: 1.65 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100%13; Flow: 1 mL/min; Detection: MS and UV (220 nm). Injection 2 results: Purity: 100.0%; Observed Mass: 428.13; Retention Time: 1.69 min. Proton NMR signal intensities proximal to the water suppression frequency may be affected and were uncorrected: $^1$H NMR (DMSO-$d_6$) δ 8.25 (d, J=8.8 Hz, 1H), 8.09 (d, J=8.8 Hz, 1H), 3.93 (s, 3H), 3.85-3.92 (m, J=4.8 Hz, 4H), 3.60-3.70 (m, J=3.7 Hz, 4H), 3.56 (s, 3H), 1.45 (s, 9H).

Intermediate 22 methyl 7-cyano-5-methyl-6-oxo-8-(piperazin-1-yl)-5,6-dihydro-1,5-naphthyridine-2-carboxylate, HCl

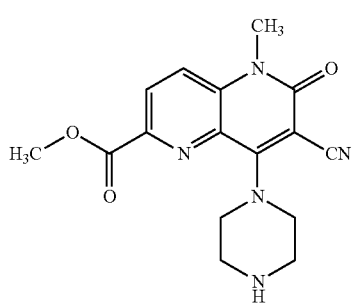

(I-22)

In a 2 dram vial containing methyl 8-(4-(tert-butoxycarbonyl)piperazin-1-yl)-7-cyano-5-methyl-6-oxo-5,6-dihydro-1,5-naphthyridine-2-carboxylate (109 mg, 0.255 mmol) was added dioxane (1.5 mL). The mixture was heated to dissolve the solids. Next, the mixture was cooled to provide a precipitation, followed by the addition of 3 mL of 4 N HCl in dioxane. The vial was capped and the reaction mixture was stirred at room temperature for 1.45 hours. Reaction monitoring by HPLC indicated that the reaction was complete. The reaction mixture was transfer to a round bottom flask. Volatiles were removed in vacuo using a rotary evaporator. The material was dried in vacuo at room temperature to give the 94 mg of the product as a light pink solid. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 μL. Retention Time=0.812 min.; Obs. Adducts: [M+H]; Obs. Masses: 328.2. $^1$H NMR (DMSO-$d_6$) δ 9.22-9.43 (m, 2H), 8.30 (d, J=9.0 Hz, 1H), 8.16 (d, J=9.0 Hz, 1H), 4.01-4.15 (m, 4H), 3.93 (s, 3H), 3.58 (s, 3H), 3.42 (br. s., 4H).

Intermediate 23 tert-butyl 4-(3-cyano-6-(methoxy(methyl)carbamoyl)-1-methyl-2-oxo-1,2-dihydro-1,5-naphthyridin-4-yl)piperazine-1-carboxylate

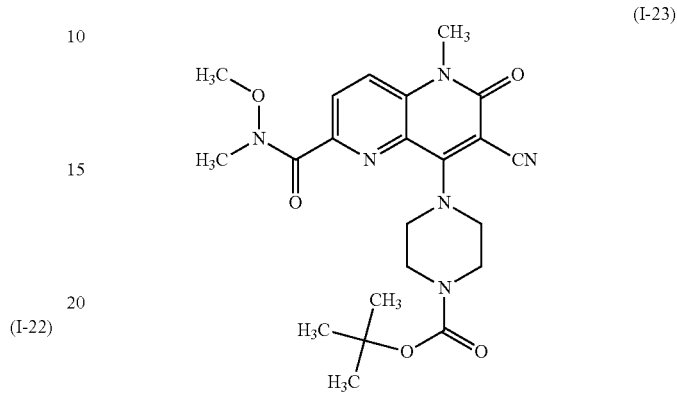

(I-23)

A two dram vial fitted with a septa cap was charged with palladium(II) acetate (1.5 mg, 6.68 μmol), 4,5-bis(diphenylphosphino)-9,9-dimethylxanthine (39 mg, 6.74 μmol), tert-butyl 4-(6-bromo-3-cyano-1-methyl-2-oxo-1,2-dihydro-1,5-naphthyridin-4-yl)piperazine-1-carboxylate (30 mg, 0.067 mmol) and N,O-dimethylhydroxylamine hydrochloride (10.2 mg, 0.105 mmol). DMF (1.0 mL) (sparged with nitrogen for 30 min) was added and the vial was evacuated and back filled with carbon monoxide from balloon (10×) through needle and 3-way valve. Next, triethylamine (30 μl, 0.215 mmol) was added to the reaction mixture. The reaction mixture was heated in an oil bath (60° C.) and stirred under 1 atm of carbon monoxide (balloon pressure) for 18 hours. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 20-60% B over 20 minutes, then a 5 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 457.12; Retention Time: 1.48 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C. Gradient: 0% B to 100% B over 3 min, then a 0.75 min hold at 100% B; Flow: 1 mL/min; Detection: MS and UV (220 nm). Injection 2 results: Purity: 100.0%; Observed Mass: 457.15; Retention Time: 1.59 min. Proton NMR signal intensities proximal to the water suppression frequency were affected and were uncorrected in this measurement. $^1$H NMR (DMSO-$d_6$) δ

8.08 (d, J=8.8 Hz, 1H), 7.90 (d, J=8.4 Hz, 1H), 3.79-3.88 (m, J=4.8 Hz, 4H), 3.61 (s, 2H), 3.53-3.59 (m, 6H), 3.31 (s, 2H), 1.45 (s, 9H).

Intermediate 24

8-(4-(tert-butoxycarbonyl)piperazin-1-yl)-7-cyano-5-methyl-6-oxo-5,6-dihydro-1,5-naphthyridine-2-carboxylic acid

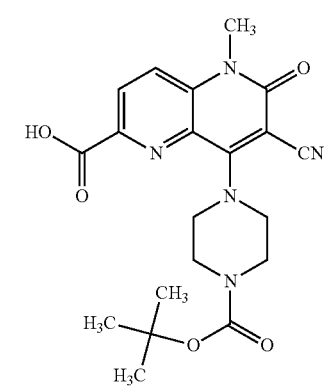

(I-24)

Intermediate 24 was isolated as a by-product of the reaction for the above product tert-butyl 4-(3-cyano-6-(methoxy(methyl)carbamoyl)-1-methyl-2-oxo-1,2-dihydro-1,5-naphthyridin-4-yl)piperazine-1-carboxylate. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 20-60% B over 20 minutes, then a 5 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; RT: 1.5; Obs. Adducts: [M+Na]; Obs. Masses: 436.05. Proton NMR signal intensities proximal to the water suppression frequency are affected and are uncorrected. $^1$H NMR (500 MHz, DMSO-d$_6$) δ 8.21 (d, J=8.8 Hz, 1H), 8.04 (d, J=9.2 Hz, 1H), 3.87 (br s, 4H), 3.62 (br s, 2H), 3.54 (s, 1H), 1.43 (s, 9H).

Intermediate 25

Ethyl 3-acetamidopicolinate

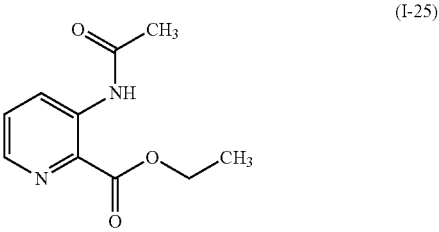

(I-25)

Ethyl 3-aminopicolinate (5.0 g, 30.1 mmol) was dissolved in THF (35 mL) with heating. Next, acetic anhydride (13 mL, 138 mmol) was added to the reaction mixture. The reaction mixture was placed under a nitrogen atmosphere and heated to reflux for 3 hours. The reaction mixture was cooled and volatiles were removed in vacuo using a rotary evaporator. The colorless product was dried in vacuo at room temperature to yield 6.228 g of the title compound. LCMS: Column: Waters Acquity UPLC BEH C18, 2.1×50 mm, 1.7 lcm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 nm. Retention Time=0.85 min.; Obs. Adducts: [M+H]; Obs. Masses: 209.1. $^1$H NMR (DMSO-d$_6$) δ 10.35 (br. s., 1H), 8.33-8.40 (m, 2H), 7.59 (dd, J=8.4, 4.5 Hz, 1H), 4.32 (q, J=7.1 Hz, 2H), 2.11 (s, 3H), 1.32 (t, J=7.2 Hz, 3H).

Intermediate 26

Ethyl 3-(N-methylacetamido)picolinate

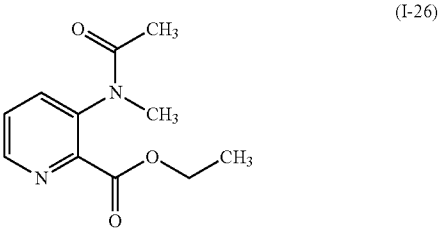 [SMILES: CCOC(=O)c1ncccc1N(C)C(C)=O]

(I-26)

Ethyl 3-acetamidopicolinate (1.0 g, 4.80 mmol) was dissolved in DMF (48.0 mL). Cesium carbonate (2.191 g, 6.72 mmol) was added, followed by the addition of methyl iodide (0.480 mL, 7.68 mmol). The reaction vial was capped and the reaction mixture was stirred at room temperature for 225 hours. The volatiles were removed in vacuo using a rotary evaporator/vacuum pump combination. The residue was partitioned between ethyl acetate and saturated aqueous sodium bicarbonate. The aqueous phase was extracted with ethyl acetate. The organic extracts were combined and washed sequentially with saturated aqueous sodium bicarbonate, then brine. The organic extract was dried over magnesium sulfate, filtered and solvent was removed in vacuo using a rotary evaporator. The title compound was obtained as a light brown solid (891 mg). LCMS: Column:

Waters Acquity UPLC BEH C18, 2.1×50 mm, 1.7 μm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 nm. Retention Time=0.80 min.; Obs. Adducts: [M+H]; Obs. Masses: 223.1. $^1$H NMR (Acetonitrile-d$_3$) δ 8.47-8.70 (m, 1H), 7.66-7.88 (m, 1H), 7.50-7.65 (m, 1H), 4.24-4.41 (m, 2H), 3.04-3.38 (m, 3H), 1.69 (s, 2H), 1.32 (t, J=7.0 Hz, 3H).

Intermediate 27

4-hydroxy-1-methyl-1,5-naphthyridin-2(1H)-one

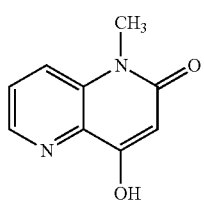

(I-27)

In a 100 mL round bottom flask, a solution of KHMDS (4.1 mL, 4.10 mol) in THF (1.0 M) was place under nitrogen and cooled to −78° C. Next, a solution of ethyl 3-(N-methylacetamido)picolinate (805 mg, 3.62 mmol) in THF (36.5 mL) was added over 26 minutes. The reaction mixture was stirred at −78° C. for one hour. The flask was removed from dry ice bath. The reaction mixture was warmed to room temperature with stirring for 1.5 hours. Ethyl acetate and 30 mL of deionized water were added to the reaction mixture, which was then transferred to a separatory funnel and gently shaken. The aqueous phase was partitioned into an Erlenmeyer flask, acidified by the addition of 1 N hydrochloric acid (4.1 mL, 4.10 mmol), and stirred at room temperature. A precipitate formed and was filtered off using a Buchner funnel. The pH of the filtrate was measured by a pH indicator strip and found to be approximately 4. The colorless precipitate was dried in vacuo at room temperature to yield 531 mg of the title compound as a colorless solid. LCMS: Column: Waters Acquity UPLC BEH C18, 2.1×50 mm, 1.7 μm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection UV at 220 nm. Retention Time=0.56 min.; Obs. Adducts: [M+1-H]; Obs. Masses: 177.0. $^1$H NMR (DMSO-d$_6$) δ 10.97 (br. s., 1H), 8.51 (dd, J=4.3, 1.0 Hz, 1H), 7.96 (dd, J=8.5, 1.0 Hz, 1H), 7.68 (dd, J=8.5, 4.5 Hz, 1H), 6.06 (s, 1H), 3.53 (s, 3H).

Intermediate 28

4-chloro-1-methyl-1,5-naphthyridin-2(1H)-one

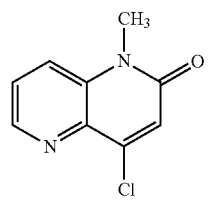

(I-28)

A suspension was prepared containing 4-hydroxy-1-methyl-1,5-naphthyridin-2(1H)-one (100 mg, 0.568 mmol) in acetonitrile (2.8 mL). Phosphorous oxychloride (0.423 mL, 4.54 mmol) was added to the suspension. The reaction vessel was capped under a nitrogen atmosphere and heat at 80° C. for 4 hours. The reaction mixture was cooled and analyzed by HPLC. Additional phosphorous oxychloride (0.2 mL, 2.146 mmol) was added to the reaction mixture and the reaction vessel was capped under a nitrogen atmosphere and heated to 80° C. for 2 hours. The reaction mixture was cooled, and volatiles removed in vacuo using a rotary evaporator. The reaction residue was partitioned between ethyl acetate and 1.5 M aqueous K$_2$HPO$_4$. The aqueous phase (pH ~7, pH indicator strip) was made more basic by the addition of saturated aqueous sodium bicarbonate and then extracted with ethyl acetate. The organic extracts were combined and washed sequentially with saturated aqueous sodium bicarbonate and brine. The organic extract was dried over magnesium sulfate, filtered and solvent removed in vacuo to yield 138 mg of product. LCMS: Column: Phenomenex LUNA C18, 2 mm×50, 3 μm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. Retention Time=1.69 min.; Obs. Adducts: [M+H]; Obs. Masses: 194.9. $^1$H NMR (DMSO-d$_6$) δ 8.64 (dd, J=4.4, 1.3 Hz, 1H), 8.10 (dd, J=8.7, 1.3 Hz, 1H), 7.76 (dd, J=8.6, 4.3 Hz, 1H), 7.23 (s, 1H), 3.63 (s, 3H).

Intermediate 29

3-bromo-4-hydroxy-1-methyl-1,5-naphthyridin-2(1H)-one

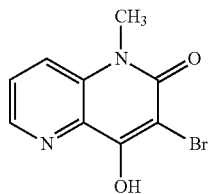

(I-29)

4-hydroxy-1-methyl-1,5-naphthyridin-2(1H)-one (500 rug, 2.84 mmol) was dissolved in DMF (8 mL), followed by the addition of NBS (535 ng, 3.01 mmol). The reaction vessel was capped under a nitrogen atmosphere. The reaction mixture was stirred at room temperature for 2 hours. Solvent was removed in vacuo using a rotary evaporator and 8 mL of deionized water was added to crude reaction product. The suspension was swirled and ultrasonicated (5-10 see pulse), then filtered through a Buchner funnel, and rinsed with deionized water (8-10 mL in three portions). The colorless product was dried in vacuo to give 681 mg of the title compound as a colorless solid. LCMS; Column: Waters Acquity BEH C18 2.1 mm×50 mm, 1.7 μm particles; Mobile Phase A: 100% water with 0.05% TFA; Mobile Phase B: 100% acetonitrile with 0.05% TFA; Temperature: 40° C.; Gradient 2% B to 98% B over 1.5 minutes, then 0.5 min hold at 98% B; Flow: 0.8 mL/min; Detection: MS and UV (220 nm). Injection volume: 3 μL. Results: Retention Time=0.64 min.; Obs. Adducts: [M+H]; Obs. Masses: 254.9. $^1$H NMR (DMSO-d$_6$) δ 11.86 (br. s., 1H), 8.57 (d, J=3.5 Hz, 1H), 8.06 (d, J=8.5 Hz, 1H), 7.76 (dd, J=8.5, 4.4 Hz, 1H), 3.65 (s, 3H).

Intermediate 30

3-bromo-1-methyl-2-oxo-1,2-dihydro-1,5-naphthyridin-4-yl trifluoromethanesulfonate

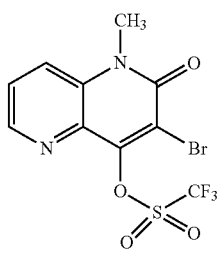

(I-30)

3-bromo-4-hydroxy-1-methyl-1,5-naphthyridin-2(1H)-one (200 mg, 0.784 mmol) was dissolved in acetonitrile (5 mL) with DIEA (0.548 mL, 3.14 mmol) at room temperature. The reaction mixture was placed under a nitrogen atmosphere and cooled to 0° C. Triflic anhydride (0.265 mL, 1.568 mmol) in acetonitrile (2 mL) was added slowly with a syringe (dropwise) to the reaction mixture. The reaction mixture was stirred at 0° C. for 30 minutes, then warmed to room temperature over 40 minutes, and stirred at room temperature for 30 minutes. Volatiles were removed from the reaction mixture using a rotary evaporator and the crude reaction mixture was partitioned between ethyl acetate and 1.5 M dipotassium phosphate. The aqueous phase was extracted with ethyl acetate and the organic extracts combined and sequentially washed with 1.5 M dipotassium phosphate and brine. The organic extract was dried over magnesium sulfate, then filtered, and volatiles removed from the filtrate using a rotary evaporator to give the crude product as a dark brown amorphous solid. The crude product was estimated by LCMS to be approximately 78% pure by UV at 220 nm. The crude product was used without further purification. LCMS; Column: Waters Acquity BEH C18 2.1 mm×50 mm, 1.7 μm particles; Mobile Phase A: 100% water with 0.05% TFA; Mobile Phase B: 100% acetonitrile with 0.05% TFA; Temperature: 40° C.; Gradient 2% B to 98% B over 1.5 minutes, then 0.5 min hold at 98% B; Flow: 0.8 mL/min; Detection: MS and UV (220 n). Injection volume: 3 μL. Results: Retention Time=1.01 min.; Obs. Adducts: [M+H]; Obs. Masses: 386.9.

Intermediate 31 tert-butyl 4-(1-methyl-2-oxo-1,2-dihydro-1,5-naphthyridin-4-yl)piperazine-1-carboxylate

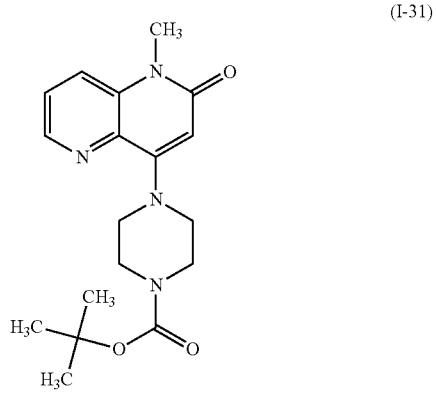 [SMILES: Cn1c(=O)cc(N2CCN(C(=O)OC(C)(C)C)CC2)c2ncccc21]

(I-31)

A solution was prepared by dissolving 4-chloro-1-methyl-1,5-naphthyridin-2(1H)-one (15 mg, 0.077 mmol) in DMF (0.7 mL). Next, 1-BOC-piperazine (27.7 mg, 0.149 mmol) was added and dissolved with stirring, followed by the addition of potassium carbonate (19.2 mg, 0.139 mmol). The reaction vessel was capped under a nitrogen atmosphere. The reaction mixture was heated at 85° C. for 16.5 hrs. LCMS analysis of the reaction mixture indicated 45% conversion to product. The reaction mixture was again placed under a nitrogen atmosphere and heated to 85° C. for 71 hours. The reaction mixture was diluted with 1 mL of acetonitrile and filtered through a syringe filter. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 25-65% B over 15 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. (Purity: 99.1%; RT: 1.61; Obs. Adducts: [M+H]; Obs. Masses: 345.18). Injection 2 conditions: Column: Waters Acquity UPLC BEH C18, 2.1×50 mm, 1.7 μm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. (Purity: 99.2%; RT: 1.48; Obs. Adducts: [M+H]; Obs. Masses: 345.18). Proton NMR signal intensities proximal to the water suppression frequency were affected and were uncorrected: $^1$H NMR (DMSO-d$_6$) δ 8.49 (dd, J=4.2, 1.3 Hz, 1H), 7.86-8.04 (m, 1H), 7.61 (dd, J=8.6, 4.2 Hz, 1H), 6.04 (s, 1H), 3.53 (s, 4H), 1.42 (s, 9H).

Intermediate 32

4-(4-(bis(4-fluorophenyl)methyl)piperazin-1-yl)-1-methyl-1,5-naphthyridin-2(1H)-one

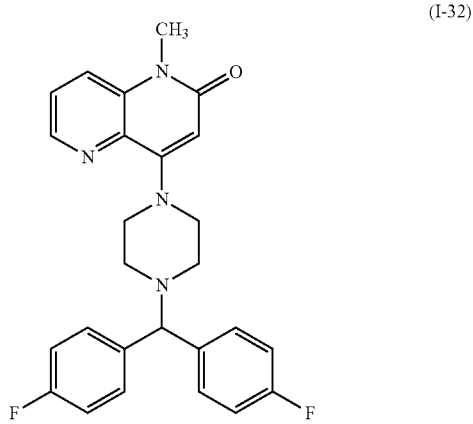 [SMILES: Cn1c(=O)cc(N2CCN(C(c3ccc(F)cc3)c3ccc(F)cc3)CC2)c2ncccc21]

(I-32)

A solution was prepared by dissolving 4-chloro-1-methyl-1,5-naphthyridin-2(1H)-one (12.3 mg, 0.063 mmol) in DMF (632). Next, 1-(4,4-difluorobenzhydryl) piperazine (22.9 mg, 0.079 mmol) and potassium carbonate (18.7 mg, 0.135 mmol) were added. The reaction mixture was placed under a nitrogen atmosphere and heated at 80° C. for 18 hours. HPLC analysis indicated approximate 50% conversion to product. To the reaction mixture was added potassium carbonate (8.2 mg, 0.059 mmol). The reaction mixture was capped under nitrogen and heated at 85° C. for 19 hours. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate: Gradient: 50-90% B over 15 minutes, then a 5 minute hold at 100% B; Flow: 20 mL/min. Fractions containing the product were combined and dried via centrifugal evaporation. The yield of the product was 21.1 mg, and its estimated purity by LCMS analysis was 100%. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. LCMS: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Retention Time=1.42 min.; Obs. Adducts: [M+H]; Obs. Masses: 447.1. LCMS: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Retention Time=2.25 min.; Obs. Adducts: [M+H]; Obs. Masses: 447.1. Proton NMR signal intensities proximal to the water suppression frequency were affected and were uncorrected: $^1$H NMR (DMSO-$d_6$) δ 8.42 (d, J=2.9 Hz, 1H), 7.91 (d, J=8.8 Hz, 1H), 7.57 (dd, J=8.8, 4.4 Hz, 1H), 7.48 (dd, J=8.6, 5.7 Hz, 4H), 7.14 (t, J=8.8 Hz, 4H), 5.98 (s, 1H), 4.47 (s, 1H), 3.51 (s, 2H).

Intermediate 33

Ethyl 6-bromo-3-(N-methylacetamido)picolinate

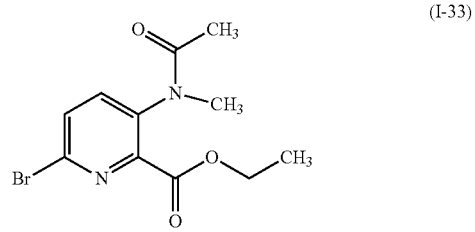 [SMILES: CCOC(=O)c1nc(Br)ccc1N(C)C(C)=O]

(I-33)

A solution was prepared by dissolving ethyl 3-acetamido-6-bromopicolinate (5 g, 17.41 mmol) into DMF (100 mL). Next, cesium carbonate (8.15 g, 25.01 mmol) and methyl iodide (1.75 mmol, 28.0 mmol) were added. The reaction mixture was placed under a nitrogen atmosphere and stirred at room temperature for 2 hours and 40 minutes. Solvent was removed in vacuo using a rotary evaporator/vacuum pump combination. Ethyl acetate and DCM were added to the reaction residue along with chloroform and toluene. The mixture was filtered through a celite pad to remove salts. Solvents were again removed in vacuo using a rotary evaporator. The reaction residue was again dissolved in chloroform and toluene and filtered through a celite bed to remove trace insolubles still present. Removal of solvents in vacuo yielded 5.35 g of the product as an orange oil. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 μL. Retention Time=1.07 min.; Obs. Adducts: [M+H]; Obs. Masses: 301.1. Proton NMR shows characteristics of restricted rotation (rotamers); 1H NMR (500 MHz, CHLOROFORM-d) δ 7.72 (d, J=8.4 Hz, 0.8H), 7.66 (d, J=8.4 Hz, 0.2H), 7.51 (d, J=8.4 Hz, 0.8H), 7.45 (d, J=8.4 Hz, 0.2H), 4.50-4.36 (m, 2.0H), 3.37 (s, 0.6H), 3.19 (s, 2.4H), 2.24 (s, 0.6H), 1.82 (s, 2.5H), 1.43-1.36 (m, 3.1H).

Intermediate 34

Ethyl 6-methyl-3-(N-methylacetamido)picolinate

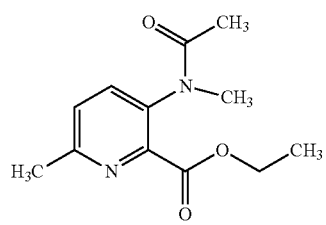

(I-34)

Ethyl 6-bromo-3-(N-methylacetamido)picolinate (3.01 g, 10.00 mmol) was dissolved in THF (100 mL). The solution was sparged with nitrogen for 20 min, followed by the addition of tetrakis(triphenylphosphine)palladium(0) (235 mg, 0.203 mmol). The reaction headspace was flushed with nitrogen and dimethylzinc (12 mL, 12.00 mmol) was added via syringe. The reaction mixture was heated under a nitrogen atmosphere at 70° C. for 2 hours. The reaction mixture was cooled and transferred to a 500 mL Erlenmeyer flask containing a magnetic stir bar. Ethyl acetate was added and a saturated solution of sodium bicarbonate was added slowly with stirring. The organic phase was separated from the aqueous phase, then washed with brine, and dried over magnesium sulfate. The drying agent was filtered from the organic extract and the solvent removed in vacuo using a rotary evaporator to give 2.23 g of product as a yellow oil. The crude product was purified on a 80 g Isco Redi-sep silica gel cartridge eluting with a gradient of 20%-50% ethyl acetate in dichloromethane. Fractions containing product by TLC analysis were combined and the solvent removed in vacuo to give 1.937 g of the title compound as a pale yellow oil. HPLC purity of this product was approximately 92% by UV at 220 nm. An analytically pure sample was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 5-45% B over 20 minutes, then a 5 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 237.17; Retention Time: 1.05 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 237.18; Retention Time: 1.01 min. $^1$H NMR (400 MHz, DMSO-$d_6$) δ 7.87 (d, J=8.1 Hz, 0.8H), 7.68 (d, J=8.1 Hz, 0.2H), 7.56 (d, J=8.1 Hz, 0.8H), 7.49 (d, J=8.3 Hz, 0.2H), 4.31 (q, J=7.1 Hz, 1.6H), 4.24 (q, J=7.1 Hz, 0.4H), 3.29 (s, 0.6H), 3.04 (s, 2.4H), 2.55 (s, 2.4H), 2.12 (s, 0.6H), 1.66 (s, 2.4H), 1.27 (t, J=7.1 Hz, 3.0H).

Intermediate 35

Ethyl 6-methyl-3-(methylamino)picolinate

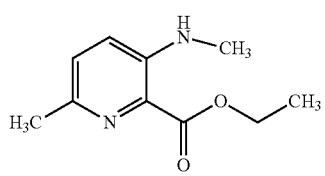

(I-35)

To a solution of ethyl 6-methyl-3-(N-methylacetamido)picolinate (1 g, 3.68 mmol) in ethanol (20 mL) was added HCl (1.841 mL, 22.09 mmol). The reaction mixture was stirred at 80° C. for 6 h. The solvents was removed under vacuum, the residue obtained was dissolved in water (10 ml), made basic with 10% NaHCO$_3$ (20 mL) and extracted with DCM (3×20 mL). The combined organic layers were washed with 10% NaHCO$_3$ (20 mL), water (20 mL), and brine (20 mL). The organic portion was dried over sodium sulphate and concentrated to afford the crude product (0.8 g). The crude product was purified by chromatography on a g silica gel column with 40% ethyl acetate in petroleum ether to isolate the desired product (0.5 g, 2.55 mmol, 69.2% yield). $^1$H NMR (Acetonitrile-$d_3$) δ 7.38 (br s, 1H), 7.23 (d, J=8.7 Hz, 1H), 7.11 (d, J=8.7 Hz, 1H), 4.32 (q, J=7.1 Hz, 2H), 2.87 (d, J=5.2 Hz, 3H), 2.36 (s, 3H), 134 (t, J=7.1 Hz, 3H).

Intermediate 36

1,6-Dimethyl-2,4-dioxo-1,2,3,4-tetrahydro-1,5-naphthyridine-3-carbonitrile

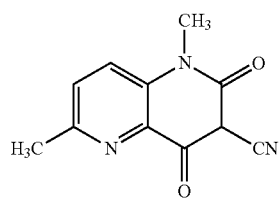

(I-36)

To a solution of ethyl 6-methyl-3-(methylamino)picolinate (3.0 g, 15.45 mmol), 2-cyanoacetic acid (1.445 g, 16.99 mmol) and PYBROP (7.20 g, 15.45 mmol) in dichloromethane (77 mL) was added triethylamine (5.40 mL, 30.9 mmol). The reaction mixture was stirred overnight. The reaction mixture was washed with aqueous saturated NaHCO$_3$ solution (30 mL) followed by brine (30 mL), and the organic layer was dried (sodium sulfate), filtered, and evaporated to obtain the crude product. The crude product was dissolved in a minimal amount of dichloromethane and purified by flash silica gel chromatography. The chromatography column was preconditioned with 1% TEA/5% EA/94% Hexanes 94:5:1 (v/v) hexane/ethyl acetate and 1% TEA, and the pure compound was eluted following a stepwise gradient of 20-100% ethylacetate/hexane/1% TEA and then 0-20% (v/v) methanol in dichloromethane with 1% TEA. The pure fractions of the product were combined, concentrated on a rotatory evaporator, and dried under high vacuum to obtain a pale yellow solid (6 g). The solid was redissolved in DCM and washed by 1 N NaOH. After shaking, white solid precipitated from the mixture. The solid was filtered from the mixture and dried under vacuum to give 1,6-dimethyl-2,4-dioxo-1,2,3,4-tetrahydro-1,5-naphthyridine-3-carbonitrile (3.1 g, 14.40 mmol, 93% yield). LCMS: Method S1; RT 1.027, M$^+$ 216. $^1$H NMR (500 MHz, methanols-d$_4$) δ 7.87-7.73 (m, 1H), 7.47 (d, J=8.7 Hz, 1H), 3.56 (s, 3H), 2.61 (s, 3H).

Intermediate 37

4-Chloro-1,6-dimethyl-2-oxo-1,2-dihydro-1,5-naphthyridine-3-carbonitrile

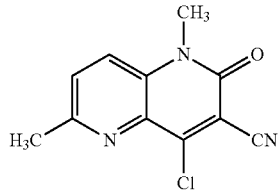

(I-37)

A suspension of 4-hydroxy-1,6-dimethyl-2-oxo-1,2-dihydro-1,5-naphthyridine-3-carbonitrile (600 mg, 2.79 mmol) was dissolved in POCl$_3$ (2.86 mL, 30.7 mmol). The reaction mixture was stirred at 120° C. for 2 h. The reaction mixture was cooled to room temperature and poured into ice cold solution of 1 N NaOH (20 mL). The solid separated was filtered and washed with ether and dried under vacuum overnight to afford 4-chloro-1,6-dimethyl-2-oxo-1,2-dihydro-1,5-naphthyridine-3-carbonitrile (400 ng, 1.712 mmol, 61.4% yield). LCMS: Method S1; RT 1.274, M$^+$ 262. $^1$H NMR (500 MHz, DMSO-d$_6$) δ 8.25-8.04 (m, 1H), 7.77 (d, J=8.7 Hz, 1H), 3.64 (s, 3H), 2.63 (s, 3H).

Intermediate 38

4-hydroxy-1,6-dimethyl-1,5-naphthyridin-2(1H)-one

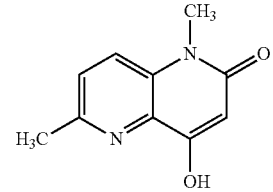

(I-38)

To a 1.0 M THF solution of NaHMDS (9 mL, 9.00 mmol) at −78° C. under a nitrogen atmosphere was added a solution of ethyl 6-methyl-3-(N-methylacetamido) picolinate (1.825 g, 7.51 mmol) in THF (60 mL) dropwise via cannula over 50 minutes with magnetic stirring. The reaction mixture was stirred at −78° C. for another 70 minutes, then the cold bath was removed, and the reaction mixture was warmed to room temperature over 30 minutes. Ethyl acetate was added to the reaction mixture followed by 45 mL of deionized water. The mixture was transferred to a separatory funnel, agitated and the aqueous layer partitioned to an Erlenmeyer flask. The aqueous layer was acidified with stirring by the addition of 1.0 N hydrochloric acid (9.0 mL, 9.00 mmol). The aqueous solution was stirred for several minutes to allow for precipitation of the product as an orange solid from the aqueous mixture with a pH measured to be 4 by pH strip. The orange product was filtered off using a Buchner funnel rinsing with a very small amount of deionized water. The product was dried in vacuo at room temperature to give 840 mg of the title compound as an orange solid. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 μL. Retention Time 1.12 min.; Obs. Adducts: [M+H]; Obs. Masses: 191.2. $^1$H NMR (DMSO-d$_6$) δ 10.67 (br. s., 1H), 7.86 (d, J=8.7 Hz, 1H), 7.53 (d, J=8.8 Hz, 1H), 6.03 (s, 1H), 3.51 (s, 3H), 2.57 (s, 3H).

Intermediate 39

4-chloro-1,6-dimethyl-1,5-naphthyridin-2(1H)-one

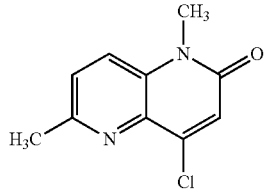

(I-39)

In a 2 dram pressure vial fitted with a pressure cap 4-hydroxy-1,6-dimethyl-1,5-naphthyridin-2(1H)-one (54.5 mg, 0.287 mmol) was suspended in acetonitrile (1.3 mL). Next, POCl$_3$ (0.3 mL, 3.22 mmol) and a magnetic stir bar were added. The vial was capped under a nitrogen atmosphere and the reaction mixture was heated at 80° C. for 3 hours. Analysis of reaction by LCMS indicates approximately 40% conversion. The reaction mixture was heated under nitrogen at 80° C. for an additional 2 hours. The reaction was quenched by the addition of ice and then ethyl acetate. The mixture was transferred to a separatory funnel, additional ethyl acetate was added, and washed with 1.5M dipotassium phosphate. The aqueous layer was extracted with ethyl acetate. The organic extracts were combined and washed sequentially with a small amount of 1.5 M dipotassium phosphate and brine. The organic extract was dried over magnesium sulfate, then the drying agent was filtered off, and solvent was removed from the filtrate in vacuo using a rotary evaporator to afford 51 mg of the title compound as a beige solid. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 μL. Retention Time=0.99 min.; Obs. Adducts: [M+H]; Obs. Masses: 209.3. $^1$H NMR (CHLOROFORM-d) δ 7.64 (d, J=8.7 Hz, 1H), 7.43 (d, J=8.7 Hz, 1H), 7.13 (s, 1H), 3.69 (s, 3H), 2.71 (s, 3H).

Intermediate 40

4-(4-(bis(4-fluorophenyl)methyl)piperazin-1-yl)-1,6-dimethyl-1,5-naphthyridin-2(1H)-one

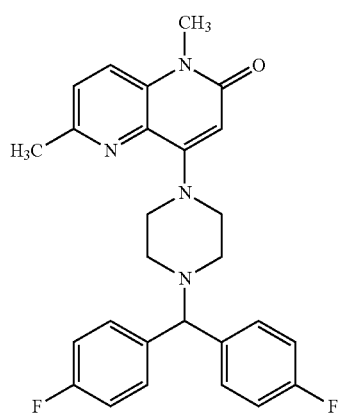

(I-40)

In a 20 mL pressure vial charged with 2nd generation RuPhos precatalyst (27.9 mg, 0.036 mmol), 4-chloro-1,6-dimethyl-1,5-naphthyridin-2(1H)-one (150 mg, 0.719 mmol), 1-(4,4-difluorobenzhydryl)piperazine (249 mg, 0.863 mmol), and cesium carbonate (703 mg, 2.157 mmol), 7.1 mL of solvent (DMA/t-BuOH; 1:4) was added. The reaction vial was capped under a nitrogen atmosphere and immersed in an oil bath at 70° C. The bath temperature was raised to 90° C. The reaction mixture was heated at 90° C. for 18 hours. Volatiles were removed from the reaction mixture in vacuo using a rotary evaporator/vacuum pump combination. Chloroform and dichloromethane were added to the reaction mixture and the mixture was heated with vortex mixing before being filtered through a 0.45 μm Whatman autovial filter with a celite prefilter plug. Removal of solvent from the filtrate afforded the crude product as an orange oil. The crude product was purified using silica gel column chromatography eluting with 15% ethyl acetate in dichloromethane. Pure fractions as analyzed by TLC were combined and solvent removed in vacuo using a rotary evaporator gave 290 mg of product as an orange oil. Removal of solvent in vacuo provided the product (217 mg) as a pale yellow foam. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 mini hold at 100% B; Flow: 1 mL/min; Detection: MS and UV (220 nm). Injection volume: 1 μL. Retention Time=1.18 min.; Obs. Adducts: [M+H]; Obs. Masses: 4613. LCMS; Column: Phenomenex Luna C18, 2 mm×50 mm, 3 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient 0% B to 100% B over 4 minutes, then 1 min hold at 100% B; Flow: 0.8 mL/min; Detection: MS and UV (220 nm). Injection volume: 3 μL. Retention Time=3.61 min.; Obs. Adducts: [M+H]; Obs. Masses: 461.2. $^1$H NMR (Chloroform-d) δ 7.56 (d, J=8.7 Hz, 1H), 7.38-7.43 (m, 4H), 7.29 (d, J=8.7 Hz, 1H), 6.97-7.03 (m, 4H), 6.16 (s, 1H), 4.31 (s, 1H), 3.62 (s, 3H), 3.57 (br. s., 4H), 2.63 (t, J=4.8 Hz, 4H), 2.57 (s, 3H).

Intermediate 41 tert-butyl 4-(1,6-dimethyl-2-oxo-1,2-dihydro-1,5-naphthyridin-4-yl)piperazine-1-carboxylate

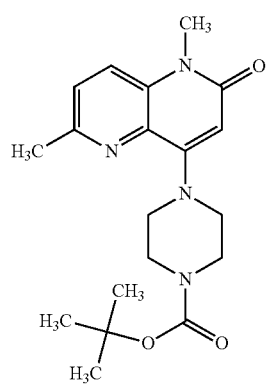

(I-41)

In a 30 mL vial charged with 2nd generation RuPhos precatalyst (46.5 mg, 0.060 mmol), 1-BOC-piperazine (268 mg, 1.438 mmol) and 4-chloro-1,6-dimethyl-1,5-naphthyridin-2(1H)-one (250 mg, 1.198 mol), was added cesium carbonate (1171 mg, 3.59 mmol) and a magnetic stir bar. To the reaction mixture was added 12 mL of 4/1 mixture of tert-butanol/dimethyl acetamide. The vial w as capped under a nitrogen atmosphere and immersed in an oil bath (75° C.). The bath temperature was raised to 90° C. The reaction mixture was heated at 90° C. for 19 hours. The reaction mixture was cooled and filtered through a celite plug to remove salts and rinsed with dichloromethane. Volatiles were removed from the filtrate in vacuo using a rotary evaporator to afford the crude product as an orange solid. The crude reaction mixture was subject to silica gel chromatography eluting with 70% ethyl acetate in dichloromethane. Product fractions were combined based on TLC analysis and solvent was removed in vacuo using a rotary evaporator to afford 304 mg as an orange solid. LCMS analysis of the chromatographed product indicated 70% purity. An analytical pure sample was prepared by further purification employing preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 0-65% B over 20 minutes, then a 4 minute hold at 100% B; Flow: 20 mL/min. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Retention Time=1.69 min.; Obs. Adducts: [M+H]; Obs. Masses: 359.2. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Retention Time=1.68 min.; Obs. Adducts: [M+H]; Obs. Masses: 359.2. Proton NMR signal intensities proximal to the water suppression frequency are affected and are uncorrected: ¹H NMR (DMSO-d₆) δ 7.84 (d, J=8.8 Hz, 1H), 7.47 (d, J=8.4 Hz, 1H), 5.99 (s, 1H), 3.48-3.57 (m, 4H), 3.41-3.47 (m, 1H), 2.54 (s, 3H), 1.43 (s, 91H). The remainder of the product mixture was subject to bromination and purified at that stage.

Intermediate 42 tert-butyl 4-(3-bromo-1,6-dimethyl-2-oxo-1,2-dihydro-1,5-naphthyridin-4-yl)piperazine-1-carboxylate

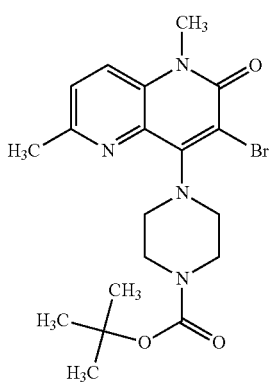

(I-42)

A solution was prepared by dissolving tert-butyl 4-(1,6-dimethyl-2-oxo-1,2-dihydro-1,5-naphthyridin-4-yl)piperazine-1-carboxylate (575 mg, 1.364 mmol) in DMF (12 mL). The reaction mixture was cooled to 0° C. under a nitrogen atmosphere, NBS (270 mg, 1.517 mmol) was added, and the reaction mixture was stirred at 0° C. for 2 hours. A small amount of saturated sodium bicarbonate solution was added to the reaction mixture and the mixture was stirred for several minutes before solvents/volatiles were removed using rotary evaporator/vacuum pump combination. The reaction residue was partitioned between ethyl acetate and 1.5 M dipotassium phosphate. The organic extract was sequentially washed with 1.5 M dipotassium phosphate solution and brine. The organic extract was dried over magnesium sulfate, filtered, and solvent was removed from the filtrate using a rotary evaporator. The crude product was purified on a silica gel column eluting with 15% ethyl acetate in dichloromethane. Pure product fractions by TLC analysis were combined and the solvents were removed in vacuo using a rotary evaporator providing 611 mg of the title compound as a pale yellow sold. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 1.5 minutes, then 0.5 min hold at 100% B; Flow: 1 mL/min; Detection: MS and UV (220 nm). Injection volume: 1 μL. Retention Time=1.44 min.; Obs. Adducts: [M+H]; Obs. Masses: 437.2. ¹H NMR (CHLOROFORM-d) δ 7.57 (d, J=8.7 Hz, 1H), 7.33 (d, J=8.7 Hz, 1H), 3.73 (s, 3H), 3.64-3.70 (m, 4H), 3.60 (br s, 4H), 2.62 (s, 3H), 1.52 (s, 9H).

Intermediate 43

3-bromo-1,6-dimethyl-4-(piperazin-1-yl)-1,5-naphthyridin-2(1H)-one, TFA

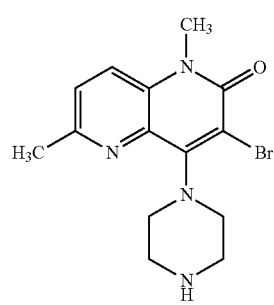

(I-43)

A solution was prepared by dissolving tert-butyl 4-(3-bromo-1,6-dimethyl-2-oxo-1,2-dihydro-1,5-naphthyridin-4-yl)piperazine-1-carboxylate (572 mg, 1.308 mmol) in dichloromethane (6 mL) and then adding TFA (6.00 mL). The reaction mixture was placed under a nitrogen atmosphere and stirred at room temperature for 1.5 hours. Volatiles were removed from the using a rotary evaporator. The reaction product was redissolved in DCM and volatiles were removed in vacuo several times to remove excess TFA. The product (1.086 g) was obtained as an orange oil having a mass indicating 4.4 equivalents of TFA. LCMS; Column: Phenomenex Luna C18, 2 mm×50 mm, 3 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient 0% B to 100% B over 4 minutes, then 1 min hold at 100% B; Flow: 0.8 mL/min; Detection: MS and UV (220 nm). Injection volume: 3 μL. Retention Time 1.88 min.; Obs. Adducts: [M+H]; Obs. Masses: 337.0

Intermediate 44

Ethyl 6-bromo-3-(2-cyanoacetamido)picolinate

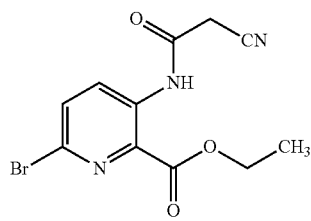

(I-44)

In a 25 mL round bottom flask charged with ethyl 3-amino-6-bromopicolinate (1.0 g, 4.08 mmol) and cyanoacetic acid (0.417 g, 4.90 mmol), DCM (14 mL) and N,N-dimethylaniline (0.622 mL, 5.30 mmol) were added. The flask was capped and cooled to 0° C., then EDC (1.172 g, 6.11 mmol) was added. The reaction mixture was stirred at 0° C. for 10 minutes, then warmed to room temperature and stirred for 2.5 hours. The reaction mixture was transferred to a separatory funnel, diluted with dichloromethane, and washed sequentially with 1.0 N hydrochloric acid (3×)

and brine (1×). The organic extract was dried over sodium sulfate, filtered, and solvent was removed from the filtrate using a rotary evaporator to give 1.177 g of the title compound as a beige solid. LCMS; Column: Waters Acquity BEH C18 2.1 mm×50 mm, 1.7 μm particles; Mobile Phase A: 100% water with 0.05% TFA; Mobile Phase B: 100% acetonitrile with 0.05% TFA; Temperature: 40° C.; Gradient 2% B to 98% B over 1.5 minutes, then 0.5 min hold at 98% B; Flow: 0.8 mL/min; Detection: MS and UV (220 nm). Injection volume: 3 μL. Results: Retention Time=0.95 min.; Obs. Adducts: [M+H]; Obs. Masses: 312.0. $^1$H NMR (500 MHz, DMSO-d$_6$) δ 10.67 (s, 1H), 8.23 (d, J=8.7 Hz, 1H), 7.89 (d, J=8.7 Hz, 1H), 4.34 (q, =7.1 Hz, 2H), 4.06 (s, 2H), 1.33 (t, J=7.2 Hz, 3H).

Intermediate 45

6-bromo-4-hydroxy-2-oxo-1,2-dihydro-1,5-naphthyridine-3-carbonitrile

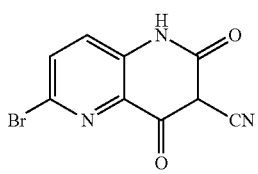

(I-45)

A solution was prepared by dissolving ethyl 6-bromo-3-(2-cyanoacetamido) picolinate (1.091 g, 3.50 mmol) in anhydrous tetrahydrofuran (35.0 mL). The reaction solution was slightly heterogeneous. To the reaction solution at room temperature was added a solution of KHMDS (3.7 mL, 3.70 mmol) in THF (1.0 M). The reaction mixture was stirred at room temperature for 1.5 hours. Next, KHMDS (0.2 mL, 0.200 mmol) was added and the reaction mixture was stirred at room temperature for several of minutes. Hydrochloric acid (4.2 mL, 4.20 mmol) was added to resulting in a pH in the range of 7-8 from pH strips, followed by the addition of 2 nL of 1 N HCl. The mixture was swirled and volatiles were removed in vacuo using a rotary evaporator/vacuum pump combination. The solid crude material was suspended in 20 mL of deionized water and cooled in an ice bath before filtering off the precipitate using a Buchner funnel. The material was rinsed with cold water which slowly percolated through the filter cake. The product was dried in vacuo at room temperature. The proton NMR in DMSO-d$_6$ was consistent with the product but showed the presence of ammonium chloride. The material was resuspended in 20 mL of 1 N hydrochloric acid and filtered through a Buchner funnel. The filter cake was rinsed with 1 N hydrochloric acid and water. The product was dried to afford 773 mg of the title compound as a light beige solid. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 μL. Retention Time 0.62 min.; Obs. Adducts: [M+H]; Obs. Masses: 266.0. $^1$H NMR (500 MHz, DMSO-d$_6$) δ 11.90 (br. s., 1H), 7.84 (d, J=8.7 Hz, 1H), 7.62 (d, J=8.8 Hz, 1H).

Intermediate 46

6-bromo-4-hydroxy-2-oxo-1-(prop-2-yn-1-yl)-1,2-dihydro-1,5-naphthyridine-3-carbonitrile

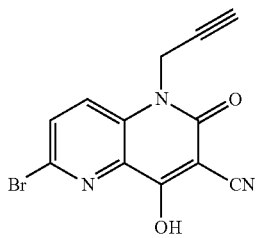

(I-46)

A solution, prepared by dissolving 6-bromo-4-hydroxy-2-oxo-1,2-dihydro-1,5-naphthyridine-3-carbonitrile (704 mg, 2.65 mmol) in DMF (24 mL), was cooled to 0° C. under a nitrogen atmosphere. Sodium hydride (60% wt in mineral oil) (270 mg, 6.75 mmol) was added as one addition. The reaction mixture was placed under a nitrogen atmosphere and stirred for 10 minutes, then removed from the ice bath, and allowed to warm to room temperature over 35 minutes. Propargyl bromide (80% in toluene) (0.737 mL, 6.62 mmol) was added and the reaction mixture was stirred at room temperature for 1 hour. Acetic acid (0.8 mL, 13.97 mmol) was added and volatiles were removed from the reaction mixture using a rotary evaporator. The crude reaction product was dried in vacuo for approximately 2 hours at room temperature to afford a brown oily residue. To the crude reaction residue, 12 mL of 1 N hydrochloric acid was added, and the mixture was swirled and briefly ultrasonicate. The mixture was cooled in an ice bath, then the product was filtered using a Buchner funnel and rinsed with 12 mL of 1 N hydrochloric acid. The product was dried in vacuo at room temperature gave 879 mg of the title compound as a tan solid. The proton NMR was consistent with the desired product. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 am). Injection volume: 1 μL. Retention Time=0.91 min.; Obs. Adducts: [M+H]; Obs. Masses: 304.0. LCMS; Column: Phenomenex Luna C18, 2 mm×50 mm, 3 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient 0% B to 100% B over 4 minutes, then 1 min hold at 100% B; Flow: 0.8 mL/min; Detection: MS and UV (220 nm). Injection volume: 5 μL. Retention Time=1.48 min.; Obs. Adducts: [M+H]; Obs. Masses: 303.8. $^1$H NMR (DMSO-d$_6$) δ 7.94-8.02 (m, 2H), 5.00 (d, J=2.4 Hz, 2H), 3.33 (t, J=2.4 Hz, 1H).

Intermediate 47

6-bromo-4-chloro-2-oxo-1-(prop-2-yn-1-yl)-1,2-dihydro-1,5-naphthyridine-3-carbonitrile

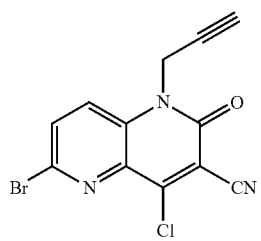

(I-47)

A suspension was prepared by adding 6-bromo-4-hydroxy-2-oxo-1-(prop-2-yn-1-yl)-1,2-dihydro-1,5-naphthyridine-3-carbonitrile (874 mg 2.87 mmol) to acetonitrile (29 ml). Next, DIEA (3.1 mL, 17.75 mmol) was added and the reaction mixture was stirred for a few minutes to ensure dissolution. Phosphorous oxychloride (POCl$_3$) (1.1 mL, 11.80 mmol) and benzyltriethylammonium chloride (790 mg, 3.47 mmol) were added to the reaction mixture. The reaction mixture was capped under a nitrogen atmosphere and stirred at room temperature for 19 hours. Volatiles were removed from the reaction mixture in vacuo using a rotary evaporator. Ice was added to the reaction residue, then dichloromethane, and the mixture transferred to a separatory funnel. An aqueous solution of 1.5 M dipotassium phosphate was added, the phases were separated, and the organic extract was washed with 1.5 M dipotassium phosphate. The aqueous washes were combined and extracted with dichloromethane. The combined organic extracts were sequentially washed with 1.5 M dipotassium phosphate and brine. The organic extract was dried over sodium sulfate, and the drying agent filtered off. Volatiles were removed from the filtrate in vacuo using a rotary evaporator to afford a sticky brown solid. The crude product was purified using normal phase silica gel chromatography eluting the mixture with dichloromethane. Pure product fractions by TLC were combined and the solvent removed in vacuo using a rotary evaporator to give 652 mg of the title compound as a pale yellow solid. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 μL. Retention Time=1.30 min.; Obs. Adducts: [M+H]; Obs. Masses: 321.95. $^1$H NMR (CHLOROFORM-d) δ 7.76-7.89 (m, 2H), 5.08 (d, J=2.5 Hz, 2H), 2.39 (t, J=2.5 Hz, 1H).

Intermediate 48 tert-butyl 4-(6-bromo-3-cyano-2-oxo-1-(prop-2-yn-1-yl)-1,2-dihydro-1,5-naphthyridin-4-yl)piperazine-1-carboxylate

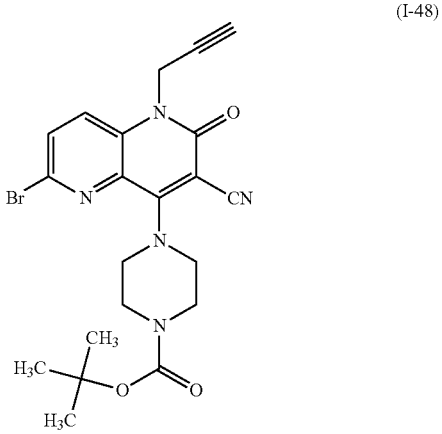 [SMILES: C#CCn1c(=O)c(C#N)c(N2CCN(C(=O)OC(C)(C)C)CC2)c2nc(Br)ccc21]

(I-48)

A solution was prepared by dissolving 6-bromo-4-chloro-2-oxo-1-(prop-2-yn-1-yl)-1,2-dihydro-1,5-naphthyridine-3-carbonitrile (502 mg, 1.556 mmol) in DMF (15 mL). Next, 1-BOC-piperazine (296 mg, 1.588 mmol) was added followed by the addition of potassium carbonate (323 ng, 2.335 mmol). The reaction mixture was stirred at room temperature under a nitrogen atmosphere for 2 hours. DMF was removed in vacuo using a rotary evaporator and vacuum pump combination. The reaction residue was partitioned between ethyl acetate and water. THF was added to improve solubility. An aqueous solution of 1.5 M dipotassium phosphate was added to effect better phase separation. The organic extract was washed sequentially with 1.5 M dipotassium phosphate and brine. The organic phase was dried over magnesium sulfate and filtered. Solvent was removed in vacuo using a rotary evaporator. The product was dried in vacuo at room temperature to give the title compound as a yellow greenish solid. LCMS; Column: Phenomenex LUNA C18, 2 mm×50 mm, 3 μm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. Retention Time=3.10 min.; Obs. Adducts: [M+H]; Obs. Masses: 471.9. $^1$H NMR (CHLOROFORM-d) δ 7.64-7.77 (m, 2H), 5.01 (d, J=2.4 Hz, 2H), 3.93 (br. s., 4H), 3.6.

79

Intermediate 49

6-bromo-2-oxo-4-(piperazin-1-yl)-1-(prop-2-yn-1-yl)-1,2-dihydro-1,5-naphthyridine-3-carbonitrile

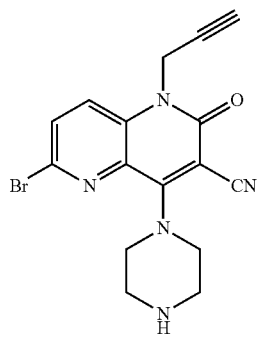

(I-49)

A solution was prepared by dissolving tert-butyl 4-(6-bromo-3-cyano-2-oxo-1-(prop-2-yn-1-yl)-1,2-dihydro-1,5-naphthyridin-4-yl)piperazine-1-carboxylate and tetrahydrofuran (25 mg, 0.052 mmol) in DCM (260 µl). Next, TFA (260 µl) was added. The reaction mixture was placed under a nitrogen atmosphere and stirred at room temperature for 1.5 hours. Volatiles were removed from the reaction mixture in vacuo using a rotary evaporator. The crude reaction mixture was dissolved in DMF/acetonitrile. The crude material was purified via preparative LC/MS with the following conditions: Column: XBridge C18, 19×200 mm, 5 µm particles; Mobile Phase A: 5:95 acetonitrile: water with 10 mM ammonium acetate; Mobile Phase B: 95:5 acetonitrile:water with 10 mM ammonium acetate; Gradient: 10-50% B over 15 minutes, then a 5 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 371.98; Retention Time: 1.09 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 mi, then a 0.75 min hold at 100% B; Flow: 1 mL/min; Detection: MS and UV (220 nm). Injection 2 results: Purity: 100.0%; Observed Mass: 371.97; Retention Time: 1.04 min. Proton NMR signal intensities proximal to the water suppression frequency were affected and were uncorrected: $^1$H NMR (DMSO-$d_6$) δ 7.85-8.05 (n 2H), 4.99 (d, J=2.6 Hz, 2H), 3.73-3.84 (n, 4H), 3.17-3.26 (m, 1H), 2.90-3.01 (m, 4l).

80

Intermediate 50 tert-butyl 4-(6-bromo-1-methyl-3-nitro-2-oxo-1,2-dihydro-1,5-naphthyridin-4-yl) piperazine-1-carboxylate

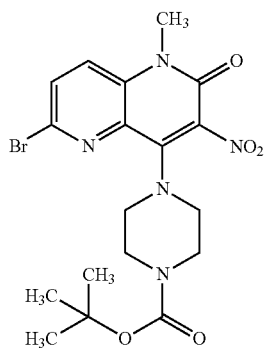

(I-50)

To a DMF (1 mL) solution of 6-bromo-4-chloro-1-methyl-3-nitro-1,5-naphthyridin-2(1H)-one (20 mg, 0.063 mmol) were added tert-butyl piperazine-1-carboxylate (11.70 mg, 0.063 mmol) and DIPEA (0.033 mL, 0.188 mmol). The reaction mixture was heated at 35° C. overnight. LC/MS analysis indicated the reaction was complete. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 40-80% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 1 results: Purity: 100%; Observed Mass: 468.0; Retention Time: 2.1 minutes. Injection 2 results: Purity: 99.1%; Observed Mass: 468.0; Retention Time: 2.1 minutes. The title compound (11.7 mg) was isolated in 39.7% yield.

Intermediate 51

6-bromo-1-methyl-3-nitro-4-(piperazin-1-yl)-1,5-naphthyridin-2(1H)-one

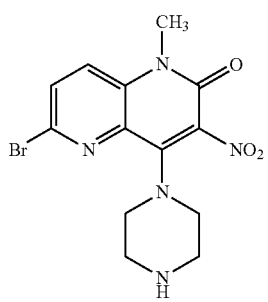

(I-51)

To a dichloromethane (2 mL) solution of tert-butyl 4-(6-bromo-1-methyl-3-nitro-2-oxo-1,2-dihydro-1,5-naphthyridin-4-yl)piperazine-1-carboxylate (10.43 mg, 0.022 mmol) was added trifluoroacetic acid (1.716 µl, 0.022 mmol) and the solution was stirred at room temperature for 2 hours. LC/MS analysis indicated the reaction was complete. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 5-40% B over 15 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 nM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 1 results: Purity: 100%; Observed Mass: 367.9; Retention Time: 1.0 minutes. Injection 2 results: Purity: 98.8%; Observed Mass: 367.9; Retention Time: 0.9 minutes. The title compound (5.2 mg) was isolated in 64.2% yield.

Intermediate 52

(1R,5S)-tert-butyl 3-(6-chloro-3-cyano-1-methyl-2-oxo-1,2-dihydro-1,5-naphthyridin-4-yl)-3,8-diazabicyclo[3.2.1]octane-8-carboxylate

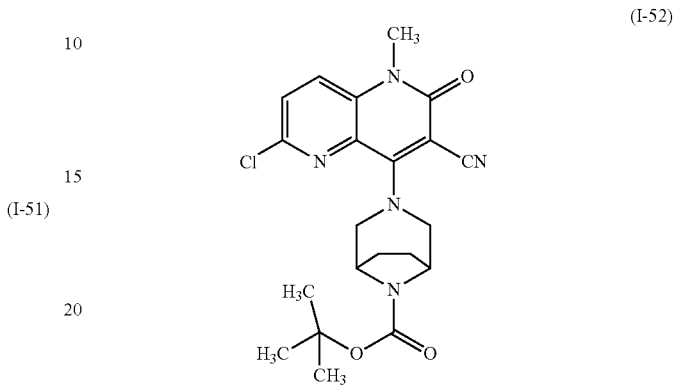

(I-52)

(1R,5S)-Tert-butyl 3,8-diazabicyclo[3.2.1]octane-8-carboxylate (137 mg, 0.645 mmol) was added to a solution of 4,6-dichloro-1-methyl-2-oxo-1,2-dihydro-1,5-naphthyridine-3-carbonitrile (164 mg, 0.645 mmol) and triethylamine (0.270 mL, 1.936 mmol) in DMF (2 mL) and the resulting mixture was stirred at room temperature overnight. LC/IS analysis indicated conversion to product with the observed mass corresponding to that of the product minus a t-butyl moiety. The crude reaction mixture was evaporated under reduced pressure and the residue was dissolved in dichloromethane and then adsorbed onto silica gel and subjected to flash chromatography using 100% ethyl acetate as eluent and silica gel as the stationary phase. Homogeneous fractions were combined and evaporated in vacuo to give 200 mg of a yellow solid. Analytical LC/MS conditions: Injection Vol 1:8; 3 µL, Start % B; 2, Final % B; 98, Gradient Time; 1.5 min, Flow Rate; 0.8 mL/min, Wavelength; 220 nm, Solvent Pair; Water/Acetonitrile/TFA, Solvent A; 100% Water/0.05% TFA. Solvent B; 100% Acetonitrile/0.05% TFA, Column; Waters Aquity BEH C18 2.1×50 mm, 1.7U MW1, Oven Temp; 40]; $R_T$: 0794 min. (M+H-boc)$^+$; 329. Purity estimated to be 77%. $^1$H NMR (500 MHz, DMSO-$d_6$) δ 8.11 (d, J=9.1 Hz, 1H), 7.84 (d, J=9.0 Hz, 1H), 4.25 (br. s., 2H), 4.12 (s, 2H), 3.61-3.47 (m, 4H), 2.22 (d, J=7.6 Hz, 2H), 1.88-1.80 (m, 2H), 1.46 (s, 9H). Next, 10 mg of this material was purified via preparative LC/MS with the following conditions: Column: XBridge C18, 19×200 mm, 5 µm particles Mobile Phase A: 5:95 acetonitrile:water with 0.1% trifluoroacetic acid; Mobile Phase B: 95:5 acetonitrile:water with 0.1% trifluoroacetic acid; Gradient: 35-75% B over 15 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile: water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 1 results: Purity: 100.0% 2.04 minutes; [M+Na]; 452.06 Injection 2 results: Purity: 100.0%; 2.14 minutes; [M+Na]; 452.05.

Intermediate 53 tert-butyl 4-(6-bromo-3-cyano-1-methyl-2-oxo-1,2-dihydro-1,5-naphthyridin-4-yl) piperazine-1-carboxylate

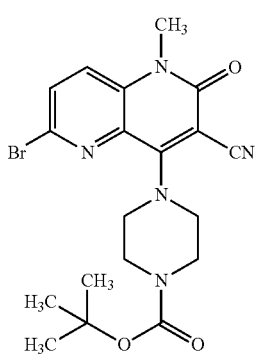

(I-53)

Tert-butyl piperazine-1-carboxylate (62.4 mg, 0.335 mmol) was added to a solution of 6-bromo-4-chloro-1-methyl-2-oxo-1,2-dihydro-1,5-naphthyridine-3-carbonitrile (100 mg, 0.335 mmol) and triethylamine (0.047 mL, 0.335 mmol) in DMF (5 mL). The resultant mixture was stirred at room temperature under nitrogen overnight. DMF was then removed under vacuum. The residue dissolved in dichlorourethane and the resultant solution was washed successively with water (ix) and then brine. The organic layer was then dried over magnesium sulfate, filtered, and evaporated under reduced pressure to give the product as a yellow/orange solid (125 mg, 79%). Analytical LC/MS conditions: Injection Vol; 3 μL, Start % B; 2, Final % B; 98, Gradient Time; 1.5 min, Flow Rate; 0.8 mL/min, Wavelength; 20 nm, Solvent Pair; Water/Acetonitrile/TFA, Solvent A; 100% Water/0.05% TFA, Solvent B: 100% Acetonitrile/0.05% TFA, Column; Waters Aquity BEH C18 2.1×50 mm, 1.7U MW1, Oven Temp; 40. LC/MS results; 1.207 min. (M-tBu)+; 391.85. $^1$H NMR (400 MHz, DMSO-d$_6$) δ 8.05-7.85 (m, 2H), 3.81 (hr. s., 4H), 3.67-3.44 (m, 7H), 1.45 (s, 9H).

Intermediate 55 tert-butyl 4-(6-cyano-1-methyl-3-nitro-2-oxo-1,2-dihydro-1,5-naphthyridin-4-yl) piperazine-1-carboxylate

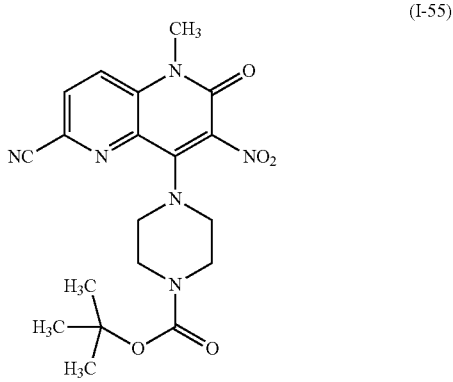 [SMILES: Cn1c(=O)c([N+](=O)[O-])c(N2CCN(C(=O)OC(C)(C)C)CC2)c2nc(C#N)ccc21]

(I-55)

To a DMF (3 mL) solution of 8-chloro-5-methyl-7-nitro-6-oxo-5,6-dihydro-1,5-naphthyridine-2-carbonitrile (270 mg, 1.020 mmol) was added Hunig's Base (0.535 mL, 3.06 mmol) followed by the addition of tert-butyl piperazine-1-carboxylate (209 mg, 1.122 mmol). The reaction mixture was shaken at room temperature for 2 hrs. LC/MS indicated the reaction was complete. The solvent was removed under vacuum. The residue was purified by eluting with 1:1 hexanes: ethyl acetate from a 40 g silica gel column. Fractions containing the title compound were combined to give a yellow solid (320 mg, 76%$_1$ yield). Analytical LC/MS conditions: Column: Phenomenex LUNA C18, 50×2, 3 μm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. Analytical LC/MS results were consistent with the title compound: 1.8 minutes, 475 (M+H), 473 (M−H).

Intermediate 56

5-methyl-7-nitro-6-oxo-8-(piperazin-1-yl)-5,6-dihydro-1,5-naphthyridine-2-carbonitrile

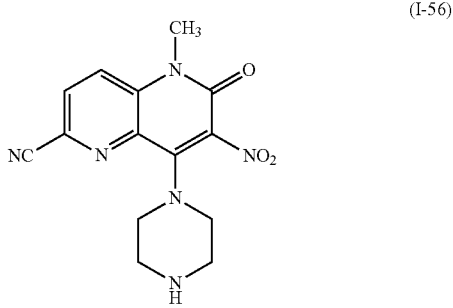 [SMILES: Cn1c(=O)c([N+](=O)[O-])c(N2CCNCC2)c2nc(C#N)ccc21]

(I-56)

To a dichloromethane (4 mL) solution of tert-butyl 4-(6-cyano-1-methyl-3-nitro-2-oxo-1,2-dihydro-1,5-naphthyridin-4-yl)piperazine-1-carboxylate (320 mg, 0.772 mmol) was added TFA (0.059 mL, 0.772 mmol) and the reaction mixture was stirred at room temperature for 2 hrs. LC/MS analysis showed that the reaction was complete. The reaction mixture was concentrated under vacuum to give a yellow solid (240 mg, 73% yield) that used without further purification. Analytical LC/MS conditions: Waters Acquity UPLC BEH C18, 2.1×50 mm, 1.7 µm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 nm. Analytical LC/MS results were consistent with the title compound: 1.0 minutes, 315 (M+H).

Intermediate 57

6-bromo-1-methyl-2,4-dioxo-1,2,3,4-tetrahydro-1,5-naphthyridine-3-carbonitrile

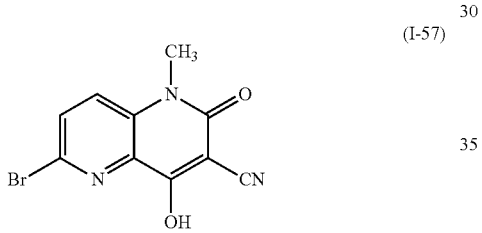

(I-57)

To a solution of 6-bromo-2,4-dioxo-1,2,3,4-tetrahydro-1,5-naphthyridine-3-carbonitrile (250 mg, 0.940 mmol) in DMF (5 mL), 60% sodium hydride (113 mg, 2.82 mmol) in mineral oil was added in portions. The reaction mixture was stirred at room temperature for 30 minutes. Iodomethane (0.176 mL, 2.82 mmol) was added and the reaction mixture was stirred at room temperature overnight. LC/MS analysis showed unreacted starting material. An equivalent of sodium hydride and iodomethane was added. The reaction mixture was stirred at room temperature for 4 hours. The reaction was then quenched by addition of water. The reaction mixture was acidified with 1 N hydrochloric acid solution to pH~3. An off-white solid was collected as final product (163 mg, 61.9% yield). Analytical LC/MS conditions: Column: Phenomenex LUNA C18, 50×2, 3 µm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. Analytical LC/MS results were consistent with the title compound: 1.9 minutes, 280, 282 (M+H).

Intermediate 58

6-methoxy-1-methyl-2,4-dioxo-1,2,3,4-tetrahydro-1,5-naphthyridine-3-carbonitrile

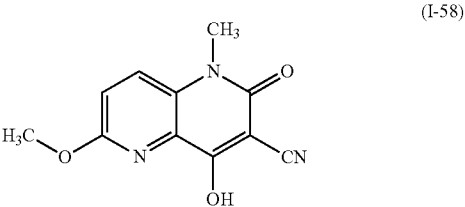 [SMILES: COc1ccc2c(n1)c(Cl)c(C#N)c(=O)n2C]

(I-58)

In a DMF (1 mL) solution, 6-bromo-1-methyl-2,4-dioxo-1,2,3,4-tetrahydro-1,5-naphthyridine-3-carbonitrile (100 mg, 0.357 mmol) was combined with sodium methoxide (0.5 N in methanol) (2.142 mL, 1.071 mmol) and the mixture was heated at 85° C. in microwave reactor for 5 hours, then at 100° C. for 2 hours. LC/MS analysis indicated the reaction was complete. The solid product (40 mg, 50% yield) was collected by filtration.

Intermediate 59

4-chloro-6-methoxy-1-methyl-2-oxo-1,2-dihydro-1,5-naphthyridine-3-carbonitrile

(I-59)

To an acetonitrile (1.5 mL) solution containing 6-methoxy-1-methyl-2,4-dioxo-1,2,3,4-tetrahydro-1,5-naphthyridine-3-carbonitrile (70 mg, 0.245 mmol) was added DIPEA (0.427 mL, 2.447 mmol) followed by the addition of phosphorous oxychloride (0.160 mL, 1.713 mmol). The mixture was stirred at room temperature for 2 hours. LC/MS analysis indicated a new peak was formed consistent with complete reaction. The volatile components were removed under vacuum. The residue was redissolved in ethyl acetate and washed with water and brine and dried over magnesium sulfate. The solvent was removed under vacuum to give a light yellow solid (40 mg, 74% yield).

Intermediate 60

1,6-Dichloro-1-methyl-2-oxo-1,2-dihydro-1,5-naphthyridine-3-carbonitrile

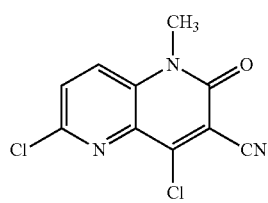
(I-60)

A 4 M solution of HCl (20 mL, 80 mmol) in dioxane was added to 6-bromo-4-chloro-1-methyl-2-oxo-1,2-dihydro-1-naphthyridine-3-carbonitrile (1 g, 3.35 mmol). The reaction mixture was heated in a seal tube at 85° C. for 4 days. The reaction mixture was concentrated and triturated with methanol. The solid was collected by filtration to give the hydrochloride salt of the title compound as a yellow solid (810 mg, 83% yield). Analytical LC/MS conditions: Column: Phenomenex LUNA C18, 2.0×50 mm, 3 μm particles; Mobile Phase A: 10:90 methanol:water with 0.100 TFA; Mobile Phase B: 90:10 methanol:water with 0.1% TFA; Gradient: 0-100% B over 4 minutes, then a 1 minute hold at 100% B; Flow: 0.8 mL/min; Detection: UV at 220 nm. LC/MS results: 2.9 min, 253.9 (M+H)+. $^1$H NMR (400 MHz, chloroform-d) δ 7.80-7.76 (m, 1H), 7.71-7.68 (m, 1H), 3.77 (s, 3H).

Intermediate 61

Tert-butyl 4-(6-bromo-3-cyano-1-methyl-2-oxo-1,2-dihydro-1,5-naphthyridin-4-yl) piperazine-1-carboxylate

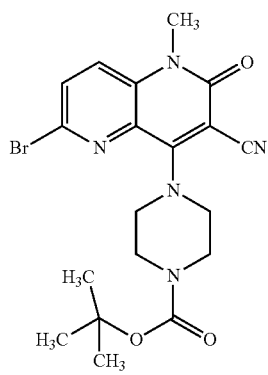
(I-61)

To a solution of 6-bromo-4-chloro-1-methyl-2-oxo-1,2-dihydro-1,5-naphthyridine-3-carbonitrile (1.2 g, 4.02 mmol) in DMF (10 mL), tert-butyl piperazine-1-carboxylate (0.824 g, 4.42 mmol) and triethylamine (1.681 mL, 12.06 mmol) were added. The reaction was quenched by the addition of 1N HCl solution. A yellow colored solid separated from solution and was collected by filtration to give the title compound (1.775 g, 98% yield). Analytical LC/MS conditions: Column: Phenomenex LUNA C18, 2.0×50 mm, 3 μm particles; Mobile Phase A: 10:90 methanol:water with 0.1% TFA; Mobile Phase B: 90:10 methanol:water with 0.1% TFA; Gradient: 0-100% B over 4 minutes, then a 1 minute hold at 100% B; Flow: 0.8 mL/min; Detection: UV at 220 nm. LC/MS results: 4.0 min, 448.0 (M+H)+. $^1$H NMR (400 MHz, chloroform-d) δ 7.67 (d, J=9.0 Hz, 1H), 7.55 (d, J=8.8 Hz, 1H), 3.93 (br s, 4H), 3.79-3.69 (m, 4H), 3.64 (s, 3H), 1.52 (s, 9H).

Intermediate 62

6-Bromo-1-methyl-2-oxo-4-(piperazin-1-yl)-1,2-dihydro-1,5-naphthyridine-3-carbonitrile

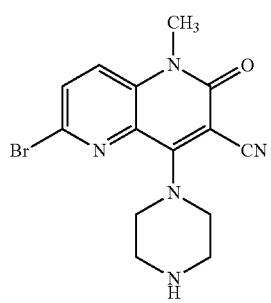
(I-62)

Trifluoroacetic acid (3 mL, 38.9 mmol) was added to a solution of tert-butyl 4-(6-bromo-3-cyano-1-methyl-2-oxo-1,2-dihydro-1,5-naphthyridin-4-yl)piperazine-1-carboxylate (700 mg, 1.561 mmol) in dichloromethane (5 mL). The reaction mixture was stirred at room temperature for 2 h, after which it was concentrated under vacuum to give the bis-TFA salt of the title compound as a brownish solid (858 mg, 1.489 mmol, 95% yield). Analytical LC/MS conditions: Column: Phenomenex LUNA C18, 2.0×50 mm, 3 μm particles; Mobile Phase A: 10:90 methanol:water with 0.1% TFA; Mobile Phase B: 90:10 methanol:water with 0.1% TFA; Gradient: 0-100% B over 4 minutes, then a 1 minute hold at 100% B; Flow: 0.8 mL/min; Detection: UV at 220 nm. LC/MS results: 1.7 min, 348.0 (MH+). $^1$H NMR (400 MHz, methanol-d$_4$) δ 7.99 (d, J=9.0 Hz, 1H), 7.88 (d, J=9.0 Hz, 1H), 4.27-4.07 (m, 4H), 3.67 (s, 3H), 3.59-3.46 (m, 4H).

Intermediate 63

5-Methyl-6-oxo-8-(piperazin-1-yl)-5,6-dihydro-1,5-naphthyridine-2,7-dicarbonitrile

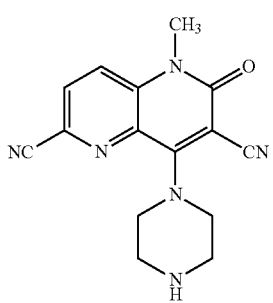
(I-63)

Tert-butyl 4-(6-bromo-3-cyano-1-methyl-2-oxo-1,2-dihydro-1,5-naphthyridin-4-yl)piperazine-1-carboxylate (100 mg, 0.223 mmol), zinc (2.92 mg, 0.045 mmol), zinc cyanide (15.72 mg, 0.134 mmol), and 1,1'-bis(diphenylphosphino)ferrocene-palladium(II)dichloride dichloromethane complex (18.22 ng, 0.022 mmol) were added to a sealed vial. The vessel was sequentially evacuated and flushed with nitrogen three times. NMP (2 mL) was added and the mixture was heated at 75° C. for 1 hour. Methanol was added and the resulting suspension was filtered and the filtrate purified by reverse phase preparative HPLC using methanol-H$_2$O-TFA as eluent. Homogeneous fractions were combined and then concentrated in vacuo overnight to give a light yellow-colored solid. This material was dissolved in dichloromethane (3 ml), and TFA (3 mL, 38.9 mmol) was added. The reaction mixture was stirred at room temperature for 3 h and was then evaporated under reduced pressure to give the bis-TFA salt of the title compound as a reddish solid (53 mg, 45.5% yield). Analytical LC/MS conditions: Phenomenex LUNA C18, 50×2, 3 µm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS results: 1.8 min, 295.1 (M+H)$^+$. $^1$H NMR (500 MHz, DMSO-d$_6$) δ 8.22 (d, J=8.8 Hz, 1H), 8.13 (d, J=9.2 Hz, 1H), 3.87-3.75 (m, 4H), 3.55 (s, 3H), 3.08-2.92 (m, 4H).

Intermediate 64

6-Chloro-1-methyl-2-oxo-4-(piperazin-1-yl)-1,2-dihydro-1,5-naphthyridine-3-carbonitrile

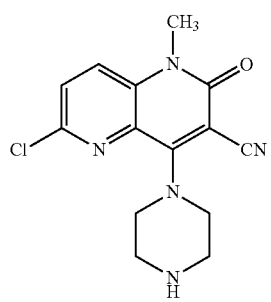

(I-64)

To a solution of 4,6-dichloro-1-methyl-2-oxo-1,2-dihydro-1,5-naphthyridine-3-carbonitrile (115 mg, 0.453 mmol) in DMF (2 mL), tert-butyl piperazine-1-carboxylate (84 ng, 0.453 mmol) and triethylamine (0.189 mL, 1.358 mmol) were added. The reaction mixture was stirred at room temperature for 2 hours. The reaction was quenched by the addition of water. A beige solid separated from solution and was collected by filtration. This material was then dissolved in dichloromethane (5 mL) and a 2 M solution of HCl in ether (2.263 mL, 4.53 mmol) was added. The resulting mixture was stirred at room temperature for 2 days, and then concentrated in vacuo to give the tribasic hydrochloride salt of the title compound as a beige colored solid (133 ng, 71.1% yield). Analytical LC/MS conditions: Column: Phenomenex LUNA C18, 2.0×50 mm, 3 µm particles; Mobile Phase A: 10:90 methanol:water with 0.1%0 TFA; Mobile Phase B: 90:10 methanol:water with 0.1% TFA; Gradient: 0-100% B over 4 minutes, then a 1 minute hold at 100% B: Flow: 0.8 mL/min; Detection: UV at 220 nm. LC/MS results: 1.8 min, 304.0 (M+H)$^+$. $^1$H NMR (400 MHz, DMSO-d$_6$) δ 9.30 (br. s., 2H), 8.13 (d, J=9.0 Hz, 1H), 7.86 (d, J=9.0 Hz, 1H), 4.10-3.89 (m, 4H), 3.57 (s, 3H), 3.36 (br. s., 4H).

Intermediate 65

2,4-Dioxo-1,2,3,4-tetrahydro-1,5-naphthyridine-3-carbonitrile

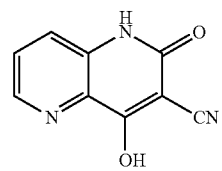

(I-65)

2-Cyanoacetic acid was converted to the related acid chloride by treatment of a solution of 2-cyanoacetic acid (1.388 g, 16.32 mmol) in dichloromethane (10 mL) containing a few drops of DMF with a mixture of 2 M oxalyl chloride in dichloromethane (10.83 mL, 21.66 mmol). The resulting solution was stirred at room temperature for 3 hours. The mixture was then concentrated and the residue subjected to vacuum overnight. This material was dissolved in dichloromethane (10 mL) and added dropwise to a solution of ethyl 3-aminopicolinate (1.5 g, 9.03 mmol) in dichloromethane (10 mL) containing DIPEA (6.31 mL, 36.1 mmol). The reaction mixture was stirred at room temperature over the weekend and then quenched by the addition of water. The resulting mixture was extracted with dichloromethane. The aqueous layer was then acidified with 1N HCl solution to pH-2 whereupon a precipitate formed that was collected by filtration to provide the hydrochloride salt of the title compound as a brown colored solid (689 mg, 40.8% yield). Analytical LC/MS conditions: Column: Phenomenex LUNA C18, 2.0×50 mm, 3 Lim particles; Mobile Phase A: 10:90 methanol:water with 0.1% TFA; Mobile Phase B: 90:10 methanol:water with 0.1% TFA; Gradient: 0-100% B over 4 minutes, then a 1 minute hold at 100% B; Flow: 0.8 mL/min; Detection: UV at 220 nm. LC/MS results: 0.44 in, 188.1 (MH$^+$), $^1$H NMR (400 MHz, DMSO-d$_6$) δ 11.56 (br s, 1H), 8.51 (dd, J=4.9, 1.2 Hz, 1H), 7.96 (dd, J=8.4, 1.1 Hz, 1H), 7.85 (dd, J=8.6, 4.9 Hz, 1H).

Intermediate 66

1-methyl-2,4-dioxo-1,2,3,4-tetrahydro-1,5-naphthyridine-3-carbonitrile

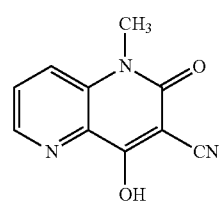

(I-66)

Sodium hydride (60%, 278 mg, 6.95 mmol) in mineral oil was added in portions to a solution of 2,4-dioxo-1,2,3,4-tetrahydro-1,5-naphthyridine-3-carbonitrile (650 mg, 3.47 mmol) in DMF (8 mL). The resulting mixture was stirred at room temperature for 30 min. Iodomethane (0.651 mL, 10.42 mmol) was then added, and stirring was continued overnight. The reaction was then quenched by the addition of water. The pH of the mixture was adjusted to ~3 by the dropwise addition of 1N HCl solution. Solid separated from the mixture and was collected by filtration to provide the hydrochloride salt of the title compound as a solid powder (403 mg, 57.7%).

Intermediate 67

4-Chloro-1-methyl-2-oxo-1,2-dihydro-1,5-naphthyridine-3-carbonitrile

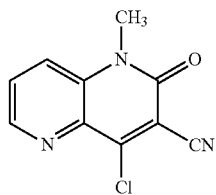

(I-67)

In a sealed tube, 1-methyl-2,4-dioxo-1,2,3,4-tetrahydro-1,5-naphthyridine-3-carbonitrile (250 mg, 1.243 mmol) and phosphorus oxychloride (2 mL, 21.46 mmol) were heated at 95° C. for 5 hours. The reaction mixture was then concentrated under reduced pressure, the residue poured into ice-water, and then neutralized by the addition of solid NaHCO$_3$. The resultant mixture was extracted with dichloromethane (2×20 mL) and the organic layers were combined, dried over MgSO$_4$, and filtered. The filtrates were concentrated in vacuo to give the title compound as a brown colored solid (105 mg, 38.5% yield). Analytical LC/MS conditions: Column: Phenomenex LUNA C18, 2.0×50 mm, 3 μm particles; Mobile Phase A: 10:90 methanol:water with 0.1% TFA; Mobile Phase B: 90:10 methanol:water with 0.100 TFA; Gradient: 0-100% B over 4 minutes, then a 1 minute hold at 100% B; Flow: 0.8 mL/min; Detection: UV at 220 nm. LC/MS results: 2.3 min, 220.0 (MH$^+$). $^1$H NMR (400 MHz, chloroform-d) δ 8.80 (dd, J=4.4, 1.2 Hz, 1H), 783 (dd, J=8.8, 1.2 Hz, 1H), 7.72 (dd, J=8.6, 4.4 Hz, 1H), 3.78 (s, 3H).

Intermediate 71

Ethyl 6-bromo-4-hydroxy-2-oxo-1,2-dihydro-1,5-naphthyridine-3-carboxylate

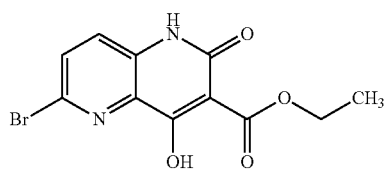

(I-71)

To a solution of ethyl 3-amino-6-bromopicolinate (500 mg, 2.040 mmol) and DIPEA (1.069 mL, 6.12 mmol) in dichloromethane (10 mL), ethyl 3-chloro-3-oxopropanoate (0.313 mL, 2.448 mmol) was added dropwise at 0° C. The reaction mixture was then warmed to room temperature and stirred for 1 hour. Then 21 wt % of sodium ethoxide (0.914 mL, 2.448 mmol) in ethanol was added drop wise and the reaction mixture was stirred at room temperature for 3 hours. The reaction was then quenched by the addition of water. The reaction mixture was acidified to pH~4 using 1 N HCl solution. Solid material separated from solution and was collected by filtration to give the title compound as a brown-colored solid (400 mg, 62.6% yield). Analytical LC/MS conditions: Phenomenex L UNA C18, 50×2, 3 μm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS results: 1.5 min, 312.9 (M+H)$^+$. $^1$H NMR (400 MHz, methanol-d$_4$) δ 7.81 (d, J=8.8 Hz, 1H), 7.64 (d, J=8.8 Hz, 1H), 4.45 (d, J=7.1 Hz, 2H), 1.42 (t, J=7.2 Hz, 3H).

Intermediate 72

Ethyl 6-bromo-4-hydroxy-1-methyl-2-oxo-1,2-dihydro-1,5-naphthyridine-3-carboxylate

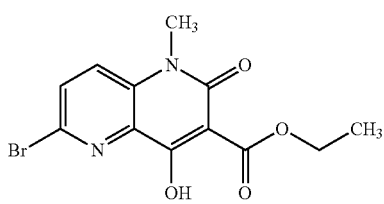

(I-72)

To a solution of ethyl 6-bromo-4-hydroxy-2-oxo-1,2-dihydro-1,5-naphthyridine-3-carboxylate (400 mg, 1.278 mol) in DMF (5 mL), 60% sodium hydride (128 mg, 3.19 mmol) in mineral oil was added in portions. The reaction mixture was stirred at room temperature for 30 min, after which iodomethane (0.200 mL, 3.19 mmol) was added. The mixture was stirred at room temperature for an additional 1 hour. The reaction was quenched by the addition of water. The reaction mixture was acidified to pH3 by the addition of 1 N HCl solution to pH3. The solution was extracted with ethyl acetate (2×40 mL) and the organic layers were combined, dried (MgSO$_4$), and concentrated in vacuo to give an orange oil. The material was purified using reverse phase preparative HPLC using CH$_3$OH—H$_2$O-TFA as eluent. Homogeneous fractions were combined, neutralized with saturated NaHCO$_3$ solution and concentrated under reduced pressure to remove acetonitrile. The resultant mixture was extracted with ethyl acetate (2×40 mL) and the organic layers were combined, dried (MgSO$_4$) and concentrated in vacuo to give the title compound as a yellow solid (190 mg, 45.5% yield). Analytical LC/MS conditions: Column: Phenomenex LUNA C18, 2.0×50 mm, 3 μm particles; Mobile Phase A: 10:90 methanol:water with 0.1% TFA; Mobile Phase B: 90:10 methanol:water with 0.1% TFA; Gradient: 0-100% B over 4 minutes, then a 1 minute hold at 100% B; Flow: 0.8 mL/min; Detection: UV at 220 nm. LC/MS results: 3.1 min, 326.8 (M+H)$^+$. $^1$H NMR (400 MHz, chloroform-d) δ 7.78 (d, J=8.8 Hz, 1H), 7.60 (d, J=8.8 Hz, 1H), 4.54 (q, J=7.2 Hz, 2H), 3.68 (s, 3H), 1.49 (t, J=7.1 Hz, 3H).

Intermediate 73

Tert-butyl 4-((1H-indol-4-yl)methyl)piperazine-1-carboxylate

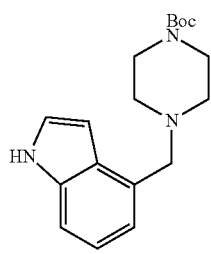

(I-73)

1H-indole-4-carbaldehyde (1.5 g, 10.33 mmol) was added to a solution of tert-butyl piperazine-1-carboxylate (2.89 g, 15.50 mmol) in DMF (10 mL). The reaction mixture was stirred at room temperature for 1 h, and sodium cyanoborohydride (1.948 g, 31.0 mmol) was added and the mixture was stirred at room temperature for 7 days. Water was then added and solid material separated which was collected by filtration. The crude product was fractionated using flash chromatography on silica gel using 35% ethyl acetate in hexanes as eluent. Homogenous fractions were combined and evaporated to give the title compound as a white solid (405 mg, 12.43% yield). Analytical LC/MS conditions: Phenomenex LUNA C18 column, 50×2, 3 µm particles Mobile Phase A: 5% acetonitrile: 95% water: 10 mM ammonium acetate; Mobile Phase B: 95% acetonitrile:5% water: 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS results: 2.9 min, 316 (M+H)$^+$. $^1$H NMR (400 MHz, chloroform-d) δ 8.23 (br. s., 1H), 7.35 (d, J=8.1 Hz, 1H), 7.23 (br. s., 1H), 7.18 (t, J=7.7 Hz, 1H), 7.13-7.05 (m, 1H), 6.76 (br. s., 1H), 3.83 (s, 2H), 3.51-3.40 (m, 4H), 2.53-2.40 (m, 4H), 1.48 (s, 9H).

Intermediate 74

1-Ethyl-4-(piperazin-1-ylmethyl)-1H-indole bis(2,2,2-trifluoroacetate)

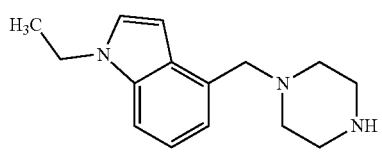

(I-74)

Sodium hydride (0.061 g, 1.522 mmol, 60% in mineral oil) was added in portions to a solution of tert-butyl 4-((1-indol-4-yl)methyl)piperazine-1-carboxylate (0.4 g, 1.268 mmol) in DMF (5 mL) at 0° C. The reaction mixture was then warmed to room temperature and stirred for 30 min. Ethyl iodide (0.205 mL, 2.54 mmol) was then added and the reaction mixture was stirred at room temperature for 10 min before being quenched by the addition of water. The resulting mixture was extracted with ethyl acetate (2×40 mL). The extracts were combined, dried (MgSO$_4$), filtered and concentrated in vacuo to give an orange colored oil. The material was fractionated using preparative HPLC using acetonitrile-water-TFA as eluent. Homogeneous fractions were combined and concentrated under reduced pressure to give a dark brown thick oil. This material was dissolved in dichloromethane (3 mL) and TFA (1 mL) was added. The reaction mixture was stirred at room temperature for 2 hr. It was then concentrated under vacuum to give a dark purple oil. This material was fractionated be reverse phase preparative HPLC using acetonitrile-water-TFA as eluent. Homogeneous fractions were combined and concentrated in vacuo to the title compound as a viscous, purple colored oil (373 mg, 62.4% yield). Analytical LC/MS conditions: Column: Phenomenex LUNA C18, 2.0×50 mm, 3 µm particles; Mobile Phase A: 10:90 methanol:water with 0.1% TFA; Mobile Phase B: 90:10 methanol:water with 0.1% TFA; Gradient: 0-100% B over 4 minutes, then a 1 minute hold at 100% B; Flow: 0.8 mL/min; Detection: UV at 220 nm. LC/MS results: 1.9 min, 244 (M+H)$^+$. $^1$H NMR (400 MHz, methanol-d$_4$) δ 7.60 (d, J=7.8 Hz, 1H), 743 (d, J=1.0 Hz, 1H), 7.35-7.15 (m, 2H), 6.74 (d, J=2.7 Hz, 1H), 4.68 (s, 2H), 4.29 (q, J=7.1 Hz, 2H), 3.68-3.43 (m, 8H), 1.45 (t, J=7.2 Hz, 3H).

Intermediate 75

2-(phenyl(piperazin-1-yl)methyl)phenol

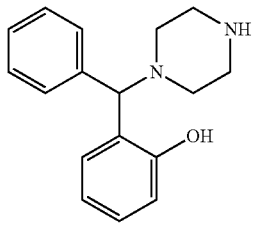

(I-75)

In a round-bottomed flask, phenylboronic acid (1.309 g, 10.74 mmol), salicylaldehyde (1.311 g, 10.74 mmol) and tert-butyl piperazine-1-carboxylate (2 g, 10.74 mmol) were dissolved in DMF (12 mL). The reaction mixture was heated at 120° C. in an oil bath for over the weekend. The reaction mixture was diluted with ethyl acetate and washed sequentially with water and brine. The organic layer was then dried (MgSO$_4$), filtered and concentrated in vacuo to a yellow viscous oil. This oil was subjected to flash chromatography using silica gel and 20% ethyl acetate in hexanes as eluent. Homogeneous fractions were combined and concentrated under vacuum to give the protected derivative as a yellow oil. This material was dissolved in dichloromethane (10 mL) and TFA (5 mL) was added. The reaction mixture was stirred at room temperature for 4 days and concentrated under reduced pressure. The residue was dissolved in ethyl acetate. This mixture was washed with saturated NaHCO$_3$ solution and the organic layer was dried over MgSO$_4$, filtered and evaporated to dryness under vacuum. The resultant residue was triturated with 25% ethyl acetate in hexanes, and a solid was collected by filtration to give the title compound as an off-white powder (0.506 g, 17.56% yield). Analytical LC/MS conditions: Column: Phenomenex LUNA C18, 2.0× 50 mm, 3 µm particles; Mobile Phase A: 10:90 methanol:water with 0.1% TFA; Mobile Phase B: 90:10 methanol:water with 0.1% TFA; Gradient: 0-100% B over 4 minutes, then a 1 minute hold at 100% B; Flow: 0.8 mL/min; Detection: UV at 220 nm. LC/MS results: 2.5 min, 267.3 (M–H⁻). ¹H NMR (400 MHz, methanol-d$_4$) δ 7.55-7.43 (m, 2H), 7.36-7.27 (m, 3H), 7.27-7.20 (m, 1H), 7.08 (td, J=7.7, 1.5 Hz, 1H), 6.86-6.66 (m, 2H), 4.85 (s, 1H), 3.28 (t, J=5.3 Hz, 4H), 2.84-2.61 (m, 4H).

Intermediate 78

Tert-butyl 4-((2-hydroxynaphthalen-1-yl)methyl)piperazine-1-carboxylate

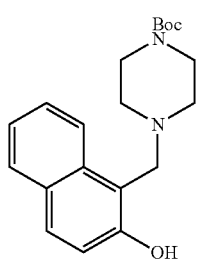

(I-78)

2-Hydroxy-1-naphthaldehyde (600 mg, 3.48 mmol) was added to a solution of tert-butyl piperazine-1-carboxylate (779 mg, 4.18 mmol) in DMF (10 mL). The reaction mixture was stirred at room temperature for 1 hour. Sodium cyanoborohydride (657 mg, 10.45 mmol) was added and the reaction mixture was stirred at room temperature for 6 days. The reaction was quenched by the addition of water. The mixture was extracted with ethyl acetate (2×40 mL). The organic layers were combined, dried (MgSO$_4$), filtered and concentrated in vacuo to give an orange oil. This material was fractionated using reverse phase preparative HPLC using acetonitrile-water-TFA as eluent. Homogeneous fractions were collected, neutralized with saturated NaHCO$_3$ solution and then concentrated under reduced pressure to remove acetonitrile. A beige solid separated and was collected by filtration, which on drying gave the title compound as a powder (498 mg, 41.7% yield). Analytical LC/MS conditions: Phenomenex LUNA C18 column, 50×2, 3 µm particles Mobile Phase A: 5% acetonitrile: 95% water: 10 mM ammonium acetate; Mobile Phase B: 95% acetonitrile: 5% water. 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS results: 3.6 min, 343.2 (M+H)⁺. ¹H NMR (400 MHz, methanol-d$_4$) δ 7.96 (d, J=8.6 Hz, 1H), 7.82-7.62 (m, 2H), 745 (td, J=7.7, 1.2 Hz, 1H), 7.29 (t, J=7.5 Hz, 1H), 7.06 (d, J=9.0 Hz, 1H), 4.17 (s, 2H), 3.60-3.43 (m, 4H), 2.63 (t, J=5.0 Hz, 4H), 1.48 (s, 9H).

Intermediate 79

1-(Piperazin-1-ylmethyl)naphthalen-2-ol bis(2,2,2-trifluoroacetate)

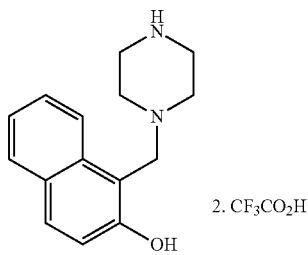

(I-79)

2. CF$_3$CO$_2$H

TFA (2 mL, 26.0 mmol) was added to a solution of tert-butyl 4-((2-hydroxynaphthalen-1-yl)methyl)piperazine-1-carboxylate (494 mg, 1.443 mmol) in dichloromethane (3 mL). The reaction mixture was stirred at room temperature overnight, and was then concentrated under reduced pressure to give the title compound as a purple colored solid (670 mg, 99% yield). Analytical LC/MS conditions: Column: Phenomenex LUTA C18, 2.0×50 mm, 3 µm particles; Mobile Phase A: 10:90 methanol:water with 0.1% TFA; Mobile Phase B: 90:10 methanol:water with 0.1% TFA; Gradient: 0-100% B over 4 minutes, then a 1 minute hold at 100% B; Flow: 0.8 mL/min; Detection: UV at 220 nm. LC/MS results: 2.1 min, 243.0 (M+H)⁺. ¹H NMR (400 MHz, methanol-d$_4$) δ 8.03 (d, J=8.6 Hz, 1H), 7.91 (d, J=8.8 Hz, 1H), 7.85 (d, J=8.1 Hz, 1H), 7.64-7.54 (m, 1H), 7.39 (t, J=7.5 Hz, 1H), 7.23 (d, J=8.8 Hz, 1H), 4.84 (s, 2H), 3.67-3.56 (m, 4H), 3.55-3.45 (m, 4H).

Intermediate 80

1-(2-(4-fluorophenyl)propan-2-yl)-4-tosylpiperazine

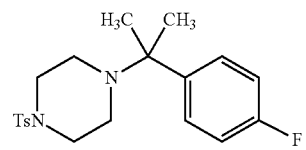

(I-80)

A mixture of 2-(4-fluorophenyl)propan-2-amine hydrochloride (0.5 g, 264 mmol), N,N-bis(2-chloroethyl)-4-methylbenzenesulfonamide (0.820 g, 2.77 mmol) and DIPEA (1.381 mL, 7.91 mmol) was heated under microwave radiation at 125° C. for 20 h. Water was added and the mixture extracted using dichloromethane (2×30 mL). The organic layers were combined, dried (MgSO$_4$), filtered and concentrated under reduced pressure to give a yellow oil. The oil was triturated with 25% ethyl acetate in hexanes and an off-white solid separated which was collected by filtration to give the title compound (505 mg, 50.9% yield). Analytical LC/MS conditions: Phenomenex LUNA C18, 50×2, 3 µm particles; Mobile Phase A: 5% acetonitrile: 95% water: 10 nM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm.

LC/MS results: 3.7 min, 377.1 (M+H)+. 1H NMR (400 MHz, DMSO-d6) δ 7.61 (d, J=8.1 Hz, 2H), 7.47 (d, J=8.1 Hz, 2H), 7.40 (dd, J=8.6, 5.9 Hz, 21-1), 707 (t, J=8.8 Hz, 2H), 2.83 (br s, 4H), 2.44 (s, 7H), 1.25 (s, 6H).

Intermediate 81

1-(2-(4-fluorophenyl)propan-2-yl)piperazine

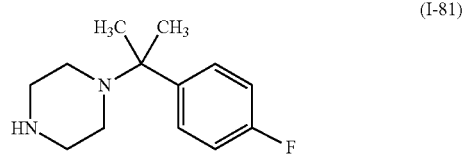 [SMILES: CC(C)(c1ccc(F)cc1)N1CCNCC1]

(I-81)

A solution of hydrogen bromide (6 mL, 33.1 mmol, 33 wt. %) in acetic acid was added to a mixture of 1-(2-(4-fluorophenyl)propan-2-yl)-4-tosylpiperazine (495 mg, 1.315 mmol) and 4-hydroxybenzoic acid (545 mg, 3.94 mmol). The reaction mixture was stirred at room temperature over the weekend. Water was then slowly added and the resultant mixture was stirred for 2 h. A white precipitate formed that was collected by filtration. The precipitate was washed sequentially with cold water and then toluene. The aqueous filtrate and washings were then cooled in an ice bath and basified with NaOH pellets to pH>10. This mixture was extracted with ethyl acetate (2×20 mL) and the combined extracts washed with brine, dried (MgSO4), filtered and concentrated under reduced pressure to give the title compound as an off-white solid (195 mg, 66.7% yield). Analytical LC/MS conditions: Phenomenex LUNA C18, 50×2, 3 µm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS results: 1.8 min, 223.1 (M+H)+. 1H NMR (400 MHz, chloroform-d) δ 7.51 (dd, J=8.6, 5.6 Hz, 2H), 6.99 (t, J=8.7 Hz, 2H), 2.96-2.73 (m, 4H), 2.52-2.36 (m, 4H), 1.34 (s, 6H).

Intermediate 82

1-(1-(4-fluorophenyl)cyclopropyl)-4-tosylpiperazine

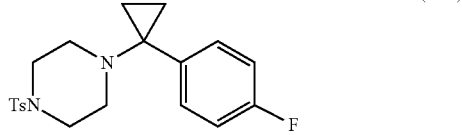

(I-82)

Intermediate 82 was prepared according to the general procedure used to synthesize 1-(2-(4-fluorophenyl)propan-2-yl)piperazine but using 1-(4-fluorophenyl) cyclopropan-1-amine hydrochloride (0.5 g, 2.66 mmol). The title compound was synthesized as a light yellow colored solid (651 mg, 65.2% yield). Analytical LC/MS conditions: Phenomenex LUNA CIS, 50×2, 3 µm particles; Mobile Phase A: 5% acetonitrile: 95% water: 10 mM ammonium acetate; Mobile Phase B: 95% acetonitrile:5% water: 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS results: 3.6 min, 375.1 (M+H)+. 1H NMR (400 MHz, chloroform-d) δ 7.61 (d, J=8.3 Hz, 2H), 7.31 (d, J=8.3 Hz, 2H), 7.20 (dd, J=8.4, 5.5 Hz, 2H), 7.01 (t, J=8.6 Hz, 2H), 3.15-2.78 (m, 4H), 2.58 (br in, 4H), 2.44 (s, 3H), 0.90-0.72 (m, 4H).

Intermediate 83

1-(1-(4-fluorophenyl)cyclopropyl)piperazine

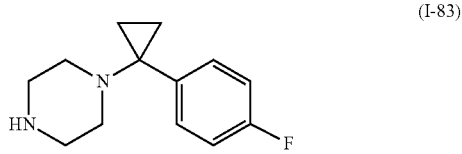 [SMILES: Fc1ccc(C2(N3CCNCC3)CC2)cc1]

(I-83)

Intermediate 83 was prepared according to the general procedure used to synthesize 1-(2-(4-fluorophenyl)propan-2-yl)piperazine but using 1-(I-(4-fluorophenyl) cyclopropyl)-4-tosylpiperazine (600 mg, 1.602 mmol) to afford as a brown colored solid (235 mg, 66.6% yield). Analytical LC/MS conditions: Phenomenex L UNA C18, 50×2, 3 µm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS results: 1.8 min, 221.1 (M+H)+. 1H NMR (400 MHz, methanol-d4) δ 7.34 (br s, 2H), 7.06 (br d, J=2.0 Hz, 2H), 3.01-2.13 (m, 8H), 1.20-0.37 (m, 4H).

Intermediate 84

1-(1-(4-fluorophenyl)-2-methylpropyl)piperazine bis(2,2,2-trifluoroacetate)

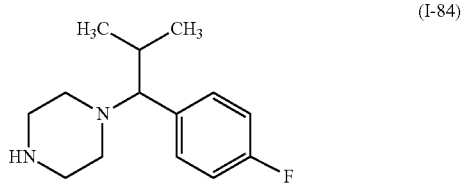 [SMILES: CC(C)C(c1ccc(F)cc1)N1CCNCC1]

(I-84)

Titanium (IV) chloride (1.0 N in dichloromethane) (1.956 mL, 1.956 mmol) was added to a solution of 1-(4-fluorophenyl)-2-methylpropan-1-one (250 mg, 1.504 mmol) in TI-IF (4 mL). The reaction mixture was stirred at room temperature for 0.5 h. Tert-butyl piperazine-1-carboxylate (336 mg, 1.805 mmol) in THF (4 mL) was added. The reaction mixture changed color from green to yellow. The reaction mixture was stirred for 1 h and then sodium cyanoborohydride (123 mg, 1.956 mmol) was added and stirring was continued for an additional 3 days. Acetic acid was added to terminate the reaction. Ethyl acetate was added to dilute the mixture. The resultant solution was washed with brine and the organic layer was separated, dried (MgSO4), filtered and evaporated under reduced pressure to give a viscous yellow oil. The crude product was dissolve in dichloromethane (4 mL) and TFA (2 mL) was added. The reaction mixture was then stirred at room temperature overnight before being concentrated to dryness under reduced pressure. The residue was fractionated using reverse phase preparative HPLC using acetonitrile-water-TFA as eluent. Homogeneous fractions were combined and concentrated in vacuo to give the title compound as a white solid (103 ng, 14.74% yield). Analytical LC/MS conditions: Phenomenex LUNA C18, 50×2, 3 μm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS results: 2.3 min, 237.1 $(M+H)^+$. $^1$H NMR (400 MHz, methanol-$d_4$) δ 7.28 (dd, J=8.6, 5.4 Hz, 2H), 7.19-7.01 (m, 2H), 3.33-3.17 (m, 5H), 2.78-2.60 (br m, 4H), 2.36 (dt, J=9.5, 6.6 Hz, 1H), 1.07 (d, J=6.6 Hz, 31H), 0.76 (d, J=6.6 Hz, 3H).

Intermediate 85

1-(cyclobutyl(4-fluorophenyl)methyl)piperazine bis(2,2,2-trifluoroacetate)

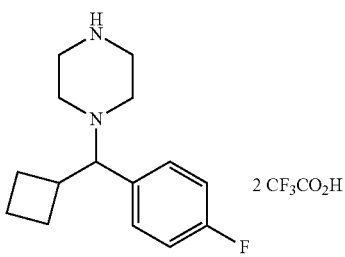

(I-85)

Intermediate 85 was prepared according to the general procedure for synthesizing 1-(2-(4-fluorophenyl)propan-2-yl)piperazine but using cyclobutyl(4-fluorophenyl) methanone (300 mg, 1.683 mmol). The title compound was synthesized as a white colored solid (40.2 mg, 5.01% yield). Analytical LC/MS conditions: Phenomenex LUNA C18, 50×2, 3 μm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS results: 2.3 min, 249.1 $(M+H)^+$. $^1$H NMR (400 MHz, methanol-$d_4$) δ 7.48 (dd, J=8.6, 5.4 Hz, 2H), 7.20 (t, J=8.6 Hz, 2H), 4.22 (d, J=10.5 Hz, 1H), 3.54-3.43 (m, 4H), 3.41-3.28 (m, 2H), 3.27-3.11 (m, 3H), 2.55-2.29 (m, 1H), 2.16 (quin, J=9.8 Hz, 1H), 2.06-1.88 (m, 11H), 1.86-1.72 (m, 1H), 1.71-1.61 (m, 1H), 1.60-1.46 (m, 1H).

Intermediate 86

Tert-butyl 4-(3-cyano-1,6-dimethyl-2-oxo-1,2-dihydro-1,5-naphthyridin-4-yl)piperazine-1-carboxylate

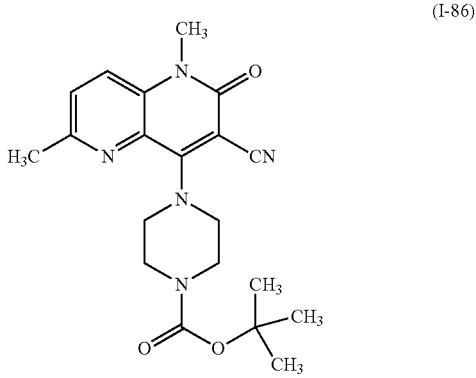 [SMILES: Cc1ccc2c(n1)c(N1CCN(C(=O)OC(C)(C)C)CC1)c(C#N)c(=O)n2C]

(I-86)

Intermediate 86 was prepared by the general methods described for Intermediates 55 and 61. LCMS. [Injection Vol=3 μL, Start % B=2, Final % B=98, Gradient Time=1.5 min, Flow Rate=0.8 mL/min, Wavelength=220 nm, Solvent Pair=Water/Acetonitrile/TFA, Solvent A=100% Water/0.05% TFA, Solvent B=100% Acetonitrile/0.05% TFA, Column=Waters Aquity BEH C18 2.1×50 mm, 1.7U MW1, Oven Temp=40] $R_T$=1.170 min. $(M+H)^+$=384.05

Intermediate 87

1,6-Dimethyl-2-oxo-4-(piperazin-1-yl)-1,2-dihydro-1,5-naphthyridine-3-carbonitrile 2,2,2-trifluoroacetate

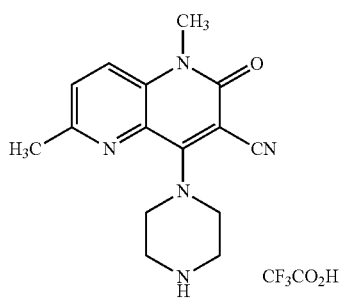

(I-87)

Tert-butyl 4-(3-cyano-1,6-dimethyl-2-oxo-1,2-dihydro-1, 5-naphthyridin-4-yl) piperazine-1-carboxylate (26 mg, 0.068 mmol) was dissolved in DCM (1 mL) and trifluoroacetic acid (1.045 mL, 13.56 mmol) was added. The mixture was stirred at room temperature for about 1 hr. The solvent and excess acid were removed under vacuum to afford the product as an oil. LCMS. [Injection Vol=3 μL, Start % B=2, Final % B=98, Gradient Time=1.5 min, Flow Rate=0.8 mL/min, Wavelength=220 nm, Solvent Pair=Water/Acetonitrile/TFA, Solvent A=100% Water/0.05% TFA, Solvent B=100% Acetonitrile/0.05% TFA, Column=Waters Aquity BEH C18 2.1×50 mm, 1.7U MW1, Oven Temp=40] $R_T$=0.799 min. $(M+H)^+$=284.05 (Free base).

Intermediate 88

Tert-butyl (1R,5S)-3-(6-chloro-3-cyano-1-methyl-2-oxo-1,2-dihydro-1,5-naphthyridin-4-yl)-3,8-diazabicyclo[3.2.1]octane-8-carboxylate

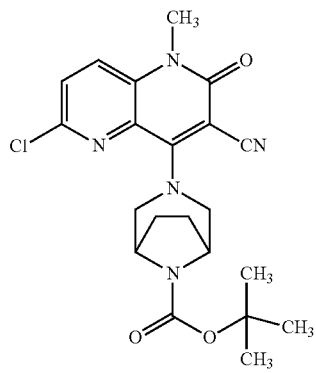

(I-88)

(1R,5S)-Tert-butyl 3,8-diazabicyclo[3.2.1]octane-8-carboxylate (137 mg, 0.645 mmol) was added to a solution of 4,6-dichloro-1-methyl-2-oxo-1,2-dihydro-1,5-naphthyridine-3-carbonitrile (164 mg, 0.645 mmol) and triethylamine (0.270 mL, 1.936 mmol) in DMF (2 mL) and the resultant mixture was stirred at room temperature overnight. The crude reaction mixture was adsorbed onto silica gel and subjected to flash chromatography using EtOAc as eluent. Homogeneous fractions were combined and evaporated in vacuo to give the product as a yellow solid (200 mg). LCMS. [Injection Vol=3 μL, Start % B=2, Final % B=98, Gradient Time=1.5 min, Flow Rate=0.8 mL/min, Wavelength=220 nm, Solvent Pair=Water/Acetonitrile/TFA, Solvent A=100% Water/0.05% TFA, Solvent B=100% Acetonitrile/0.05?% TFA. Column=Waters Aquity BEH C18 2.1×50 mm, 1.7U MW1, Oven Temp 40] $R_T$=1.260 min. (M-tBu+H)$^+$=373.95. $^1$H NMR (500 MHz, DMSO-d$_6$) δ 8.11 (d, J=9.1 Hz, 1H), 7.84 (d, J=9.0 Hz, 1H), 4.25 (br. s., 2H), 4.12 (s, 2H), 3.61-3.47 (m, 4H), 2.22 (d, J=7.6 Hz, 2H), 1.88-1.80 (m, 21H), 1.46 (s, 9H).

Intermediate 89

4-((1R,5S)-3,8-Diazabicyclo[3.2.1]octan-3-yl)-6-chloro-1-methyl-2-oxo-1,2-dihydro-1,5-naphthyridine-3-carbonitrile 2,2,2-trifluoroacetate

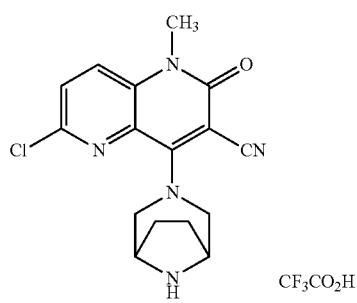

(I-89)

Trifluoroacetic acid (0.717 mL, 9.30 mmol) was diluted with DCM (0.8 mL) and the resultant mixture was added to a flask containing (1R,5S)-tert-butyl 3-(6-chloro-3-cyano-1-methyl-2-oxo-1,2-dihydro-1,5-naphthyridin-4-yl)-3,8-diazabicyclo[3.2.1]octane-8-carboxylate (200 mg, 0.465 mmol). The yellow solution was stirred at room temperature for 30 mins, after which it was evaporated under vacuum to give the title compound as a brown colored oil. LCMS. [Injection Vol=3 μL, Start % B=2, Final % B=98, Gradient Time=1.5 min, Flow Rate=0.8 mL/min, Wavelength=220 m, Solvent Pair=Water/Acetonitrile/TFA, Solvent A=100% Water/0.05% TFA, Solvent B=100% Acetonitrile/0.05% TFA, Column Waters Aquity BEH C18 2.1×50 mm, 1.7U MW1, Oven Temp=40] $R_T$=0.756 min, (M+H)$^+$=331.00. $^1$H NMR (DMSO-d$_6$) δ 8.14 (d, J=9.0 Hz, 1H), 7.87 (d, J=8.8 Hz, 1H), 4.23 (br d, J=11.2 Hz, 4H), 3.84 (br d, J=13.0 Hz, 2H), 3.57 (s, 3H), 2.42 (br d, J=7.8 Hz, 2H), 1.84-2.03 (m, 2H).

Intermediate 90

Cyclohexyl(phenyl)methanol

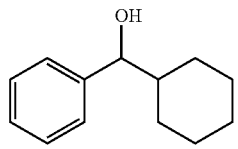

(I-90)

Sodium borohydride (0.201 g, 5.31 mmol) was added to a solution of cyclohexyl (phenyl)methanone (1 g, 5.31 mmol) in ethanol (20 mL) and the mixture was stirred at room temperature overnight. The reaction mixture was evaporated under vacuum. The residue was dissolved in DCM and washed sequentially with water and brine. The organic layer was then dried over MgSO$_4$, filtered and evaporated under reduced pressure to give the product as a colorless oil (1.01 g). LCMS. [Injection Vol=3 μL, Start % B=2, Final % B=98, Gradient Time==1.5 min, Flow Rate=0.8 mL/min, Wavelength=220 nm, Solvent Pair=Water/Acetonitrile/TFA, Solvent A=100% Water/0.05% TFA, Solvent B=100% Acetonitrile/0.05% TFA. Column=Waters Aquity BEH C18 2.1×50 mm, 1.7U MW1, Oven Temp=40] $R_T$=1.255 min. Mass not observed as MWt<200. $^1$H NMR (400 MHz, DMSO-d$_6$) δ 7.34-7.17 (m, 5H), 5.01 (d, J=4.4 Hz, 1H), 4.23 (dd, J=6.4, 4.6 Hz, 1H), 1.89-0.85 (m, 1H).

Intermediate 91

Bromo(cyclohexyl)methyl)benzene

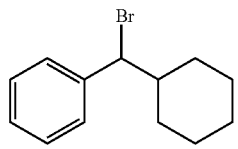

(I-91)

To a mixture of pentabromophosphorane (3.43 g, 7.96 mmol) in 20 mL of DCM was added slowly a solution of cyclohexyl(phenyl)methanol (1.01 g, 5.31 mmol) in 10 mL of DCM at room temperature. After 1 hr, the reaction mixture was washed with water (1×30 mL), 10% NaHSO₃ solution (1×25 mL) and water (1×30 mL). The material was dried over MgSO₄, filtered, and evaporated under reduced pressure to give the product as a colorless oil (1.32 g). LCMS. [Injection Vol=3 μL, Start % B=2, Final % B=98, Gradient Time=1.5 min, Flow Rate=0.8 mL/min, Wavelength=220 nm, Solvent Pair=Water/Acetonitrile/TFA, Solvent A: 100% Water/0.05% TFA, Solvent B=100% Acetonitrile/0.05% TFA, Column=Waters Aquity BEH C18 2.1×50 mm, 1.7U MW1, Oven Temp=40] $R_T$=1.609 min. Mass not observed under the ionization conditions used. ¹H NMR (400 MHz, DMSO-d₆) δ 7.52-7.18 (m, 5H), 5.03 (d, J=9.3 Hz, 1H), 2.26-0.75 (m, 11H).

Intermediate 92

Tert-butyl 4-(cyclohexyl(phenyl)methyl)piperazine-1-carboxylate

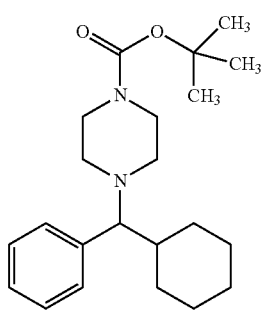

(I-92)

A mixture of potassium carbonate (218 mg, 1.580 mmol), tert-butyl piperazine-1-carboxylate (147 mg, 0.790 mmol) and (bromo(cyclohexyl)methyl)benzene (200 mg, 0.790 mmol) in acetonitrile (10 mL) was heated at reflux under nitrogen overnight. NaI was added (~2 mg) and the mixture was heated under reflux for an additional 24 hr. The reaction mixture was filtered and the filtrate evaporated to dryness. The residue was dissolved in 30% EtOAc in hexanes and the mixture filtered through a plug of silica gel. The eluted material was evaporated under reduced pressure and the residue placed under high vacuum for 1 hr to give the title compound (223 mg). LCMS. [Injection Vol=3 μL, Start % B=2, Final % B=98, Gradient Time=1.5 min, Flow Rate=0.8 mL/min, Wavelength=220 nm, Solvent Pair=Water/Acetonitrile/TFA, Solvent A=100% Water/0.05% TFA, Solvent B=100% Acetonitrile/0.05% TFA, Column=Waters Aquity BEH C18 2.1×50 mm, 1.7U MW1, Oven Temp=40] $R_T$=0.857 min. (M-Boc+AcOH+ACN)=403.25.

Intermediate 93

1-(Cyclohexyl(phenyl)methyl)piperazine bis(2,2,2-trifluoroacetate)

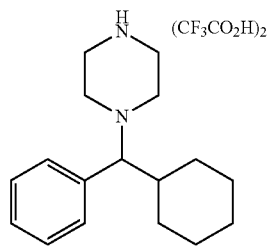

(I-93)

Trifluoroacetic acid (0.479 mL, 6.22 mmol) was added to a solution of tert-butyl 4-(cyclohexyl(phenyl)methyl)piperazine-1-carboxylate (223 mg, 0.622 mmol) in DCM (0.5 mL) and the resultant mixture was stirred at room temperature for 1 hr. The reaction mixture was evaporated to dryness. LCMS. [Injection Vol=3 μL, Start. % B=2, Final % B=98, Gradient Time=1.5 min, Flow Rate=0.8 mL/min, Wavelength=220 nm, Solvent Pair=Water/Acetonitrile/TFA, Solvent A=100% Water/0.05% TFA, Solvent B=100% Acetonitrile/0.05% TFA, Column=Waters Aquity BEH CIS 2.1×50 mm, 1.7U MW1, Oven Temp=40] $R_T$=0.850 min. (M+H)=259.1 (Free base).

Intermediate 94

Tert-butyl 4-(2-hydroxybenzyl)piperazine-1-carboxylate

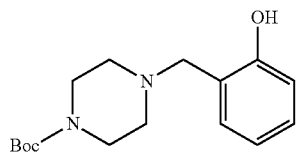

(I-94)

Acetic acid (0.307 mL, 5.37 mmol) was added to a solution of tert-butyl piperazine-1-carboxylate (1 g, 5.37 mmol) and 2-hydroxybenzaldehyde (0.656 g, 5.37 mmol) in DCE over 4 Om molecular sieves. The mixture was stirred for 1 hr at room temperature and sodium triacetoxyborohydride (0.993 mL, 5.37 mmol) was added. After stirring the reaction mixture over the weekend, the reaction was quenched by the addition of MeOH (10 mL). The reaction mixture was stirred for 30 min, and filtered. The filtrate was concentrated in vacuo. The crude residue was purified by column chromatography using 5-50% EtOAc in hexanes as eluent. Homogeneous fractions were combined and concentrated under reduced pressure to give the title compound as a pale yellow-colored oil (684 ng). LCMS. [Injection Vol=3 μL, Start % B=2, Final % B=98, Gradient Time 1.5 min, Flow Rate=0.8 mL/mm, Wavelength=220 nm, Solvent Pair=Water/Acetonitrile/TFA, Solvent A=100% Water/ 0.05% TFA, Solvent B=100% Acetonitrile/0.05% TFA, Column=Waters Aquity BEH C18 2.1×50 mm, 1.7U MW1, Oven Temp=40] $R_T$=0.810 min. (M+H)⁺=293.40. ¹H NMR (400 MHz, DMSO-d$_6$) δ 10.11-9.89 (s, 1H), 7.20-7.01 (m, 2H), 6.85-6.69 (m, 2H), 3.60 (s, 2H), 3.41-3.27 (m, 4H), 2.39 (t, J=4.9 Hz, 4H), 1.48-1.34 (m, 9H).

Intermediate 95

2-(Piperazin-1-ylmethyl)phenol bis(2,2-trifluoroacetate)

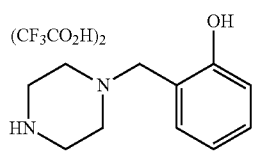

(I-95)

Trifluoroacetic acid (1.792 mL, 23.26 mmol) was added to a solution of tert-butyl 4-(2-hydroxybenzyl)piperazine-1-carboxylate (680 mg, 2.326 mmol) in DCM (2 mL) and the resultant mixture was stirred at room temperature for 1 hr. The mixture was concentrated under vacuum to give the product as a red-colored oil, which crystallized slowly on standing. LCMS. [Injection Vol=3 μL, Start % B=2, Final % B=98, Gradient Time=1.5 min, Flow Rate=0.8 mL/min, Wavelength=220 m, Solvent Pair=Water/Acetonitrile/TFA, Solvent A=100% Water/0.05% TFA, Solvent B=100% Acetonitrile/0.05% TFA, Column=Waters Aquity BEH C18 2.1×50 mm, 1.7U MW1, Oven Temp=40] R$_T$=0.599 min.

Intermediate 96

8-hydroxy-5-methyl-6-oxo-5,6-dihydro-1,5-naphthyridine-2-carbonitrile

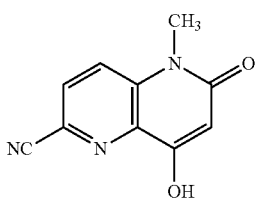

(I-96)

In a round bottom flask fitted with a reflux condenser, 8-hydroxy-5-methyl-6-oxo-5,6-dihydro-1,5-naphthyridine-2-carbonitrile (1 g, 4.97 mmol) was suspended in acetonitrile (25 mL). To this solution POCl$_3$ (6.02 mL, 64.6 mmol) was added. The reaction mixture was heated under a nitrogen atmosphere at 85° C. for 3.5 hours. To the reaction added ice followed by 5 N aqueous sodium hydroxide and saturated sodium bicarbonate until CO$_2$ gas evolution ceased. The aqueous portion was extracted with chloroform. The organic portions were combined and washed sequentially with 1.5M K$_2$HPO$_4$ and brine. After drying the organic portion over sodium sulfate, the drying agent was filtered off from the extract and the solvent removed in vacuo using a rotary evaporator. The title compound (958 mg, 72% yield) was isolated as a yellow green solid. LC/MS analysis was consistent with the desired product: Gradient Time=4 min, Flow Rate=0.8 mL/min, Wavelength 220, Solvent Pair=ACN: Water: Ammonium Acetate, Solvent A=5% ACN: 95% Water: 10 mM Ammonium Acetate, Solvent B=95% ACN: 5% Water: 10 mM Ammonium Acetate, Column Phenomenex LUNA C18, 50×2, 3 u, Oven Temp.=40. LC/MS results: 1.9 min, 220.0 (M+H)$^+$.

Intermediate 97

Tert-butyl 4-(6-bromo-3-cyano-1-methyl-2-oxo-1,2-dihydro-1,5-naphthyridin-4-yl)piperazine-1-carboxylate

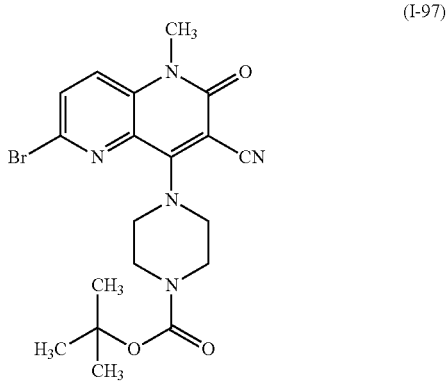 [SMILES: Cn1c(=O)c(C#N)c(N2CCN(C(=O)OC(C)(C)C)CC2)c2nc(Br)ccc21]

(I-97)

To a dimethylformamide (20 mL) solution of 6-bromo-4-chloro-1-methyl-2-oxo-1,2-dihydro-1,5-naphthyridine-3-carbonitrile (5 g, 16.75 mmol) was added tert-butyl piperazine-1-carboxylate (3.12 g, 16.75 mmol) and Hunig's base (5.85 ml, 33.5 mmol). A large amount of precipitate was formed immediately. LC/MS analysis indicated the reaction was complete. The precipitate was collected and washed with ether, EtOAC, and DCM to afford the title compound (6.2 g, 83% yield). LC/MS analysis was used to determine identity and purity. Injection conditions: Column: Waters Aquity BEH C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 40° C.; Gradient: 0% B to 100% B over 1.5 min, then a 0.75 min hold at 100% B; Flow: 1 mL/min; Detection: MS and UV (220 nm). Injection results: Purity: >90%; Observed Mass: 448.1; Retention Time: 1.4 min.

Intermediate 98

Tert-butyl 4-(3-cyano-6-methoxy-1-methyl-2-oxo-1,2-dihydro-1,5-naphthyridin-4-yl) piperazine-1-carboxylate

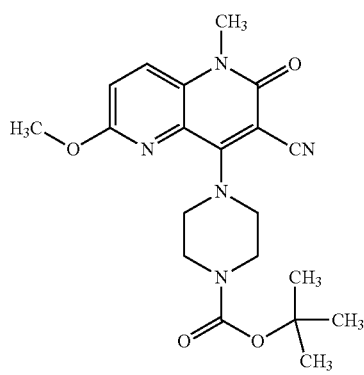

(I-98)

In a sealed reaction vial, tert-butyl 4-(6-bromo-3-cyano-1-methyl-2-oxo-1,2-dihydro-1,5-naphthyridin-4-yl)piperazine-1-carboxylate (500 mg, 1.115 mmol), palladium(II) acetate (12.52 mg, 0.056 mmol), cesium carbonate (363 mg, 1.115 mmol) and 5-[di(1-adamantyl)phosphino]-1',3',5'-triphenyl-1'h-[1,4']bipyrazole (73.9 mg, 0.112 mmol) placed under vacuum and sealed nitrogen. Methanol (0.2 mL) and acetonitrile (4 mL) were added and the reaction heated at 80° C. overnight. LC/MS analysis indicated the reaction was complete. The mixture was diluted with ethyl acetate, filtered, concentrated and the residue was purified using silica gel chromatography (hexane/ethyl acetate, 40 g silica column, 30 to 100% EtOAc). The title compound was isolated yellow solid (360 mg, 81% yield). Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 400.05; Retention Time: 1.69 min. Injection 2 conditions: Column: Waters XBridge C18, 2.1 mm×50 mm, 1.7 urn particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 400.06; Retention Time: 1.72 min.

Intermediate 99

6-methoxy-1-methyl-2-oxo-4-(piperazin-1-yl)-1,2-dihydro-1,5-naphthyridine-3-carbonitrile

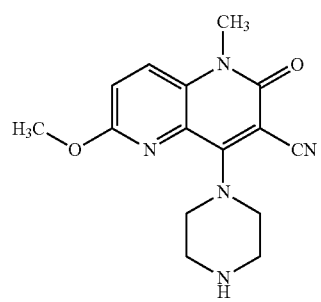

(I-99)

To dichloromethane (3 mL) solution of tert-butyl 4-(3-cyano-6-methoxy-1-methyl-2-oxo-1,2-dihydro-1,5-naphthyridin-4-yl)piperazine-1-carboxylate (350 mg, 0.876 mmol) was added trifluoroacetic acid (0.675 mL, 8.76 mmol). The reaction mixture was stirred at room temperature for 2 hours. LC/MS analysis indicated the reaction was complete. The solvent was removed and the crude residue was diluted with ethyl acetate. This solution was washed with sodium bicarbonate and brine, and dried over sodium sulfate to afford yellow solid (250 mg, 90% yield). Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 300.11; Retention Time: 0.95 min. Injection 2 conditions: Column: Waters Bridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.8%; Observed Mass: 300.09; Retention Time: 0.81 min.

Intermediate 100

(4-fluorophenyl)(2-methoxypyridin-3-yl)methanol

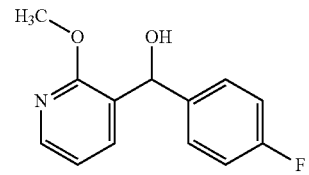

(I-100)

In a 500 mL round bottom flask, 2-methoxynicotinaldehyde (2.5 g, 18.23 mmol) was dissolved in TI-F (36.5 mL) and cooled on an ice bath. After 5 minutes, (4-fluorophenyl) magnesium bromide in diethyl ether (10.94 mL, 21.88 mmol) was added via a syringe and the reaction mixture was stirred for 50 minutes. The cooling bath was removed and the reaction mixture was stirred for 10 minutes. The reaction was quenched by sequential addition of 1 mL saturated aqueous ammonium chloride and 50 mL ethyl acetate. The solids were removed by decanting. The solvent was removed by rotary evaporation and the crude residue was chromatographed on silica gel with 5-15% methanol in ethyl acetate. The fractions containing the product were combined. The solvent was removed to afford (4-fluorophenyl)(2-methoxypyridin-3-yl)methanol (3 g, 12.22 mmol, 67.0% yield) as a yellow solid. NMR analysis showed this material to be >95% pure. $^1$H NMR (400 MHz, chloroform-d) δ 8.12 (d, J=4.9 Hz, 1H), 7.54 (d, J=7.1 Hz, 1H), 7.37 (dd, J=8.3, 5.6 Hz, 2H), 7.05 (t, J=8.6 Hz, 2H), 6.91 (dd, J=7.3, 5.1 Hz, 1H), 5.98 (d, J=4.6 Hz, 1H), 3.98 (s, 3H), 2.92 (d, J=4.6 Hz, 1H).

Intermediate 101

(cyanomethyl)trimethylphosphonium iodide

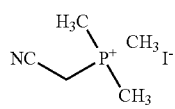

(I-101)

The title compound was prepared according to the method of Zaragoza and Stephensen (*J. Org. Chem.* 2001, 66, 2518-2521). In a 1 L round bottom flask, trimethyl phosphane in toluene (80 mL, 80 mmol) was diluted with THF (40 mL) and toluene (40 mL) and cooled on an ice bath. The reaction mixture was stirred vigorously while (cyanomethyl)trimethylphosphonium iodide was added dropwise to produce a tan precipitate. The cooling bath was removed and the reaction stirred overnight at room temperature. The reaction mixture was placed in a sonicator to break up any clumped solids and the reaction mixture was stirred an additional 4 hours. The solids were collected by filtration and dried under vacuum to afford the title compound (17.1 g, 88%). NMR consistent with pure desired product. TH NMR (400 MHz, DMSO-d$_6$) δ 4.03 (d, J=16.4 Hz, 2H), 2.05 (d, J=15.4 Hz, 9H).

Intermediate 102

(4-fluorophenyl)(3-methoxypyridin-2-yl)methanol

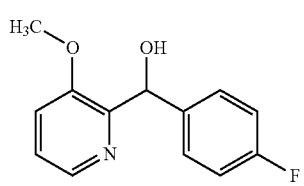

(I-102)

Intermediate 102 was prepared according to the general procedure described in Intermediate 100 from appropriate starting materials. $^1$H NMR (500 MHz, chloroform-d) δ 8.21 (dd, J=4.8, 1.1 Hz, 1H), 7.39-7.32 (m, 2H), 7.25 (dd, J=8.3, 4.8 Hz, 1H), 7.15 (dd, J=8.2, 1.1 Hz, 1H), 7.01-6.94 (m, 2H), 5.94 (d, J=6.9 Hz, 1H), 5.50 (d, J=7.0 Hz, 1H), 3.79 (s, 3H).

Intermediate 103

(4-fluorophenyl)(pyridin-2-yl)methanol

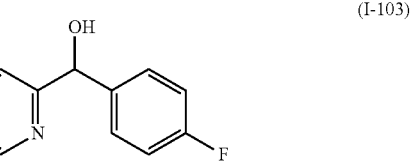

(I-103)

Intermediate 103 was prepared according to the general procedure described in Intermediate 100 from appropriate starting materials. $^1$H NMR (500 MHz, chloroform-d) δ 8.59 (d, J=4.9 Hz, 1H), 7.65 (td, J=7.6, 1.7 Hz, 1H), 7.36 (dd, J=8.6, 5.4 Hz, 2H), 7.23 (dd, J=72, 5.0 Hz, 1H), 7.14 (d, J=7.8 Hz, 1H), 7.04 (t, J=8.7 Hz, 2H), 5.75 (d, J=2.0 Hz, 1H), 5.43-5.14 (m, 1H).

Intermediate 104

(4-fluoro-2-methoxyphenyl)(pyrindin-2-yl)methanol

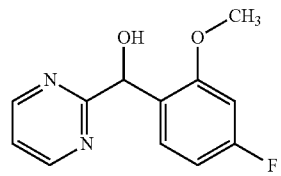

(I-104)

Intermediate 104 was prepared according to the general procedure described in Intermediate 100 from appropriate starting materials. $^1$H NMR (500 MHz, chloroform-d) δ 8.77 (d, J=4.9 Hz, 2H), 7.24 (t, J=4.9 Hz, 1H), 7.18 (dd, J=89, 6.7 Hz, 1H), 6.69-6.61 (m, 2H), 6.15 (d, J=5.4 Hz, 1H), 4.77 (d, J=5.6 Hz, 1H), 3.79 (s, 3H).

Intermediate 105

Bis(4-fluoro-2-methoxyphenyl)methano

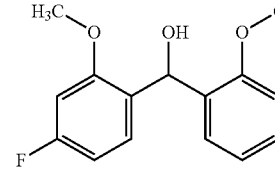

(I-105)

Intermediate 105 was prepared according to the general procedure described in Intermediate 100 from appropriate starting materials. $^1$H NMR (500 MHz, chloroform-d) δ 7.17 (dd, J=8.9, 7.0 Hz, 2H), 6.72-6.58 (m, 4H), 6.26 (d, J=3.2 Hz, 1H), 3.83 (s, 6H), 3.26 (br d, J=4.4 Hz, 1H).

Intermediate 106 tert-butyl 4-(3,6-dicyano-1-methyl-2-oxo-1,2-dihydro-1,5-naphthyridin-4-yl)piperazine-1-carboxylate

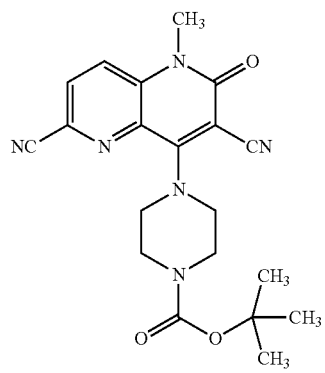

(I-106)

In a sealed reaction vial, tert-butyl 4-(6-bromo-3-cyano-1-methyl-2-oxo-1,2-dihydro-1,5-naphthyridin-4-yl)piperazine-1-carboxylate (150 ng, 0.335 mmol), zinc (2.92 ng, 0.045 mmol), zinc cyanide (15.72 mg, 0.134 mmol) and 1,1-bis(diphenylphosphino)ferrocene-palladium(ii)dichloride dichloromethane complex (54.6 mg, 0.067 mmol) were combined. The reaction mixture was placed under vacuum and sealed under nitrogen. The solids were suspended in NMP (2 mL) from a new, unopened bottle. The reaction vial was heated at 80° C. for 2.5 hours. LC/MS analysis showed the reaction was complete. The crude was purified by preparative HPLC (MeOH/water) using TFA as the buffer to obtain the desired product as yellow solid (95 mg, 67%). Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 in, then a 0.75 min hold at 100% B; Flow: 1 mL/min; Detection: MS and UV (220 nm). Injection 1 results: Purity: 98.1%; Observed Mass: 395.12; Retention Time: 1.66 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.4%; Observed Mass: 395.15; Retention Time: 1.66 min. $^1$H NMR (500 MHz, DMSO-d$_6$) δ 8.26 (d, J=8.9 Hz, 1H), 8.16 (d, J=8.8 Hz, 1H), 3.83 (br s, 4H), 3.69-3.36 (m, 3H), 1.44 (s, 91H).

Intermediate 107

5-methyl-6-oxo-8-(piperazin-1-yl)-5,6-dihydro-1,5-naphthyridine-2,7-dicarbonitrile

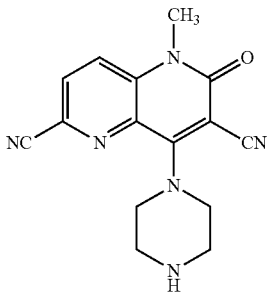

(I-107)

Intermediate 107 was prepared according to the general procedure described in Intermediate 99 from tert-butyl 4-(3,6-dicyano-1-methyl-2-oxo-1,2-dihydro-1,5-naphthyridin-4-yl)piperazine-1-carboxylate. Analytical LC/MS was used to determine the final purity. Injection conditions: Column: Waters Aquity BEH C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 40° C.; Gradient: 0% B to 100% B over 1.5 min, then a 0.75 min hold at 100% B; Flow: 0.8 mL/min; Detection: MS and UV (220 nm). Injection results: Purity: 91%; Observed Mass: 294.8, Retention Time: 0.87 min.

Intermediate 108

(4-fluoro-2-methoxyphenyl)(4-fluorophenyl)methanol

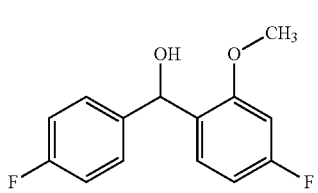

(I-108)

Intermediate 108 was prepared according to the general procedure described in Intermediate 100 from appropriate starting materials. $^1$H NMR (400 MHz, chloroform-d) δ 7.35 (dd, J=8.3, 5.6 Hz, 2H), 7.20 (t, J=7.6 Hz, 1H), 7.03 (t, J=8.7 Hz, 2H), 6.71-6.58 (m, 2H), 6.03 (d, J=4.6 Hz, 1H), 3.83 (s, 3H), 2.78 (d, J=4.9 Hz, 1H, OH).

Intermediate 109

Ethyl 4-((4-fluoro-2-methoxyphenyl)(4-fluorophenyl)methyl)piperazine-1-carboxylate

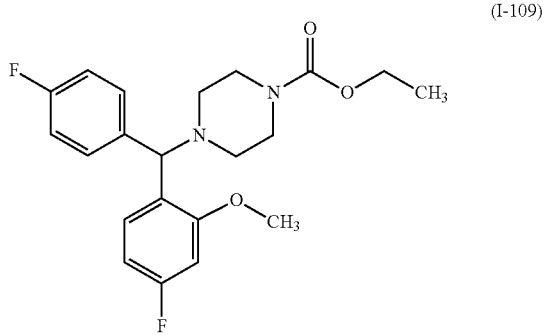 [SMILES: CCOC(=O)N1CCN(C(c2ccc(F)cc2)c2ccc(F)cc2OC)CC1]

(I-109)

Intermediate 109 was prepared according to the general procedure described in Intermediate 100 from appropriate starting materials. $^1$H NMR (400 MHz, chloroform-d) δ 7.58-7.46 (m, 1H), 7.36 (dd, J=8.3, 5.6 Hz, 2H), 6.96 (t 0.1=8.6 Hz, 2H), 6.67 (td, J=8.3, 2.2 Hz, 1H), 6.56 (dd, J=10.8, 2.2 Hz, 1H), 4.74 (s, 1H), 4.19-4.08 (m, 2H), 3.79 (s, 3H), 3.47 (br t, J=4.6 Hz, 4H), 2.46-2.24 (m, 4H), 1.26 (t, J=7.1 Hz, 3H).

Intermediates 110 and 111

1-((4-fluoro-2-methoxyphenyl)(4-fluorophenyl)methyl)piperazine

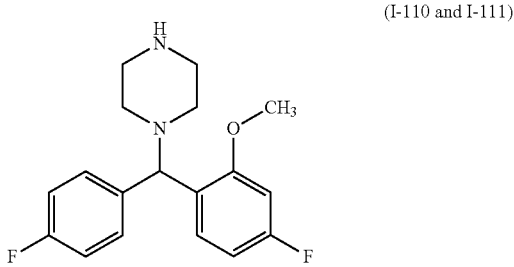 [SMILES: COc1cc(F)ccc1C(c1ccc(F)cc1)N1CCNCC1]

(I-110 and I-111)

In a 500 mL round bottom flask, ethyl 4-((4-fluoro-2-methoxyphenyl)(4-fluorophenyl)methyl)piperazine-1-carboxylate (3.6 g, 9.22 mmol) was combined with water (23.05 mL) and methanol (69.2 mL). Next, potassium hydroxide (7.76 g, 138 mmol) was added. The reaction mixture was heated at reflux and monitored by LC\MS analysis. After 7 days at reflux the reaction appeared complete. The reaction mixture was extracted 5×30 mL with diethyl ether. The combined organic portions were concentrated, redissolved in diethyl ether and dried over magnesium sulfate. Removal of the solvent gave 2.9 g of a pale yellow oil that was dried under high vacuum overnight. LCMS and NMR analysis were consistent with the desired racemic product. Four extra hydrogens were present in the aliphatic region of the H NMR. $^1$H NMR (500 MHz, chloroform-d) δ 7.54 (t, J=7.8 Hz, 1H), 7.36 (dd, J=8.2, 5.6 Hz, 2H), 6.95 (t, J=8.5 Hz, 2H), 6.66 (td, J=8.3, 2.3 Hz, 1H), 6.55 (dd, J=10.9, 2.4 Hz, 1H), 4.71 (s, 1H), 3.79 (d, J=1.1 Hz, 3H), 2.90 (t, J=4.8 Hz, 4H), 2.50-2.25 (m, 4H), 1.68 (br s, 3H). The enantiomers were separated by chiral chromatography under the following conditions: Column: Chiralpak AD-H, 30×250 mm, 5 μm, Mobile Phase: 10% MeOH w/0.2% DEA/90% $CO_2$, Pressure: 150 bar, Temperature: 30° C., Flow Rate: 100 mL/min UV: 275 nm, Injection: 0.5 mL (~75 mg/mL in EtOH:CHCl$_3$ (~9:1)), Fraction Collection: Slope and Level with no make-up flow, First eluting enantiomer: 4.00'-6.00', second eluting enantiomer: 5.30'-10.00'.

Intermediate 110 (1.1 g, 75% yield) was isolated as the first eluting enantiomer. Intermediate 111 (1.1 g, 75% yield) was isolated as the second eluting enantiomer.

Example 1

Ethyl 4-(4-(bis(4-fluorophenyl)methyl)piperazin-1-yl)-6-bromo-1-methyl-2-oxo-1,2-dihydro-1,5-naphthyridine-3-carboxylate

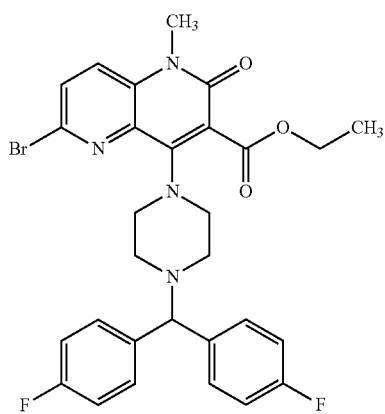

(1)

1,1,1-Trifluoro-N-phenyl-N-(trifluoromethyl)sulfonyl methanesulfonamide (82 tug, 0.229 mmol) was added to a solution of ethyl 6-bromo-4-hydroxy-1-methyl-2-oxo-1,2-dihydro-1,5-naphthyridine-3-carboxylate (25 mg, 0.076 mmol) and DIPEA (0.053 mL, 0.306 mmol) in THF (3 mL). The resulting solution was stirred at room temperature overnight. 1-(Bis(4-fluorophenyl)methyl)piperazine (22.04 mg, 0.076 mmol) and DIPEA (0.053 mL, 0.306 mmol) were added and the resultant mixture was stirred at room temperature for 2 hours. The reaction mixture was then concentrated in vacuo, and the crude material was purified via preparative HPLC using acetonitrile-water-ammonium acetate as eluent. Homogeneous fractions were combined and evaporated under vacuum to give the title compound (4.4 mg, 9.2% yield). Analytical LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). LC/MS results: 2.6 min, 597.0 (M+H)$^+$. $^1$H NMR (500 MHz, DMSO-d$_6$) δ 7.89 (d, J=8.8 Hz, 1H), 7.79 (d, J=9.2 Hz, 1H), 7.49 (dd, J=8.3, 5.7 Hz, 4H), 7.14 (t, J=8.8 Hz, 4H), 4.51 (s, 1H), 4.27 (q, J=7.3 Hz, 2H), 3.52 (s, 3H), 3.42 (br s, 4H), 2.51 (br s, 4H), 1.28 (t, J=7.0 Hz, 3H).

Example 2

6-Bromo-4-(4-(2-hydroxybenzyl)piperazin-1-yl)-1-methyl-2-oxo-1,2-dihydro-1,5-naphthyridine-3-carbonitrile

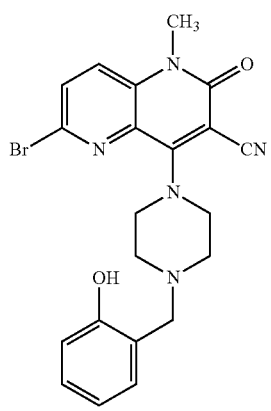

(2)

2-Hydroxybenzaldehyde (7.95 mg, 0.065 mmol) was added to a solution of 6-bromo-1-methyl-2-oxo-4-(piperazin-1-yl)-1,2-dihydro-1,5-naphthyridine-3-carbonitrile bis(2,2,2-trifluoroacetate (25 mg, 0.043 mmol) in DMF (1.5 mL). The reaction mixture was stirred at room temperature for 1 hr. Sodium cyanoborohydride (8.18 mg, 0.130 mmol) was added and the reaction mixture was stirred at room temperature for an additional 2 h. Methanol was added and the resultant mixture was filtered and then fractionated using preparative LC/MS under the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 60-100% B over 20 minutes, then a 4 minute hold at 100% B; Flow: 20 mL/min. Homogeneous fractions were combined and evaporated under centrifugal evaporation to the title compound (9.3 mg, 44.8% yield). Analytical LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). LC/MS results: 1.9 min, 454.0 (M+H)$^+$. $^1$H NMR (500 MHz, DMSO-d$_6$) δ 8.00-7.94 (m, 1H), 7.93-7.88 (m, 1H), 7.19 (br d, J=7.7 Hz, 1H), 7.13 (br t, J=7.5 Hz, 1H), 6.89-6.66 (m, 2H), 3.88 (br s, 4H), 3.70 (br s, 2H), 3.52 (s, 3H), 2.71 (br s, 4H).

Example 3

4-(4-(bis(4-fluorophenyl)methyl)piperazin-1-yl)-1-methyl-3-nitro-1,5-naphthyridin-2(1H)-one

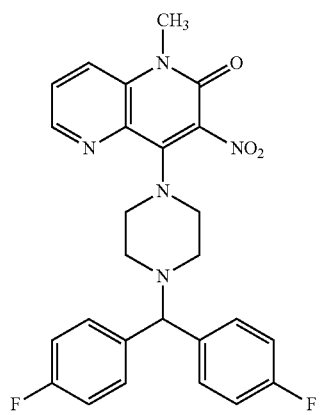

(3)

In a round bottom flask, 4-(4-(bis(4-fluorophenyl)methyl)piperazin-1-yl)-3-nitro-1,5-naphthyridin-2(1H)-one (400 mg, 0.838 mmol) and potassium carbonate (463 mg, 3.35 mmol) were combined in DMF (4189 pal). Iodomethane (119 ng, 0.838 mmol) was added and the reaction mixture was heated at 50° C. overnight. The reaction mixture was cooled and diluted with water. The yellow solids (0.26 g, 63%) were collected by filtration and dried under high vacuum. $^1$H NMR (400 MHz, DMSO-d$_6$) δ 8.57 (dd, J=44, 1.2 Hz, 1H), 8.04 (dd J=8.8, 1.2 Hz, 1H), 7.72 (dd, J=8.7, 4.3 Hz, 1H), 7.49 (dd, J=8.6, 5.6 Hz, 4H), 7.15 (t, J=8.8 Hz, 4H), 4.51 (s, 1H), 3.58 (s, 3H), 3.49 (br. s., 4H). C NMR (101 MHz, chloroform-d) δ 163.2, 160.7, 155.8, 148.3, 143.2, 137.9, 137.8, 136.3, 134.6, 132.3, 129.3, 129.2, 125.8, 122.4, 115.7, 115.5, 74.5, 51.9, 50.9, 29.3. Analytical LC/MS conditions: column: Phenomenex Luna C18, 2.0×50 mm, 3.0 μm particles; Mobile Phase A: 5:95 methanol:water with 0.1% trifluoroacetic acid; Mobile Phase B: 95:5 methanol:water with 0.1% trifluoroacetic acid; Gradient: 0-100% B over 4 minutes, then a 0.75 minute hold at 100% B; Flow: 0.8 mL/min; Detection: UV at 220 nm. LC/MS results: 3.2 minutes, 492 (M+H).

Examples 5 to 7

6-bromo-4-{4-[(4-fluorophenyl) [2-(prop-2-yn-1-yloxy)phenyl]methyl]piperazin-1-yl}-1-methyl-2-oxo-1,2-dihydro-1,5-naphthyridine-3-carbonitrile

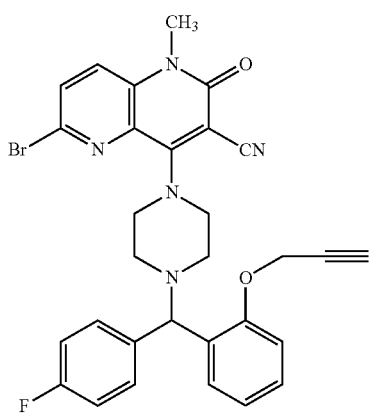

(5)

To a DMF (1 mL) solution of 6-bromo-4-chloro-1-methyl-2-oxo-1,2-dihydro-1,5-naphthyridine-3-carbonitrile (25 mg, 0.084 mmol) was added potassium carbonate (23.15 mg, 0.167 mmol) and 1-((4-fluorophenyl)(2-(prop-2-yn-1-yloxy)phenyl)methyl) piperazine, 2 TFA (55.1 mg, 0.126 mmol). The reaction mixture was mixed by shaking at room temperature for 2 hours. LC/MS analysis indicated the reaction was complete. The crude material was purified via preparative LC/MS with the following conditions: Column: XBridge C18, 19×200 mm, 5 µm particles; Mobile Phase A: 5:95 acetonitrile:water with 10 mM ammonium acetate: Mobile Phase B: 95:5 acetonitrile:water with 10 mM ammonium acetate: Gradient: 35-100% B over 15 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 µm particles. Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 in particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 2 results: Purity: 100.0%; retention time: 1.7; Obs. Adducts: [M+H]; Obs. Masses: 585.97. Injection 1 results: Purity: 100.0%; retention time: 2.4; Obs. Adducts: [M+H]; Obs. Masses: 585.99. The title compound (29.2 mg) was isolated in 59.3% yield. The racemic compound was purified using SFC-chiral chromatography.

Example 6 (first eluting isomer) and Example 7 (second eluting isomer) were isolated from the racemate using SFC-chiral chromatography. Analytical LC/MS was used to determine the final purity.

Injection 1 conditions: Column: Waters XBridge C18, 2.1 mm×50 nm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and IV (220 nm).

Example 6: Injection 1 results: Purity: 100.0%; Observed Mass: 585.99; Retention Time: 2.32 minutes. Injection 2 results: Purity: 100.0%; Observed Mass: 585.94; Retention Time: 1.66 minutes. Injection 1 results: Purity: 100.0%; retention time: 2.32; Obs. Adducts: [M+H]; Obs. Masses: 585.99. Example 6 (7.4 mg) was isolated in 15% yield.

Example 7: Injection 1 results: Purity: 100.0%; Observed Mass: 585.97; Retention Time: 2.32 minutes. Injection 2 results: Purity: 100.0%; Observed Mass: 585.96; Retention Time: 1.66 minutes. Example 7 (7.3 ng) was isolated in 14.8% yield.

Examples 8 to 10

6-bromo-4-{4-[(4-fluorophenyl)(2-hydroxyphenyl) methyl]piperazin-1-yl}-1-methyl-2-oxo-1,2-dihydro-1,5-naphthyridine-3-carbonitrile

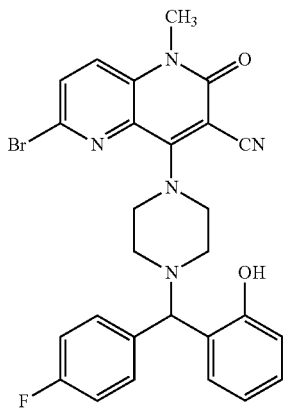

(8)

To a DMF solution (1 mL) of 6-bromo-4-chloro-1-methyl-2-oxo-1,2-dihydro-1,5-naphthridine-3-carbonitrile (50 mg, 0.167 mmol) were added potassium carbonate (93 mg, 0.670 mmol) and 2-((4-fluorophenyl)(piperazin-1-yl)

methyl)phenol, 2 TFA (86 mg, 0.167 mmol). The reaction mixture was mixed by shaking at room temperature for 2 hours. LC/MS analysis indicated that the reaction was complete. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 60-100% B over 20 minutes, then a 4 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 548.05; Retention Time: 2.24 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 548.05; Retention Time: 1.47 The title racemic compound (25.8 rug) was isolated in 28% yield. The racemic material was further purified by using SFC-chiral chromatography to give isomers.

Example 9 (first eluting isomer) and Example 10 (second eluting isomer) were isolated from the racemate using SFC-chiral chromatography. Analytical LC/MS was used to determine the final purity.

Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Example 9: Injection 1 results: Purity: 100.0%; Observed Mass: 548.11; Retention Time: 1.78 min. Injection 2 results: Purity: 94.5%/o; Observed Mass: 548.08; Retention Time: 2.66 min. Example 9 (11.1 mg) was isolated with 94% purity.

Example 10: Injection 1 results: Purity: 100.0%; Observed Mass: 548.08; Retention Time: 1.78 min. Injection 2 results: Purity: 100.0%; Observed Mass: 548.08; Retention Time: 2.66 min. Example 10 (1.8 mg) was isolated with 100% purity.

Example 11

8-{4-[(4-fluorophenyl)(2-hydroxyphenyl)methyl] piperazin-1-yl}-5-methyl-6-oxo-5,6-dihydro-1,5-naphthyridine-2,7-dicarbonitrile

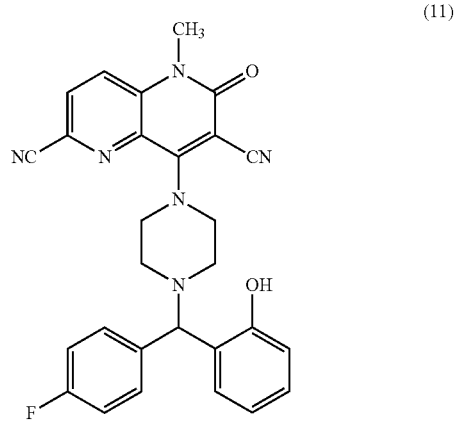 [SMILES: Cn1c(=O)c(C#N)c(N2CCN(C(c3ccc(F)cc3)c3ccccc3O)CC2)c2nc(C#N)ccc21]

(11)

A DMF solution (1 mL) of 5-methyl-6-oxo-8-(piperazin-1-yl)-5,6-dihydro-1,5-naphthyridine-2,7-dicarbonitrile, TFA (20 mg, 0.049 mmol), (4-fluorophenyl)boronic acid (6.85 mg, 0.049 mmol), and 2-hydroxybenzaldehyde (5.98 mg, 0.049 mmol) was sealed in microwave tube and heated at 150° C. for 2 hours. LC/MS analysis indicated that some product was formed, but starting material (5-methyl-6-oxo-8-(piperazin-1-yl)-5,6-dihydro-1,5-naphthyridine-2,7-dicarbonitrile, TFA) remained. More 2-hydroxybenzaldehyde (5.98 mg, 0.049 mmol) and (4-fluorophenyl)boronic acid (6.85 mg, 0.049 mmol) were added and the reaction mixture was heated at 150° C. for 2 hours. LC/MS analysis indicated that approximately 20% converted to the desired product. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 38-78% B over 22 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 495.14; Retention Time: 1.41 minutes. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 98.6%; Observed Mass: 495.14; Retention Time: 2.06 minutes. The title compound (1.5 mg) was isolated in 6.2% yield.

Examples 12 to 14

6-bromo-4-{4-[(4-fluorophenyl)(2-methoxyphenyl)methyl]piperazin-1-yl}-1-methyl-2-oxo-1,2-dihydro-1,5-naphthyridine-3-carbonitrile

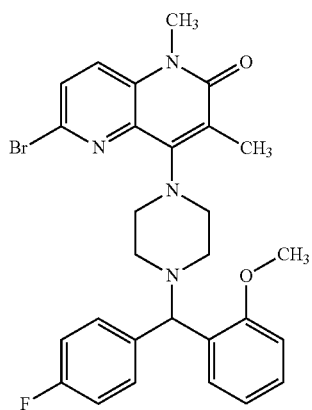

(12)

To a DMF solution (1.5 mL) of 6-bromo-4-chloro-1-methyl-2-oxo-1,2-dihydro-1,5-naphthyridine-3-carbonitrile (50 mg, 0.167 mmol) was added Hunig's base (0.15 mL, 0.84 mmol) followed by the addition of 1-((4-fluorophenyl)(2-methoxyphenyl)methyl) piperazine, 2 TFA (89 mg, 0.167 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 50-100% B over 20 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 562.12; Retention Time: 2.46 minutes. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 562.12; Retention Time: 1.59 minutes. The racemic title compound (50.4 mg) was isolated in 53.7% yield. The racemic material was further purified by using SFC-chiral chromatography to give isomers.

Example 13 (first eluting isomer) and Example 14 (second eluting isomer) were isolated from the racemate using SFC-chiral chromatography. Analytical LC/MS was used to determine the final purity.

Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Example 13: Injection 1 results: Purity: 100.0%; Observed Mass: 561.99; Retention Time: 2.4 minutes. Injection 2 results: Purity: 100.0%; Observed Mass: 562; Retention Time: 1.55 minutes. Example 13 (15.2 mg) was isolated in 16.2% yield.

Example 14: Injection 1 results: Purity: 100.0%; Observed Mass: 562; Retention Time: 2.4 minutes. Injection 2 results: Purity: 99.1%; Observed Mass: 562; Retention Time: 1.55 minutes. Example 14 (15.3 mg) was isolated in 16.3% yield.

Examples 15 to 17

6-bromo-4-{4-[(4-fluoro-2-methoxyphenyl)(4-fluorophenyl)methyl]piperazin-1-yl}-1-methyl-2-oxo-1,2-dihydro-1,5-naphthyridine-3-carbonitrile

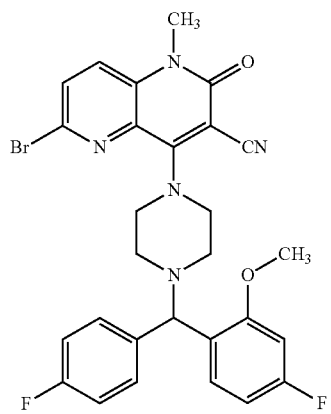

(15)

To a DMF (1.5 mL) solution of 6-bromo-4-chloro-1-methyl-2-oxo-1,2-dihydro-1,5-naphthyridine-3-carbonitrile (50 mg, 0.167 mmol) was added potassium carbonate (93 mg, 0.670 mmol) followed by the addition of 1-((4-fluoro-2-methoxyphenyl)(4-fluorophenyl)methyl)piperazine, 2 TFA (92 mg, 0.167 mmol). The reaction mixture was mixed by shaking at room temperature overnight. LC/MS analysis indicated the reaction was complete. A precipitate was formed. DMF (2 mL) was added followed by ethyl acetate and washed with water and brine. The crude material was purified via preparative LC/MS with the following conditions: Column: XBridge C18, 19×200 mm, 5 μm particles; Mobile Phase A: 5:95 acetonitrile:water with 10 mM ammonium acetate: Mobile Phase B: 95:5 acetonitrile:water with 10 mM ammonium acetate; Gradient: 50-100% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate: Mobile Phase B: 95:5 acetonitrile: water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 98.6%; Observed Mass: 580.12; Retention Time: 2.49 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 580.05; Retention Time: 1.7 minutes. The racemic title compound (22.7 mg) was isolated in 23.4% yield. The racemic material was further purified by using SFC-chiral chromatography to give isomers.

Example 16 (first eluting isomer) and Example 17 (second eluting isomer) were isolated from the racemate using SFC-chiral chromatography. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Example 16: Injection 1 results: Purity: 100.0%; Observed Mass: 580.07; Retention Time: 2.49 minutes. Injection 2 results: Purity: 99.4%; Observed Mass: 580.09; Retention Time: 1.66 minutes. Example 16 (7.5 mg) was isolated in 7.7% yield.

Example 17: Injection 1 results: Purity: 100.0%; Observed Mass: 580.1; Retention Time: 2.49 minutes. Injection 2 results: Purity: 100.0%; Observed Mass: 580.1; Retention Time: 1.66 minutes. Example 17 (7.4 mg) was isolated in 7.6% yield.

Examples 18 to 20

8-{4-[(4-fluorophenyl)(2-methoxyphenyl)methyl]piperazin-1-yl}-5-methyl-7-nitro-6-oxo-5,6-dihydro-1,5-naphthyridine-2-carbonitrile

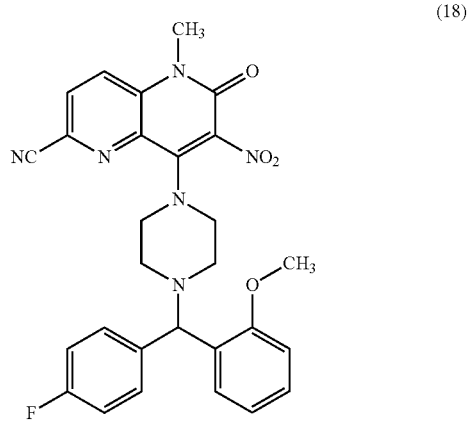 [SMILES: COc1ccccc1C(c1ccc(F)cc1)N1CCN(c2c([N+](=O)[O-])c(=O)n(C)c3ccc(C#N)nc23)CC1]

(18)

To a DMF (1 mL) solution of 8-chloro-5-methyl-7-nitro-6-oxo-5,6-dihydro-1,5-naphthyridine-2-carbonitrile (30 ng, 0.113 mmol) was added Hunig's Base (0.099 mL, 0.567 mmol) followed by the addition of 1-((4-fluorophenyl)(2-methoxyphenyl)methyl) piperazine, 2 TFA (59.9 mg, 0.113 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 47-87% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 529.17; Retention Time: 2.38 minutes. Injection 2 conditions: Column: Waters XBridge C18, 2.1 mm×50 mm, 1.7 μm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 529.15; Retention Time: 1.62 minutes. The racemic title compound (42.4 mug) was isolated in 70% yield. The racemic material was further purified by using SFC-chiral chromatography to give isomers.

Example 19 (first eluting isomer) and Example 20 (second eluting isomer) were isolated from the racemate using SFC-chiral chromatography. Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 nm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Example 19: Injection 1 results: Purity: 100.0%; Observed Mass: 529.16; Retention Time: 2.38 minutes. Injection 2 results: Purity: 99.4%; Observed Mass: 529.18; Retention Time: 1.62 minutes. Example 19 (9 mg) was isolated in 29% yield.

Example 20: Injection 1 results: Purity: 100.0%; Observed Mass: 529.17; Retention Time: 2.38 minutes. Injection 2 results: Purity: 100.0%; Observed Mass: 529.15; Retention Time: 1.62 minutes. Example 20 (9.9 mg) was isolated in 33% yield.

Example 21

6-bromo-4-[4-(6-methoxy-2,3-dihydro-1H-inden-1-yl)piperazin-1-yl]-1-methyl-2-oxo-1,2-dihydro-1,5-naphthyridine-3-carbonitrile

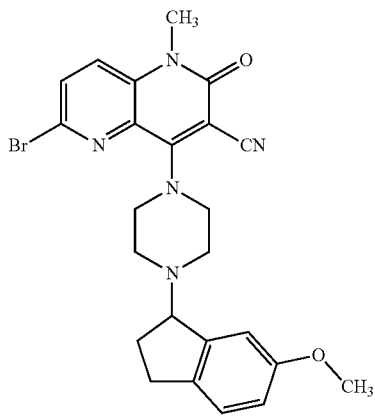

(21)

To a DMF (1.5 mL) solution of 6-bromo-4-chloro-1-methyl-2-oxo-1,2-dihydro-1,5-naphthyridine-3-carbonitrile (50 mg, 0.167 mmol) was added potassium carbonate (93 mg, 0.670 mmol) followed by the addition of 1-(6-methoxy-2,3-dihydro-1H-inden-1-yl)piperazine 2 TFA (77 mg, 0.167 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 40-80% B over 22 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 98.0%; Observed Mass: 494.06; Retention Time: 1.35 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 97.9%; Observed Mass: 494.08; Retention Time: 2.09 minutes. The title compound (19.7 mg) was isolated in 59.5% yield.

Examples 22-24

6-bromo-4-{4-[1-(4-fluorophenyl)ethyl]piperazin-1-yl}-1-methyl-2-oxo-1,2-dihydro-1,5-naphthyridine-3-carbonitrile

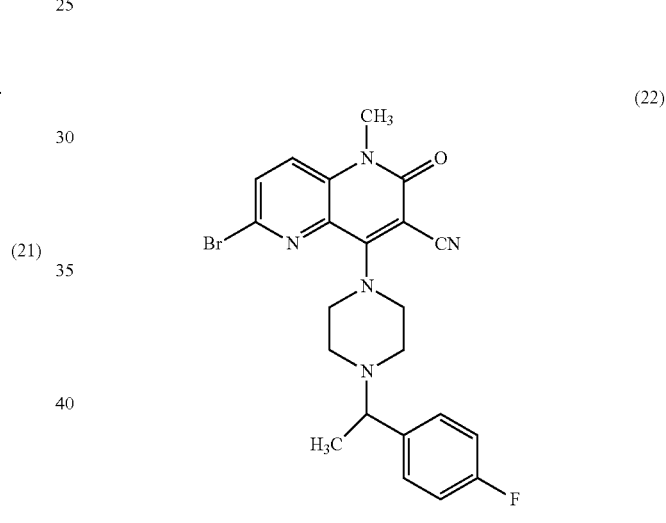

(22)

To a DMF (1 mL) solution of 6-bromo-4-chloro-1-methyl-2-oxo-1,2-dihydro-1,5-naphthyridine-3-carbonitrile (20 mg, 0.067 mmol) and 1-(1-(4-fluorophenyl)ethyl) piperazine (27.9 mg, 0.134 mmol) was added Hunig's Base (0.035 mL, 0.201 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 42-82% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 470.05; Retention Time: 2.11 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 470.05; Retention Time: 1.3 minutes. The title compound (19.8 mg) was isolated in 62.8% yield. The racemic material was further purified by using SFC-chiral chromatography to give isomers.

Example 23 (first eluting isomer) and Example 24 (second eluting isomer) were isolated from the racemate using SFC-chiral chromatography. Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Example 23: Injection 1 results: Purity: 100.0%; Observed Mass: 470.06; Retention Time: 2.11 minutes. Injection 2 results: Purity: 100.0%; Observed Mass: 470.05; Retention Time: 1.26 minutes. Example 23 (6.2 mg) was isolated in 19.7% yield.

Example 24: Injection 1 results: Purity: 100.0%; Observed Mass: 470.03; Retention Time: 2.11 minutes. Injection 2 results: Purity: 98.5%; Observed Mass: 470.04; Retention Time: 1.26 minutes. Example 24 (6.3 mg) was isolated in 20% yield.

Examples 25 to 27

6-bromo-4-{4-[1-(4-fluorophenyl)propyl]piperazin-1-yl}-1-methyl-2-oxo-1,2-dihydro-1,5-naphthyridine-3-carbonitrile (25)

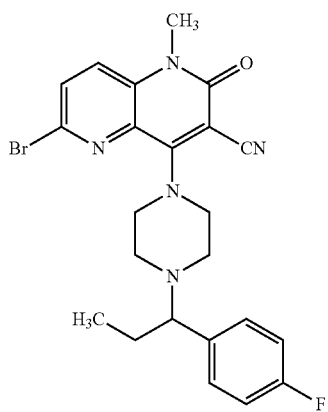

To a DMF (0.5 mL) solution of 6-bromo-4-chloro-1-methyl-2-oxo-1,2-dihydro-1,5-naphthyridine-3-carbonitrile (15 mg, 0.050 mmol) were added Hunig's Base (0.026 mL, 0.151 mmol) and 1-(1-(4-fluorophenyl)propyl)piperazine (22.34 mg, 0.100 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 41-81% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 minutes, then a 0.75 minute hold at 100% B; Flow: 1 mL/minute; Detection: MS and UV (220 nm). Injection 1 results: Purity 100.0%; Observed Mass: 484.1; Retention Time: 1.4 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 484.06; Retention Time: 2.26 minutes. The racemic title compound (20.4 mug) was isolated in 84.2% yield. The racemic material was further purified by using SFC-chiral chromatography to give isomers.

Example 26 (first eluting isomer) and Example 27 (second eluting isomer) were isolated from the racemate using SFC-chiral chromatography. Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Example 26: Injection 1 results: Purity: 96.7%; Observed Mass: 483.96; Retention Time: 1.53 minutes. Injection 2 results: Purity: 100.0%; Observed Mass: 483.97; Retention Time: 2.19 minutes. Example 26 (7.6 mg) was isolated in 31.4% yield.

Example 27: Injection 1 results: Purity: 97.3%; Observed Mass: 483.96; Retention Time: 1.34 minutes. Injection 2 results: Purity: 97.7%; Observed Mass: 483.97; Retention Time: 2.19 minutes. Example 27 (7.4 mg) was isolated in 30.6% yield.

Examples 28 to 30

6-bromo-4-{4-[2-(4-fluorophenyl)-2-hydroxyethyl]piperazin-1-yl}-1-methyl-2-oxo-1,2-dihydro-1,5-naphthyridine-3-carbonitrile

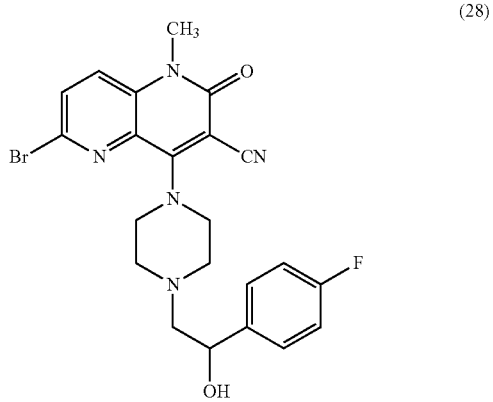 [SMILES: Cn1c(=O)c(C#N)c(N2CCN(CC(O)c3ccc(F)cc3)CC2)c2nc(Br)ccc21]

(28)

To a DMF (0.5 mL) solution of 6-bromo-4-chloro-1-methyl-2-oxo-1,2-dihydro-1,5-naphthyridine-3-carbonitrile (15 mg, 0.050 mmol) were added Hunig's Base (0.026 mL, 0.151 mmol) and a mixture of 1-(4-fluorophenyl)-2-(piperazin-1-yl)ethan-1-ol, TFA and 2-(4-fluorophenyl)-2-(piperazin-1-yl)ethanol TFA (34.0 mg, 0.100 mmol). The reaction mixture was mixed by shaking at room temperature for 1 hour. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 25-70% B over 20 minutes, then a 6-minute hold at 100% B; Flow: 20 mL/minute. Fractions containing the secondary alcohol isomer were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 2 results: Purity: 98.9%: retention time: 1.16; Obs. Adducts: [M+H]; Obs. Masses: 485.91. Injection 1 results: Purity: 100.0%; retention time: 1.61; Obs. Adducts: [M+H]; Obs. Masses: 485.93. The racemic title compound (15.4 mg) was isolated in 62% yield. The racemic material was further purified by using SFC-chiral chromatography to give isomers. The isomer 6-bromo-4-{4-[1-(4-fluorophenyl)-2-hydroxyethyl]piperazin-1-yl}-1-methyl-2-oxo-1,2-dihydro-1,5-naphthyridine-3-carbonitrile was also isolated.

Example 29 (first eluting isomer) and Example 30 (second eluting isomer) were isolated from the racemate using SFC-chiral chromatography. Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Example 29: Injection 1 results: Purity: 98.3%; Observed Mass: 486.06; Retention Time: 1.65 minutes. Injection 2 results: Purity: 98.0%; Observed Mass: 486.05; Retention Time: 1.21 minutes. Example 29 (6.2 mg) was isolated in 25.5% yield.

Example 30: Injection 1 results: Purity: 98.2%; Observed Mass: 486.06; Retention Time: 1.65 minutes. Injection 2 results: Purity: 97.9%; Observed Mass: 486.03; Retention Time: 1.21 minutes. Example 30 (5.3 mg) was isolated in 21.8% yield.

Example 31

6-bromo-4-{4-[1-(4-fluorophenyl)-2-hydroxyethyl]piperazin-1-yl}-1-methyl-2-oxo-1,2-dihydro-1,5-naphthyridine-3-carbonitrile

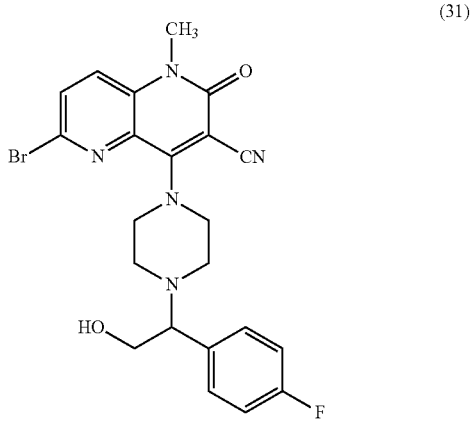 [SMILES: Cn1c(=O)c(C#N)c(N2CCN(C(CO)c3ccc(F)cc3)CC2)c2nc(Br)ccc21]

(31)

Fractions containing the primary alcohol isomer were combined and dried via centrifugal evaporation. Two analytical LC/MS injections were used to determine the final purity. Injection 1 conditions: Column: Waters Acquity UPLC BEH C18, 2.1×50 nm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 nm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute;

Detection: UV at 220 nm. Injection 2 results: Purity: 94.2%; retention time: 1.2; Obs. Adducts: [M+H]; Obs. Masses: 485.93. Injection 1 results: Purity: 95.2%; retention time: 1.72; Obs. Adducts: [M+H]; Obs. Masses: 485.95. The title compound (3.5 mg) was isolated in 14.4% yield.

Examples 32 to 34

8-{4-[1-(4-fluorophenyl)propyl]piperazin-1-yl}-5-methyl-7-nitro-6-oxo-5,6-dihydro-1,5-naphthyridine-2-carbonitrile

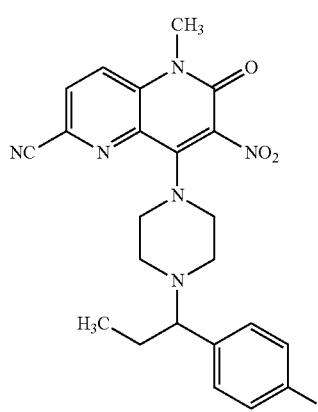

(32)

To a DMF (1 mL) solution of 8-chloro-5-methyl-7-nitro-6-oxo-5,6-dihydro-1,5-naphthyridine-2-carbonitrile (20 mg, 0.076 mmol) was added 1-(1-(4-fluorophenyl) propyl)piperazine (18.48 mg, 0.083 mmol)) followed by Hunig's Base (0.040 mL, 0.227 mmol). The reaction mixture was mixed by shaking at room temperature for 2 hours. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 40-80% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 451.14; Retention Time: 1.33 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 451.15; Retention Time: 2.17 minutes. The racemic title compound (27.3 mg) was isolated in 79.7% yield. The racemic material was further purified by using SFC-chiral chromatography to give isomers.

Example 33 (first eluting isomer) and Example 34 (second eluting isomer) were isolated from the racemate using SFC-chiral chromatography. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and IV (220 nm).

Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Example 33: Injection 1 results: Purity: 98.9%; Observed Mass: 451.11; Retention Time: 1.33 minutes. Injection 2 results: Purity: 100.0%; Observed Mass: 451.15; Retention Time: 2.17 minutes. Example 33 (7.7 mg) was isolated in 22.5% yield.

Example 34: Injection 1 results: Purity: 100.0%; Observed Mass: 451.13; Retention Time: 1.33 minutes. Injection 2 results: Purity: 100.0%; Observed Mass: 451.14; Retention Time: 2.17 minutes. Example 34 (8.4 mg) was isolated in 24.5% yield.

Example 35

6-bromo-4-{4-[cyclopropyl(4-fluorophenyl)methyl]piperazin-1-yl}-1-methyl-2-oxo-1,2-dihydro-1,5-naphthyridine-3-carbonitrile

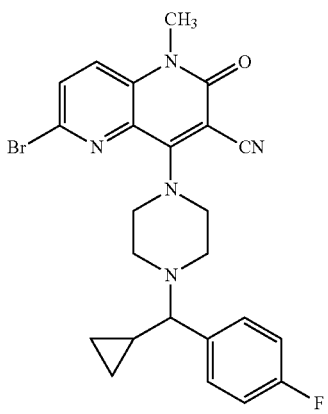

(35)

To a DMF (1 mL) solution of 1-(cyclopropyl(4-fluorophenyl)methyl)piperazine, TFA (23.34 mg, 0.067 mmol) and 6-bromo-4-chloro-1-methyl-2-oxo-1,2-dihydro-1,5-naphthyridine-3-carbonitrile (20 mg, 0.067 mmol) was added Hunig's Base (0.012 mL, 0.067 mmol). The reaction mixture was mixed by shaking at room temperature for 2 hours. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient:

43-83% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 496.13; Retention Time: 2.25 minutes. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 496.07; Retention Time: 1.39 minutes. The title compound (5.1 mg) was isolated in 15.3% yield.

Example 36

8-{4-[2-(4-fluorophenyl)-2-hydroxyethyl]piperazin-1-yl}-5-methyl-7-nitro-6-oxo-5,6-dihydro-1,5-naphthyridine-2-carbonitrile

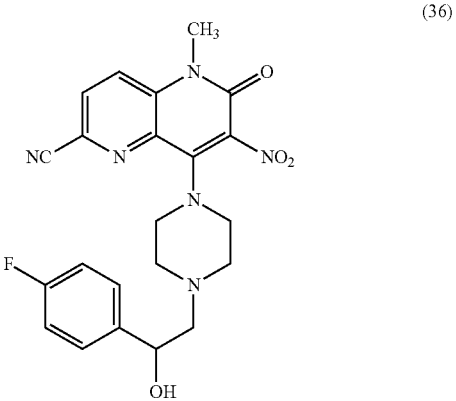 [SMILES: Cn1c(=O)c([N+](=O)[O-])c(N2CCN(CC(O)c3ccc(F)cc3)CC2)c2nc(C#N)ccc21]

(36)

An ethanol (2 mL) mixture of 5-methyl-7-nitro-6-oxo-8-(piperazin-1-yl)-5,6-dihydro-1,5-naphthyridine-2-carbonitrile (20 mg, 0.064 mmol) and 2-(4-fluorophenyl) oxirane (26.4 mg, 0.191 mmol) was heated at reflux overnight. DMF (2 mL) was added and the reaction mixture was heated in microwave at 110° C. for 45 minutes. LC/MS analysis indicated approximately 50% conversion. The reaction mixture was heated at 120° C. in microwave for 1 h. LC/MS analysis indicated that approximately 80% of the desired product had formed. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 20-80% B over 22 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 453.11; Retention Time: 1.2 minutes. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 98.6%; Observed Mass: 453.13; Retention Time: 1.74 minutes. The title compound (3.2 mg) was isolated in 11.1% yield.

Example 37

8-{4-[1-(4-fluorophenyl)-2-hydroxyethyl]piperazin-1-yl}-5-methyl-7-nitro-6-oxo-5,6-dihydro-1,5-naphthyridine-2-carbonitrile

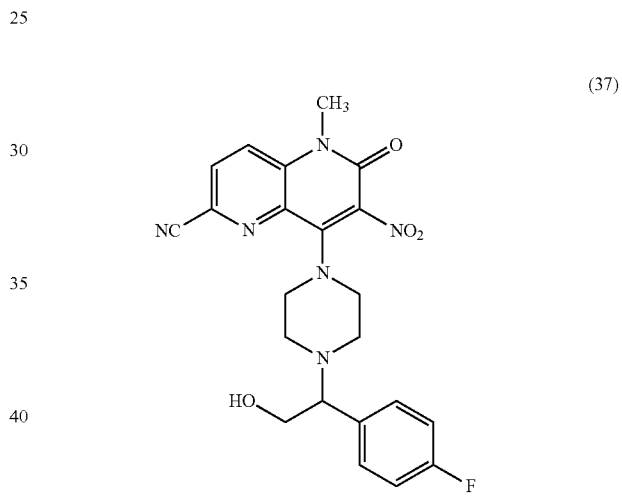

(37)

A second isomer was isolated in the synthesis of 8-{4-[2-(4-fluorophenyl)-2-hydroxyethyl]piperazin-1-yl}-5-methyl-7-nitro-6-oxo-5,6-dihydro-1,5-naphthyridine-2-carbonitrile and purified via preparative LC/MS with the following conditions: Column: XBridge C18, 19×200 mm, 5 µm particles; Mobile Phase A: 5:95 acetonitrile: water with 10 mM ammonium acetate; Mobile Phase B: 95:5 acetonitrile:water with 10 mM ammonium acetate; Gradient: 20-80% B over 22 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 nm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 96.8%; Observed Mass: 453.16; Retention Time: 1.16 minutes. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 453.1; Retention Time: 1.61 minutes. The title compound (1.2 mg) was isolated in 4.1% yield.

Example 38

1-methyl-4-{4-[(naphthalen-1-yl)methyl]piperazin-1-yl}-3-nitro-1,2-dihydro-1,5-naphthyridin-2-one

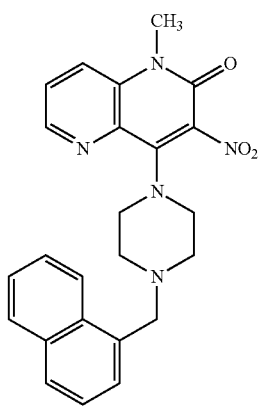

(38)

To a DMF (1 mL) solution of 4-(4-(napthalen-1-ylmethyl)piperazin-1-yl)-3-nitro-1,5-naphthyridin-2(1H)-one (20 mg, 0.048 mmol) was added sodium hydride (2.311 mg, 0.096 mmol). The reaction mixture was stirred at room temperature for 5 minutes. Iodomethane (6.02 μl, 0.096 mmol) was added and the reaction mixture was stirred at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 35-75% B over 15 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH CIS, 2.1×50 mm, 1.7 in particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 1 results: Purity: 100%; Observed Mass: 430.0; Retention Time: 2.5 minutes. Injection 2 results: Purity: 94.7%; Observed Mass: 430.0; Retention Time: 1.5 minutes. The title compound (5.4 ng) was isolated in 26.2% yield.

Example 39

6-chloro-4-{4-[(4-fluorophenyl)[2-(prop-2-yn-1-yloxy)phenyl]methyl]piperazin-1-lv}-1-methyl-2-oxo-1,2-dihydro-1,5-naphthyridine-3-carbonitrile

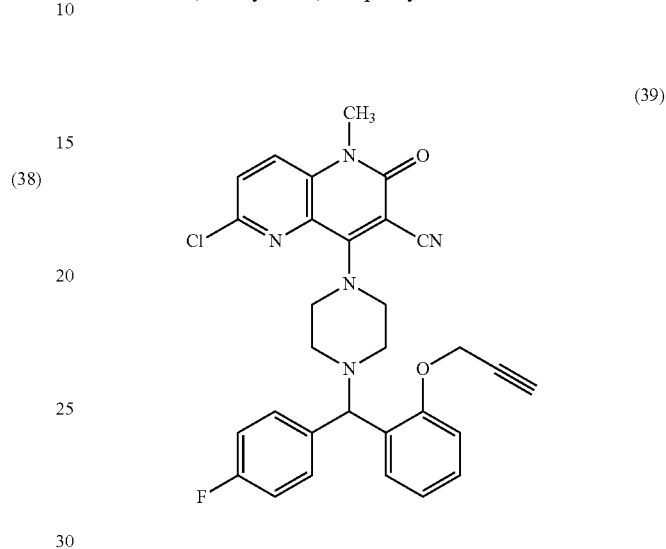

(39)

To a DMF (1 mL) solution of 4,6-dichloro-1-methyl-2-oxo-1,2-dihydro-1,5-naphthyridine-3-carbonitrile (32 ng, 0.126 mmol) was added DIPEA (0.066 mL, 0.378 mmol) followed with 1-((4-fluorophenyl)(2-(prop-2-yn-1-yloxy)phenyl)methyl) piperazine, TFA (60.7 mg, 0.139 mmol). The reaction mixture was mixed by shaking at room temperature for 2 hours and LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-90% B over 15 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 542.05; Retention Time: 1.54 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.: Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 542.05; Retention Time: 2.32 minutes. The title compound (33.8 mg) was isolated in 49.5% yield.

Example 40

8-(4-(bis(4-fluorophenyl)methyl)piperazin-1-yl)-5-methyl-7-nitro-6-oxo-5,6-dihydro-1,5-naphthyridine-2-carbonitrile

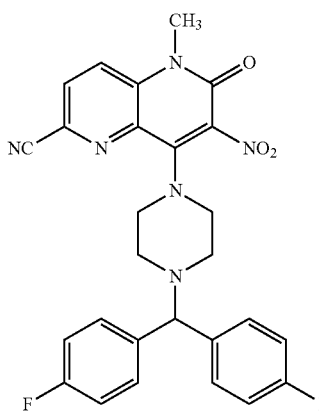

(40)

DMF was sparged with nitrogen for 1 hour. In a 1 dram vial was charged with zinc (0.95 mg, 0.015 mmol), bromo(tri-tert-butylphosphine)palladium(I) dimer (9.96 mg, 0.013 mmol) and 4-(4-(bis(4-fluorophenyl)methyl)piperazin-1-yl)-6-bromo-1-methyl-3-nitro-1,5-naphthyridin-2(1H)-one (21.38 mg, 0.037 mmol). The sparged DMF (0.3 mL) was added and the mixture was capped under nitrogen and immersed in a 50° C. oil bath for 15 minutes. Dicyanozinc (2.86 mg, 0.024 mmol) was added. The reaction mixture was capped under nitrogen and immersed in 50° C. oil bath for 3 hours. LC/MS analysis indicated the reaction was complete. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 50-90% B over 15 minutes, then a 5 minute hold at 100% B; Flow: 20 mL/minute. Fractions containing the product were combined and dried via centrifugal evaporation. The title compound (11.4 mg) was isolated in 59.7% yield.

Alternative synthesis: A DMF (6 mL) solution of 8-chloro-5-methyl-7-nitro-6-oxo-5,6-dihydro-1,5-naphthyridine-2-carbonitrile (750 mg, 2.83 mmol) was combined with 1-(bis(4-fluorophenyl)methyl)piperazine (899 mg, 3.12 mmol)) followed by the addition of Hunig's Base (0.990 mL, 5.67 mmol). The reaction mixture was stirred at room temperature overnight. LC/MS analysis indicated the reaction was completed. The crude material was filtered and purified by preparative HPLC employing aqueous acetonitrile with ammonium acetate as the buffer to afford 1.02 g of yellow solid. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 1 results: Purity: 100%; Observed Mass: 517.0; Retention Time: 2.4 minutes. Injection 2 results: Purity: 98.4%; Observed Mass: 517.0; Retention Time: 1.7 minutes. $^1$H NMR (500 MHz, chloroform-d) δ 7.88 (d, J=8.7 Hz, 1H), 7.76 (d, J=8.9 Hz, 1H), 7.40 (dd, J=8.5, 5.5 Hz, 4H), 7.02 (t, J=8.7 Hz, 4H), 4.34 (s, 1H), 3.68 (s, 3H), 3.62-3.55 (m, 4H), 2.64 (br s, 4H). $^{13}$C NMR (126 MHz, chloroform-d) δ 163.0, 161.0, 155.4, 147.0, 138.0, 137.7, 137.7, 135.9, 132.4, 129.5, 1292, 129.2, 126.0, 123.1, 116.5, 115.8, 115.6, 74.3, 51.6, 51.2, 29.7.

Example 41

8-(4-benzhydrylpiperazin-1-yl)-5-methyl-7-nitro-6-oxo-5,6-dihydro-1,5-naphthyridine-2-carbonitrile

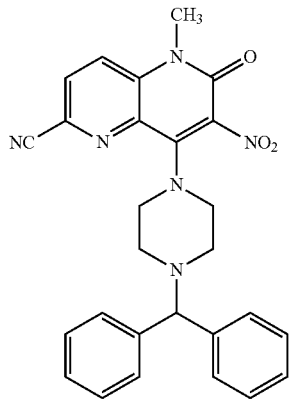

(41)

DMF was sparged with nitrogen for 1 hour. In 1 dram vial, zinc (1.2 mg, 0.018 mmol), bromo(tri-tert-butylphosphine)palladium(i) dimer (16 mg, 0.021 mmol), and 4-(4-benzhydrylpiperazin-1-yl)-6-bromo-1-methyl-3-nitro-1,5-naphthyridin-2(1H)-one (22.82 mg, 0.043 mmol) was charged. The sparged DMF (0.3 mL) was added and the mixture was capped under nitrogen. The vial was immersed in a 50° C. oil bath for 15 minutes. Dicyanozinc (3.7 mg, 0.032 mmol) was added. The vial was sealed under nitrogen and immersed in 50° C. oil bath for 3 hours. LC/MS analysis indicated the reaction was complete. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 50-100% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column:

Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0-100% B over 3 minutes, then a 0.75 minute hold at 100% B; Flow: 1.0 mL/minute; Detection: UV at 220 nm. Injection 1 results: Purity: 100%; Observed Mass: 481.0; Retention Time: 2.4 minutes. Injection 2 results: Purity: 100%; Observed Mass: 481.0; Retention Time: 1.6 minutes. The title compound (13 mg) was isolated in 62.9% yield.

Example 42

8-(4-((2-hydroxyphenyl)(phenyl)methyl)piperazin-1-yl)-5-methyl-7-nitro-6-oxo-5,6-dihydro-1,5-naphthyridine-2-carbonitrile

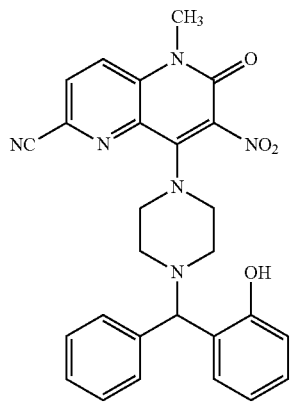

(42)

DMF was sparged with nitrogen for 1 hour. In a 1 dram vial, zinc (0.95 mg, 0.015 mmol), bromo(tri-tert-butylphosphine)palladium(I) dimer (9.96 mg, 0.013 mmol), and 6-bromo-4-(4-((2-hydroxyphenyl)(phenyl)methyl)piperazin-1-yl)-1-methyl-3-nitro-1,5-naphthyridin-2(1H)-one (22.02 mg, 0.040 mmol) were combined. DMF (0.3 mL) was added. The vial was capped under nitrogen and immersed in a 50° C. oil bath for 15 minutes. Dicyanozinc (2.86 mg, 0.024 mmol) was added. The vial was sealed under nitrogen and immersed in a 50° C. oil bath for 3 hours. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 40-90% B over 20 minutes, then a 5 minute hold at 100% 13; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 1 results: Purity: 95.4%; Observed Mass: 550.0; Retention Time: 2.3 minutes. Injection 2 results: Purity: 96.0%; Observed Mass: 550.0; Retention Time: 1.6 minutes. The title compound (5 mg) was isolated in 25.2% yield.

Examples 43 to 45

8-(4-(1-(4-fluorophenyl)ethyl)piperazin-1-yl)-5-methyl-7-nitro-6-oxo-5,6-dihydro-1,5-naphthyridine-2-carbonitrile

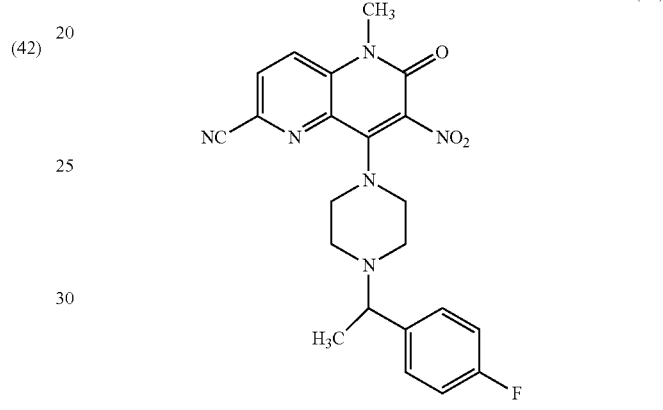

(43)

To a DMF (1 mL) solution of 8-chloro-5-methyl-7-nitro-6-oxo-5,6-dihydro-1,5-naphthyridine-2-carbonitrile (20 mg, 0.060 mmol) and 1-(1-phenylethyl)piperazine (50.6 mg, 0.121 mmol) was added Hunig's Base (0.032 mL, 0.181 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 37-77% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 437.11; Retention Time: 2.05 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 437.11; Retention Time: 1.23 minutes. The racemic title compound (18 mg) was isolated in 68.7% yield. The racemic material was further purified by using SFC-chiral chromatography to give isomers.

Example 44 (first eluting isomer) and Example 45 (second eluting isomer) were isolated from the racemate using SFC-chiral chromatography. Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 m/minute; Detection: MS and UV (220 nm).

Example 44: Injection 1 results: Purity: 97.5%; Observed Mass: 437.14; Retention Time: 1.24 minutes. Injection 2 results: Purity: 98.4%; Observed Mass: 437.11; Retention Time: 2.06 minutes. Example 44 (6.7 mg) was isolated in 25.6% yield.

Example 45: Injection 1 results: Purity: 97.5%; Observed Mass: 437.14; Retention Time: 1.24 minutes. Injection 2 results: Purity: 98.4%; Observed Mass: 437.11; Retention Time: 2.06 minutes. Example 45 (7.2 mg) was isolated in 27.5% yield.

Example 46

8-(4-(6-methoxy-2,3-dihydro-1H-inden-1-yl)piperazin-1-yl)-5-methyl-7-nitro-6-oxo-5,6-dihydro-1,5-naphthyridine-2-carbonitrile

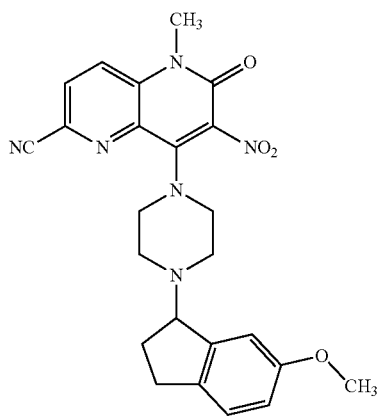

(46)

To a DMF (1 mL) solution of 8-chloro-5-methyl-7-nitro-6-oxo-5,6-dihydro-1,5-naphthyridine-2-carbonitrile (20 mg, 0.060 mmol) and 1-(6-methoxy-2,3-dihydro-1H-inden-1-yl) piperazine (55.7 mg, 0.121 mmol) was added Hunig's Base (0.032 mL, 0.181 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles;

Mobile Phase A: 5:95 acetonitrile:water with 10 mM ammonium acetate; Mobile Phase B: 95:5 acetonitrile:water with 10 mM ammonium acetate; Gradient: 41-81% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 99.3%; Observed Mass: 461.15; Retention Time: 2.03 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 461.15; Retention Time: 1.29 minutes. The title compound (16.1 mg) was isolated in 58.3% yield.

Example 47

8-(4-(2-hydroxy-1-phenylethyl)piperazin-1-yl)-5-methyl-7-nitro-6-oxo-5,6-dihydro-1,5-naphthyridine-2-carbonitrile

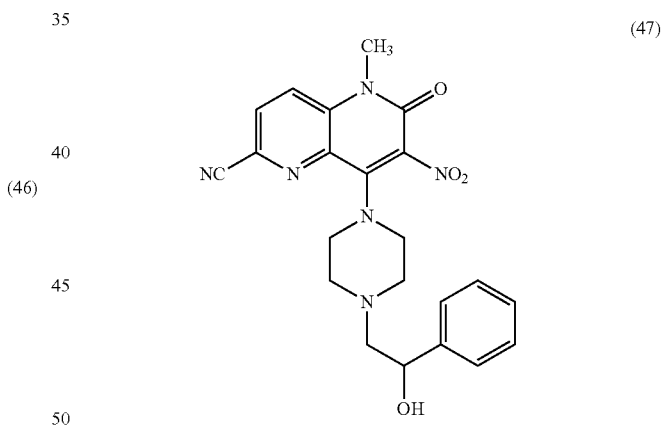

(47)

To an ethanol (2 mL) mixture of 5-methyl-7-nitro-6-oxo-8-(piperazin-1-yl)-5,6-dihydro-1,5-naphthyridine-2-carbonitrile (20 mg, 0.064 mmol) was added 2-phenyloxirane (15.29 mg, 0.127 mmol). The reaction mixture was heated at reflux overnight. LC/MS analysis indicated the absence of the desired product. DMF (2 mL) was added and the reaction mixture was heated in microwave at 100° C. for 30 minutes. LC/MS analysis indicated approximately 50% conversion. The reaction mixture was heated at 120° C. for 45 minutes. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 25-75% B over 25 minutes, then a 4 minute hold at 100% B;

Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 435.14; Retention Time: 1.68 minutes. Injection 2 conditions: Column: Waters XBridge C18, 2.1 mm×50 mm, 1.7 μm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and IV (220 nm). Injection 2 results: Purity: 100.0%; Observed Mass: 435.16; Retention Time: 1.16 minutes. The title compound (7.1 mg) was isolated in 25.5% yield.

Example 48

8-(4-(2-hydroxy-2-phenylethyl)piperazin-1-yl)-5-methyl-7-nitro-6-oxo-5,6-dihydro-1,5-naphthyridine-2-carbonitrile

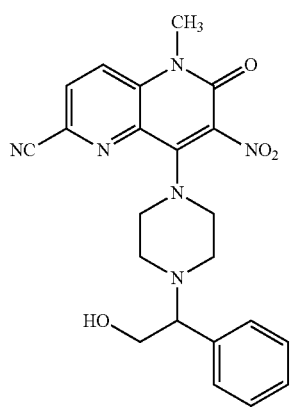

(48)

A second isomer was isolated from the synthesis of 8-[4-(2-hydroxy-2-phenylethyl)piperazin-1-yl]-5-methyl-7-nitro-6-oxo-5,6-dihydro-1,5-naphthyridine-2-carbonitrile. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 435.12; Retention Time: 1.56 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 435.12; Retention Time: 1.13 minutes. The title compound (2.2 mg) was isolated in 8% yield.

Examples 49 to 51

8-(4-(cyclopropyl(4-fluorophenyl)methyl)piperazin-1-yl)-5-methyl-7-nitro-6-oxo-5,6-dihydro-1,5-naphthyridine-2-carbonitrile

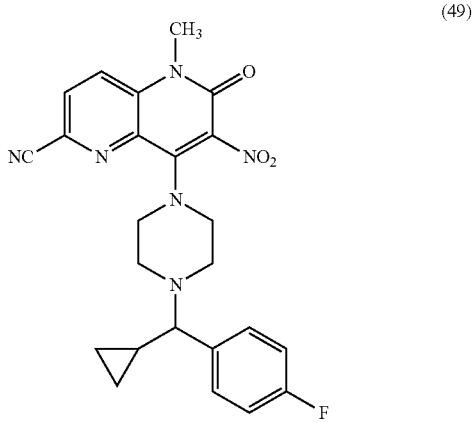 [SMILES: Cn1c(=O)c([N+](=O)[O-])c(N2CCN(C(c3ccc(F)cc3)C3CC3)CC2)c2nc(C#N)ccc21]

(49)

To a DMF (1 mL) solution of 1-(cyclopropyl(4-fluorophenyl)methyl)piperazine, TFA (26.3 mg, 0.076 mmol) and 8-chloro-5-methyl-7-nitro-6-oxo-5,6-dihydro-1,5-naphthyridine-2-carbonitrile (20 mg, 0.076 mmol) was added Hunig's Base (0.013 mL, 0.076 mmol). The reaction mixture was mixed by shaking at room temperature for 2 hours. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 41-81% B over 20 minutes, then a 4 minute hold at 100% B; Flow: 20 mL/minute. Fractions containing the product were combined and dried via centrifugal evaporation. The material was further purified via preparative LC/MS with the following conditions: Column: XBridge C18, 19×200 mm, 5 μm particles; Mobile Phase A: 5:95 acetonitrile:water with 10 mM ammonium acetate: Mobile Phase B: 95:5 acetonitrile:water with 10 mM ammonium acetate; Gradient: 32-72'% B over 25 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 463.12; Retention Time: 1.35 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0%

B to 100% B over 3 minutes, then a 0.75 minute hold at 100% B; Flow: 1 mL/minute; Detection: MS and UV (220 nm). Injection 2 results: Purity: 100.0%; Observed Mass: 463.12; Retention Time: 2.18 minutes. The racemic title compound (13.7 mg) was isolated in 39% yield. The racemic material was further purified by using SFC-chiral chromatography to give isomers.

Example 50 (first eluting isomer) and Example 51 (second eluting isomer) were isolated from the racemate using SFC-chiral chromatography. Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Example 50: Injection 1 results: Purity: 100.0%; Observed Mass: 463.03; Retention Time: 1.35 minutes. Injection 2 results: Purity: 100.0%; Observed Mass: 463.03; Retention Time: 2.15 minutes. Example 50 (6.7 mg) was isolated in 19.1% yield.

Example 51: Injection 1 results: Purity: 100.0%; Observed Mass: 463.02; Retention Time: 1.35 minutes. Injection 2 results: Purity: 100.0%; Observed Mass: 463.02; Retention Time: 2.16 minutes. Example 51 (6.5 mg) was isolated in 18.5% yield.

Example 52

4-(4-benzhydrylpiperazin-1-yl)-6-bromo-1-methyl-3-nitro-1,5-naphthyridin-2(1H)-one

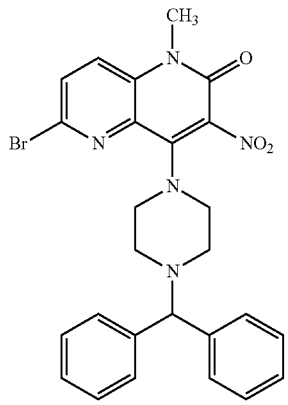

(52)

To a DMF (mL) solution of 6-bromo-4-chloro-1-methyl-3-nitro-1,5-naphthyridin-2(1H)-one (20 mg, 0.063 mmol) were added DIPEA (0.033 mL, 0.188 mmol) and 1-benzhydrylpiperazine (15.85 mg, 0.063 mmol). The reaction mixture was mixed by shaking at 35° C. overnight. LC/MS analysis indicated the reaction was complete. The clear yellow solution was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-90% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles: Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 1 results: Purity: 100%; Observed Mass: 534.0; Retention Time: 2.6 minutes. Injection 2 results: Purity: 83.0%; Observed Mass: 534.0; Retention Time: 1.6 minutes. The title compound (9.8 mg) was isolated in 29.1% yield.

Example 53

4-(4-(bis(4-fluorophenyl)methyl)piperazin-1-yl)-6-bromo-1-methyl-3-nitro-1,5-naphthyridin-2(1H)-one

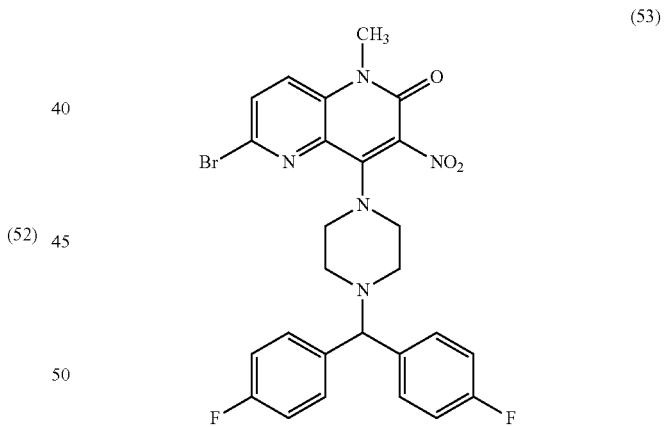

(53)

To a DMF (1 mL) solution of 6-bromo-4-chloro-1-methyl-3-nitro-1,5-naphthyridin-2(1H)-one (20 ng, 0.063 mmol) were added DIPEA (0.033 mL, 0.188 mmol) and 1-(bis(4-fluorophenyl)methyl)piperazine (18.11 mg, 0.063 mmol). The reaction mixture was mixed by shaking at 35° C. overnight. LC/MS analysis indicated the reaction was complete. The clear yellow solution was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 55-95% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 nm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 1 results: Purity: 100%; Observed Mass: 570.0; Retention Time: 2.6 minutes. Injection 2 results: Purity: 100.0%; Observed Mass: 570.0; Retention Time: 1.8 minutes. The title compound (16.4 mg) was isolated in 45.6% yield.

Example 54

6-bromo-4-(4-((1-ethyl-H-indol-4-yl)methyl)piperazin-1-yl)-1-methyl-3-nitro-1,5-naphthyridin-2(1H)-one

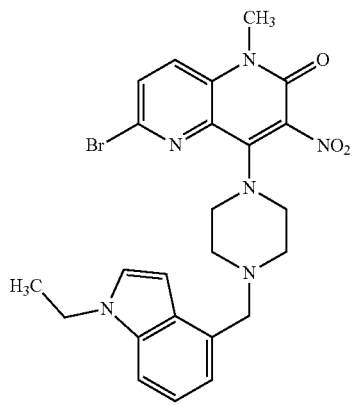

(54)

To a DMF (1 mL) solution of 6-bromo-4-chloro-1-methyl-3-nitro-1,5-naphthyridin-2(1H)-one (20 mg, 0.063 mmol) were added DIPEA (0.033 mL, 0.188 mmol) and 1-ethyl-4-(piperazin-1-ylmethyl)-1-indole, 2 TFA (29.6 mg, 0.063 mmol). The reaction mixture was mixed by shaking at 35° C. overnight. LC/MS analysis indicated the reaction was complete. The clear yellow solution was purified using reverse phase HPLC for purification. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 50-90% B over 15 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 21×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 1 results: Purity: 100%; Observed Mass: 524.9; Retention Time: 2.3 minutes. Injection 2 results: Purity: 99.1%; Observed Mass: 524.9; Retention Time: 1.5 minutes. The title compound (14.9 mg) was isolated in 45% yield.

Example 55

6-bromo-1-methyl-4-(4-(naphthalen-1-ylmethyl)piperazin-1-yl)-3-nitro-1,5-naphthyridin-2(1H)-one

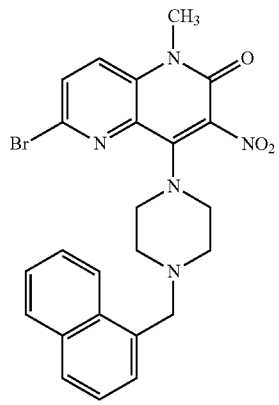

(55)

To a DMF (1 mL) solution of 6-bromo-4-chloro-r-methyl-3-nitro-1,5-naphthyridin-2(1H)-one (20 mg, 0.063 mmol) was added 1-(naphthalen-1-ylmethyl) piperazine (17.05 mg, 0.075 mmol), followed by the addition of DIPEA (0.033 mL, 0.188 mmol). The reaction mixture was mixed by shaking at 35° C. overnight. LC/MS analysis indicated the reaction was complete. The crude material was purified via preparative LC/MS with the following conditions: Column: XBridge C18, 19×200 mm, 5 pam particles; Mobile Phase A: 5:95 acetonitrile:water with 10 mM ammonium acetate; Mobile Phase B: 95:5 acetonitrile:water with 10 mM ammonium acetate; Gradient: 55-95% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100%

B; Flow: 1.0 mL/minute; Detection: UV at 220 nm. Injection 1 results: Purity: 100%; Observed Mass: 508.0; Retention Time: 2.5 minutes. Injection 2 results: Purity: 100%; Observed Mass: 508.0; Retention Time: 1.5 minutes. The title compound (18.3 mg) was isolated in 57.1% yield.

Examples 56 to 58

6-bromo-4-(4-((4-fluoro-2-methoxyphenyl)(4-fluorophenyl)methyl)piperazin-1-yl)-1-methyl-3-nitro-1,5-naphthyridin-2(1H)-one

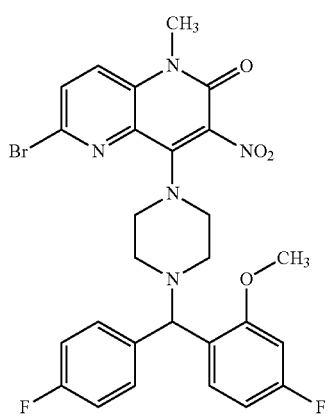

(56)

To a DMF (1 mL) solution of 6-bromo-4-chloro-1-methyl-3-nitro-1,5-naphthyridin-2(1H)-one (50 mg, 0.157 mmol) were added 1-((4-fluoro-2-methoxyphenyl) (4-fluorophenyl)methyl)piperazine, TFA (102 mg, 0.235 mmol) and DIPEA (0.082 mL, 0.471 mmol). The reaction mixture was mixed by shaking at 35° C. overnight. LC/MS analysis indicated the reaction was complete. The crude material was purified via preparative LC/MS with the following conditions: Column: XBridge C18, 19×200 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: 18-58% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 pin particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: IV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 1 results: Purity: 99.0%; retention time: 2.57; Obs. Adducts: [M+H]; Obs. Masses: 599.97. Injection 2 results: Purity: 95.5%; retention time: 1.69; Obs. Adducts: [M+H]; Obs. Masses: 600. The racemic title compound (52.5 mg) was isolated in 55.7% yield. The racemic material was further purified by using SFC-chiral chromatography to give isomers.

Example 57 (first eluting isomer) and Example 58 (second eluting isomer) were isolated from the racemate using SFC-chiral chromatography. Two analytical LC/MS injections were used to determine the final purity.

Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm.

Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm.

Example 57: Injection 1 results: Purity: 100.0%; retention time: 2.71; Obs. Adducts: [M+H]; Obs. Masses: 599.95. Injection 2 results: Purity: 100.0%; retention time: 1.76; Obs. Adducts: [M+H]; Obs. Masses: 599.98. Example 57 (13.2 mg) was isolated in 14% yield.

Example 58: Injection 1 results: Purity: 100.0%; retention time: 2.71; Obs. Adducts: [M+H]; Obs. Masses: 599.96. Injection 2 results: Purity: 99.1%; retention time: 1.75; Obs. Adducts: [M+H]; Obs. Masses: 599.98. Example 58 (13.7 mg) was isolated in 14.5% yield.

Examples 59 to 61

6-bromo-4-(4-((4-fluorophenyl)(2-methoxy-6-methylphenyl)methyl)piperazin-1-yl)-1-methyl-3-nitro-1,5-naphthyridin-2(1H)-one

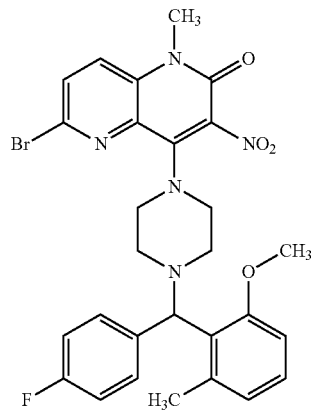

(59)

To a DMF (2 mL) solution of 6-bromo-4-(4-((4-fluorophenyl)(2-hydroxy-6-methylphenyl)methyl)piperazin-1-yl)-1-methyl-3-nitro-1,5-naphthyridin-2(1H)-one (30 mg, 0.052 mmol) was added cesium carbonate (50.3 mg, 0.155 mmol).

The reaction mixture was stirred at room temperature for 20 minutes and methyl iodide (9.66 W, 0.155 mmol) was added. The reaction mixture was stirred at room temperature for 1 hour. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 55-95% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 2 results: Purity: 100.0%; retention time: 1.67; Obs. Adducts: [M+H]; Obs. Masses: 595.95. Injection 1 results: Purity: 100.0%; retention time: 2.73; Obs. Adducts: [M+H]; Obs. Masses: 595.96. The racemic title compound (17.1 mg) was isolated in 55.1% yield. The racemic material was further purified by using SFC-chiral chromatography to give isomers.

Example 60 (first eluting isomer) and Example 61 (second eluting isomer) were isolated from the racemate using SFC-chiral chromatography. Two analytical LC/MS injections were used to determine the final purity.

Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm.

Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm.

Example 60: Injection 1 results: Purity: 100.0%; retention time: 2.65; Obs. Adducts: [M+H]; Obs. Masses: 595.97. Injection 2 results: Purity: 100.0%; retention time: 1.67; Obs. Adducts: [M+H]; Obs. Masses: 595.96. Example 60 (5.4 mg) was isolated in 17.4% yield.

Example 61: Injection 1 results: Purity: 100.0%; retention time: 2.65; Obs. Adducts: [M+H]; Obs. Masses: 595.96. Example 61 (5.1 mg) was isolated in 16.4% yield.

Example 62 tert-butyl (8-(4-(bis(4-fluorophenyl)methyl)piperazin-1-yl)-5-methyl-7-nitro-6-oxo-5,6-dihydro-1,5-naphthyridin-2-yl)carbamate

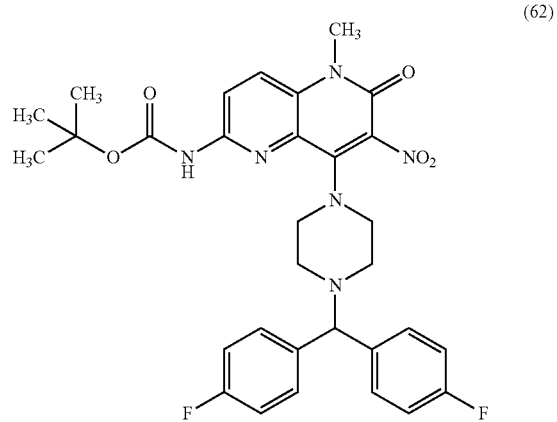 [SMILES: Cn1c(=O)c([N+](=O)[O-])c(N2CCN(C(c3ccc(F)cc3)c3ccc(F)cc3)CC2)c2nc(NC(=O)OC(C)(C)C)ccc21]

(62)

A mixture of tris(dibenzylideneacetone)dipalladium(0) (9.38 mg, 10.24 μmol), 4,5-bis(diphenylphosphino)-9,9-dimethylxanthine (17.77 mg, 0.031 mmol), tert-butyl carbamate (39.0 mg, 0.333 mmol), cesium carbonate (125 mg, 0.384 mmol) and 4-(4-(bis(4-fluorophenyl)methyl)piperazin-1-yl)-6-bromo-1-methyl-3-nitro-1,5-naphthyridin-2 (1H)-one (146 mg, 0.256 mmol) was placed under argon. Dioxane (2560 μl) and H$_2$O (5.53 μl, 0.307 mmol) were added. The reaction mixture was sealed under argon and heated at 100° C. overnight. LC/MS indicated the reaction was complete. The solvent was removed. The residue was purified via Biotage® MPLC system with 1:1 hexanes: ethyl acetate; 24 g silica column). Fractions were collected to afford 160 mg of a light yellow film consistent with the title compound. A sample of 10 mg was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 60-100% B over 15 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 11×50 mm, 1.7 μm particles: Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 1 results: Purity: 98.7%; retention time: 2.55; Obs. Adducts: [M+H]; Obs. Masses: 607.03. Injection 2 results: Purity:

Example 63

6-amino-4-(4-(bis(4-fluorophenyl)methyl)piperazin-1-yl)-1-methyl-3-nitro-1,5-naphthyridin-2(1H)-one

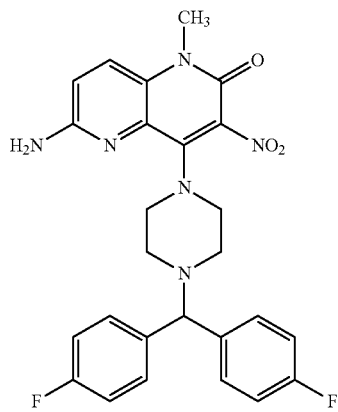

(63)

A dichloromethane (3 mL) solution of tert-butyl (8-(4-(bis(4-fluorophenyl) methyl)piperazin-1-yl)-5-methyl-7-nitro-6-oxo-5,6-dihydro-1,5-naphthyridin-2-yl) carbamate (150 mg, 0.247 mmol) was combined with TFA (0.5 mL, 6.49 mmol). The reaction mixture was stirred at room temperature for 2 hours. LC/MS indicated the reaction was complete. The solvent was removed to afford a yellow solid. A sample of 6 mg was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 35-75% B over 20 minutes, then a 4 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 pnm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 1 results: Purity: 98.8%; retention time: 2.16; Obs. Adducts: [M+H]; Obs. Masses: 507.1. Injection 2 results: Purity: 100.0%; retention time: 1.7; Obs. Adducts: [M+H]; Obs. Masses: 507.08. The title compound (3.4 mg) was isolated in 55.9% yield.

Example 64

6-bromo-4-(4-(2-(difluoromethyl)benzyl)piperazin-1-yl)-2-oxo-1-(prop-2-yn-1-yl)-1,2-dihydro-1,5-naphthyridine-3-carbonitrile

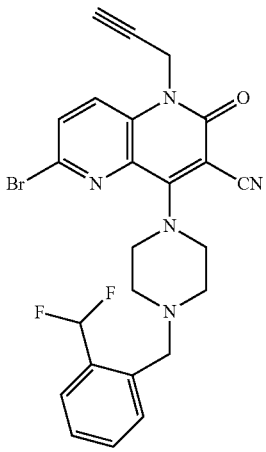

(64)

Polymeric N,N,N-trimethyl-1-(p-tolyl)methanamonium cyanoborohydride (4.1 mmol/g) (35 mg, 0.144 mmol) was added to 2-(difluoromethyl)benzaldehyde (16.05 mg, 0.103 mmol). A mixture of 6-bromo-2-oxo-4-(piperazin-1-yl)-1-(prop-2-yn-1-yl)-1,2-dihydro-1,5-naphthyridine-3-carbonitrile, TFA (25 mg, 0.051 mmol) in dichloromethane (2 mL) and acetic acid (0.250 mL) was added. The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate: Mobile Phase B: 95:5 acetonitrile:water with 10 mM ammonium acetate; Gradient: 45-85% B over 18 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 512.04; Retention Time: 2.39 minutes. Injection 2 conditions: Column: Waters XBridge C18, 2.1 mm×50 mm, 1.7 μm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 512.05; Retention Time: 1.68 minutes. The title compound (16.6 mg) was isolated in 63.5% yield.

Example 65

6-bromo-4-(4-(2-hydroxy benzyl)piperazin-1-yl)-2-oxo-1-(prop-2-yn-1-yl)-1,2-dihydro-1,5-naphthyridine-3-carbonitrile

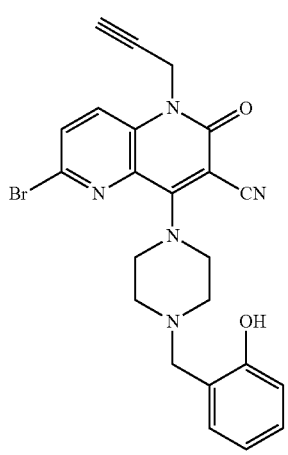

(65)

A dichloromethane (2 mL) solution of 2-hydroxybenzaldehyde (22.60 mg, 0.185 mmol), 6-bromo-2-oxo-4-(piperazin-1-yl)-1-(prop-2-yn-1-yl)-1,2-dihydro-1,5-naphthyridine-3-carbonitrile, TFA (60 mg, 0.123 mmol) and sodium cyanoborohydride (15.51 mg, 0.247 mmol) was mixed by shaking at room temperature overnight. LC/MS analysis indicated approximately 30% conversion. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 38-78% B over 19 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 477.99; Retention Time: 1.97 minutes. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 477.98; Retention Time: 1.18 minutes. The title compound (16.7 mg) was isolated in 28.4% yield.

Example 66

6-bromo-4-(4-(2-hydroxy-4-methylbenzyl)piperazin-1-yl)-2-oxo-1-(prop-2-yn-1-yl)-1,2-dihydro-1,5-naphthyridine-3-carbonitrile

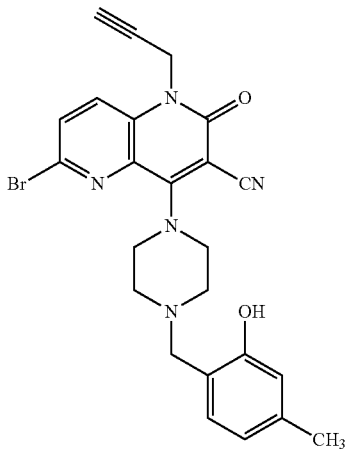

(66)

A DMF (2 mL) solution of 2-hydroxy-4-methylbenzaldehyde (7.56 mg, 0.056 mmol) and 6-bromo-2-oxo-4-(piperazin-1-yl)-1-(prop-2-yn-1-yl)-1,2-dihydro-1,5-naphthyridine-3-carbonitrile, TFA (18 mg, 0.037 mmol) was mixed by shaking at room temperature for 1 hour. Sodium cyanoborohydride (4.65 mg, 0.074 mmol) was added. The reaction mixture was mixed by shaking at room temperature overnight. LC/MS analysis indicated the reaction was complete. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 47-87% B over 19 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 492.02; Retention Time: 2.19 minutes. Injection 2 conditions: Column: Waters XBridge C18, 2.1 mm×50 mm, 1.7 µmm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and IV (220 nm). Injection 2 results: Purity: 100.0%; Observed Mass: 492.05; Retention Time: 1.33 minutes. The title compound (8 mg) was isolated in 43.9% yield.

Example 67

6-bromo-4-(4-(4-fluoro-2-hydroxybenzyl)piperazin-1-yl)-2-oxo-1-(prop-2-yn-1-yl)-1,2-dihydro-1,5-naphthyridine-3-carbonitrile

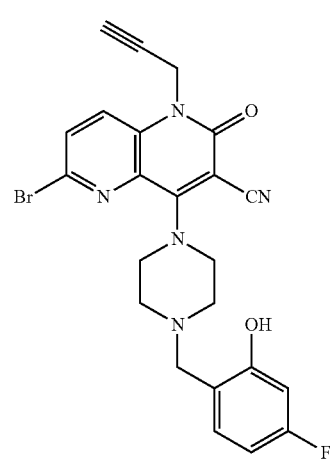

(67)

A DMF (2 mL) solution of 4-fluoro-2-hydroxybenzaldehyde (7.78 mg, 0.056 mmol) and 6-bromo-2-oxo-4-(piperazin-1-yl)-1-(prop-2-yn-1-yl)-1,2-dihydro-1,5-naphthyridine-3-carbonitrile, TFA (18 mg, 0.037 mmol) was mixed by shaking at room temperature for 1 hour. Sodium cyanoborohydride (4.65 mg, 0.074 mmol) was added. The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 42-82% B over 19 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 496.05; Retention Time: 1.28 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 496.04; Retention Time: 2.11 minutes. The title compound (9.8 ng) was isolated in 53.4% yield.

Example 68

6-bromo-4-(4-(4-fluoro-2-methoxybenzyl)piperazin-1-yl)-2-oxo-1-(prop-2-yn-1-yl)-1,2-dihydro-1,5-naphthyridine-3-carbonitrile

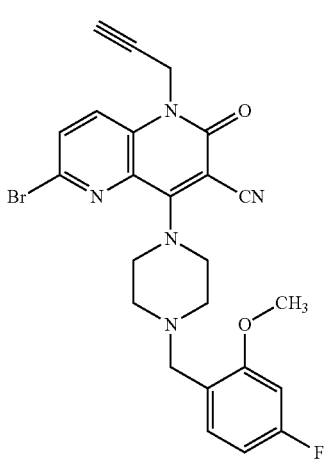

(68)

A DMF (2 mL) solution of 4-fluoro-2-methoxybenzaldehyde (8.56 mg, 0.056 mmol) and 6-bromo-2-oxo-4-(piperazin-1-yl)-1-(prop-2-yn-1-yl)-1,2-dihydro-1,5-naphthyridine-3-carbonitrile, TFA (18 mg 0.037 mmol) was mixed by shaking at room temperature for 1 hour. Sodium cyanoborohydride (4.65 mg, 0.074 mmol) was added. The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 42-82% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 510.09; Retention Time: 2.11 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid. Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0 ?%; Observed Mass: 510.07; Retention Time: 1.41 minutes. The title compound (4.9 mg) was isolated in 25.9% yield.

Example 69

6-bromo-4-(4-(2-hydroxy-4,6-dimethylbenzyl)piperazin-1-yl)-2-oxo-1-(prop-2-yn-1-yl)-1,2-dihydro-1,5-naphthyridine-3-carbonitrile

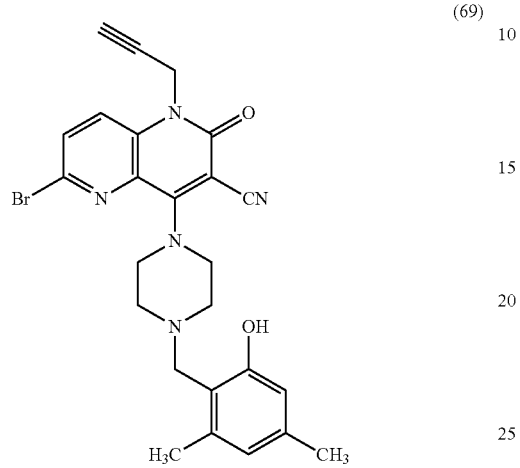

(69)

A DMF (2 mL) solution of 2-hydroxy-4,6-dimethylbenzaldehyde (11.58 mg, 0.077 mmol) and 6-bromo-2-oxo-4-(piperazin-1-yl)-1-(prop-2-yn-1-yl)-1,2-dihydro-1,5-naphthyridine-3-carbonitrile, TFA (25 mg, 0.051 mmol) was mixed by shaking at room temperature for 1 hour. Sodium cyanoborohydride (6.46 mg, 0.103 mmol) was added. The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 35-83% B over 20 minutes, then a 6-minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 506.04; Retention Time: 2.27 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 506.08; Retention Time: 1.46 minutes. The title compound (9.9 mg) was isolated in 38.3% yield.

Example 70

6-bromo-4-(4-((4-fluorophenyl)(2-hydroxyphenyl)methyl)piperazin-1-yl)-1-methyl-3-nitro-1,5-naphthyridin-2(1H)-one

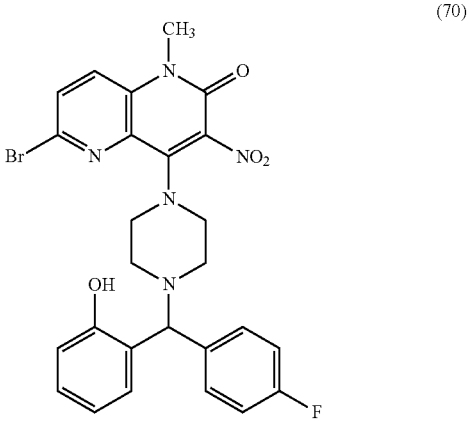 [SMILES: Cn1c(=O)c([N+](=O)[O-])c(N2CCN(C(c3ccc(F)cc3)c3ccccc3O)CC2)c2nc(Br)ccc21]

(70)

A microwave vial was charged with (4-fluorophenyl)boronic acid (13.99 mg, 0.100 mmol), salicylaldehyde (12.21 mg, 0.100 mmol) and 6-bromo-1-methyl-3-nitro-4-(piperazin-1-yl)-1,5-naphthyridin-2(1H)-one (36.8 mg, 0.1 mmol). The reaction vessel was sealed and submitted to microwave irradiation at 150° C. for 2 hours in a Biotage™ Initiator microwave oven. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 45-85% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 2 results: Purity: 98.0%; retention time: 1.59; Obs. Adducts: [M+H]; Obs. Masses: 567.99. Injection 1 results: Purity: 100.0%; retention time: 2.42; Obs. Adducts: [M+H]; Obs. Masses: 568.02. The title compound (3 mg) was isolated in 5.3% yield.

Example 71

6-bromo-4-(4-((2-fluoro-4-methylphenyl)(2-hydroxyphenyl)methyl)piperazin-1-yl)-1-methyl-3-nitro-1,5-naphthyridin-2(1H)-one

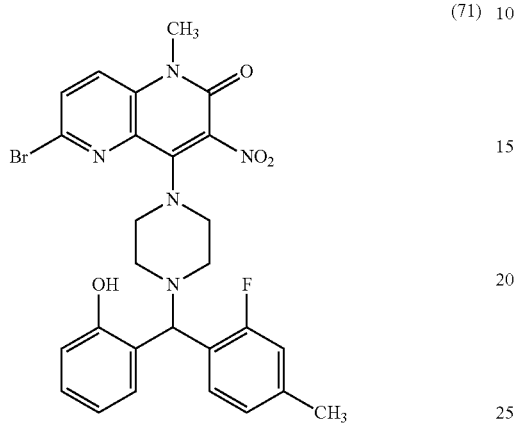

A microwave vial was charged with (2-fluoro-4-methylphenyl)boronic acid (15.39 mg, 0.100 mmol), salicylaldehyde (12.21 mg, 0.100 mmol) and 6-bromo-1-methyl-3-nitro-4-(piperazin-1-yl)-1,5-naphthyridin-2(1H)-one (36.8 mg, 0.1 mmol). The reaction vessel was sealed and submitted to microwave irradiation at 150° C. for 2 h in a Biotage™ Initiator microwave oven. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-100% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 2 results: Purity: 100.0% retention time: 1.69, 1.72; Obs. Adducts: [M+H], Obs. Masses: 582, 582. Injection 1 results: Purity: 98.1%: retention time: 2.51, 2.56; Obs. Adducts: [M+H]; Obs. Masses: 582. The title compound (2.1 mg) was isolated in 3.6% yield.

Example 72

6-bromo-4-(4-((2,4-dimethylphenyl)(2-hydroxyphenyl)methyl)piperazin-1-yl)-1-methyl-3-nitro-1,5-naphthyridin-2(1H)-one

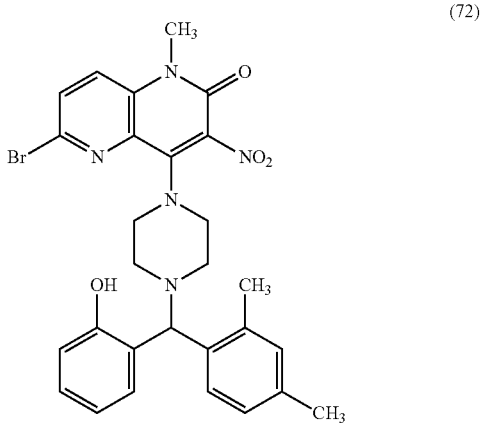 [SMILES: Cc1ccc(C(c2ccccc2O)N2CCN(c3c([N+](=O)[O-])c(=O)n(C)c4ccc(Br)nc34)CC2)c(C)c1]

Example 72 was prepared according to the general method for the synthesis of 6-bromo-4-{4-[(2-fluoro-4-methylphenyl)(2-hydroxyphenyl)methyl]piperazin-1-yl}-1-methyl-3-nitro-1,2-dihydro-1,5-naphthyridin-2-one. The crude material was purified via preparative LC/MS with the following conditions: Column: XBridge C18, 19×200 mm, 5 μm particles; Mobile Phase A: 5:95 acetonitrile:water with 10 mM ammonium acetate: Mobile Phase B: 95:5 acetonitrile:water with 10 mM ammonium acetate: Gradient: 50-100% B over 20 minutes, then a 5 minute hold at 100% B: Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid: Mobile Phase B: 95:5 acetonitrile:water with 0.1% trifluoroacetic acid: Temperature: 50° C.; Gradient: 0-100% B over 3 minutes, then a 0.75 minute hold at 100% B; Flow: 1.0 mL/minute; Detection: UV at 220 nm. Injection 1 results: Purity: 100.0%; retention time: 2.59; Obs. Adducts: [M+H]; Obs. Masses: 577.98. Injection 2 results: Purity: 98.3%; retention time: 1.72; Obs. Adducts: [M+H]; Obs. Masses: 577.99. The title compound (2.1 mg) was isolated in 3.6% yield.

Example 73

6-bromo-4-(4-((2-hydroxyphenyl)(o-tolyl)methyl) piperazin-1-yl)-1-methyl-3-nitro-1,5-naphthyridin-2 (1H)-one

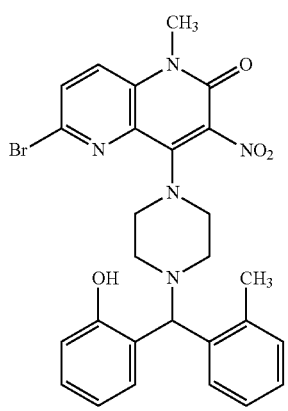

(73)

Example 73 was prepared according to the general method for the synthesis of 6-bromo-4-{4-[(2-fluoro-4-methylphenyl)(2-hydroxyphenyl)methyl]piperazin-1-yl}-1-methyl-3-nitro-1,2-dihydro-1,5-naphthyridin-2-one. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-90% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid: Mobile Phase B: 95:5 acetonitrile:water with 0.1% trifluoroacetic acid: Temperature: 50° C.; Gradient: 0-100% B over 3 minutes, then a 0.75 minute hold at 100% B; Flow: 1.0 mL/minute; Detection: UV at 220 nm. Injection 1 results: Purity: 100.0%; retention time: 2.48; Obs. Adducts: [M+H]; Obs. Masses: 564.01. Injection 2 results: Purity: 95.2%; retention time: 1.59; Obs. Adducts: [M+H]; Obs. Masses: 564.01. The title compound (6.2 mg) was isolated in 15% yield.

Examples 74 to 76

6-bromo-4-(4-((3-fluoro-2-hydroxyphenyl)(4-fluorophenyl)methyl)piperazin-1-yl)-1-methyl-3-nitro-1,5-naphthyridin-2(1H)-one

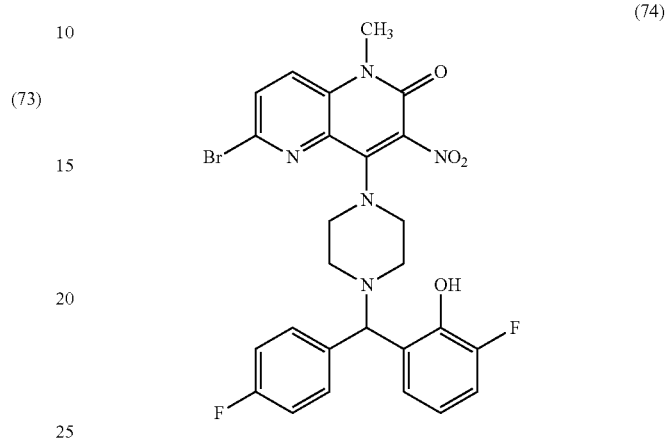

(74)

To a DMF (1 mL) solution of 6-bromo-4-chloro-1-methyl-3-nitro-1,5-naphthyridin-2(1H)-one (50 mg, 0.157 mmol) were added 2-fluoro-6-((4-fluorophenyl) (piperazin-1-yl)methyl)phenol, TFA (99 mg, 0.235 mmol) and DIPEA (0.082 mL, 0.471 mmol). The reaction mixture was mixed by shaking at 35° C. overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate: Mobile Phase B: 95:5 acetonitrile:water with 10 mM ammonium acetate; Gradient: 50-90% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1× 50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 2 results: Purity: 92.2%; retention time: 1.73; Obs. Adducts: [M+H]; Obs. Masses: 585.98. Injection 1 results: Purity: 100.0%; retention time: 2.42; Obs. Adducts: [M+H]; Obs. Masses: 585.95. The title compound (60.7 mg) was isolated in 65.9% yield. The racemic material was further purified by using SFC-chiral chromatography to give isomers.

Example 75 (first eluting isomer) and Example 76 (second eluting isomer) were isolated from the racemate using SFC-chiral chromatography. Two analytical LC/MS injections were used to determine the final purity.

Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0-100% B over 3 minutes, then a 0.75 minute hold at 100% B; Flow: 1.0 mL/minute; Detection: UV at 220 nm.

Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm.

Example 75: Injection 1 results: Purity: 100.0%; retention time: 2.31; Obs. Adducts: [M+H]; Obs. Masses: 585.97. Injection 2 results: Purity: 100.0%; retention time: 1.7; Obs. Adducts: [M+I-]; Obs. Masses: 585.98. Example 75 (21 mg) was isolated in 22.8% yield.

Example 76: Injection 1 results: Purity: 1000%; retention time: 2.31; Obs. Adducts: [M+H]; Obs. Masses: 585.97. Injection 2 results: Purity: 100.0%; retention time: 1.67, 1.7; Obs. Adducts: [M+H], [M+H]; Obs. Masses: 585.98, 585.98. Example 76 (21.8 mg) was isolated in 23.7% yield.

Examples 77 to 79

6-bromo-4-(4-((2-hydroxyphenyl)(phenyl)methyl) piperazin-1-yl)-1-methyl-3-nitro-1,5-naphthyridin-2 (1H)-one

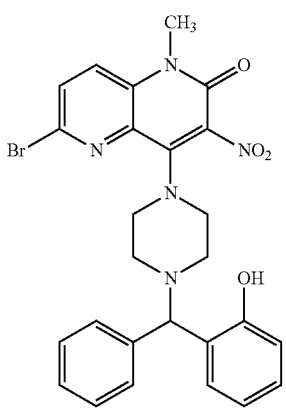

(77)

To a DMF (1 mL) solution of 6-bromo-4-chloro-1-methyl-3-nitro-1,5-naphthyridin-2(1H)-one (50 mg, 0.157 mmol) were added 2-(phenyl(piperazin-1-yl) methyl)phenol, TFA (90 mg, 0.235 mmol) and DIPEA (0.082 mL, 0.471 mmol). The reaction mixture was mixed by shaking at 35° C. overnight. LC/MS analysis indicated the reaction was complete. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 45-95% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. LC/MS results (acetonitrile TFA)-2: Purity: 96.3%; retention time: 1.65; Obs. Adducts: [M+H]; Obs. Masses: 550. LC/MS results (acetonitrile ammonium acetate)-2: Purity: 100.0%; retention time: 234; Obs. Adducts: [M+H]; Obs. Masses: 550. The racemic title compound (27 mg) was isolated in 31% yield. The racemic material w as further purified by using SFC-chiral chromatography to give isomers.

Example 78 (first eluting isomer) and Example 79 (second eluting isomer) were isolated from the racemate using SFC-chiral chromatography. Two analytical LC/MS injections were used to determine the final purity.

Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0-100% B over 3 minutes, then a 0.75 minute hold at 100% B; Flow: 1.0 mL/minute; Detection: UV at 220 nm.

Injection 2 conditions: Column: Waters Acquity UPLC BEH C18, 2.1×50 mm, 1.7 urn particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm.

Example 78: LC/MS results (acetonitrile TFA)-2: Purity: 96.3%; retention time: 1.65; Obs. Adducts: [M+H]; Obs. Masses: 550) LC/MS results (acetonitrile ammonium acetate)-2: Purity: 100.0%; retention time: 2.34 Obs. Adducts: [M+H]; Obs. Masses: 550. Example 78 (11.4 mg) was isolated in 13.2% yield.

Example 79: LC/MS results (acetonitrile TFA)-2: Purity: 95.4%; retention time: 1.63; Obs. Adducts: [M+H]; Obs. Masses: 550.04) LC/MS results (acetonitrile ammonium acetate)-2: Purity: 96.2%; retention time: 2.35; Obs. Adducts: [M+H]; Obs. Masses: 550.01. Example 79 (11.3 mg) was isolated in 13.1% yield.

Examples 80 to 82

6-bromo-4-(4-((4-fluoro-2-hydroxyphenyl)(4-fluorophenyl)methyl)piperazin-1-yl)-1-methyl-3-nitro-1,5-naphthyridin-2(1H)-one

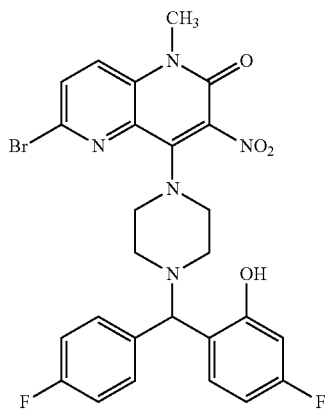

(80)

To a DMF (1 mL) solution of 6-bromo-4-chloro-1-methyl-3-nitro-1,5-naphthyridin-2(1H)-one (50 mg, 0.157 mmol) were added 5-fluoro-2-((4-fluorophenyl) (piperazin-1-yl)methyl)phenol, TFA (99 mg, 0.235 mmol) and DIPEA (0.082 mL, 0.471 mmol). The reaction mixture was mixed by shaking at 35° C. overnight. LC/MS analysis indicated the reaction was complete. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 45-85% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 1(00% B; Flow: 1.0 mL/minute; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 1 results: Purity: 93.2%4; retention time: 2.43; Obs. Adducts: [M+1H]; Obs. Masses: 585.96. Injection 2 results: Purity 91.7%; retention time: 1.7; Obs. Adducts: [M+H]; Obs. Masses: 585.95. The racemic title compound (17 mg) was isolated in 19% yield. The racemic material was further purified by using SFC-chiral chromatography to give isomers.

Example 81 (first eluting isomer) and Example 82 (second eluting isomer) were isolated from the racemate using SFC-chiral chromatography. Two analytical LC/MS injections were used to determine the final purity.

Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm.

Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm.

Example 81: Injection 1 results: Purity: 93.2%; retention time: 2.43; Obs. Adducts: [M+H]; Obs. Masses: 585.96. Injection 2 results: Purity: 91.7%; retention time: 1.7; Obs. Adducts: [M+H]; Obs. Masses: 585.95. Example 81 (7.2 mg) was isolated in 7.8% yield.

Example 82: Injection 1 results: Purity: 90.8%; retention time: 2.43; Obs. Adducts: [M+H]; Obs. Masses: 585.92. Injection 2 results: Purity: 95.9%; retention time: 1.7; Obs. Adducts: [M+H]; Obs. Masses: 585.9. Example 82 (5.3 mg) was isolated in 5.8% yield.

Examples 83 to 85

6-bromo-4-(4-((4-fluorophenyl)(2-hydroxy-3-methylphenyl)methyl)piperazin-1-yl)-1-methyl-3-nitro-1,5-naphthyridin-2(1H)-one

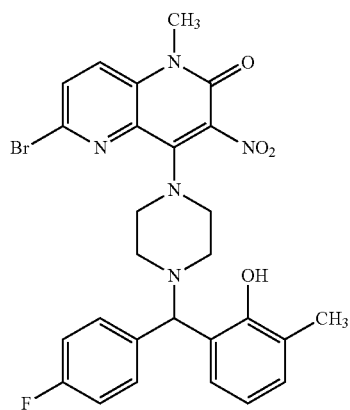

(83)

To a DMF (1 mL) solution of 6-bromo-4-chloro-1-methyl-3-nitro-1,5-naphthyridin-2(1H)-one (50 mg, 0.157 mmol) was added 2-((4-fluorophenyl)(piperazin-1-yl) methyl)-6-methylphenol (70.7 mg, 0.235 mmol), followed by the addition of DIPEA (0.027 mL, 0.157 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-90% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles. Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Injection 2 results: Purity: 96.0%; retention time: 1.85: Obs. Adducts: [M+H]; Obs. Masses: 582. Injection 1 results: Purity: 97.8%; retention time: 2.53, 2.6: Obs. Adducts: [M+H]; Obs. Masses: 581.98. The racemic title compound (15.7 tug) was isolated in 17.2% yield. The racemic material was further purified by using SFC-chiral chromatography to give isomers.

Example 84 (first eluting isomer) and Example 85 (second eluting isomer) were isolated from the racemate using SFC-chiral chromatography. Two analytical LC/MS injections were used to determine the final purity.

Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm.

Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm.

Example 84: Injection 1 results: Purity: 100.0%; retention time: 2.53; Obs. Adducts: [M+H]; Obs. Masses: 581.96. Injection 2 results: Purity: 100.0%; retention time: 1.84; Obs. Adducts: [M+H]; Obs. Masses: 581.97. Example 84 (5.1 mg) was isolated in 5.6% yield.

Example 85: Injection 1 results: Purity: 100.0%; retention time: 2.53; Obs. Adducts: [M+H]; Obs. Masses: 581.95. Injection 2 results: Purity: 99.0%; retention time: 1.83; Obs. Adducts: [M+H]; Obs. Masses: 581.97. Example 85 (5.3 mg) was isolated in 5.8% yield.

Example 86

6-bromo-4-(4-((4-fluorophenyl)(2-hydroxy-5-methylphenyl)methyl)piperazin-1-yl)-1-methyl-3-nitro-1,5-naphthyridin-2(1H)-one

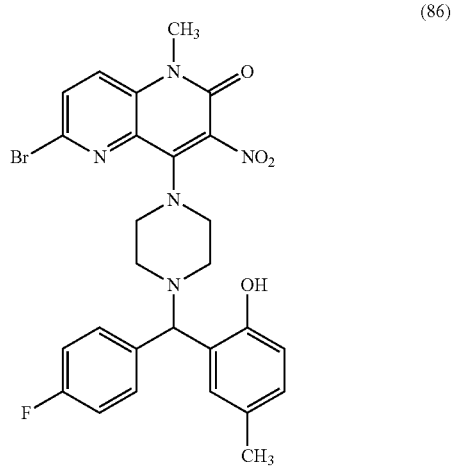 [SMILES: Cc1ccc(O)c(C(c2ccc(F)cc2)N2CCN(c3c([N+](=O)[O-])c(=O)n(C)c4ccc(Br)nc34)CC2)c1]

(86)

To a DMF (1.5 mL) solution of 6-bromo-4-chloro-1-methyl-3-nitro-1,5-naphthyridin-2(1H)-one (50 mg, 0.157 mmol) was added 2-((4-fluorophenyl)(piperazin-1-yl)methyl)-4-methylphenol (70.7 mg, 0.235 mmol) followed by the addition of DIPEA (0.082 mL, 0.471 mmol). The reaction mixture w as mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-90% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/minute; Detection: UV at 220 nm. Injection 2 conditions: Column: Waters CSH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/minute; Detection: UV at 220 nm. Purity: 100.0%; retention time: 2.5; Obs. Adducts: [M+H]; Obs. Masses: 582.08. Injection 2 results: Purity: 97.4%; retention time: 1.82; Obs. Adducts: [M+H]; Obs. Masses: 581.86. The title compound (5.3 mg) was isolated in 5.8% yield.

Example 87

6-bromo-4-(4-((4-fluorophenyl)(2-hydroxy-6-methylphenyl)methyl)piperazin-1-yl)-1-methyl-3-nitro-1,5-naphthyridin-2(1H)-one

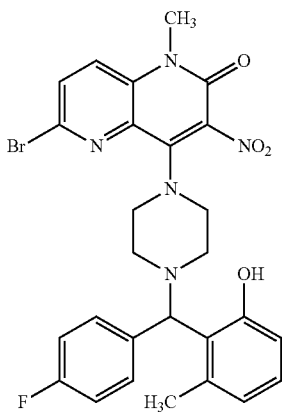

(87)

To a DMF (2 ml) solution of 6-bromo-4-chloro-1-methyl-3-nitro-1,5-naphthyridin-2(1H)-one (100 mg, 0.314 mmol) was added 2-((4-fluorophenyl)(piperazin-1-yl)methyl)-3-methylphenol (141 mg, 0.471 mmol), followed by the addition of DIPEA (0.165 mL, 0.942 mmol). The reaction mixture was mixed by shaking at room temperature overnight. LC/MS analysis indicated the reaction was complete. The crude material was diluted with ethyl acetate, washed with water and brine, and dried over magnesium sulfate. The residue was purified via Biotage™ MPLC system with 1:1 hexanes: ethyl acetate; 40 g silica column. Fractions containing the product were combined to afford the desired yellow product. The title compound (100 mg) was isolated in 54.7% yield. Approximately third of the yellow solid was purified via preparative LC/MS with the following conditions: Column: XBridge C18, 19×200 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 20 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B: Flow: 1.0 mL/minute; Detection: UV at 220 nm. Injection 1 results: Purity: 100.0% retention time: 2.4: Obs. Adducts: [M+H]; Obs. Masses: 582. Injection 2 results: Purity: 97.2%; retention time: 1.7; Obs. Adducts: [M+H]; Obs. Masses: 581.94. The title compound (33.4 mg) was isolated.

Examples 88 to 90

5-((2-((4-(6-bromo-1-methyl-3-nitro-2-oxo-1,2-dihydro-1,5-naphthyridin-4-yl)piperazin-1-yl)(4-fluorophenyl)methyl)-3-methylphenoxy)methyl)nicotinonitrile

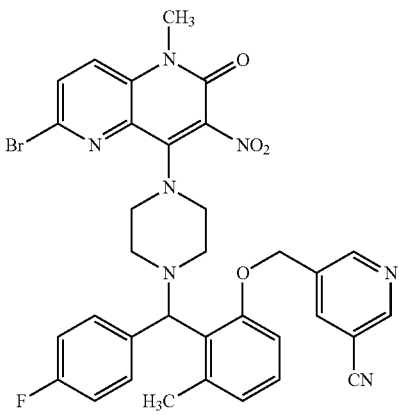

(88)

To a DMF (2 mL) solution of 6-bromo-4-(4-((4-fluorophenyl)(2-hydroxy-6-methylphenyl)methyl)piperazin-1-yl)-1-methyl-3-nitro-1,5-naphthyridin-2(1H)-one (30 mg, 0.052 mmol) was added cesium carbonate (50.3 mg, 0.155 mmol). The reaction mixture was stirred at room temperature for 20 minutes, 5-(Chloromethyl)nicotinonitrile (23.58 mg, 0.155 mmol) was added and the reaction mixture was heated at 75° C. for 3 hours. LC/MS analysis indicated approximately 40% conversion. The reaction mixture was mixed by shaking at 75° C. overnight. LC/MS analysis indicated approximately 75% conversion. The reaction mixture was mixed by shaking at 75° C. for an additional 24 hours. LC/MS analysis indicated that the reaction was almost complete. The crude material was purified via preparative LC/MS with the following conditions: Column: Waters CSH C18, 19×200 mm, 5 μm particles; Mobile Phase A: 5:95 acetonitrile: water with 0.1% trifluoroacetic acid; Mobile Phase B: 95:5 acetonitrile:water with 0.1% trifluoroacetic acid; Gradient: 18-58% B over 28 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles; Mobile Phase A: 5:95 acetonitrile: water with 0.1% trifluoroacetic acid; Mobile Phase B: 95:5 acetonitrile:water with 0.10% trifluoroacetic acid; Temperature: 50° C.; Gradient: 0-100% B over 3 minutes, then a 0.75 minute hold at 100% B; Flow: 1.0 mL/minute; Detection: UV at 220 nm. LC/MS results (acetonitrile TFA)-3: Purity: 98.7%; retention time: 1.72; Obs. Adducts: [M+H]; Obs. Masses: 697.92) LC/MS results (acetonitrile ammonium acetate)-3: Purity: 96.6%; retention time: 2.49; Obs. Adducts: [M+H]; Obs. Masses: 697.9. The racemic title compound (21.7 mg) was isolated in 59.7% yield. The racemic material was further purified by using SFC-chiral chromatography to give isomers.

Example 89 (first eluting isomer) and Example 90 (second eluting isomer) were isolated from the racemate using SFC-chiral chromatography. Two analytical LC/MS injections were used to determine the final purity.

Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 min.

Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm.

Example 89: Injection 1 results: Purity: 98.3%; retention time: 2.51; Obs. Adducts: [M+H]; Obs. Masses: 697.93. Injection 2 results: Purity: 99.0%; retention time: 1.68; Obs. Adducts: [M+H]; Obs. Masses: 697.93. Example 89 (5.4 mg) was isolated in 14.9% yield.

Example 90: Injection 1 results: Purity: 99.2%; retention time: 2.51; Obs. Adducts: [M+H]; Obs. Masses: 697.9. Injection 2 results: Purity: 100.0%; retention time: 1.69; Obs. Adducts: [M+H]; Obs. Masses: 697.92. Example 90 (5.9 mg) was isolated in 16.2% yield.

Examples 91 to 93

5-((2-((4-(6-bromo-1-methyl-3-nitro-2-oxo-1,2-dihydro-1,5-naphthyridin-4-yl)piperazin-1-yl)(4-fluorophenyl)methy)-5-fluorophenoxy)methyl)nicotinonitrile

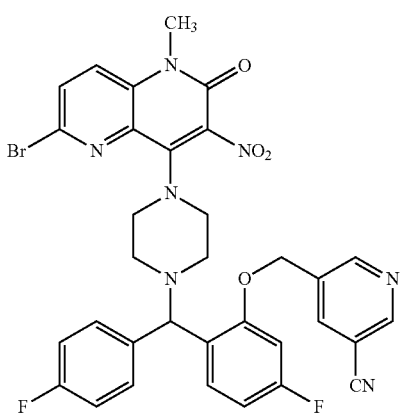

(91)

To a DMF (1.6 mL) solution of 6-bromo-4-(4-((4-fluoro-2-hydroxyphenyl)(4-fluorophenyl)methyl)piperazin-1-yl)-1-methyl-3-nitro-1,5-naphthyridin-2(1H)-one (20 mg, 0.034 mmol) was added cesium carbonate (33.3 mg, 0.102 mmol). The reaction mixture was stirred at room temperature for 20 minutes, 5-(Chloromethyl)nicotinonitrile (15.61 mg, 0.102 mmol) was added and the reaction mixture was heated at 75° C. overnight. LC/MS analysis indicated the reaction was complete. The crude material was purified via preparative LC/MS with the following conditions: Column: Waters CSH C18, 19×200 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 25 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. LC/MS results (acetonitrile TFA)-2: Purity: 99.00%; retention time: 1.74; Obs. Adducts: [M+H]; Obs. Masses: 701.88; LC/MS results (acetonitrile ammonium acetate)-2: Purity: 98.8%; retention time: 2.4 Obs. Adducts: [M+H]; Obs. Masses: 701.91. The racemic title compound (5.2 mg) was isolated in 21.8% yield. The racemic material was further purified by using SFC-chiral chromatography to give isomers.

Example 92 (first eluting isomer) and Example 93 (second eluting isomer) were isolated from the racemate using SFC-chiral chromatography. Two analytical LC/MS injections were used to determine the final purity.

Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm.

Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm.

Example 92: Injection 1 results: Purity: 100.0%; retention time: 2.4; Obs. Adducts: [M+H]; Obs. Masses: 701.91. Injection 2 results: Purity: 100.0%; retention time: 1.7; Obs. Adducts: [M+H]; Obs. Masses: 701.81. Example 92 (1.4 mg) was isolated in 5.9% yield.

Example 93: Injection 1 results: Purity: 100.0%; retention time: 2.4; Obs. Adducts: [M+1-H]; Obs. Masses: 701.92. Injection 2 results: Purity: 100.0%; retention time: 1.7; Obs. Adducts: [M+H]; Obs. Masses: 701.94. Example 93 (1.5 mg) was isolated in 6.3% yield.

Examples 94 to 96

4-(4-((2-(allyloxy)-6-methylphenyl)(4-fluorophenyl)methyl)piperazin-1-yl)-6-bromo-1-methyl-3-nitro-1,5-naphthyridin-2(1-H)-one

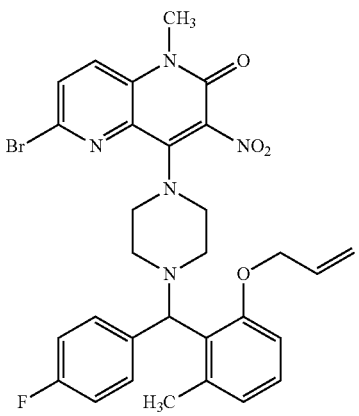

(94)

To a DMF (1.6 mL) solution of 6-bromo-4-(4-((4-fluorophenyl)(2-hydroxy-6-methylphenyl)methyl)piperazin-1-yl)-1-methyl-3-nitro-1,5-naphthyridin-2(1H)-one (20 mg, 0.034 mmol) was added cesium carbonate (33.6 mg, 0.103 mmol). The reaction mixture was stirred at room temperature for 20 minutes. Allyl bromide (8.91 µL, 0.103 mmol) was added and the reaction mixture was stirred at 60° C. overnight. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 50-100% B over 15 minutes, then a 5 minute hold at 100% B; Flow: 20 mL/minute. Fractions containing the product were combined and dried via centrifugal evaporation. The material was further purified via preparative LC/MS with the following conditions: Column: XBridge C18, 19×200 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: 7-47% B over 25 minutes, then a 5 minute hold at 100% B; Flow: 20 mL/minute. Fractions containing the product were combined and dried via centrifugal evaporation. Two analytical LC/MS injections were used to determine the final purity Injection 1 conditions: Column: Waters Acquity UPLC BEH C18, 2.1×50 mm, 1.7 µmm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.10 trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm. Purity: 100.0%; retention time: 1.59; Obs. Adducts: [M+H]; Obs. Masses: 621.9. Injection 1 results: Purity: 100.0%; retention time: 2.4; Obs. Adducts: [M+H]; Obs. Masses: 621.92. The racemic title compound (16.9 mg) was isolated in 79.9% yield. The racemic material was further purified by using SFC-chiral chromatography to give isomers.

Example 95 (first eluting isomer) and Example 96 (second eluting isomer) were isolated from the racemate using SFC-chiral chromatography. Two analytical LC/MS injections were used to determine the final purity.

Injection 1 conditions: Column: Waters Acquity UPLC BEH C18, 2.1×50 mm, 1.7 urn particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm.

Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/minute; Detection: UV at 220 nm.

Example 95: Injection 1 results: Purity: 97.8%; retention time: 2.77; Obs. Adducts: [M+1-H]; Obs. Masses: 621.94. Injection 2 results: Purity: 100.0%; retention time: 1.83; Obs. Adducts: [M+H]; Obs. Masses: 621.96. Example 95 (5.3 mg) was isolated in 25% yield.

Example 96: Injection 1 results: Purity: 98.4%; retention time: 2.77; Obs. Adducts: [M+H]; Obs. Masses: 621.94. Injection 2 results: Purity: 100.0%; retention time: 1.83; Obs. Adducts: [M+H]; Obs. Masses: 621.93. Example 96 (5.3 mg) was isolated in 25% yield.

Examples 97 to 99

8-(4-((4-fluorophenyl)(2-hydroxyphenyl)methyl)piperazin-1-yl)-5-methyl-7-nitro-6-oxo-5,6-dihydro-1,5-naphthyridine-2-carbonitrile

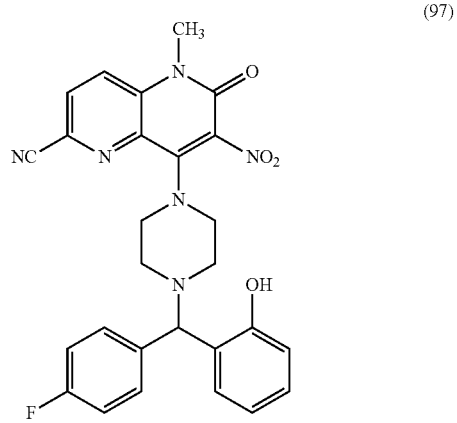

(97)

To a DMF (3 mL) solution of 8-chloro-5-methyl-7-nitro-6-oxo-5,6-dihydro-1,5-naphthyridine-2-carbonitrile (300 mg, 1.134 mmol) was added 2-((4-fluorophenyl) (piperazin-1-yl)methyl)phenol (390 mg, 1.360 mmol) followed by the addition of potassium carbonate (313 mg, 2.267 mmol). The reaction mixture was stirred at room temperature overnight. LC/MS analysis indicated the reaction was complete. The crude material was diluted with ethyl acetate, washed with brine, and dried over magnesium sulfate. The residue was purified via Biotage™ MPLC system with gradient of 1:1 hexanes: ethyl acetate to 100% ethyl acetate; 24 g silica column. Fractions were collected to afford the desired product as light yellow solid. This material was further purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 43-83% B over 15 minutes, then a 5 minute hold at 100% B; Flow: 20 mL/minute. Fractions containing the product were combined and dried via centrifugal evaporation. Two analytical LC/MS injections were used to determine the final purity. Injection 1 conditions: Column: Waters Acquity UPLC BEH C18, 2.1× 50 mm, 1.7 µm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B: Flow: 1.0 mL/minute; Detection: UV at 220 nm. Injection 1 results: Purity: 100.0%; retention time: 2.17; Obs. Adducts: [M+H]; Obs. Masses: 514.99. Injection 2 results: Purity: 98.1%; retention time: 1.51; Obs. Adducts: [M+H]; Obs. Masses: 515.01. The racemic title compound (220 mg) was isolated in 37.7% yield. The racemic material was further purified by using SFC-chiral chromatography to give isomers.

A 30 ng portion of racemic material was further purified by using SFC-chiral chromatography to afford Example 98 (first eluting isomer) and Example 99 (second eluting isomer). Two analytical LC/MS injections were used to determine the final purity.

Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/minute; Detection: UV at 220 nm.

Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C. Gradient: 0-100% B over 3 minutes, then a 0.75 minute hold at 100% B; Flow: 1.0 mL/minute; Detection: UV at 220 nm. Injection 2 results: Purity: 100.0%; retention time: 1.55; Obs. Adducts: [M-]; Obs. Masses: 515.03.

Example 98: Injection 1 results: Purity: 100.0%; retention time: 2.2; Obs. Adducts: [M+1-H]; Obs. Masses: 515.03. Example 98 (3.3 mg) was isolated in 11% yield.

Example 99: Injection 1 results: Purity: 100.0%; retention time: 2.17; Obs. Adducts: [M+H]; Obs. Masses: 515.01. Injection 2 results: Purity: 100.0%; retention time: 1.5; Obs. Adducts: [M+H]; Obs. Masses: 515.01. Example 99 (4.2 mg) was isolated in 14% yield.

Example 100

8-(4-((4-fluorophenyl)(2-(prop-2-yn-1-yloxy)phenyl) methyl)piperazin-1-yl)-5-methyl-7-nitro-6-oxo-5,6-dihydro-1,5-naphthyridine-2-carbonitrile

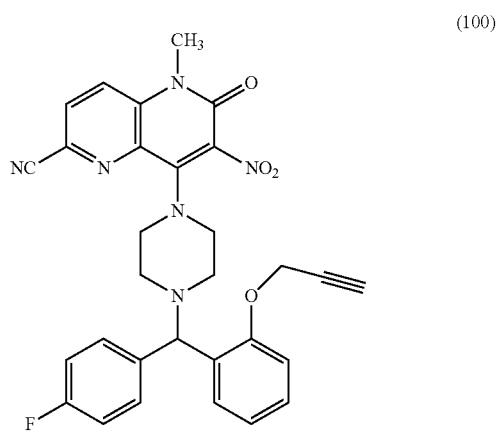 [SMILES: C#CCOc1ccccc1C(c1ccc(F)cc1)N1CCN(c2c([N+](=O)[O-])c(=O)n(C)c3ccc(C#N)nc23)CC1]

(100)

To a DMF (1 mL) solution of 8-(4-((4-fluorophenyl)(2-hydroxyphenyl)methyl) piperazin-1-yl)-5-methyl-7-nitro-6-oxo-5,6-dihydro-1,5-naphthyridine-2-carbonitrile (40 mg, 0.078 mmol) was added potassium carbonate (32.2 mg, 0.233 mmol) followed by the addition of propargyl bromide (80 wt % in toluene) (0.026 mL, 0.233 mmol). The reaction mixture was mixed by shaking at 75° C. over a weekend. LC/MS analysis indicated that approximately 40% of the starting material was converted to the desired product. Additional propargyl bromide (80 wt % in toluene) (0.026 mL, 0.233 mmol) was added, along with the addition of cesium carbonate (38.0 mg, 0.117 mmol). The reaction mixture was mixed by shaking at 75° C. overnight. LC/MS analysis indicated that the starting material was completely consumed. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 40-85% B over 20 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid. Mobile Phase B: 95:5 acetonitrile:water with 0.1% trifluoroacetic acid; Temperature: 50° C.; Gradient: 0%=B to 100% B over 3 minutes, then a 0.75 minute hold at 100% B; Flow: 1 mL/minute; Detection: MS and UV (220 nm). Injection 1 results: Purity: 100.0%; Observed Mass: 553.08; Retention Time: 1.61 minutes. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0% B to 100%1B over 3 minutes, then a 0.75 minute hold at 100% B; Flow: 1 mL/minute; Detection: MS and UV (220 nm). Injection 2 results: Purity: 100.0%; Observed Mass: 553.07; Retention Time: 2.41 minutes. The racemic title compound (13.5 mg) was isolated with a yield of 31.3%. The racemic material was further purified by using SFC-chiral chromatography to give isomers.

Example 101

8-(4-((4-fluorophenyl)(2-(prop-2-yn-1-yloxy)phenyl)methyl)piperazin-1-yl)-5-methyl-7-nitro-6-oxo-5,6-dihydro-1,5-naphthyridine-2-carbonitrile (first eluting isomer)

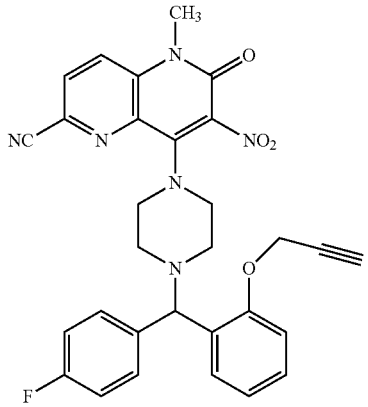

(101)

The racemic material was further purified by using SFC-chiral chromatography. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 553.08; Retention Time: 1.66 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 553.12; Retention Time: 2.33 minutes. The title compound (4 mg) was isolated in 9.3% yield.

Example 102

8-(4-((4-fluorophenyl)(2-(prop-2-yn-1-yloxy)phenyl)methyl)piperazin-1-yl)-5-methyl-7-nitro-6-oxo-5,6-dihydro-1,5-naphthyridine-2-carbonitrile (second eluting isomer)

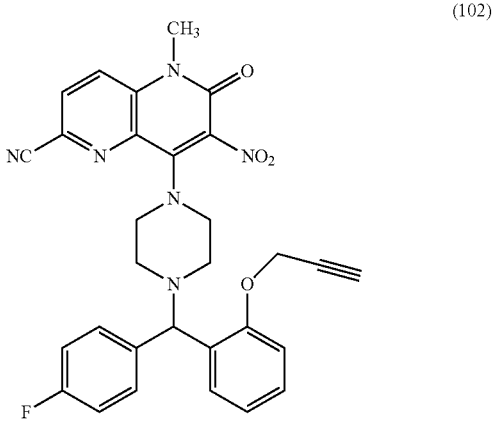 [SMILES: C#CCOc1ccccc1C(c1ccc(F)cc1)N1CCN(c2c([N+](=O)[O-])c(=O)n(C)c3ccc(C#N)nc23)CC1]

(102)

The racemic material was further purified by using SFC-chiral chromatography. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 40-85% B over 20 minutes, then a 5 minute hold at 100% B; Flow: 20 mL/minute. Fractions containing the product were combined and dried via centrifugal evaporation. Analytical LC/MS was used to determine the final purity. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 553.07; Retention Time: 2.33 minutes. The title compound (3.7 mg) was isolated in 8.6% yield.

Example 103

4-(4-(bis(4-fluorophenyl)methyl)piperazin-1-yl)-6-methoxy-1-methyl-2-oxo-1,2-dihydro-1,5-naphthyridine-3-carbonitrile

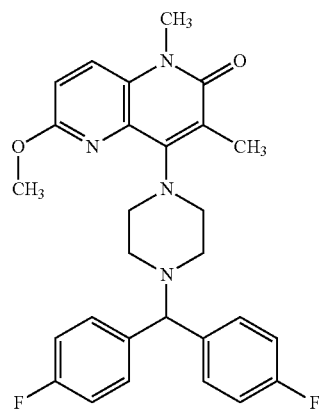

(103)

To a DMF (1 mL) solution of 4-chloro-6-methoxy-1-methyl-2-oxo-1,2-dihydro-1,5-naphthyridine-3-carbonitrile (20 mg, 0.080 mmol) was added Hunig's Base (0.014 mL, 0.080 mmol) followed by the addition of 1-(bis(4-fluorophenyl)methyl)piperazine (23.10 mg, 0.080 mmol). The reaction mixture was mixed by shaking at room temperature for 2 hours. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 45-85% B over 20 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 99.0%; Observed Mass: 502.09; Retention Time: 1.5 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% NB; Flow: 1 mL/minute; Detection: MS and UV (220 nm). Injection 2 results: Purity: 100.0%; Observed Mass: 502.09; Retention Time: 2.25 minutes. The title compound (3.4 mg) was isolated in 8.5% yield.

Example 104

4-(4-((4-fluorophenyl)(2-hydroxyphenyl)methyl)piperazin-1-yl)-6-methoxy-1-methyl-2-oxo-1,2-dihydro-1,5-naphthyridine-3-carbonitrile

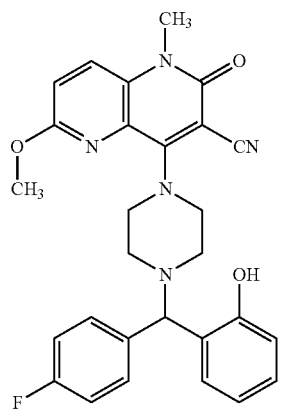

(104)

To a DMF (1 mL) solution of 4-chloro-6-methoxy-1-methyl-2-oxo-1,2-dihydro-1,5-naphthyridine-3-carbonitrile (20 mg, 0.080 mmol) was added Hunig's Base (0.014 mL, 0.080 mmol) followed by the addition of 2-((4-fluorophenyl)(piperazin-1-yl)methyl) phenol, 2 TFA (41.2 mg, 0.080 mmol). The reaction mixture was mixed by shaking at room temperature for 2 hours. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 17-57% B over 15 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 500.09; Retention Time: 2.1 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 500.09; Retention Time: 1.4 minutes. The title compound (2.2 mg) was isolated in 5.5% yield.

Examples 105 to 107

6-bromo-4-(4-((4-fluorophenyl)(2-hydroxyphenyl)methyl)piperazin-1-yl)-2-oxo-1-(prop-2-yn-1-yl)-1,2-dihydro-1,5-naphthyridine-3-carbonitrile

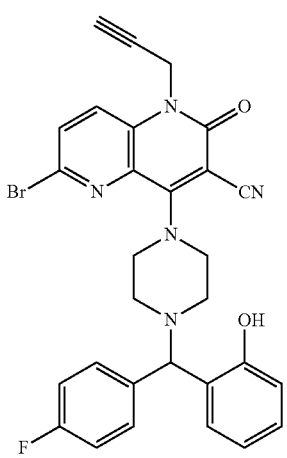

(105)

A DMF (1 mL) solution of 2-hydroxybenzaldehyde (15.07 mg, 0.123 mmol), 6-bromo-2-oxo-4-(piperazin-1-yl)-1-(prop-2-yn-1-yl)-1,2-dihydro-1,5-naphthyridine-3-carbonitrile, TFA (60 mg, 0.123 mmol) and (4-fluorophenyl) boronic acid (17.27 mg, 0.123 mmol) was heated in microwave at 150° C. for 2 hours. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-90% B over 18 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 97.3%; Observed Mass: 572.05; Retention Time: 1.85 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 97.4%; Observed Mass: 572.1; Retention Time: 2.75 minutes. The racemic title compound (15.3 mg) was isolated in 21.7% yield. The racemic material was further purified by using SFC-chiral chromatography to give isomers.

The racemic material of Example 105 was further purified by using SFC-chiral chromatography to afford Example 106 (first eluting isomer) and Example 107 (second eluting isomer). Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 pam particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Example 106: Injection 1 results: Purity: 100.0%; Observed Mass: 572.1; Retention Time: 1.91 minutes. Injection 2 results: Purity: 100.0%; Observed Mass: 572.08; Retention Time: 2.72 minutes. Example 106 (6.8 mg) was isolated in 9.7% yield.

Example 107: Injection 1 results: Purity: 100.0%; Observed Mass: 572.06; Retention Time: 1.91 minutes. Injection 2 results: Purity: 100.0%; Observed Mass: 572.09; Retention Time: 2.72 minutes. Example 107 (7.4 mg) was isolated in 10.5% yield.

Example 113

4-(4-(bis(4-fluorophenyl)methyl)piperazin-1-yl)-6-bromo-1-(2-methoxyethyl)-2-oxo-1,2-dihydro-1,5-naphthyridine-3-carbonitrile

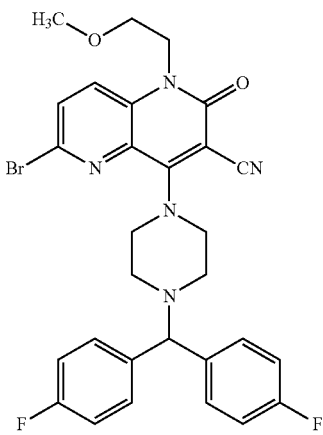

(113)

To a solution of triethylamine (0.017 mL, 0.123 mmol), 1-methylpiperidine (0.015 mL, 0.123 mmol), and 6-bromo-4-hydroxy-1-(2-methoxyethyl)-2-oxo-1,2-dihydro-1,5-naphthyridine-3-carbonitrile (20 mg, 0.062 mmol) in acetonitrile (1 mL) was added 4-methylbenzene-1-sulfonyl chloride (23.53 mg, 0.123 mmol). The reaction mixture was mixed by shaking at room temperature for 30 minutes, 1-(bis(4-fluorophenyl)methyl) piperazine (35.6 mg, 0.123 mmol) was then added. The reaction mixture was mixed by shaking at room temperature overnight. LC/MS analysis indicated that the starting material was all consumed. The desired product was detected as a small peak and purified using reverse phase HPLC for purification. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-100% B over 20 minutes, then a 4 minute hold at 100% B: Flow: 20 mL/minute. Fractions containing the product were combined and dried via centrifugal evaporation. The material was further purified via preparative LC/MS with the following conditions: Column: XBridge C18, 19×200 mm, 5 μm particles; Mobile Phase A: 5:95 acetonitrile:water with 0.100 trifluoroacetic acid; Mobile Phase B: 95:5 acetonitrile:water with 0.1'% trifluoroacetic acid; Gradient: 25-65% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% NB over 3 minutes, then a 0.75 minute hold at 100% B; Flow: 1 mL/minute; Detection: MS and UV (220 nm). Injection 1 results: Purity: 100.0%; Observed Mass: 594.09; Retention Time: 1.78 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C. Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 594.1; Retention Time: 2.56 minutes. The title compound (1.8 mg) was isolated in 4.9% yield.

Examples 114 to 116

6-bromo-4-(4-((4-fluoro-2-methoxyphenyl)(4-fluorophenyl)methyl)piperazin-1-yl)-1-(2-methoxyethyl)-2-oxo-1,2-dihydro-1,5-naphthyridine-3-carbonitrile

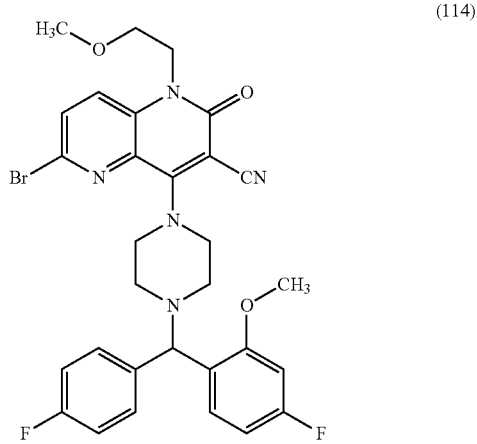 [SMILES: COCCn1c(=O)c(C#N)c(N2CCN(C(c3ccc(F)cc3)c3ccc(F)cc3OC)CC2)c2nc(Br)ccc21]

(114)

To a DMF (1 mL) solution of 6-bromo-4-chloro-1-(2-methoxyethyl)-2-oxo-1,2-dihydro-1,5-naphthyridine-3-carbonitrile (20 mg, 0.058 mmol) were added Hunig's Base (0.051 mL, 0.292 mmol) and 1-((4-fluoro-2-methoxyphenyl)(4-fluorophenyl)methyl) piperazine, 2 TFA (31.9 mg, 0.058 mmol). The reaction mixture was mixed by shaking at room temperature overnight. LC/IS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 60-100% B over 19 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 624.06; Retention Time: 1.76 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 624.07; Retention Time: 2.59 minutes. The racemic compound, Example 114, (19.7 mg) was isolated in 54.4% yield.

Example 114 was further purified by using SFC-chiral chromatography to afford Example 115 (first eluting isomer) and Example 116 (second eluting isomer). Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 101 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and IV (220 nm).

Example 115: Injection 1 results: Purity: 100.0%; Observed Mass: 624.05; Retention Time: 1.76 minutes. Injection 2 results: Purity: 100.0%; Observed Mass: 624.06; Retention Time: 2.58 minutes. Example 115 (4.5 mg) was isolated in 12.4% yield.

Example 116: Injection 1 results: Purity: 100.0%; Observed Mass: 624.05; Retention Time: 1.76 minutes. Injection 2 results: Purity: 100.0%; Observed Mass: 624.07; Retention Time: 2.58 minutes. Example 116 (4.2 mg) was isolated in 11.6% yield.

Example 117

6-bromo-4-(4-((4-fluorophenyl)(2-hydroxyphenyl)methyl)piperazin-1-yl)-1-(2-methoxyethyl)-2-oxo-1,2-dihydro-1,5-naphthyridine-3-carbonitrile

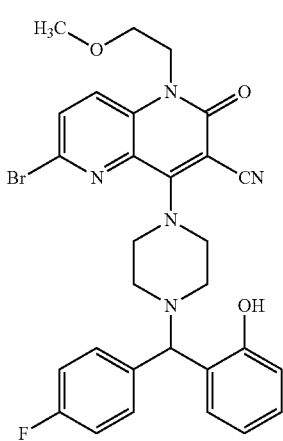

(117)

Example 118

8-(4-(bis(4-fluorophenyl)methyl)piperazin-1-yl)-7-nitro-6-oxo-5-(prop-2-yn-1-yl)-5,6-dihydro-1,5-naphthyridine-2-carbonitrile

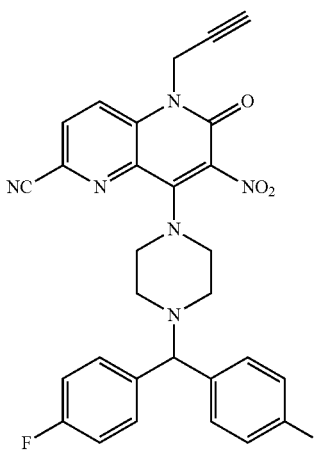

(118)

To a DMF (1 mL) solution of 6-bromo-4-chloro-1-(2-methoxyethyl)-2-oxo-1,2-dihydro-1,5-naphthyridine-3-carbonitrile (20 mg, 0.058 mmol) were added Hunig's Base (0.041 mL, 0.234 mmol) and 2-((4-fluorophenyl)(piperazin-1-yl)methyl)phenol (16.72 mg, 0.058 mmol). The reaction mixture was mixed by shaking at room temperature for 1 hour. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-90% B over 20 minutes, then a 5 minute hold at 100% B; Flow: 20 mL/minute. Fractions containing the product were combined and dried via centrifugal evaporation. Analytical LC/MS was used to determine the final purity Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 592.04; Retention Time: 2.29 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 592.03; Retention Time: 1.54 minutes. The title compound (6.4 mg) was isolated in 18.6% yield.

To a DMF (1.5 mL) solution of 8-chloro-7-nitro-6-oxo-5-(prop-2-yn-1-yl)-5,6-dihydro-1,5-naphthyridine-2-carbonitrile (25 mg, 0.087 mmol) was added 1-(bis(4-fluorophenyl)methyl)piperazine (24.97 mg, 0.087 mmol) followed by the addition of Hunig's base (0.08 mL, 0.43 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-90% B over 22 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 am). Injection 1 results: Purity: 100.0%; Observed Mass: 541.08; Retention Time: 1.74 minutes. Injection 2 conditions: Column: Waters XBridge C18, 2.1 mm×50 mm, 1.7 μm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 541.09; Retention Time: 2.38 minutes. The title compound (32.4 ng) was isolated in 68.9% yield.

Examples 119 to 121

8-(4-((4-fluoro-2-hydroxyphenyl)(4-fluorophenyl)methyl)piperazin-1-yl)-7-nitro-6-oxo-5-(prop-2-yn-1-yl)-5,6-dihydro-1,5-naphthyridine-2-carbonitrile

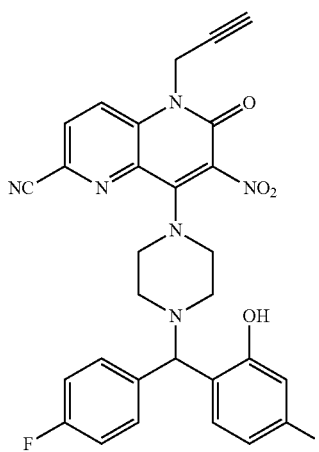

(119)

To a DMF (1.5 mL) solution of 8-chloro-7-nitro-6-oxo-5-(prop-2-yn-1-yl)-5,6-dihydro-1,5-naphthyridine-2-carbonitrile (25 mg, 0.087 mmol) was added Hunig's Base (0.076 mL, 0.433 mmol) followed by the addition of 5-fluoro-2-((4-fluorophenyl)(piperazin-1-yl)methyl)phenol, TFA (36.2 mg, 0.087 mmol). The reaction mixture was mixed by shaking at room temperature overnight. LC/MS analysis indicated that 2 major peaks were obtained. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-100% B over 20 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 557.11; Retention Time: 2.31 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 557.11; Retention Time: 1.69 minutes. The title compound (10.5 mg) was isolated in 21.7% yield.

A 8.37 mg portion of racemic material was further purified by using SFC-chiral chromatography to afford Example 120 (first eluting isomer) and Example 121 (second eluting isomer). Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μLm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Example 120: Injection 1 results: Purity: 100.0%; Observed Mass: 557.13; Retention Time: 1.7 minutes. Injection 2 results: Purity: 98.6%; Observed Mass: 557.17; Retention Time: 2.32 minutes. Example 120 (3.5 mug) was isolated in 41.9% yield.

Example 121: Injection 1 results: Purity: 100.0%; Observed Mass: 557.16; Retention Time: 1.7 minutes. Injection 2 results: Purity: 100.0%; Observed Mass: 557.12; Retention Time: 2.32 minutes. Example 121 (3.2 mug) was isolated in 38.3% yield.

Example 122

8-(4-((4-fluoro-2-hydroxyphenyl)(4-fluorophenyl)methyl)piperazin-1-yl)-5-methyl-7-nitro-6-oxo-5,6-dihydro-1,5-naphthyridine-2-carbonitrile

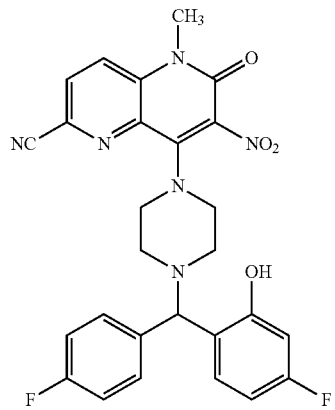

(122)

To a DMF (1.5 mL) solution of 8-chloro-5-methyl-7-nitro-6-oxo-5,6-dihydro-1,5-naphthyridine-2-carbonitrile (15 mg, 0.057 mmol) was added potassium carbonate (23.50 mg, 0.170 mmol) followed by the addition of 5-fluoro-2-((4-fluorophenyl)(piperazin-1-yl)methyl)phenol, TFA (23.71 mg, 0.057 mmol). The reaction mixture was mixed by shaking at room temperature overnight. LC/MS analysis indicated that 2 major peaks were obtained. The crude material was purified via preparative LC/MS with the following conditions: Column: XBridge C18, 19×200 mm, 5 in particles; Mobile Phase A: 5:95 acetonitrile:water with 0.1% trifluoroacetic acid; Mobile Phase B: 95:5 acetonitrile:water with 0.1% trifluoroacetic acid; Gradient: 10-80% B over 27 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 nm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 98.2%; Observed Mass: 533.11; Retention Time: 1.53 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 97.8%; Observed Mass: 533.09; Retention Time: 2.17 minutes. The title compound (3.4 mg) was isolated in 11.2% yield.

Examples 123 to 125

8-(4-((4-fluoro-2-methoxyphenyl)(4-fluorophenyl)methyl)piperazin-1-yl)-5-methyl-7-nitro-6-oxo-5,6-dihydro-1,5-naphthyridine-2-carbonitrile

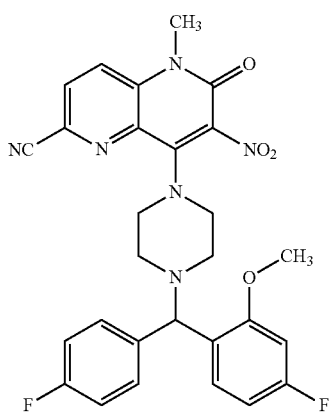

(123)

To a DMF (1 mL) solution of 8-chloro-5-methyl-7-nitro-6-oxo-5,6-dihydro-1,5-naphthyridine-2-carbonitrile (30 mg, 0.113 mmol) was added Hunig's Base (0.099 mL, 0.567 mmol) followed by the addition of 1-((4-fluoro-2-methoxyphenyl)(4-fluorophenyl) methyl)piperazine, 2 TFA (61.9 mg, 0.113 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 48-88% B over 19 minutes, then a 4 minute hold at 100% B; Flow: 20 ml/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 547.16; Retention Time: 2.41 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 547.15; Retention Time: 1.67 minutes. The racemic title compound (18 mg) was isolated in 29.1% yield.

The racemic material was further purified by using SFC-chiral chromatography to afford Example 124 (first eluting isomer) and Example 125 (second eluting isomer). Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 547.14; Retention Time: 2.41 minutes.

Example 124: Injection 1 results: Purity: 100.0%; Observed Mass: 547.15; Retention Time: 1.66 minutes. Injection 2 results: Purity: 100.0%; retention time: 1.66; Obs. Adducts: [M+H]; Obs. Masses: 547.15). Example 124 (8.1 mg) was isolated in 13.1% yield.

Example 125: Injection 1 results: Purity: 100.0%; Observed Mass: 547.21; Retention Time: 1.66 minutes. Injection 2 results: Purity: 100.0%; Observed Mass: 547.14; Retention Time: 2.41 minutes. Example 125 (8.1 mg) was isolated in 13.1% yield.

Examples 126 to 128

8-(4-((4-fluoro-2-methoxyphenyl)(4-fluorophenyl)methyl)piperazin-1-yl)-7-nitro-6-oxo-5-(prop-2-yn-1-yl)-5,6-dihydro-1,5-naphthyridine-2-carbonitrile

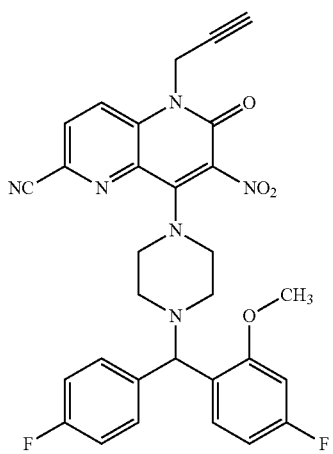

(126)

To a DMF (1.5 mL) solution of 8-chloro-7-nitro-6-oxo-5-(prop-2-yn-1-yl)-5,6-dihydro-1,5-naphthyridine-2-carbonitrile (25 mg, 0.087 mmol) was added 1-((4-fluoro-2-methoxyphenyl)(4-fluorophenyl)methyl)piperazine, 2 TFA (47.3 mg, 0.087 mmol) followed by the addition of Hunig's Base (0.08 mL, 0.43 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 50-100% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 571.14; Retention Time: 2.47 minutes. Injection 2 conditions: Column: Waters XBridge C18, 2.1 mm×50 mm, 1.7 µL m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% NB to 100% B over 3 minutes, then a 0.75 minute hold at 100% B; Flow: 1 mL/minute; Detection: MS and UV (220 mu). Injection 2 results: Purity: 100.0%; Observed Mass: 571.17; Retention Time: 1.73 minutes. The racemic title compound (21.3 mg) was isolated in 42.9% yield.

The racemic material was further purified by using SFC-chiral chromatography to afford Example 127 (first eluting isomer) and Example 128 (second eluting isomer). Analytical LC/MS was used to determine the final purity.

Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 nm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Example 127: Injection 1 results: Purity: 100.0%: Observed Mass: 571.12; Retention Time: 1.75 minutes. Injection 2 results: Purity: 100.0%; Observed Mass: 571.16; Retention Time: 2.48 minutes. Example 127 (7.7 mg) was isolated in 15.5% yield.

Example 128: Injection 1 results: Purity: 100.0%; Observed Mass: 571.15; Retention Time: 1.74 minutes. Injection 2 results: Purity: 100.0%; Observed Mass: 571.16; Retention Time: 2.48 minutes. Example 128 (7.5 mg) was isolated in 15.1% yield.

Examples 129 to 131

8-(4-((4-fluorophenyl)(2-methoxyphenyl)methyl)piperazin-1-yl)-7-nitro-6-oxo-5-(prop-2-yn-1-yl)-5,6-dihydro-1,5-naphthyridine-2-carbonitrile

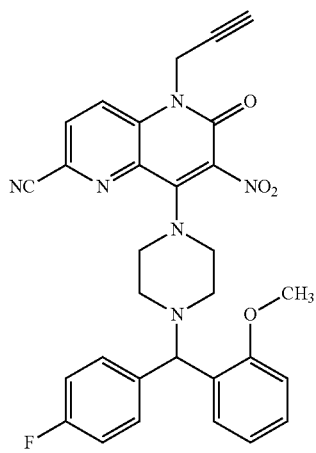

(129)

To a DMF (1.5 mL) solution of 8-chloro-7-nitro-6-ox-5-(prop-2-yn-1-yl)-5,6-dihydro-1,5-naphthyridine-2-carbonitrile (25 mg, 0.087 mmol) was added 1-((4-fluorophenyl)(2-methoxyphenyl)methyl)piperazine, 2 TFA (45.8 mg, 0.087 mmol) followed by the addition of Hunig's Base (0.08 mL, 0.43 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-95° % B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 553.15; Retention Time: 1.67 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 553.15; Retention Time: 2.45 minutes. The racemic title compound (27.3 mg) was isolated in 56.8% yield.

The racemic material was further purified by using SFC-chiral chromatography to afford Example 130 (first eluting isomer) and Example 131 (second eluting isomer). Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Example 130: Injection 1 results: Purity: 100.0%: Observed Mass: 553.15; Retention Time: 2.45 minutes. Injection 2 results: Purity: 100.0%; Observed Mass: 553.13; Retention Time: 1.68 minutes. Example 130 (8 mg) was isolated in 16.6% yield.

Example 131: Injection 1 results: Purity: 100.0%; Observed Mass: 553.14; Retention Time: 2.45 minutes. Injection 2 results: Purity: 100.0%; Observed Mass: 553.17; Retention Time: 1.71 minutes. Example 131 (2.3 mg) was isolated in 4.8% yield.

Examples 132 to 134

8-(4-((4-fluorophenyl)(2-hydroxyphenyl)methyl) piperazin-1-yl)-7-nitro-6-oxo-5-(prop-2-yn-1-yl)-5, 6-dihydro-1,5-naphthyridine-2-carbonitrile

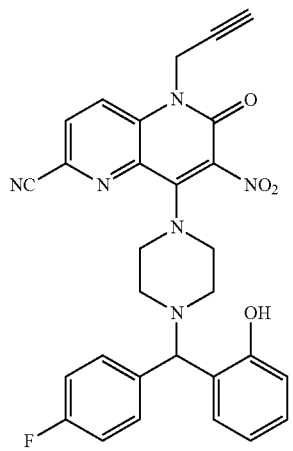

(132)

To a DMF (1.5 mL) solution of 8-chloro-7-nitro-6-oxo-5-(prop-2-yn-1-yl)-5,6-dihydro-1,5-naphthyridine-2-carbonitrile (25 ng, 0.087 mmol) was added 2-((4-fluorophenyl)(piperazin-1-yl)methyl)phenol, 2 TFA (44.6 mg, 0.087 mmol) followed by the addition of Hunig's Base (0.08 ml, 0.43 mmol). The reaction mixture was mixed by shaking at room temperature for 1 hour. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 n ammonium acetate; Mobile Phase B: 95:5 acetonitrile:water with 10 mM ammonium acetate; Gradient: 50-90% B over 20 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 539.13; Retention Time: 2.26 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 539.14; Retention Time: 1.62 minutes. The racemic title compound (9.7 mug) was isolated in 20.7% yield.

The racemic material was further purified by using SFC-chiral chromatography to afford Example 133 (first eluting isomer) and Example 134 (second eluting isomer). Analytical LC/MS was used to determine the final purity.

Injection 1 conditions: Column: Waters XBridge C18, 2.1 mm×50 mm, 1.7 pam particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Example 133: Injection 1 results: Purity: 100.0%; Observed Mass: 539.17; Retention Time: 2.25 minutes. Injection 2 results: Purity: 100.0%; Observed Mass: 539.15; Retention Time: 1.61 minutes. Example 133 (4.3 mg) was isolated in 9.2% yield.

Example 134: Injection 1 results: Purity: 100.0%; Observed Mass: 539.12; Retention Time: 2.25 min. Injection 2 results: Purity: 100.0%; Observed Mass: 539.19; Retention Time: 1.6 min. Example 134 (2.8 mg) was isolated in 6% yield.

Examples 135 to 137

8-(4-(1-(4-fluorophenyl)ethyl)piperazin-1-yl)-7-nitro-6-oxo-5-(prop-2-yn-1-yl)-5,6-dihydro-1,5-naphthyridine-2-carbonitrile

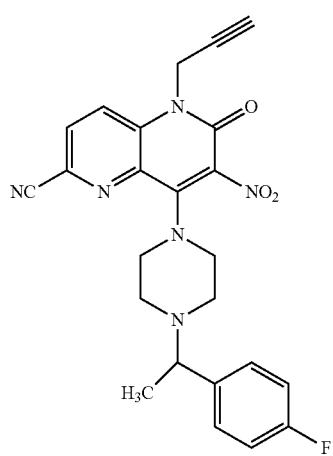

(135)

To a DMF (1 mL) solution of 8-chloro-7-nitro-6-oxo-5-(prop-2-yn-1-yl)-5,6-dihydro-1,5-naphthyridine-2-carbonitrile (20 mg, 0.055 mmol) and 1-(1-phenylethyl) piperazine (46.4 mg, 0.111 mmol) were added Hunig's Base (0.029 mL, 0.166 mmol) and 1-(1-phenylethyl)piperazine (46.4 mg, 0.111 mmol). The reaction mixture was mixed by shaking at room temperature for 2 hours. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 13-53% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B: Flow: 1 mL/minute; Detection: MS and UV (220 nm). Injection 1 results: Purity: 100.0%; Observed Mass: 461.16; Retention Time: 1.33 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 461.11; Retention Time: 2.15 minutes. The racemic title compound (20.5 mg) was isolated in 80.9% yield.

The racemic material was further purified by using SFC-chiral chromatography to afford Example 136 (first eluting isomer) and Example 137 (second eluting isomer). Analytical LC/MS was used to determine the final purity.

Injection 1 conditions: Column: Waters XBridge C18, 2.1 mm×50 mm, 1.7 Lm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 nm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 m/minute; Detection: MS and UV (220 nm).

Example 136: Injection 1 results: Purity: 99.0%; Observed Mass: 461.12; Retention Time: 1.35 minutes. Injection 2 results: Purity: 98.8%; Observed Mass: 461.12; Retention Time: 2.15 minutes. Example 136 (6.1 mg) was isolated in 24.1% yield.

Example 137: Injection 1 results: Purity: 98.6%; Observed Mass: 461.14; Retention Time: 1.35 minutes. Injection 2 results: Purity: 100.0%; Observed Mass: 461.13; Retention Time: 2.15 minutes. Example 137 (5.7 mg) was isolated in 22.5% yield.

Example 138

8-(4-(6-methoxy-2,3-dihydro-1H-inden-1-yl)piperazin-1-yl)-7-nitro-6-oxo-5-(prop-2-yn-1-yl)-5,6-dihydro-1,5-naphthyridine-2-carbonitrile

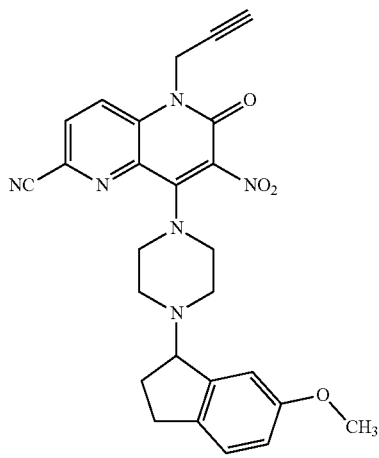

(138)

To a DMF (1 mL) solution of 8-chloro-7-nitro-6-oxo-5-(prop-2-yn-1-yl)-5,6-dihydro-1,5-naphthyridine-2-carbonitrile (20 mg, 0.055 mmol) and Hunig's Base (0.029 mL, 0.166 mmol) was added 1-(6-methoxy-2,3-dihydro-1H-inden-1-yl)piperazine (51.0 mg, 0.111 mmol). The reaction mixture was mixed by shaking at room temperature for 2 hours. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 21 mm×50 mm, 1.7 μm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 485.18; Retention Time: 2.13 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 485.16; Retention Time: 1.4 minutes. The title compound (24 mg) was isolated in 90.1% yield.

Examples 139 to 141

8-{4-[1-(4-fluorophenyl)propyl]piperazin-1-yl}-7-nitro-6-oxo-5-(prop-2-yn-1-yl)-5,6-dihydro-1,5-naphthyridine-2-carbonitrile

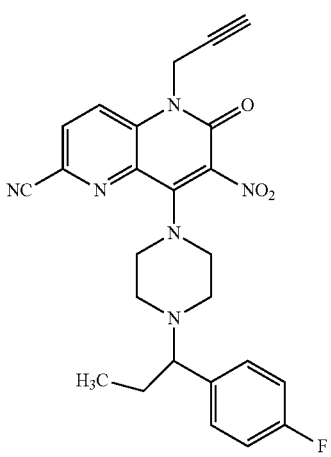

(139)

To a DMF (1 mL) solution of 8-chloro-7-nitro-6-oxo-5-(prop-2-yn-1-yl)-5,6-dihydro-1,5-naphthyridine-2-carbonitrile (20 mg, 0.055 mmol) and 1-(1-phenylpropyl) piperazine, 2 TFA (35.9 mg, 0.083 mmol) were added Hunig's Base (0.048 mL, 0.277 mmol) and 1-(l-phenylpropyl)piperazine, 2 TFA (35.9 mg, 0.083 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 45-85% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 475.16; Retention Time: 1.45 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 475.16; Retention Time: 2.29 minutes. The racemic title compound (15.3 mg) was isolated in 58.6% yield.

The racemic material was further purified by using SFC-chiral chromatography to afford Example 140 (first eluting isomer) and Example 141 (second eluting isomer). Analytical LC/MS was used to determine the final purity. Injection 1 conditions: Column: Waters XBridge C18, 2.1 mm×50 mm, 1.7 μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Example 140: Injection 1 results: Purity: 100.0%; Observed Mass: 475.19; Retention Time: 2.28 minutes. Injection 2 results: Purity: 97.3%; Observed Mass: 475.19; Retention Time: 1.47 minutes. Example 140 (6.9 mg) was isolated in 26.4% yield.

Example 141: Injection 1 results: Purity: 98.2%; Observed Mass: 475.17; Retention Time: 2.28 minutes. Injection 2 results: Purity: 98.5%; Observed Mass: 475.18; Retention Time: 1.47 minutes. Example 141 (6.4 mg) was isolated in 24.5% yield.

Examples 142 to 144

8-(4-(cyclopropyl(4-fluorophenyl)methyl)piperazin-1-yl)-7-nitro-6-oxo-5-(prop-2-yn-1-yl)-5,6-dihydro-1,5-naphthyridine-2-carbonitrile

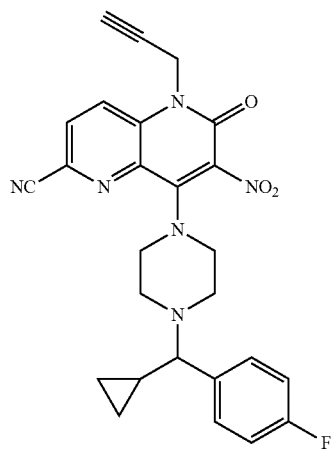

(142)

To a DMF (1 mL) solution of 1-(cyclopropyl(4-fluorophenyl)methyl)piperazine, TFA (24.14 mg, 0.069 mmol) and 8-chloro-7-nitro-6-oxo-5-(prop-2-yn-1-yl)-5,6-dihydro-1,5-naphthyridine-2-carbonitrile (20 mg, 0.069 mmol) was added Hunig's Base (0.036 mL, 0.208 mmol). The reaction mixture was mixed by shaking at room temperature for 2 hours. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 45-85% B over 20 minutes, then a 6-minute hold at 100% B; Flow: 20 mL/minute. Fractions containing the product were combined and dried via centrifugal evaporation.

The racemic material was purified by using SFC-chiral chromatography to afford Example 143 (first eluting isomer) and Example 144 (second eluting isomer). Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Example 143: Injection 1 results: Purity: 100.0%; Observed Mass: 487.02; Retention Time: 1.56 minutes. Injection 2 results: Purity: 100.0%; Observed Mass: 487.02; Retention Time: 2.23 minutes. Example 143 (3.8 mg) was isolated in 11.3% yield.

Example 144: Injection 1 results: Purity: 100.0%; Observed Mass: 487.03; Retention Time: 1.41 minutes. Injection 2 results: Purity: 99.1%; Observed Mass: 487.03; Retention Time: 2.23 minutes. Example 144 (4 mg) was isolated in 119% yield.

Example 145

8-(4-((4-fluorophenyl)(2-hydroxyphenyl)methyl)piperazin-1-yl)-5-(2-methoxyethyl)-7-nitro-6-oxo-5,6-dihydro-1,5-naphthyridine-2-carbonitrile

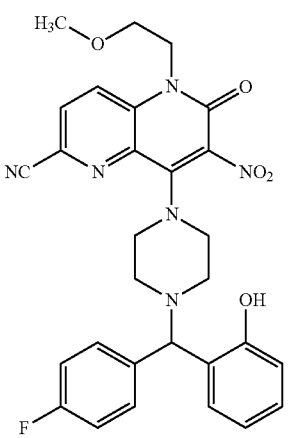

(145)

To a DMF (0.5 mL) solution of 8-chloro-5-(2-methoxyethyl)-7-nitro-6-oxo-5,6-dihydro-1,5-naphthyridine-2-carbonitrile (5 mg, 0.016 mmol) were added Hunig's Base (8.49 μl, 0.049 mmol) and 2-((4-fluorophenyl)(piperazin-1-yl)methyl)phenol (9.28 mg 0.032 mmol). The reaction mixture was mixed by shaking at room temperature for 1 hour. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 38-78% B over 20 minutes, then a 4 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 21 min×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 559.23; Retention Time: 1.6 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 559.19; Retention Time: 2.27 minutes. The title compound (1.5 mg) was isolated in 16.8% yield.

Example 146

8-(4-(6-methoxy-2,3-dihydro-1H-inden-1-yl)piperazin-1-yl)-5-(2-methoxyethyl)-7-nitro-6-oxo-5,6-dihydro-1,5-naphthyridine-2-carbonitrile

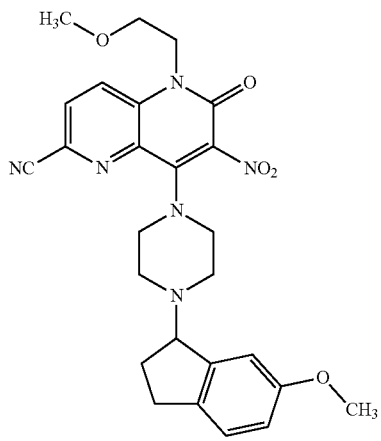

(146)

To a DMF (0.5 mL) solution of 8-chloro-5-(2-methoxyethyl)-7-nitro-6-oxo-5,6-dihydro-1,5-naphthyridine-2-carbonitrile (15 mg, 0.049 mmol) were added Hunig's Base (0.025 mL, 0.146 n mol) and 1-(6-methoxy-2,3-dihydro-1H-inden-1-yl)piperazine (16.93 mug, 0.073 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 40-80% B over 20 minutes, then a 4 minute hold at 100% B: Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 505.21; Retention Time: 1.41 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 505.2; Retention Time: 2.13 minutes. The title compound (12.5 mg) was isolated in 50.6% yield.

Example 147

8-(4-(bis(4-fluorophenyl)methyl)piperazin-yl)-5-(2-methoxyethyl)-7-nitro-6-oxo-5,6-dihydro-1,5-naphthyridine-2-carbonitrile

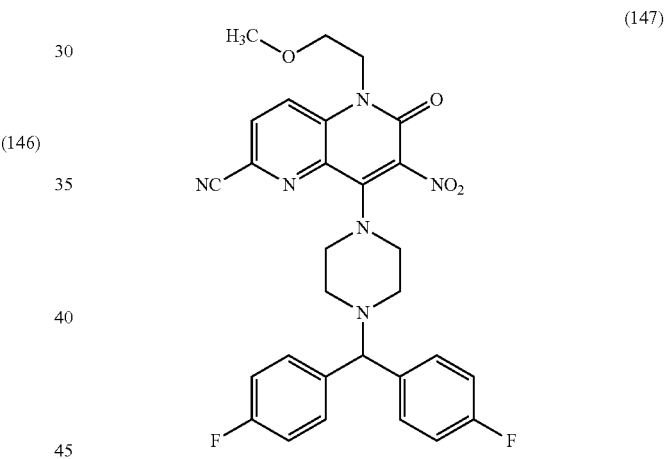

(147)

To a DMF (0.5 mL) solution of 8-chloro-5-(2-methoxyethyl)-7-nitro-6-oxo-5,6-dihydro-1,5-naphthyridine-2-carbonitrile (15 tug, 0.049 mmol) were added Hunig's Base (0.025 mL, 0.146 mmol) and 1-(bis(4-fluorophenyl)methyl)piperazine (21.02 mg, 0.073 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 46-86% B over 20 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 561.17; Retention Time: 1.79 minutes. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 561.17; Retention Time: 2.46 minutes. The title compound (13.5 mug) was isolated in 49.1% yield.

Examples 148 to 150

8-(4-(1-(4-fluorophenyl)ethyl)piperazin-1-yl)-5-(2-methoxyethyl)-7-nitro-6-oxo-5,6-dihydro-1,5-naphthyridine-2-carbonitrile

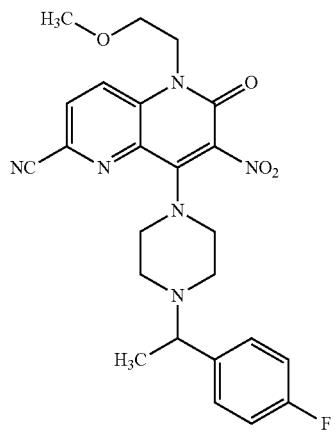

(148)

To a DMF (0.5 mL) solution of 8-chloro-5-(2-methoxyethyl)-7-nitro-6-oxo-5,6-dihydro-1,5-naphthyridine-2-carbonitrile (15 mg, 0.049 mmol) were added Hunig's Base (0.051 mL, 0.292 mmol) and 1-(1-(4-fluorophenyl)ethyl) piperazine, 2 aqueous hydrochloric acid (20.50 mg, 0.073 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 38-78% B over 22 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 pam particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 481.19; Retention Time: 1.36 minutes. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 am). Injection 2 results: Purity: 100.0%; Observed Mass: 481.17; Retention Time: 2.16 minutes. The racemic title compound (11.5 mg) was isolated in 48.8% yield.

The racemic material was further purified by using SFC-chiral chromatography to afford Example 149 (first eluting isomer) and Example 150 (second eluting isomer). Analytical LC/MS was used to determine the final purity.

Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Example 149: Injection 1 results: Purity: 97.1%; Observed Mass: 481.18; Retention Time: 2.17 minutes. Injection 2 results: Purity: 97.4%; Observed Mass: 481.16; Retention Time: 1.36 minutes. Example 149 (3.7 mg) was isolated in 15.7% yield.

Example 150: Injection 1 results: Purity: 97.1%; Observed Mass: 481.2; Retention Time: 2.17 minutes. Injection 2 results: Purity: 97.3%; Observed Mass: 481.18; Retention Time: 1.36 minutes. Example 150 (3.6 mg) was isolated in 15.3% yield.

Example 151

5-(cyanomethyl)-8-(4-(1-(4-fluorophenyl)ethyl)piperazin-1-yl)-7-nitro-6-oxo-5,6-dihydro-1,5-naphthyridine-2-carbonitrile

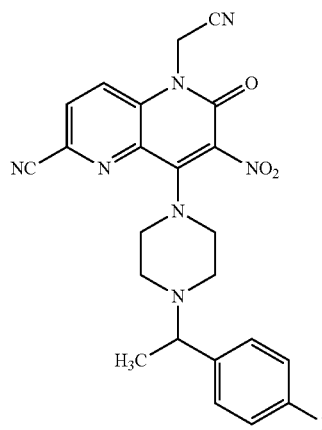

(151)

To a DMF (0.5 mL) solution of 8-chloro-5-(cyanomethyl)-7-nitro-6-oxo-5,6-dihydro-1,5-naphthyridine-2-carbonitrile (15 mg, 0.052 mmol) were added Hunig's Base (0.027 mL, 0.155 mmol) and 1-(1-(4-fluorophenyl)ethyl)piperazine (16.18 mg, 0.078 mmol). The reaction mixture was mixed by shaking at room temperature for 1 hr. LC/MS analysis indicated that the reaction was approximately 80% complete. The reaction mixture was mixed by shaking at room temperature for 3 more hours. The crude material was purified via preparative LC/MS with the following conditions: Column: XBridge C18, 19×200 mm, 5 μm particles; Mobile Phase A: 5:95 acetonitrile: water with 10 mM ammonium acetate; Mobile Phase B: 95:5 acetonitrile:water with 10 mM ammonium acetate; Gradient: 28-68% B over 20 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 462.14; Retention Time: 1.28 minutes. Injection 2 conditions: Column: Waters XBridge C18, 2.1 mm×50 mm, 1.7 μm particles; Mobile Phase A: 5:95 acetonitrile:water with 10 nM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 462.15; Retention Time: 2.07 minutes. The title compound (6.6 mg) was isolated in 27.5% yield.

Example 152

8-(4-(bis(4-fluorophenyl)methyl)piperazin-1-yl)-5-(cyanomethyl)-7-nitro-6-oxo-5,6-dihydro-1,5-naphthyridine-2-carbonitrile

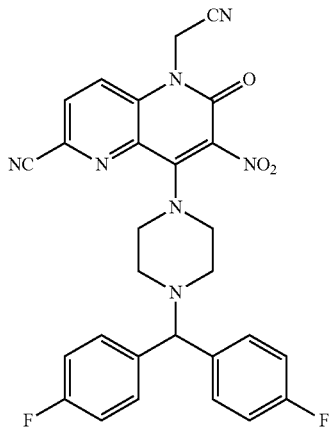

(152)

To a DMF (0.5 mL) solution of 8-chloro-5-(cyanomethyl)-7-nitro-6-oxo-5,6-dihydro-1,5-naphthyridine-2-carbonitrile (15 mg, 0.052 mmol) were added Hunig's Base (0.027 mL, 0.155 mmol) and 1-(bis(4-fluorophenyl)methyl)piperazine (22.40 mg, 0.078 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 41-81% B over 23 minutes, then a 6-minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 542.09; Retention Time: 1.71 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 542.11; Retention Time: 2.32 minutes. The title compound (5.3 mg) was isolated in 18.8% yield.

Example 153

4-(4-(bis(4-fluorophenyl)methyl)piperazin-1-yl)-6-bromo-1-(cyanomethyl)-2-oxo-1,2-dihydro-1,5-naphthyridine-3-carbonitrile

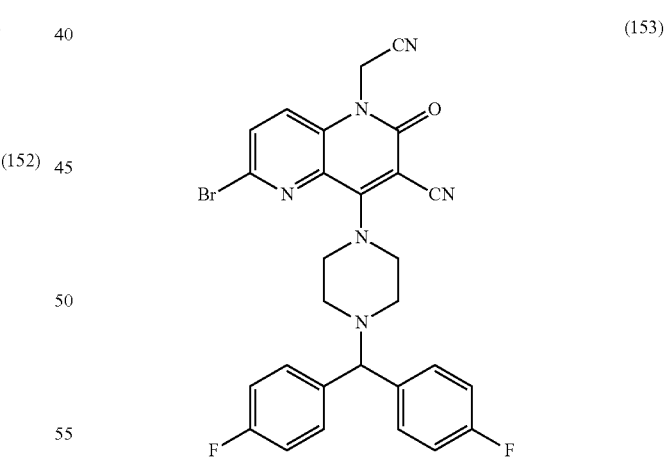

(153)

To a DMF (0.5 mL) solution of 6-bromo-4-chloro-1-(cyanomethyl)-2-oxo-1,2-dihydro-1,5-naphthyridine-3-carbonitrile (15 mg, 0.046 mmol) were added Hunig's Base (0.024 mL, 0.139 mmol) and 1-(bis(4-fluorophenyl)methyl)piperazine (20.05 mg, 0.070 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 43-83% B over 20 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 97.1%; Observed Mass: 577.13; Retention Time: 2.39 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 97.7%; Observed Mass: 575.07; Retention Time: 1.74 minutes. The title compound (6.3 mg) was isolated in 23.8% yield.

Example 154

6-bromo-1-(cyanomethyl)-4-(4-(1-(4-fluorophenyl)ethyl)piperazin-1-yl)-2-oxo-1,2-dihydro-1,5-naphthyridine-3-carbonitrile

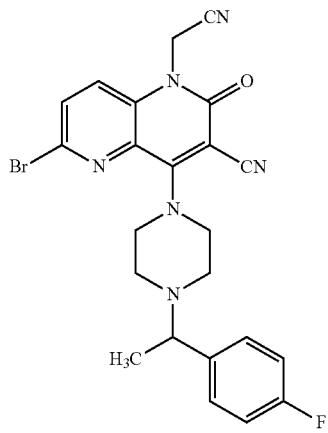

(154)

To a DMF (0.5 mL) solution of 6-bromo-4-chloro-1-(cyanomethyl)-2-oxo-1,2-dihydro-1,5-naphthyridine-3-carbonitrile (15 mg, 0.046 mmol) were added Hunig's Base (0.024 mL, 0.139 mmol) and 1-(1-(4-fluorophenyl)ethyl)piperazine (14.48 mg, 0.070 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 38-78% B over 20 minutes, then a 6-minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 494.97; Retention Time: 2.05 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 494.95; Retention Time: 1.26 minutes. The title compound (6.6 mg) was isolated in 29% yield.

Example 155

6-bromo-1-(cyanomethyl)-4-(4-(1-(4-fluorophenyl)propyl)piperazin-1-yl)-2-oxo-1,2-dihydro-1,5-naphthyridine-3-carbonitrile

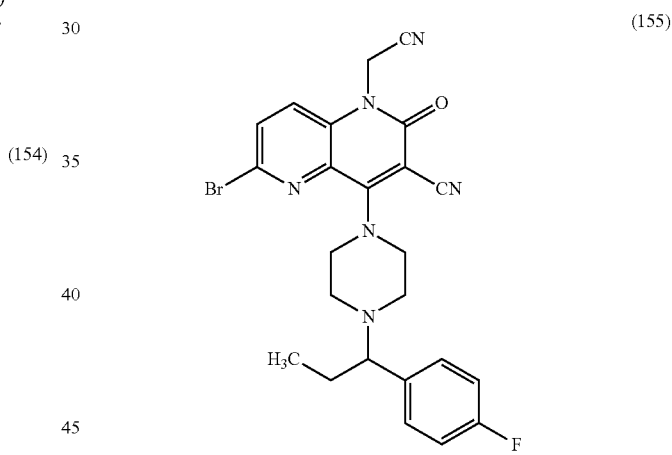

(155)

To a DMF (0.5 mL) solution of 6-bromo-4-chloro-1-(cyanomethyl)-2-oxo-1,2-dihydro-1,5-naphthyridine-3-carbonitrile (15 mg, 0.046 mmol) were added Hunig's Base (0.024 mL, 0.139 mmol) and 1-(1-(4-fluorophenyl)propy)piperazine (15.46 mg, 0.070 mmol). The reaction mixture was mixed by shaking at room temperature overnight. LC/MS analysis indicated that the reaction is complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 38-78% B over 25 minutes, then a 6-minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 509.07; Retention Time: 1.43 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 509.1; Retention Time: 2.26 minutes. The title compound (6.8 mg) was isolated in 29% yield.

Example 156

6-bromo-1-(cyanomethyl)-4-(4-(6-methoxy-2,3-dihydro-1H-inden-1-yl)piperazin-1-yl)-2-oxo-1,2-dihydro-1,5-naphthyridine-3-carbonitrile

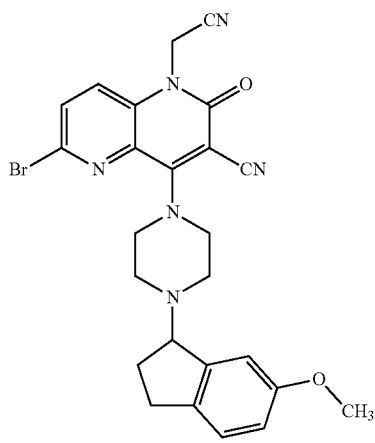

(156)

To a DMF (0.5 mL) solution of 6-bromo-4-chloro-1-(cyanomethyl)-2-oxo-1,2-dihydro-1,5-naphthyridine-3-carbonitrile (15 mg, 0.046 mmol) were added Hunig's Base (0.024 mL, 0.139 mmol) and 1-(6-methoxy-2,3-dihydro-1H-inden-1-yl)piperazine (16.16 mg, 0.070 mmol). The reaction mixture was mixed by shaking at room temperature overnight. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 32-72% B over 20 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 97.0%; Observed Mass: 519.08; Retention Time: 2.06 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 97.6%; Observed Mass: 519.04; Retention Time: 136 minutes. The title compound (2.8 mg) was isolated in 11.7% yield.

Example 157

6-bromo-1-(cyanomethyl)-4-(4-((4-fluorophenyl)(2-hydroxyphenyl)methyl)piperazin-1-yl)-2-oxo-1,2-dihydro-1,5-naphthyridine-3-carbonitrile

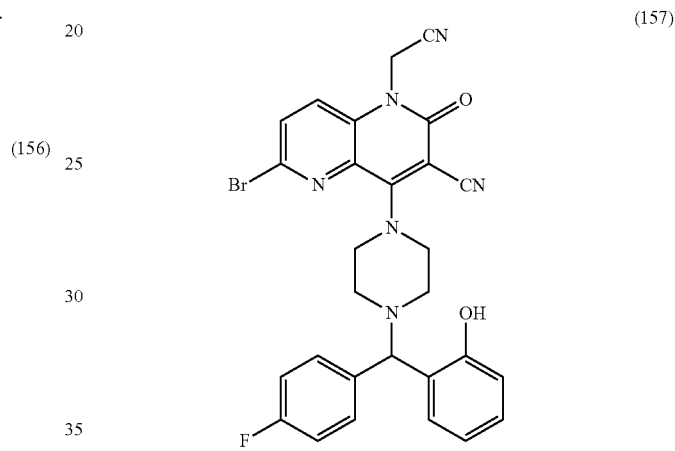

(157)

To a DMF (0.5 mL) solution of 6-bromo-4-chloro-1-(cyanomethyl)-2-oxo-1,2-dihydro-1,5-naphthyridine-3-carbonitrile (25 mg, 0.077 mmol) were added Hunig's Base (0.040 mL, 0.232 mmol) and 2-((4-fluorophenyl)(piperazin-1-yl)methyl)phenol, TFA (37.1 mg, 0.093 mmol). The reaction mixture was mixed by shaking at room temperature for 1 hour. LC/MS analysis indicated that the desired product was detected. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 36-76% B over 20 minutes, then a 5 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 573.08; Retention Time: 2.26 minutes. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 573.1; Retention Time: 1.58 minutes. The title compound (4.5 mg) was isolated in 10.2% yield.

Examples 158 to 160

6-bromo-1-(cyclopropylmethyl)-4-(4-((4-fluorophenyl)(2-methoxyphenyl) methyl)piperazin-1-yl)-2-oxo-1,2-dihydro-1,5-naphthyridine-3-carbonitrile

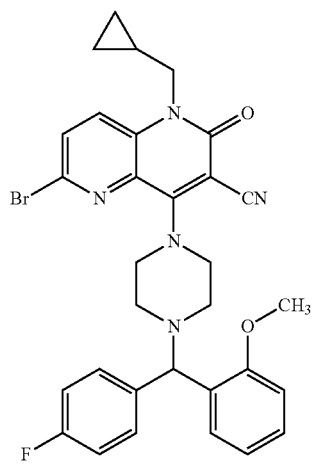

(158)

To a DMF (1 mL) solution of 6-bromo-4-chloro-1-(cyclopropylmethyl)-2-oxo-1,2-dihydro-1,5-naphthyridine-3-carbonitrile (15 mg, 0.044 mmol) was added 1-((4-fluorophenyl)(2-methoxyphenyl)methyl)piperazine, TFA (18.36 mg, 0.044 mmol)) followed by the addition of Hunig's Base (0.023 mL, 0.133 mmol). The reaction mixture was mixed by shaking at room temperature for 2 hours. LC/MS analysis indicated the reaction was complete. The crude material was purified via preparative LC/MS with the following conditions: Column: XBridge C18, 19×200 mm, 5 in particles; Mobile Phase A: 5:95 acetonitrile:water with 10 mM ammonium acetate; Mobile Phase B: 95:5 acetonitrile:water with 10 mM ammonium acetate; Gradient: 50-100% B over 20 minutes, then a 6-minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 602.08; Retention Time: 1.78 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 602.13; Retention Time: 2.68 minutes. The racemic title compound (16.8 mg) was isolated in 63.4% yield.

The racemic material was further purified by using SFC-chiral chromatography to afford Example 159 (first eluting isomer) and Example 160 (second eluting isomer). Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Example 159: Injection 1 results: Purity: 100.0%; Observed Mass: 602.08; Retention Time: 1.78 minutes. Injection 2 results: Purity: 100.0%; Observed Mass: 602.09; Retention Time: 2.68 minutes. Example 159 (6.6 mg) was isolated in 24.9% yield.

Example 160: Injection 1 results: Purity: 100.0%; Observed Mass: 602.08; Retention Time: 1.78 minutes. Injection 2 results: Purity: 100.0%; Observed Mass: 602.11; Retention Time: 2.68 minutes. Example 160 (5.2 mg) was isolated in 19.6% yield.

Example 161

4-(4-(bis(4-fluorophenyl)methyl)piperazin-1-yl)-6-bromo-1-(cyclopropylmethyl)-2-oxo-1,2-dihydro-1,5-naphthyridine-3-carbonitrile

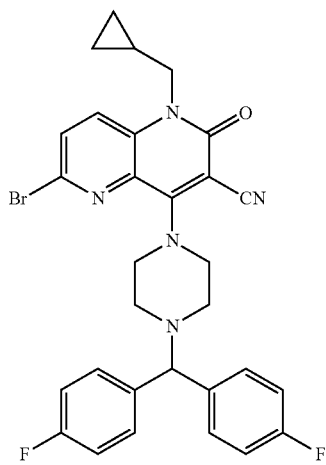

(161)

To a DMF (15 mL) solution of 6-bromo-4-chloro-1-(cyclopropylmethyl)-2-oxo-1,2-dihydro-1,5-naphthyridine-3-carbonitrile (15 mg, 0.044 mmol) was added 1-(bis(4-fluorophenyl)methyl)piperazine, TFA (17.83 mg, 0.044 mmol)) followed by Hunig's Base (0.023 mL, 0.133 mmol). The reaction mixture was mixed by shaking at room temperature for 2 hours. LC/MS analysis indicated the reaction was complete. The crude material was purified via preparative LC/MS with the following conditions: Column: XBridge C18, 19×200 mm, 5 μm particles; Mobile Phase A:

5:95 acetonitrile:water with 10 mM ammonium acetate; Mobile Phase B: 95:5 acetonitrile:water with 10 mM ammonium acetate; Gradient: 55-100% B over 20 minutes, then a 6-minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 590.11; Retention Time: 2.66 minutes. Injection 2 conditions: Column: Waters XBridge C18, 2.1 mm×50 mm, 1.7 μm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 590.1; Retention Time: 1.9 minutes. The title compound (14.5 mg) was isolated in 55.8% yield.

Examples 162 to 164

6-bromo-1-(cyclopropylmethyl)-4-(4-(1-(4-fluorophenyl)ethyl)piperazin-1-yl)-2-oxo-1,2-dihydro-1,5-naphthyridine-3-carbonitrile

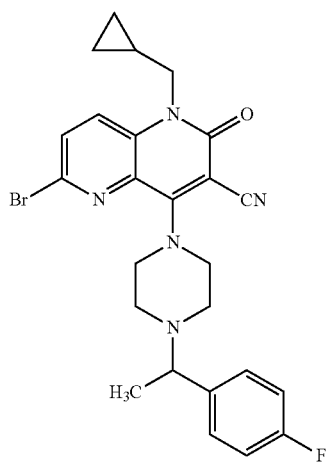

(162)

To a DMF (15 mL) solution of 6-bromo-4-chloro-1-(cyclopropylmethyl)-2-oxo-1,2-dihydro-1,5-naphthyridine-3-carbonitrile (15 mg, 0.044 mmol) was added 1-(1-(4-fluorophenyl)ethyl)piperazine, TFA (14.28 mg, 0.044 mmol)) followed by Hunig's Base (0.023 mL, 0.133 mmol). The reaction mixture was mixed by shaking at room temperature for 2 hours. LC/MS analysis indicated the reaction was complete. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-90% B over 20 minutes, then a 4 minute hold at 100% B; Flow: 20 mL/minute. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm). Injection 1 results: Purity: 100.0%; Observed Mass: 510.07; Retention Time: 1.49 minutes. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm). Injection 2 results: Purity: 100.0%; Observed Mass: 510.09; Retention Time: 2.38 minutes. The racemic title compound (14.8 mg) was isolated in 65.9% yield.

The racemic material was further purified by using SFC-chiral chromatography to afford Example 163 (first eluting isomer) and Example 164 (second eluting isomer). Analytical LC/MS was used to determine the final purity.

Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 minutes, then a 0.75 minute hold at 100% B; Flow: 1 mL/minute; Detection: MS and UV (220 nm).

Injection 2 conditions: Column: Waters XBridge C18, 2.1 mm×50 mm, 1.7 μm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0% B to 100% B over 3 minutes, then a 0.75 minute hold at 100% B; Flow: 1 mL/minute; Detection: MS and UV (220 nm).

Example 163: Injection 1 results: Purity: 97.5%; Observed Mass: 510.13; Retention Time: 2.37 minutes. Injection 2 results: Purity: 98.3%; Observed Mass: 510.11; Retention Time: 1.51 minutes. Example 163 (3.5 mg) was isolated in 15.6% yield.

Example 164: Injection 1 results: Purity: 99.0%; Observed Mass: 510.13; Retention Time: 2.37 minutes. Injection 2 results: Purity: 100.0%; Observed Mass: 510.11; Retention Time: 1.51 minutes. Example 164 (4.5 mg) was isolated in 20% yield.

General Process for Preparing Example 204 and 4-(4-benzhydrylpiperazin-1-yl)-1-alkyl-3-nitro-1,5-naphthyridin-2 (1H)-one analogues:

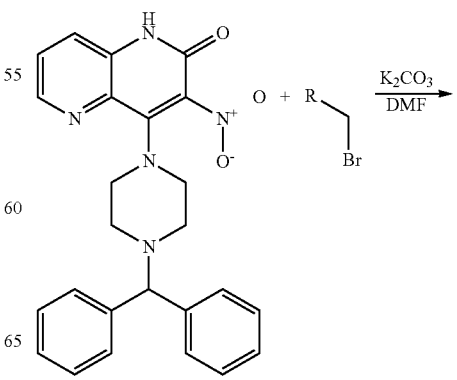

-continued

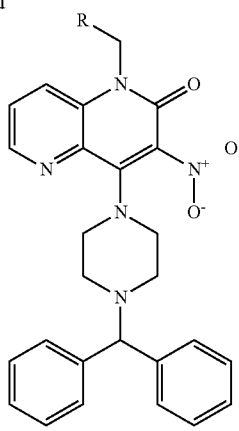

A DMF (15.5 mL) solution of 4-(4-benzhydrylpiperazin-1-yl)-3-nitro-1,5-naphthyridin-2(1H)-one was prepared. To each of the alkyl halides weighed into 16×100 mm threaded vials were added 0.500 mL of the 4-(4-benzhydrylpiperazin-1-yl)-3-nitro-1,5-naphthyridin-2(1H)-one solution, potassium carbonate (25 mg, 0.18 mmol), and a stir bar. The vials were capped and allowed to shake at room temperature for 4 hours before heating to 50° C. with stirring overnight. The mixtures were transferred to empty 6-mL SPE cartridges for filtration, collecting into 16×48 mm threaded vials. The reaction vials were each rinsed with 0.5 mL of DMF. The rinses were transferred to the filter cartridges. Crude mixtures were purified by preparative HPLC using the conditions described for each example.

Example 165

4-(4-benzhydrylpiperazin-1-yl)-3-nitro-1-(prop-2-yn-1-yl)-1,5-naphthyridin-2(1H)-one

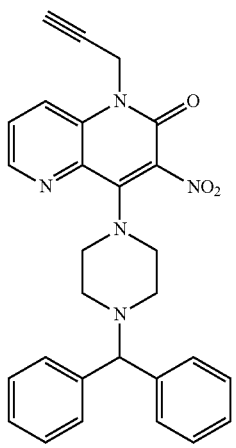

(165)

The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 55-100% B over 20 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.75 minute hold at 100% B; Flow: 1 mL/min; Detection: UV at 220 nm. Injection 2 conditions: Column: Waters BEH C18, 2.0×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B, 0-100% B over 3 minutes, then a 0.75 minute hold at 100% B; Flow: 1.0 mL/min; Detection: UV at 220 nm. The title compound was isolated in 54.7% yield (11.8 mg).

Example 166

1-(2-(1,3-dioxan-2-yl)ethyl)-4-(4-benzhydrylpiperazin-1-yl)-3-nitro-1,5-naphthyridin-2(1H)-one

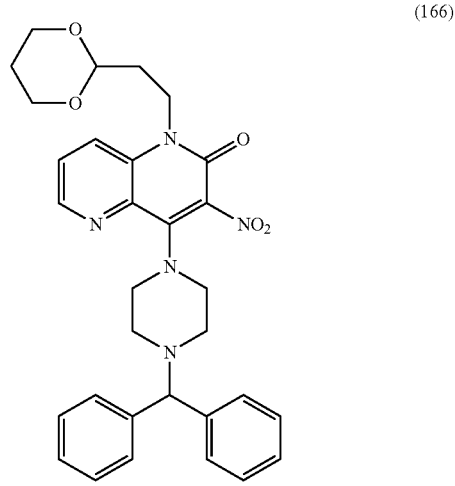 [SMILES: O=c1c([N+](=O)[O-])c(N2CCN(C(c3ccccc3)c3ccccc3)CC2)c2ncccc2n1CCC1OCCCO1]

(166)

The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 70-100% B over 15 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.75 minute hold at 100% B; Flow: 1 mL/min; Detection: UV at 220 nm. Injection 2 conditions: Column: Waters BEH C18, 2.0×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B, 0-100% B over 3 minutes, then a 0.75 minute hold at 100% B; Flow: 1.0 mL/min; Detection: UV at 220 nm. The title compound was isolated in 36% yield (9 mg).

Example 176

1-all-4-(4-benzhydrylpiperazin-1-yl)-3-nitro-1,5-naphthyridin-2(1H)-one

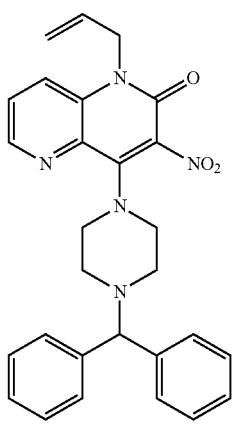

(176)

The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 70-100% B over 15 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters BEH C18, 2.0 20×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.75 minute hold at 100% B; Flow: 1 mL/min; Detection: UV at 220 nm. Injection 2 conditions: Column: Waters BEH C18, 2.0×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B, 0-100% B over 3 minutes, then a 0.75 minute hold at 100% B; Flow: 1.0 mL/min; Detection: UV at 220 nm. The title compound was isolated in 37.4% yield (8.1 mg).

Example 177

4-(4-benzhydrylpiperazin-1-yl)-1-butyl-3-nitro-1,5-naphthyridin-2(1H)-one

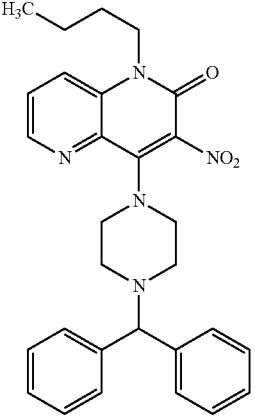

(177)

The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 70-100% B over 15 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.75 minute hold at 100% B; Flow: 1 ml/min; Detection: UV at 220 nm. Injection 2 conditions: Column: Waters BEH C18, 2.0×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B, 0-100% B over 3 minutes, then a 0.75 minute hold at 100% B; Flow: 1.0 mL/min; Detection: UV at 220 nm. The title compound was isolated in 26.3% yield (5.9 mg).

Example 183

4-(4-(4-benzhydrylpiperazin-1-yl)-3-nitro-2-oxo-1,5-naphthyridin-1(2H)-yl)butanenitrile

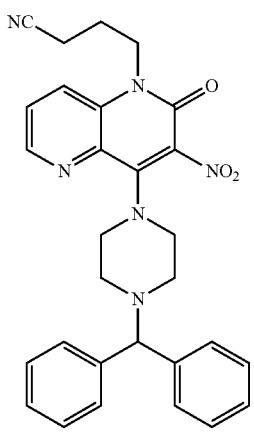

(183)

The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-90% B over 15 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1× 50 mm, 1.7 μm particles; Mobile Phase A: 5:95 acetonitrile:water with 0.1% trifluoroacetic acid; Mobile Phase B: 95:5 acetonitrile:water with 0.100 trifluoroacetic acid; Temperature: 50° C.; Gradient: 0-100% B over 3 minutes, then a 0.75 minute hold at 100% B; Flow: 1.0 mL/min; Detection: UV at 220 nm. The title compound was isolated in 36.3% yield (8.3 mg).

Example 185

4-(4-benzhydrylpiperazin-1-yl)-3-nitro-1-(3,3,3-trifluoropropyl)-1,5-naphthyridin-2(1H)-one (185)

The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 70-100% B over 15 minutes, then a 5 minute hold at 100% B; Flow: 20 mL/min. Fractions containing the product were combined and dried via centrifugal evaporation. Two analytical LC/S injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.75 minute hold at 100% B; Flow: 1 mL/min; Detection: UV at 220 nm. Injection 2 conditions: Column: Waters BEH C18, 2.0×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B, 0-100% B over 3 minutes, then a 0.75 minute hold at 100% B; Flow: 1.0 mL/min; Detection: UV at 220 nm. The title compound was isolated in 22.7% n yield (5.5 mg).

Example 186

4-(4-benzhydrylpiperazin-1-yl)-1-(4,4-difluorobut-3-en-1-yl)-3-nitro-1,5-naphthyridin-2(1H)-one

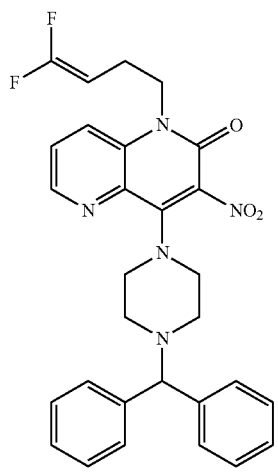

(186)

The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 70-100% B over 15 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 nM ammonium acetate; Temperature: 50° C.; Gradient: 0% B, 0-100% B over 3 minutes, then a 0.75 minute hold at 100% B; Flow: 1 mL/min; Detection: UV at 220 nm. Injection 2 conditions: Column: Waters BEH C18, 2.0×50 mm, 1.7 μm particles; Mobile Phase A: 5:95 acetonitrile:water with 0.1% trifluoroacetic acid: Mobile Phase B: 95:5 acetonitrile:water with 0.100 trifluoroacetic acid; Temperature: 50° C.; Gradient: 0% B, 0-100% B over 3 minutes, then a 0.75 minute hold at 100% B; Flow: 1.0 mL/min; Detection: UV at 220 nm. The title compound was isolated in 32.6% yield (7.8 mg).

Example 187

4-(4-benzhydrylpiperazin-1-yl)-3-nitro-1-(4-oxopentyl)-1,5-naphthyridin-2(1H)-one

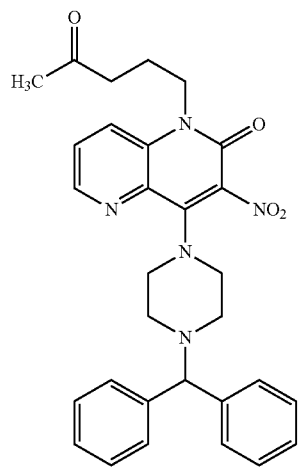

(187)

The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 70-100% B over 15 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters BEH C18, 2.0×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.75 minute hold at 100% B; Flow: 1 mL/min; Detection: UV at 220 nm. Injection 2 conditions: Column: Waters BEH C18, 2.0×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.: Gradient: 0% B, 0-100% B over 3 minutes, then a 0.75 minute hold at 100% B; Flow: 1.0 mL/min; Detection: UV at 220 nm. The title compound was isolated in 22% yield (5.2 mg).

Example 189

4-(4-benzhydrylpiperazin-1-yl)-1-(3-(2-methoxyethoxy)propyl)-3-nitro-1,5-naphthyridin-2(1H)-one

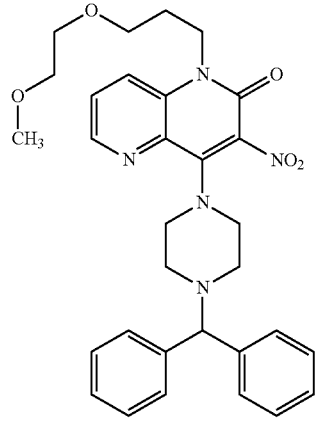

(189)

The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 65-100% B over 15 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.75 minute hold at 100% B; Flow: 1 mL/min; Detection: UV at 220 nm. Injection 2 conditions: Column: Waters BEH C18, 2.0×50 mm, 1.7 µm particles; Mobile Phase A: 5:95 acetonitrile:water with 0.1% trifluoroacetic acid; Mobile Phase B: 95:5 acetonitrile:water with (0.1% trifluoroacetic acid; Temperature: 50° C.; Gradient: 0%1B, 0-100% B over 3 minutes, then a 0.75 minute hold at 100% B; Flow: 1.0 mL/min; Detection: UV at 220 nm. The title compound was isolated in 32.3% yield (8.1 mg).

Example 190

4-(4-benzhydrylpiperazin-1-yl)-1-(3-methoxypropyl)-3-nitro-1,5-naphthyridin-2(1H)-one

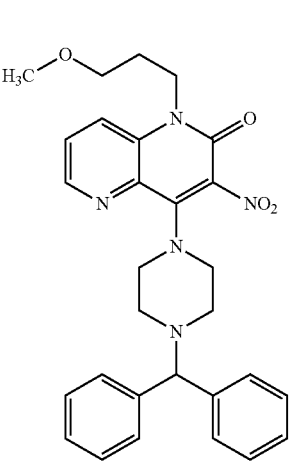

(190)

The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 65-100% B over 15 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters BEH C18, 2.0×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 00B, 0-100% B over 3 minutes, then a 0.75 minute hold at 100% B; Flow: 1 mL/min; Detection: UV at 220 nm. Injection 2 conditions: Column: Waters BEH C18, 2.0×50 mm, 1.7 µm particles; Mobile Phase A: 5:95 acetonitrile:water with 0.100 trifluoroacetic acid; Mobile Phase B: 95:5 acetonitrile:water with 0.1% trifluoroacetic acid; Temperature: 50° C.; Gradient: 0%1B, 0-100% B over 3 minutes, then a 0.75 minute hold at 100% B; Flow: 1.0 mL/min; Detection: UV at 220 nm. The title compound was isolated in 32.9% yield (7.6 mg).

Example 191

4-(4-benzhydrylpiperazin-1-yl)-6-bromo-1-methyl-2-oxo-1,2-dihydro-1,5-naphthyridine-3-carbonitrile

Example 192

6-bromo-4-(4-(4-fluoro-2-hydroxybenzyl)piperazin-1-yl)-1-methyl-2-oxo-1,2-dihydro-1,5-naphthyridine-3-carbonitrile

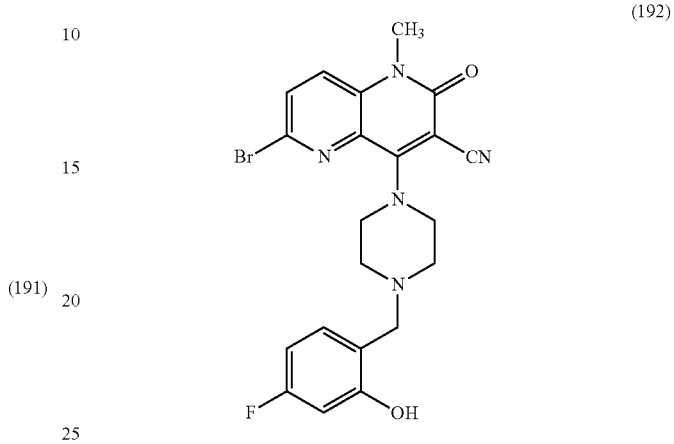

(192)

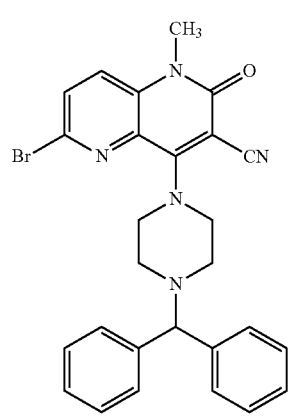

(191)

1-Benzhydrylpiperazine (85 mg, 0.335 mmol) was added in a single portion to a solution of 6-bromo-4-chloro-1-methyl-2-oxo-1,2-dihydro-1,5-naphthyridine-3-carbonitrile (100 mg, 0.335 mmol) and Hunig's Base (0.117 mL, 0.670 mmol) in DMF (5 mL) under nitrogen. The reaction was monitored by HPLC. After 2 hr, the reaction was complete. The reaction mixture was then diluted with chloroform and washed (2×) with saturated aqueous $NaHCO_3$. The organic layer was then dried over $MgSO_4$, filtered and evaporated under reduced pressure overnight to afford the product as an off-white solid (132 mg, 770%). LC/MS conditions: Injection Vol; 3 μL, Start % B; 2, Final % B; 98, Gradient Time; 1.5 min, Flow Rate; 0.8 mL/min, Wavelength; 220 nm, Solvent Pair; Water/Acetonitrile/TFA, Solvent A; 100% Water/0.05% TFA, Solvent B; 100% Acetonitrile/0.05% TFA, Column; Waters Aquity BEH C18 2.1×50 mm, 1.7U MW1, Oven Temp; 40. LC/MS results: 0.990 min. $(M+H)^+$; 514. $^1H$ NMR (400 MHz, chloroform-d) δ 7.62 (d, J=8.8 Hz, 1H), 7.53-7.46 (m, 5H), 7.32 (t, J=7.6 Hz, 4H), 7.25-7.20 (m, 2H), 4.35 (s, 1H), 4.08-3.95 (m, 4H), 3.61 (s, 3H).

5-Fluoro-2-(piperazin-1-ylmethyl)phenol 2,2,2-trifluoroacetate (109 mg, 0.335 mmol) was added to a solution of 6-bromo-4-chloro-1-methyl-2-oxo-1,2-dihydro-1,5-naphthyridine-3-carbonitrile (100 mg, 0.335 mmol) and triethylamine (0.140 mL, 1.005 mmol) in DMF (2 mL) and the resultant mixture was stirred at room temperature over the weekend. The crude material was purified via preparative LC/IS with the following conditions: Column: XBridge C18, 19×200 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 23 minutes, then a 5 minute hold at 100% B; Flow: 20 mL/min. Fractions containing the product were combined and dried via centrifugal evaporation. The yield of the product was 9.1 mg, and its estimated purity by LC/MS analysis was 96%. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. $^1H$ NMR (500 MHz, DMSO-$d_6$) δ 7.95-7.92 (m, 1H), 7.88-7.85 (m, 1H), 7.20 (t, J=8.1 Hz, 1H), 6.63-6.57 (m, 2H), 3.91-3.85 (m, 4H), 3.67 (s, 2H), 3.53 (s, 3H), 2.74-2.69 (m, 4H).

Example 193

6-chloro-4-(4-(4-fluoro-2-hydroxybenzyl)piperazin-1-yl)-1-methyl-2-oxo-1,2-dihydro-1,5-naphthyridine-3-carbonitrile

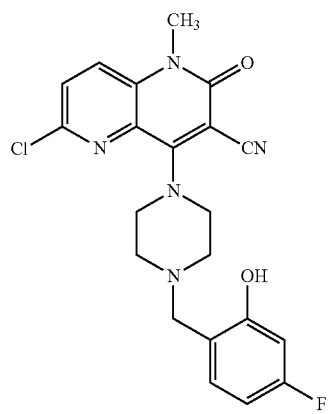

(193)

5-Fluoro-2-(piperazin-1-ylmethyl)phenol (828 ng, 0.039 mmol) was added to a solution of 4,6-dichloro-1-methyl-2-oxo-1,2-dihydro-1,5-naphthyridine-3-carbonitrile (10 mg, 0.039 mmol) and triethylamine (0.016 mL, 0.118 mmol) in DMF (2 mL) and the resultant mixture was stirred at room temperature overnight. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 35-75% B over 20 minutes, then a 5 minute hold at 100% B; Flow: 20 mL/min. Fractions containing the product were combined and dried via centrifugal evaporation. The material was further purified via preparative LC/MS with the following conditions: Column: XBridge C18, 19×200 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-40% B over 20 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Injection 2 results: 1.32 minutes, [M+H]: 428.05 Injection 1 results 2.04 minutes, [M+H]: 428.04. $^1$H NMR (500 MHz, DMSO-$d_6$) δ 8.10 (d, J=8 Hz, 1H), 7.82 (d, J=8 Hz, 1H), 7.42 (br. s., 1H), 6.74 (d, J=9.5 Hz, 2H), 4.25 (br. s., 2H), 4.14-3.91 (m, 2H), 3.57 (s, 3H), 2.55 (s, 2H).

Example 194

4-(4-(4-fluoro-2-hydroxybenzyl)piperazin-1-yl)-1,6-dimethyl-2-oxo-1,2-dihydro-1,5-naphthyridine-3-carbonitrile

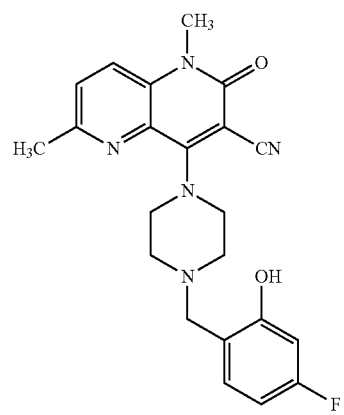

(194)

Hunig's Base (10.48 μl, 0.060 mmol) was added to a solution of 5-fluoro-2-(piperazin-1-ylmethyl)phenol 2,2,2-trifluoroacetate (19.46 ng, 0.060 mmol) and 4-chloro-1,6-dimethyl-2-oxo-1,2-dihydro-1,5-naphthyridine-3-carbonitrile (14.02 mg, 0.06 mmol) in DMF (2 mL) and the resultant mixture was stirred at room temperature overnight, under nitrogen. The crude material was purified via preparative LC/MS with the following conditions: Column: XBridge C18, 19×200 nm 5 μm particles; Mobile Phase A: 5:95 acetonitrile:water with 10 mM ammonium acetate: Mobile Phase B: 95:5 acetonitrile:water with 10 mM ammonium acetate; Gradient: 30-70% B over 20 minutes, then a 5 minute hold at 100% B; Flow: 20 mL/min. Fractions containing the product were combined and dried via centrifugal evaporation. The yield of the product was 6.6 mg, (27%) and its estimated purity by LC/MS analysis was 99%. Analytical LC/MS was used to determine the final purity. Injection 1 conditions: Column: Waters XBridge C18, 2.1 mm×50 mm, 1.7 mm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.8%; Observed Mass: 408.01; Retention Time: 1.21 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 408.02; Retention Time: 1.8 min. $^1$H NMR (500 MHz, DMSO-$d_6$) δ 7.91 (d, J=8.8 Hz, 1H), 7.59 (d, J=8.8 Hz, 1H), 7.20 (t, J=7.5 Hz, 1H), 6.64-6.58 (m, 2H), 3.91 (br. s., J=3.3 Hz, 4H), 3.66 (s, 2H), 2.70 (br. s., 4H), 2.54 (s, 3H).

Example 195

4-(4-(1-(2-(allyloxy)-4-fluorophenyl)ethyl)piperazin-1-yl)-6-chloro-1-methyl-2-oxo-1,2-dihydro-1,5-naphthyridine-3-carbonitrile

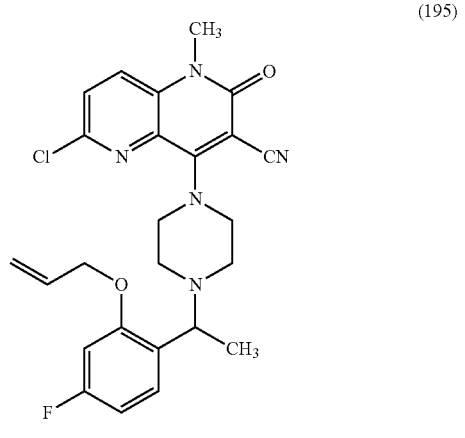 [SMILES: C=CCOc1cc(F)ccc1C(C)N1CCN(c2c(C#N)c(=O)n(C)c3ccc(Cl)nc23)CC1]

(195)

Potassium carbonate (82 mg, 0.590 mmol) was suspended in anhydrous DMF (4 mL). 4,6-Dichloro-1-methyl-2-oxo-1,2-dihydro-1,5-naphthyridine-3-carbonitrile (50 mg, 0.197 mmol) and 1-(1-(2-(allyloxy)-4-fluorophenyl)ethyl)piperazine (52.0 mg, 0.197 mmol) were then added and the resultant mixture was stirred at room temperature under nitrogen overnight. The mixture was filtered and concentrated under high vacuum. The residue was dissolved in DMF and the crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 42-82% B over 19 minutes, then a 4 minute hold at 100% B; Flow: 20 mL/min. Fractions containing the product were combined and dried via centrifugal evaporation. The yield of the product was 6.5 mg, and its estimated purity by LC/MS analysis was 100%. Analytical LC/MS was used to determine the purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and IV (220 nm). Injection 1 results: Purity: 100.0%; Observed Mass: 482.08; Retention Time: 1.54 min. $^1$H NMR (500 MHz, DMSO-$d_6$) δ 8.04 (d, J=92 Hz, 1H), 778 (d, J=8.8 Hz, 1H), 7.43 (s, 1H), 6.89 (dd, J=11.6, 2.4 Hz, 1H), 6.79 (s, 1H), 6.15-5.95 (m, 1H), 5.44 (s, 1H), 5.28 (d, J=10.6 Hz, 1H), 4.61 (br. s., 2H), 4.02-3.92 (m, 1H), 3.83 (br. s., 4H), 2.69-2.55 (m, 4H), 1.29 (d, J=6.6 Hz, 3H). The N—CH$_3$ resonance was not clearly observed due to the water suppression used in the acquisition of the spectrum.

Example 196

4-(4-benzhydrylpiperazin-1-yl)-1-methyl-2-oxo-1,2-dihydro-1,5-naphthyridine-3-carbonitrile

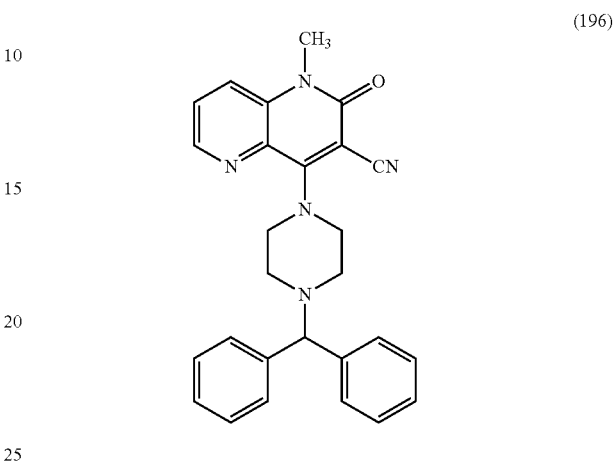

(196)

4-(4-Benzhydrylpiperazin-1-yl)-6-bromo-1-methyl-2-oxo-1,2-dihydro-1,5-naphthyridine-3-carbonitrile (20 mg, 0.039 mmol) was suspended in THF (2 mL). Diethylzinc (0.093 mL, 0.093 mmol) and tetrakis(triphenylphosphine)palladium(0) (4.49 mg, 3.89 μmol) were then added and the reaction mixture was heated at 70° C. in a sealed tube overnight. On initial heating, the suspension became a yellow colored solution which darkened on heating overnight. The mixture was then cooled, filtered, and evaporated to dryness, and the residue dissolved in 2 mL of DMF. The crude solution was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 45-90% B over 20 minutes, then a 5 minute hold at 100% B; Flow: 20 mL/min. Fractions containing the product were combined and dried via centrifugal evaporation. The yield of the product was 5.2 ng, and its estimated purity by LC/MS analysis was 99%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.3%; Observed Mass: 436.17; Retention Time: 1.34 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 ml/min; Detection: MS and UV (220 nm). Injection 2 results: Purity: 100.0%; Observed Mass: 436.15; Retention Time: 2.17 min. $^1$H NMR (500 MHz, DMSO-$d_6$) δ 8.51 (d, J=2.9 Hz, 1H), 7.97 (d, J=8.8 Hz, 1H), 7.68 (dd, J=8.8, 4.4 Hz, 1H), 7.50 (d, J=7.3 Hz, 4H), 7.33 (t, J=7.7 Hz, 4H), 7.25-7.12 (m, 2H), 4.40 (s, 1H).

Example 198

6-chloro-4-(4-(2-hydroxybenzyl)piperazin-1-yl)-1-methyl-2-oxo-1,2-dihydro-1,5-naphthyridine-3-carbonitrile

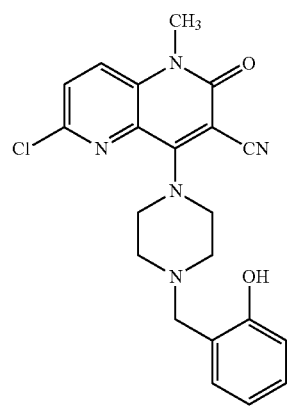

(198)

2-(Piperazin-1-ylmethyl)phenol-2,2,2,-trifluoroacetate (27.7 mg, 0.091 mmol) was added to a solution of triethylamine (0.050 mL, 0.362 mmol) and 4,6-dichloro-1-methyl-2-oxo-1,2-dihydro-1,5-naphthyridine-3-carbonitrile (23 mg, 0.091 mmol) in DMF (4 mL) and the reaction mixture was stirred at room temperature overnight. The resultant mixture was evaporated to dryness and then dissolved in 2 mL of DMF and this was fractionated via preparative LC/MS with the following conditions: Column: XBridge C18, 19×200 mm, 5 μm particles; Mobile Phase A: 5:95 acetonitrile:water with 0.1% trifluoroacetic acid: Mobile Phase B: 95:5 acetonitrile:water with 0.1% trifluoroacetic acid; Gradient: 10-60% B over 20 minutes, then a 5 minute hold at 100% B; Flow: 20 mL/min. Fractions containing the product were combined and dried via centrifugal evaporation. The yield of the product was 10.6 mg, and its estimated purity by LC/MS analysis was 95%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 410.04; Retention Time: 1.36 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.1%; Observed Mass: 410.09; Retention Time: 1.9 min. 11 NMR (500 MI-z, DMSO-$d_6$) δ 8.10 (d, J=9.2 Hz, 1H), 7.82 (d, J=8.8 Hz, 1H), 7.38 (d, J=7.3 Hz, 1H), 7.29 (t, J=7.5 Hz, 1H), 6.96 (d, J=8.1 Hz, 1H), 6.90 (t, J=7.3 Hz, 1H), 4.29 (br. s., 2H), 4.05 (br. s., 2H), 3.57 (s, 3H), 2.55 (s, 2H). 4H'S of the piperazine are missing due to the water suppression peak.

Example 199

6-chloro-4-(4-(3-(ethyl(methyl)amino)benzyl)piperazin-1-yl)-1-methyl-2-oxo-1,2-dihydro-1,5-naphthyridine-3-carbonitrile

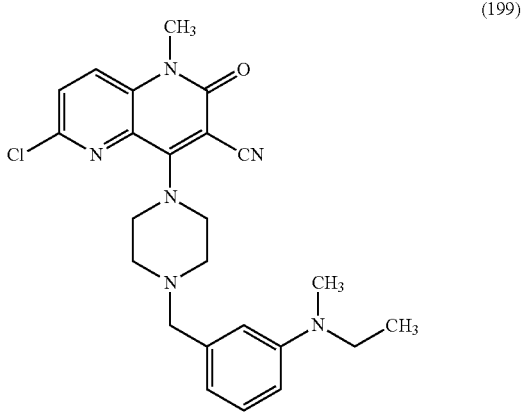 [SMILES: CCN(C)c1cccc(CN2CCN(c3c(C#N)c(=O)n(C)c4ccc(Cl)nc34)CC2)c1]

(199)

4,6-Dichloro-1-methyl-2-oxo-1,2-dihydro-1,5-naphthyridine-3-carbonitrile (20 mg, 0.079 mmol) and Hunig's Base (0.030 mL, 0.173 mmol) were dissolved in DMF (2 mL). N-Ethyl-N-methyl-3-(piperazin-1-ylmethyl)aniline 2,2,2-trifluoroacetate (27.3 mg, 0.079 mmol) was then added and the reaction mixture was stirred at room temperature under nitrogen. After 4 h the reaction had proceeded to completion. The crude reaction product was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 38-78% B over 19 minutes, then a 4 minute hold at 100% B; Flow: 20 mL/min. Fractions containing the product were combined and dried via centrifugal evaporation. The yield of the product was 2.2 mg, and its estimated purity by LC/MS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 mi hold at 100% B; Flow: 1 mL/min; Detection: MS and UV (220 nm). Injection 1 results: Purity: 100.0%₀; Observed Mass: 451.13; Retention Time: 1.02 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 451.11; Retention Time: 2.19 min. The water suppression technique used in the acquisition of the product's spectrum prevented a full assignment being made, with only the aromatic signals being described. $^1$H NMR (DMSO-$d_6$) δ 8.09 (br d, J=8.8 Hz, 1H), 7.83 (br d, J=8.8 Hz, 1H), 7.05-7.28 (nm 1H), 6.57-6.87 (m, 3H). The title compound 2.2 was isolated in 6.2% yield.

Example 200

4-(4-(7-(allyloxy)-5-fluoro-2,3-dihydro-1H-inden-1-yl)piperazin-1-yl)-6-chloro-1-methyl-2-oxo-1,2-dihydro-1,5-naphthyridine-3-carbonitrile

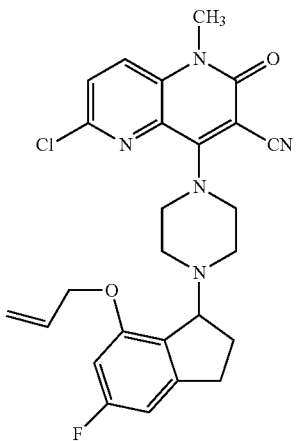

(200)

A solution of 4,6-dichloro-1-methyl-2-oxo-1,2-dihydro-1,5-naphthyridine-3-carbonitrile (54 mg, 0.213 mmol), 1-(7-(allyloxy)-5-fluoro-2,3-dihydro-1H-inden-1-yl)piperazine (58.7 ng, 0.213 mmol) and triethylamine (0.059 mL, 0.425 mmol) in DMF (5 mL) was stirred under nitrogen over the weekend. The solvent was then removed under vacuum and the residue dissolved in dichloromethane. The organic layer was washed with 1.5 M potassium phosphate buffer (2×) and was then dried over $MgSO_4$, filtered and concentrated in vacuo to give 159 mg of the crude product. 127 mg of this material was fractionated using flash chromatography; 1-5% methanol in dichloromethane as eluent, and a Biotage 24 g silica gel column. Homogeneous fractions were combined and evaporated under reduced pressure to give the product as a brown colored oil, 73 mg, 87%. 32 mg of the above crude reaction product was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 50-90% B over 20 minutes, then a 5 minute hold at 100% B; Flow: 20 mL/min. Fractions containing the product were combined and dried via centrifugal evaporation. The yield of the product was 9.8 mg, and its estimated purity by LC/MS analysis was 100%. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 494.05; Retention Time: 1.41 min. Injection 2 conditions: Column: Waters XBridge C18, 2.1 mm×50 mm, 1.7 µm particles. Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 494.05; Retention Time: 2.22 min. $^1$H NMR (400 MHz, chloroform-d) δ 7.64 (d, J=8.8 Hz, 1H), 7.51 (d, J=9.0 Hz, 1H), 6.56 (d, J=0.7 Hz, 1H), 6.44 (d, J=11.0 Hz, 1H), 6.13-6.00 (m, 1H), 5.52-5.41 (m, 1H), 5.29 (d, J=10.5 Hz, 1H), 4.62-4.50 (m, 2H), 4.37 (d, J=7.1 Hz, 1H), 4.03-3.86 (m, 41), 3.81-3.68 (m, 1H), 3.61 (s, 3H), 3.03 (dt, J=16.4, 8.3 Hz, 1H), 2.85-2.69 (m, 5H), 2.31-2.06 (m, 2H).

Example 201

6-chloro-4-(4-(5-fluoro-7-hydroxy-2,3-dihydro-1H-inden-1-yl)piperazin-1-yl)-1-methyl-2-oxo-1,2-dihydro-1,5-naphthyridine-3-carbonitrile

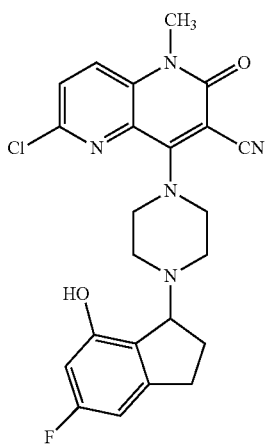

(201)

To a solution of 4-(4-(7-(allyloxy)-5-fluoro-2,3-dihydro-H-inden-1-yl)piperazin-1-yl)-6-chloro-1-methyl-2-oxo-1,2-dihydro-1,5-naphthyridine-3-carbonitrile (75 mg, 0.152 mmol) in THF (3 mL) under nitrogen was added a catalytic amount of tetrakis(triphenylphosphine)palladium(0) (3.51 mg, 3.04 µmol). The slightly brown solution was stirred for 5 min, after which, sodium borohydride (8.62 mg, 0.228 mmol) and the reaction mixture was left to stir at room temperature overnight. The reaction mixture was transferred to a preparative silica gel TLC plate that was eluted using 30% acetone in hexanes. Two fractions were eluted from the plate with the lower $R_f$ material being further purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 40-80% B over 20 minutes, then a 5 minute hold at 100% B; Flow: 20 mL/min. Fractions containing the product were combined and dried via centrifugal evaporation. The yield of the product was 3.4 mg, and its estimated purity by LC/MS analysis was 94%. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.6%; Observed Mass: 453.97; Retention Time: 2.09 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.2%; Observed Mass: 453.95; Retention Time: 1.27 min. $^1$H NMR (500 MHz, DMSO-$d_6$) δ 8.04 (d, J=8.8 Hz, 1H), 7.78 (d, J=8.8 Hz, 1H), 6.53 (d, J=−8.8 Hz, 1H), 6.41 (d, J=10.6 Hz, 1H), 4.46 (s, 1H), 3.84 (br. s., 2H), 3.58 (br. s., 1H), 3.09-3.01 (m, 1H), 2.88 (br. s., 1H), 2.83-2.68 (m, 2H), 2.65-2.55 (m, 2H), 2.15-1.97 (m, 2H).

Example 202

4-(4-benzhydrylpiperazin-1-yl)-6-ethyl-1-methy-2-oxo-1,2-dihydro-1,5-naphthyridine-3-carbonitrile

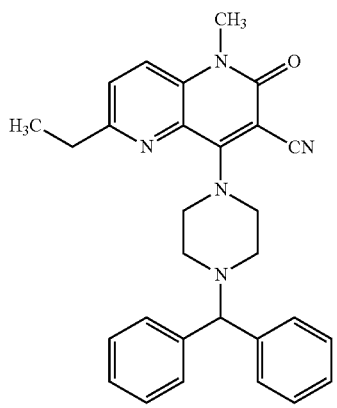

(202)

4-(4-Benzhydrylpiperazin-1-yl)-6-bromo-1-methyl-2-oxo-1,2-dihydro-1,5-naphthyridine-3-carbonitrile (20 mg, 0.039 mmol) were suspended in THF (2 mL). Diethylzinc (0.093 mL, 0.093 mmol) and tetrakis(triphenylphosphine)palladium(0) (4.49 mg, 3.89 μmol) were then added and the reaction mixture was heated at 70° C. in a sealed tube overnight. On initial heating the suspension became a yellow colored solution. The reaction mixture was then cooled, filtered and evaporated to dryness. The residue was dissolved in 2 mL of DMF and this solution purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 45-90% B over 20 minutes, then a 5 minute hold at 100% B; Flow: 20 mL/min. Fractions containing the product were combined and dried via centrifugal evaporation. The yield of the product was 7.3 mg, and its estimated purity by LC/MS analysis was 100%. Analytical LC/MS was used to determine the final purity. Injection 1 conditions: Column: Waters XBridge C18, 2.1 mm×50 mm, 1.7 μm particles. Mobile Phase A: 5:95 acetonitrile:water with 0.1% trifluoroacetic acid; Mobile Phase B: 95:5 acetonitrile:water with 0.1% trifluoroacetic acid. Temperature: 50° C.; Gradient: 0% B to 100° % B over 3 min, then a 0.75 min hold at 100% B; Flow: 1 mL/min; Detection: MS and UV (220 nm). Injection 1 results: Purity: 100.0%; Observed Mass: 464.16; Retention Time: 1.52 min. Injection 2 conditions: Column: Waters XBridge C18, 2.1 mm×50 mm, 1.7 μm particles; Mobile Phase A: 5:95 acetonitrile:water with 10 mM ammonium acetate. Mobile Phase B: 95:5 acetonitrile:water with 10 mM ammonium acetate; Temperature: 50° C.; Gradient: 0% B to 100% NB over 3 min, then a 0.75 min hold at 100% B; Flow: 1 mL/min; Detection: MS and UV (220 nm). Injection 2 results: Purity: 100.0%; Observed Mass: 464.14; Retention Time: 2.4 min. $^1$H NMR (500 MHz, DMSO-$d_6$) δ 7.90 (d, J=8.8 Hz, 1H), 7.57 (d, J=8.4 Hz, 1H), 7.50 (d, J=7.3 Hz, 4H), 7.33 (t, J=7.7 Hz, 4H), 7.24-7.18 (m, 2H), 4.42 (s, 1H), 3.95 (br. s., 2H), 3.50 (s, 3H), 3.43 (br. s., 2H), 2.80 (q, J=7.5 Hz, 2H), 2.60-2.53 (m, 4H), 1.20 (t, J=7.5 Hz, 3H).

Example 204

4-(4-benzhydrylpiperazin-1-yl)-1,6-dimethyl-2-oxo-1,2-dihydro-1,5-naphthyridine-3-carbonitrile

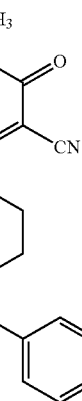

(204)

(Bromomethylene)dibenzene (16.17 mg, 0.065 mmol) was added to a solution of 1,6-dimethyl-2-oxo-4-(piperazin-1-yl)-1,2-dihydro-1,5-naphthyridine-3-carbonitrile 2,2,2-trifluoroacetate (26 mg, 0.065 mmol) and triethylamine (0.027 mL, 0.196 mmol) in DMF (2 mL). The resultant mixture was stirred at room temperature under nitrogen overnight. An additional equivalent of (bromomethylene)dibenzene (16.17 ng, 0.065 mmol) was added together with 1 further equivalent of triethylamine and reaction mixture was left to stir at room temperature for a further 48 h. The crude reaction mixture was then fractionated via preparative LC/MS with the following conditions: Column: XBridge C18, 19×200 mm, 5 μm particles; mobile Phase A: 5:95 acetonitrile:water with 10 mM ammonium acetate; Mobile Phase B: 95:5 acetonitrile:water with 10 mM ammonium acetate; Gradient: 50-90% B over 20 minutes, then a 5 minute hold at 100% B; Flow: 20 mL/min. Fractions containing the product were combined and dried via centrifugal evaporation. The yield of the product was 3.3 mg, and its estimated purity by LC/MS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 450.14; Retention Time: 2.35 min. Injection 2 conditions: Column:

Waters XBridge C18, 2.1 mm×50 mm, 1.7 Lµm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 450.12; Retention Time: 1.53 min. $^1$H NMR (500 MHz, DMSO-$d_6$) δ 7.87 (d, J=8.8 Hz, 1H), 7.55 (d, J=8.8 Hz, 1H), 7.51 (d, J=7.7 Hz, 4H), 7.33 (t, J=7.5 Hz, 4H), 725-7.19 (m, 1H), 4.45 (s, 1H), 3.96 (br. s., 4H), 3.51 (s, 3H), 2.60 (br. s., 4H), 2.51 (s, 3H).

Example 208

4-(4-benzhydrylpiperazin-1-yl)-1-methyl-2-oxo-6-vinyl-1,2-dihydro-1,5-naphthyridine-3-carbonitrile

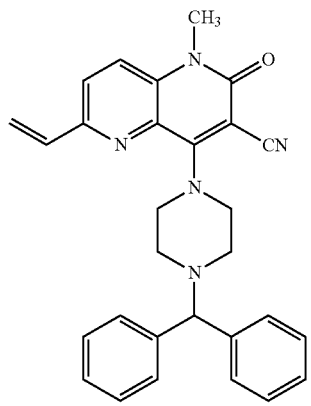

(208)

A mixture of 4-(4-Benzhydrylpiperazin-1-yl)-6-bromo-1-methyl-2-oxo-1,2-dihydro-1,5-naphthyridine-3-carbonitrile (30 mg, 0.058 mmol), potassium vinyltrifluoroborate (9.37 ng, 0.070 mmol), and PdCl$_2$ (dppf) (4.27 mg, 5.83 mol) was placed in a dry microwave vial which was then sealed. BuOH (2 mL) and TEA (0.012 mL, 0.087 mmol) were added and the vial was evacuated and filled with nitrogen (3×). The reaction mixture was heated in microwave at 110° C. for 2 hr before being allowed to cool and evaporated to dryness in vacuo. The residual material was then dissolved in DMF (2 mL) and this solution was fractionated via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile: water with 10 mM ammonium acetate; Gradient: 50-90% B over 20 minutes, then a 5 minute hold at 100% B; Flow: 20 mL/min. Fractions containing the product were combined and dried via centrifugal evaporation. The yield of the product was 15.7 mg, and its estimated purity by LC/MS analysis was 100%. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 462.17, 462.17, 462.17; Retention Time: 2.34, 2.42, 2.49 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 462.19; Retention Time: 1.5 min. $^1$H NMR (DMSO-$d_6$) δ 7.93 (d, J=8.8 Hz, 1H), 7.81 (d, J=8.8 Hz, 1H), 7.49 (d, J=7.7 Hz, 4H), 7.32 (t, J=7.7 Hz, 4H), 7.14-7.25 (m, 2H), 6.75-6.85 (m, 1H), 6.13 (d, J=18.0 Hz, 1H), 5.50 (d, J=11.7 Hz, 1H), 4.40 (s, 1H). Due to the water suppression technique used in the acquisition of the products spectrum, detection of the piperazine and the N-Me protons was obscured.

Example 209

6-chloro-4-(4-(cyclohexyl(phenyl)methyl)piperazin-1-yl)-1-methyl-2-oxo-1,2-dihydro-1,5-naphthyridine-3-carbonitrile

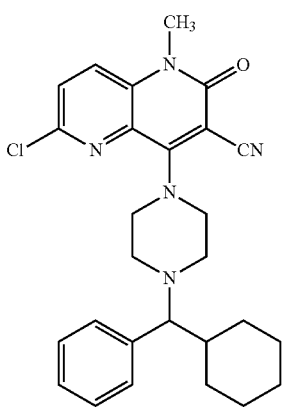

(209)

Triethylamine (0.016 mL, 0.11 mmol) was added to a solution of 1-(cyclohexyl (phenyl)methyl)piperazine 2,2,2-trifluoroacetate (16.12 mg, 0.043 mmol) and 4,6-dichloro-1-methyl-2-oxo-1,2-dihydro-1,5-naphthyridine-3-carbonitrile (10 mg, 0.039 mmol) in DMF (1 mL). The reaction mixture was stirred at room temperature overnight. The crude reaction mixture was then fractionated via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 60-100% B over 20 minutes, then a 5 minute hold at 100% B; Flow: 20 mL/min. Fractions containing the product were combined and dried via centrifugal evaporation. The yield of the product was 3.7 mg, and its estimated purity by LC/MS analysis was 98%. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 min). Injection 1 results: Purity: 98.5%; Observed Mass: 476.1; Retention Time: 1.72 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 nL/mm; Detection: MS and UV (220 nm). Injection 2 results: Purity: 99.2%; Observed Mass: 476.11; Retention Time: 2.81 min. NMR data could not be fully interpreted due to the concentration of the test sample being too dilute. $^1$H NMR (DMSO-$d_6$) δ 8.00 (d, J=9. Hz, 1H), 7.72 (d, J=8.8 Hz, 1H), 7.30-7.38 (m, 2H), 7.21 (br d, J=7.3 Hz, 3H), 3.83 (br t, J=5.0 Hz, 4H), 3.50 (s, 3H).

Example 210

(R)-4-(4-benzyl-3-((benzyloxy)methyl)piperazin-1-yl)-6-chloro-1-methyl-2-oxo-1,2-dihydro-1,5-naphthyridine-3-carbonitrile

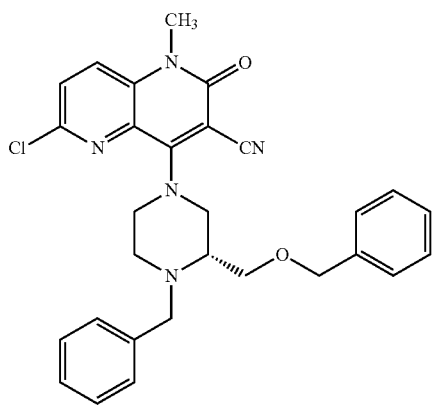

(210)

4,6-Dichloro-1-methyl-2-oxo-1,2-dihydro-1,5-naphthyridine-3-carbonitrile (20 mg, 0.079 mmol) was dissolved in dry DMF (2 mL) and potassium carbonate (32.6 mg, 0.236 mmol). (R)-1-benzyl-2-((benzyloxy)methyl)piperazine (25.7 mg, 0.087 mmol) were added and the reaction mixture was stirred at 60° C. in a sealed vial over the weekend. The reaction mixture was allowed to cool, and was then filtered and the crude product was fractionated via preparative LC/MS with the following conditions: Column: XBridge C18, 19×200 mm, 5 Lμm particles; Mobile Phase A: 5:95 acetonitrile:water with 10 mM ammonium acetate; Mobile Phase B: 95:5 acetonitrile:water with 10 mM ammonium acetate; Gradient: 60-100% B over 20 minutes, then a 5 minute hold at 100% B; Flow: 20 mL/min. Fractions containing the product were combined and dried via centrifugal evaporation. The yield of the product was 1.2 mg, and its estimated purity by LC/MS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 514; Retention Time: 1.8 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 514.04; Retention Time: 2.8 min.

Example 211

4-(4-(2-aminobenzyl)piperazin-1-yl)-6-bromo-1-methyl-2-oxo-1,2-dihydro-1,5-naphthyridine-3-carbonitrile

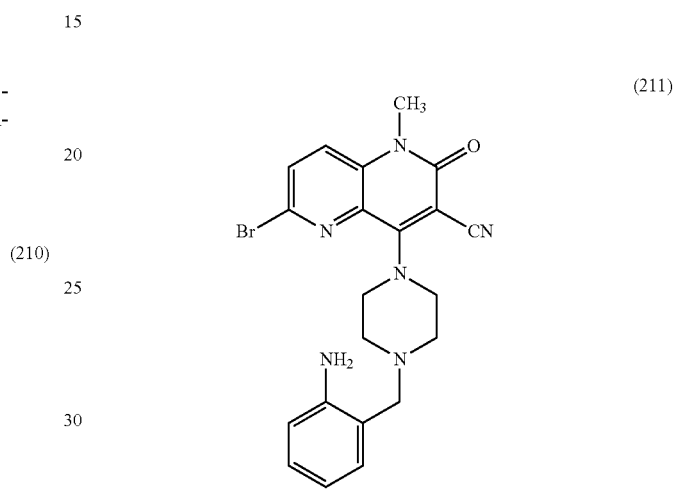

(211)

Tert-butyl (2-formylphenyl)carbamate (92 mg, 0.416 mmol) was added to a solution of 6-bromo-1-methyl-2-oxo-4-(piperazin-1-yl)-1,2-dihydro-1,5-naphthyridine-3-carbonitrile bis(2,2,2-trifluoroacetate) (200 mg, 0.347 mmol) in DMF (5 mL). The reaction mixture was stirred at room temperature for 1 h, after which sodium cyanoborohydride (65.4 mg, 1.041 mmol) was added and the reaction mixture was stirred at room temperature overnight. Methanol was then added and the resultant mixture was filtered and the filtrate fractionated using reverse phase preparative HPLC using $CH_3OH$—$H_2O$-TFA as eluent. Homogeneous fractions were combined and concentrated in vacuo to give tert-butyl (2-((4-(6-bromo-3-cyano-1-methyl-2-oxo-1,2-dihydro-1,5-naphthyridin-4-yl)piperazin-1-yl)methyl)phenyl) carbamate as a yellow solid. The material was dissolved in dichloromethane (5 mL) and TFA (3 mL, 38.9 mmol) was added. The reaction mixture was stirred at room temperature for 2 h, and was then concentrated under vacuum to give an orange oil. This material was further purified by using reverse phase preparative HPLC using $CH_3OH$—$H_2O$-TFA as eluent. Homogeneous fractions were combined and concentrated in vacuo to give a TFA salt of the title compound as a light yellow-colored solid (70 mg, 29.6% yield). Analytical LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). LC/MS results: 2.3 min, 453.0 (M+H)$^+$. $^1$H NMR (500 MHz, DMSO-$d_6$) δ 7.96-7.90 (m, 1H), 7.88-7.83 (m, 1H), 7.10-6.86 (m, 2H), 6.67 (d, J=7.7 Hz, 1H), 6.54 (t, J=7.5 Hz, 1H), 3.88-3.81 (m, 4H), 3.52 (s, 3H), 3.0 (s, 2H), 2.56-2.64 (m, 4H).

Example 212

N-(2-((4-(6-bromo-3-cyano-1-methyl-2-oxo-1,2-dihydro-1,5-naphthyridin-4-yl) piperazin-1-yl)methyl)phenyl)methanesulfonamide

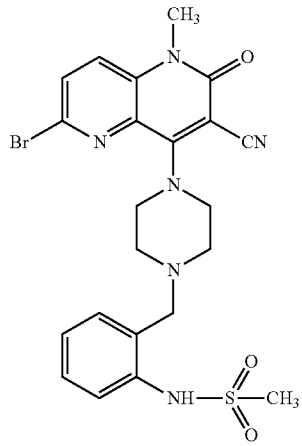

(212)

Methanesulfonyl chloride (2.74 µl, 0.035 mmol) was added to a solution of 4-(4-(2-aminobenzyl)piperazin-1-yl)-6-bromo-1-methyl-2-oxo-1,2-dihydro-1,5-naphthyridine-3-carbonitrile bis(2,2,2-trifluoroacetate) (12 mg, 0.018 mmol) and triethylamine (0.012 mL, 0.088 mmol) in dichloromethane (2 mL). The reaction mixture was stirred at room temperature overnight, after which it was concentrated and the residue dissolved in a DMF-methanol mixture. This solution was fractionated by reverse phase preparative LC/MS under the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 36-76% B over 19 minutes, then a 4 minute hold at 100% B; Flow: 20 mL/min. Homogeneous Fractions containing the product were combined and dried via centrifugal evaporation to give the title compound (1.8 mg, 18.3% yield). Analytical LC/MS conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). LC/MS results: 1.8 min, 531.1 (M+H)⁺. ¹H NMR (500 MHz, DMSO-d₆) δ 7.99-7.92 (m, 1H), 7.91-7.82 (m, 1H), 7.43 (br d, J=7.7 Hz, 1H), 7.39-7.28 (m, 2H), 7.15 (br d, J=6.2 Hz, 1H), 3.95-3.70 (m, 6H), 3.54 (s, 3H), 3.12 (s, 3H), 2.81-2.65 (m 4H).

Example 213

N-(2-((4-(6-bromo-3-cyano-1-methyl-2-oxo-1,2-dihydro-1,5-naphthyridin-4-yl) piperazin-1-yl)methyl)phenyl)benzamide

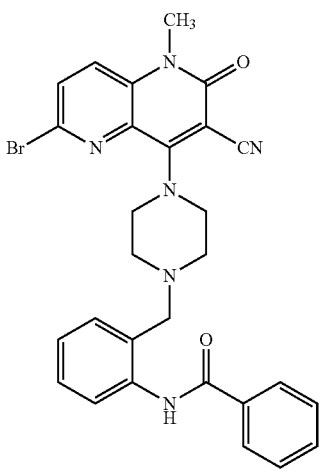

(213)

Benzoyl chloride (4.34 µl, 0.037 mmol) was added to a solution of 4-(4-(2-aminobenzyl)piperazin-1-yl)-6-bromo-1-methyl-2-oxo-1,2-dihydro-1,5-naphthyridine-3-carbonitrile bis(2,2,2-trifluoroacetamide) (17 mg, 0.025 mmol) and triethylamine (0.017 mL, 0.125 mmol) in dichloromethane (2 mL). The reaction mixture was stirred at room temperature for 1 hr, after which it was concentrated under vacuum, and the residue dissolved in DMF-methanol and this solution was fractionated using preparative LC/MS under the following conditions: Column: XBridge C18, 19×200 mm, 5 µm particles: Mobile Phase A: 5:95 acetonitrile:water with 10 mM ammonium acetate; Mobile Phase B: 95:5 acetonitrile:water with 10 mM ammonium acetate; Gradient: 40-80% B over 23 minutes, then a 4 minute hold at 100% B; Flow: 20 mL/min. Homogeneous Fractions containing the product were combined and dried via centrifugal evaporation to give the title compound (7.5 mg, 51.2% yield). Analytical LC/MS conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). LC/MS results: 2.5 min, 557.1 (M+H)⁺. ¹H NMR (500 MHz, DMSO-d₆) δ 11.20 (br s, 1H), 8.31 (br d, J=8.1 Hz, 1H), 8.01 (br d, J=7.0 Hz, 2H), 7.97-7.91 (m, 1H), 7.90-7.83 (m, 1H), 7.69-7.50 (m, 3H), 7.44-7.26 (m, 2H), 7.12 (br t, J=7.3 Hz, 1H), 3.85 (br m, 6H), 3.53 (s, 3H), 2.74 (br s, 4H).

Example 214

1-(2-((4-(6-bromo-3-cyano-1-methyl-2-oxo-1,2-dihydro-1,5-naphthyridin-4-yl)piperazin-1-yl)methyl)phenyl)-3-phenylurea

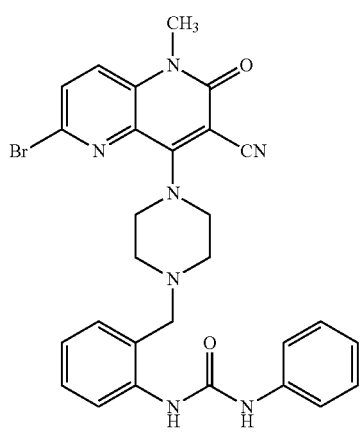

(214)

Phenyl isocyanate (4.09 µl, 0.037 mmol) was added to a solution of 4-(4-(2-aminobenzyl)piperazin-1-yl)-6-bromo-1-methyl-2-oxo-1,2-dihydro-1,5-naphthyridine-3-carbonitrile bis(2,2,2-trifluoroacetamide) (17 mg, 0.025 mmol) and triethylamine (0.017 mL, 0.125 mmol) in TI-IF (2 mL). The reaction mixture was stirred at room temperature for 1 h, after which it was concentrated under vacuum. The residue was dissolved in a mixture of DMF and methanol. This solution was fractionated using preparative LC/MS under the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 37-77% B over 22 minutes, then a 4 minute hold at 100% B; Flow: 20 mL/min. Homogeneous fractions containing the product were combined and dried via centrifugal evaporation to give the title compound (6.8 mg, 45.2% yield). Analytical LC/MS conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). LC/MS results: 2.4 min, 572.2 (M+H)$^+$. $^1$H NMR (500 MHz, DMSO-d$_6$) δ 9.07 (s, 1H), 8.81 (br s, 1H), 7.98-7.90 (m, 2H), 7.89-7.80 (m, 1H), 7.50 (d, J=7.7 Hz, 2H), 7.37-7.18 (m, 4H), 7.07-6.84 (m, 21H), 3.91 (br s, 4H), 3.65 (br s, 2H), 3.52 (s, 3H), 2.65 (br s, 4H).

Example 215

N-(2-((4-(6-bromo-3-cyano-1-methyl-2-oxo-1,2-dihydro-1,5-naphthyridin-4-yl)piperazin-1-yl)methyl)phenyl)acetamide

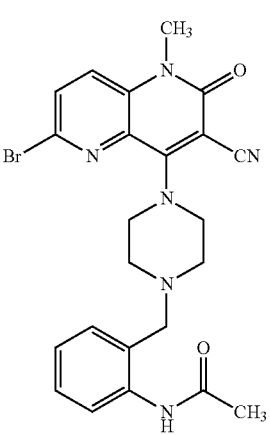

(215)

Acetyl chloride (1.878 µl, 0.026 mmol) was added to a solution of 4-(4-(2-aminobenzyl)piperazin-1-v)-6-bromo-1-methyl-2-oxo-1,2-dihydro-1,5-naphthyridine-3-carbonitrile bis(2,2,2-trifluoroacetamide) and triethylamine (0.012 mL, 0.088 mmol) (12 mg, 0.018 mmol) in dichloromethane (2 mL). The reaction mixture was stirred at room temperature overnight, after which it was concentrated under vacuum and the residue dissolved in a mixture of DMF and methanol. This solution was fractionated using preparative LC/MS under the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 26-76% B over 19 minutes, then a 4 minute hold at 100% B; Flow: 20 mL/min. Homogeneous fractions containing the product were combined and dried via centrifugal evaporation to give the title compound (4.2 mg 45.7% yield). Analytical LC/MS conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). LC/MS results: 2.1 min, 495.1 (M+H)$^+$. $^1$H NMR (500 MHz, DMSO-d$_6$) δ 10.15 (br s, 1H), 7.97-7.89 (m, 2H), 7.88-7.81 (m, 1H), 7.38-7.19 (m, 2H), 7.07 (t, J=7.5 Hz, 1H), 3.90 (br s, 4H), 3.67 (s, 2H), 3.52 (s, 3H), 2.61-2.71 (br m, 4H), 2.13 (s, 3H).

Example 216

6-chloro-4-(4-(indolin-7-ylmethyl)piperazin-1-yl)-1-methyl-2-oxo-1,2-dihydro-1,5-naphthyridine-3-carbonitrile

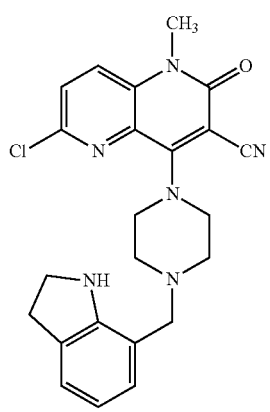

(216)

Tert-butyl 7-formylindoline-1-carboxylate (13.95 mg, 0.056 mmol) was added to a solution of 6-chloro-1-methyl-2-oxo-4-(piperazin-1-yl)-1,2-dihydro-1,5-naphthyridine-3-carbonitrile bis(2,2,2-trifluoroacetate) (20 mg, 0.038 mmol) in DMF (1.5 mL). The reaction mixture was stirred at room temperature for 1 h. Sodium cyanoborohydride (7.09 mg, 0.113 mmol) was added and the reaction mixture was stirred at room temperature overnight. Methanol w as then added and the resultant mixture was filtered, and the filtrate fractionated by reverse phase preparative HPLC using $CH_3OH$—$H_2O$-TFA as eluent. Homogeneous fractions were collected and concentrated under reduced pressure overnight, to afford tert-butyl 7-((4-(6-chloro-3-cyano-1-methyl-2-oxo-1,2-dihydro-1,5-naphthyridin-4-yl)piperazin-1-yl)methyl)indoline-1-carboxylate as a yellow colored solid. This material was dissolved in dichloromethane (2 mL) and TFA (1 mL, 12.98 mmol) was added. The reaction mixture was stirred at room temperature overnight, and then concentrated under reduced pressure. The residue was then fractionated using preparative LC/MS under the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 38-78% B over 19 minutes, then a 4 minute hold at 100% B; Flow: 20 mL/min. Homogeneous fractions were combined and evaporated in vacuo to give the title compound (5.0 mg, 29% yield). Analytical LC/MS conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). LC/MS results: 1.9 min, 435.0 (M+H)+. $^1$H NMR (500 MHz, DMSO-$d_6$) δ 8.04 (d, J=9.2 Hz, 1H), 7.77 (d, J=8.8 Hz, 1H), 6.98 (d, J=6.6 Hz, 1H), 6.87 (d, J=7.3 Hz, 1H), 6.53 (t, J=7.3 Hz, 1H), 4.00-3.75 (m, 4H), 3.56-3.47 (m, 4H), 3.45 (s, 3H), 2.99-2.90 (m, 2H), 2.58-2.66 (br m, 4H).

Example 217

8-(4-(bis(4-fluorophenyl)methyl)piperazin-1-yl)-5-methy-6-oxo-5,6-dihydro-1,5-naphthyridine-2,7-dicarbonitrile

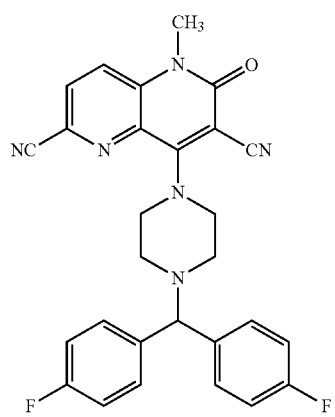

(217)

In a microwave tube, 4-(4-(bis(4-fluorophenyl)methyl)piperazin-1-yl)-6-chloro-1-methyl-2-oxo-1,2-dihydro-1,5-naphthyridine-3-carbonitrile (30 mg, 0.059 mmol), zinc (0.775 mg, 0.012 mmol), zinc cyanide (4.18 mg, 0.036 mmol), and 1,1-bis(diphenylphosphino)ferrocene-palladium(II)dichloride dichloromethane complex (4.84 mg, 5.93 µmmol) were added. The vessel was sealed, sequentially evacuated, and flushed with nitrogen three times. NMP (2 mL) was added and the reaction mixture was heated at 75° C. for 1 hr. The reaction mixture was then cooled, acetonitrile was added, and the resultant mixture was filtered. The filtrate was fractionated using reverse phase preparative HPLC using acetonitrile-water-ammonium acetate as eluent. Homogeneous fractions were combined and concentrated under vacuum overnight to give the title compound as a light-yellow colored solid (22.3 mg, 72.0% yield). Analytical LC/MS conditions: Column: Phenomenex LUNA C18, 2.0×50 mm, 3 µm particles; Mobile Phase A: 10:90 methanol:water with 0.1% TFA; Mobile Phase B: 90:10 methanol:water with 0.1% TFA; Gradient: 0-100% B over 4 minutes, then a 1 minute hold at 100% B; Flow: 0.8 mL/min; Detection: UV at 220 nm. LC/MS results: 3.3 min, 497.1 (M+H)+. $^1$H NMR (400 MHz, DMSO-$d_6$) δ 8.28-8.22 (m, 1H), 8.17-8.12 (m, 1H), 7.53 (dd, J=8.6, 5.6 Hz, 4H), 7.16 (t, J=8.8 Hz, 4H), 4.54 (s, 1H), 3.91 (br. s., 4H), 2.56 (br. s., 4H).

The following examples where prepared using method analogous to those already described from appropriate starting materials.

Example 218

4-(4-(bis(4-fluorophenyl)methyl)piperazin-1-yl)-6-chloro-1-methyl-2-oxo-1,2-dihydro-1,5-naphthyridine-3-carbonitrile

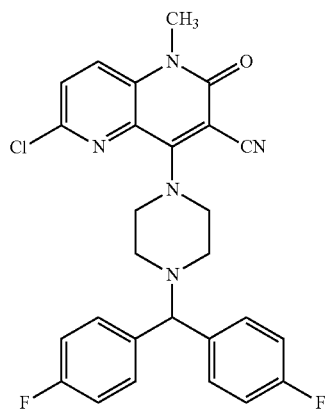

(218)

Analytical LC/MS conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. LC/MS results: 2.4 min, 506.0 (M+H)$^+$. $^1$H NMR (500 MHz, DMSO-d$_6$) δ 8.04 (d, J=9.2 Hz, 1H), 7.78 (d, =8.8 Hz, 1H), 7.52 (dd, J=8.6, 5.7 Hz, 4H), 7.16 (t, J=8.8 Hz, 4H), 4.51 (s, 1H), 3.88 (br. s., 4H), 3.51 (s, 3H), 2.56-2.53 (m, 4H).

Example 219

6-chloro-4-(4-((2-hydroxyphenyl)(phenyl)methyl)piperazin-1-yl)-1-methyl-2-oxo-1,2-dihydro-1,5-naphthyridine-3-carbonitrile

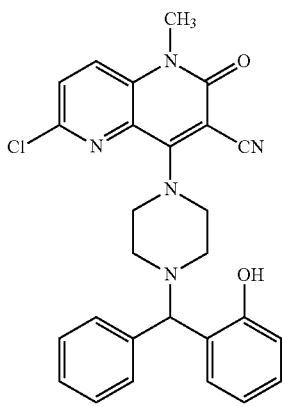

(219)

LC/MS (Method LC-2): 2.1 min, 486.1 (M+H)$^+$. $^1$H NMR (500 MHz, DMSO-d$_6$) δ 8.06 (d, J=8.8 Hz, 1H), 7.79 (d, J=9.2 Hz, 1H), 7.54-7.46 (m, 2H), 7.42-7.35 (m, 1H), 7.33 (t, J=7.7 Hz, 2H), 726-7.17 (m, 1H), 7.10-6.97 (m, 1H), 6.84-6.73 (m, 2H), 4.78 (s, 1H), 3.90 (br. s, 4H), 3.52 (s, 3H), 2.69-2.56 (m, 4H).

Example 220

6-chloro-4-(4-((1-ethyl-1H-indol-4-yl)methyl)piperazin-1-yl)-1-methyl-2-oxo-1,2-dihydro-1,5-naphthyridine-3-carbonitrile

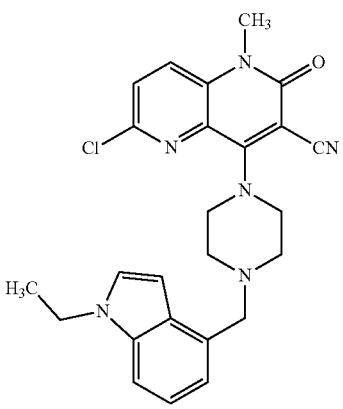

(220)

Analytical LC/MS conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. LC/MS results: 2.1 min, 461.1 (M+H)$^+$. $^1$H NMR (500 MHz, DMSO-d$_6$) δ 8.05 (d, J=9.2 Hz, 1H), 7.79 (d, J=9.2 Hz, 1H), 7.45-7.33 (m, 2H), 7.12 (t, J=7.5 Hz, 1H), 7.03 (d, J=7.3 Hz, 1H), 6.65 (d, J=2.6 Hz, 1H), 4.21 (q, J=7.1 Hz, 2H), 3.90-3.74 (m, 6H), 3.52 (s, 3H), 2.68 (br. s., 4H), 1.37 (t, J=7.2 Hz, 3H).

Example 221

6-chloro-1-methyl-4-(4-(naphthalen-1-ylmethyl)piperazin-1-yl)-2-oxo-1,2-dihydro-1,5-naphthyridine-3-carbonitrile

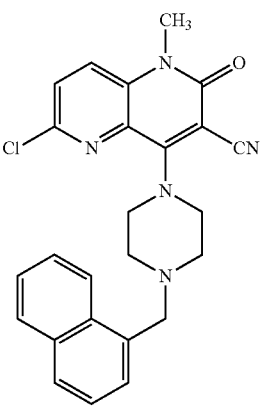

(221)

Analytical LC/MS conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. LC/MS results: 2.3 min, 444.1 (M+H)+. ¹H NMR (500 MHz, DMSO-d₆) δ 8.36 (d, J=8.8 Hz, 1H), 8.06 (d, J=8.8 Hz, 1H), 7.94 (d, J=8.4 Hz, 1H), 7.88 (d, J=8.8 Hz, 1H), 7.80 (d, J=8.8 Hz, 1H), 7.62-7.44 (m, 4H), 4.00 (s, 2H), 3.83 (br. s., 4H), 3.53 (s, 3H), 2.72 (br. s., 4H).

Example 222

6-chloro-4-(4-((4-fluoro-2-hydroxyphenyl)(4-fluorophenyl)methyl)piperazin-1-yl)-1-methyl-2-oxo-1,2-dihydro-1,5-naphthyridine-3-carbonitrile

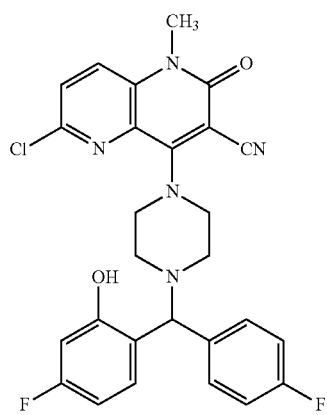

(222)

Analytical LC/MS conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. LC/MS results: 2.4 min, 522.1 (M+H)+. ¹H NMR (500 MHz, DMSO-d₆) δ 8.06 (d, J=9.2 Hz, 1H), 7.79 (d, J=8.8 Hz, 1H), 7.49 (dd, J=8.6, 5.7 Hz, 2H), 7.43-7.34 (m, 1H), 7.16 (t, J=8.8 Hz, 21-1), 6.72-6.53 (m, 2H), 4.79 (s, 1H), 3.89 (br. s., 4H), 3.52 (s, 3H), 2.62 (br. s., 2H), 2.57-2.51 (m, 2H).

Example 223

8-(4-benzhydrylpiperazin-1-yl)-5-methyl-7-nitro-6-oxo-5,6-dihydro-1,5-naphthyridine-2-carbonitrile

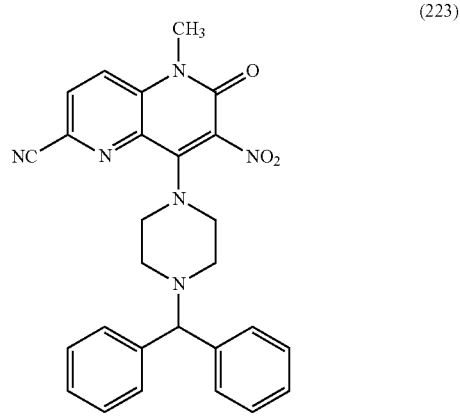

(223)

A solution was prepared by dissolving 8-chloro-5-methyl-7-nitro-6-oxo-5,6-dihydro-1,5-naphthyridine-2-carbonitrile, 0.22 ethyl acetate (94 mg, 0.331 mmol) in DMF (3.3 mL). To the solution were added a magnetic stir bar, 1-(diphenylmethyl)piperazine (89 mg, 0.353 mmol), and then potassium carbonate (91 mg, 0.662 mmol). The reaction mixture was placed under a nitrogen atmosphere and stirred at room temperature over a weekend. The reaction solution was pipetted off from the inorganic salts. Several drop of water and TFA (0.076 mL, 0.993 mmol) were added and the mixture was diluted to 6 mL using DMF and filtered through 0.45 μm syringe filter into three 2 mL sample vials. The sample was purified by reverse phase HPLC under the following conditions: Shimadzu Prep HPLC system using discovery software: Column: Waters Sunfire C18, 19 mm×150 mm; Flow Rate: 25 mL/min; Solvent % A: 10% acetonitrile-90% water-0.1% TFA; Solvent % B: 90% acetonitrile-10% water-0.1% TFA; Detection: UV at 220 nm; Gradient 20% B to 100% B over 20 minutes, Hold at 100% B for 5 minutes. Retention time of product=6.48 minutes to 7.31 minutes. The product was collected and solvent removed in vacuo to give 156 mg of the title compound as a yellow solid. LCMS: Column: Waters Acquity UPLC BEH C18, 2.1×50 mm, 1.7 μm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 nm. Retention Time==0.96 min.; Obs. Adducts: [M+H]; Obs. Masses: 481.2. ¹H NMR (Acetonitrile-d₃) δ 8.00-8.04 (m, 1H), 7.94-8.00 (m, 1H), 7.69 (d, J=7.6 Hz, 4H), 7.40-7.47 (m, 4H), 7.32-7.39 (m, 2H), 5.08 (br. s., 1H), 3.71 (t, J=4.5 Hz, 4H), 3.60 (s, 3H), 3.15 (br. s., 4H).

Example 224

3-bromo-4-(4-(1-(4-fluorophenyl)ethyl)piperazin-1-yl)-1,6-dimethyl-1,5-naphthyridin-2(1H)-one

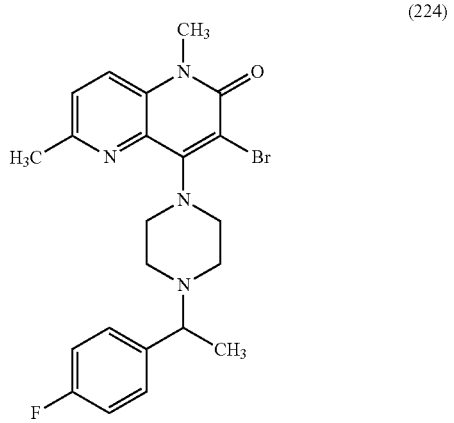 [SMILES: Cc1ccc2c(n1)c(N1CCN(C(C)c3ccc(F)cc3)CC1)c(Br)c(=O)n2C]

(224)

In a 1 dram vial containing 1-(1-bromoethyl)-4-fluorobenzene (21 mg, 0.103 mmol), DMF (0.7 mL) and 3-bromo-1,6-dimethyl-4-(piperazin-1-yl)-1,5-naphthyridin-2(1H)-one (30.6 mg, 0.091 mmol) were added followed by the addition of potassium carbonate (25.6 mg, 0.185 mmol). The reaction mixture was stirred in a capped vial at room temperature for 4.5 hours. HPLC analysis indicated the reaction proceeded to completion. The volatiles were removed from the reaction in vacuo using a rotary evaporator. The crude reaction product was partitioned between ethyl acetate and saturated sodium bicarbonate. The organic extract was washed with brine and dried over magnesium sulfate. The drying agent was removed by filtration. The solvent was removed from the filtrate to afford the crude product as 31 mg of amber oil. The Rf of the product on silica gel plate is ~0.26 in 20% ethyl acetate in chloroform. The sample was dissolved in DME/acetonitrile and the crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 30-78% B over 20 minutes, then a 4 minute hold at 100% B; Flow: 20 mL/min. Fractions containing the product were combined and dried via centrifugal evaporation. The NMR data is reported uncorrected for the effects of water suppression. $^1$H NMR (DMSO-$d_6$) δ 7.83 (d, J=8.9 Hz, 1H), 7.37 (br dd, J=8.2, 5.8 Hz, 2H), 7.13 (br t, J=8.9 Hz, 2H), 3.58 (s, 2H), 3.51 (br t, J=4.4 Hz, 3H), 2.59 (br s, 2H), 2.51 (br s, 4H), 1.32 (br d, J=6.7 Hz, 3H). Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.4%; Observed Mass: 458.92; Retention Time: 1.91 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.3%; Observed Mass: 459.04; Retention Time: 1.19 min.

Example 225

6-bromo-4-(4-((1-ethyl-1H-indol-4-yl)methyl)piperazin-1-yl)-1-methyl-2-oxo-1,2-dihydro-1,5-naphthyridine-3-carbonitrile

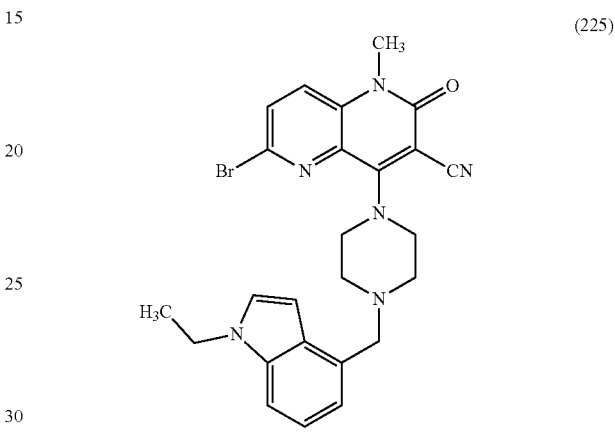

(225)

A solution was prepared by dissolving 6-bromo-4-chloro-1-methyl-2-oxo-1,2-dihydro-1,5-naphthyridine-3-carbonitrile (15 mg, 0.050 mmol) in DMF (0.5 mL). Next, 1-ethyl-4-(piperazin-1-ylmethyl)-1H-indole, 2 HCl (16.5 mg, 0.052 mmol) was added followed by the addition of potassium carbonate (31 mg, 0.224 mmol). The reaction mixture was placed under nitrogen at room temperature for 1.75 hours. Acetic acid (20 μl, 0.349 mmol) was added to the reaction mixture. The reaction mixture was diluted to 1.2 mL using acetonitrile and filtered through syringe filter. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 45-85% B over 18 minutes, then a 4 minute hold at 100% B; Flow: 20 mL/min. Fractions containing the product were combined and dried via centrifugal evaporation. $^1$H NMR (DMSO-$d_6$) δ 7.89-7.95 (m, 1H), 7.81-7.88 (m, 1H), 7.30-7.41 (m, 2H), 7.07-7.15 (m, 1H), 7.03 (d, J=6.6 Hz, 1H), 6.66 (d, J=2.6 Hz, 1H), 4.20 (q, J=7.2 Hz, 2H), 3.74-3.95 (m, 6H), 3.51 (s, 3H), 2.69 (br. s., 2H), 1.39 (t, J=7.0 Hz, 3H). Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 505.01; Retention Time: 2.16 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B: Flow: 1 mL/min; Detection: MS and UV (220 nm). Injection 2 results: Purity: 100.0%; Observed Mass: 505.02; Retention Time: 1.50 min. Proton NMR: Signal intensity is diminished (integration) adjacent to water suppression frequency. $^1$H NMR (DMSO-$d_6$) δ 7.89-7.95 (m, 1H), 7.81-7.88 (m, 1H), 7.30-7.41 (m, 2H), 7.07-7.15 (m, 1H), 7.03 (d, J=6.6 Hz, 1H), 6.66 (d, J=2.6 Hz, 1H), 4.20 (q, J=7.2 Hz, 2H), 3.74-3.95 (m, 6H), 3.51 (s, 3H), 2.69 (br. s., 2H), 1.39 (t, J=7.0 Hz, 3H).

Example 226

4-(4-(bis(4-fluorophenyl)methyl)piperazin-1-yl)-1,6-dimethyl-2-oxo-1,2-dihydro-1,5-naphthyridine-3-carbonitrile

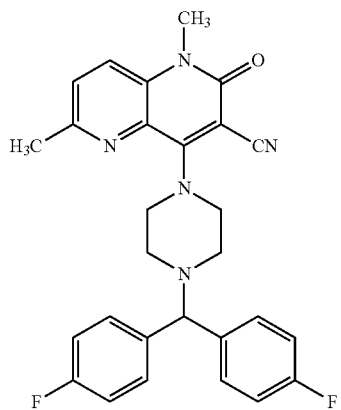

(226)

A solution was prepared by dissolving 4-chloro-1,6-dimethyl-2-oxo-1,2-dihydro-1,5-naphthyridine-3-carbonitrile (6.5 mg, 0.028 mmol) and 1-(4,4'-difluorobenzhydryl) piperazine (8.8 mg, 0.031 mmol) in DMF (0.3 mL). Next, potassium carbonate (8 mg, 0.058 mmol) was added. The reaction mixture was stirred at room temperature for 2 hours. Analysis by LCMS indicated approximately 80% conversion. Additional 1-(4,4'-difluorobenzhydryl)piperazine (2.3 mg, 7.98 µmol) was added to the reaction mixture. The reaction vessel was capped. The reaction mixture was stirred at room temperature overnight. The reaction mixture was diluted with acetonitrile and filtered through a syringe filter. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 48-88% B over 20 minutes, then a 4 minute hold at 100% B; Flow: 20 mL/min. Fractions containing the product were combined and dried via centrifugal evaporation. Analytical LC/MS was used to determine the final purity. Injection 1 conditions: Column: Waters XBridge C18 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 n/min; Detection: MS and UV (220 nm). Injection 1 results: Purity: 100.0%; Observed Mass: 486.13; Retention Time: 2.36 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 486.16; Retention Time: 1.59 min. Proton NMR signal intensities proximal to the water suppression frequency were affected and were uncorrected: $^1$H NMR (DMSO-$d_6$) δ 7.86 (d, J=8.8 Hz, 1H), 7.44-7.58 (m, 5H), 7.09-7.18 (m, 4H), 4.52 (s, 1H), 3.90-3.97 (m, 4H), 3.50 (s, 2H), 2.53-2.60 (m, 4H).

Example 227

4-(4-(bis(4-fluorophenyl)methyl)piperazin-1-yl)-1-methyl-3-(2,2,2-trifluoroacetyl)-1,5-naphthyridin-2(1H)-one

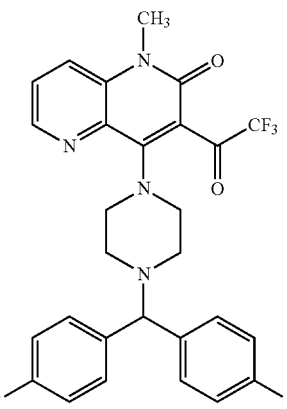

(227)

A solution was prepared by dissolving 4-(4-(bis(4-fluorophenyl)methyl)piperazin-1-yl)-1-methyl-1,5-naphthyridin-2(1H)-one (25 mg, 0.056 mmol) in dioxane (0.5 mL). Next, pyridine (0.023 mL, 0.280 mmol) was added followed by the addition of trifluoroacetic anhydride (0.016 mL, 0.112 mmol). The reaction mixture was placed under nitrogen and stirred at room temperature for 4 hours. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 60-100% B over 18 minutes, then a 5 minute hold at 100% B; Flow: 20 mL/min. Fractions containing the product were combined and dried via centrifugal evaporation. Two analytical LC/MS injections were used to determine the final purity Injection 1 conditions: Column: Waters Acquity UPLC BEH C18, 2.1×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. (Purity: 95.0%; RT: 2.54; Obs. Adducts: [M+H]; Obs. Masses: 543.07) Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B:

95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. (Purity: 100.0%; RT: 1.7; Obs. Adducts: [M+H]; Obs. Masses: 543.24). Proton NMR signal intensities proximal to the water suppression frequency were affected and were uncorrected: H NMR (DMSO-$d_6$) δ 8.54 (d, J=4.0 Hz, 1H), 8.01 (d, J=8.8 Hz, 1H), 7.70 (dd, J=8.8, 4.0 Hz, 1H), 7.49 (dd, J=8.3, 5.7 Hz, 4H), 7.14 (t, J=8.8 Hz, 4H), 4.48 (s, 1H), 3.52 (s, 3H).

Example 228

4-(4-(bis(4-fluorophenyl)methyl)piperazin-1-yl)-1,6-dimethyl-3-(2,2,2-trifluoroacetyl)-1,5-naphthyridin-2(1H)-one

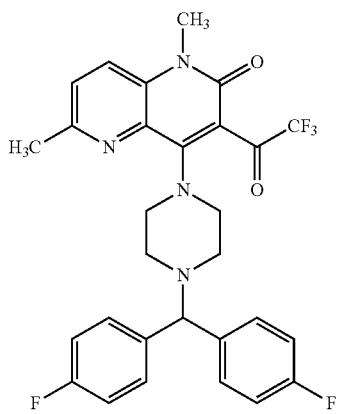

(228)

A solution was prepared by dissolving 4-(4-(bis(4-fluorophenyl)methyl)piperazin-1-yl)-1,6-dimethyl-1,5-naphthyridin-2(1H)-one (25 mg, 0.054 mmol) in dioxane (0.5 mL). Next, pyridine (0.022 mL, 0.271 mmol) was added followed by the addition of trifluoroacetic anhydride (0.015 mL, 0.109 mol). The reaction mixture was placed under nitrogen and stirred at room temperature for 5.5 hours. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 60-100% B over 18 minutes then a 7 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 93.9%; Observed Mass: 557.14; Retention Time: 2.63 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 91.9%; Observed Mass: 557.14; Retention Time: 1.79 min. Proton NMR signal intensities proximal to the water suppression frequency were affected and were uncorrected: $^1$H NMR (DMSO-$d_6$) δ 7.87 (d, J=8.8 Hz, 1H), 7.54 (d, J=8.8 Hz, 1H), 7.47 (dd, J=8.6, 5.7 Hz, 4H), 7.12 (t, J=8.8 Hz, 4H), 4.48 (s, 1H), 3.49 (s, 2H), 3.29 (s, 3H), 2.51-2.54 (m, 4H).

Example 229

4-(4-(bis(4-fluorophenyl)methyl)piperazin-1-yl)-6-bromo-2-oxo-1-(prop-2-yn-1-yl)-1,2-dihydro-1,5-naphthyridine-3-carbonitrile

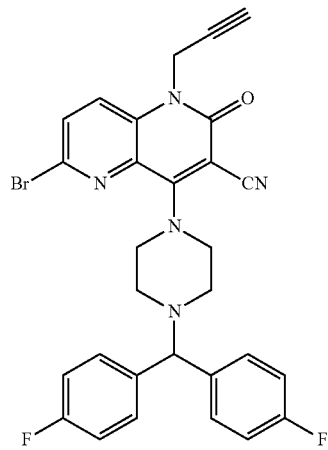

(229)

A solution was prepared by dissolving 6-bromo-4-chloro-2-oxo-1-(prop-2-yn-1-yl)-1,2-dihydro-1,5-naphthyridine-3-carbonitrile (16 mg, 0.050 mmol) in DMF (0.5 mL). Next, 1-(4,4'-difluorobenzhydryl)piperazine (14.6 mg, 0.051 mmol) was added followed by the addition of potassium carbonate (13.9 mg, 0.101 mmol). The reaction mixture was placed under nitrogen and stirred at room temperature for 3.5 hours. Acetic acid (10 μl, 0.175 mmol) was added to the reaction mixture. The reaction mixture was then diluted to 1 mL using acetonitrile and filtered. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 55-95% B over 20 minutes, then a 5 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 573.96; Retention Time: 1.9 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100%

B; Flow: 1 mL/min; Detection: MS and UV (220 nm). Injection 2 results: Purity: 100.0%; Observed Mass: 573.96; Retention Time: 2.55 min. Proton NMR signal intensities proximal to the water suppression frequency were affected and were uncorrected: $^1$H NMR (DMSO-$d_6$) δ 7.86-8.00 (m, 2H), 7.50 (dd, J=8.4, 5.9 Hz, 4H), 7.14 (t, J=8.8 Hz, 4H), 5.00 (d, J=1.8 Hz, 2H), 4.53 (s, 1H), 3.91 (br. s., 4H), 2.56 (br. s., 4H).

Example 230

4-(4-(bis(4-fluorophenyl)methyl)piperazin-1-yl)-3-bromo-1-methyl-1,5-naphthyridin-2(1H)-one

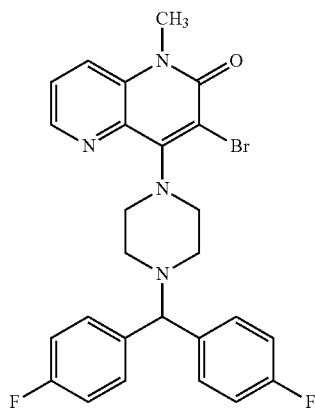

(230)

A solution was prepared by dissolving 4-(4-(bis(4-fluorophenyl)methyl)piperazin-1-yl)-1-methyl-1,5-naphthyridin-2(1H)-one (26.5 mg, 0.059 mmol) in DMF (0.2 mL) followed by the addition of NBS (12.6 mg, 0.071 mmol). The reaction mixture was placed under a nitrogen atmosphere and stirred at room temperature for 2.5 hours. The reaction mixture was diluted to 1 mL using acetonitrile and then filtered through a syringe filter. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 50-100% B over 20 minutes, then a 5 minute hold at 100% B; Flow: 20 mL/min. Fractions containing the product were combined and dried via centrifugal evaporation. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. (Purity: 98.8%; RT: 261; Obs. Adducts: [M+H]; Obs. Masses: 524.99). Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. (Purity: 100.0%; RT: 1.44; Obs. Adducts: [M+H]; Obs. Masses: 525.02). Proton NMR signal intensities proximal to the water suppression frequency were affected and were uncorrected: $^1$H NMR (DMSO-$d_6$) δ 8.54 (d, J=4.4 Hz, 1H), 7.98 (d, J=8.8 Hz, 1H), 7.63 (dd, J=8.6, 4.2 Hz, 1H), 7.51 (dd, J=8.4, 5.5 Hz, 4H), 7.14 (t, J=8.8 Hz, 4H), 4.46 (s, 1H), 3.63 (s, 3H), 3.56 (t, J=5.0 Hz, 4H).

Example 231

8-(4-(bis(4-fluorophenyl)methyl)piperazin-1-yl)-7-cyano-N,N,5-trimethyl-6-oxo-5,6-dihydro-1,5-naphthyridine-2-carboxamide

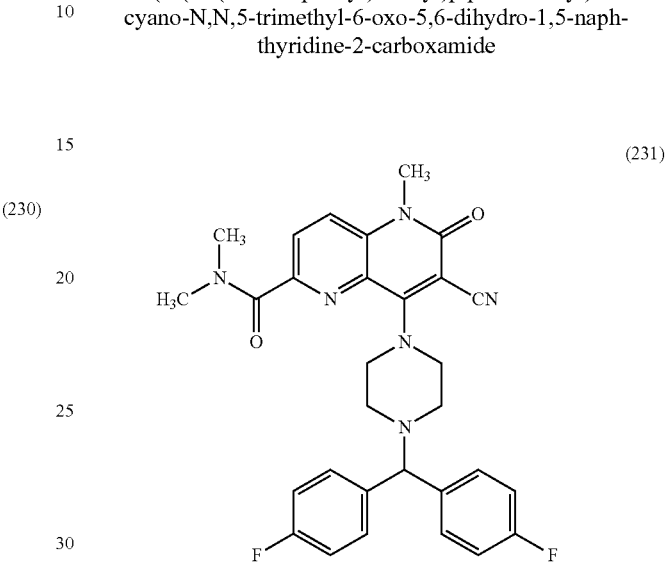

(231)

A solution was prepared by dissolving 8-(4-(bis(4-fluorophenyl)methyl)piperazin-1-yl)-7-cyano-5-methyl-6-oxo-5,6-dihydro-1,5-naphthyridine-2-carboxylic acid (15 mg, 0.029 mmol) and aza-HOBt (5.0 mg, 0.037 mmol) in DMF (0.3 mL). To the reaction mixture was added DIEA (5.4 μl, 0.031 mmol) followed by the addition of EDC (9.1 mg, 0.047 mmol). The reaction mixture was stirred at room temperature for 5 minutes, and then dimethylamine (29.1 μl, 0.058 mmol) was added. The reaction vessel was capped and the reaction mixture was stirred at room temperature for 2 hours. Acetic acid (7 μl, 0.122 mmol) added and the reaction mixture was diluted with acetonitrile. The crude material w as purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 38-78% B over 20 minutes, then a 4 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 543.18; Retention Time: 1.41 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0%1B to 100% B over 3 min. then a 0.75 min hold at 100% B; Flow: 1 mL/min; Detection: MS and UV (220 nm).

Injection 2 results: Purity: 100.0%; Observed Mass: 543.24; Retention Time: 2.01 min. Proton NMR signal intensities proximal to the water suppression frequency were affected and were uncorrected: $^1$H NMR (DMSO-$d_6$) δ 8.04 (d, J=9.2 Hz, 1H), 7.80 (d, J=8.8 Hz, 1H), 7.49 (dd, J=8.6, 5.7 Hz, 4H), 7.14 (t, J=8.8 Hz, 4H), 4.55 (s, 1H), 3.84-3.95 (m, 4H), 3.54 (s, 3H), 3.00 (br s, 2H), 2.91 (br s, 2H), 2.52-2.57 (m, 4H).

Example 232

4-(4-(bis(4-fluorophenyl)methyl)piperazin-1-yl)-1,6-dimethyl-3-(trifluoromethyl)-1,5-naphthyridin-2(1H)-one

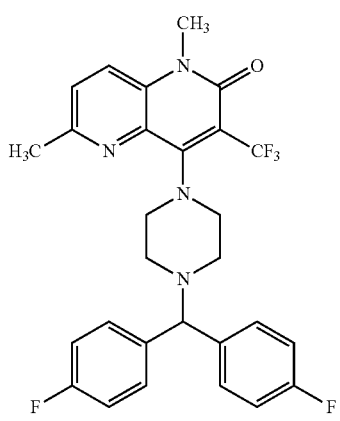

(232)

References: Togni et. al. J. Fluorine Chem. 131 (2010) 951-957. Onset observed >135° C.; Haller, *J. Org. Process Res. Dev.*, 2013, 17 (3), pp 318-319.

In a 1 dram pressure vial containing a new Teflon magnetic stir bar, 4-(4-(bis(4-fluorophenyl)methyl)piperazin-1-yl)-1,6-dimethyl-1,5-naphthyridin-2(1H)-one (15 mg, 0.033 mmol) and chlorotris(triethylsilyl)silane (16.2 mg, 0.057 mmol) were added and dissolve in acetonitrile (0.35 mL). Next, 1-trifluoromethyl-3,3-dimethyl-1,2-benziodoxole (21.5 mg, 0.065 mmol) was added. The vial was closed with a pressure cap and heated in an oil bath, pre-equilibrated to 80° C., behind a blast shield for 24 hours. The crude material was purified via preparative LC/IS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 60-100% B over 22 minutes, then a 4 minute hold at 100% B; Flow: 20 mL/min. Fractions containing the product were combined and dried via centrifugal evaporation. Analytical LC/MS was used to determine the final purity.

Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 529.16; Retention Time: 2.67 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 529.22; Retention Time: 1.71 min. Proton NMR signal intensities proximal to the water suppression frequency were affected and were uncorrected: $^1$H NMR (DMSO-$d_6$) δ 7.85 (d, J=8.8 Hz, 1H), 7.50 (dt, J=8.5, 5.6 Hz, 5H), 7.13 (t, J=8.8 Hz, 4H), 4.49 (s, 1H), 3.67 (br s, 4H), 3.50 (s, 3H), 2.52-2.58 (m, 4H).

Example 233

4-(4-(bis(4-fluorophenyl)methyl)piperazin-1-yl)-3-chloro-1,6-dimethyl-1,5-naphthyridin-2(1H)-one

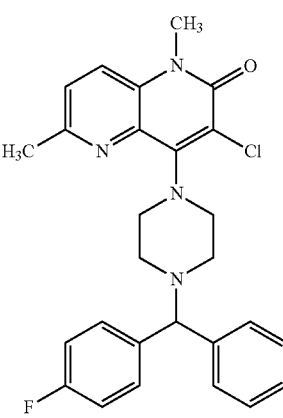

(233)

A solution was prepared by dissolving 4-(4-(bis(4-fluorophenyl)methyl)piperazin-1-yl)-1,6-dimethyl-1,5-naphthyridin-2(1H)-one (15 mg, 0.033 mmol) in DMF (0.33 mL). The solution was cooled to 0° C., and then n-chlorosuccinimide (5.0 mg, 0.037 mmol) was added. The reaction mixture was placed under nitrogen, stirred at 0° C. for one hour, then removed from the ice bath, warmed to room temperature, and stirred for an additional hour. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile: water with 10 mM ammonium acetate; Gradient: 50-100% B over 20 minutes, then a 5 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 495.1; Retention Time: 1.53 min. Injection 2 conditions: Column: Waters XBridge C18, 2.1 mm×50 mm, 1.7 µm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0% B to 100% B over 3 min then a 0.75 min hold at 100% B; Flow: 1 mL/min; Detection:

MS and UV (220 nm). Injection 2 results: Purity: 100.0%; Observed Mass: 495.09; Retention Time: 2.49 min. Proton NMR signal intensities proximal to the water suppression frequency were affected and were uncorrected: $^1$H NMR (DMSO-d$_6$) δ 7.84 (d, J=8.4 Hz, 1H), 7.40-7.54 (m, 5H), 7.13 (t, J=8.8 Hz, 4H), 4.48 (s, 1H), 3.54-3.64 (m, 6H), 2.54 (s, 3H).

Example 234

4-(4-(bis(4-fluorophenyl)methyl)piperazin-1-yl)-3-fluoro-1,6-dimethyl-1,5-naphthyridin-2(1H)-one

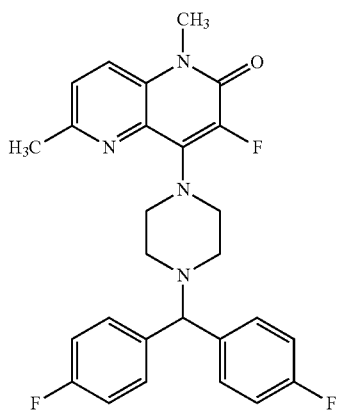

(234)

A solution was prepared by dissolving 4-(4-(bis(4-fluorophenyl)methyl)piperazin-1-yl)-1,6-dimethyl-1,5-naphthyridin-2(1H)-one (20 mg, 0.043 mmol) in acetonitrile (0.4 nL). The solution was cooled to 0° C., and 1-chloromethyl-4-fluoro-1,4-diazoniabicyclo [2.2.2]octane bis(tetrafluoroborate) (15.39 mg, 0.043 mmol) dissolved in water (0.15 mL) and THF (0.15 mL) was added. The reaction mixture was placed under nitrogen, stirred at 0° C., warmed to room temperature over 1.5 hours, and then stirred for 3 hours. HPLC analysis of the reaction showed approximately 25% conversion to product. The reaction mixture was cooled to 0° C., and additional 1-chloromethyl-4-fluoro-1,4-diazoniabicyclo [2.2.2]octane bis(tetrafluoroborate) (16.3 mg, 0.046 mmol) in 0.2 mL of water was added. The reaction vessel was capped and the reaction mixture was stirred at 0° C. for 25 minutes. The reaction vessel was removed from the ice bath. The reaction mixture was stirred for 35 minutes warming to room temperature. HPLC analysis indicated approximately 50% conversion to product. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 45-85% B over 23 minutes, then a 4 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.4%; Observed Mass: 479.2; Retention Time: 2.42 min. Injection 2 conditions: Column: Waters XBridge C18, 2.1 mm×50 min, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.3%; Observed Mass: 479.2; Retention Time: 1.48 min. Proton NMR signal intensities proximal to the water suppression frequency are affected and are uncorrected: $^1$H NMR (DMSO-d$_6$) δ 7.81 (d, J=8.4 Hz, 1H), 7.48 (dd, J8.6, 5.7 Hz, 4H), 7.41 (d, J=8.8 Hz, 1H), 7.12 (t, J=8.8 Hz, 4H), 4.48 (s, 1H), 3.58 (br s, 3H), 3.56 (s, 3H).

Example 235

4-(4-(bis(4-fluorophenyl)methyl)piperazin-1-yl)-6-bromo-1-methyl-2-oxo-1,2-dihydro-1,5-naphthyridine-3-carbonitrile, TFA

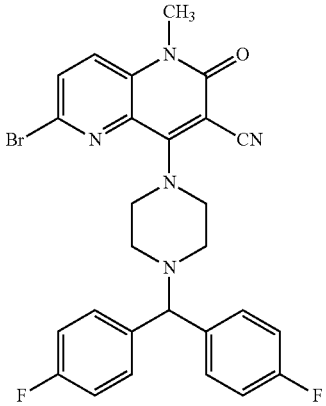

(235)

In a 1 dram vial charged with 6-bromo-1-methyl-2,4-dioxo-1,2,3,4-tetrahydro-1,5-naphthyridine-3-carbonitrile (39.7 mg, 0.142 mmol) in acetonitrile (1.4 mL) was add DIEA (0.149 mL, 0.850 mmol). The reaction mixture was stirred for several minutes and tosyl chloride (81 mg, 0.425 mmol) was added. The reaction mixture was capped under a nitrogen atmosphere and stirred at room temperature for 20 hours. One half of the above reaction volume (the reaction mixture was heterogeneous and amber in color) was added to a one dram vial containing 1-(4,4'-difluorobenzhydryl)piperazine (26.6 mg, 0.092 mmol), acetonitrile (0.2 mL), and 1-methylpiperidine (0.011 mL, 0.092 mmol). The reaction mixture was capped under a nitrogen atmosphere and stirred at room temperature for 3 hours. After HPLC analysis, 1-(4,4'-difluorobenzhydryl)piperazine (20.47 mg, 0.071 mmol) was added to the reaction mixture. The reaction vessel was capped. The reaction mixture was stirred at room temperature for an additional 1.5 hours. Acetic acid (0.020 ml, 0.355 mmol) was added to the reaction mixture along with DMF and filtered through a syringe filter. The crude material was purified via preparative LC/MS with the following conditions: Column: XBridge C18, 19×200 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 20 minutes, then a 5 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.4%; Observed Mass: 549.94; Retention Time: 2.5 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 549.95; Retention Time: 1.8 min. $^1$H NMR (DMSO-$d_6$) δ 7.89-7.96 (m, 1H), 7.81-7.88 (m, 1H), 754 (dd, J=8.3, 5.7 Hz, 4H), 7.17 (t, J=8.8 Hz, 4H), 4.73 (br. s., 1H), 3.91 (br. s., 4H), 3.51 (s, 3H), 2.68 (br. s., 4H).

Example 236

3-bromo-4-(4-((1-ethyl-1H-indol-4-yl)methyl)piperazin-1-yl)-1-methyl-1,5-naphthyridin-2(1H)-one

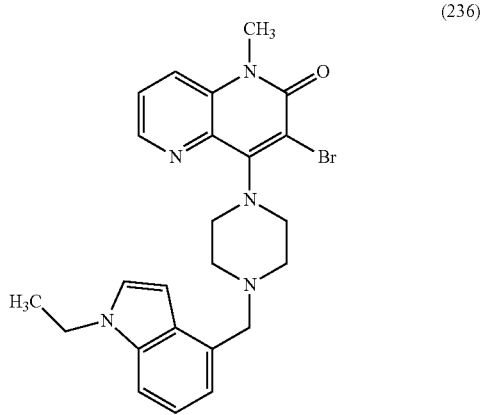 [SMILES: CCn1ccc2c(CN3CCN(c4c(Br)c(=O)n(C)c5cccnc45)CC3)cccc21]

(236)

In a 1 dram vial containing 3-bromo-4-hydroxy-1-methyl-1,5-naphthyridin-2(1H)-one (16.4 mg, 0.064 mmol), acetonitrile (0.5 mL) was added followed by the addition of DIEA (44.9 μl, 0.257 mmol). To reaction mixture was added triflic anhydride (13.04 μl, 0.077 mmol). The reaction mixture was placed under a nitrogen atmosphere and stirred at room temperature for 55 minutes. HPLC analysis of the reaction indicated approximately 60% conversion to product. The reaction mixture was stirred at room temperature under a nitrogen atmosphere overnight. HPLC analysis the following morning showed no significant change in the reaction composition. Triflic anhydride (5.5 μl, 0.033 mmol) was added to the reaction mixture. The reaction mixture was stirred under a nitrogen atmosphere for 45 minutes. Subsequent HPLC analysis estimated conversion to product at 91%. Volatiles were removed from the reaction in vacuo using a rotary evaporator. The crude product was partitioned between ethyl acetate and 1.5 M dipotassium phosphate. The organic extract was washed sequentially with 1.5 M dipotassium phosphate and brine, and dried over magnesium sulfate. The drying agent was removed by filtration. The solvents were removed in vacuo using a rotary evaporator to afford the intermediate product, 3-bromo-1-methyl-2-oxo-1,2-dihydro-1,5-naphthyridin-4-yl trifluoromethanesulfonate, as a brown film (26 mg). LCMS; Column: Waters Acquity BEH C18 2.1 mm×50 mm, 1.7 μm particles; Mobile Phase A: 100% water with 0.05% TFA; Mobile Phase B: 100% acetonitrile with 0.05% TFA; Temperature: 40° C.; Gradient 2% B to 98% B over 1.5 minutes, then 0.5 min hold at 98% B; Flow: 0.8 mL/min; Detection: MS and UV (220 nm). Injection volume: 3 μL. Retention Time=1.01 min.; Obs. Adducts: [M+H]; Obs. Masses: 386.85.

A solution of 3-bromo-1-methyl-2-oxo-1,2-dihydro-1,5-naphthyridin-4-yl trifluoromethanesulfonate (26 mg, 0.067 mmol) in DCM (0.45 mL) was added to a 1 dram vial containing 1-ethyl-4-(piperazin-1-ylmethyl)-1H-indole, 2 TFA (44.3 mg, 0.094 mmol) and DIEA (0.059 mL, 0.336 mmol). The vial was capped and the reaction mixture was stirred at room temperature for 2 hours. Volatiles were removed from the reaction mixture in vacuo using a rotary evaporator. The crude reaction product was dissolved in DMF/acetonitrile (1:1, 1 mL). The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 40-80% B over 15 minutes, then a 5 minute hold at 100% B; Flow: 20 mL/min. Fractions containing the product were combined and dried via centrifugal evaporation.

Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. (Purity: 100.0%; RT: 1.88; Obs. Adducts: [M+H]; Obs. Masses: 480.04). Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 min hold at 100% B; Flow: 1.0 mL/min; Detection: UV at 220 nm, (Purity: 100.0%; RT: 1.29; Obs. Adducts: [M+H]; Obs. Masses: 480.04). Proton NMR signal intensities proximal to the water suppression frequency were affected and were uncorrected: $^1$H NMR (DMSO-$d_6$) δ 8.53 (d, J=2.9 Hz, 1H), 7.99 (d, J=7.7 Hz, 1H), 7.63 (dd, J=8.6, 4.2 Hz, 1H), 732-7.44 (m, 2H), 7.11 (t, J=7.5 Hz, 1H), 7.03 (d, J=5.9 Hz, 1H), 6.65 (br. s., 1H), 4.20 (q, 0.1=7.3 Hz, 2H), 3.79 (br. s., 1H), 3.64 (s, 3H), 3.53 (br. s., 2H), 2.63 (br. s., 2H), 1.37 (t, J=7.2 Hz, 3H).

Example 237

6-bromo-1-methyl-4-(4-(naphthalen-1-ylmethyl)piperazin-1-yl)-2-oxo-1,2-dihydro-1,5-naphthyridine-3-carbonitrile

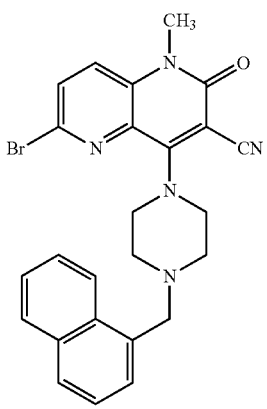

(237)

A solution was prepared by dissolving 6-bromo-4-chloro-1-methyl-2-oxo-1,2-dihydro-1,5-naphthyridine-3-carbonitrile (15 mg, 0.050 mmol) in DMF (0.5 mL). Next, 1-(naphthalen-1-ylmethyl)piperazine, 3 TFA (28.6 mg, 0.050 mmol) was added followed by the addition of potassium carbonate (34.7 mg, 0.251 mmol). The reaction mixture was placed under a nitrogen atmosphere and stirred at room temperature for 2 hours. The reaction mixture was diluted with acetonitrile and 15 µl of acetic acid was added. The reaction mixture was stirred and then filtered through a syringe filter. The crude material was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 50-90% B over 15 minutes, then a 5 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1 N trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 487.9; Retention Time: 1.35 min. $^1$H NMR (DMSO-$d_6$) δ 8.36 (d, J=9.2 Hz, 1H), 7.92 (d, J=9.2 Hz, 21H), 7.82-7.88 (m, 2H), 7.43-7.62 (m, 4H), 4.00 (s, 2H), 3.83 (d, J=4.8 Hz, 4H), 3.52 (s, 3H), 2.67-2.77 (m, 4H).

Example 238

4-(4-([1,1'-biphenyl]-2-ylmethyl)piperazin-1-yl)-6-bromo-1-methyl-2-oxo-1,2-dihydro-1,5-naphthyridine-3-carbonitrile, TFA (238)

A solution was prepared by dissolving 6-bromo-4-chloro-1-methyl-2-oxo-1,2-dihydro-1,5-naphthyridine-3-carbonitrile (15 mg, 0.050 mmol) in DMF (0.5 mL). Next, 1-([1,1'-biphenyl]-2-ylmethyl)piperazine, 2 TFA (24.14 mg, 0.050 mmol) was added followed by the addition of potassium carbonate (29 mg, 0.210 mmol). The reaction mixture was capped under a nitrogen atmosphere and stirred at room temperature for 2 hours. The reaction mixture was diluted in DMF and acetonitrile, and two drops of water and 30 µL of acetic acid were added. The reaction mixture was heated to dissolve solids and filtered through a syringe filter. Upon cooling a very small amount or material was precipitated out and 15 µL of TFA was added to help solubilization. The solution re-filtered through a syringe filter. The crude material was purified via preparative LC/MS with the following conditions: Column: XBridge C18, 19×200 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 18 minutes, then a 4 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 513.93; Retention Time: 2.42 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 514.18; Retention Time: 1.46 min. Proton NMR signal intensities proximal to the water suppression frequency were affected and were uncorrected: $^1$H NMR (DMSO-d$_6$) δ 7.90-7.97 (m, 1H), 7.83-7.89 (m, 1H), 7.71 (d, J=7.3 Hz, 1H), 7.48 (t, J=7.3 Hz, 4H), 7.35-7.43 (m, 3H), 7.28-7.34 (m, 1H), 4.08 (br. s., 1H), 3.89 (br. s., 3H), 3.51 (s, 2H), 2.93 (br. s., 1H).

Example 239

4-(4-(bis(4-fluorophenyl)methyl)piperazin-1-yl)-3-bromo-1,6-dimethyl-1,5-naphthyridin-2(1H)-one

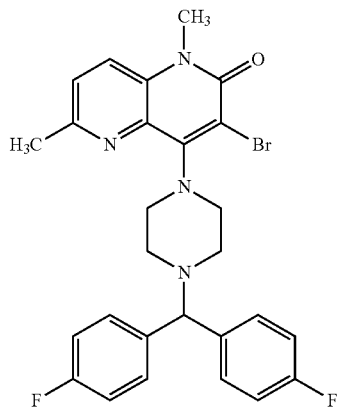

(239)

A solution was prepared by dissolving 4-(4-(bis(4-fluorophenyl)methyl)piperazin-1-yl)-1,6-dimethyl-1,5-naphthyridin-2(1H)-one (25 mg, 0.054 mmol) in DMF (0.25 mL). Next, NBS (12.3 mg, 0.069 mmol) was added. The reaction mixture was capped and stirred at room temperature for 1.5 hours. The crude material was purified via preparative LC/MS with the following conditions: Column: XBridge C18, 19×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 55-95% B over 20 minutes, then a 5 minute hold at 100% B; Flow: 20 mL/min. Fractions containing the product were combined and dried via centrifugal evaporation. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then 0.75 min hold at 100% B; Flow: 1 mL/min; Detection: MS and UV (220 nm). Injection 1 results: Purity: 100.0%; Observed Mass: 539.07; Retention Time: 2.58 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 539.06; Retention Time: 1.65 min. $^1$H NMR (CHLOROFORM-d) δ 7.55 (d, J=8.7 Hz, 1H), 7.39-7.47 (m, 4H), 7.30 (d, J=8.7 Hz, 1H), 6.96-7.05 (m, 4H), 4.32 (s, 1H), 3.71 (s, 3H), 3.65-3.70 (m, 4H), 2.56-2.64 (m, 7H).

Example 240 methyl 8-(4-(bis(4-fluorophenyl)methyl)piperazin-1-yl)-7-cyano-5-methyl-6-oxo-5,6-dihydro-1,5-naphthyridine-2-carboxylate

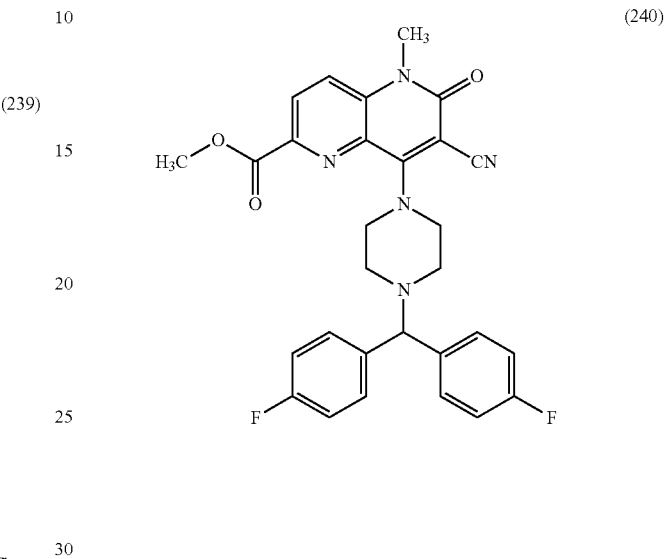

(240)

To a 2 dram vial containing methyl 7-cyano-5-methyl-6-oxo-8-(piperazin-1-yl)-5,6-dihydro-1,5-naphthyridine-2-carboxylate, HCl (52 mg, 0.143 mmol), 1.5 mL of DCM and 1.5 mL of 1.0M sodium carbonate were added. Next, 4,4'-(bromomethylene)bis (fluorobenzene) (59.5 mg, 0.210 mmol) was added. The reaction vessel was capped. The reaction mixture was stirred at room temperature for 2 days. The reaction mixture was further diluted with DCM and brine. The product was extracted into ethyl acetate. The organic extract, was dried over magnesium sulfate, filtered, and solvent was removed in vacuo to afford the crude product. The crude mixture was purified using silica gel chromatography eluting first with DCM to remove non-polar impurities and then 15° % ethyl acetate in DCM. The pure product fractions (TLC) were combined and solvent removed in vacuo to afford the product as a beige solid. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 μL. Retention Time=1.90 min.; Obs. Adducts: [M+H]; Obs. Masses: 530.20. LCMS; Column: Phenomenex Luna C18, 2 mm×50 mm, 3 μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient 0%=B to 100%=B over 4 minutes, then 1 min hold at 100% B; Flow: 0.8 mL/min; Detection: MS and UV (220 nm). Injection volume: 3 μL. Retention Time==3.43 min.; Obs. Adducts: [M+H]; Obs. Masses: 530.21.

Example 241

8-(4-(bis(4-fluorophenyl)methyl)piperazin-1-yl)-7-cyano-5-methyl-6-oxo-5,6-dihydro-1,5-naphthyridine-2-carboxylic acid

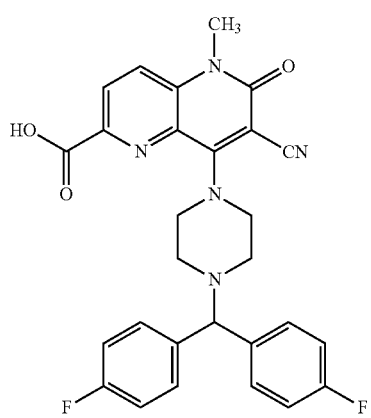

(241)

In a 1 dram vial containing methyl 8-(4-(bis(4-fluorophenyl)methyl)piperazin-1-yl)-7-cyano-5-methyl-6-oxo-5,6-dihydro-1,5-naphthyridine-2-carboxylate (50 mg, 0.094 mmol), 0.5 mL of T-IF was added, resulting in the formation of a suspension. Next, 0.5 mL of DCM was added to help solubilization. Additional THF (0.45 mL) was added, which precipitated more starting material from solution. DCM was added in 0.1 nL increments to solubilize starting material. Solubilization was achieved after an additional 0.4 mL of DCM. The reaction solution composition was 0.9 mL DCM and 0.95 mL THF. Potassium trimethylsilanolate (15.7 mg, 0.122 mmol) was added to the reaction mixture and the reaction mixture was capped and stirred at room temperature for 4 hours. Hydrochloric acid (IM, 0.123 mL, 0.123 mmol) was added to the reaction mixture and the reaction mixture was stirred for several minutes. Chloroform was added. The reaction mixture was transferred to a separatory funnel and additional chloroform added along with some water. After mixing, the organic phase was partitioned and the aqueous phase extracted with chloroform. The organic extracts were combined and washed with brine and dried over magnesium sulfate. The drying agent was filtered off and solvent from the filtrate removed in vacuo using a rotary evaporator. The crude material was purified via preparative reverse phase HPLC using acetonitrile/water/0.1% TFA solvent system with UV detection at 220 nm. Fractions were analyzed by LCMS and solvent was removed from the product fraction in vacuo using a rotary evaporator to afford the product as an off white solid. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 mi hold at 100% B; Flow: 1 mL/min; Detection: MS and UV (220 nm). Injection volume: 1 μL. Results: Retention Time=1.70 min.; Obs. Adducts: [M+H]; Obs. Masses: 516.20. $^1$H NMR (Acetonitrile-d$_3$) δ 8.25 (d, J=8.8 Hz, 1H), 7.92 (d, J=9.0 Hz, 1H), 7.64-7.78 (m, 4H), 7.17 (t, J=8.7 Hz, 4H), 5.05 (br. s., 1H), 4.16 (br. s., 4H), 3.57 (s, 3H), 3.15 (br. s., 4H).

Example 242

4-[4-(diphenylmethyl)piperazin-1-yl]-1-methyl-3-nitro-1,2-dihydro-1,5-naphthyridin-2-one

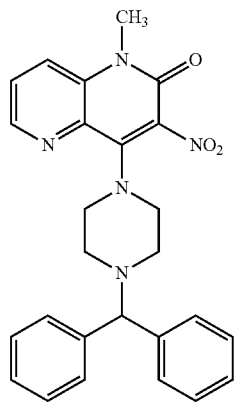

(242)

The title compound was prepared according to the general method used to prepare Example 165. The compound (1.8 mg) was isolated in 0.9% yield. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm.

Example 243

4-[4-(diphenylmethyl)piperazin-1-yl]-1-ethyl-3-nitro-1,2-dihydro-1,5-naphthyridin-2-one

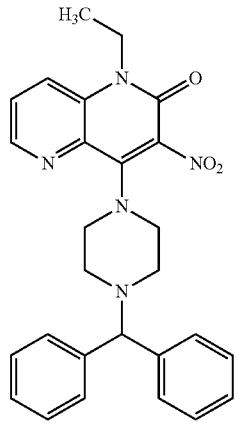

(243)

The title compound was prepared according to the general method used to prepare Example 165. The compound (5 mg) was isolated in 23.7% yield. Two analytical LC/MS injections were used to determine the final purity. Injection 1 conditions: Column: Waters Acquity UPLC BEH C18, 2.1× 50 mm, 1.7 µm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-1000% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm.

Example 244

4-[4-(diphenylmethyl)piperazin-1-yl]-1-(2-methoxyethyl)-3-nitro-1,2-dihydro-1,5-naphthyridin-2-one

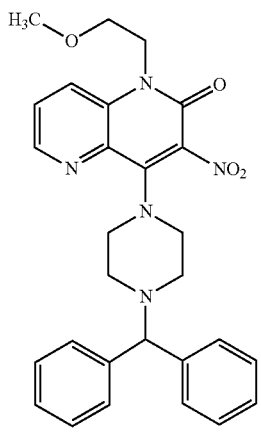

(244)

The title compound was prepared according to the general method used to prepare Example 165. The compound (10.1 mg) was isolated in 35.5% yield. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm.

Example 245

2-{4-[4-(diphenylmethyl)piperazin-1-yl]-3-nitro-2-oxo-1,2-dihydro-1,5-naphthyridin-1-yl}acetonitrile

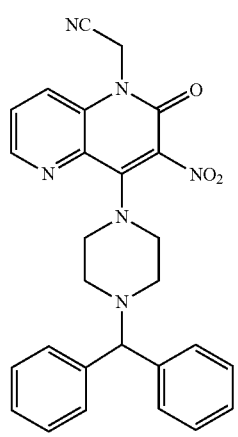

(245)

The title compound was prepare according to the general method used to prepare Example 165. The compound (5.9 mg) was isolated in 21.5% yield. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm.

Example 246

Ethyl 2-{4-[4-(diphenylmethyl)piperazin-1-yl]-3-nitro-2-oxo-1,2-dihydro-1,5-naphthyridin-1-yl}acetate

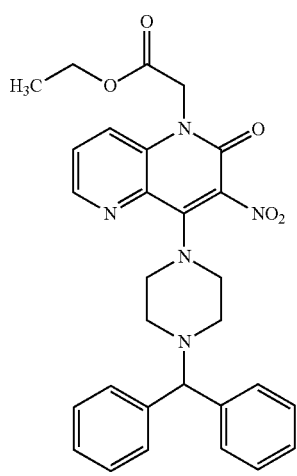
(246)

The title compound was prepared according to the general method used to prepare Example 165. The compound (7.5 mg) was isolated in 50.8% yield. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm.

Example 248

4-[4-(diphenylmethyl)piperazin-1-yl]-3-nitro-1-propyl-1,2-dihydro-1,5-naphthyridin-2-one

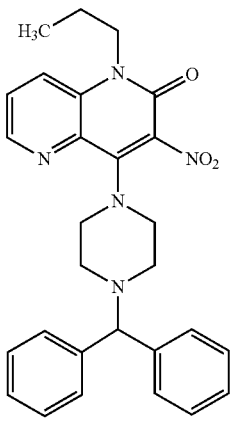
(248)

The title compound was prepared according to the general method used to prepare Example 165. The compound (9.5 mg) was isolated in 27.9% yield. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1%/trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm.

Example 250

4-{4-[cyclopropyl(4-fluorophenyl)methyl]piperazin-1-yl}-1,6-dimethyl-2-oxo-1,2-dihydro-1,5-naphthyridine-3-carbonitrile

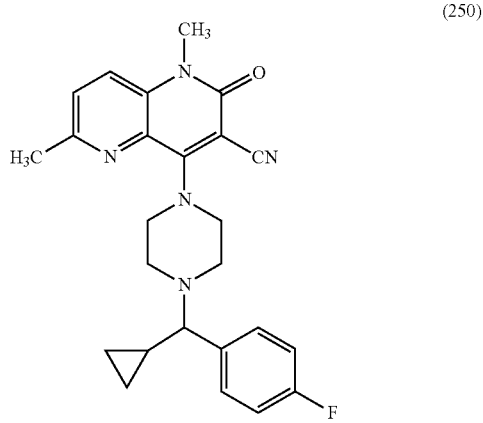 [SMILES: Cc1ccc2c(n1)c(N1CCN(C(c3ccc(F)cc3)C3CC3)CC1)c(C#N)c(=O)n2C]
(250)

In a 2 dram sealed reaction vessel 1,6-dimethyl-2-oxo-4-(piperazin-1-yl)-1,2-dihydro-1,5-naphthyridine-3-carbonitrile, TFA (20 mg, 0.050 mmol), cyclopropyl(4-fluorophenyl)methanol (11.71 mg, 0.070 mmol), (cyanomethyl)trimethylphosphonium iodide (24.46 mg, 0.101 mmol) were combined in propionitrile (252 µl). Hunig's Base (75 µl, 0.429 mmol) was added and the reaction mixture was heated at 110° C. for 4 hours. LCMS analysis showed the starting material was consumed. The reaction mixture was diluted with ethyl acetate (5 mL) and extracted 3× with water. The organic portion was concentrated under a stream of nitrogen. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 30% B, 30-70% B over 23 minutes, then a 5 minute hold at 100% B; Flow Rate: 20 mL/min; Column Temperature: 25° C. Fraction collection was triggered by MS and UV signals. Fractions containing the product were combined and dried via centrifugal evaporation. The compound (1.8 mg) was isolated in 8.3% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 min hold at 100% B; Flow: 1 mL/min; Detection: MS and UV (220 nm). Injection 1 results: Purity: 98.0%; Observed Mass: 432.16; Retention Time: 1.42 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.4%; Observed Mass: 432.2; Retention Time: 2.03 min.

Example 251

4-{4-[bis(4-fluoro-2-methoxyphenyl)methyl]piperazin-1-yl}-1,6-dimethyl-2-oxo-1,2-dihydro-1,5-naphthyridine-3-carbonitrile

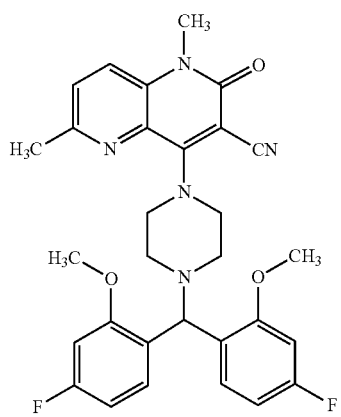

(251)

The title compound was prepared according to the general method used to prepare Example 250. The compound (23.2 mg) was isolated in 42.5% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.1%; Observed Mass: 546.16; Retention Time: 2.31 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 546.19; Retention Time: 1.51 min.

Example 252

4-[4-(4-methoxybutan-2-yl)piperazin-1-yl]-1,6-dimethyl-2-oxo-1,2-dihydro-1,5-naphthyridine-3-carbonitrile

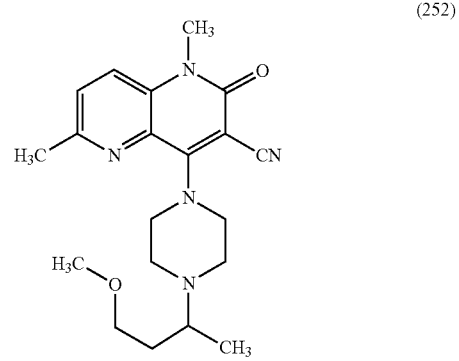 [SMILES: COCCC(C)N1CCN(c2c(C#N)c(=O)n(C)c3ccc(C)nc23)CC1]

(252)

The title compound was prepared according to the general method used to prepare Example 250. The compound (1.7 mg) was isolated in 9.2% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 mi hold at 100% B; Flow: 1 mL/min; Detection: MS and UV (220 nm). Injection 1 results: Purity: 92.7%; Observed Mass: 370.2; Retention Time: 1.02 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.3%; Observed Mass: 370.21; Retention Time: 1.37 min.

Example 253

4-[4-(3,4-dihydro-2H-1-benzopyran-4-yl)piperazin-1-yl]-1,6-dimethyl-2-oxo-1,2-dihydro-1,5-naphthyridine-3-carbonitrile

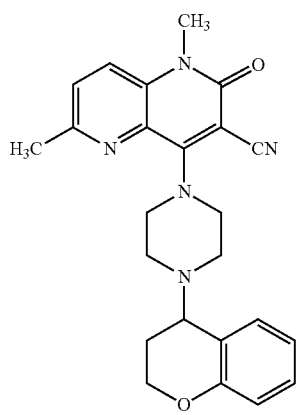

(253)

The title compound was prepared according to the general method used to prepare Example 250. The compound (2.1 mg) was isolated in 10.1% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 416.16; Retention Time: 1.19 mini. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 416.14; Retention Time: 204 min.

Example 254

4-{4-[(4-fluorophenyl)(2-methoxypyridin-3-yl)methyl]piperazin-1-yl}-1,6-dimethyl-2-oxo-1,2-dihydro-1,5-naphthyridine-3-carbonitrile

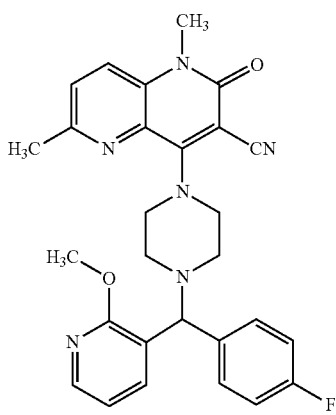

(254)

The title compound was prepared according to the general method used to prepare Example 250. The compound (0.8 mg) was isolated in 3.2% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 mii hold at 100% B; Flow: 1 mL/min; Detection: MS and UV (220 nm). Injection 1 results: Purity: 97.5%; Observed Mass: 499.22; Retention Time: 1.44 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.3%; Observed Mass: 499.19; Retention Time: 2.2 min.

Example 255

4-{4-[(4-fluorophenyl)(3-methoxypyridin-2-yl)methyl]piperazin-1-yl}-1,6-dimethyl-2-oxo-1,2-dihydro-1,5-naphthyridine-3-carbonitrile

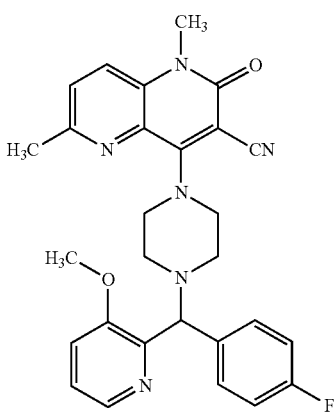

(255)

The title compound was prepared according to the general method used to prepare Example 250. The compound (9.5 mg) was isolated in 19.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.3%; Observed Mass: 499.2; Retention Time: 1.93 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.6%; Observed Mass: 499.2; Retention Time: 1.37 min.

Example 256

4-{4-[(4-fluorophenyl)(pyridin-2-yl)methyl]piperazin-1-yl}-1,6-dimethyl-2-oxo-1,2-dihydro-1,5-naphthyridine-3-carbonitrile

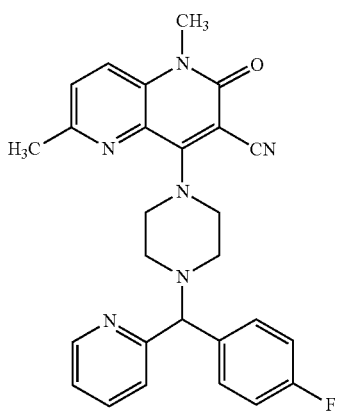

(256)

The title compound was prepared according to the general method used to prepare Example 250. The compound (17.2 mg) was isolated in 36.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.6%; Observed Mass: 469.18; Retention Time: 1.89 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 469.19; Retention Time: 1.33 min.

Example 258

4-{4-[(2-bromo-6-hydroxyphenyl)methyl]piperazin-1-yl}-6-chloro-1-methyl-2-oxo-1,2-dihydro-1,5-naphthyridine-3-carbonitrile

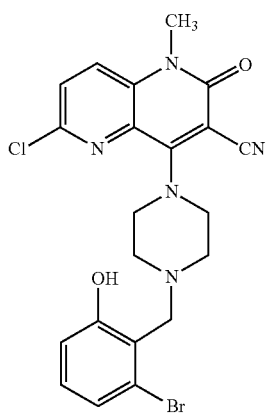

(258)

The title compound was prepared according to the general method used to prepare Example 257. The compound (13 mg) was isolated in 70% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 487.93; Retention Time: 1.19 min. Injection 2 conditions: Column: Waters XBridge C18, 2.1 mm×50 nm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 487.92; Retention Time: 181 min.

Example 259

6-bromo-4-{4-[(2-hydroxy-6-methylphenyl)methyl]piperazin-yl}-1-methyl-2-oxo-1,2-dihydro-1,5-naphthyridine-3-carbonitrile

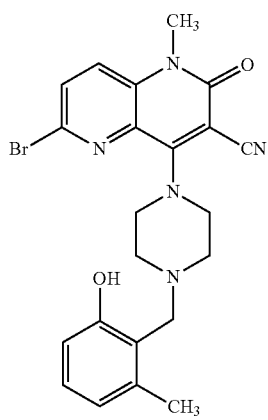

(259)

The title compound was prepared according to the general method used to prepare Example 2. The compound (4.9 mg) was isolated in 20.1% yield. Analytical LC/MS was used to determine the final purity. Injection 1 conditions: Column: Waters XBridge C18, 2.1 mm×50 mm, 1.7 Pin particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 467.99; Retention Time: 1.18 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 467.99; Retention Time: 1.71 min.

Example 260

8-{4-[2-(4-fluorophenyl)propan-2-yl]piperazin-1-yl}-5-methyl-7-nitro-6-oxo-5,6-dihydro-1,5-naphthyridine-2-carbonitrile

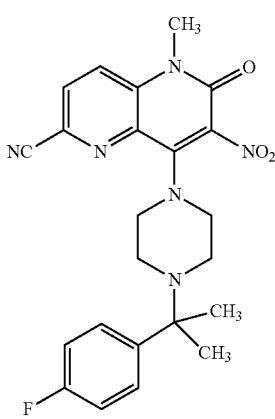
(260)

The title compound was prepared according to the general method used to prepare Example 18 using Intermediate 81. The compound (18.3 mg) was isolated in 71.3% yield. Analytical LC/MS was used to determine the final purity. Injection 1 conditions: Column: Waters XBridge C18, 21 mm×50 mm, 1.7 μm particles; Mobile Phase A: 5:95 acetonitrile:water with 10 mM ammonium acetate; Mobile Phase B: 95:5 acetonitrile:water with 10 nM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.4%; Observed Mass: 451.22; Retention Time: 2.23 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.3%; Observed Mass: 451.21; Retention Time: 1.14 min.

Example 261

4-{4-[(4-tert-butyl-2-hydroxyphenyl)methyl]piperazin-1-yl}-6-chloro-1-methyl-2-oxo-1,2-dihydro-1,5-naphthyridine-3-carbonitrile

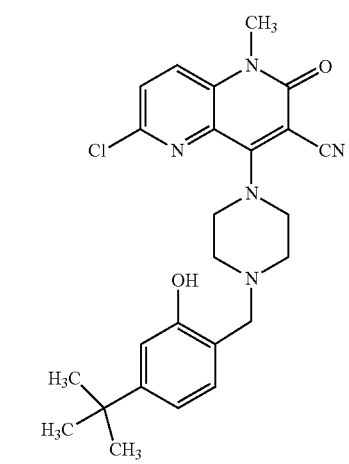
(261)

The title compound was prepared according to the general method used to prepare Example 216. The compound (8.4 mg) was isolated in 47.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 466.15; Retention Time: 1.51 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 466.17; Retention Time: 2.39 min.

Example 262

4-(4-{[2-hydroxy-5-(trifluoromethoxy)phenyl]methyl}piperazin-1-yl)-1,6-dimethyl-2-oxo-1,2-dihydro-1,5-naphthyridine-3-carbonitrile

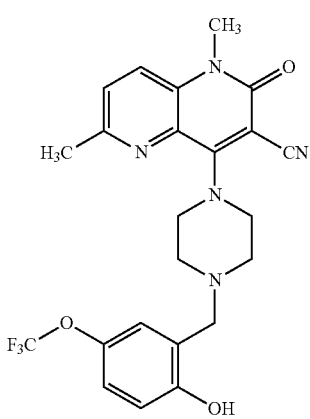
(262)

The title compound was prepared according to the general method used to prepare Example 216 from 1,6-dimethyl-2-oxo-4-(piperazin-1-yl)-1,2-dihydro-1,5-naphthyridine-3-carbonitrile. The compound (9.4 mg) was isolated in 37.5% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 474.14; Retention Time: 2.5 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100%=B over 3 min, then a 0.75 min hold at 100% B; Flow: 1 mL/min; Detection: MS and UV (220 nm). Injection 2 results: Purity: 100.0%; Observed Mass: 474.14; Retention Time: 1.59 min.

Example 263

8-{4-[(4-bromo-2-hydroxyphenyl)methyl]piperazin-1-yl}-5-methyl-6-oxo-5,6-dihydro-1,5-naphthyridine-2,7-dicarbonitrile

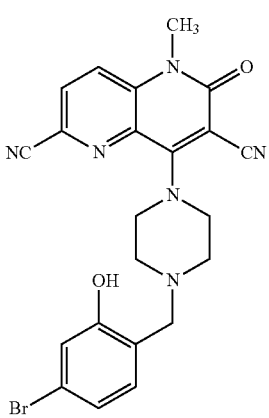
(263)

The title compound was prepared according to the general method used to prepare Example 216 from 5-methyl-6-oxo-8-(piperazin-1-yl)-5,6-dihydro-1,5-napthyridine-2,7-dicarbonitrile, 2 TFA. The compound (6.6 mg) was isolated in 36.2% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 min hold at 100% B; Flow: 1 mL/min; Detection: MS and UV (220 nm). Injection 1 results: Purity: 95.0%; Observed Mass: 478.91; Retention Time: 1.18 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.4%; Observed Mass: 478.94; Retention Time: 1.89 min.

Example 264

6-chloro-4-{4-[(2-hydroxy-6-methoxyphenyl)methyl]piperazin-1-yl}-1-methyl-2-oxo-1,2-dihydro-1,5-naphthyridine-3-carbonitrile

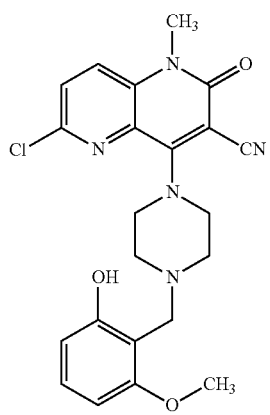

(264)

The title compound was prepared according to the general method used to prepare Example 216. The compound (5.9 ng) was isolated in 35.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 mm hold at 100% B; Flow: 1 mL/min; Detection: MS and UV (220 nm). Injection 1 results: Purity: 100.0%; Observed Mass: 440.12; Retention Time: 1.19 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100 ?% B; Flow: 1 mL/min; Detection: MS and UV (220 nm). Injection 2 results: Purity: 100.0%; Observed Mass: 440.12; Retention Time: 1.88 min.

Example 265

8-(4-{[2-hydroxy-4-(trifluoromethoxy)phenyl]methyl}piperazin-1-yl)-5-methyl-6-oxo-5,6-dihydro-1,5-naphthyridine-2,7-dicarbonitrile

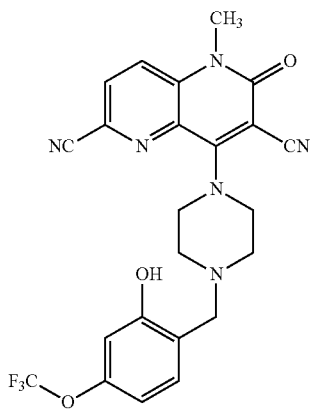

(265)

The title compound was prepared according to the general method used to prepare Example 216 from 5-methyl-6-oxo-8-(piperazin-1-yl)-5,6-dihydro-1,5-napthyridine-2,7-dicarbonitrile, 2 TFA. The compound (5 mg) was isolated in 18.5% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.4%; Observed Mass: 485.01; Retention Time: 1.99 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 485.01; Retention Time: 1.3 min.

Example 266

6-bromo-4-{4-[(4-chloro-2-hydroxyphenyl)methyl]piperazin-1-yl}-1-methyl-2-oxo-1,2-dihydro-1,5-naphthyridine-3-carbonitrile

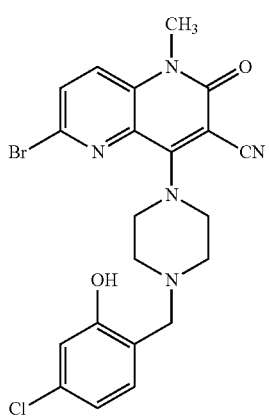

(266)

The title compound was prepared according to the general method used to prepare Example 2. The compound (7.9 mg) was isolated in 37.60% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 487.93; Retention Time: 1.26 min. Injection 2 conditions: Column: Waters XBridge C18, 2.1 mm×50 nm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 487.97; Retention Time: 2.15 min.

Example 267

6-chloro-4-{4-[(2-chloro-6-hydroxyphenyl)methyl]piperazin-1-yl}-1-methyl-2-oxo-1,2-dihydro-1,5-naphthyridine-3-carbonitrile

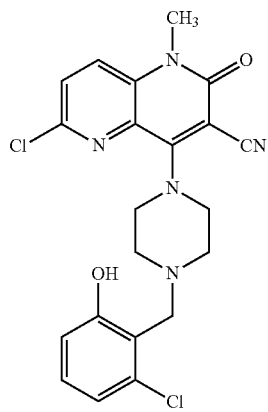

(267)

The title compound was prepared according to the general method used to prepare Example 216. The compound (11.7 mg) was isolated in 69.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 443.96; Retention Time: 1.77 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 443.96; Retention Time: 1.18 min.

Example 268

4-{4-[(3-bromo-2-hydroxyphenyl)methyl]piperazin-1-yl}-6-chloro-1-methyl-2-oxo-1,2-dihydro-1,5-naphthyridine-3-carbonitrile

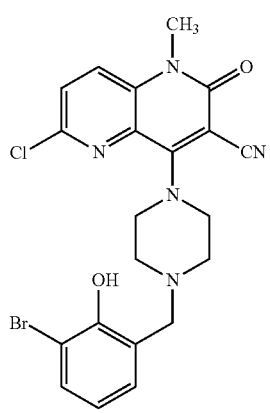

(268)

The title compound was prepared according to the general method used to prepare Example 216. The compound (13.8 mg) was isolated in 74.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.2%; Observed Mass: 488.04; Retention Time: 2.49 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.1%; Observed Mass: 487.98; Retention Time: 1.5 min.

Example 269

8-{4-[(4-chloro-2-hydroxyphenyl)methyl]piperazin-1-yl}-5-methyl-6-oxo-5,6-dihydro-1,5-naphthyridine-2,7-dicarbonitrile

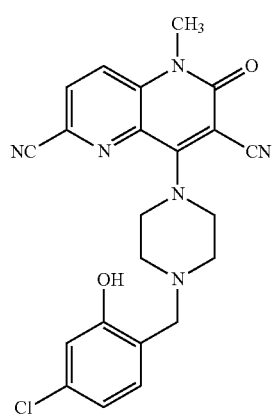

(269)

The title compound was prepared according to the general procedure used to prepare Example 216 from 5-methyl-6-oxo-8-(piperazin-1-yl)-5,6-dihydro-1,5-naphthyridine-2,7-dicarbonitrile, 2 TFA. The compound (6.5 mg) was isolated in 39.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.4%; Observed Mass: 434.97; Retention Time: 1.86 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 min hold at 100% B; Flow: 1 mL/min; Detection: MS and UV (220 nm). Injection 2 results: Purity: 95.9%; Observed Mass: 434.96; Retention Time: 1.15 min.

Example 270

6-bromo-4-(4-{[2-hydroxy-5-(trifluoromethoxy)phenyl]methyl}piperazin-1-yl)-1-methyl-2-oxo-1,2-dihydro-1,5-naphthyridine-3-carbonitrile

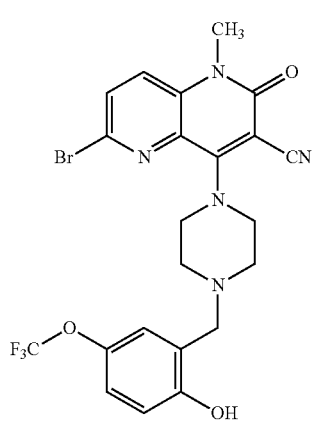

(270)

The title compound was prepared according to the general method used to prepare Example 2. The compound (4.8 mg) was isolated in 20.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.6%; Observed Mass: 538.04; Retention Time: 2.63 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 538.03; Retention Time: 1.67 min.

Example 271

6-bromo-4-{4-[(2-bromo-6-hydroxyphenyl)methyl]piperazin-1-yl}-1-methyl-2-oxo-1,2-dihydro-1,5-naphthyridine-3-carbonitrile

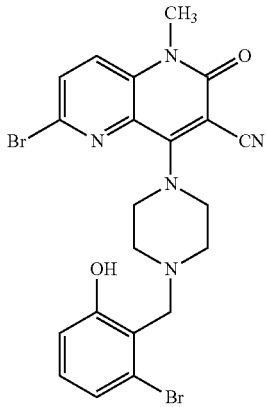

(271)

The title compound was prepared according to the general method used to prepare Example 2. The compound (2.7 mg) was isolated in 14.5% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100° % B over 3 min, then a 0.75 min hold at 100% B; Flow: 1 mL/min; Detection: MS and UV (220 nm). Injection 1 results: Purity: 100.0%; Observed Mass: 531.89; Retention Time: 1.21 min. Injection 2 conditions: Column: Waters XBridge C18, 2.1 mm×50 nm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 531.93; Retention Time: 1.84 min.

Example 272

6-chloro-4-{4-[(2-chlorophenyl)methyl]piperazin-1-yl}-1-methyl-2-oxo-1,2-dihydro-1,5-naphthyridine-3-carbonitrile

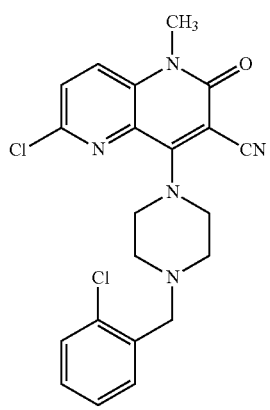
(272)

The title compound was prepared according to the general method used to prepare Example 216. The compound (5.7 mg) was isolated in 47.5% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0% c; Observed Mass: 428.07; Retention Time: 2.19 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 428.05; Retention Time: 1.25 min.

Example 273

6-chloro-4-{4-[(2-hydroxy-4-methylphenyl)methyl]piperazin-1-yl}-1-methyl-2-oxo-1,2-dihydro-1,5-naphthyridine-3-carbonitrile

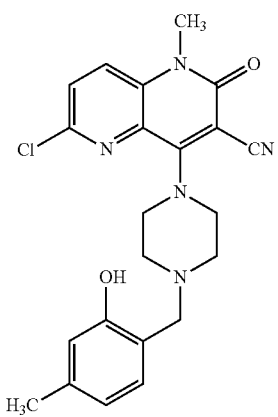
(273)

The title compound was prepared according to the general method used to prepare Example 216. The compound (8.1 mg) was isolated in 68.2% yield. Analytical LC/MS was used to determine the final purity. Injection 1 conditions: Column: Waters XBridge C18, 2.1 m×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 424; Retention Time: 1.71 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0% a; Observed Mass: 423.99; Retention Time: 1.16 min.

Example 274

6-chloro-4-{4-[(3-fluoro-2-methoxyphenyl)methyl]piperazin-1-yl}-1-methyl-2-oxo-1,2-dihydro-1,5-naphthyridine-3-carbonitrile

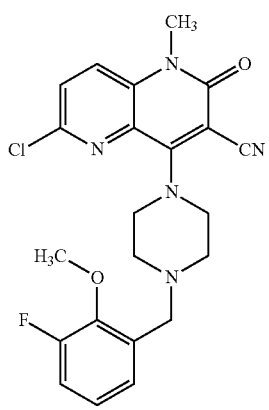

(274)

The title compound was prepared according to the general method used to prepare Example 216. The compound (9.7 mg) was isolated in 41.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 mi hold at 100% B; Flow: 1 mL/min; Detection: MS and UV (220 nm). Injection 1 results: Purity: 100.0%; Observed Mass: 442.12; Retention Time: 1.29 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 442.12; Retention Time: 204 min.

Example 275

4-{4-[(5-bromo-2-hydroxyphenyl)methyl]piperazin-1-yl}-6-chloro-1-methyl-2-oxo-1,2-dihydro-1,5-naphthyridine-3-carbonitrile

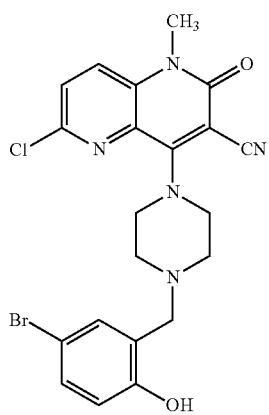

(275)

The title compound was prepared according to the general method used to prepare Example 216. The compound (14.7 ng) was isolated in 79.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 488.02; Retention Time: 1.52 mini. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.3%; Observed Mass: 487.99; Retention Time: 2.51 min.

Example 276

4-{4-[(4-bromo-2-hydroxyphenyl)methyl]piperazin-1-yl}-6-chloro-1-methyl-2-oxo-1,2-dihydro-1,5-naphthyridine-3-carbonitrile

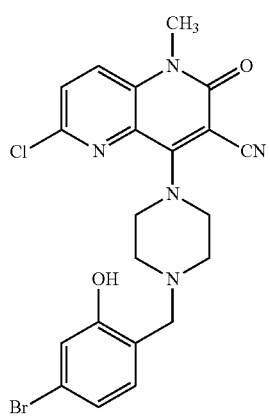

(276)

The title compound was prepared according to the general method used to prepare Example 216. The compound (6.3 mg) was isolated in 46% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 488; Retention Time: 1.28 min. Injection 2 conditions: Column: Waters XBridge C18, 2.1 mm×50 mm, 1.7 μm particles; Mobile Phase A: 5:95 acetonitrile:water with 10 mM ammonium acetate Mobile Phase B: 95:5 acetonitrile:water with 10 mM ammonium acetate; Temperature: 50° C.; Gradient: 0% B to 100% B over 3 min, then a 0.75 mini hold at 100% B; Flow: 1 mL/min; Detection: MS and UV (220 nm). Injection 2 results: Purity: 100.0%; Observed Mass: 488.02; Retention Time: 2.17 min.

Example 277

4-{4-[(5-bromo-2-hydroxyphenyl)methyl]piperazin-1-yl}-1,6-dimethyl-2-oxo-1,2-dihydro-1,5-naphthyridine-3-carbonitrile

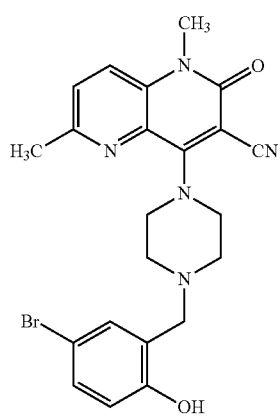

(277)

The title compound was prepared according to the general method used to prepare Example 216 from 1,6-dimethyl-2-oxo-4-(piperazin-1-v)-1,2-dihydro-1,5-naphthyridine-3-carbonitrile. The compound (14.4 mg) was isolated in 78.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 468; Retention Time: 1.2 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 468.02; Retention Time: 2.01 min.

Example 278

6-bromo-4-{4-[(3-chloro-2-hydroxyphenyl)methyl]piperazin-1-yl}-1-methyl-2-oxo-1,2-dihydro-1,5-naphthyridine-3-carbonitrile

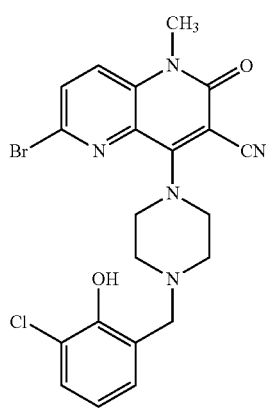

(278)

The title compound was prepared according to the general method used to prepare Example 2. The compound (5.6 ng) was isolated in 26.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 488.05; Retention Time: 2.48 min. Injection 3 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 mi, then a 0.75 min hold at 100% B; Flow: 1 mL/min; Detection: MS and UV (220 nm). Injection 3 results: Purity: 99.3%; Observed Mass: 488.01; Retention Time: 1.48 min.

Example 279

6-chloro-4-{4-[(3-fluoro-4-methoxyphenyl)methyl]piperazin-1-yl}-1-methyl-2-oxo-1,2-dihydro-1,5-naphthyridine-3-carbonitrile

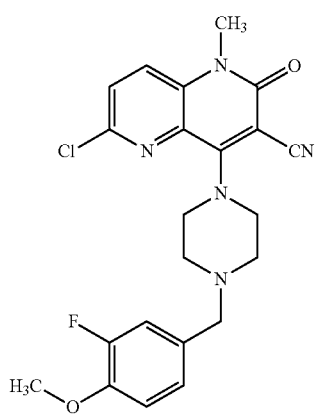

(279)

The title compound was prepared according to the general method used to prepare Example 216. The compound (6 mg) was isolated in 35.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100'% B; Flow: 1 mL/min; Detection: MIS and UV (220 nm). Injection 1 results: Purity: 100.0%; Observed Mass: 442.09; Retention Time: 1.91 min. Injection 2 conditions: Column. Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 442.13; Retention Time: 1.22 min.

Example 280

6-chloro-4-{4-[(2-fluoro-6-hydroxyphenyl)methyl]piperazin-1-yl}-1-methyl-2-oxo-1,2-dihydro-1,5-naphthyridine-3-carbonitrile

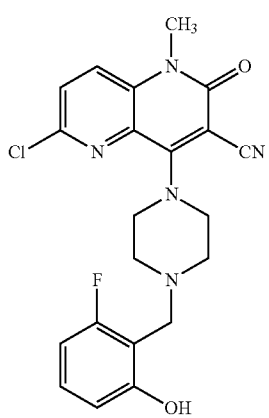

(280)

The title compound was prepared according to the general method used to prepare Example 216. The compound (6.2 ng) was isolated in 38.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 mm hold at 100% B; Flow: 1 mL/min; Detection: MS and UV (220 nm). Injection 1 results: Purity: 100.0%; Observed Mass: 428.01; Retention Time: 1.11 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100 ?% B; Flow: 1 mL/min; Detection: MS and UV (220 nm). Injection 2 results: Purity: 100.0%; Observed Mass: 428.01; Retention Time: 1.86 min.

Example 281

6-chloro-4-{4-[(2-fluoro-3-methylphenyl)methyl]piperazin-1-yl}-1-methyl-2-oxo-1,2-dihydro-1,5-naphthyridine-3-carbonitrile

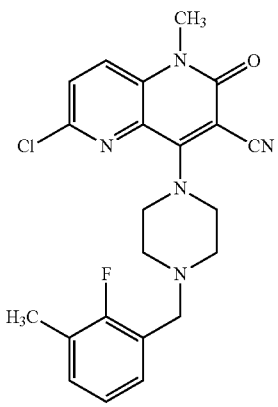

(281)

The title compound was prepared according to the general method used to prepare Example 216. The compound (10.8 mg) was isolated in 47.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0% c; Observed Mass: 425.97; Retention Time: 1.25 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 425.97; Retention Time: 2.02 min.

Example 282

6-bromo-4-{4-[(5-bromo-2-hydroxyphenyl)methyl]piperazin-1-yl}-1-methyl-2-oxo-1,2-dihydro-1,5-naphthyridine-3-carbonitrile

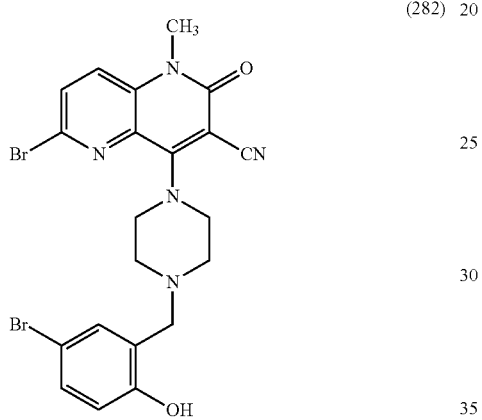

(282)

The title compound was prepared according to the general method used to prepare Example 2. The compound (7.4 mg) was isolated in 32.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 531.96; Retention Time: 2.6 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 531.98; Retention Time: 1.55 min.

Example 283

6-chloro-4-{4-[(2-hydroxy-5-methylphenyl)methyl]piperazin-1-yl}-1-methyl-2-oxo-1,2-dihydro-1,5-naphthyridine-3-carbonitrile

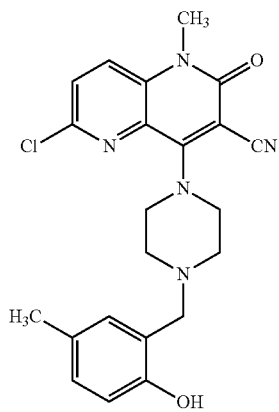

(283)

The title compound was prepared according to the general method used to prepare Example 216. The compound (7.5 mg) was isolated in 46.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 424.11; Retention Time: 2.03 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 424.11; Retention Time: 1.21 min.

Example 284 tert-butyl N-(2-{[4-(6-bromo-3-cyano-1-methyl-2-oxo-1,2-dihydro-1,5-naphthyridin-4-yl)piperazin-1-yl]methyl}phenyl)carbamate

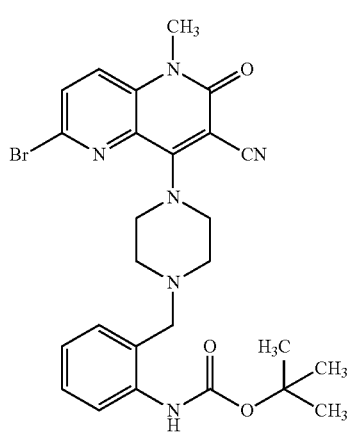

(284)

The title compound was prepared according to the general method used to prepare Example 2. The compound (8.1 mg) was isolated in 34% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity 100.0%; Observed Mass: 553.06; Retention Time: 2.48 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 553.07; Retention Time: 1.43 min.

Example 285

6-chloro-1-methyl-2-oxo-4-(4-{[2-(trifluoromethoxy)phenyl]methyl}piperazin-1-yl)-1,2-dihydro-1,5-naphthyridine-3-carbonitrile

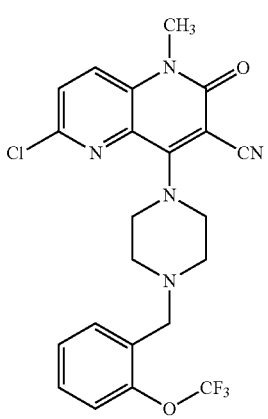

(285)

The title compound was prepared according to the general method used to prepare Example 216. The compound (9.8 ng) was isolated in 38.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 478.13; Retention Time: 2.28 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 478.12; Retention Time: 1.4 min.

Example 286

4-{4-[(3-bromo-2-hydroxyphenyl)methyl]piperazin-1-yl}-1,6-dimethyl-2-oxo-1,2-dihydro-1,5-naphthyridine-3-carbonitrile

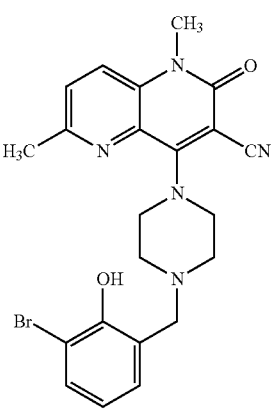
(286)

The title compound was prepared according to the general method used to prepare Example 216 from 1,6-dimethyl-2-oxo-4-(piperazin-1-yl)-1,2-dihydro-1,5-naphthyridine-3-carbonitrile. The compound (4.3 mg) was isolated in 23.5% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 468.01; Retention Time: 1.97 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 467.99; Retention Time: 1.16 min.

Example 287

6-chloro-4-{4-[(2-chloro-4-fluorophenyl)methyl]piperazin-1-yl}-1-methyl-2-oxo-1,2-dihydro-1,5-naphthyridine-3-carbonitrile

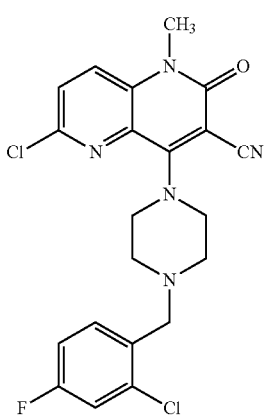
(287)

The title compound was prepared according to the general method used to prepare Example 216. The compound (9.6 ng) was isolated in 40.6% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% % B over 3 min, then a 0.75 min hold at 100% B; Flow: 1 mL/min; Detection: MS and UV (220 nm). Injection 1 results: Purity: 100.0%; Observed Mass: 445.92; Retention Time: 1.26 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 445.91; Retention Time: 2.17 min.

Example 288

6-chloro-4-{4-[(4-chloro-2-hydroxyphenyl)methyl]piperazin-1-yl}-methyl-2-oxo-1,2-dihydro-1,5-naphthyridine-3-carbonitrile

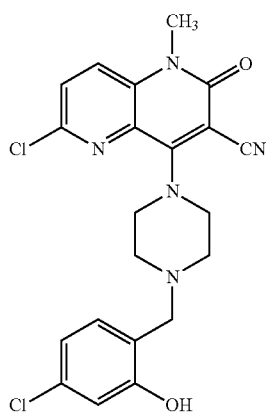

(288)

The title compound was prepared according to the general method used to prepare Example 216. The compound (9.6 mg) was isolated in 77.2% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 443.96; Retention Time: 1.78 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 443.95; Retention Time: 1.18 min.

Example 289

6-chloro-4-{4-[(3-fluoro-4-methylphenyl)methyl]piperazin-1-yl}-1-methyl-2-oxo-1,2-dihydro-1,5-naphthyridine-3-carbonitrile

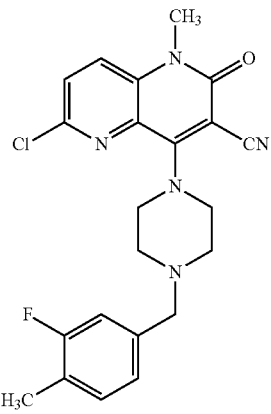

(289)

The title compound was prepared according to the general method used to prepare Example 216. The compound (5.3 mg) was isolated in 23.5% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.9%; Observed Mass: 426.11; Retention Time: 2.15 min. Injection 2 conditions: Column: Waters XBridge C18, 2.1 mm×50 mm, 1.7 µm particles; Mobile Phase A: 5:95 acetonitrile:water with 0.1% r trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.2%; Observed Mass: 426.08; Retention Time: 1.32 min.

Example 290

6-chloro-4-{4-[(3-fluoro-5-methylphenyl)methyl]piperazin-1-yl}-1-methyl-2-oxo-1,2-dihydro-1,5-naphthyridine-3-carbonitrile

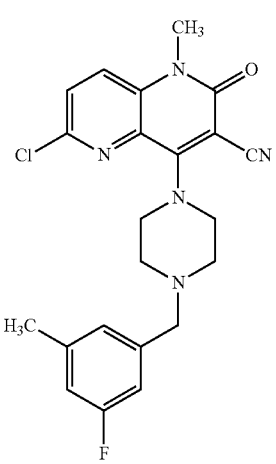

(290)

The title compound was prepared according to the general method used to prepare Example 216. The compound (4.5 mg) was isolated in 37.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 426; Retention Time: 1.28 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 nL/mm; Detection: MS and UV (220 nm). Injection 2 results: Purity: 100.0%; Observed Mass: 426; Retention Time: 2.09 min.

Example 291

6-chloro-4-{4-[(3,5-difluorophenyl)methyl]piperazin-1-yl}-1-methyl-2-oxo-1,2-dihydro-1,5-naphthyridine-3-carbonitrile

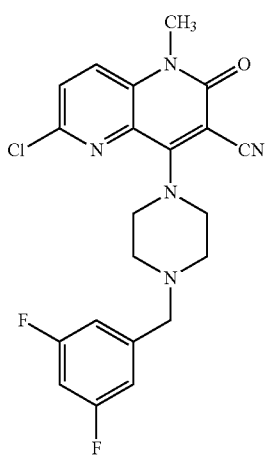

(291)

The title compound was prepared according to the general method used to prepare Example 216. The compound (7.3 mg) was isolated in 44.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 430.11; Retention Time: 1.26 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 nL/mm; Detection: MS and UV (220 nm). Injection 2 results: Purity: 100.0%; Observed Mass: 430.07; Retention Time: 2.11 min.

Example 292

6-chloro-4-{4-[(2-hydroxy-6-methylphenyl)methyl]piperazin-1-yl}-1-methyl-2-oxo-1,2-dihydro-1,5-naphthyridine-3-carbonitrile

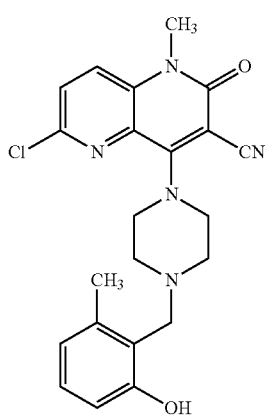

(292)

The title compound was prepared according to the general method used to prepare Example 216. The compound (11.2 mg) was isolated in 45.2% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0° % B to 100% B over 3 min, then a 0.75 min hold at 100% B; Flow: 1 mL/min; Detection: MS and UV (220 nm). Injection 1 results: Purity: 100.0%; Observed Mass: 424.02; Retention Time: 1.16 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.7%; Observed Mass: 424.01; Retention Time: 1.69 min.

Example 293

6-chloro-4-{4-[(3-chloro-2-hydroxyphenyl)methyl]piperazin-1-yl}-1-methyl-2-oxo-1,2-dihydro-1,5-naphthyridine-3-carbonitrile

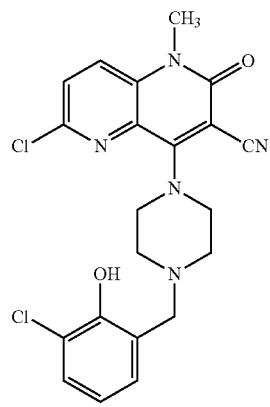

(293)

The title compound was prepared according to the general method used to prepare Example 216. The compound (12.9 mg) was isolated in 76.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 444.09; Retention Time: 1.42 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 444.08; Retention Time: 2.46 min.

Example 294

6-bromo-4-{4-[(2-fluoro-6-hydroxyphenyl)methyl]piperazin-1-yl}-1-methyl-2-oxo-1,2-dihydro-1,5-naphthyridine-3-carbonitrile

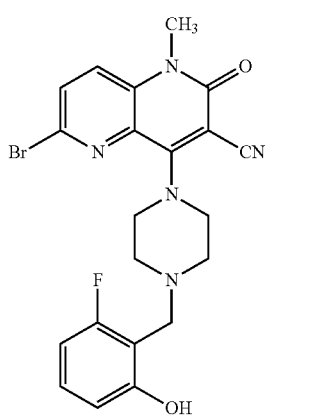

(294)

The title compound was prepared according to the general method used to prepare Example 2. The compound (10.5 mg) was isolated in 63.5% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 mm hold at 100% B; Flow: 1 mL/min; Detection: MS and UV (220 am). Injection 1 results: Purity: 100.0%; Observed Mass: 471.93; Retention Time: 1.13 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 471.92; Retention Time: 1.9 min.

Example 295

6-bromo-4-{4-[(2-hydroxy-4-methoxyphenyl)methyl]piperazin-1-yl}-1-methy-2-oxo-1,2-dihydro-1,5-naphthyridine-3-carbonitrile

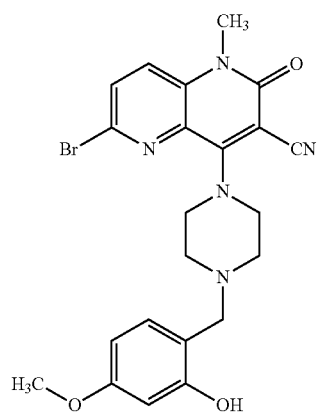

(295)

The title compound was prepared according to the general method used to prepare Example 2. The compound (12.5 mg) was isolated in 60% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 mm, then a 0.75 min hold at 100% B; Flow: 1 mL/min; Detection: MS and UV (220 nm). Injection 1 results: Purity: 98.3%; Observed Mass: 483.97; Retention Time: 1.81 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.1%; Observed Mass: 483.96; Retention Time: 1.14 min.

Example 296

4-{4-[(5-chloro-2-hydroxyphenyl)methyl]piperazin-1-yl}-1,6-dimethyl-2-oxo-1,2-dihydro-1,5-naphthyridine-3-carbonitrile

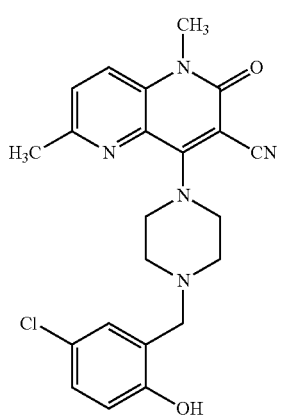

(296)

The title compound was prepared according to the general method used to prepare Example 216 from 1,6-dimethyl-2-oxo-4-(piperazin-1-yl)-1,2-dihydro-1,5-naphthyridine-3-carbonitrile. The compound (10.5 mg) was isolated in 46.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 424.09; Retention Time: 2.4 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100%=B over 3 min, then a 0.75 min hold at 100% B; Flow: 1 mL/min; Detection: MS and UV (220 nm). Injection 2 results: Purity: 100.0%; Observed Mass: 424.11; Retention Time: 1.43 min.

Example 297

6-bromo-4-{4-[4(2-methoxyphenyl)methyl]piperazin-1-yl}-1-methyl-2-oxo-1,2-dihydro-1,5-naphthyridine-3-carbonitrile

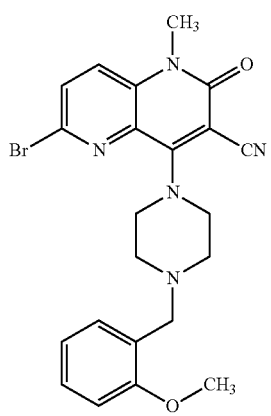

(297)

The title compound was prepared according to the general method used to prepare Example 2. The compound (5.2 mg) was isolated in 31.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100° % B over 3 min, then a 0.75 min hold at 100% B; Flow: 1 mL/min; Detection: MS and UV (220 nm). Injection 1 results: Purity: 95.8%; Observed Mass: 468; Retention Time: 1.22 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.2%; Observed Mass: 468; Retention Time: 1.8 min.

Example 298

6-chloro-4-{4-[(3,5-difluoro-2-hydroxyphenyl)methyl]piperazin-1-yl}-1-methyl-2-oxo-1,2-dihydro-1,5-naphthyridine-3-carbonitrile

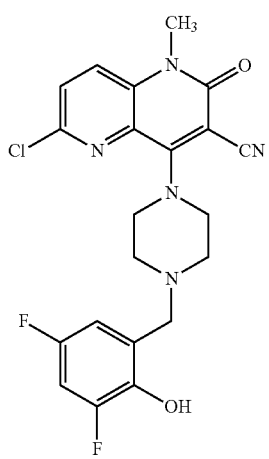

(298)

The title compound was prepared according to the general method used to prepare Example 216. The compound (11.6 mg) was isolated in 68.5% yield. Analytical LC/MS was used to determine the final purity. Injection 1 conditions: Column: Waters XBridge CIS, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0% B to 100% B over 3 min, then a 0.75 min hold at 100% B; Flow: 1 mL/min; Detection: MS and UV (220 nm). Injection 1 results: Purity: 96.6%; Observed Mass: 446.07; Retention Time: 2.32 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.9%; Observed Mass: 446.1; Retention Time: 1.4 min.

Example 299

6-bromo-4-{4-[(2,3-dihydro-1H-indol-7-yl)methyl]piperazin-1-yl}-1-methyl-2-oxo-1,2-dihydro-1,5-naphthyridine-3-carbonitrile

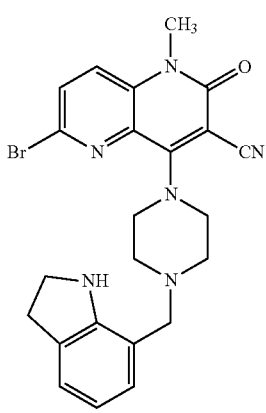

(299)

The title compound was prepared according to the general method used to prepare Example 2. The compound (5.4 mg) was isolated in 26.2%4 yield. Analytical LC/IS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 478.98; Retention Time: 1.19 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 478.99; Retention Time: 1.94 min.

Example 300

6-bromo-4-{4-[(2-chlorophenyl)methyl]piperazin-1-yl}-1-methyl-2-oxo-1,2-dihydro-1,5-naphthyridine-3-carbonitrile

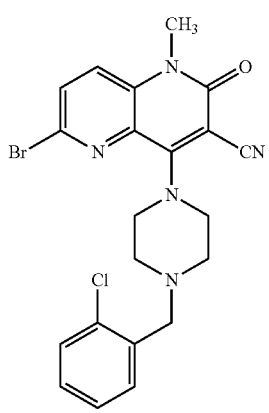

(300)

The title compound was prepared according to the general method used to prepare Example 2. The compound (7.3 mg) was isolated in 44.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 472; Retention Time: 2.23 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 471.99; Retention Time: 1.3 min.

Example 301

6-chloro-4-{4-[(2-hydroxy-4-methoxyphenyl)methyl]piperazin-1-yl}-1-methyl-2-oxo-1,2-dihydro-1,5-naphthyridine-3-carbonitrile

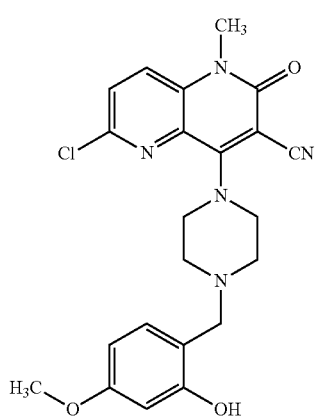

(301)

The title compound was prepared according to the general method used to prepare Example 216. The compound (6.9 mg) was isolated in 56% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 440.01; Retention Time: 1.58 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 439.98; Retention Time: 1.13 min.

Example 302

6-chloro-4-{4-[(3-chlorophenyl)methyl]piperazin-1-yl}-1-methyl-2-oxo-1,2-dihydro-1,5-naphthyridine-3-carbonitrile

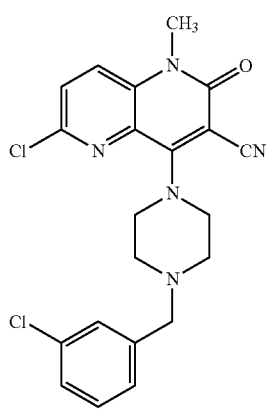

(302)

The title compound was prepared according to the general method used to prepare Example 216. The compound (14.3 mg) was isolated in 69.6% yield. Analytical LC/MS was used to determine the final purity. Injection 1 conditions: Column: Waters XBridge C18, 2.1 mm×50 mm, 1.7 μmm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (22) nm). Injection 1 results: Purity: 100.0%; Observed Mass: 428.05; Retention Time: 1.3 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 428.07; Retention Time: 2.17 min.

Example 303

6-chloro-4-{4-[_(1H-indol-7-yl)methyl]piperazin-1-yl}-1-methyl-2-oxo-1,2-dihydro-1,5-naphthyridine-3-carbonitrile

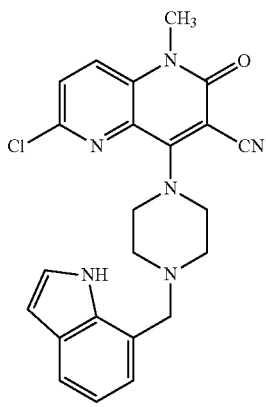

(303)

The title compound was prepared according to the general method used to prepare Example 216. The compound (6.3 mg) was isolated in 38.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: NIS and UV (220 nm). Injection 1 results: Purity: 100.0%; Observed Mass: 433.02; Retention Time: 2.03 min. Injection 3 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 3 results: Purity: 100.0%; Observed Mass: 432.99; Retention Time: 1.25 min.

Example 304

6-bromo-4-{4-[(3-fluoro-2-hydroxyphenyl)methyl]piperazin-1-yl}-1-methyl-2-oxo-1,2-dihydro-1,5-naphthyridine-3-carbonitrile

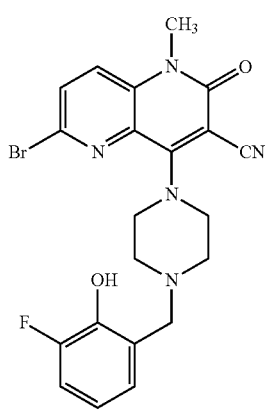

(304)

The title compound was prepared according to the general method used to prepare Example 2. The compound (6.6 mg) was isolated in 32.5% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.2%; Observed Mass: 472.04; Retention Time: 2.33 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° ° C.; Gradient: 0% B to 100% B over 3 mi, then a 0.75 min hold at 100% B; Flow: 1 mL/min; Detection: MS and UV (220 nm). Injection 2 results: Purity: 100.0%; Observed Mass: 472.06; Retention Time: 1.37 min.

Example 305

6-chloro-4-{4-[(2-hydroxy-5-methoxyphenyl)methyl]piperazin-1-yl}-1-methyl-2-oxo-1,2-dihydro-1,5-naphthyridine-3-carbonitrile

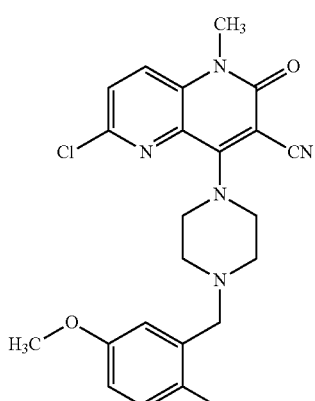

(305)

The title compound was prepared according to the general method used to prepare Example 216. The compound (8.7 mg) was isolated in 52% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 440.13; Retention Time: 1.13 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100 ?% B; Flow: 1 mL/min; Detection: MS and UV (220 nm). Injection 2 results: Purity: 100.0%; Observed Mass: 440.12; Retention Time: 1.8 min.

Example 306

6-chloro-4-{4-[(3-fluoro-2-hydroxyphenyl)methyl]piperazin-1-yl}-1-methyl-2-oxo-1,2-dihydro-1,5-naphthyridine-3-carbonitrile

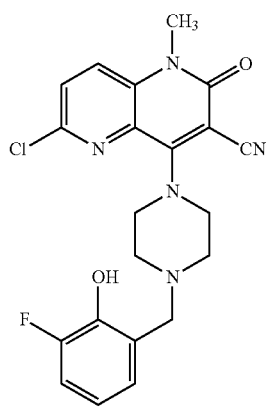

(306)

The title compound was prepared according to the general method used to prepare Example 216. The compound (11.6 mg) was isolated in 71.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 428.09; Retention Time: 1.32 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 428.1; Retention Time: 2.28 min.

Example 307

6-chloro-4-{4-[(3,5-dichloro-2-hydroxyphenyl)methyl]piperazin-1-yl}-1-methyl-2-oxo-1,2-dihydro-1,5-naphthyridine-3-carbonitrile

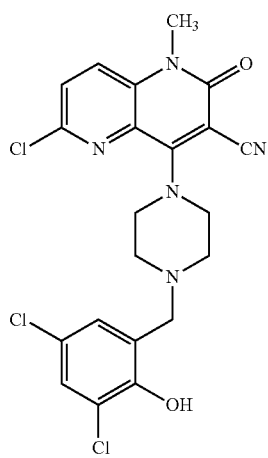

(307)

The title compound was prepared according to the general method used to prepare Example 216. The compound (7.9 mg) was isolated in 43.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 mi, then a 0.75 min hold at 100% B; Flow: 1 mL/min; Detection: MS and UV (220 nm). Injection 1 results: Purity: 100.0%; Observed Mass: 478.02; Retention Time: 1.65 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min then a 0.75 min hold at 100% B; Flow: 1 mL/min; Detection: MS and UV (220 nm). Injection 2 results: Purity: 100.0%; Observed Mass: 478.03; Retention Time: 2.66 min.

Example 308

6-chloro-4-{4-[(4-fluorophenyl)methyl]piperazin-1-yl}-1-methyl-2-oxo-1,2-dihydro-1,5-naphthyridine-3-carbonitrile

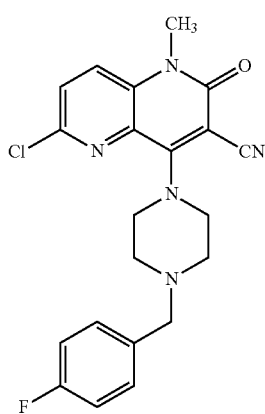

(308)

The title compound was prepared according to the general method used to prepare Example 216. The compound (12.2 mg) was isolated in 61.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 412.1; Retention Time: 1.97 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 91.9%; Observed Mass: 412.07; Retention Time: 1.21 min.

Example 309

6-bromo-4-{4-[(3-tert-butyl-2-hydroxyphenyl)methyl]piperazin-1-yl}-1-methyl-2-oxo-1,2-dihydro-1,5-naphthyridine-3-carbonitrile

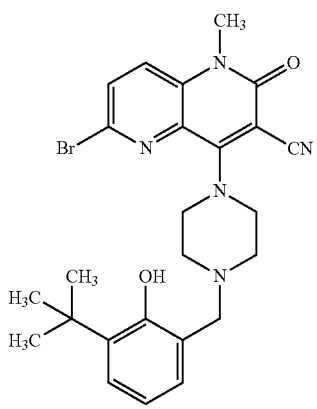

(309)

The title compound was prepared according to the general method used to prepare Example 2. The compound (3.6 mg) was isolated in 16.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/mi; Detection: MS and UV (220 nm). Injection 1 results: Purity: 100.0%; Observed Mass: 510.09; Retention Time: 3.04 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 mi, then a 0.75 min hold at 100% B; Flow: 1 mL/min; Detection: MS and UV (220 nm). Injection 2 results: Purity: 100.0%; Observed Mass: 510.12; Retention Time: 1.96 min.

Example 310

6-chloro-4-{4-[(2,4-dichlorophenyl)methyl]piper-azin-1-yl}-1-methyl-2-oxo-1,2-dihydro-1,5-naphthy-ridine-3-carbonitrile

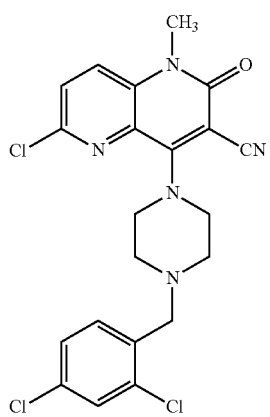

(310)

The title compound was prepared according to the general method used to prepare Example 216. The compound (3.1 ng) was isolated in 12.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 462.03; Retention Time: 2.46 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 462.07; Retention Time: 1.43 min.

Example 311

6-chloro-4-(4-{[2-hydroxy-4-(trifluoromethyl)phe-nyl]methyl}piperazin-1-yl)-1-methyl-2-oxo-1,2-dihydro-1,5-naphthyridine-3-carbonitrile

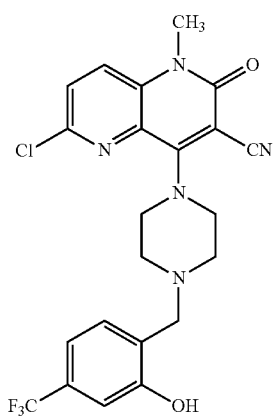

(311)

The title compound was prepared according to the general method used to prepare Example 216. The compound (4.8 mg) was isolated in 26.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 min). Injection 1 results: Purity: 100.0%; Observed Mass: 478.07; Retention Time: 2.18 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 478.11; Retention Time: 1.34 min.

Example 312

6-chloro-4-{4-[(5-fluoro-2-hydroxyphenyl)methyl]piperazin-1-yl}-1-methyl-2-oxo-1,2-dihydro-1,5-naphthyridine-3-carbonitrile

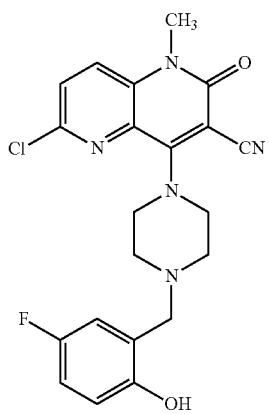

(312)

Example 313

6-chloro-4-(4-{[3-fluoro-5-(trifluoromethyl)phenyl]methyl}piperazin-1-yl)-1-methyl-2-oxo-1,2-dihydro-1,5-naphthyridine-3-carbonitrile

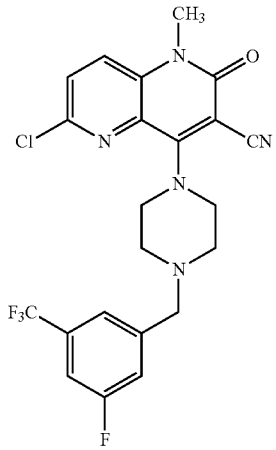

(313)

The title compound was prepared according to the general method used to prepare Example 216. The compound (8.6 mg) was isolated in 52.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 428.12; Retention Time: 1.92 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 428.1; Retention Time: 1.14 min.

The title compound was prepared according to the general method used to prepare Example 216. The compound (7.4 mg) was isolated in 40.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 480.09; Retention Time: 1.44 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 min). Injection 2 results: Purity: 100.0%; Observed Mass: 480.09; Retention Time: 2.3 min.

Example 314

6-bromo-4-{4-[(2-hydroxy-6-methoxyphenyl)methyl]piperazin-1-yl}-1-methyl-2-oxo-1,2-dihydro-1,5-naphthyridine-3-carbonitrile

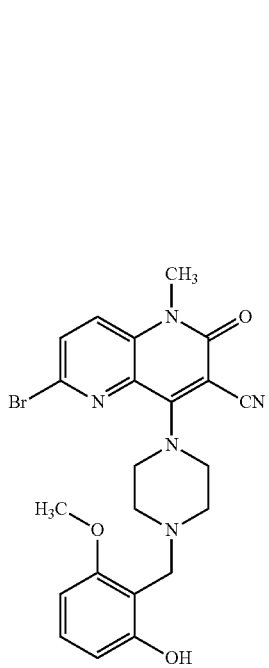

(314)

The title compound was prepared according to the general method used to prepare Example 2. The compound (7.4 mg) was isolated in 43.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 483.98; Retention Time: 1.17 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 483.98; Retention Time: 1.79 min.

Examples 315 and 316

6-chloro-4-{4-[1-(4-fluorophenyl)-2-methylpropyl]piperazin-1-yl}-methyl-2-oxo-1,2-dihydro-1,5-naphthyridine-3-carbonitrile

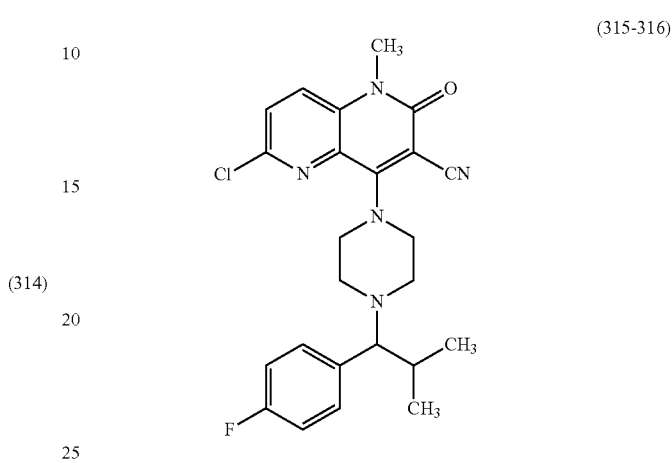

(315-316)

The title compound was prepared according to the general method used to prepare Example 193. The racemic compound (17.5 mg) was isolated in 55.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient 0% B to 100% B over 3 min, then a 0.75 min hold at 100% B; Flow: 1 mL/min; Detection: MS and UV (220 nm). Injection 1 results: Purity: 100.0%; Observed Mass: 454.17; Retention Time: 2.46 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 454.14; Retention Time: 1.39 min. The racemic mixture was separated into Example 315 (Isomer 1) and Example 316 (Isomer 2).

Example 315 (4.3 mg) was isolated in 27.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 454.42; Retention Time: 2.61 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 mi hold at 100% B; Flow: 1 mL/min; Detection: MS and UV (220 nm). Injection 2 results: Purity: 100.0%; Observed Mass: 454.15; Retention Time: 1.34 min.

Example 316 (4.2 mg) was isolated in 26.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 mi, then a 0.75 min hold at 100% B; Flow: 1 mL/min; Detection: MS and UV (220 nm). Injection 1 results: Purity: 100.0%; Observed Mass: 454.1; Retention Time: 2.62 min. Injection 2 conditions: Column: Waters XBridge C18, 2.1 mm×50 am, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.4%; Observed Mass: 454.26; Retention Time: 1.35 min.

Example 317

8-{4-[(2-hydroxyphenyl)methyl]piperazin-1-yl}-5-methyl-6-oxo-5,6-dihydro-1,5-naphthyridine-2,7-dicarbonitrile

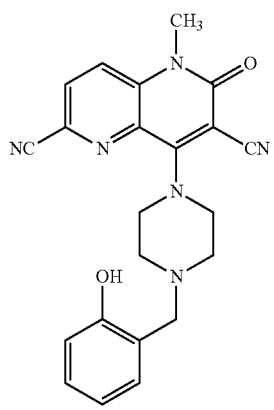

(317)

The title compound was prepared according to the general method used to prepare Example 216 from 5-methyl-6-oxo-8-(piperazin-1-vi)-5,6-dihydro-1,5-naphthyridine-2,7-dicarbonitrile, 2 TFA. The compound (6 mg) was isolated in 39.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0% B to 100% B over 3 mm, then a 0.75 min hold at 100% B; Flow: 1 mL/min; Detection: MS and UV (220 nm). Injection 1 results: Purity: 99.1%; Observed Mass: 400.98; Retention Time: 1.02 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.8%; Observed Mass: 400.99; Retention Time: 1.62 min.

Example 318

6-chloro-4-{4-[(2,5-difluorophenyl)methyl]piperazin-1-yl}-1-methyl-2-oxo-1,2-dihydro-1,5-naphthyridine-3-carbonitrile

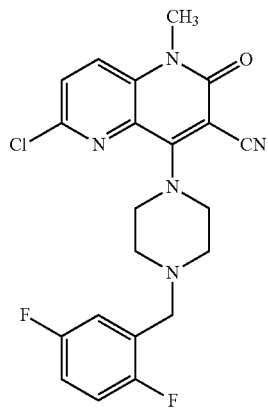

(318)

The title compound was prepared according to the general method used to prepare Example 216. The compound (13.2 mg) was isolated in 64% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 430.05; Retention Time: 2 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C. Gradient: 0% B to 100% B over 3 min, then a 0.75 min hold at 100% B; Flow: 1 mL/min; Detection: MS and UV (220 nm). Injection 2 results: Purity: 100.0%; Observed Mass: 430.08; Retention Time: 1.2 min.

Example 319

6-chloro-4-{4-[(3,4-difluorophenyl)methyl]piperazin-1-yl}-1-methyl-2-oxo-1,2-dihydro-1,5-naphthyridine-3-carbonitrile

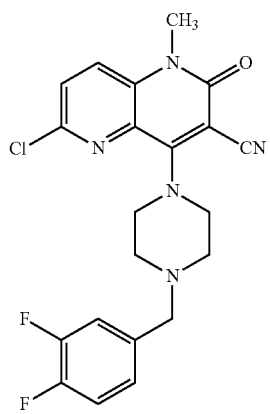

(319)

The title compound was prepared according to the general method used to prepare Example 216. The compound (3.9 mg) was isolated in 32.4% yield. Analytical LC/IS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 430.07; Retention Time: 1.25 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 430.09; Retention Time: 2.07 min.

Example 320

6-bromo-4-{4-[(3,5-difluoro-2-hydroxyphenyl)methyl]piperazin-1-yl}-1-methyl-2-oxo-1,2-dihydro-1,5-naphthyridine-3-carbonitrile

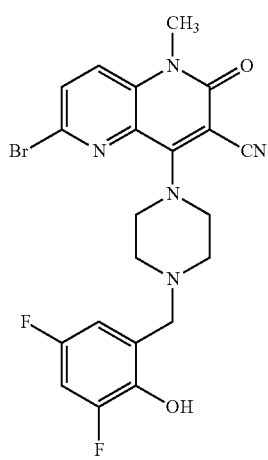

(320)

The title compound was prepared according to the general method used to prepare Example 2. The compound (9.8 mg) was isolated in 46.5% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.9%; Observed Mass: 490.02; Retention Time: 2.39 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C. Gradient: 0% B to 100% B over 3 min, then a 0.75 min hold at 100% B; Flow: 1 mL/min; Detection: MS and UV (220 nm). Injection 2 results: Purity: 98.9%; Observed Mass: 489.98; Retention Time: 1.42 min.

Example 321

6-chloro-4-{4-[(3-fluorophenyl)methyl]piperazin-1-yl}-1-methyl-2-oxo-1,2-dihydro-1,5-naphthyridine-3-carbonitrile

Example 322

6-chloro-4-{4-[(1H-indazol-7-yl)methyl]piperazin-1-yl}-1-methyl-2-oxo-1,2-dihydro-1,5-naphthyridine-3-carbonitrile

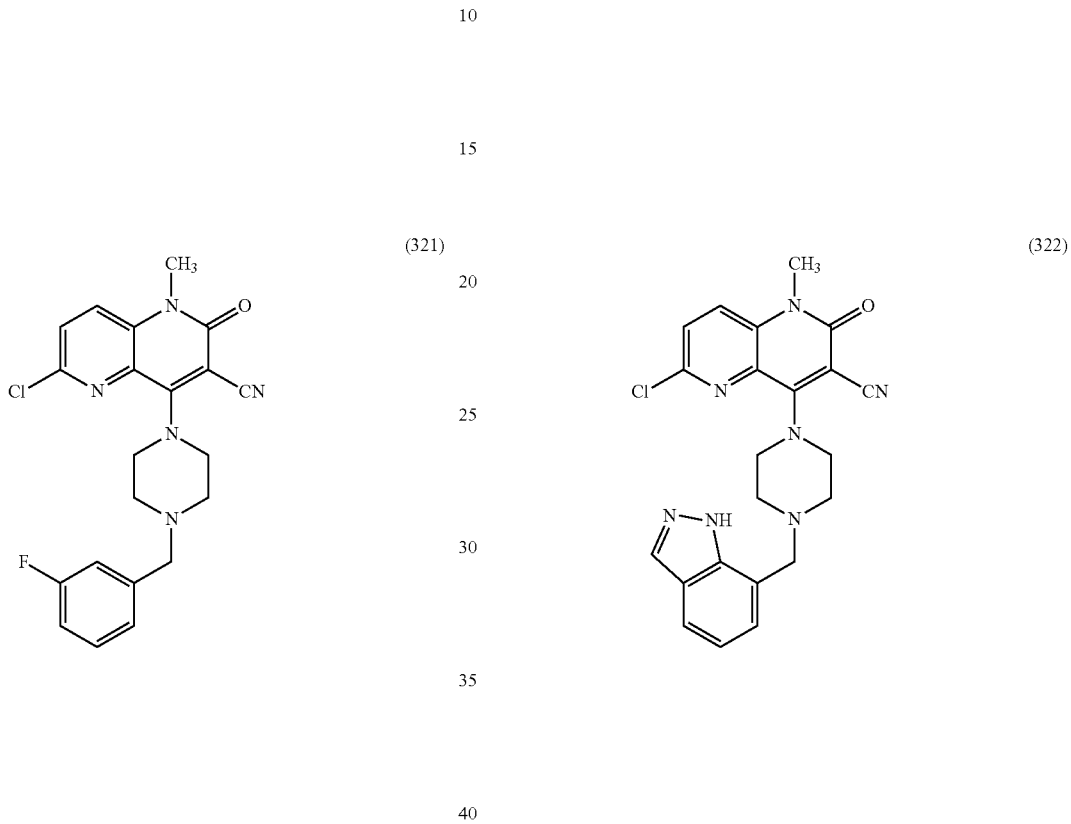

(321)

(322)

The title compound was prepared according to the general method used to prepare Example 216. The compound (4.5 mg) was isolated in 390 yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min then a 0.75 min hold at 100% B; Flow: 1 mL/min; Detection: MS and UV (220 nm). Injection 1 results: Purity: 100.0%; Observed Mass: 412.07; Retention Time: 1.2 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 412.13; Retention Time: 2.02 min.

The title compound was prepared according to the general method used to prepare Example 216. The compound (3 mg) was isolated in 24.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 434.11; Retention Time: 1.8 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 434.07; Retention Time: 1 min.

Example 323

6-chloro-4-{4-[(4-chloro-3-hydroxyphenyl)methyl]piperazin-1-yl}-1-methyl-2-oxo-1,2-dihydro-1,5-naphthyridine-3-carbonitrile

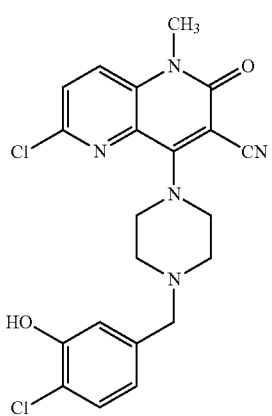

(323)

The title compound was prepared according to the general method used to prepare Example 216. The compound (5 mg) was isolated in 40.2% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 444.08; Retention Time: 1.77 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 444.06; Retention Time: 1.19 min.

Example 324

6-chloro-4-{4-[(3-chloro-5-fluorophenyl)methyl]piperazin-1-yl}-1-methyl-2-oxo-1,2-dihydro-1,5-naphthyridine-3-carbonitrile

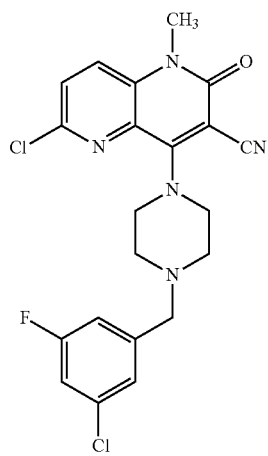

(324)

The title compound was prepared according to the general method used to prepare Example 216. The compound (4.3 mg) was isolated in 25.4% yield. Analytical LC/MS was used to determine the final purity. Injection 1 conditions: Column: Waters XBridge C18, 2.1 mm×50 mm, 1.7 in particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 min, then a 0.75 min hold at 100) % B; Flow: 1 mL/min; Detection: MS and UV (220 n). Injection 1 results: Purity: 100.0%; Observed Mass: 446.05; Retention Time: 2.27 min. Injection 2 conditions: Column: Waters XBridge C18, 2.1 mm×50 mm, 1.7 μm particles: Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 446.04; Retention Time: 1.34 min.

Example 325

8-[4-(diphenylmethyl)piperazin-1-yl]-5-methyl-6-oxo-5,6-dihydro-1,5-naphthyridine-2,7-dicarbonitrile

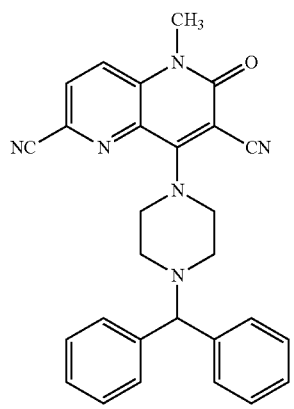

(325)

In a microwave vial, zinc (0.696 mg, 10.64 µmol), bromo(tri-tert-butylphosphine) palladium(i) dimer (8.27 mg, 10.64 µmol), dicyanozinc (1.999 mg, 0.017 mmol) and 4-(4-benzhydrylpiperazin-1-yl)-6-chloro-1-methyl-2-oxo-1,2-dihydro-1,5-naphthyridine-3-carbonitrile (10 mg, 0.021 mmol) were added. The vial was sealed, placed under vacuum and filled with nitrogen. DMF (0.5 mL) was added and the reaction mixture was heated at 50° C. for 2 hours. LC/MS analysis indicated the reaction was complete. The reaction mixture was diluted with CH$_3$CN, filtered and the filtrate was purified via preparative LC/MS with the following conditions: Column: XBridge C18, 19×200 mm, 5 µm particles; Mobile Phase A: 5:95 acetonitrile:water with 10 mM ammonium acetate; Mobile Phase B: 95:5 acetonitrile:water with 10 mM ammonium acetate; Gradient: 50-90% B over 15 minutes, then a 5 minute hold at 100% B; Flow: 20 mL/min. Fractions containing the product were combined and dried via centrifugal evaporation. The compound (4 mg) was isolated in 41.4% yield. Two analytical LC/MS injections were used to determine the final purity. Injection 1 conditions: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm.

Example 326

6-chloro-4-{4-[(4-chloro-3-fluorophenyl)methyl]piperazin-1-yl}-1-methyl-2-oxo-1,2-dihydro-1,5-naphthyridine-3-carbonitrile

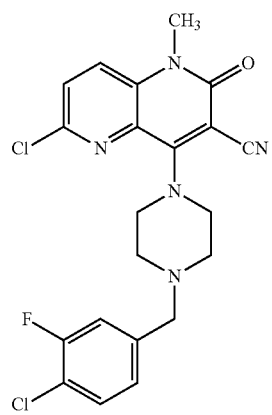

(326)

The title compound was prepared according to the general method used to prepare Example 216. The compound (5.6 mg) was isolated in 33% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 446.09; Retention Time: 1.36 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 446.08; Retention Time: 2.22 min.

Example 327

6-chloro-4-{4-[(3-methoxyphenyl)methyl]piperazin-1-yl}-1-methyl-2-oxo-1,2-dihydro-1,5-naphthyridine-3-carbonitrile

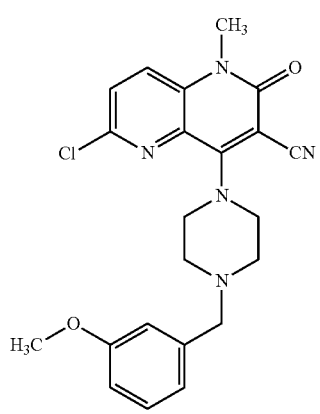
(327)

The title compound was prepared according to the general method used to prepare Example 216. The compound (5.3 mg) was isolated in 31.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0% c; Observed Mass: 424.1; Retention Time: 1.91 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 424.09; Retention Time: 1.24 min.

Example 328

6-chloro-4-{4-[(3-hydroxy-4-methylphenyl)methyl]piperazin-1-yl}-1-methyl-2-oxo-1,2-dihydro-1,5-naphthyridine-3-carbonitrile

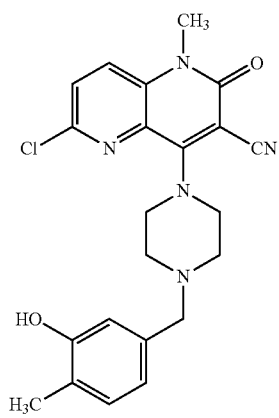
(328)

The title compound was prepared according to the general method used to prepare Example 216. The compound (6.3 mg) was isolated in 53.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100%13 Flow: 1 mL/min; Detection: MS and UV (220 nm). Injection 1 results: Purity: 100.0%; Observed Mass: 424.1; Retention Time: 1.19 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 in, then a 0.75 min hold at 100% B; Flow: 1 mL/min; Detection: MS and UV (220 nm). Injection 2 results: Purity: 100.0%; Observed Mass: 424.08; Retention Time: 1.72 min.

Example 329

4-{4-[(3-fluoro-2-hydroxyphenyl)methyl]piperazin-1-yl}-1,6-dimethyl-2-oxo-1,2-dihydro-1,5-naphthyridine-3-carbonitrile

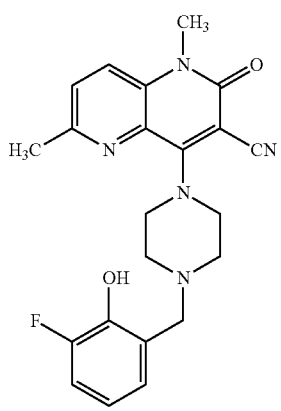

(329)

The title compound was prepared according to the general method used to prepare Example 216 from 1,6-dimethyl-2-oxo-4-(piperazin-1-yl)-1,2-dihydro-1,5-naphthyridine-3-carbonitrile. The compound (9.6 mg) was isolated in 44.5% yield. Analytical LC/IS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100%13 Flow: 1 mL/min; Detection: MS and UV (220 nm). Injection 1 results: Purity: 100.0%; Observed Mass: 408.16; Retention Time: 1.27 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 408.16; Retention Time: 2.11 min.

Example 330

6-chloro-4-{4-[(2,3-difluorophenyl)methyl]piperazin-1-yl}-1-methyl-2-oxo-1,2-dihydro-1,5-naphthyridine-3-carbonitrile

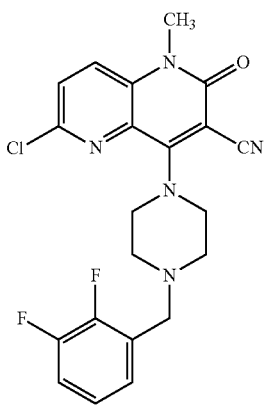

(330)

Example 330 was prepared according to the general method used to prepare Example 216. The compound (6.1 mg) was isolated in 26.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.1%; Observed Mass: 429.94; Retention Time: 1.94 min. Injection 2 conditions: Column: Waters XBridge C18, 2.1 mm×50 mm, 1.7 Um particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 mi, then a 0.75 min hold at 100% B; Flow: 1 mL/min; Detection: MS and UV (220 nm). Injection 2 results: Purity: 97.3%; Observed Mass: 429.94; Retention Time: 1.19 min.

Example 331

6-chloro-4-{4-[(2-methoxyphenyl)methyl]piperazin-1-yl}-1-methyl-2-oxo-1,2-dihydro-1,5-naphthyridine-3-carbonitrile

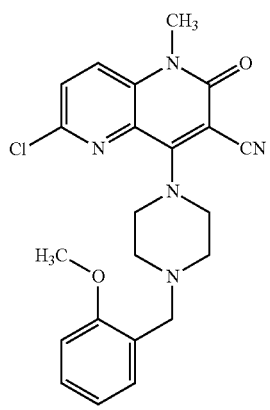
(331)

Example 331 was prepared according to the general method used to prepare Example 216. The compound (2.9 mg) was isolated in 18% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 424.03; Retention Time: 1.2 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 424.02; Retention Time: 1.76 min.

Example 332

8-{4-[(4-chloro-3-hydroxyphenyl)methyl]piperazin-1-yl}-5-methyl-6-oxo-5,6-dihydro-1,5-naphthyridine-2,7-dicarbonitrile

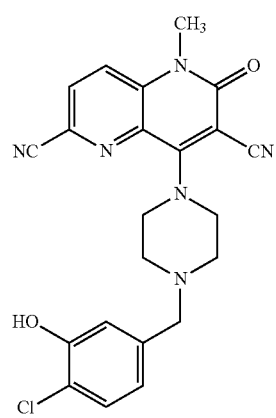
(332)

Example 332 was prepared according to the general method used to prepare Example 216 from 5-methyl-6-oxo-8-(piperazin-1-yl)-5,6-dihydro-1,5-naphthyridine-2,7-dicarbonitrile, 2 TFA. The compound (14 mg) was isolated in 84.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.9%; Observed Mass: 434.94; Retention Time: 1.54 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.8%; Observed Mass: 434.96; Retention Time: 1.1 min.

Example 333

6-bromo-4-{4-[(1H-indazol-7-yl)methyl]piperazin-1-yl}-1-methyl-2-oxo-1,2-dihydro-1,5-naphthyridine-3-carbonitrile

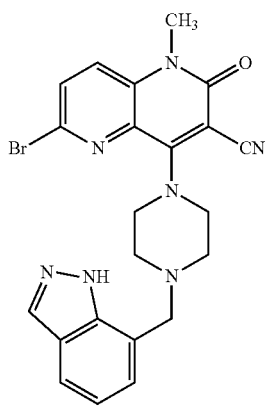
(333)

Example 334

4-{4-[(1-ethyl-1H-indol-4-yl)methyl]piperazin-1-yl}-1-methyl-2-oxo-1,2-dihydro-1,5-naphthyridine-3-carbonitrile

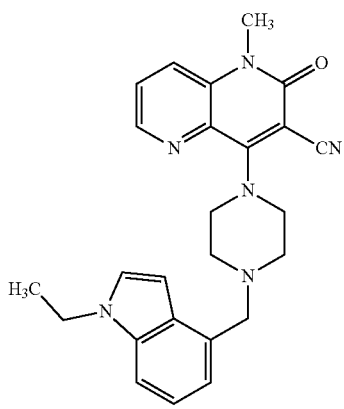
(334)

Example 333 was prepared according to the general method used to prepare Example 2. The compound (3.5 mg) was isolated in 20.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.5%; Observed Mass: 478.04; Retention Time: 1.14 min. Injection 2 conditions: Column: Waters XBridge C18, 2.1 mm×50 mm, 1.7 min particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0% B to 100% B over 3 min, then a 0.75 min hold at 100% B; Flow: 1 mL/min; Detection: MS and UV (220 nm). Injection 2 results: Purity: 98.6%; Observed Mass: 478.08; Retention Time: 1.84 min.

Example 334 was prepared according to the general method used to prepare Example 66. The compound (21.3 mg) was isolated in 73.4% yield. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm.

Example 335

6-chloro-4-{4-[(2-fluor-6-methoxyphenyl)methyl]piperazin-1-yl}-1-methyl-2-oxo-1,2-dihydro-1,5-naphthyridine-3-carbonitrile

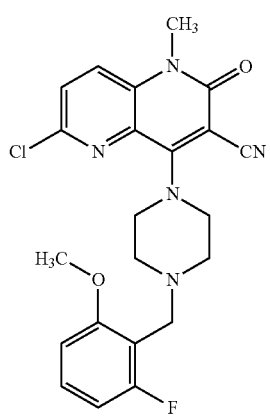

(335)

Example 336

6-chloro-4-{4-[(2-hydroxynaphthalen-1-yl)methyl]piperazin-1-yl}-1-methyl-2-oxo-1,2-dihydro-1,5-naphthyridine-3-carbonitrile

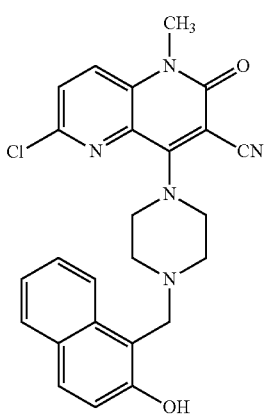

(336)

Example 335 was prepared according to the general method used to prepare Example 216. The compound (8.7 mg) was isolated in 37.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 442.13; Retention Time: 1.89 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 442.1; Retention Time: 1.25 min.

Example 336 was prepared according to the general method used to prepare Example 216. The compound (10.4 mg) was isolated in 19.2% yield. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm.

Example 337

4-{4-[(2-hydroxyphenyl)methyl]piperazin-1-yl}-1,6-dimethyl-2-oxo-1,2-dihydro-1,5-naphthyridine-3-carbonitrile

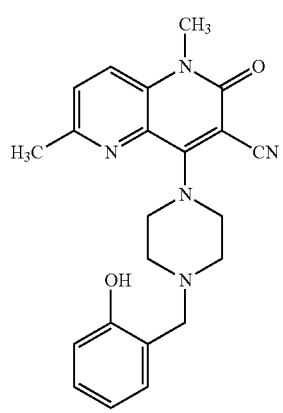

(337)

Example 337 was prepared according to the general method used to prepare Example 216 from 1,6-dimethyl-2-oxo-4-(piperazin-1-yl)-1,2-dihydro-1,5-naphthyridine-3-carbonitrile. The compound (5.9 mg) was isolated in 28.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 390.16; Retention Time: 2.13 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.3%; Observed Mass: 390.15; Retention Time: 1.27 mm.

Example 338

6-chloro-4-{4-[(3-fluoro-5-hydroxyphenyl)methyl]piperazin-1-yl}-1-methyl-2-oxo-1,2-dihydro-1,5-naphthyridine-3-carbonitrile

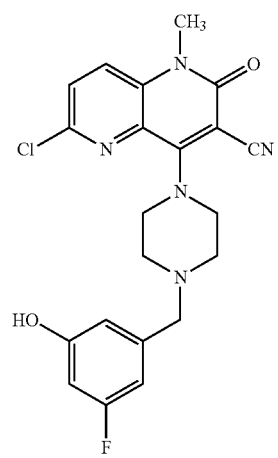

(338)

Example 338 was prepared according to the general method used to prepare Example 216. The compound (4.9 mg) was isolated in 40.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.9%; Observed Mass: 428.07; Retention Time: 1.13 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: IS and UV (220 nm). Injection 2 results: Purity: 98.2%; Observed Mass: 428.07; Retention Time: 1.68 min.

Example 339

6-chloro-4-{4-[(2-fluorophenyl)methyl]piperazin-1-yl}-1-methyl-2-oxo-1,2-dihydro-1,5-naphthyridine-3-carbonitrile

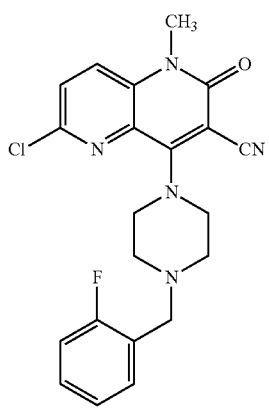

(339)

Example 340

6-chloro-4-{4-[(5-cyano-2-fluoro-phenyl)methyl]piperazin-1-yl}-1-methyl-2-oxo-1,2-dihydro-1,5-naphthyridine-3-carbonitrile

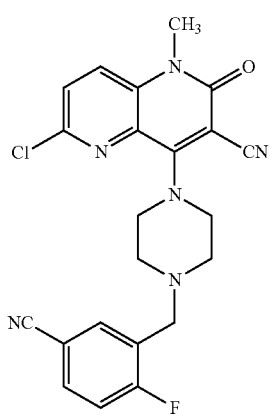

(340)

Example 339 was prepare according to the general method used to prepare Example 216. The compound (5.9 mug) was isolated in 51.2% yield. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% 3 over 3 minutes, then a 0.75 minute hold at 100% B; Flow: 1.0 mL/min; Detection: UV at 220 nm.

Example 340 was prepared according to the general method used to prepare Example 216. The compound (7.4 mg) was isolated in 32% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.2%; Observed Mass: 437.09; Retention Time: 1.13 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.2%; Observed Mass: 437.07; Retention Time: 1.83 min.

Example 341

6-chloro-4-{4-[(4-methoxyphenyl)methyl]piperazin-1-yl}-1-methyl-2-oxo-1,2-dihydro-1,5-naphthyridine-3-carbonitrile

Example 342

8-{4-[1-(4-fluorophenyl)cyclopropyl]piperazin-1-yl}-5-methyl-7-nitro-6-oxo-5,6-dihydro-1,5-naphthyridine-2-carbonitrile

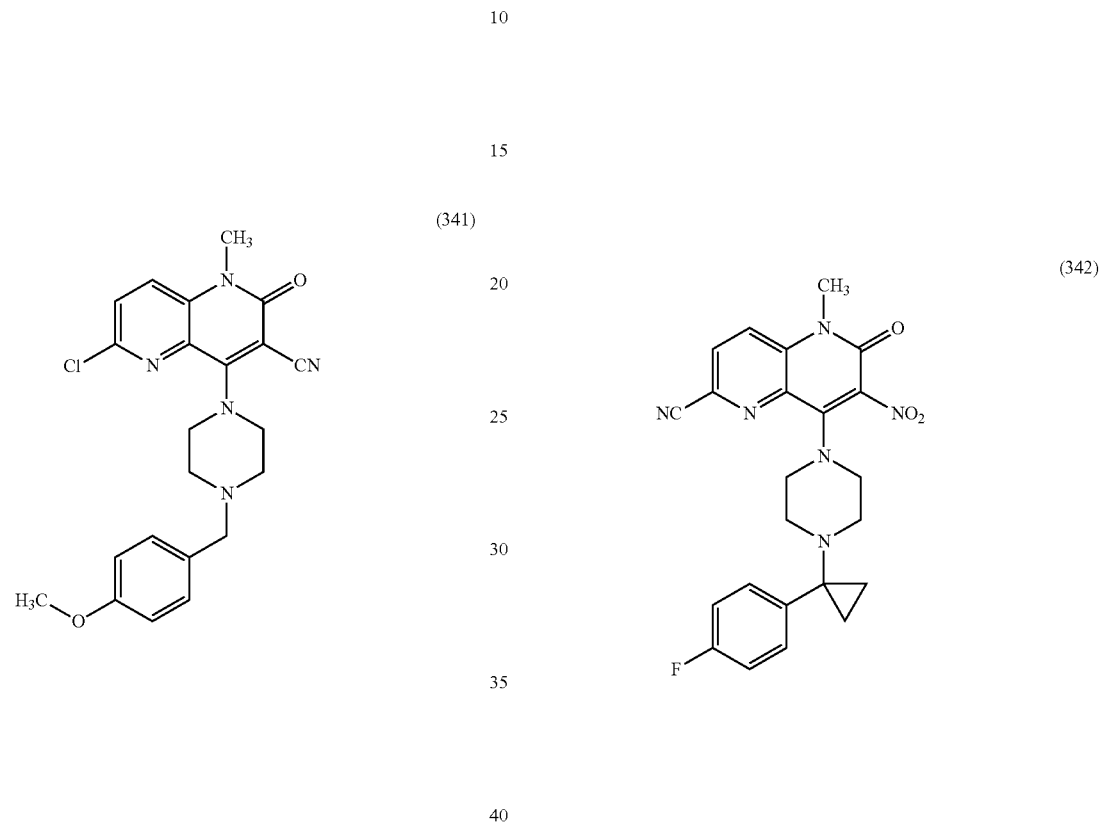

Example 341 was prepared according to the general method used to prepare Example 216. The compound (5.2 mg) was isolated in 30.7% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 424.1; Retention Time: 1.86 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 424.11; Retention Time: 1.22 min.

Example 342 was prepared according to the general method used to prepare Example 221. The compound (14.8 mg) was isolated in 57.9% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 449.23; Retention Time: 1.27 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.4%; Observed Mass: 449.1; Retention Time: 2.14 min.

Example 343

4-(4-benzylpiperazin-1-yl)-6-chloro-1-methyl-2-oxo-1,2-dihydro-1,5-naphthyridine-3-carbonitrile

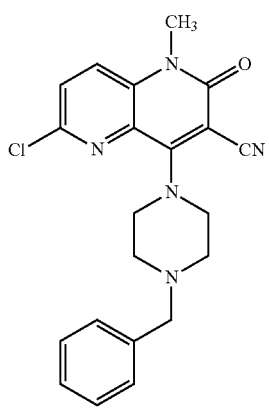

(343)

Example 343 was prepared according to the general method used to prepare Example 216. The compound (6.9 mg) was isolated in 46.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 394.1; Retention Time: 1.19 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 394.1; Retention Time: 1.95 min.

Example 344

6-bromo-4-{4-[(2-fluorophenyl)methyl]piperazin-1-yl}-1-methyl-2-oxo-1,2-dihydro-1,5-naphthyridine-3-carbonitrile

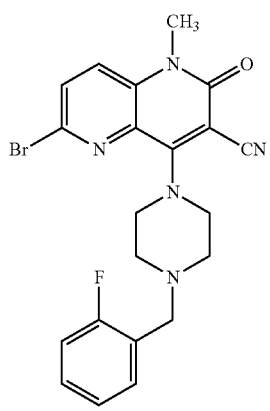

(344)

Example 344 was prepared according to the general method used to prepare Example 2. The compound (8.6 mg) was isolated in 53.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 455.96; Retention Time: 1.91 min. Injection 2 conditions: Column: Waters XBridge C18, 21 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 455.96; Retention Time: 1.17 min.

Example 345

6-chloro-4-{4-[(3-chloro-5-hydroxyphenyl)methyl]piperazin-1-yl}-1-methyl-2-oxo-1,2-dihydro-1,5-naphthyridine-3-carbonitrile

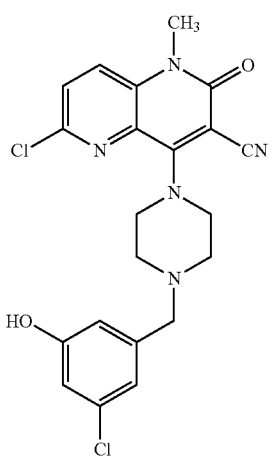

(345)

Example 345 was prepared according to the general method used to prepare Example 216. The compound (4.4 mg) was isolated in 35.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: NIS and UV (220 nm). Injection 1 results: Purity: 99.3%; Observed Mass: 444.09; Retention Time: 1.82 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.0%; Observed Mass: 444.1; Retention Time: 1.22 min.

Example 346

6-chloro-1-methyl-4-{4-[(2-methylphenyl)methyl]piperazin-1-yl}-2-oxo-1,2-dihydro-1,5-naphthyridine-3-carbonitrile

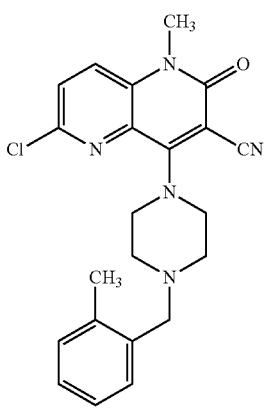

(346)

Example 346 was prepared according to the general method used to prepare Example 216. The compound (7.4 mg) was isolated in 64.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 408.11; Retention Time: 1.26 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 408.12; Retention Time: 2.22 min.

Example 347

4-{4-[bis(4-fluorophenyl)methyl]piperazin-1-yl}-1-methyl-2-oxo-1,2-dihydro-1,5-naphthyridine-3-carbonitrile

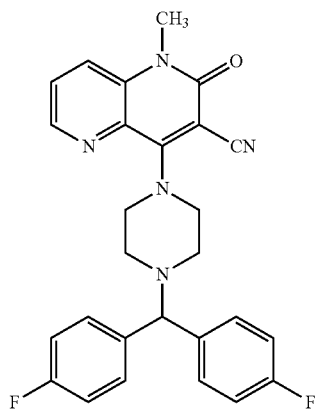

(347)

Example 347 was prepared according to the general method used to prepare Example 66. The compound (23.1 mg) was isolated in 72% yield. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.: Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm.

Example 348

6-chloro-4-{4-[(4-fluoro-3-hydroxyphenyl)methyl]piperazin-1-yl}-1-methyl-2-oxo-1,2-dihydro-1,5-naphthyridine-3-carbonitrile

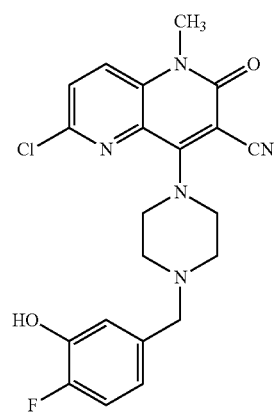

(348)

Example 348 was prepared according to the general method used to prepare Example 216. The compound (6.7 mg) was isolated in 41.2% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 428.08; Retention Time: 1.09 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 428.1; Retention Time: 1.62 min.

Example 349

4-{4-[(2-hydroxyphenyl)(phenyl)methyl]piperazin-1-yl}-1-methyl-2-oxo-1,2-dihydro-1,5-naphthyridine-3-carbonitrile

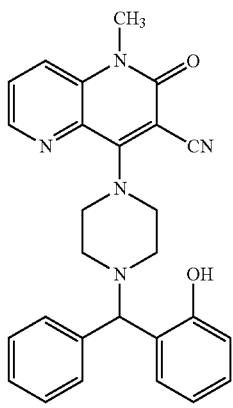
(349)

Example 349 was prepared according to the general method used to prepare Example 66. The compound (22.2 mg) was isolated in 72.3% yield. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.100 trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm.

Example 350

6-chloro-4-{4-[(2,4-difluorophenyl)methyl]piperazin-1-yl}-1-methyl-2-oxo-1,2-dihydro-1,5-naphthyridine-3-carbonitrile

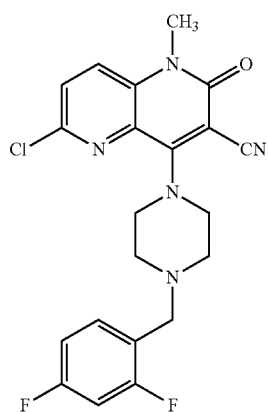
(350)

Example 350 was prepared according to the general method used to prepare Example 216. The compound (5.9 mg) was isolated in 34.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 430.07; Retention Time: 2 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 430.06; Retention Time: 1.23 min.

Example 351

6-chloro-4-{4-[(3-hydroxyphenyl)methyl]piperazin-1-yl}-1-methyl-2-oxo-1,2-dihydro-1,5-naphthyridine-3-carbonitrile

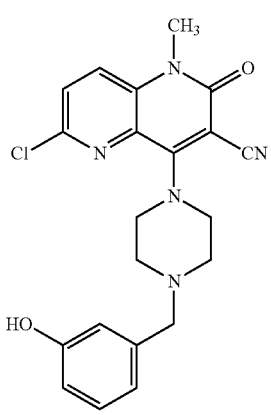

(351)

Example 352

4-{4-[(2-hydroxy-3-methoxyphenyl)methyl]piperazin-1-yl}-1,6-dimethyl-2-oxo-1,2-dihydro-1,5-naphthyridine-3-carbonitrile

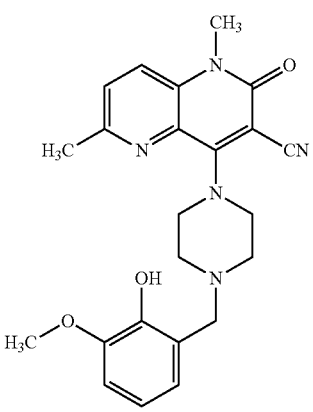

(352)

Example 351 was prepared according to the general method used to prepare Example 216. The compound (4.5 mg) was isolated in 39.2% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 nM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 410.11; Retention Time: 1.56 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 410.06; Retention Time: 1.06 min.

Example 352 was prepared according to the general method used to prepare Example 216 from 1,6-dimethyl-2-oxo-4-(piperazin-1-yl)-1,2-dihydro-1,5-naphthyridine-3-carbonitrile. The compound (6.6 mg) was isolated in 29.7% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 420.14; Retention Time: 1.41 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 420.15; Retention Time: 2.04 min.

Example 353

6-chloro-4-{4-[(3-hydroxy-4-methoxyphenyl)methyl]piperazin-1-yl}-1-methyl-2-oxo-1,2-dihydro-1,5-naphthyridine-3-carbonitrile

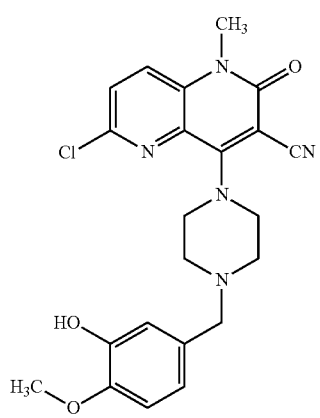

(353)

Example 353 was prepared according to the general method used to prepare Example 216. The compound (6.8 mg) was isolated in 40.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.8%; Observed Mass: 440.08; Retention Time: 1.55 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.9%; Observed Mass: 440.12; Retention Time: 1.08 min.

Example 354

6-chloro-4-{4-[(3-chloro-4-hydroxyphenyl)methyl]piperazin-1-yl}-1-methyl-2-oxo-1,2-dihydro-1,5-naphthyridine-3-carbonitrile

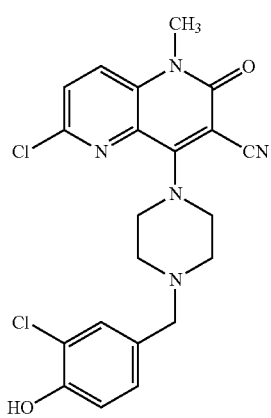

(354)

Example 354 was prepared according to the general method used to prepare Example 216. The compound (6.5 mg) was isolated in 36.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 444.09; Retention Time: 1.66 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 444.09; Retention Time: 1.14 min.

Example 355

6-chloro-4-(4-{[4-hydroxy-3-(trifluoromethyl)phenyl]methyl}piperazin-1-yl)-1-methyl-2-oxo-1,2-dihydro-1,5-naphthyridine-3-carbonitrile

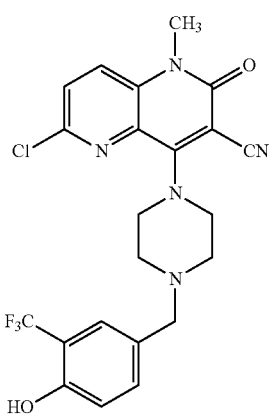

(355)

Example 355 was prepared according to the general method used to prepare Example 216. The compound (5.4 mg) was isolated in 21.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 mi hold at 100% B; Flow: 1 mL/min; Detection: MS and UV (220 nm). Injection 1 results: Purity: 99.3%; Observed Mass: 478.11; Retention Time: 1.27 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100 ?% B; Flow: 1 mL/min; Detection: MS and UV (220 nm). Injection 2 results: Purity: 99.4%; Observed Mass: 478.13; Retention Time: 1.79 min.

Example 356

6-chloro-4-{4-[(4-hydroxy-3-methylphenyl)methyl]piperazin-1-yl}-1-methyl-2-oxo-1,2-dihydro-1,5-naphthyridine-3-carbonitrile

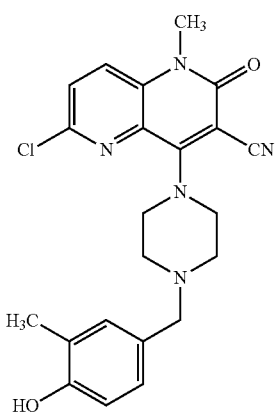

(356)

Example 356 was prepared according to the general method used to prepare Example 216. The compound (8.7 mg) was isolated in 38.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 423.99; Retention Time: 1.49 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 424; Retention Time: 1.09 min.

Example 357

6-chloro-4-{4-[(3-fluoro-4-hydroxyphenyl)methyl]piperazin-1-yl}-1-methyl-2-oxo-1,2-dihydro-1,5-naphthyridine-3-carbonitrile

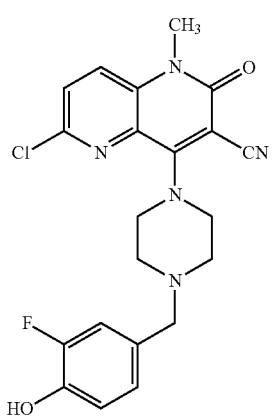

(357)

Example 357 was prepared according to the general method used to prepare Example 216. The compound (5.9 ng) was isolated in 49.2% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 mi hold at 100% B; Flow: 1 mL/min; Detection: MS and UV (220 nm). Injection 1 results: Purity: 100.0%; Observed Mass: 428.07; Retention Time: 1.06 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100 ?% B; Flow: 1 mL/min; Detection: MS and UV (220 nm). Injection 2 results: Purity: 100.0%; Observed Mass: 428.07; Retention Time: 1.56 min.

Example 358

6-chloro-4-[4-(diphenylmethyl)piperazin-1-yl]-1-methyl-2-oxo-1,2-dihydro-1,5-naphthyridine-3-carbonitrile

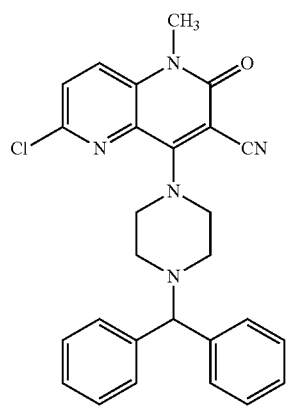

(358)

Example 358 was prepared according to the general method used to prepare Example 191. The compound (4.2 mg) was isolated in 15.1% yield. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1%/trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B. Flow: 1.0 mL/min; Detection: UV at 220 nm.

Example 359

4-{4-[(1H-1,3-benzodiazol-7-yl)methyl]piperazin-1-yl}-6-chloro-1-methyl-2-oxo-1,2-dihydro-1,5-naphthyridine-3-carbonitrile

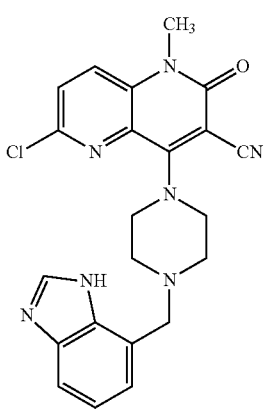

(359)

Example 359 was prepared according to the general method used to prepare Example 216. The compound (4.5 mg) was isolated in 27.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.2%; Observed Mass: 434.09; Retention Time: 0.94 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.4%; Observed Mass: 434.1; Retention Time: 1.47 min.

Example 360

4-{4-([(1H-1,3-benzodiazol-7-yl)methyl]piperazin-1-yl}-6-bromo-1-methyl-2-oxo-1,2-dihydro-1,5-naphthyridine-3-carbonitrile

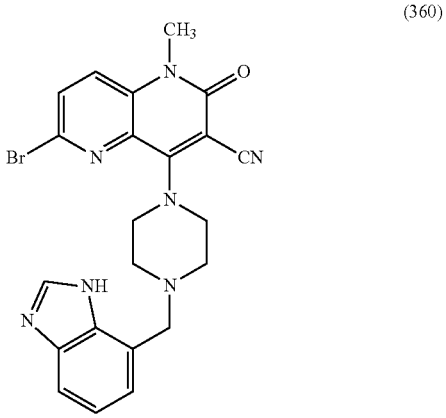 [SMILES: Cn1c(=O)c(C#N)c(N2CCN(Cc3cccc4nc[nH]c34)CC2)c2nc(Cl)ccc21]

(360)

Example 360 was prepared according to the general method used to prepare Example 2. The compound (3.6 mg) was isolated in 21.5% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 478.01; Retention Time: 1.5 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 478.04; Retention Time: 0.95 min.

Example 362

6-chloro-4-{4-[(4-hydroxyphenyl)methyl]piperazin-1-yl}-1-methyl-2-oxo-1,2-dihydro-1,5-naphthyridine-3-carbonitrile

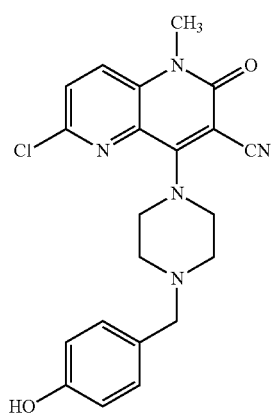

(362)

Example 363

8-{4-[(3-fluoro-4-hydroxyphenyl)methyl]piperazin-1-yl}-5-methyl-6-oxo-5,6-dihydro-1,5-naphthyridine-2,7-dicarbonitrile

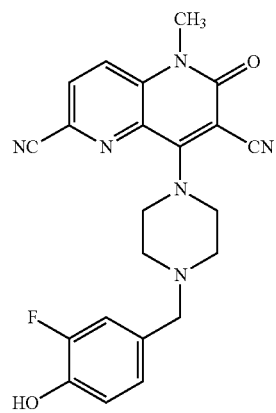

(363)

Example 362 was prepared according to the general method used to prepare Example 216. The compound (5.7 mg) was isolated in 36.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 mi, then a 0.75 min hold at 100% B; Flow: 1 mL/min; Detection: MS and UV (220 nm). Injection 1 results: Purity: 100.0%: Observed Mass: 41012; Retention Time: 1.46 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 410.12; Retention Time: 1.03 min.

Example 363 was prepared according to the general method used to prepare Example 216 from 5-methyl-6-oxo-8-(piperazin-1-yl)-5,6-dihydro-1,5-naphthyridine-2,7-dicarbonitrile, 2 TFA. The compound (7.4 mg) was isolated in 30.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 419.01; Retention Time: 0.95 min. Injection 2 conditions: Column: Waters XBridge C1, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 419.01; Retention Time: 1.32 min.

Example 364

6-chloro-4-{4-[(2-fluoro-5-methylphenyl)methyl]piperazin-1-yl}-1-methyl-2-oxo-1,2-dihydro-1,5-naphthyridine-3-carbonitrile

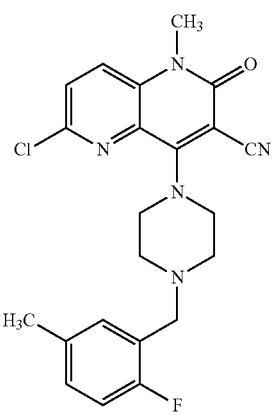

(364)

Example 364 was prepared according to the general method used to prepare Example 216. The compound (9.1 mg) was isolated in 40.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.4%; Observed Mass: 426.14; Retention Time: 1.29 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 426.11; Retention Time: 2.1 min.

Example 365

6-chloro-4-{4-[(2-chloro-6-methoxyphenyl)methyl]piperazin-1-yl}-1-methyl-2-oxo-1,2-dihydro-1,5-naphthyridine-3-carbonitrile

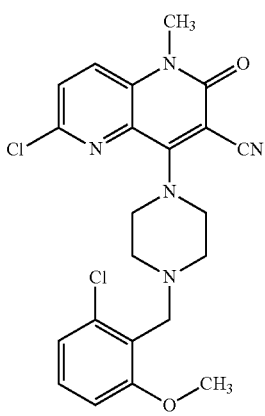

(365)

Example 365 was prepared according to the general method used to prepare Example 216. The compound (10.1 mg) was isolated in 41.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.2%; Observed Mass: 458.09; Retention Time: 2.13 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.2%; Observed Mass: 458.06; Retention Time: 1.34 min.

Example 366

6-bromo-4-{4-[(3,5-dichloro-2-hydroxyphenyl)methyl]piperazin-1-yl}-1-methyl-2-oxo-1,2-dihydro-1,5-naphthyridine-3-carbonitrile

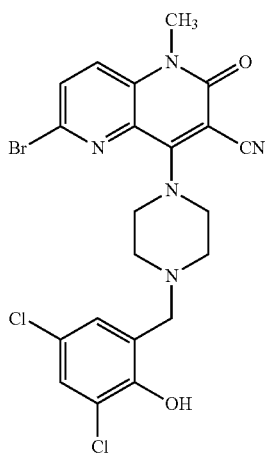

(366)

Example 366 was prepared according to the general method used to prepare Example 2. The compound (8.3 mg) was isolated in 36.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.3%; Observed Mass: 521.97; Retention Time: 2.76 min.

Example 367

6-bromo-4-{4-[(5-chloro-2-hydroxyphenyl)methyl]piperazin-1-yl}-1-methyl-2-oxo-1,2-dihydro-1,5-naphthyridine-3-carbonitrile

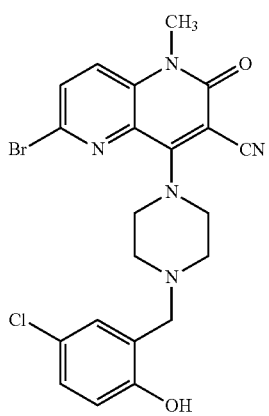

(367)

Example 367 was prepared according to the general method used to prepare Example 2. The compound (11.1 mg) was isolated in 52.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B: Flow: 1 mL/min; Detection: MS and UV (220 nm). Injection 1 results: Purity: 100.0%; Observed Mass: 488; Retention Time: 2.56 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 mi hold at 100% B; Flow: 1 mL/min; Detection: MS and UV (220 nm). Injection 2 results: Purity: 100.0%; Observed Mass: 488; Retention Time: 1.5 min.

Example 368

6-bromo-4-{4-[(2-hydroxy-3-methoxyphenyl)methyl]piperazin-1-yl}-1-methyl-2-oxo-1,2-dihydro-1,5-naphthyridine-3-carbonitrile

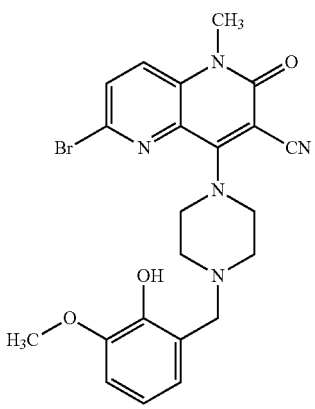

(368)

Example 368 was prepared according to the general method used to prepare Example 2. The compound (14 mg) was isolated in 67.2% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.6%; Observed Mass: 484.05; Retention Time: 1.41 min. Injection 2 conditions: Column: Waters XBridge C18, 2.1 mm×50 mm, 1.7 μm particles; Mobile Phase A: 5:95 acetonitrile:water with 10 mM ammonium acetate: Mobile Phase B: 95:5 acetonitrile:water with 10 mM ammonium acetate: Temperature: 50° C.; Gradient: 0% B to 100% B over 3 min, then a 0.75 min hold at 100%

Example 369

6-chloro-4-(4-{[2-hydroxy-5-(trifluoromethoxy)phenyl]methyl}piperazin-1-yl)-1-methyl-2-oxo-1,2-dihydro-1,5-naphthyridine-3-carbonitrile

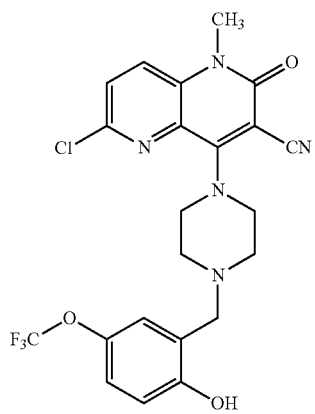

(369)

Example 370

6-chloro-4-{4-[(5-chloro-2-hydroxyphenyl)methyl]piperazin-1-yl}-1-methyl-2-oxo-1,2-dihydro-1,5-naphthyridine-3-carbonitrile

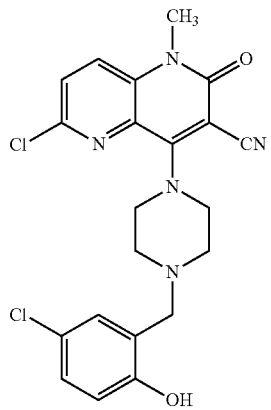

(370)

Example 369 was prepared according to the general method used to prepare Example 216. The compound (12.5 mg) was isolated in 66.6% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 494.05; Retention Time: 1.64 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.0%; Observed Mass: 494.08; Retention Time: 2.6 min.

Example 370 was prepared according to the general method used to prepare Example 216. The compound (11.7 mg) was isolated in 69.3% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 444.1; Retention Time: 2.5 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 444.07; Retention Time: 1.48 min.

Example 371

6-chloro-4-{4-[(2-hydroxy-3-methoxyphenyl)methyl]piperazin-1-yl}-1-methyl-2-oxo-1,2-dihydro-1,5-naphthyridine-3-carbonitrile

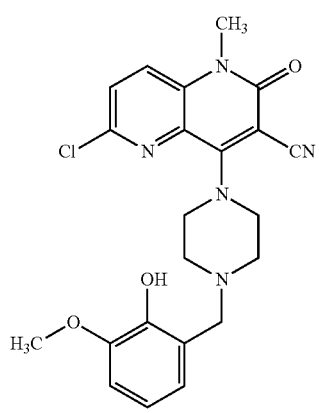

(371)

Example 371 was prepared according to the general method used to prepare Example 216. The compound (9.4 mg) was isolated in 56.2% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 440.11; Retention Time: 1.37 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 440.11; Retention Time: 213 min.

Example 372

6-bromo-4-{4-[(2-hydroxy-4-methylphenyl)methyl]piperazin-1-yl}-1-methyl-2-oxo-1,2-dihydro-1,5-naphthyridine-3-carbonitrile

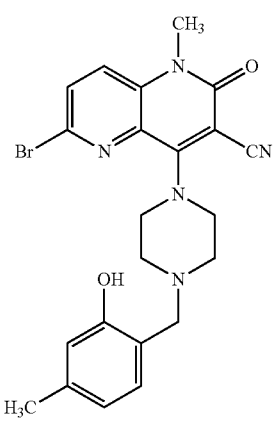

(372)

Example 372 was prepared according to the general method used to prepare Example 2. The compound (10.1 mg) was isolated in 50.2% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 n). Injection 1 results: Purity: 100.0%; Observed Mass: 468.07; Retention Time: 1.22 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 468.05; Retention Time: 2.07 min.

Example 373

6-bromo-4-{4-[(1H-indol-7-yl)methyl]piperazin-1-yl}-1-methyl-2-oxo-1,2-dihydro-1,5-naphthyridine-3-carbonitrile

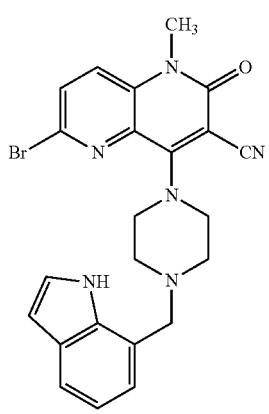

(373)

Example 373 was prepared according to the general method used to prepare Example 2. The compound (11.3 mg) was isolated in 55.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.8%; Observed Mass: 477.08; Retention Time: 2.13 min. Injection 2 conditions: Column: Waters XBridge C18, 2.1 mm×50 mm, 1.7 μmm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 477.08; Retention Time: 1.31 min.

Example 374

6-bromo-1-methyl-2-oxo-4-{4-[(2-oxo-2,3-dihydro-1H-indol-7-yl)methyl]piperazin-1-yl}-1,2-dihydro-1,5-naphthyridine-3-carbonitrile

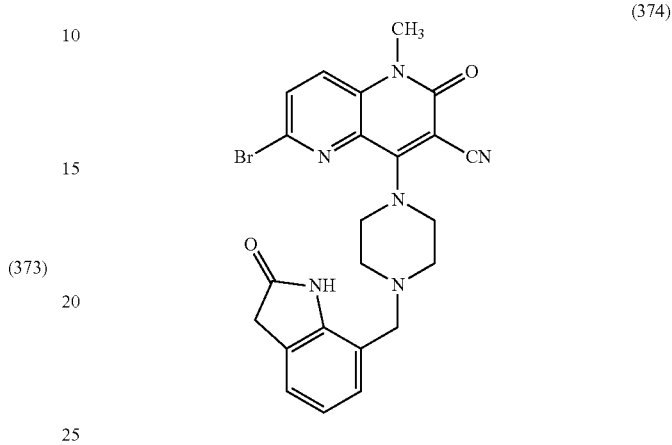

(374)

Example 374 was prepared according to the general method used to prepare Example 2. The compound (5.8 mg) was isolated in 27.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 493.37; Retention Time: 0.91 min.

Example 375

6-chloro-4-(4-{[3-fluoro-4-(trifluoromethyl)phenyl]methyl}piperazin-1-yl)-1-methyl-2-oxo-1,2-dihydro-1,5-naphthylidine-3-carbonitrile

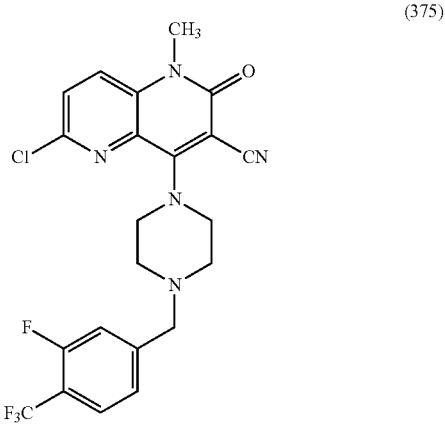 [SMILES: Cn1c(=O)c(C#N)c(N2CCN(Cc3ccc(C(F)(F)F)c(F)c3)CC2)c2nc(Cl)ccc21]

(375)

Example 375 was prepared according to the general method used to prepare Example 216. The compound (8.1 mg) was isolated in 44.4% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 480.1; Retention Time: 1.47 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 480.1; Retention Time: 2.27 min.

Example 376

6-chloro-1-methyl-2-oxo-4-{4-[(2-oxo-2,3-dihydro-1H-indol-7-yl)methyl]piperazin-1-yl}-1,2-dihydro-1,5-naphthyridine-3-carbonitrile

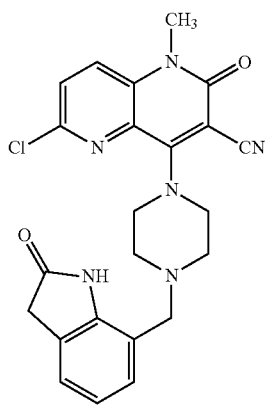

(376)

Example 376 was prepared according to the general method used to prepare Example 216. The compound (4 mg) was isolated in 31.8% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 448.98; Retention Time: 1.44 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 449; Retention Time: 1.07 min.

Example 377 and 378

6-chloro-4-{4-[1-(4-fluorophenyl)-3,3-dimethyl-butyl]piperazin-1-yl}-1-methyl-2-oxo-1,2-dihydro-1,5-naphthyridine-3-carbonitrile

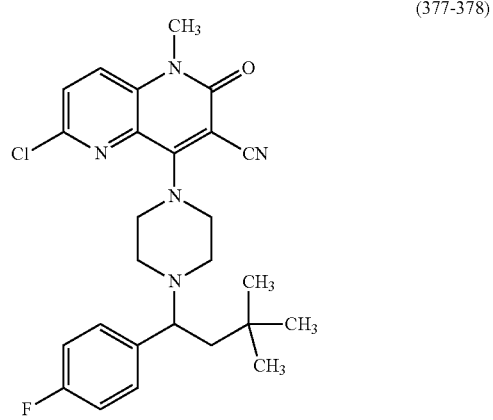 [SMILES: Cn1c(=O)c(C#N)c(N2CCN(C(CC(C)(C)C)c3ccc(F)cc3)CC2)c2nc(Cl)ccc21]

(377-378)

Example 3 377-378 were prepared according to the general method used to prepare Example 68. The racemic compound (25 mg) was isolated in 603% yield. Analytical LC/MS was used to determine the final purity. Injection 1 conditions: Column: Waters XBridge C18, 2.1 mm×50 mm, 1.7 mm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.1%; Observed Mass: 482.32; Retention Time: 2.52 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.4%; Observed Mass: 482.06; Retention Time: 1.69 min.

The racemic material was further purified by using SFC-chiral chromatography to afford Example 377 (first eluting isomer) and Example 378 (second eluting isomer).

Example 377: The compound (9.4 mg) was isolated in 22.7% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.0%; Observed Mass: 482.31; Retention Time: 2.51 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 482.36; Retention Time: 1.56 min.

Example 378: The compound (9.5 mg) was isolated in 22.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0% B to 100% B over 3 min, then a 0.75 min hold at 100% B; Flow: 1 mL/min; Detection: MS and UV (220 nm). Injection 1 results: Purity: 98.1%; Observed Mass: 482.32; Retention Time: 2.51 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.3%; Observed Mass: 482.31; Retention Time: 1.56 min.

Example 379

6-chloro-4-{4-[(4-cyano-2-fluorophenyl)methyl]piperazin-1-yl}-1-methyl-2-oxo-1,2-dihydro-1,5-naphthyridine-3-carbonitrile

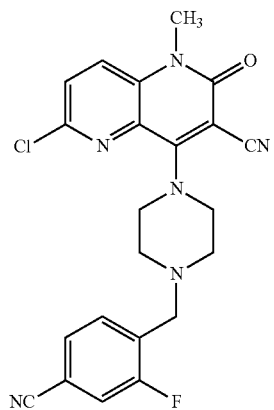

(379)

Example 379 was prepared according to the general method used to prepare Example 216. The compound (1.8 ng) was isolated in 7.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.1%; Observed Mass: 436.92; Retention Time: 1.13 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100 ?% B; Flow: 1 mL/min; Detection: MS and UV (220 nm). Injection 2 results: Purity: 98.7%; Observed Mass: 436.93; Retention Time: 1.8 min.

Example 380

6-bromo-4-{4-[(3-bromo-2-hydroxyphenyl)methyl]piperazin-1-yl}-1-methyl-2-oxo-1,2-dihydro-1,5-naphthyridine-3-carbonitrile

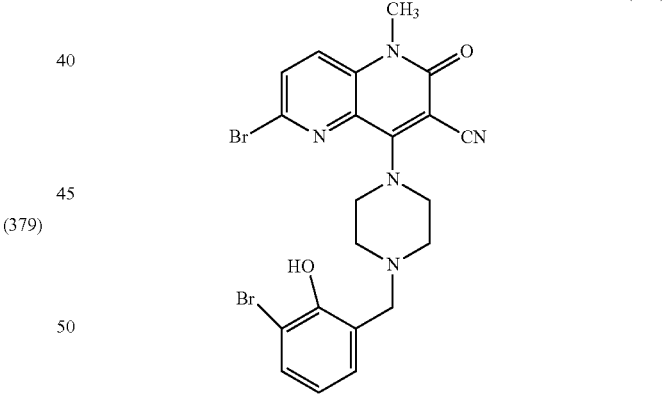

(380)

Example 380 was prepared according to the general method used to prepare Example 2. The compound (2.3 mg) was isolated in 10% yield. Analytical LC/MS was used to determine the final purity. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.2%; Observed Mass: 531.93; Retention Time: 1.52 min.

Example 381

6-chloro-4-(4-{[2-hydroxy-4-(trifluoromethoxy)phenyl]methyl}piperazin-1-yl)-1-methyl-2-oxo-1,2-dihydro-1,5-naphthyridine-3-carbonitrile

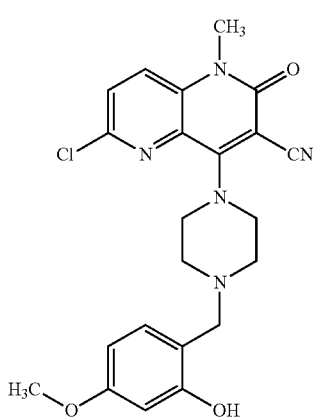

(381)

Example 381 was prepared according to the general method used to prepare Example 216. The compound (4.3 mg) was isolated in 22.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 494.1; Retention Time: 2.23 min. Injection 2 conditions: Column: Waters XBridge C18, 2.1 mm×50 mm, 1.7 μm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C. Gradient: 0% B to 100% B over 3 min, then a 0.75 min hold at 100% B; Flow: 1 mL/min; Detection: MS and UV (220 nm). Injection 2 results: Purity: 100.0%; Observed Mass: 494.09; Retention Time: 1.4 min.

Examples 382A, 382, and 383

6-chloro-4-{4-[cyclobutyl(4-fluorophenyl)methyl]piperazin-1-yl}-1-methyl-2-oxo-1,2-dihydro-1,5-naphthyridine-3-carbonitrile

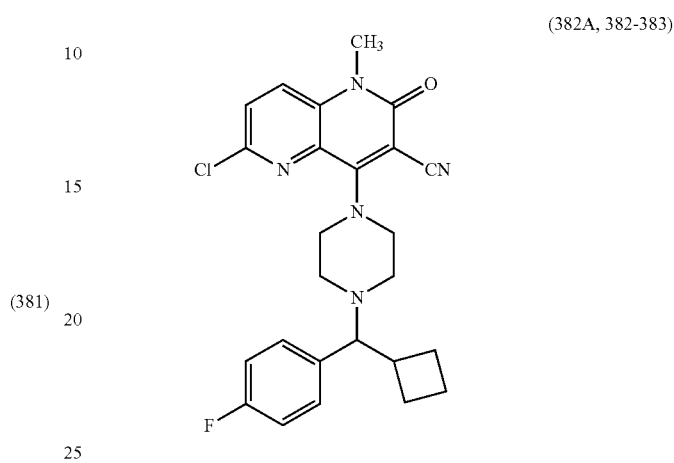

(382A, 382-383)

Example 382A were prepared according to the general method used to prepare Example 68. The compound (24.6 mg) was isolated in 63.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 466.12; Retention Time: 2.39 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 466.08; Retention Time: 1.38 min. The racemic material was separated by using SFC-chiral chromatography to afford Example 382 (first eluting isomer) and Example 383 (second eluting isomer).

Example 382: The compound (7.7 mg) was isolated in 19.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.5%; Observed Mass: 466.06; Retention Time: 2.63 mi Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 95.4%; Observed Mass: 466.08; Retention Time: 1.55 min.

Example 383: The compound (7.7 mg) was isolated in 19.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.7%; Observed Mass: 466.04; Retention Time: 2.63 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.2%; Observed Mass: 466.08; Retention Time: 1.55 min.

Example 384

4-{4-[(3-tert-butyl-2-hydroxyphenyl)methyl]piperazin-1-yl}-6-chloro-1-methyl-2-oxo-1,2-dihydro-1,5-naphthyridine-3-carbonitrile

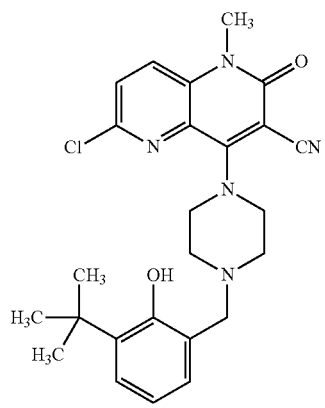

(384)

Example 384 was prepared according to the general method used to prepare Example 216. The compound (1.3 mg) was isolated in 7.3% yield. Analytical LC/MS was used to determine the final purity. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 mi hold at 100% B; Flow: 1 mL/min; Detection: MS and UV (220 nm). Injection 2 results: Purity: 100.0%; Observed Mass: 466.17; Retention Time: 1.86 min.

Example 385

6-chloro-1-methyl-1-{4-4[(3-methylphenyl)methyl]piperazin-1-yl}-2-oxo-1,2-dihydro-1,5-naphthyridine-3-carbonitrile

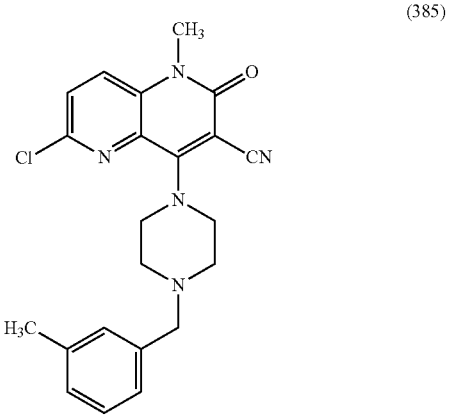 [SMILES: Cc1cccc(CN2CCN(c3c(C#N)c(=O)n(C)c4ccc(Cl)nc34)CC2)c1]

(385)

Example 385 was prepared according to the general method used to prepare Example 216. The compound (9.5 mug) was isolated in 48.5% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 408.12; Retention Time: 1.3 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 408.13; Retention Time: 2.08 min.

Example 386

6-chloro-1-methyl-4-{4-[(4-methylphenyl)methyl]piperazin-1-yl}-2-oxo-1,2-dihydro-1,5-naphthyridine-3-carbonitrile

Examples 387A, 387, and 388

6-chloro-4-{4-[1-(4-fluorophenyl)ethyl]piperazin-1-yl}-1-methyl-2-oxo-1,2-dihydro-1,5-naphthyridine-3-carbonitrile

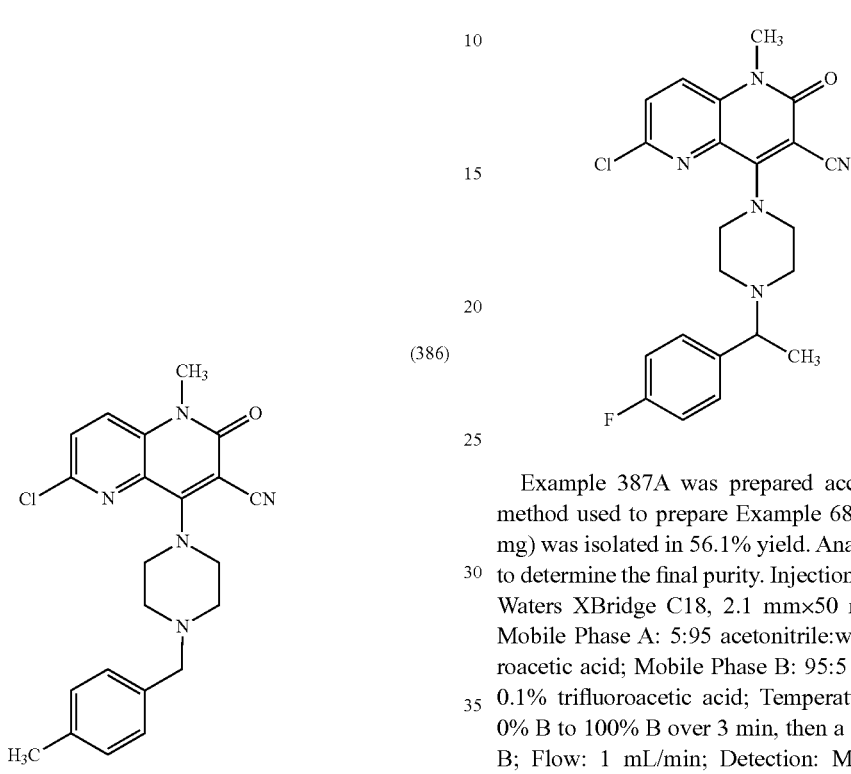

Example 386 was prepared according to the general method used to prepare Example 216. The compound (18.8 mg) was isolated in 29% yield. Two analytical LC/MS injections were used to determine the final purity. Injection 1 conditions: Column: Waters Acquity UPLC BEH C18, 2.1×50 mm, 1.7 pin particles Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm.

Example 387A was prepared according to the general method used to prepare Example 68. The compound (16.5 mg) was isolated in 56.1% yield. Analytical LC/IS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 425.97; Retention Time: 1.37 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 425.98; Retention Time: 2 min. The racemic material was further purified by using SFC-chiral chromatography to afford Example 387 (first eluting isomer) and Example 388 (second eluting isomer).

Example 387: The compound (4.4 mg) was isolated in 15.9% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mi M ammonium acetate; Temperature: 50° C.: Gradient: 0% B to 100% B over 3 min, then a 0.75 min hold at 100% B; Flow: 1 mL/min; Detection: MS and UV (220 nm). Injection 1 results: Purity: 98.4%; Observed Mass: 426.18; Retention Time: 2.05 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.7%; Observed Mass: 426.21; Retention Time: 1.15 min.

Example 388: The compound (1.7 mg) was isolated in 6.1% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.1%; Observed Mass: 426.16; Retention Time: 2.05 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.8%; Observed Mass: 426.2; Retention Time: 1.15 min.

Example 389

4-{4-[(3-chloro-2-hydroxyphenyl)methyl]piperazin-1-yl}-1,6-dimethyl-2-oxo-1,2-dihydro-1,5-naphthyridine-3-carbonitrile

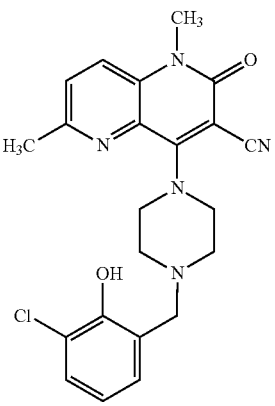

(389)

Example 389 was prepared according to the general method used to prepare Example 216 from 1,6-dimethyl-2-oxo-4-(piperazin-1-li)-1,2-dihydro-1,5-naphthyridine-3-carbonitrile. The compound (4.4 mg) was isolated in 10.8% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 424.14; Retention Time: 1.51 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 424.11; Retention Time: 2.39 min.

Example 390

6-bromo-4-{4-[(2-chloro-6-hydroxyphenyl)methyl]piperazin-1-yl}-1-methyl-2-oxo-1,2-dihydro-1,5-naphthyridine-3-carbonitrile

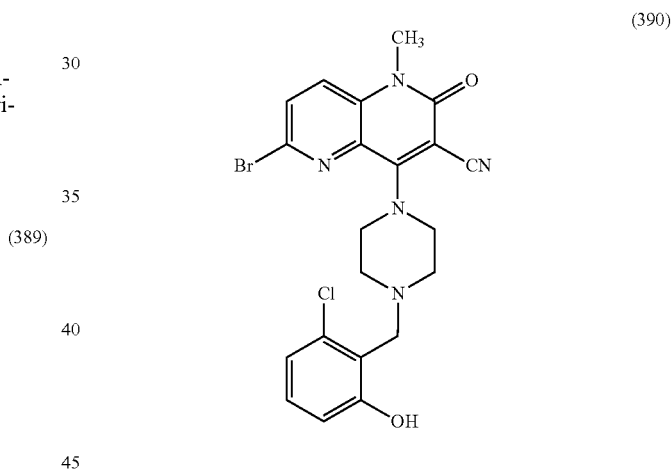

(390)

Example 390 was prepared according to the general method used to prepare Example 2. The compound (0.8 mg) was isolated in 4.7% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 488; Retention Time: 1.25 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 488; Retention Time: 2.14 mm.

Example 391

6-chloro-4-{4-[(2-hydroxy-3-methylphenyl)methyl]piperazin-1-yl}-1-methyl-2-oxo-1,2-dihydro-1,5-naphthyridine-3-carbonitrile

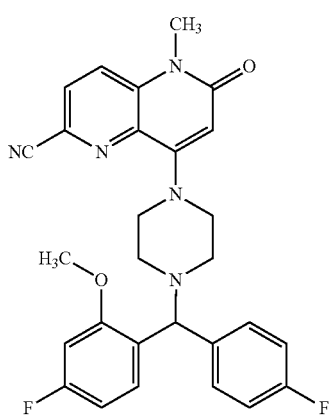

(391)

Example 391 was prepared according to the general method used to prepare Example 216. The compound (5.6 mg) was isolated in 34.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 424.08; Retention Time: 2.12 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 424.08; Retention Time: 1.23 min.

Example 392

8-{4-[(4-fluoro-2-methoxyphenyl)(4-fluorophenyl)methyl]piperazin-1-yl}-5-methyl-6-oxo-5,6-dihydro-1,5-naphthyridine-2-carbonitrile

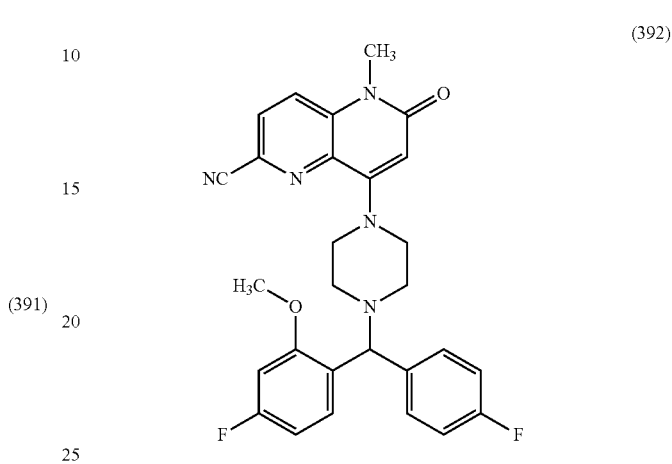

(392)

In a 1 dram vial, 8-chloro-5-methyl-6-oxo-5,6-dihydro-1,5-naphthyridine-2-carbonitrile (19.8 mg, 0.090 mmol) was suspended in DMF (0.9 mL). To this mixture were added 1-((4-fluoro-2-methoxyphenyl)(4-fluorophenyl)methyl)piperazine, 2 HC (42.3 mg, 0.108 mmol) and potassium carbonate (62.3 mg, 0.451 mmol). The reaction mixture was sealed under nitrogen and immersed in oil bath at 120° C. for 6 hrs. LC/MS analysis displayed a new peak with molecular weight for the desired product. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 27% B, 27-77% B over 25 minutes, then a 4-minute hold at 100% B; Flow Rate: 20 mL/min; Column Temperature: 25 C. Fraction collection was triggered by MS and UV signals. Fractions containing the product were combined and dried via centrifugal evaporation. The compound (12.7 mg) was isolated in 28.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% N trifluoroacetic acid; Temperature: 50° C.; Gradient: 0% B to 100%/(B over 3 min, then a 0.75 min hold at 100% B; Flow: 1 mL/min; Detection: MS and UV (220 nm). Injection 1 results: Purity: 100.0%; Observed Mass: 502.19; Retention Time: 1.47 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 ruin hold at 100% B; Flow: 1 mL/min; Detection: MS and UV (220 nm). Injection 2 results: Purity: 100.0%; Observed Mass: 502.19; Retention Time: 2.27 min. $^1$H NMR (500 MHz, DMSO-$d_6$)

δ 8.21-8.12 (m, 1.0H), 8.10-8.03 (m, 1.0H), 7.60 (br t, J=7.6 Hz, 1.0H), 7.45-7.38 (m, 2.1H), 7.13 (br t, J=8.7 Hz, 2.1H), 6.87 (br d, J=11.3 Hz, 1.0H), 6.81 (br t, J=8.2 Hz, 1.1H), 6.09 (s, 1.0H), 4.76 (s, 1.0H), 3.80 (s, 2.9H), 3.53 (s, 1.9H), 3.47 (br s, 0.9H), 2.60-2.53 (m, 2.0H), 2.47-2.39 (m, 2.0H).

Example 393

4-{4-[bis(4-chlorophenyl)methyl]piperazin-1-yl}-6-bromo-1-methyl-2-oxo-1,2-dihydro-1,5-naphthyridine-3-carbonitrile

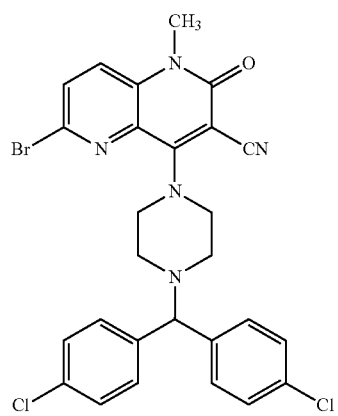

(393)

The title compound was prepared according to the general method used to prepare Example 191. The compound (35.8 mg) was isolated in 61.4% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 582.01; Retention Time: 2.01 min. Injection 2 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 581.98; Retention Time: 2.72 min.

Example 394

8-{4-[bis(4-chlorophenyl)methyl]piperazin-1-yl}-5-methyl-6-oxo-5,6-dihydro-1,5-naphthyridine-2,7-dicarbonitrile

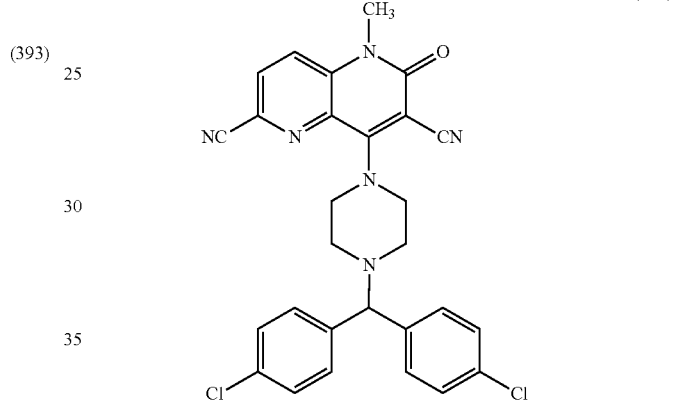

(394)

Example 394 was prepared according to the general method used to prepare Example 325. The compound (8.4 mg) was isolated in 58.8% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 529.13; Retention Time: 2.52 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.9%; Observed Mass: 529.11; Retention Time: 1.89 min.

Example 395

4-{4-[bis(4-chlorophenyl)methyl]piperazin-1-yl}-6-methoxy-1-methy-2-oxo-1,2-dihydro-1,5-naphthyridine-3-carbonitrile

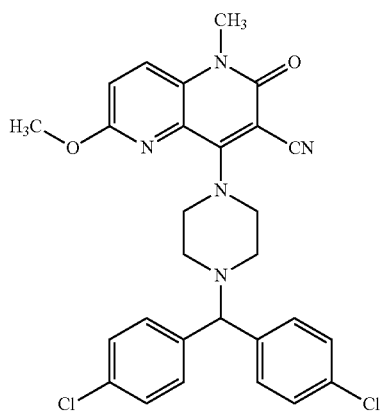

(395)

Into a microwave vial were added 4-(4-(bis(4-chlorophenyl)methyl)piperazin-1-yl)-6-bromo-1-methyl-2-oxo-1,2-dihydro-1,5-naphthyridine-3-carbonitrile (15 mg, 0.026 mmol), palladium(II) acetate (0.577 mg, 2.57 µmol), cesium carbonate (8.38 mg, 0.026 mmol) and 5-[di(1-adamantyl)phosphino]-1',3',5'-triphenyl-1'h-[1,4']bipyrazole (3.41 mg, 5.14 µmol). The vial was placed under vacuum, refilled the nitrogen and sealed. Methanol (0.1 mL) and acetonitrile (2 mL) were added and the reaction mixture was heated at 80° C. overnight. LC/MS analysis indicated completion of the reaction. The crude material was purified via preparative LC/MS with the following conditions: Column: XBridge C18, 200 mm×19 mm, 5 µm particles; Mobile Phase A: 5:95 acetonitrile:water with 0.1% trifluoroacetic acid: Mobile Phase B: 95:5 acetonitrile water with 0.1% trifluoroacetic acid; Gradient: a 0-minute hold at 28%/p B, 28-68% B over 20 minutes, then a 5 minute hold at 100% B; Flow Rate: 20 mL/min; Column Temperature: 25 C. Fraction collection was triggered by MS and UV signals. Fractions containing the product were combined and dried via centrifugal evaporation. The title compound (13.5 mg) was isolated in 97.2% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 534.17; Retention Time: 2.59 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 534.17; Retention Time: 1.87 min.

Example 396

4-{4-[(4-fluorophenyl)(2-methoxypyridin-3-yl)methyl]piperazin-1-yl}-6-methoxy-1-methyl-2-oxo-1,2-dihydro-1,5-naphthyridine-3-carbonitrile

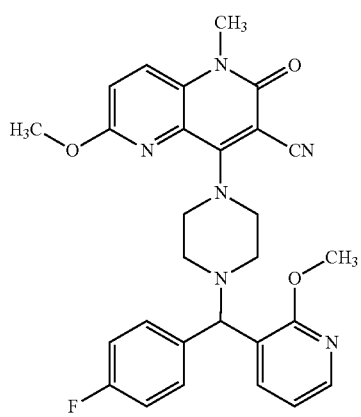

(396)

In a 2 mL sealed vial, 6-methoxy-1-methyl-2-oxo-4-(piperazin-1-yl)-1,2-dihydro-1,5-naphthyridine-3-carbonitrile (30 mg, 0.100 mmol), (4-fluorophenyl)(2-methoxypyridin-3-yl)methanol (28.1 mg, 0.120 mmol), (cyanomethyl)trimethylphosphonium iodide (48.7 mg, 0.200 mmol) were combined in propionitrile (0.8 mL). Hunig's Base (0.053 mL, 0.301 mmol) was added and the reaction mixture was sealed and heated at 110° C. in a microwave reactor for 4 hours. LC/MS analysis indicated completion of the reaction. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 32% B, 32-72% B over 25 minutes, then a 4-minute hold at 100% B; Flow Rate: 20 mL/min; Column Temperature: 25 C. Fraction collection was triggered by MS and UV signals. Fractions containing the product were combined and dried via centrifugal evaporation. The compound (11.4 mg) was isolated in 22.2% yield. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0% B to 100% B over 3 min, then a 0.75 min hold at 100% B; Flow: 1 mL/min; Detection: MS and UV (220 nm). Injection 1 results: Purity: 98.2%; Observed Mass: 515.2; Retention Time: 2.14 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.2%; Observed Mass: 515.22 Retention Time: 1.41 min.

Example 397

4-{4-[(4-fluorophenyl)(3-methoxypyridin-2-yl)methyl]piperazin-1-yl}-6-methoxy-1-methyl-2-oxo-1,2-dihydro-1,5-naphthyridine-3-carbonitrile

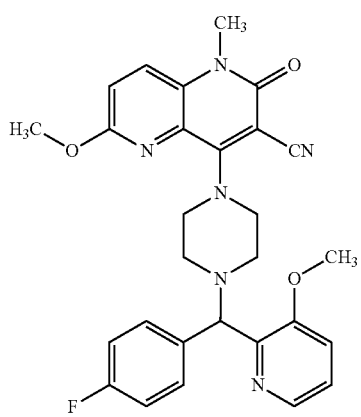

(397)

Example 397 was prepared according to the general method used to prepare Example 396. The compound (4.8 mg) was isolated in 9.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: NIS and UV (220 nm). Injection 1 results: Purity: 99.1%; Observed Mass: 515.13; Retention Time: 1.86 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.9%; Observed Mass: 515.13; Retention Time: 1.36 min.

Examples 398, 398A, and 398B

4-{4-[1-(4-fluorophenyl)propyl]piperazin-1-yl}-1,6-dimethyl-2-oxo-1,2-dihydro-1,5-naphthyridine-3-carbonitrile

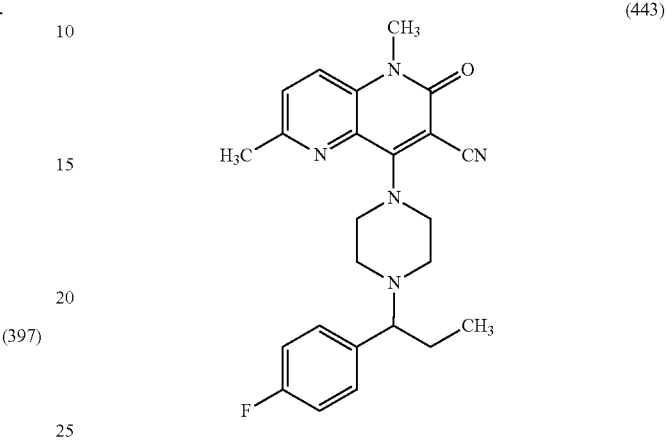

(443)

Example 398 was prepared according to the general method used to prepare Example 226. The compound (28.8 mg) was isolated in 64.2% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 420.18; Retention Time: 2.08 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.9%; Observed Mass: 420.18; Retention Time: 1.37 min. The racemic material was further purified by using SFC-chiral chromatography to afford Example 398A (first eluting isomer) and Example 398B (second eluting isomer).

Example 398A (9.5 mg) was isolated in 33.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 420.11; Retention Time: 2.21 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 420.31; Retention Time: 1.23 min.

Example 398B (10.2 ng) was isolated in 36.3% yield. Analytical LC/MS was used to determine the final purity. Injection 1 conditions: Column: Waters XBridge C18, 2.1 mm×50 nm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 420.1; Retention Time: 2.21 min. Injection 2 conditions: Column: Waters XBridge C18, 2.1 mm×50 mm, 1.7 μm particles: Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 420.29; Retention Time: 1.23 min.

Example 399

8-{4-[(S)-(4-chlorophenyl)(phenyl)methyl]piperazin-1-yl}-5-methyl-7-nitro-6-oxo-5,6-dihydro-1,5-naphthyridine-2-carbonitrile

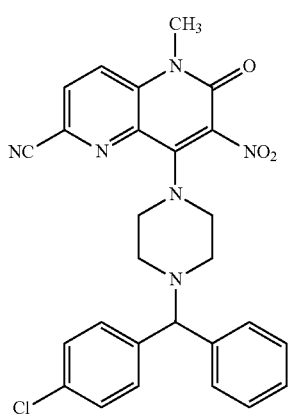

(399)

Example 399 was prepared according to the general method used to prepare Example 18. The compound (8.5 mg) was isolated in 43.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate: Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 515.14; Retention Time: 2.5 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid: Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 515.17; Retention Time: 1.72 min.

Example 400

8-{4-[(4-fluorophenyl)(pyridin-2-yl)methyl]piperazin-1-yl}-5-methyl-6-oxo-5,6-dihydro-1,5-naphthyridine-2,7-dicarbonitrile

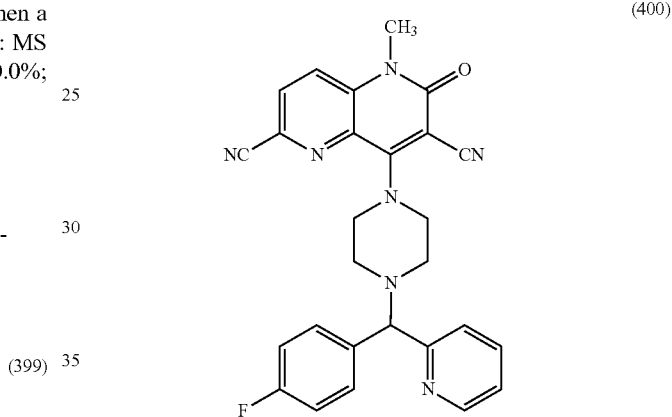

(400)

Example 400 was prepared from 5-methyl-6-oxo-8-(piperazin-1-yl)-5,6-dihydro-1,5-naphthyridine-2,7-dicarbonitrile in according to the general procedure used for the preparation of Example 396. The compound (5.5 mg) was isolated in 23.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.9%; Observed Mass: 480.16; Retention Time: 1.81 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.1%; Observed Mass: 480.16; Retention Time: 1.29 min.

Example 401

4-{4-[(4-fluoro-2-methoxyphenyl)(pyrimidin-2-yl)methyl]piperazin-1-yl}-6-methoxy-1-methyl-2-oxo-1,2-dihydro-1,5-naphthyridine-3-carbonitrile

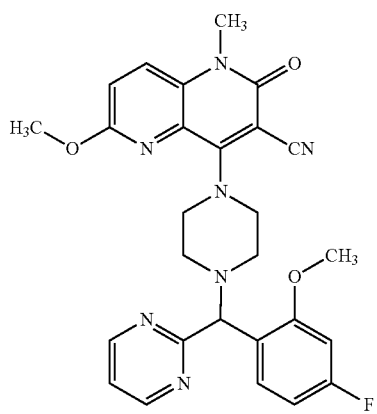
(401)

Example 401 was prepared according to the general method used to prepare Example 396. The compound (12.6 mg) was isolated in 24.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.1%; Observed Mass: 516.21; Retention Time: 1.64 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C. Gradient: 0% B to 100% B over 3 min, then a 0.75 min hold at 100% B; Flow: 1 mL/min; Detection: MS and UV (220 nm). Injection 2 results: Purity: 96.8%; Observed Mass: 516.2; Retention Time: 1.22 min.

Example 402

4-{4-[bis(4-fluoro-2-methoxyphenyl)methyl]piperazin-1-yl}-6-methoxy-1-methyl-2-oxo-1,2-dihydro-1,5-naphthyridine-3-carbonitrile

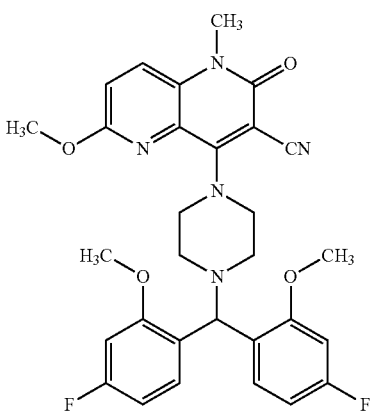
(402)

Example 402 was prepared according to the general method used to prepare Example 396. The compound (33.9 mg) was isolated in 60.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 5622; Retention Time: 1.56 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 562.19; Retention Time: 2.31 min.

Example 403

4-{4-[(4-fluorophenyl)(pyridin-2-yl)methyl]piperazin-1-yl}-6-methoxy-1-methyl-2-oxo-1,2-dihydro-1,5-naphthyridine-3-carbonitrile

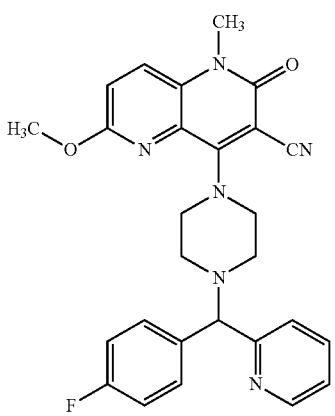
(403)

Example 403 was prepared according to the general method used to prepare Example 396. The compound (10.8 mg) was isolated in 22.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.6%; Observed Mass: 485.17; Retention Time: 1.85 min. Injection 2 conditions: Column: Waters XBridge C18, 2.1 mm×50 mm, 1.7 μm particles; Mobile Phase A: 5:95 acetonitrile:water with 0.1% r trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.9%; Observed Mass: 485.18; Retention Time: 1.32 min.

Example 404

5-methyl-8-{4-[(naphthalen-1-yl)methyl]piperazin-1-yl}-6-oxo-5,6-dihydro-1,5-naphthyridine-2,7-dicarbonitrile

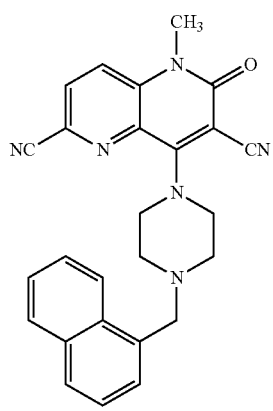
(404)

Example 404 was prepared according to the general method used to prepare Example 52 from 6-bromo-1-methyl-4-(4-(naphthalen-1-ylmethyl)piperazin-1-yl)-2-oxo-1,2-dihydro-1,5-naphthyridine-3-carbonitrile. The compound (3.7 mg) was isolated in 8.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C. Gradient: 0% B to 100% B over 3 min, then a 0.75 min hold at 100% B; Flow: 1 mL/min; Detection: MS and UV (220 nm). Injection 1 results: Purity: 90.2%; Observed Mass: 435.14; Retention Time: 1.27 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% NB to 100% B over 3 min, then a 0.75 min hold at 100% B; Flow: 1 mL/min; Detection: MS and UV (220 nm). Injection 2 results: Purity: 90.1%; Observed Mass: 435.16; Retention Time: 2.07 min.

Examples 405-407

8-{4-[(4-fluoro-2-methoxyphenyl)(4-fluorophenyl)methyl]piperazin-1-yl}-5-methy-6-oxo-5,6-dihydro-l,5-naphthyridine-2,7-dicarbonitrile

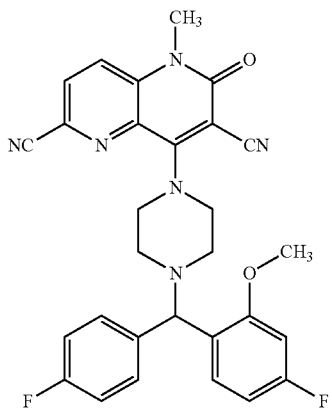

(405-407)

Example 405-407 were prepared according to the general method used to prepare Example 52 from 6-bromo-4-(4-((4-fluoro-2-methoxyphenyl)(4-fluorophenyl)methyl) piperazin-1-yl)-1-methyl-2-oxo-1,2-dihydro-1,5-naphthyridine-3-carbonitrile. The compound (12.1 mg) was isolated in 33.3% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 955 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.8%; Observed Mass: 527.16; Retention Time: 1.65 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.1% r; Observed Mass: 527.17; Retention Time: 2.24 min. The racemic material was further purified by using SFC-chiral chromatography to afford Example 406 (first eluting isomer) and Example 407 (second eluting isomer).

Example 406: The title compound (3.5 mg) was isolated in 31.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.2%; Observed Mass: 527.08; Retention Time: 2.15 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.9%; Observed Mass: 526.97; Retention Time: 2.06 min.

Example 407: The title compound (27.8 mg) was isolated in 61.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 527.14; Retention Time: 1.5 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 527.14; Retention Time: 2.25 min.

Example 408

5-methyl-8-{4-[(4-methylphenyl)(phenyl)methyl]piperazin-1-yl}-6-oxo-5,6-dihydro-1,5-naphthyridine-2,7-dicarbonitrile

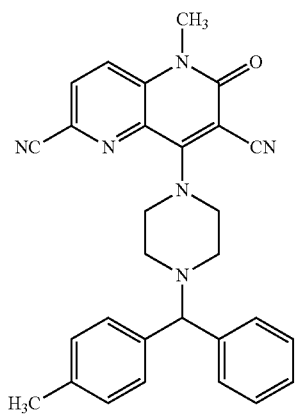

(408)

Example 408 was prepared according to the general method used to prepare Example 52. The compound (2.6 ng) was isolated in 45.7% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100%

B: Flow: 1 mL/min; Detection: MS and UV (220 nm). Injection 1 results: Purity: 100.0%; Observed Mass: 475.25; Retention Time: 1.52 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.1%; Observed Mass: 475.24; Retention Time: 2.32 min.

Example 409

8-{4-[bis(4-fluoro-2-methoxyphenyl)methyl]piperazin-1-yl}-5-methyl-6-oxo-5,6-dihydro-1,5-naphthyridine-2,7-dicarbonitrile

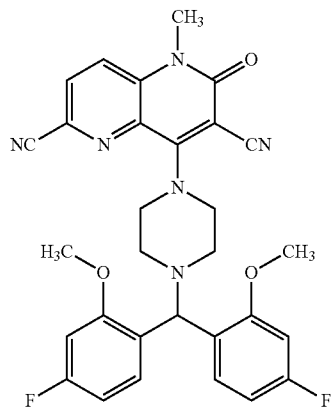

(409)

Example 409 was prepared according to the general method used to prepare Example 396. The compound (0.8 mg) was isolated in 2.9% yield. Analytical LC/MS was used to determine the final purity. Injection 1 conditions: Column: Waters XBridge CIS, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.0%; Observed Mass: 557.21; Retention Time: 1.56 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 557.17; Retention Time: 2.24 min.

Example 410

8-{4-[(4-fluorophenyl)(3-methoxypyridin-2-yl)methyl]piperazin-1-yl}-5-methyl-6-oxo-5,6-dihydro-1,5-naphthyridine-2,7-dicarbonitrile

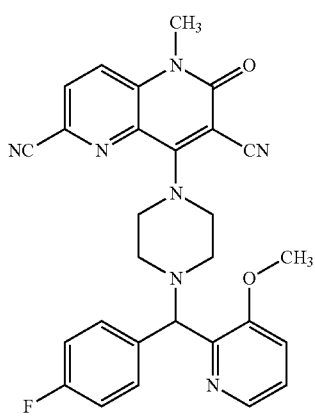

(410)

Example 410 was prepared according to the general method used to prepare Example 396. The compound (1.9 mg) was isolated in 7.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.7%; Observed Mass: 510.22; Retention Time: 1.83 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.4%; Observed Mass: 510.19; Retention Time: 1.36 min.

Example 411

8-{4-[(4-fluorophenyl)(phenyl)methyl]piperazin-1-yl}-5-methyl-6-oxo-5,6-dihydro-1,5-naphthyridine-2,7-dicarbonitrile

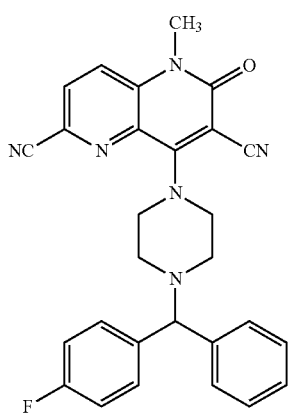

(411)

Example 411 was prepared according to the general method used to prepare Example 52. The compound (11.6 mg) was isolated in 48.5% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.9%; Observed Mass: 479.2; Retention Time: 1.48 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 479.21; Retention Time: 2.22 min.

Example 412

4-{4-[(4-fluoro-2-methoxyphenyl)(4-fluorophenyl)methyl]piperazin-1-yl}-6-methoxy-1-methyl-2-oxo-1,2-dihydro-1,5-naphthyridine-3-carbonitrile

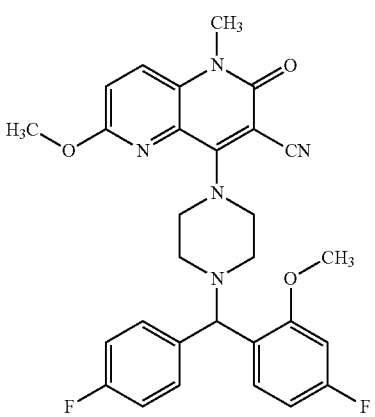

(412)

Example 412 was prepared according to the general method used to prepare Example 395 from racemic 1-((4-fluoro-2-methoxyphenyl)(4-fluorophenyl)methyl) piperazine. The compound (8.4 ng) was isolated in 19.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 532.2; Retention Time: 1.54 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 532.18; Retention Time: 2.3 min.

Example 413

4-{4-[(4-fluoro-2-methoxyphenyl)(4-fluorophenyl)methyl]piperazin-1-yl}-6-methoxy-1-methyl-2-oxo-1,2-dihydro-1,5-naphthyridine-3-carbonitrile

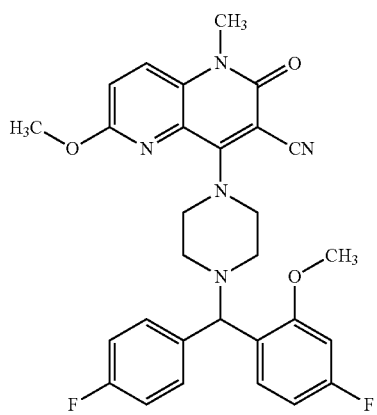

(413)

Example 413 was prepared according to the general method used to prepare Example 395 from homochiral 1-((4-fluoro-2-methoxyphenyl)(4-fluorophenyl)methyl) piperazine (Intermediate 110). The compound (13.8 mg) was isolated in 60.4% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 532.18; Retention Time: 2.32 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 mu). Injection 2 results: Purity: 100.0%; Observed Mass: 532.19; Retention Time: 1.53 min.

Example 414

8-{4-[(S)-(4-chlorophenyl)(phenyl)methyl]piperazin-1-yl}-5-methyl-6-oxo-5,6-dihydro-1,5-naphthyridine-2,7-dicarbonitrile

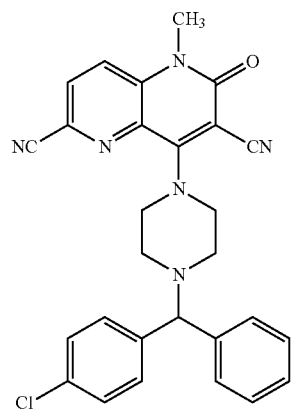

(414)

Example 414 was prepared according to the general method used to prepare Example 52. The compound (10 mg) was isolated in 63.1% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 96.9%; Observed Mass: 495.12; Retention Time: 2.33 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100 ?% B; Flow: 1 mL/min; Detection: MS and UV (220 nm). Injection 2 results: Purity: 97.4%; Observed Mass: 495.14; Retention Time: 1.62 min.

Example 415

5-methyl-8-{4-[(naphthalen-1-yl)methyl]piperazin-1-yl}-7-nitro-6-oxo-5,6-dihydro-1,5-naphthyridine-2-carbonitrile

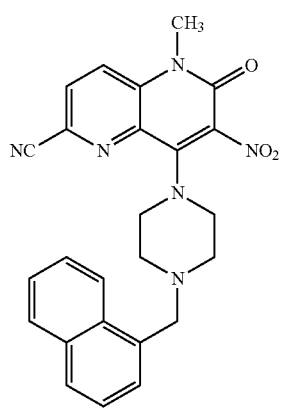

(415)

Example 416

8-{4-[(4-fluorophenyl)(2-methoxy-4-methylphenyl)methyl]piperazin-1-yl}-5-methyl-7-nitro-6-oxo-5,6-dihydro-1,5-naphthyridine-2-carbonitrile

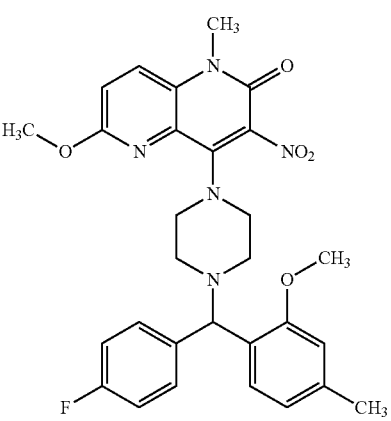

(416)

Example 415 was prepared according to the general method used to prepare Example 18. The compound (10.1 mg) was isolated in 390 yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 99.0%; Observed Mass: 455.13; Retention Time: 1.34 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: mL/min; Detection: MS and UV (220 nm). Injection 2 results: Purity: 99.0%; Observed Mass: 455.13; Retention Time: 2.31 min.

Example 416 was prepared according to the general method used to prepare Example 18. The compound (21.7 mg) was isolated in 52.6% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 543.2; Retention Time: 2.48 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 543.22; Retention Time: 1.64 min.

Example 417

6-chloro-4-{4-[(4-chlorophenyl)methyl]piperazin-1-yl}-1-methyl-2-oxo-1,2-dihydro-1,5-naphthyridine-3-carbonitrile

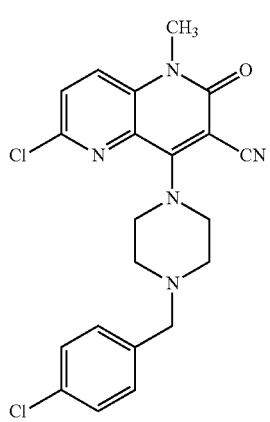

(417)

To a solution of 6-chloro-1-methyl-2-oxo-4-(piperazin-1-yl)-1,2-dihydro-1,5-naphthyridine-3-carbonitrile, 2 HCl (15 mg, 0.040 mmol) in DMF (1.5 mL), 4-chlorobenzaldehyde (8.40 mg, 0.060 mmol) was added. The reaction mixture was stirred at room temperature for 1 hour. Sodium cyanoborohydride (7.51 mg, 0.119 mmol) was added and the reaction mixture was stirred at room temperature for overnight. The reaction mixture was diluted with methanol, filtered and a light yellow solid was obtained as the final product (2.6 mg, 5.77 µmol, 14.5% yield). Analytical LC/MS conditions: Column: Phenomenex LUNA C18, 2.0×50 mm, 3 µm particles; Mobile Phase A: 10:90 methanol: water with 0.1%0 TFA; Mobile Phase B: 90:10 methanol:water with 0.10% TFA; Gradient: 0-100% B over 4 minutes, then a 1 minute hold at 100% B. Flow: 0.8 mL/min; Detection: UV at 220 nm. LC/MS Results: Retention Time=2.6 min.; Obs. Adducts: [M+H]; Obs. Masses: 427.9. Analytical HPLC conditions: Column: XTERRA 3.0×50 mm s7; Mobile Phase A: 10:90 acetonitrile:water with 0.1% TFA; Mobile Phase B: 90:10 acetonitrile:water with 0.1% TFA; Gradient: 0-100% B over 4 minutes, then a 2 minute hold at 100% B; Flow: 5 mL/min; Detection: UV at 220 nm. HPLC result: 100% pure.

Example 418

8-{4-[(2-hydroxyphenyl)(phenyl)methyl]piperazin-1-yl}-5-methyl-6-oxo-5,6-dihydro-1,5-naphthyridine-2,7-dicarbonitrile

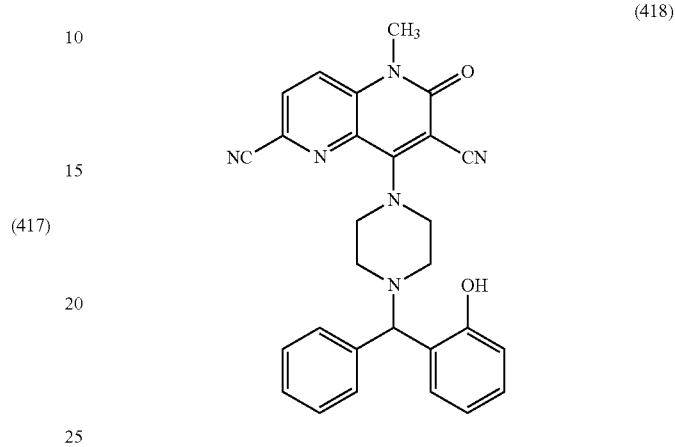

(418)

Example 418 was prepared according to the general method used to prepare Example 52. The compound (1.2 mg) was isolated in 12% yield. Analytical LC/MS conditions: Column: Phenomenex LUNA C18, 2×50 mm, 3 µm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS Results: Retention Time=3.2 min.; Obs. Adducts: [M+H]; Obs. Masses: 477.1

Example 419

6-chloro-4-{4-[(2-chloro-6-methylphenyl)methyl]piperazin-1-yl}-1-methyl-2-oxo-1,2-dihydro-1,5-naphthyridine-3-carbonitrile

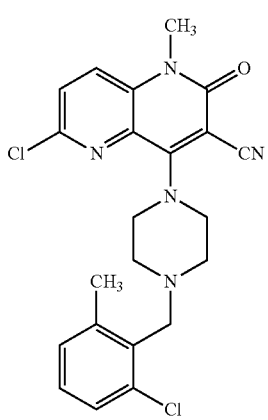

(419)

Example 419 was prepare according to the general method used to prepare Example 417. The compound (6.8 mg) was isolated in 28% yield. Analytical LC/MS conditions: Column: Phenomenex LUNA C18, 2×50 mm, 3 μm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS Results: Retention Time=3.7 min.; Obs. Adducts: [M+H]; Obs. Masses: 442.0.

Example 420

6-chloro-4-{4-[(2-chloro-6-fluoro phenyl)methyl]piperazin-1-yl}-1-methyl-2-oxo-1,2-dihydro-1,5-naphthyridine-3-carbonitrile

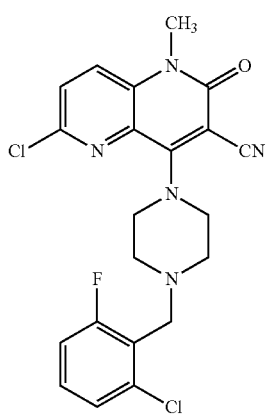

(420)

Example 420 was prepared according to the general method used to prepare Example 417. The compound (10.1 mg) was isolated in 42.7% yield. Analytical LC/MS conditions: Column: Phenomenex LUNA C18, 2.0×50 mm, 3 μm particles; Mobile Phase A: 10:90 methanol: water with 0.1% TFA; Mobile Phase B: 90:10 methanol:water with 0.1% TFA; Gradient: 0-100% B over 4 minutes, then a 1 minute hold at 100% B; Flow: 0.8 mL/min; Detection: UV at 220 nm. LC/MS Results: Retention Time=2.4 min.; Obs. Adducts: [M+H]; Obs. Masses: 445.9.

Example 421

6-chloro-4-{4-[1-(4-fluorophenyl)cyclopropyl]piperazin-1-yl}-1-methyl-2-oxo-1,2-dihydro-1,5-naphthyridine-3-carbonitrile

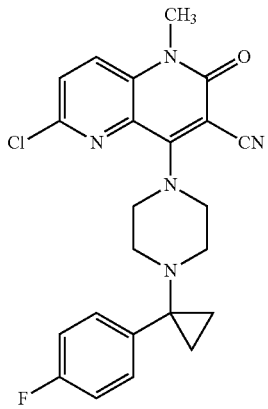

(421)

Example 421 was prepared according to the general method used to prepare Example 193 from 4,6-dichloro-1-methyl-2-oxo-1,2-dihydro-1,5-naphthylidine-3-carbonitrile. The compound (14.1 mg) was isolated in 54.5% yield. Analytical LC/MS conditions: Column: Phenomenex LUNA C18, 2 mm×50, 3 μm particles; Mobile Phase A: 5% acetonitrile: 95% water: 10 mM ammonium acetate; Mobile Phase B: 95% acetonitrile: 5% water: 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS Results: Retention Time=3.5 min.; Obs. Adducts: [M+H]; Obs. Masses: 438.0.

Example 422

6-chloro-4-{4-[(2,6-difluorophenyl)methyl]piperazin-1-yl}-1-methyl-2-oxo-1,2-dihydro-1,5-naphthyridine-3-carbonitrile

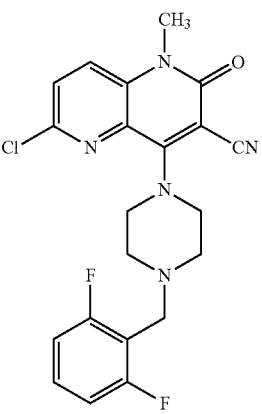

(422)

Example 422 was prepared according to the general method used to prepare Example 417. The compound (7.3 mg) was isolated in 300 yield. Analytical LC/MS conditions: Column: Phenomenex LUNA C18, 2.0×50 mm, 3 μm particles; Mobile Phase A: 10:90 methanol: water with 0.1% TFA; Mobile Phase B: 90:10 methanol: water with 0.1% TFA; Gradient: 0-100% B over 4 minutes, then a 1 minute hold at 100% B; Flow: 0.8 mL/min; Detection: UV at 220 nm. LC/MS Results: Retention Time=2.2 min.; Obs. Adducts: [M+H]; Obs. Masses: 429.9.

Example 423

6-chloro-4-{4-[(2-fluoro-4-methylphenyl)methyl] piperazin-1-yl}-1-methyl-2-oxo-1,2-dihydro-1,5-naphthyridine-3-carbonitrile

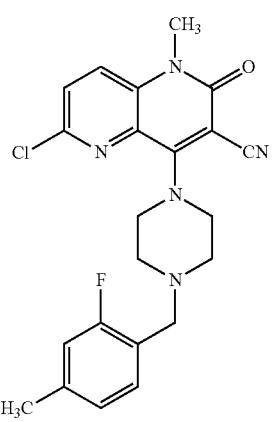

(423)

Example 423 was prepared according to the general method used to prepare Example 417. The compound (9.4 mg) was isolated in 40.3% yield. Analytical LC/MS conditions: Column: Phenomenex LUNA C18, 2 mm×50, 3 μm particles; Mobile Phase A: 5% acetonitrile: 95% water: 10 mM ammonium acetate; Mobile Phase B: 95% acetonitrile: 5% water: 10 mM ammonium acetate; Temperature: 40; Gradient: 0-100% B over 4 minutes, then a 1 minute hold at 100% B; Flow: 0.8 mL/min; Detection: UV at 220 min. LC/MS Results: Retention Time=3.2 min.; Obs. Adducts: [M+H]; Obs. Masses: 426.1.

Example 424

6-chloro-4-{4-[(4-cyano-2-methoxyphenyl)methyl] piperazin-1-yl}-1-methyl-2-oxo-1,2-dihydro-1,5-naphthyridine-3-carbonitrile

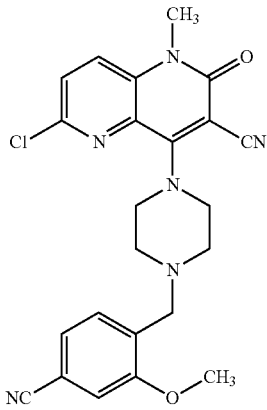

(424)

Example 424 was prepared according to the general method used to prepare Example 417. The compound (10.2 mg) was isolated in 41.5% yield. Analytical LC/MS conditions: Column: Phenomenex LUNA C18, 2 mm×50, 3 μm particles; Mobile Phase A: 5% acetonitrile: 95% water: 10 nM ammonium acetate; Mobile Phase B: 95% acetonitrile: 50% water: 10 mM ammonium acetate; Temperature: 40° C.; Gradient: 0-100% B over 4 minutes, then a 1 minute hold at 100% B; Flow: 0.8 mL/min; Detection: UV at 220 nm. LC/MS Results: Retention Time=2.9 min.; Obs. Adducts: [M+H]; Obs. Masses: 449.1.

Example 425

6-chloro-4-{4-[2-(4-fluorophenyl)propan-2-yl]piperazin-1-yl}-1-methyl-2-oxo-1,2-dihydro-1,5-naphthyridine-3-carbonitrile

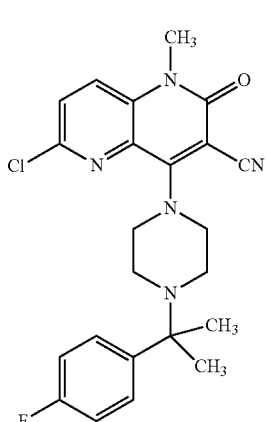

(425)

Example 425 was prepared according to the general method used to prepare Example 193 from 4,6-dichloro-1- methyl-2-oxo-1,2-dihydro-1,5-naphthylidine-3-carbonitrile. The compound (11.8 mg) was isolated in 52.0% yield. Analytical LC/MS conditions: Column: Phenomenex LUNA C18, 2.0×50 mm, 3 μm particles; Mobile Phase A: 10:90 methanol: water with 0.1%0 TFA; Mobile Phase B: 90:10 methanol:water with 0.1% TFA; Gradient: 0-100% B over 4 minutes, then a 1 minute hold at 100% B; Flow: 0.8 mL/min; Detection: UV at 220 nm. LC/MS Results: Retention Time=3.0 min.; Obs. Adducts: [M+H]; Obs. Masses: 439.9.

Example 426

4-(4-(bis(4-fluorophenyl)methyl)piperazin-1-yl)-1-methyl-1,5-naphthyridin-2(1H)-one

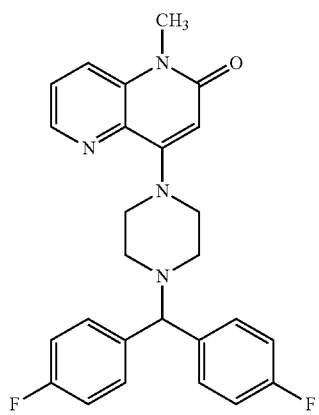

(426)

A solution was prepared by dissolving 4-chloro-1-methyl-1,5-naphthyridin-2(1H)-one (12.3 mg, 0.063 mmol) in DMF (632 μL). Next, 1-(4,4'-difluorobenzhydryl) piperazine (22.9 mg, 0.079 mmol) and potassium carbonate (18.7 mg, 0.135 mmol) were added. The reaction mixture was placed under a nitrogen atmosphere and heated at 80° C. for 18 hours. HPLC analysis indicated approximate 50% conversion to product. To the reaction mixture was added potassium carbonate (8.2 mg, 0.059 mmol). The reaction mixture was capped under nitrogen and heated at 85° C. for 19 hours. The crude material was purified via preparative LC/MS with the following conditions: Column: XBridge C18, 19×200 rum, 5 μm particles; Mobile Phase A: 5:95 acetonitrile:water with 10 mM ammonium acetate; Mobile Phase B: 95:5 acetonitrile:water with 10 mM ammonium acetate; Gradient: 50-90% B over 15 minutes, then a 5 minute hold at 100% B; Flow: 20 mL/min. Fractions containing the desired product were combined and dried via centrifugal evaporation. The yield of the product was 21.1 rug, and its estimated purity by LCMS analysis was 100%. Two analytical LC/MS injections were used to determine the final purity. Injection 1 conditions: Column: Waters Acquity UPLC BEH C18, 2.1×50 mm, 1.7 μm particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Injection 2 conditions: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. LCMS: Column: Waters Acquity UPLC BEH C18, 2.1×50 mm, 1.7 μm particles; Mobile Phase A: 5:95 acetonitrile: water with 0.1% trifluoroacetic acid: Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.0 mL/min; Detection: UV at 220 nm. Retention Time=1.42 min. Obs. Adducts: [M+H]; Obs. Masses: 447.1. LCMS: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75 minute hold at 100% B; Flow: 1.0 mL/min; Detection: UV at 220 nm. Retention Time=2.25 min.; Obs. Adducts: [M+H]; Obs. Masses: 447.1. Proton NMR signal intensities proximal to the water suppression frequency were affected and were uncorrected: $^1$H NMR (DMSO-$d_6$) δ 8.42 (d, J=2.9 Hz, 1H), 791 (d, J=8.8 Hz, 1H), 7.57 (dd, J=8.8, 4.4 Hz, 1H), 7.48 (dd, J=8.6, 5.7 Hz, 4H), 7.14 (t, J=8.8 Hz, 4H), 5.98 (s, 1H), 4.47 (s, 1H), 3.51 (s, 2H).

Example 427

4-{4-[bis(4-fluorophenyl)methyl]piperazin-1-yl}-1,6-dimethyl-1,2-dihydro-1,5-naphthyridin-2-one

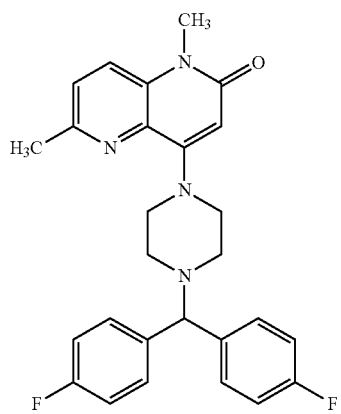

(427)

In a 20 mL vial, 2nd generation RuPhos precatalyst (CAS No. 1375325-68-0, 27.9 mg, 0.036 mmol), 4-chloro-1,6-dimethyl-1,5-naphthyridin-2(1H)-one (150 mg, 0.719 mmol), 1-(4,4'-difluorobenzhydryl)piperazine (249 mg, 0.863 mmol) and cesium carbonate (703 mg, 2.157 mmol) were combined in 7.1 mL of solvent (DMA/t-BuOH; 1:4). The mixture was capped under a nitrogen atmosphere and heated at 90° C. for 72 hours. LC/MS analysis showed the reaction was complete. The volatiles were removed in vacuo using a rotary evaporator/vacuum pump combination. The residue suspended in DCM and CHCl$_3$ and filtered through a plug of celite. The mixture was adsorbed onto 1.3 g of silica gel and chromatographed on 13.6 g of silica gel slurry loaded in 15% ethyl acetate in dichloromethane, eluted with 15% ethyl acetate in dichloromethane. After drying under vacuum, the title compound (217 mg) was isolated in 62.3% yield. $^1$H NMR (chloroform-d) δ 7.56 (d, J=8.7 Hz, 1H), 7.38-7.43 (m, 4H), 7.29 (d, J=8.7 Hz, 1H), 6.97-7.03 (m, 4H), 6.16 (s, 1H), 4.31 (s, 1H), 3.62 (s, 3H), 3.57 (br. s., 4H), 2.63 (t, J=4.8 Hz, 4H), 2.57 (s, 3H).

Example 428

6-bromo-4-{4-[(S)-(4-chlorophenyl)(phenyl)methyl] piperazin-1-yl}-1-methyl-2-oxo-1,2-dihydro-1,5-naphthyridine-3-carbonitrile

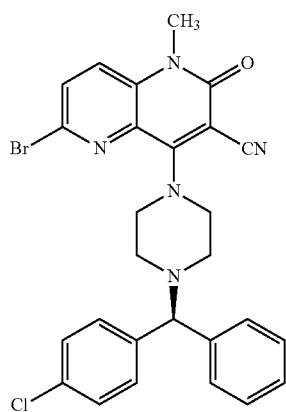

(428)

Example 428 was prepared according to the general method used to prepare Example 393 from (S)-1-((4-chlorophenyl)(phenyl)methyl)piperazine. The compound (23 mg) was isolated in 41.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 548.07; Retention Time: 2.59 min. Injection 2 conditions: Column: Waters XBridge C18, 2.1 mm×50 mm, 1.7 μm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 548.06; Retention Time: 1.72 min.

Example 429

6-bromo-4-{4-[(4-chlorophenyl)(phenyl)methyl] piperazin-1-yl}-1-methyl-2-oxo-1,2-dihydro-1,5-naphthyridine-3-carbonitrile

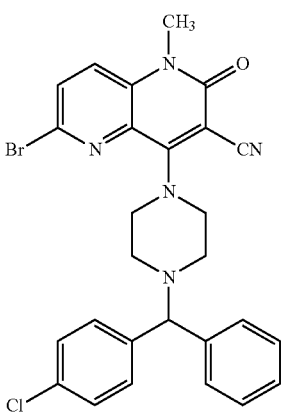

(429)

Example 429 was prepared according to the general method used to prepare Example 393 from racemic 1-((4-chlorophenyl)(phenyl)methyl)piperazine. The compound (29 mg) was isolated in 52.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 548.09; Retention Time: 1.73 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 548.06; Retention Time: 2.56 min.

Example 430

6-bromo-4-{4-[(4-fluorophenyl)(phenyl)methyl]piperazin-1-yl}-1-methyl-2-oxo-1,2-dihydro-1,5-naphthyridine-3-carbonitrile

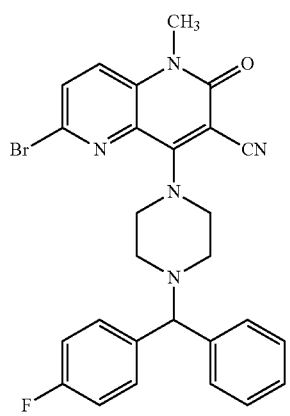

(430)

Example 430 was prepared according to the general method used to prepare Example 393 from racemic 1-((4-fluorophenyl)(phenyl)methyl)piperazine. The compound (30.8 mg) was isolated in 57.8% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 532.08; Retention Time: 2.41 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 532.09; Retention Time: 1.58 min.

Example 431

6-bromo-1-methyl-4-{4-[(4-methylphenyl)(phenyl)methyl]piperazin-1-yl}-2-oxo-1,2-dihydro-1,5-naphthyridine-3-carbonitrile

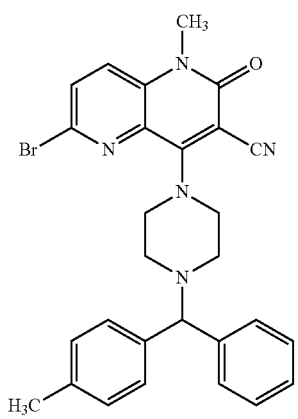

(431)

Example 431 was prepared according to the general method used to prepare Example 393. The compound (12.1 mg) was isolated in 22.9% yield. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 94.8%; Observed Mass: 528.15; Retention Time: 1.6 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 94.9%; Observed Mass: 528.09; Retention Time: 2.54 min.

Example 432

8-{4-[bis(4-fluorophenyl)methyl]piperazin-1-yl}-5-methyl-6-oxo-5,6-dihydro-1,5-naphthyridine-2-carbonitrile

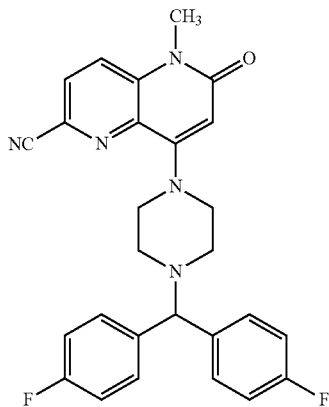
(432)

Example 432 was isolated as the major product in the attempted synthesis of (4-(4-(bis(4-fluorophenyl)methyl)piperazin-1-yl)-6-cyano-1-methyl-2-oxo-1,2-dihydro-1,5-naphthyridin-3-yl)boronic acid. To a −78° C. solution. of 8-(4-(bis(4-fluorophenyl) methyl)piperazin-1-yl)-7-bromo-5-methyl-6-oxo-5,6-dihydro-1,5-naphthyridine-2-carbonitrile (0.065 g, 0.118 mmol) in THF (1.181 mL) was added, dropwise, a 2.5 M solution of n-butyllithium (0.052 mL, 0.130 mmol). The reaction mixture was stirred at −78° C. for 1 hour, followed by the addition of trimethyl borate (0.020 mL, 0.177 mmol). The reaction mixture was stirred at −78° C. for 30 min, and then at room temperature for 16 hours. LC/MS analysis showed the hydro-dehalogenated product. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 37% B, 37-77% B over 22 minutes, then a 5-minute hold at 100% B; Flow Rate: 20 mL/min; Column Temperature: 25° C. Fraction collection was triggered by MS and UV signals. Fractions containing the product were combined and dried via centrifugal evaporation. The compound (22.6 mg) was isolated in 40.6% yield. Analytical LC/MS was used to determine the final purity Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.6%; Observed Mass: 472.18; Retention Time: 1.46 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 97.3%; Observed Mass: 472.19; Retention Time: 2.23 min.

Biological Assays

The pharmacological properties of the compounds of this invention may be confirmed by a number of biological assays. The exemplified biological assays, which follow, have been carried out with compounds of the invention.

1. In vitro DGK Inhibition Assays

The DGKα and DGKζ reactions were performed using either extruded liposome (DGKα and DGKζ LIPGLO assays) or detergent/lipid micelle substrate (DGKα and DGKζ assays). The reactions were carried out in 50 mM MOPS pH 7.5, 100 mM NaCl, 10 mM $MgCl_2$, 1 μM $CaCl_2$, and 1 mM DTT (assay buffer). The reactions using a detergent/lipid micelle substrate also contained 50 mM octyl B-D-glucopyranoside. The lipid substrate concentrations were 11 mM PS and 1 mM DAG for the detergent/lipid micelle reactions. The lipid substrate concentrations were 2 nM PS, 0.25 mM DAG, and 2.75 mM PC for the extruded liposome reactions. The reactions were carried out in 150 μM ATP. The enzyme concentrations for the DGKα and DGKζ were 5 nM The compound inhibition studies were carried out as follows: 50 nL droplets of each test compound (top concentration 10 mM with 11 point, 3-fold dilution series for each compound) solubilized in DMSO were transferred to wells of a white 1536 well plate (Corning 3725). A 5 mL enzyme/substrate solution at 2× final reaction concentration was prepared by combining 2.5 mL 4× enzyme solution (20 nM DGKα or DGKζ (prepared as described below) in assay buffer) and 2.5 mL of either 4× liposome or 4× detergent/lipid micelle solution (compositions described below) and incubated at room temperature for 10 minutes. Next, 1 μL 2× enzyme/substrate solution was added to wells containing the test compound and reactions were initiated with the addition of 1 μL 300 uM ATP. The reactions were allowed to proceed for 1 hr, after which 2 μL Glo Reagent (Promega V9101) was added and incubated for 40 minutes. Next, 4 μL Kinase Detection Reagent was added and incubated for 30 minutes. Luminescence was recorded using an EnVision microplate reader. The percent inhibition was calculated from the ATP conversion generated by no enzyme control reactions for 100% inhibition and vehicle-only reactions for 0% inhibition. The compounds were evaluated at 11 concentrations to determine $IC_{50}$.

4× Detergent/Lipid Micelle Preparation

The detergent/lipid micelle was prepared by combining 15 g phosphatidylserine (Avanti 840035P) and 1 g diacylglycerol (800811O) and dissolving into 150 mL chloroform in a 2 L round bottom flask. Chloroform was removed under high vacuum by rotary evaporation. The resulting colorless, tacky oil was resuspended in 400 mL 50 mM MOPS pH 7.5, 100 mM NaCl, 20 mM NaF, 10 mM $MgCl_2$, 1 μM $CaCl_2$), 1 mM DTT, and 200 mM octyl glucoside by vigorous mixing. The lipid/detergent solution was split into 5 mL aliquots and stored at −80° C.

4× Liposome Preparation

The lipid composition was 5 mol % DAG (Avanti 800811O), 40 mol % PS (Avanti 840035P), and 55 mol % PC (Avanti 850457) at a total lipid concentration of 15.2 mg/mL for the 4× liposome solution. The PC, DAG, and PS were dissolved in chloroform, combined, and dried in vacuo to a thin film. The lipids were hydrated to 20 mM in 50 mM MOPS pH 7.5, 100 mM NaCl, 5 mM $MgCl_2$, and were freeze-thawed five times. The lipid suspension was extruded through a 100 nm polycarbonate filter eleven times. Dynamic light scattering was carried out to confirm liposome size (50-60 nm radius). The liposome preparation was stored at 4° C. for as long as four weeks.

Baculovirus Expression of Human DGKα and DGKζ

Human DGK-alpha-TVMV-His-pFBgate and human DCK-zeta-transcript variant-2-TVMV-His-pFBgate baculovirus samples were generated using the Bac-to-Bac baculovirus expression system (Invitrogen) according to the manufacturer's protocol. The DNA used for expression of DGK-alpha and DGK-zeta have SEQ ID NOs: 1 and 3, respectively. Baculovirus amplification was achieved using infected Sf9 cells at 1:1500 virus/cell ratios, and grown for 65 hours at 27° C. post-transfection.

The expression scale up for each protein was carried out in the Cellbag 50 L WAVE-Bioreactor System 20/50 from GE Healthcare Bioscience. 12 L of $2×10^6$ cells/mL Sf9 cells (Expression System, Davis, Calif.) grown in ESF921 insect medium (Expression System) were infected with virus stock at 1:200 virus/cell ratios, and grown for 66-68 hours at 27° C. post-infection. The infected cell culture was harvested by centrifugation at 2000 rpm for 20 min 4° C. in a SORVALL® RC12BP centrifuge. The cell pellets were stored at −70° C. until purification.

Purification of Human DGK-Alpha and DGK-Zeta

Full length human DGKα and DGKζ, each expressed containing a TVMV-cleavable C-terminal Hexa-His tag sequence (SEQ ID NOs: 2 and 4, respectively) and produced as described above, were purified from Sf) baculovirus-infected insect cell paste. The cells were lysed using nitrogen cavitation method with a nitrogen bomb (Parr Instruments), and the lysates were clarified by centrifugation. The clarified lysates were purified to ~90% homogeneity, using three successive column chromatography steps on an ÄKTA Purifier Plus system. The three steps column chromatography included nickel affinity resin capture (i.e. HisTrap FF crude, GE Healthcare), followed by size exclusion chromatography (i.e. HiLoad 26/600 Superdex 200 prep grade, GE Healthcare for DGK-alpha, and HiPrep 26/600 Sephacryl S 300_HR, GE Healthcare for DGK-zeta). The third step was ion exchange chromatography, and differed for the two isoforms. DGKα was polished using Q-Sepharose anion exchange chromatography (GE Healthcare). DGKζ was polished using SP Sepharose cation exchange chromatography (GE Healthcare). The proteins were delivered at concentrations of ≥2 mg/mL. The formulation buffers were identical for both proteins: 50 mM Hepes, pH 7.2, 500 mM NaCl, 10% v/v glycerol, 1 mM TCEP, and 0.5 mM EDTA.

2. Raji CD4 T Cell IL2 Assay

A 1536-well IL-2 assay was performed in 4 µl volume using pre-activated CD4 T cells and Raji cells. Prior to the assay, CD4 T cells were pre-activated by treatment with α-CD3, α-CD28 and PHA at 1.5 µg/mL, 1 µg/mL, and 10 µg/mL, respectively. Raji cells were treated with Staphylococcal enterotoxin B (SEB) at 10,000 ng/mL. Serially diluted compounds were first transferred to 1536-well assay plate (Corning, #3727), followed by addition of 2 µl of pre-activated CD4 T cells (final density at 6000 cells/well) and 2 µl of SEB-treated Raji cells (2000 cells/well). After 24 hours incubation at a 37° C./5% $CO_2$ incubator, 4 µl of IL-2 detection reagents were added to the assay plate (Cisbio, #64IL2PEC). The assay plates were read on an Envision reader. To assess compound cytotoxicity, either Raji or CD4 T cells were incubated with the serially diluted compounds. After 24 hours incubation, 4 µl of Cell Titer Glo (Promega, #G7572) were added, and the plates were read on an Envision reader. The 50% effective concentration ($IC_{50}$) was calculated using the four-parameter logistic formula y=A+ ((B−A)/(1+((C/x)^D))), where A and B denote minimal and maximal % activation or inhibition, respectively, C is the $IC_{50}$, D is hill slope and x represent compound concentration.

3. CellTiter-Glo CD8 T Cell Proliferation Assay

Frozen naïve human CD8 T cells were thawed in RPMI+ 10% FBS, incubated for 2 h in 37° C., and counted. The 384-well tissue culture plate was coated overnight at 4° C. with 20 µl anti-human CD3 at 0.1 µg/mL in plain RPMI, which was removed off the plate before 20 k/40 µl CD8 T cells with 0.5 µg/mL soluble anti-human CD28 were added to each well. The compounds were echoed to the cell plate immediately after the cells were plated. After 72 h incubation at 37° C. incubator, 10 µl CellTiter-glo reagent (Promega catalog number G7570) was added to each well. The plate was vigorously shaken for 5 mins, incubated at room temperature for another 15 mins and read on Envision for CD8 T cell proliferation. In analysis, 0.1 µg/mL anti-CD3 and 0.5 µg/mL anti-CD28 stimulated CD8 T cell signal was background. Example 40 at 3 µM was used to set the 100% range and $EC_{50}$ was at absolute 50% to normalize the data.

4. DGK AP1-Reporter Assay

The Jurkat AP1-luciferase Reporter was generated using the Cignal Lenti AP1 Reporter (luc) Kit from SABiosciences (CLS-011L).

The compounds were transferred from an Echo LDV plate to individual wells of a 384-well plate (white, solid-bottom, opaque PE CulturPlate 6007768) using an Echo550 instrument. The sample size was 30 nl per well; and one destination plate per source plate. The cell suspensions were prepared by transferring 40 mL cells (2×20 mL) to clean 50 mL conical tubes. The cells were concentrated by centrifugation (1200 rpm; 5 mins; ambient temperature). The supernatant was removed and all cells were suspended in RPMI (Gibco 11875)+10% FBS to make a $1.35×10^6$ cells/mL concentration. The cells were added manually using a multichannel pipette, 30 µl/well of cell suspension to a 384-well TC plate containing the compounds, $4.0×10^4$ cells per well. The cell plates were incubated for 20 minutes at 37° C., and 5% $CO_2$.

During the incubation, anti-CD3 antibody (αCD3) solutions were prepared by mixing 3 µl αCD3 (1.3 mg/mL) with 10 mL medium [final conc=0.4 µg/mL]. Next, 1.5 µl αCD3 (1.3 mg/mL) was mixed with 0.5 mL medium [final conc=4 µg/mL]. After 20 minutes, 10 µl medium was added to all wells in column 1, wells A to M, and 10 μl αCD3 (4 μg/mL) per well was added in column 1, rows N to P for reference. Then using a multi-channel pipette, 10 μl αCD3 (0.4 μg/mL) per well was added. The αCD3 stimulated +/− compound-treated cells were incubated at 37° C., 5% $CO_2$ for 6 hours.

During this incubation period. Steady-Glo (Promega E2520) reagent was slowly thawed on to ambient temperature. Next, 20 μl Steady-Glo reagent per well was added using a multi-drop Combi-dispenser. Bubbles were removed by centrifugation (2000 rpm, ambient temperature, 10 secs). The cells were incubated at room temperature for 5 minutes. Samples were characterized by measuring the Relative Light Units (RLU) with an using Envision Plate Reader Instrument on a luminescence protocol. The data was analyzed using the compound of Example 40 to normalize 100% inhibition.

5. Murine Cytotoxic T Lymphocyte Assay

An antigen-specific cytolytic T-cell (CTL) assay was developed to evaluate functionally the ability of DGKα and DGKζ inhibitors to enhance effector T cell mediated tumor cell killing activity. CD8+ T-cells isolated from the OT-1 transgenic mouse recognize antigen presenting cells, MC38, that present the ovalbumin derived peptide SIINFEKL. Recognition of the cognate antigen initiates the cytolytic activity of the OT-1 antigen-specific CD8+ T cells.

Functional CTL cells were generated as follows: OT-1 splenocytes from 8-12 week old mice were isolated and expanded in the presence of the SIINFEKL peptide at 1 μg/mL and mIL2 at 10 U/mL. After three days, fresh media with mIL2 U/mL was added. On day 5 of the expansion, the CD8+ T cells were isolated and ready for use. Activated CTL cells may be stored frozen for 6 months. Separately, one million MC38 tumor cells were pulsed with 1 μg/mL of SIINFEKL-OVA peptide for 3 hours at 37° C. The cells were washed (3×) with fresh media to remove excess peptide. Finally, CTL cells that were pretreated with DGK inhibitors for 1 hour in a 96-well U bottom plate were combined with the antigen loaded MC38 tumor cells at a 1:10 ratio. The cells were then spun at 700 rpm for 5 min and placed in an incubator overnight at 37° C. After 24 hours, the supernatant was collected for analysis of IFN-γ cytokine levels by AlphaLisa purchased from Perkin Elmer.

6. PHA Proliferation Assay

Phytohaemagglutinin (PHA)-stimulated blast cells from frozen stocks were incubated in RPMI medium (Gibco, ThermoFisher Scientific, Waltham, Mass.) supplemented with 10% fetal bovine serum (Sigma Aldrich, St. Louis, Mo.) for one hour prior to adding to individual wells of a 384-well plate (10,000 cells per well). The compounds were transferred to individual wells of a 384-well plate and the treated cells are maintained at 37° C., 5% $CO_2$ for 72 h in culture medium containing human IL2 (20 ng/mL) prior to measuring growth using MTS reagent [3-(4,5-dimethyl-2-yl)-5-(3-carboxymethoxyphenyl)-2-(4-sulfophenyl)-2H-tetrazolium] following manufacturer's instructions (Promega, Madison, Wis.). Percent inhibition was calculated comparing values between IL2 stimulated (0% inhibition) and unstimulated control (100% inhibition). Inhibition concentration ($IC_{50}$) determinations were calculated based on 50% inhibition on the fold-induction between IL2 stimulated and unstimulated treatments.

7. Human CD8 T cells IFN-γ Assay

Frozen naïve human CD8 T cells were thawed in ATM-V media, incubated for 2 h in 37° C., and counted. The 384-well tissue culture plate was coated overnight at 4° C. with 20 μl anti-human CD3 at 0.05 μg/mL in PBS, which was removed off the plate before 40,000 cells per 40 microliters CD8 T cells with 0.1 μg/mL soluble anti-human CD28 were added to each well. The compounds were transferred using an Echo liquid handler to the cell plate immediately after the cells were plated. After 20 h incubation at 37° C. incubator, 3 microliters per well supernatants transferred into a new 384-well white assay plate for cytokine measurement.

Interferon-γ (IFN-γ) was quantitated using the AlphaLISA kit (Cat #AL217) as described by the manufacturer manual (Perkin Elmer). The counts from each well were converted to IFN-γ concentration (μg/mL). The compound $EC_{50}$ values were determined by setting 0.05 μg/mL anti-CD3 plus 0.1 μg/mL anti-CD28 as the baseline, and co-stimulation of 3 μM Example 40 with anti-CD3 plus anti-CD28 as 100% activation.

8. Human CD8 T cells pERK Assay

Frozen naïve human CD8 T cells were thawed in AIM-V media, incubated for 2 h in 37° C., and counted. The CD8 positive T cells were added to 384-well tissue culture plate at 20,000 cells per well in AIM-V media. One compound was added to each well, then bead bound anti-human CD3 and anti-CD28 mAb were added at final concentration of 0.3 μg/mL. The cells were incubated at 37° C. for 10 minutes. The reaction was stopped by adding lysis buffer from the AlphaLISA Surefire kit. (Perkin Elmer, cat #ALSU-PERK-A). Lysate (5 μL per well) was transferred into a new 384-well white assay plate for pERK activation measurement.

Compound $EC_{50}$ was determined as setting anti-CD3 plus anti-CD28 as baseline, and co-stimulation of 3 μM Example 40 with anti-CD3 plus anti-CD28 as 100% activation.

9. Human Whole Blood IFN-γ Assay

Human venous whole blood (22.5 μL per well), obtained from healthy donors, was pre-treated with compounds for one hour at 37° C. in a humidified 95% air/5% $CO_2$ incubator. The blood was stimulated with 2.5 μL anti-human CD3 and anti-CD28 mAb at a final concentration of 1 μg/mL each for 24 hours at 37° C. IFN-γ in the supernatants was measured using AlphaLISA kit (Cat #AL217).

Compound $EC_{50}$ determined as setting anti-CD3 plus anti-CD28 as baseline, and co-stimulation of 3 μM Example 40 with anti-CD3 plus anti-CD28 as 10% activation.

TABLE 1

| | In vitro DGK Inhibition $IC_{50}$ Activity Vallies | | | |
|---|---|---|---|---|
| Ex. No. | DGKα LIPGLO $IC_{50}$ (μM) | DGKζ LIPGLO $IC_{50}$ (μM) | DGKα $IC_{50}$ (μM) | DGKζ $IC_{50}$ (μM) |
| 2 | — | — | 0.049 | >240 |
| 3 | 3.8 | 2.3 | 2.1 | >240 |
| 6 | — | — | 6.5 | >240 |
| 7 | — | — | 0.5 | 120 |
| 8 | 0.41 | 5.4 | 0.16 | 20 |
| 9 | — | — | 3.8 | >240 |
| 10 | 0.31 | 3.9 | 0.12 | 23 |

TABLE 1-continued

In vitro DGK Inhibition IC$_{50}$ Activity Vallies

| Ex. No. | DGKα LIPGLO IC$_{50}$ (μM) | DGKζ LIPGLO IC$_{50}$ (μM) | DGKα IC$_{50}$ (μM) | DGKζ IC$_{50}$ (μM) |
|---|---|---|---|---|
| 11 | 1.8 | 1.8 | 0.45 | 4 |
| 12 | — | — | 1 | >81 |
| 13 | 5.4 | — | 9.5 | >240 |
| 14 | 4.7 | 3.2 | 1.2 | >240 |
| 15 | — | — | 0.55 | 58 |
| 16 | 4.3 | 27 | 6.4 | >240 |
| 17 | 3.5 | 9.4 | 0.93 | 180 |
| 18 | — | — | 0.96 | 2.5 |
| 19 | — | — | 13 | 19 |
| 20 | — | — | 3.3 | 4.3 |
| 21 | — | — | 22 | 94 |
| 22 | — | — | 0.07 | >81 |
| 23 | 1.9 | 13 | 0.61 | >240 |
| 24 | 0.15 | 90 | 0.034 | >240 |
| 25 | — | — | 0.041 | >81 |
| 26 | 6.7 | 18 | 4.3 | 85 |
| 27 | 0.11 | >240 | 0.11 | >240 |
| 28 | — | — | 1.3 | >81 |
| 29 | — | — | 0.57 | >240 |
| 30 | — | — | 1.8 | 140 |
| 31 | — | — | 1.2 | >240 |
| 32 | — | — | 0.19 | 9.4 |
| 33 | 1.7 | 1.7 | 0.75 | 7.6 |
| 34 | 0.29 | 3.4 | 0.18 | 23 |
| 35 | 0.99 | 81 | 0.14 | >240 |
| 36 | 6.8 | 18 | 1.4 | 68 |
| 37 | — | — | 1.8 | 38 |
| 39 | — | — | 50 | >240 |
| 40 | 3.4 | 0.21 | 1.9 | 1.3 |
| 43 | — | — | 0.037 | 6.3 |
| 44 | 0.37 | 1.3 | 0.23 | 8.9 |
| 45 | 0.39 | 6.8 | 0.1 | 36 |
| 46 | — | — | 8.5 | 2.7 |
| 47 | — | — | 1.8 | >81 |
| 48 | 3.9 | 4.5 | >240 | >240 |
| 49 | — | — | 0.18 | >240 |
| 50 | 2.1 | 5.7 | 0.99 | 39 |
| 51 | 0.33 | 4.7 | 0.18 | 56 |
| 52 | — | — | 7.8 | 150 |
| 53 | — | — | 1.5 | 16 |
| 54 | 3.1 | 1.3 | 0.82 | 7.3 |
| 55 | 0.19 | 1.8 | — | — |
| 57 | — | — | 1.6 | 110 |
| 58 | — | — | 0.25 | 19 |
| 60 | — | — | 32 | >240 |
| 61 | — | — | 4.4 | 2.2 |
| 64 | — | — | 2.7 | 14 |
| 65 | 0.51 | 3.7 | 0.29 | 20 |
| 66 | 0.23 | 1.7 | 0.084 | 13 |
| 67 | 4.8 | 12 | 0.13 | 13 |
| 68 | — | — | 4 | 23 |
| 69 | — | — | 1.3 | 13 |
| 70 | — | — | 0.13 | 3.3 |
| 73 | — | — | 0.9 | 2.1 |
| 75 | — | — | 2.6 | 130 |
| 76 | — | — | 5.5 | 2.5 |
| 78 | — | — | 12 | >240 |
| 79 | — | — | 81 | >81 |
| 85 | — | — | 7.6 | 0.77 |
| 89 | — | — | 41 | >240 |
| 90 | >240 | 15 | 82 | 190 |
| 95 | — | — | >240 | >240 |
| 96 | — | — | 87 | 53 |
| 98 | — | — | 6.7 | 4.4 |
| 99 | 0.72 | 0.04 | 0.41 | 0.67 |
| 101 | — | — | 15 | 27 |
| 103 | 6.1 | 0.99 | — | — |
| 104 | 0.74 | 0.78 | — | — |
| 105 | — | — | 0.58 | 2.5 |
| 106 | — | — | 0.96 | 2 |
| 114 | — | — | 120 | 100 |
| 115 | — | — | 220 | >240 |
| 116 | — | — | >240 | >240 |
| 117 | — | — | 46 | 21 |
| 118 | 1.3 | 0.061 | 4.2 | 0.23 |
| 119 | — | — | 0.97 | 0.19 |
| 120 | — | — | 18 | 0.>81 |
| 121 | 6.4 | 0.055 | 1.9 | 0.>18 |
| 122 | — | — | 1 | 0.72 |
| 123 | — | — | 2.3 | 0 |
| 124 | 0.75 | 0.16 | 0.75 | 0.9 |
| 125 | 11 | 2.3 | 4.3 | 7.9 |
| 126 | — | — | 6.1 | 0.33 |
| 127 | 2.9 | 0.03 | 4.2 | 0.25 |
| 128 | 18 | 0.048 | 21 | 1.5 |
| 129 | — | — | 4.2 | 0.18 |
| 130 | — | 0.31 | 30 | 1.9 |
| 131 | — | — | 11 | 0.37 |
| 132 | — | — | 3.3 | 0.15 |
| 133 | — | — | 3.3 | 0.14 |
| 134 | — | — | 31 | 4.2 |
| 135 | — | — | 0.18 | 1.3 |
| 136 | 0.79 | 0.21 | 0.21 | 0.87 |
| 137 | 1.5 | 0.85 | 0.28 | 4.8 |
| 138 | — | — | 32 | 0.73 |
| 139 | — | — | 0.41 | 0.91 |
| 140 | 2.7 | 0.13 | 0.64 | 0.6 |
| 141 | 0.58 | 1.4 | 0.27 | 8.9 |
| 143 | 3.4 | 1.1 | 1.3 | 4.2 |
| 144 | — | — | 0.53 | 7.9 |
| 145 | — | — | 30 | 2.3 |
| 146 | — | — | >240 | 36 |
| 147 | — | — | 76 | 3.6 |
| 148 | — | — | 15 | 28 |
| 149 | — | — | 47 | 86 |
| 150 | — | — | 73 | 88 |
| 151 | 7.3 | 3.1 | 38 | 27 |
| 152 | — | — | 150 | 3.9 |
| 153 | — | — | 180 | 76 |
| 154 | 81 | 72 | 45 | >240 |
| 155 | 71 | 63 | 24 | 230 |
| 156 | — | — | 170 | 140 |
| 157 | — | — | 53 | 26 |
| 158 | — | — | >240 | >240 |
| 159 | — | — | 120 | >240 |
| 160 | — | — | 180 | 160 |
| 161 | — | — | >240 | >81 |
| 162 | — | — | 160 | >240 |
| 163 | 110 | 110 | >240 | >240 |
| 164 | 81 | 59 | >240 | >240 |
| 165 | 2.8 | 4.1 | 3.4 | 92 |
| 166 | 210 | 230 | — | — |
| 176 | >240 | 27 | — | — |
| 177 | >240 | 9.7 | — | — |
| 183 | >240 | 21 | 52 | >240 |
| 186 | — | — | >240 | >240 |
| 189 | — | — | 130 | >240 |
| 190 | — | — | 58 | >240 |
| 192 | 0.048 | 8.1 | 0.084 | >240 |
| 193 | 0.089 | 6.5 | 0.22 | >240 |
| 194 | 0.18 | 8.3 | 0.076 | 62 |
| 195 | 1.7 | 98 | 0.22 | >240 |
| 196 | 2.7 | 43 | 4 | >240 |
| 198 | — | — | 0.074 | 150 |
| 199 | — | — | 0.48 | >240 |
| 200 | — | — | 24 | >240 |
| 202 | — | — | 31 | 12 |
| 211 | — | — | 0.25 | >240 |
| 212 | — | — | 2.2 | >240 |
| 213 | — | — | 3.1 | >240 |
| 214 | — | — | 3.1 | >81 |
| 215 | — | — | 4.1 | >81 |
| 216 | 1.2 | 4.8 | 1.4 | 54 |
| 217 | 1.3 | 1.4 | 2.3 | 4.5 |
| 218 | 1.5 | 5.1 | 0.69 | >81 |
| 220 | — | — | 1.7 | 89 |
| 221 | 3.4 | 18 | 0.74 | >240 |
| 222 | — | — | 0.083 | — |

TABLE 1-continued

In vitro DGK Inhibition IC$_{50}$ Activity Vallies

| Ex. No. | DGKα LIPGLO IC$_{50}$ (μM) | DGKζ LIPGLO IC$_{50}$ (μM) | DGKα IC$_{50}$ (μM) | DGKζ IC$_{50}$ (μM) |
|---|---|---|---|---|
| 223 | 9.9 | 0.62 | 1.9 | 3.2 |
| 224 | 0.14 | 20 | 0.54 | >240 |
| 225 | 0.82 | 1.3 | 0.39 | 14 |
| 226 | 3.9 | 10 | 1.6 | 70 |
| 227 | 230 | 11 | >240 | >240 |
| 228 | >240 | 9.7 | — | >240 |
| 229 | >240 | 11 | 14 | 14 |
| 230 | — | — | 8.8 | >240 |
| 231 | — | — | 170 | >240 |
| 232 | — | — | 150 | >240 |
| 233 | 3 | 6.6 | 8.4 | >240 |
| 234 | — | — | 16 | — |
| 239 | 9.9 | 51 | 11 | >240 |
| 244 | — | — | 32 | >81 |
| 250 | 5.1 | >240 | — | — |
| 251 | >240 | 9 | — | — |
| 252 | >240 | 200 | — | — |
| 253 | 40 | 7.4 | — | — |
| 254 | 1.7 | 16 | — | — |
| 255 | 1.4 | 21 | — | — |
| 256 | 2.7 | 10 | — | — |
| 258 | 1.6 | 5.3 | 0.43 | 26 |
| 259 | 0.49 | 4 | 0.42 | 55 |
| 260 | 1.6 | 5.3 | 0.35 | — |
| 261 | 0.71 | 10 | 0.43 | >240 |
| 262 | — | — | 0.52 | >240 |
| 263 | 0.22 | 5.2 | 0.084 | 14 |
| 264 | — | — | 0.62 | >240 |
| 265 | — | — | 0.034 | 36 |
| 266 | 0.02.2 | 11 | 0.027 | >240 |
| 267 | — | — | 0.31 | >240 |
| 268 | — | — | 0.68 | 120 |
| 269 | 0.21 | 2.8 | 0.052 | 26 |
| 270 | — | — | 0.19 | >240 |
| 271 | — | — | 1.1 | 110 |
| 272 | 2.3 | 10 | 1.5 | >240 |
| 273 | 0.082 | 7.8 | 0.018 | 69 |
| 274 | 1.6 | 5.4 | 0.67 | 30 |
| 275 | 0.77 | 10 | 0.3 | 58 |
| 276 | — | — | 0.012 | >240 |
| 277 | 1.7 | 13 | 0.75 | 45 |
| 278 | — | — | 0.35 | >81 |
| 279 | 0.81 | 5.8 | 0.38 | 56 |
| 280 | — | — | 0.076 | >240 |
| 281 | 2 | 9.9 | 0.39 | 49 |
| 282 | — | — | 0.22 | >240 |
| 283 | 0.21 | 3 | 0.12 | 27 |
| 284 | — | — | 1 | >240 |
| 285 | — | — | 0.91 | >240 |
| 286 | — | — | 1.2 | 140 |
| 287 | 18 | 29 | 2.1 | >240 |
| 288 | 0.033 | 2.3 | 0.037 | >240 |
| 289 | — | — | 0.25 | >81 |
| 290 | — | — | 2.2 | >240 |
| 291 | — | — | 0.33 | >81 |
| 292 | 0.48 | 2.4 | 0.27 | 25 |
| 293 | 0.6 | 6 | 0.27 | 58 |
| 294 | — | — | 0.11 | >240 |
| 295 | 0.16 | 6.9 | 0.13 | 55 |
| 296 | — | — | 0.98 | 150 |
| 297 | — | — | 0.89 | >240 |
| 298 | — | — | 0.83 | 27 |
| 299 | — | — | 0.57 | >240 |
| 300 | 24 | 98 | 2 | >240 |
| 301 | — | — | 0.068 | >240 |
| 302 | — | — | 0.61 | >81 |
| 303 | — | — | 0.9 | >240 |
| 304 | 0.61 | 5.8 | 0.33 | 68 |
| 305 | 0.49 | 7.5 | 0.13 | 62 |
| 306 | — | — | 0.2 | >240 |
| 307 | — | — | 1.8 | >81 |
| 308 | 0.95 | 13 | 0.19 | — |
| 310 | — | — | 0.97 | >240 |
| 312 | 0.22 | 16 | 0.12 | >240 |
| 313 | 17 | 62 | 1.5 | >81 |
| 314 | — | — | 0.17 | 82 |
| 315 | — | — | 1.1 | >240 |
| 315 | >240 | 1.6 | >240 | >240 |
| 316 | 0.25 | >240 | 0.4 | >240 |
| 317 | — | — | 0.16 | 34 |
| 318 | — | — | 0.85 | 140 |
| 319 | — | — | 0.55 | 220 |
| 320 | — | — | 0.89 | >240 |
| 321 | 0.34 | 12 | 0.16 | >240 |
| 322 | — | — | 2.8 | >240 |
| 323 | 1.2 | 27 | 0.14 | 11 |
| 324 | — | — | 0.19 | >240 |
| 326 | — | — | 1.9 | >240 |
| 327 | — | — | 0.66 | 140 |
| 328 | — | — | 1 | 120 |
| 329 | 5.6 | 49 | 0.56 | 30 |
| 330 | — | — | 3.7 | >240 |
| 331 | — | — | 0.49 | >240 |
| 332 | 2.5 | 6.5 | 1.1 | 67 |
| 333 | — | — | 5 | 230 |
| 334 | 1.7 | 27 | — | — |
| 335 | 1.9 | 18 | 2.7 | >240 |
| 337 | — | — | 0.065 | >81 |
| 338 | 5.1 | 66 | 1.1 | >240 |
| 339 | — | — | 0.57 | >240 |
| 340 | 3.4 | 17 | 4.2 | >240 |
| 341 | — | — | 0.32 | >240 |
| 342 | — | — | 28 | >240 |
| 343 | — | — | 0.068 | >81 |
| 344 | — | — | 0.4 | >240 |
| 345 | — | — | 4.6 | >240 |
| 346 | — | — | 5.3 | >240 |
| 347 | 2.6 | — | — | — |
| 348 | — | — | 0.22 | 140 |
| 349 | 1.3 | 32 | — | — |
| 350 | — | — | 1.2 | >81 |
| 351 | — | — | 0.36 | 190 |
| 352 | — | — | 0.7 | >81 |
| 353 | — | — | 0.065 | >240 |
| 354 | — | — | 0.11 | >240 |
| 355 | — | — | 7.1 | >240 |
| 356 | — | — | 0.3 | >240 |
| 357 | 0.085 | 47 | 0.028 | >240 |
| 358 | >240 | >240 | — | — |
| 359 | — | — | 19 | >240 |
| 360 | — | — | 48 | >240 |
| 362 | — | — | 0.069 | >240 |
| 363 | — | — | 0.15 | >240 |
| 364 | — | — | 1.1 | >240 |
| 365 | — | — | 3.5 | 190 |
| 366 | — | — | 1.3 | 160 |
| 367 | — | — | 0.22 | >240 |
| 368 | — | — | 0.4 | >240 |
| 369 | — | — | 0.16 | >240 |
| 370 | — | — | 0.17 | >240 |
| 371 | — | — | 0.23 | 170 |
| 372 | 0.078 | 8.8 | 0.033 | 60 |
| 373 | — | — | 2.5 | 100 |
| 375 | — | — | 1.6 | >240 |
| 377 | >240 | 130 | — | — |
| 378 | 2.2 | >240 | — | — |
| 379 | — | — | 0.38 | >240 |
| 380 | — | — | 0.83 | >240 |
| 381 | 0.073 | 27 | 0.018 | >240 |
| 382 | 0.76 | >240 | — | — |
| 383 | 0.22 | >2.40 | — | — |
| 385 | — | — | 0.35 | 150 |
| 386 | 0.26 | 6.7 | 0.15 | 190 |
| 387 | — | — | 0.0041 | >240 |
| 387 | 0.27 | 1.6 | 0.46 | >240 |
| 388 | 0.051 | 130 | 0.053 | >240 |
| 389 | 1.4 | 9.4 | 0.85 | 130 |
| 390 | — | — | 0.87 | >240 |

TABLE 1-continued

In vitro DGK Inhibition IC$_{50}$ Activity Vallies

| Ex. No. | DGKα LIPGLO IC$_{50}$ (μM) | DGKζ LIPGLO IC$_{50}$ (μM) | DGKα IC$_{50}$ (μM) | DGKζ IC$_{50}$ (μM) |
|---|---|---|---|---|
| 391 | 1.8 | 2.1 | 0.26 | 36 |
| 392 | >240 | 2.3 | — | — |
| 393 | 9 | >240 | — | — |
| 394 | 3.9 | 1.2 | — | — |
| 395 | 14 | 3 | — | — |
| 396 | 21 | 5.8 | — | — |
| 397 | 16 | 13 | — | — |
| 398 | 0.097 | — | — | — |
| 398 | 0.21 | >240 | — | — |
| 398 | 1.7 | 49 | — | — |
| 399 | 6.4 | 0.16 | — | — |
| 400 | 5.4 | 2.1 | — | — |
| 401 | 81 | 7.6 | — | — |
| 402 | 160 | 3.5 | — | — |
| 403 | 26 | 5.7 | — | — |
| 404 | 4.9 | 3.9 | — | 63 |
| 405 | 0.56 | 0.86 | — | — |
| 406 | 13 | 3.1 | — | — |
| 407 | 0.96 | 0.45 | — | — |
| 408 | 9 | 1.1 | — | — |
| 409 | >240 | 0.95 | — | — |
| 410 | 5.4 | 2.2 | — | — |
| 411 | 4.9 | 1.4 | — | — |
| 412 | 1.8 | 0.6 | — | — |
| 413 | 3.3 | 0.97 | — | — |
| 414 | 9 | 1.5 | — | — |
| 415 | 0.65 | 0.66 | — | — |
| 416 | 4.8 | 0.91 | — | — |
| 417 | — | — | 0.25 | >240 |
| 419 | 49 | 15 | 81 | >81 |
| 421 | — | — | 69 | >240 |
| 422 | — | — | 1.4 | >240 |
| 423 | 2.2 | 33 | 1.4 | >81 |
| 424 | 1.4 | 27 | 0.77 | >240 |
| 425 | 20 | >240 | 1.8 | >240 |
| 426 | 170 | >240 | — | — |
| 427 | — | — | 150 | >240 |
| 428 | 10 | 5.2 | — | — |
| 429 | 1.8 | 9.4 | — | — |
| 430 | 1.9 | 3 | — | — |
| 431 | 9 | 9 | — | — |
| 432 | >240 | 5.4 | — | — |

TABLE 2

Raji CD4 T cell IL2 IC$_{50}$ Activity Values

| Ex. No. | RAJI IC$_{50}$ (μM) |
|---|---|
| 2 | 0.20 |
| 3 | 0.31 |
| 6 | 0.82 |
| 7 | 0.075 |
| 8 | 0.091 |
| 9 | >100 |
| 10 | 0.0030 |
| 13 | >100 |
| 14 | 0.026 |
| 16 | 0.021 |
| 18 | 0.023 |
| 19 | >100 |
| 20 | >100 |
| 21 | 0.41 |
| 23 | 0.041 |
| 24 | 0.012 |
| 26 | 0.14 |
| 27 | 0.057 |
| 29 | 2.3 |
| 30 | 1.1 |
| 31 | 1.8 |
| 33 | 0.018 |
| 34 | 0.035 |
| 35 | 0.21 |
| 39 | 0.64 |
| 40 | 0.037 |
| 45 | 0.062 |
| 46 | 0.13 |
| 47 | >100 |
| 50 | 0.039 |
| 51 | 0.0052 |
| 52 | 0.056 |
| 53 | 0.043 |
| 54 | 0.063 |
| 55 | 0.038 |
| 57 | 0.14 |
| 58 | 0.028 |
| 60 | 1.6 |
| 61 | 0.056 |
| 64 | 55 |
| 65 | 0.0055 |
| 66 | 0.048 |
| 67 | 0.0066 |
| 68 | 0.052 |
| 69 | >100 |
| 70 | 0.0089 |
| 73 | 0.026 |
| 75 | 0.14 |
| 76 | 0.067 |
| 78 | >100 |
| 79 | 0.067 |
| 85 | 0.1 |
| 89 | 2.8 |
| 90 | 0.63 |
| 95 | 1.1 |
| 96 | 0.36 |
| 98 | 0.13 |
| 99 | 0.0094 |
| 101 | 0.19 |
| 103 | 0.40 |
| 104 | 0.44 |
| 106 | 0.0024 |
| 115 | 3.8 |
| 116 | 0.17 |
| 117 | 0.77 |
| 118 | 0.018 |
| 122 | 0.011 |
| 125 | 0.023 |
| 127 | 0.0064 |
| 128 | 0.10 |
| 130 | 0.019 |
| 138 | >100 |
| 140 | 0.006 |
| 144 | 0.02 |
| 146 | >100 |
| 147 | 0.30 |
| 149 | 0.064 |
| 150 | 0.51 |
| 151 | 0.88 |
| 152 | 0.15 |
| 153 | 0.71 |
| 154 | 0.88 |
| 155 | 1.6 |
| 156 | >100 |
| 157 | 0.22 |
| 159 | 2.0 |
| 160 | 2.9 |
| 161 | 5.7 |
| 163 | 2.1 |
| 164 | 2.6 |
| 163 | 0.22 |
| 166 | 3.8 |
| 176 | 3.0 |
| 183 | 3.2 |
| 186 | 3.0 |
| 189 | 7.3 |
| 190 | 4.2 |
| 192 | 0.20 |

TABLE 2-continued

Raji CD4 T cell IL2 $IC_{50}$ Activity Values

| Ex. No. | RAJI $IC_{50}$ (μM) |
|---|---|
| 193 | 0.13 |
| 194 | 0.44 |
| 195 | 0.12 |
| 196 | 2.1 |
| 198 | 0.50 |
| 199 | 0.38 |
| 200 | 1.6 |
| 201 | 22 |
| 202 | 0.40 |
| 213 | 0.71 |
| 214 | 0.55 |
| 215 | 0.48 |
| 216 | 0.064 |
| 217 | 0.067 |
| 218 | 0.093 |
| 220 | 0.063 |
| 221 | 0.33 |
| 222 | 0.068 |
| 223 | 0.042 |
| 225 | 0.07 |
| 226 | 0.084 |
| 227 | 1.5 |
| 228 | 0.11 |
| 229 | 0.12 |
| 230 | 3.6 |
| 231 | 3.0 |
| 232 | 1.1 |
| 233 | 0.48 |
| 234 | 0.13 |
| 239 | 3.6 |
| 244 | 0.69 |
| 258 | 0.0053 |
| 259 | 0.016 |
| 260 | 0.018 |
| 261 | 0.021 |
| 262 | 0.028 |
| 263 | 0.035 |
| 264 | 0.036 |
| 265 | 0.039 |
| 266 | 0.041 |
| 267 | 0.048 |
| 268 | 0.051 |
| 269 | 0.057 |
| 270 | 0.059 |
| 271 | 0.061 |
| 272 | 0.064 |
| 273 | 0.064 |
| 275 | 0.073 |
| 276 | 0.079 |
| 277 | 0.079 |
| 278 | 0.087 |
| 279 | 0.092 |
| 280 | 0.092 |
| 281 | 0.093 |
| 282 | 0.094 |
| 283 | 0.094 |
| 284 | 0.098 |
| 285 | 0.10 |
| 286 | 0.10 |
| 287 | 0.10 |
| 288 | 0.10 |
| 289 | 0.11 |
| 290 | 0.11 |
| 291 | 0.11 |
| 292 | 0.11 |
| 293 | 0.11 |
| 294 | 0.14 |
| 295 | 0.14 |
| 296 | 0.15 |
| 297 | 0.16 |
| 298 | 0.16 |
| 299 | 0.16 |
| 300 | 0.16 |
| 301 | 0.17 |
| 302 | 0.18 |
| 303 | 0.18 |
| 304 | 0.19 |
| 305 | 0.21 |
| 306 | 0.21 |
| 307 | 0.21 |
| 308 | 0.21 |
| 310 | 0.22 |
| 312 | 0.24 |
| 313 | 0.25 |
| 314 | 0.25 |
| 315 | 0.25 |
| 316 | 0.41 |
| 317 | 0.29 |
| 318 | 0.29 |
| 319 | 0.30 |
| 320 | 0.30 |
| 321 | 0.31 |
| 322 | 0.32 |
| 323 | 0.34 |
| 324 | 0.35 |
| 326 | 0.38 |
| 327 | 0.43 |
| 328 | 0.44 |
| 329 | 0.47 |
| 330 | 0.50 |
| 331 | 0.52 |
| 332 | 0.53 |
| 333 | 0.54 |
| 334 | 0.54 |
| 335 | 0.54 |
| 337 | 0.55 |
| 338 | 0.58 |
| 339 | 0.65 |
| 340 | 0.69 |
| 341 | 0.73 |
| 342 | 0.79 |
| 343 | 0.81 |
| 344 | 0.82 |
| 345 | 0.99 |
| 346 | 1.1 |
| 347 | 1.2 |
| 348 | 1.3 |
| 349 | 1.4 |
| 350 | 1.5 |
| 351 | 1.5 |
| 352 | 1.6 |
| 353 | 1.9 |
| 354 | 2.5 |
| 355 | 2.8 |
| 356 | 3.0 |
| 357 | 5.0 |
| 358 | 6.5 |
| 359 | 8.0 |
| 360 | 9.6 |
| 362 | >100 |
| 363 | >100 |
| 364 | >100 |
| 365 | >100 |
| 366 | >100 |
| 367 | >100 |
| 368 | >100 |
| 369 | >100 |
| 370 | >100 |
| 371 | >100 |
| 372 | >100 |
| 373 | >100 |
| 375 | >100 |
| 417 | 0.15 |
| 421 | 2.8 |
| 422 | >100 |
| 423 | >100 |

TABLE 2-continued

Raji CD4 T cell IL2 IC$_{50}$ Activity Values

| Ex. No. | RAJI IC$_{50}$ (μM) |
|---|---|
| 424 | >100 |
| 425 | >100 |
| 274 | 0.072 |
| 419 | 0.29 |
| 426 | 20 |
| 427 | 2.4 |

TABLE 3

AP1-Luciferase Reporter IC$_{50}$ Values

| Ex. No. | AP1-Luciferase Reporter IC$_{50}$ (μM) |
|---|---|
| 11 | 0.08 |
| 12 | 0.58 |
| 13 | 1.3 |
| 15 | 1.82 |
| 17 | 0.35 |
| 19 | 0.83 |
| 20 | 0.4 |
| 22 | 1.53 |
| 25 | 1.15 |
| 28 | 4.45 |
| 32 | 0.36 |
| 36 | 1.6 |
| 37 | 2.83 |
| 43 | 0.4 |
| 44 | 0.35 |
| 47 | 2.55 |
| 48 | 2.16 |
| 69 | 0.51 |
| 78 | 0.14 |
| 113 | 0.58 |
| 114 | 4.12 |
| 120 | 1.3 |
| 121 | 0.34 |
| 123 | 0 |
| 124 | 0.1 |
| 126 | 0 |
| 129 | 0 |
| 131 | 0.5 |
| 132 | 0.08 |
| 133 | 0.28 |
| 134 | 0.6 |
| 135 | 0.34 |
| 136 | 0.23 |
| 136 | 0.23 |
| 137 | 0.19 |
| 138 | 0.66 |
| 139 | 0.13 |
| 141 | 0.24 |
| 145 | 0.57 |
| 146 | 1.87 |
| 148 | 0.87 |
| 156 | 10 |
| 158 | 4.59 |
| 162 | 4.81 |
| 188 | 10 |
| 211 | 0.52 |
| 212 | 1.14 |
| 362 | 8.37 |
| 363 | 10 |
| 364 | 1.57 |
| 365 | 2.22 |
| 372 | 0.14 |
| 373 | 0.26 |
| 374 | 7.93 |
| 376 | 10 |
| 379 | 7.84 |
| 381 | 0.19 |
| 384 | 0.18 |
| 385 | 0.06 |
| 386 | 0.05 |

TABLE 3-continued

AP1-Luciferase Reporter IC$_{50}$ Values

| Ex. No. | AP1-Luciferase Reporter IC$_{50}$ (μM) |
|---|---|
| 389 | 0.65 |
| 390 | 0.8 |
| 391 | 0.07 |
| 422 | 3.49 |
| 423 | 1.88 |
| 424 | 10 |

TABLE 4

DGKAP1 Luciferase Reporter IC$_{50}$ Values

| Ex. No. | DGKAP1 Lucif Reporter IC$_{50}$ (μM) |
|---|---|
| 17 | 1.33 |
| 49 | 1.7 |
| 124 | 0.57 |
| 129 | 0.87 |
| 143 | 1.28 |
| 156 | 10 |
| 158 | 10 |
| 162 | 10 |
| 177 | 10 |
| 224 | 10 |
| 315 | 10 |
| 364 | 10 |
| 365 | 10 |
| 377 | 10 |
| 378 | 10 |
| 382 | 10 |
| 383 | 10 |
| 387A | 10 |
| 387 | 3.33 |
| 388 | 3.33 |
| 415 | 0.42 |
| — | — |

TABLE 5

CD8 GLO Normalized EC$_{50}$ Activity Values

| Ex. No. | CD8 GLO normalized EC$_{50}$ (μM) |
|---|---|
| 32 | 0.18 |
| 49 | 0.17 |
| 124 | 0.02 |
| 129 | 0.06 |
| 141 | 0.01 |
| 143 | 0.01 |
| 156 | 0.14 |
| 158 | 0.92 |
| 162 | 10 |
| 177 | 10 |
| 224 | 4.28 |
| 315 | 1.26 |
| 377 | 10 |
| 378 | 1.74 |
| 382 | 1.79 |
| 383 | 0.06 |
| 387A | 10 |
| 387 | 0.18 |
| 388 | 0.48 |
| 405 | 0.02 |
| 412 | 0.3 |
| 415 | 0.02 |
| 425 | 0.19 |
| — | — |

TABLE 6

HuCD8 INFG Normalized EC$_{50}$ Activity Values

| Ex. No. | HuCD8 INFG Normalized EC$_{50}$ (μM) |
|---|---|
| 13 | 10 |
| 17 | 0.52 |
| 44 | 0.18 |
| 124 | 0.01 |
| 137 | 0.04 |
| 141 | 0.03 |
| 143 | 0.09 |
| 251 | 0.58 |
| 252 | 10 |
| 253 | 2.51 |
| 256 | 0.24 |
| 381 | 0.07 |
| 386 | 0.96 |
| 392 | 0.23 |
| 393 | 0.17 |
| 394 | 0.01 |
| 395 | 0.09 |
| 396 | 2.66 |
| 397 | 4.47 |
| 398 | 1.21 |
| 398B | 5.97 |
| 398B | 0.6 |
| 399 | 0.02 |
| 400 | 0.05 |
| 401 | 10 |
| 402 | 1.78 |
| 403 | 1.49 |
| 406 | 0.41 |
| 407 | 0.12 |
| 408 | 0 |
| 410 | 0.09 |
| 411 | 0.02 |
| 414 | 0.16 |
| 416 | 0.03 |
| 423 | 0.46 |
| 413 | 0.04 |
| 428 | 0.03 |
| 429 | 0.08 |
| 430 | 0.3 |
| 432 | 0.06 |

TABLE 7

HuCD8 pERK IC$_{50}$ Activity Values

| Ex. No. | HuCD8 pERK IC$_{50}$ (μM) |
|---|---|
| 124 | 0.36 |
| 143 | 0.06 |

TABLE 8

INF-γ Whole Blood Agonist EC$_{50}$ Activity Values

| Ex. No. | INF-γ Whole Blood Agonist EC$_{50}$ (uM) |
|---|---|
| 17 | 0.67 |
| 124 | 0.14 |
| 145 | 1.33 |

TABLE 9

INF-γ Whole Blood Normalized Agonist EC$_{50}$ Activity Values

| Ex. No. | INF-γ Whole Blood Normalized Agonist EC$_{50}$ (μM) |
|---|---|
| 13 | 5 |
| 17 | 1.15 |
| 44 | 0.9 |
| 121 | 0.55 |
| 124 | 0.1 |
| 136 | 1.16 |
| 137 | 5 |
| 145 | 1.87 |
| 372 | 5 |
| 386 | 1.24 |
| 391 | 3.5 |
| 406 | 2.19 |
| 407 | 0.78 |
| 412 | 3.01 |
| 423 | 10 |
| 425 | 10 |

TABLE 10

INF-γ Whole Blood Normalized Agonist EC$_{50}$ Activity Values

| Ex. No. | msCTL INF-γ IC$_{50}$ (μM) |
|---|---|
| 13 | 0.64 |
| 17 | 0.19 |
| 36 | 10 |
| 44 | 0.13 |
| 48 | 10 |
| 121 | 0.05 |
| 124 | 0.04 |
| 133 | 0.06 |
| 134 | 1.14 |
| 136 | 0.09 |
| 137 | 0.23 |
| 141 | 0.29 |
| 143 | 1.41 |
| 145 | 0.46 |
| 177 | 10 |
| 224 | 10 |
| 362 | 10 |
| 372 | 2.55 |
| 378 | 10 |
| 381 | 0.7 |
| 383 | 10 |
| 385 | 4.09 |
| 386 | 0.59 |
| 389 | 5.05 |
| 391 | 0.73 |
| 392 | 1.85 |
| 399 | 0.41 |
| 404 | 9.84 |
| 406 | 0.16 |
| 407 | 0.04 |
| 412 | 0.36 |
| 415 | 10 |
| 423 | 0.7 |
| 424 | 10 |
| 425 | 2.98 |
| 428 | 0.59 |

Table 1 lists in vitro DGK inhibition IC$_{50}$ activity values measured in the DGKα and DGKζ liposome (LIPGLO) and the Detergent/lipid Micelle assays. The compounds of the present invention, as exemplified by the Examples 2-3, 6-37, 39-40, 43-55, 57-58, 60-61, 64-70, 73, 75-76, 78-79, 85, 89-90, 95-96, 98-99, 101, 103-106, 114-115, 117-141, 143-157, 159-160, 162-166, 176-177, 183, 189-190, 192-200, 202, 211-218, 220-234, 239, 244, 250-256, 258-308, 310, 312-324, 326-335, 337-357, 359-360, 362-373, 375, 377-383, 385-417, 419, and 421-432, had IC$_{50}$ values of less than <240 μM, in one or more of DGKα and DGKζ LIPGLO assays and the DGKα and DGKζ assays, indicating inhibition of one or both of the DGKα and DGKζ enzymes.

The compounds of the present invention possess activity as an inhibitor(s) of one or both of the DGKα and DGKζ enzymes, and therefore, may be used in the treatment of diseases associated with the inhibition of DGKα and DGKζ activity.

```
Nucleotide sequence encoding hDGKα-(M1-S735)-Ct-TVMV-His:
                                                                    (SEQ ID NO: 1)
   1 ATGGCCAAGG AGAGGGGCCT AATAAGCCCC AGTGATTTTG CCCAGCTGCA
  51 AAAATACATG AATACTCCA CCAAAAAGGT CAGTGATGTC CTAAAGCTCT
 101 TCGAGGATGG CGAGATGGCT AAATATGTCC AAGGAGATGC CATTGGGTAC
 151 GAGGGATTCC AGCAATTCCT GAAAATCTAT CTCGAAGTGG ATAATGTTCC
 201 CAGACACCTA AGCCTGGCAC TGTTTCAATC CTTTGAGACT GGTCACTGCT
 251 TAAATGAGAC AAATGTGACA AAAGATGTGG TGTGTCTCAA TGATGTTTCC
 301 TGCTACTTTT CCCTTCTGGA GGGTGGTCGG CCAGAAGACA AGTTAGAATT
 351 CACCTTCAAG CTGTACGACA CGGACAGAAA TGGGATCCTG GACAGCTCAG
 401 AAGTGGACAA AATTATCCTA CAGATGATGC GAGTGGCTGA ATACCTGGAT
 451 TGGGATGTGT CTGAGCTGAG GCCGATTCTT CAGGAGATGA TGAAAGAGAT
 501 TGACTATGAT GGCAGTGGCT CTGTCTCTCA AGCTGAGTGG GTCCGGGCTG
 551 GGGCCACCAC CGTGCCACTG CTAGTGCTGC TGGGTCTGGA GATGACTCTG
 601 AAGGACGACG GACAGCACAT GTGGAGGCCC AAGAGGTTCC CCAGACCAGT
 651 CTACTGCAAT CTGTGCGAGT CAAGCATTGG TCTTGGCAAA CAGGGACTGA
 701 GCTGTAACCT CTGTAAGTAC ACTGTTCACG ACCAGTGTGC CATGAAAGCC
 751 CTGCCTTGTG AAGTCAGCAC CTATGCCAAG TCTCGGAAGG ACATTGGTGT
 801 CCAATCACAT GTGTGGGTGC GAGGAGGCTG TGAGTCCGGG CGCTGCGACC
 851 GCTGTCAGAA AAAGATCCGG ATCTACCACA GTCTGACCGG GCTGCATTGT
 901 GTATGGTGCC ACCTAGAGAT CCACGATGAC TGCCTGCAAG CGGTGGGCCA
 951 TGAGTGTGAC TGTGGGCTGC TCCGGGATCA CATCCTGCCT CCATCTTCCA
1001 TCTATCCCAG TGTCCTGGCC TCTGGACCGG ATCGTAAAAA TAGCAAAACA
1051 AGCCAGAAGA CCATGGATGA TTTAAATTTG AGCACCTCTG AGGCTCTGCG
1101 GATTGACCCT GTTCCTAACA CCCACCCACT TCTCGTCTTT GTCAATCCTA
1151 AGAGTGGCGG GAAGCAGGGG CAGAGGGTGC TCTGGAAGTT CCAGTATATA
1201 TTAAACCCTC GACAGGTGTT CAACCTCCTA AAGGATGGTC CTGAGATAGG
1251 GCTCCGATTA TTCAAGGATG TTCCTGATAG CCGGATTTTG TGTGTGGTG
1301 GAGACGGCAC AGTAGGCTGG ATTCTAGAGA CCATTGACAA AGCTAACTTG
1351 CCAGTTTTGC CTCCTGTTGC TGTGTTGCCC CTGGGTACTG GAAATGATCT
1401 GGCTCGATGC CTAAGATGGG GAGGAGGTTA TGAAGGACAG AATCTGGCAA
1451 AGATCCTCAA GGATTTAGAG ATGAGTAAAG TGGTACATAT GGATCGATGG
1501 TCTGTGGAGG TGATACCTCA ACAAACTGAA GAAAAAGTG ACCCAGTCCC
1551 CTTTCAAATC ATCAATAACT ACTTCTCTAT TGGCGTGGAT GCCTCTATTG
1601 CTCATCGATT CCACATCATG CGAGAGAAAT ATCCGGAGAA GTTCAACAGC
```

-continued

```
1651 AGAATGAAGA ACAAGCTATG GTACTTCGAA TTTGCCACAT CTGAATCCAT

1701 CTTCTCAACA TGCAAAAAGC TGGAGGAGTC TTTGACAGTT GAGATCTGTG

1751 GGAAACCGCT GGATCTGAGC AACCTGTCCC TAGAAGGCAT CGCAGTGCTA

1801 AACATCCCTA GCATGCATGG TGGCTCCAAC CTCTGGGGTG ATACCAGGAG

1851 ACCCCATGGG GATATCTATG GGATCAACCA GGCCTTAGGT GCTACAGCTA

1901 AAGTCATCAC CGACCCTGAT ATCCTGAAAA CCTGTGTACC AGACCTAAGT

1951 GACAAGAGAC TGGAAGTGGT TGGGCTGGAG GGTGCAATTG AGATGGGCCA

2001 AATCTATACC AAGCTCAAGA ATGCTGGACG TCGGCTGGCC AAGTGCTCTG

2051 AGATCACCTT CCACACCACA AAAACCCTTC CCATGCAAAT TGACGGAGAA

2101 CCCTGGATGC AGACGCCCTG TACAATCAAG ATCACCCACA AGAACCAGAT

2151 GCCCATGCTC ATGGGCCCAC CCCCCCGCTC CACCAATTTC TTTGGCTTCT

2201 TGAGCGGATC CTCGGAGACA GTGCGGTTTC AGGGACACCA CCACCATCAC

2251 CACTGA
```

Amino acid sequence of hDGKα-(M1-S735)-Ct-TVMV-His:
(SEQ ID NO: 2)
```
0001 MAKERGLISP SDFAQLQKYM EYSTKKVSDV LKLFEDGEMA KYVQGDAIGY EGFQQFLKIY 0060

0061 LEVDNVPRHL SLALFQSFET GHCLNETNVT KDVVCLNDVS CYFSLLEGGR PEDKLEFTFK 0120

0121 LYDTDRNGIL DSSEVDKIIL QMMRVAEYLD WDVSELRPIL QEMMKEIDYD GSGSVSQAEW 0180

0181 VRAGATTVPL LVLLGLEMTL KDDGQHMWRP KRFPRPVYCN LCESSIGLGK QGLSCNLCKY 0240

0241 TVHDQCAMKA LPCEVSTYAK SRKDIGVQSH VWVRGGCESG RCDRCQKKIR IYHSLIGLHC 0300

0301 VWCHLEIHDD CLQAVGHECD CGLLRDHILP PSSIYPSVLA SGPDRKNSKT SQKTMDDLNL 0360

0361 STSEALRIDP VPNTHPLLVF VNPKSGGKQG QRVLWKFQYI LNPRQVFNLL KDGPEIGLRL 0420

0421 FKDVPDSRIL VCGGDGTVGW ILETIDKANL PVLPPVAVLP LGTGNDLARC LRWGGGYEGQ 0480

0481 NLAKILKDLE MSKVVHMDRW SVEVIPQQTE EKSDPVPFQI INNYFSIGVD ASIAHRFHIM 0540

0541 REKYPEKFNS RMKNKLWYFE FATSESIFST CKKLEESLTV EICGKPLDLS NLSLEGIAVL 0600

0601 NIPSMHGGSN LWGDTRRPHG DIYGINQALG ATAKVITDPD ILKTCVPDLS DKRLEVVGLE 0660

0661 GAIEMGQIYT KLKNAGRRLA KCSEITFHTT KILPMQIDGE PWMQTPCTIK ITHKNQMPML 0720

0721 MGPPPRSTNF FGFLSGSSET VRFQGHHHHH H                              0751
```

Nucleotide sequence encoding hDGKζ-(MI-A928)-transcript variant-2 Ct-TVMV-His:
(SEQ ID NO: 3)
```
  1 ATGGAGCCGC GGGACGGTAG CCCCGAGGCC CGGAGCAGCG ACTCCGAGTC

51 GGCTTCCGCC TCGTCCAGCG GCTCCGAGCG CGACGCCGGT CCCGAGCCGG

101 ACAAGGCGCC GCGGCGACTC AACAAGCGGC GCTTCCCGGG GCTGCGGCTC

151 TTCGGGCACA GGAAAGCCAT CACGAAGTCG GGCCTCCAGC ACCTGGCCCC

201 CCCTCCGCCC ACCCCTGGGG CCCCGTGCAG CGAGTCAGAG CGGCAGATCC

251 GGAGTACAGT GGACTGGAGC GAGTCAGCGA CATATGGGGA GCACATCTGG

301 TTCGAGACCA ACGTGTCCGG GGACTTCTGC TACGTTGGGG AGCAGTACTG

351 TGTAGCCAGG ATGCTGCAGA AGTCAGTGTC TCGAAGAAAG TGCGCAGCCT

401 GCAAGATTGT GGTGCACACG CCCTGCATCG AGCAGCTGGA GAAGATAAAT

451 TTCCGCTGTA AGCCGTCCTT CCGTGAATCA GGCTCCAGGA ATGTCCGCGA

501 GCCAACCTTT GTACGGCACC ACTGGGTACA CAGACGACGC CAGGACGGCA

551 AGTGTCGGCA CTGTGGGAAG GGATTCCAGC AGAAGTTCAC CTTCCACAGC

601 AAGGAGATTG TGGCCATCAG CTGCTCGTGG TGCAAGCAGG CATACCACAG
```

```
 651 CAAGGTGTCC TGCTTCATGC TGCAGCAGAT CGAGGAGCCG TGCTCGCTGG
 701 GGGTCCACGC AGCCGTGGTC ATCCCGCCCA CCTGGATCCT CCGCGCCCGG
 751 AGGCCCCAGA ATACTCTGAA AGCAAGCAAG AAGAAGAAGA GGGCATCCTT
 801 CAAGAGGAAG TCCAGCAAGA AAGGGCCTGA GGAGGGCCGC TGGAGACCCT
 851 TCATCATCAG GCCCACCCCC TCCCCGCTCA TGAAGCCCCT GCTGGTGTTT
 901 GTGAACCCCA AGAGTGGGGG CAACCAGGGT GCAAAGATCA TCCAGTCTTT
 951 CCTCTGGTAT CTCAATCCCC GACAAGTCTT CGACCTGAGC CAGGGAGGGC
1001 CCAAGGAGGC GCTGGAGATG TACCGCAAAG TGCACAACCT GCGGATCCTG
1051 GCGTGCGGGG CGACGGCAC GGTGGGCTGG ATCCTCTCCA CCCTGGACCA
1101 GCTACGCCTG AAGCCGCCAC CCCCTGTTGC CATCCTGCCC CTGGGTACTG
1151 GCAACGACTT GGCCCGAACC CTCAACTGGG GTGGGGGCTA CACAGATGAG
1201 CCTGTGTCCA AGATCCTCTC CCACGTGGAG GAGGGGAACG TGGTACAGCT
1251 GGACCGCTGG GACCTCCACG CTGAGCCCAA CCCCGAGGCA GGGCCTGAGG
1301 ACCGAGATGA AGGCGCCACC GACCGGTTGC CCCTGGATGT CTTCAACAAC
1351 TACTTCAGCC TGGGCTTTGA CGCCCACGTC ACCCTGGAGT TCCACGAGTC
1401 TCGAGAGGCC AACCCAGAGA AATTCAACAG CCGCTTTCGG AATAAGATGT
1451 TCTACGCCGG GACAGCTTTC TCTGACTTCC TGATGGGCAG CTCCAAGGAC
1501 CTGGCCAAGC ACATCCGAGT GGTGTGTGAT GGAATGGACT TGACTCCCAA
1551 GATCCAGGAC CTGAAACCCC AGTGTGTTGT TTTCCTGAAC ATCCCCAGGT
1601 ACTGTGCGGG CACCATGCCC TGGGGCCACC CTGGGGAGCA CCACGACTTT
1651 GAGCCCCAGC GGCATGACGA CGGCTACCTC GAGGTCATTG GCTTCACCAT
1701 GACGTCGTTG GCCGCGCTGC AGGTGGGCGG ACACGGCGAG CGGCTGACGC
1751 AGTGTCGCGA GGTGGTGCTC ACCACATCCA AGGCCATCCC GGTGCAGGTG
1801 GATGGCGAGC CCTGCAAGCT TGCAGCCTCA CGCATCCGCA TCGCCCTGCG
1851 CAACCAGGCC ACCATGGTGC AGAAGGCCAA GCGGCGGAGC GCCGCCCCCC
1901 TGCACAGCGA CCAGCAGCCG GTGCCAGAGC AGTTGCGCAT CCAGGTGAGT
1951 CGCGTCAGCA TGCACGACTA TGAGGCCCTG CACTACGACA AGGAGCAGCT
2001 CAAGGAGGCC TCTGTGCCGC TGGGCACTGT GGTGGTCCCA GGAGACAGTG
2051 ACCTAGAGCT CTGCCGTGCC CACATTGAGA GACTCCAGCA GGAGCCCGAT
2101 GGTGCTGGAG CCAAGTCCCC GACATGCCAG AAACTGTCCC CCAAGTGGTG
2151 CTTCCTGGAC GCCACCACTG CCAGCCGCTT CTACAGGATC GACCGAGCCC
2201 AGGAGCACCT CAACTATGTG ACTGAGATCG CACAGGATGA GATTTATATC
2251 CTGGACCCTG AGCTGCTGGG GGCATCGGCC CGGCCTGACC TCCCAACCCC
2301 CACTTCCCCT CTCCCCACCT CACCCTGCTC ACCCACGCCC CGGTCACTGC
2351 AAGGGGATGC TGCACCCCCT CAAGGTGAAG AGCTGATTGA GGCTGCCAAG
2401 AGGAACGACT TCTGTAAGCT CCAGGAGCTG CACCGAGCTG GGGCGACCT
2451 CATGCACCGA GACGAGCAGA GTCACGCT CCTGCACCAC GCAGTCAGCA
2501 CTGGCAGCAA GGATGTGGTC CGCTACCTGC TGGACCACGC CCCCCCAGAG
2551 ATCCTTGATG CGGTGGAGGA AAACGGGGAG ACCTGTTTGC ACCAAGCAGC
2601 GGCCCTGGGC CAGCGCACCA TCTGCCACTA CATCGTGGAG GCCGGGGCCT
```

-continued

```
2651 CGCTCATGAA GACAGACCAG CAGGGCGACA CTCCCCGGCA GCGGGCTGAG

2701 AAGGCTCAGG ACACCGAGCT GGCCGCCTAC CTGGAGAACC GGCAGCACTA

2751 CCAGATGATC CAGCGGGAGG ACCAGGAGAC GGCTGTGGGA TCCTCGGAGA

2801 CAGTGCGGTT TCAGGGACAC CACCACCATC ACCACTGA
```

Amino acid sequence of hDGKζ-(MI-A928)-transcript variant-2 Ct-TVMV-His:
(SEQ ID NO: 4)

```
0001 MEPRDGSPEA RSSDSESASA SSSGSERDAG PEPDKAPERL NKRRFPGLRL FGHRKAITKS  0060

0061 GLQHLAPPPP TPGAPCSESE RQIRSTVDWS ESATYGEHIW FETNVSGDFC YVGEQYCVAR  0120

0121 MLQKSVSRRK CAACKIVVHT PCIEQLEKIN FRCKPSFRES GSRNVREPTF VRHHWVHRRR  0180

0181 QDGKCRHCGK GFQQKFTFHS KEIVAISCSW CKQAYHSKVS CEMLQQIEEP CSLGVHAAVV  0240

0241 IPPTWILRAR RPQNTLKASK KKKRASFKRK SSKKGPEEGR WRPFIIRPTP SPLMKPLLVE  0300

0301 VNPKSGGNQG AKIIQSFLWY LNPRQVFDLS QGGPKEALEM YRKVHNLRIL ACGGDGTVGW  0360

0361 ILSTLDQLRL KPPPPVAILP LGTGNDLART LNWGGGYTDE PVSKILSHVE EGNVVQLDRW  0420

0421 DLHAEPNPEA GPEDRDEGAT DRLPLDVENN YFSLGFDAHV TLEFHESREA NPEKENSRFR  0480

0481 NKMFYAGTAF SDELMGSSKD LAKHIRVVCD GMDLTPKIQD LKPQCVVFLN IPRYCAGIMP  0540

0541 WGHPGEHHDF EPQRHDDGYL EVIGFTMTSL AALQVGGHGE RLTQCREVVL TTSKAIPVQV  0600

0601 DGEPCKLAAS RIRIALRNQA TMVQKAKRES AAPLHSDQQP VPEQLRIQVS RVSMHDYEAL  0660

0661 HYDKEQLKEA SVPLGTVVVP GDSDLELCRA HIERLQQEPD GAGAKSPTCQ KLSPKWCFLD  0720

0721 ATTASRFYRI DRAQEHLNYV TEIAQDEIYI LDPELLGASA RPDLPTPTSP LPISPCSPTP  0780

0781 RSLQGDAAPP QGEELIEAAK RNDFCKLQEL HRAGGDLMHR DEQSRTLLHH AVSTGSKDVV  0840

0841 RYLLDHAPPE ILDAVEENGE TCLHQAAALG QRTICHYIVE AGASLMKIDQ QGDTPRQRAE  0900

0901 KAQDTELAAY LENRQHYQMI QREDQETAVG SSETVRFQGH HHHHH  0945
```

---

The invention claimed is:

1. A compound of Formula (I):

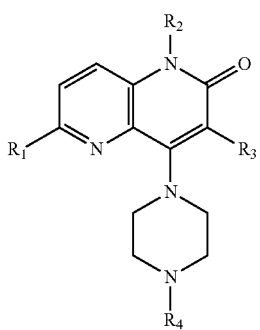

(I)

or a salt thereof, wherein:

$R_1$ is H, Cl, Br, —CN, $C_{1-4}$ alkyl, $C_{2-3}$ alkenyl, $C_{1-3}$ alkoxy, —C(O)OH, —C(O)O($C_{1-3}$ alkyl), —C(O)NR$_a$R$_a$, —NR$_a$R$_a$, —NR$_a$C(O)O($C_{1-4}$ alkyl), or —NR$_a$C(O)NR$_a$($C_{1-4}$ alkyl);

each $R_a$ is independently H or $C_{1-2}$ alkyl;

$R_2$ is $C_{1-6}$ alkyl, $C_{1-4}$ cyanoalkyl, $C_{1-4}$ fluoroalkyl, $C_{2-4}$ alkenyl, —(CH$_2$)$_{1-3}$CH=CF$_2$, $C_{3-5}$ alkynyl, —(CH$_2$)$_{1-4}$O($C_{1-3}$ alkyl), —(CH$_2$)$_{1-4}$O(CH$_2$)$_{1-3}$O($C_{1-3}$ alkyl), —(CH$_2$)$_{1-3}$C(O)($C_{1-3}$ alkyl), —(CH$_2$)$_{1-3}$C(O)O($C_{1-3}$ alkyl), —(CH$_2$)$_{1-3}$R$_b$, —(CH$_2$)$_{1-3}$OR$_b$, or —(CH$_2$)$_{1-3}$OCH$_2$R$_b$;

$R_b$ is $C_{3-6}$ cycloalkyl or dioxanyl, each substituted with zero to 2 substituents independently selected from F, —CN, —CH$_3$, and —OCH$_3$;

$R_3$ is H, F, Cl, Br, —CN, $C_{1-3}$ alkyl, $C_{1-3}$ fluoroalkyl, —NO$_2$, —C(O)($C_{1-3}$ alkyl), —C(O)O($C_{1-3}$ alkyl), or —C(O)($C_{1-3}$ fluoroalkyl);

$R_4$ is:

(a) 2,3-dihydro-1H-indenyl substituted with zero to 2 substituents independently selected from F, Cl, —OH, $C_{1-2}$ alkyl, $C_{1-2}$ fluoroalkyl, $C_{1-2}$ alkoxy, and —OCH$_2$CH=CH$_2$; or (b) —CH$_2$R$_y$, —C(CH$_3$)$_2$R$_y$, —CHR$_x$R$_y$, —CH$_2$CH(OH)R$_x$, —CH(CH$_3$)(CH$_2$CH$_2$OCH$_3$), or $C_{3-6}$ cycloalkyl substituted with fluorophenyl;

$R_x$ is $C_{1-6}$ alkyl, $C_{1-3}$ hydroxyalkyl, $C_{1-2}$ aminoalkyl, $C_{3-6}$ cycloalkyl, or phenyl substituted with zero to 2 substituents independently selected from F, Cl, —OH, $C_{1-3}$ alkyl, $C_{1-2}$ fluoroalkyl, $C_{1-2}$ alkoxy, —OCH$_2$CH=CH$_2$, and —OCH$_2$C≡CH;

$R_y$ is 1,3-benzodiazolyl, indazolyl, indolyl, indolinyl, naphthalenyl, oxoindolinyl, pyridinyl, pyrimidinyl, or phenyl, each substituted with zero to 3 substituents independently selected from F, Cl, Br, —OH, —CN, $C_{1-6}$ alkyl, $C_{1-3}$ fluoroalkyl, $C_{1-3}$ alkoxy, $C_{1-3}$ fluoroalkoxy, —OCH$_2$CH=CH$_2$, —OCH$_2$C≡CH, —OCH$_2$(cyanopyridinyl), —NR$_c$R$_c$, —NR$_a$S(O)$_2$($C_{1-3}$ alkyl), —NR$_a$C(O)($C_{1-3}$ alkyl), —NR$_a$C(O)O($C_{1-4}$ alkyl), —NR$_a$C(O)R$_d$, —NR$_a$C(O)NR$_a$R$_d$, and R$_d$;

each $R_c$ is independently H or $C_{1-2}$ alkyl; and $R_d$ is phenyl substituted with zero to 1 substituent selected from Cl, —CH$_3$, and —OCH$_3$.

2. The compound according to claim 1 or a salt thereof, $R_1$ is H, Cl, Br, —CN, $C_{1-3}$ alkyl, $C_{2-3}$ alkenyl, $C_{1-2}$ alkoxy, —C(O)OH, —C(O)O($C_{1-2}$ alkyl), —C(O)NR$_a$R$_a$, —NR$_a$R$_a$, or —NR$_a$C(O)O($C_{1-4}$ alkyl);

$R_2$ is $C_{1-4}$ alkyl, $C_{1-3}$ cyanoalkyl, $C_{1-3}$ fluoroalkyl, $C_{2-3}$ alkenyl, —CH$_2$CH$_2$CH=CF$_2$, $C_{3-4}$ alkynyl, —(CH$_2$)$_{1-3}$OCH$_3$, —(CH$_2$)$_{1-3}$O(CH$_2$)$_{1-2}$OCH$_3$, —(CH$_2$)$_{1-3}$C(O)CH$_3$, —(CH$_2$)$_{1-3}$C(O)O($C_{1-2}$ alkyl), —(CH$_2$)$_{1-2}$R$_b$, —(CH$_2$)$_{1-3}$OR$_b$, or —(CH$_2$)$_{1-3}$OCH$_2$R$_b$;

$R_b$ is $C_{3-6}$ cycloalkyl or dioxanyl, each substituted with zero to 1 substituent selected from F, —CN, —CH$_3$, and —OCH$_3$;

$R_3$ is H, F, Cl, Br, —CN, $C_{1-2}$ alkyl, $C_{1-2}$ fluoroalkyl, —NO$_2$, —C(O)O($C_{1-2}$ alkyl), or —C(O)($C_{1-2}$ fluoroalkyl);

$R_4$ is:

(a) 2,3-dihydro-1H-indenyl substituted with zero to 2 substituents independently selected from F, Cl, —OH, —CH$_3$, —CF$_3$, —OCH$_3$, and —OCH$_2$CH=CH$_2$; or (b) —CH$_2$R$_y$, —C(CH$_3$)$_2$R$_y$, —CHR$_x$R$_y$, —CH$_2$CH(OH)R$_x$, —CH(CH$_3$)(CH$_2$CH$_2$OCH$_3$), or cyclopropyl substituted with fluorophenyl;

$R_x$ is $C_{1-5}$ alkyl, $C_{1-2}$ hydroxyalkyl, $C_{1-2}$ aminoalkyl, $C_{3-6}$ cycloalkyl, or phenyl substituted with zero to 2 substituents independently selected from F, Cl, —OH, $C_{1-2}$ alkyl, —CHF$_2$, —OCH$_3$, —OCH$_2$CH=CH$_2$, and —OCH$_2$C≡CH; and $R_y$ is 1,3-benzodiazolyl, indazolyl, indolyl, indolinyl, naphthalenyl, oxoindolinyl, pyridinyl, pyrimidinyl, or phenyl, each substituted with zero to 3 substituents independently selected from F, Cl, Br, —OH, —CN, $C_{1-4}$ alkyl, $C_{1-2}$ fluoroalkyl, $C_{1-2}$ alkoxy, $C_{1-2}$ fluoroalkoxy, —OCH$_2$CH=CH$_2$, —OCH$_2$C≡CH, —OCH$_2$(cyanopyridinyl), —NR$_c$R$_c$, —NHS(O)$_2$CH$_3$, —NHC(O)(C$_{1-2}$ alkyl), —NHC(O)O(C$_{1-4}$ alkyl), —NHC(O)(phenyl), —NHC(O)NH(phenyl), and phenyl.

3. The compound according to claim 1 or a salt thereof, wherein:

$R_1$ is H, Cl, Br, —CN, $C_{1-2}$ alkyl, —CH=CH$_2$, —OCH$_3$, —C(O)OH, —C(O)OCH$_3$, —C(O)N(CH$_3$)$_2$, —NH$_2$, or —NHC(O)OC(CH$_3$)$_3$;

$R_2$ is —CH$_3$, —CH$_2$CH$_3$, —CH$_2$CH$_2$CH$_3$, —CH$_2$CH$_2$CH$_2$CH$_3$, —CH$_2$CN, —CH$_2$CH$_2$CH$_2$CN, —CH$_2$CH$_2$CF$_3$, —CH$_2$CH=CH$_2$, —CH$_2$CH$_2$CH=CF$_2$, —CH$_2$C≡CH, —CH$_2$CH$_2$OCH$_3$, —CH$_2$CH$_2$CH$_2$OCH$_3$, —CH$_2$CH$_2$CH$_2$OCH$_2$CH$_2$OCH$_3$, —CH$_2$CH$_2$CH$_2$C(O)CH$_3$, —CH$_2$C(O)OCH$_2$CH$_3$, —CH$_2$(cyclopropyl), or —CH$_2$CH$_2$(dioxanyl);

$R_3$ is H, F, Cl, Br, —CN, —CH$_3$, —CF$_3$, —NO$_2$, —C(O)OCH$_2$CH$_3$, or —C(O)CF$_3$;

$R_4$ is:

(a) 2,3-dihydro-1H-indenyl substituted with 1 to 2 substituents independently selected from F, —OH, —OCH$_3$, and —OCH$_2$CH=CH$_2$; or (b) —CH$_2$R$_y$, —C(CH$_3$)$_2$R$_y$, —CHR$_x$R$_y$, —CH$_2$CH(OH)R$_x$, —CH(CH$_3$)(CH$_2$CH$_2$OCH$_3$), or cyclopropyl substituted with fluorophenyl;

$R_x$ is $C_{1-2}$ alkyl, —CH(CH$_3$)$_2$, —C(CH$_3$)$_3$, —CH$_2$C(CH$_3$)$_3$, —CH$_2$OH, —CH$_2$NH$_2$, cyclopropyl, cyclobutyl, cyclohexyl, or phenyl substituted with zero to 2 substituents independently selected from F, Cl, —OH, and —OCH$_3$; and $R_y$ is 1,3-benzodiazolyl, indazolyl, indolyl, ethyl indolyl, indolinyl, naphthalenyl, hydroxynaphthalenyl, oxoindolinyl, pyridinyl, methoxypyridinyl, pyrimidinyl, or phenyl substituted with zero to 3 substituents independently selected from F, Cl, Br, —OH, —CN, —CH$_3$, —C(CH$_3$)$_3$, —CHF$_2$, —CF$_3$, —OCH$_3$, —OCF$_3$, —OCH$_2$CH=CH$_2$, —OCH$_2$C≡CH, —OCH$_2$(cyanopyridinyl), —NH$_2$, —NHS(O)$_2$CH$_3$, —N(CH$_3$)(CH$_2$CH$_3$), —NHC(O)CH$_3$, —NHC(O)O(C(CH$_3$)$_3$), —NHC(O)(phenyl), —NHC(O)NH(phenyl), and phenyl.

4. The compound according to claim 1 or a salt thereof, wherein $R_4$ is —CH$_2$R$_y$, —CHR$_x$R$_y$, or —CH$_2$CH(OH)R$_x$.

5. The compound according to claim 4 or a salt thereof, wherein:

$R_x$ is phenyl substituted with zero to 2 substituents independently selected from F, Cl, —OH, $C_{1-2}$ alkyl, —CHF$_2$, —OCH$_3$, —OCH$_2$CH=CH$_2$, and —OCH$_2$C≡CH; and $R_y$ is phenyl substituted with zero to 3 substituents independently selected from F, Cl, Br, —OH, —CN, $C_{1-4}$ alkyl, $C_{1-2}$ fluoroalkyl, $C_{1-2}$ alkoxy, $C_{1-2}$ fluoroalkoxy, —OCH$_2$CH=CH$_2$, —OCH$_2$C≡CH, —OCH$_2$(cyanopyridinyl), —NR$_c$R$_c$, —NHS(O)$_2$CH$_3$, —NHC(O)(C$_{1-2}$ alkyl), —NHC(O)O(C$_{1-4}$ alkyl), —NHC(O)(phenyl), —NHC(O)NH(phenyl), and phenyl.

6. The compound according to claim 1 or a salt thereof, wherein:

$R_4$ is —CHR$_x$R$_y$;

$R_x$ is phenyl substituted with zero to 2 substituents independently selected from F, Cl, —OH, and —OCH$_3$; and $R_y$ is phenyl substituted with zero to 3 substituents independently selected from F, Cl, Br, —OH, —CN, —CH$_3$, —C(CH$_3$)$_3$, —CHF$_2$, —CF$_3$, —OCH$_3$, —OCF$_3$, —OCH$_2$CH=CH$_2$, —OCH$_2$C≡CH, —OCH$_2$(cyanopyridinyl), —NH$_2$, —NHS(O)$_2$CH$_3$, —N(CH$_3$)(CH$_2$CH$_3$), —NHC(O)CH$_3$, —NHC(O)O(C(CH$_3$)$_3$), —NHC(O)(phenyl), —NHC(O)NH(phenyl), and phenyl.

7. The compound according to claim 1 or a salt thereof, wherein $R_4$ is 2,3-dihydro-1H-indenyl substituted with zero to 2 substituents independently selected from F, Cl, —OH, $C_{1-2}$ alkyl, $C_{1-2}$ fluoroalkyl, $C_{1-2}$ alkoxy, and —OCH$_2$CH=CH$_2$.

8. The compound according to claim 1 or a salt thereof, wherein said compound is:

ethyl 4-(4-(bis(4-fluorophenyl)methyl)piperazin-1-yl)-6-bromo-1-methyl-2-oxo-1,2-dihydro-1,5-naphthyridine-3-carboxylate (1);

6-bromo-4-(4-(2-hydroxybenzyl)piperazin-1-yl)-1-methyl-2-oxo-1,2-dihydro-1,5-naphthyridine-3-carbonitrile (2);

4-(4-(bis(4-fluorophenyl) methyl)piperazin-1-yl)-1-methyl-3-nitro-1,5-naphthyridin-2(1H)-one (3);

6-bromo-4-{4-[(4-fluorophenyl)[2-(prop-2-yn-1-yloxy)phenyl]methyl]piperazin-1-yl}-1-methyl-2-oxo-1,2-dihydro-1,5-naphthyridine-3-carbonitrile (5-7);

6-bromo-4-{4-[(4-fluorophenyl)(2-hydroxyphenyl)methyl]piperazin-1-yl}-1-methyl-2-oxo-1,2-dihydro-1,5-naphthyridine-3-carbonitrile (8-10);

8-{4-[(4-fluorophenyl)(2-hydroxyphenyl)methyl]piperazin-1-yl}-5-methyl-6-oxo-5,6-dihydro-1,5-naphthyridine-2,7-dicarbonitrile (11);

6-bromo-4-{4-[(4-fluorophenyl)(2-methoxyphenyl)methyl]piperazin-1-yl}-1-methyl-2-oxo-1,2-dihydro-1,5-naphthyridine-3-carbonitrile (12-14);

6-bromo-4-{4-[(4-fluoro-2-methoxyphenyl)(4-fluorophenyl) methyl]piperazin-1-yl}-1-methyl-2-oxo-1,2-dihydro-1,5-naphthyridine-3-carbonitrile (15-17);

8-{4-[(4-fluorophenyl)(2-methoxyphenyl)methyl]piperazin-1-yl}-5-methyl-7-nitro-6-oxo-5,6-dihydro-1,5-naphthyridine-2-carbonitrile (18-20);

6-bromo-4-[4-(6-methoxy-2,3-dihydro-1H-inden-1-yl)piperazin-1-yl]-1-methyl-2-oxo-1,2-dihydro-1,5-naphthyridine-3-carbonitrile (21):

6-bromo-4-{4-[1-(4-fluorophenyl)ethyl]piperazin-1-yl}-1-methyl-2-oxo-1,2-dihydro-1,5-naphthyridine-3-carbonitrile (22-24);

6-bromo-4-{4-[1-(4-fluorophenyl)propyl]piperazin-1-yl}-1-methyl-2-oxo-1,2-dihydro-1,5-naphthyridine-3-carbonitrile (25-27);

6-bromo-4-{4-[2-(4-fluorophenyl)-2-hydroxyethyl]piperazin-1-yl}-1-methyl-2-oxo-1,2-dihydro-1,5-naphthyridine-3-carbonitrile (28-30);

6-bromo-4-{4-[1-(4-fluorophenyl)-2-hydroxyethyl]piperazin-1-yl}-1-methyl-2-oxo-1,2-dihydro-1,5-naphthyridine-3-carbonitrile (31);

8-{4-[1-(4-fluorophenyl)propyl]piperazin-1-yl}-5-methyl-7-nitro-6-oxo-5,6-dihydro-1,5-naphthyridine-2-carbonitrile (32-34);

6-bromo-4-{4-[cyclopropyl(4-fluorophenyl)methyl]piperazin-1-yl}-1-methyl-2-oxo-1,2-dihydro-1,5-naphthyridine-3-carbonitrile (35);

8-{4-[2-(4-fluorophenyl)-2-hydroxyethyl]piperazin-1-yl}-5-methyl-7-nitro-6-oxo-5,6-dihydro-1,5-naphthyridine-2-carbonitrile (36);

8-{4-[1-(4-fluorophenyl)-2-hydroxyethyl]piperazin-1-yl}-5-methyl-7-nitro-6-oxo-5,6-dihydro-1,5-naphthyridine-2-carbonitrile (37);

1-methyl-4-{4-[(naphthalen-1-yl) methyl]piperazin-1-yl}-3-nitro-1,2-dihydro-1,5-naphthyridin-2-one (38);

6-chloro-4-{4-[(4-fluorophenyl)[2-(prop-2-yn-1-yloxy)phenyl]methyl]piperazin-1-yl}-1-methyl-2-oxo-1,2-dihydro-1,5-naphthyridine-3-carbonitrile (39);

8-(4-(bis(4-fluorophenyl)methyl) piperazin-1-yl)-5-methyl-7-nitro-6-oxo-5,6-dihydro-1,5-naphthyridine-2-carbonitrile (40);

8-(4-benzhydrylpiperazin-1-yl)-5-methyl-7-nitro-6-oxo-5,6-dihydro-1,5-naphthyridine-2-carbonitrile (41);

8-(4-((2-hydroxyphenyl)(phenyl)methyl)piperazin-1-yl)-5-methyl-7-nitro-6-oxo-5,6-dihydro-1,5-naphthyridine-2-carbonitrile (42);

8-(4-(1-(4-fluorophenyl)ethyl)piperazin-1-yl)-5-methyl-7-nitro-6-oxo-5,6-dihydro-1,5-naphthyridine-2-carbonitrile (43-45);

8-(4-(6-methoxy-2,3-dihydro-1H-inden-1-yl) piperazin-1-yl)-5-methyl-7-nitro-6-oxo-5,6-dihydro-1,5-naphthyridine-2-carbonitrile (46);

8-(4-(2-hydroxy-1-phenylethyl)piperazin-1-yl)-5-methyl-7-nitro-6-oxo-5,6-dihydro-1,5-naphthyridine-2-carbonitrile (47);

8-(4-(2-hydroxy-2-phenylethyl)piperazin-1-yl)-5-methyl-7-nitro-6-oxo-5,6-dihydro-1,5-naphthyridine-2-carbonitrile (48);

8-(4-(cyclopropyl(4-fluorophenyl)methyl)piperazin-1-yl)-5-methyl-7-nitro-6-oxo-5,6-dihydro-1,5-naphthyridine-2-carbonitrile (49-51);

4-(4-benzhydrylpiperazin-1-yl)-6-bromo-1-methyl-3-nitro-1,5-naphthyridin-2(1H)-one (52);

4-(4-(bis(4-fluorophenyl)methyl) piperazin-1-yl)-6-bromo-1-methyl-3-nitro-1,5-naphthyridin-2(1H)-one (53);

6-bromo-4-(4-((1-ethyl-1H-indol-4-yl)methyl)piperazin-1-yl)-1-methyl-3-nitro-1,5-naphthyridin-2(1H)-one (54);

6-bromo-1-methyl-4-(4-(naphthalen-1-ylmethyl)piperazin-1-yl)-3-nitro-1,5-naphthyridin-2(1H)-one (55);

6-bromo-4-(4-((4-fluoro-2-methoxyphenyl)(4-fluorophenyl)methyl)piperazin-1-yl)-1-methyl-3-nitro-1,5-naphthyridin-2(1H)-one (56-58);

6-bromo-4-(4-((4-fluorophenyl)(2-methoxy-6-methylphenyl)methyl)piperazin-1-yl)-1-methyl-3-nitro-1,5-naphthyridin-2(1H)-one (59-61);

tert-butyl (8-(4-(bis(4-fluorophenyl)methyl)piperazin-1-yl)-5-methyl-7-nitro-6-oxo-5,6-dihydro-1,5-naphthyridin-2-yl)carbamate (62);

6-amino-4-(4-(bis(4-fluorophenyl)methyl)piperazin-1-yl)-1-methyl-3-nitro-1,5-naphthyridin-2(1H)-one (63);

6-bromo-4-(4-(2-(difluoromethyl)benzyl)piperazin-1-yl)-2-oxo-1-(prop-2-yn-1-yl)-1,2-dihydro-1,5-naphthyridine-3-carbonitrile (64);

6-bromo-4-(4-(2-hydroxybenzyl)piperazin-1-yl)-2-oxo-1-(prop-2-yn-1-yl)-1,2-dihydro-1,5-naphthyridine-3-carbonitrile (65);

6-bromo-4-(4-(2-hydroxy-4-methylbenzyl)piperazin-1-yl)-2-oxo-1-(prop-2-yn-1-yl)-1,2-dihydro-1,5-naphthyridine-3-carbonitrile (66);

6-bromo-4-(4-(4-fluoro-2-hydroxybenzyl)piperazin-1-yl)-2-oxo-1-(prop-2-yn-1-yl)-1,2-dihydro-1,5-naphthyridine-3-carbonitrile (67);

6-bromo-4-(4-(4-fluoro-2-methoxybenzyl)piperazin-1-yl)-2-oxo-1-(prop-2-yn-1-yl)-1,2-dihydro-1,5-naphthyridine-3-carbonitrile (68);

6-bromo-4-(4-(2-hydroxy-4,6-dimethylbenzyl)piperazin-1-yl)-2-oxo-1-(prop-2-yn-1-yl)-1,2-dihydro-1,5-naphthyridine-3-carbonitrile (69);

6-bromo-4-(4-((4-fluorophenyl)(2-hydroxyphenyl)methyl)piperazin-1-yl)-1-methyl-3-nitro-1,5-naphthyridin-2(1H)-one (70);

6-bromo-4-(4-((2-fluoro-4-methylphenyl)(2-hydroxyphenyl)methyl)piperazin-1-yl)-1-methyl-3-nitro-1,5-naphthyridin-2(1H)-one (71);

6-bromo-4-(4-((2,4-dimethylphenyl)(2-hydroxyphenyl)methyl)piperazin-1-yl)-1-methyl-3-nitro-1,5-naphthyridin-2(1H)-one (72);

6-bromo-4-(4-((2-hydroxyphenyl)(o-tolyl)methyl)piperazin-1-yl)-1-methyl-3-nitro-1,5-naphthyridin-2(1H)-one (73);

6-bromo-4-(4-((3-fluoro-2-hydroxyphenyl)(4-fluorophenyl)methyl) piperazin-1-yl)-1-methyl-3-nitro-1,5-naphthyridin-2(1H)-one (74-76);

6-bromo-4-(4-((2-hydroxyphenyl)(phenyl)methyl)piperazin-1-yl)-1-methyl-3-nitro-1,5-naphthyridin-2(1H)-one (77-79);

6-bromo-4-(4-((4-fluoro-2-hydroxyphenyl)(4-fluorophenyl)methyl) piperazin-1-yl)-1-methyl-3-nitro-1,5-naphthyridin-2(1H)-one (80-82);

6-bromo-4-(4-((4-fluorophenyl)(2-hydroxy-3-methylphenyl)methyl)piperazin-1-yl)-1-methyl-3-nitro-1,5-naphthyridin-2(1H)-one (83-85);

6-bromo-4-(4-((4-fluorophenyl)(2-hydroxy-5-methylphenyl)methyl)piperazin-1-yl)-1-methyl-3-nitro-1,5-naphthyridin-2(1H)-one (86);

6-bromo-4-(4-((4-fluorophenyl)(2-hydroxy-6-methylphenyl)methyl)piperazin-1-yl)-1-methyl-3-nitro-1,5-naphthyridin-2(1H)-one (87);

5-((2-((4-(6-bromo-1-methyl-3-nitro-2-oxo-1,2-dihydro-1,5-naphthyridin-4-yl) piperazin-1-yl)(4-fluorophenyl)methyl)-3-methylphenoxy)methyl)nicotinonitrile (88-90);

5-((2-((4-(6-bromo-1-methyl-3-nitro-2-oxo-1,2-dihydro-1,5-naphthyridin-4-yl) piperazin-1-yl)(4-fluorophenyl) methyl)-5-fluorophenoxy)methyl)nicotinonitrile (91-93);

4-(4-((2-(allyloxy)-6-methylphenyl)(4-fluorophenyl) methyl)piperazin-1-yl)-6-bromo-1-methyl-3-nitro-1,5-naphthyridin-2(1H)-one (94-96);

8-(4-((4-fluorophenyl)(2-hydroxyphenyl)methyl)piperazin-1-yl)-5-methyl-7-nitro-6-oxo-5,6-dihydro-1,5-naphthyridine-2-carbonitrile (97-99);

8-(4-((4-fluorophenyl) (2-(prop-2-yn-1-yloxy)phenyl) methyl)piperazin-1-yl)-5-methyl-7-nitro-6-oxo-5,6-dihydro-1,5-naphthyridine-2-carbonitrile (100-102);

4-(4-(bis(4-fluorophenyl)methyl) piperazin-1-yl)-6-methoxy-1-methyl-2-oxo-1,2-dihydro-1,5-naphthyridine-3-carbonitrile (103);

4-(4-((4-fluorophenyl)(2-hydroxyphenyl)methyl)piperazin-1-yl)-6-methoxy-1-methyl-2-oxo-1,2-dihydro-1,5-naphthyridine-3-carbonitrile (104);

6-bromo-4-(4-((4-fluorophenyl)(2-hydroxyphenyl) methyl)piperazin-1-yl)-2-oxo-1-(prop-2-yn-1-yl)-1,2-dihydro-1,5-naphthyridine-3-carbonitrile (105-107);

4-(4-(bis(4-fluorophenyl)methyl) piperazin-1-yl)-6-bromo-1-(2-methoxyethyl)-2-oxo-1,2-dihydro-1,5-naphthyridine-3-carbonitrile (113);

6-bromo-4-(4-((4-fluoro-2-methoxyphenyl)(4-fluorophenyl)methyl) piperazin-1-yl)-1-(2-methoxyethyl)-2-oxo-1,2-dihydro-1,5-naphthyridine-3-carbonitrile (114-116);

6-bromo-4-(4-((4-fluorophenyl)(2-hydroxyphenyl) methyl)piperazin-1-yl)-1-(2-methoxyethyl)-2-oxo-1,2-dihydro-1,5-naphthyridine-3-carbonitrile (117);

8-(4-(bis(4-fluorophenyl)methyl)piperazin-1-yl)-7-nitro-6-oxo-5-(prop-2-yn-1-yl)-5,6-dihydro-1,5-naphthyridine-2-carbonitrile (118);

8-(4-((4-fluoro-2-hydroxyphenyl)(4-fluorophenyl) methyl)piperazin-1-yl)-7-nitro-6-oxo-5-(prop-2-yn-1-yl)-5,6-dihydro-1,5-naphthyridine-2-carbonitrile (119-121);

8-(4-((4-fluoro-2-hydroxyphenyl)(4-fluorophenyl) methyl) piperazin-1-yl)-5-methyl-7-nitro-6-oxo-5,6-dihydro-1,5-naphthyridine-2-carbonitrile (122);

8-(4-((4-fluoro-2-methoxyphenyl)(4-fluorophenyl) methyl)piperazin-1-yl)-5-methyl-7-nitro-6-oxo-5,6-dihydro-1,5-naphthyridine-2-carbonitrile (123-125);

8-(4-((4-fluoro-2-methoxyphenyl)(4-fluorophenyl) methyl)piperazin-1-yl)-7-nitro-6-oxo-5-(prop-2-yn-1-yl)-5,6-dihydro-1,5-naphthyridine-2-carbonitrile (126-128);

8-(4-((4-fluorophenyl)(2-methoxyphenyl)methyl)piperazin-1-yl)-7-nitro-6-oxo-5-(prop-2-yn-1-yl)-5,6-dihydro-1,5-naphthyridine-2-carbonitrile (129-131);

8-(4-((4-fluorophenyl)(2-hydroxyphenyl)methyl)piperazin-1-yl)-7-nitro-6-oxo-5-(prop-2-yn-1-yl)-5,6-dihydro-1,5-naphthyridine-2-carbonitrile (132-134);

8-(4-(1-(4-fluorophenyl)ethyl)piperazin-1-yl)-7-nitro-6-oxo-5-(prop-2-yn-1-yl)-5,6-dihydro-1,5-naphthyridine-2-carbonitrile (135-137);

8-(4-(6-methoxy-2,3-dihydro-1H-inden-1-yl)piperazin-1-yl)-7-nitro-6-oxo-5-(prop-2-yn-1-yl)-5,6-dihydro-1,5-naphthyridine-2-carbonitrile (138);

8-{4-[1-(4-fluorophenyl) propyl]piperazin-1-yl}-7-nitro-6-oxo-5-(prop-2-yn-1-yl)-5,6-dihydro-1,5-naphthyridine-2-carbonitrile (139-141);

8-(4-(cyclopropyl(4-fluorophenyl)methyl)piperazin-1-yl)-7-nitro-6-oxo-5-(prop-2-yn-1-yl)-5,6-dihydro-1,5-naphthyridine-2-carbonitrile (142-144);

8-(4-((4-fluorophenyl)(2-hydroxyphenyl)methyl)piperazin-1-yl)-5-(2-methoxyethyl)-7-nitro-6-oxo-5,6-dihydro-1,5-naphthyridine-2-carbonitrile (145);

8-(4-(6-methoxy-2,3-dihydro-1H-inden-1-yl)piperazin-1-yl)-5-(2-methoxyethyl)-7-nitro-6-oxo-5,6-dihydro-1,5-naphthyridine-2-carbonitrile (146);

8-(4-(bis(4-fluorophenyl)methyl)piperazin-1-yl)-5-(2-methoxyethyl)-7-nitro-6-oxo-5,6-dihydro-1,5-naphthyridine-2-carbonitrile (147);

8-(4-(1-(4-fluorophenyl)ethyl)piperazin-1-yl)-5-(2-methoxyethyl)-7-nitro-6-oxo-5,6-dihydro-1,5-naphthyridine-2-carbonitrile (148-150);

5-(cyanomethyl)-8-(4-(1-(4-fluorophenyl)ethyl)piperazin-1-yl)-7-nitro-6-oxo-5,6-dihydro-1,5-naphthyridine-2-carbonitrile (151);

8-(4-(bis(4-fluorophenyl)methyl)piperazin-1-yl)-5-(cyanomethyl)-7-nitro-6-oxo-5,6-dihydro-1,5-naphthyridine-2-carbonitrile (152);

4-(4-(bis(4-fluorophenyl) methyl)piperazin-1-yl)-6-bromo-1-(cyanomethyl)-2-oxo-1,2-dihydro-1,5-naphthyridine-3-carbonitrile (153);

6-bromo-1-(cyanomethyl)-4-(4-(1-(4-fluorophenyl)ethyl) piperazin-1-yl)-2-oxo-1,2-dihydro-1,5-naphthyridine-3-carbonitrile (154);

6-bromo-1-(cyanomethyl)-4-(4-(1-(4-fluorophenyl)propyl)piperazin-1-yl)-2-oxo-1,2-dihydro-1,5-naphthyridine-3-carbonitrile (155);

6-bromo-1-(cyanomethyl)-4-(4-(6-methoxy-2,3-dihydro-1H-inden-1-yl)piperazin-1-yl)-2-oxo-1,2-dihydro-1,5-naphthyridine-3-carbonitrile (156);

6-bromo-1-(cyanomethyl)-4-(4-((4-fluorophenyl)(2-hydroxyphenyl)methyl) piperazin-1-yl)-2-oxo-1,2-dihydro-1,5-naphthyridine-3-carbonitrile (157);

6-bromo-1-(cyclopropylmethyl)-4-(4-((4-fluorophenyl) (2-methoxyphenyl)methyl) piperazin-1-yl)-2-oxo-1,2-dihydro-1,5-naphthyridine-3-carbonitrile (158-160);

4-(4-(bis(4-fluorophenyl)methyl)piperazin-1-yl)-6-bromo-1-(cyclopropylmethyl)-2-oxo-1,2-dihydro-1,5-naphthyridine-3-carbonitrile (161);

6-bromo-1-(cyclopropylmethyl)-4-(4-(1-(4-fluorophenyl) ethyl)piperazin-1-yl)-2-oxo-1,2-dihydro-1,5-naphthyridine-3-carbonitrile (162-164);

4-(4-benzhydrylpiperazin-1-yl)-3-nitro-1-(prop-2-yn-1-yl)-1,5-naphthyridin-2(1H)-one (165);

1-(2-(1,3-dioxan-2-yl)ethyl)-4-(4-benzhydrylpiperazin-1-yl)-3-nitro-1,5-naphthyridin-2(1H)-one (166);

1-allyl-4-(4-benzhydrylpiperazin-1-yl)-3-nitro-1,5-naphthyridin-2(1H)-one (176);

4-(4-benzhydrylpiperazin-1-yl)-1-butyl-3-nitro-1,5-naphthyridin-2(1H)-one (177);

4-(4-(4-benzhydrylpiperazin-1-yl)-3-nitro-2-oxo-1,5-naphthyridin-1(2H)-yl) butanenitrile (183);

4-(4-benzhydrylpiperazin-1-yl)-3-nitro-1-(3,3,3-trifluoropropyl)-1,5-naphthyridin-2(1H)-one (185);

4-(4-benzhydrylpiperazin-1-yl)-1-(4,4-difluorobut-3-en-1-yl)-3-nitro-1,5-naphthyridin-2(1H)-one (186);

4-(4-benzhydrylpiperazin-1-yl)-3-nitro-1-(4-oxopentyl)-1,5-naphthyridin-2(1H)-one (187);

4-(4-benzhydrylpiperazin-1-yl)-1-(3-(2-methoxyethoxy)propyl)-3-nitro-1,5-naphthyridin-2(1H)-one (189);

4-(4-benzhydrylpiperazin-1-yl)-1-(3-methoxypropyl)-3-nitro-1,5-naphthyridin-2(1H)-one (190);

4-(4-benzhydrylpiperazin-1-yl)-6-bromo-1-methyl-2-oxo-1,2-dihydro-1,5-naphthyridine-3-carbonitrile (191);

6-bromo-4-(4-(4-fluoro-2-hydroxybenzyl)piperazin-1-yl)-1-methyl-2-oxo-1,2-dihydro-1,5-naphthyridine-3-carbonitrile (192);

6-chloro-4-(4-(4-fluoro-2-hydroxybenzyl)piperazin-1-yl)-1-methyl-2-oxo-1,2-dihydro-1,5-naphthyridine-3-carbonitrile (193);

4-(4-(4-fluoro-2-hydroxybenzyl) piperazin-1-yl)-1,6-dimethyl-2-oxo-1,2-dihydro-1,5-naphthyridine-3-carbonitrile (194);

4-(4-(1-(2-(allyloxy)-4-fluorophenyl)ethyl)piperazin-1-yl)-6-chloro-1-methyl-2-oxo-1,2-dihydro-1,5-naphthyridine-3-carbonitrile (195);

4-(4-benzhydrylpiperazin-1-yl)-1-methyl-2-oxo-1,2-dihydro-1,5-naphthyridine-3-carbonitrile (196);

6-chloro-4-(4-(2-hydroxybenzyl) piperazin-1-yl)-1-methyl-2-oxo-1,2-dihydro-1,5-naphthyridine-3-carbonitrile (198);

6-chloro-4-(4-(3-(ethyl(methyl)amino)benzyl)piperazin-1-yl)-1-methyl-2-oxo-1,2-dihydro-1,5-naphthyridine-3-carbonitrile (199);

4-(4-(7-(allyloxy)-5-fluoro-2,3-dihydro-1H-inden-1-yl) piperazin-1-yl)-6-chloro-1-methyl-2-oxo-1,2-dihydro-1,5-naphthyridine-3-carbonitrile (200);

6-chloro-4-(4-(5-fluoro-7-hydroxy-2,3-dihydro-1H-inden-1-yl) piperazin-1-yl)-1-methyl-2-oxo-1,2-dihydro-1,5-naphthyridine-3-carbonitrile (201);

4-(4-benzhydrylpiperazin-1-yl)-6-ethyl-1-methyl-2-oxo-1,2-dihydro-1,5-naphthyridine-3-carbonitrile (202);

4-(4-benzhydrylpiperazin-1-yl)-1,6-dimethyl-2-oxo-1,2-dihydro-1,5-naphthyridine-3-carbonitrile (204);

4-(4-benzhydrylpiperazin-1-yl)-1-methyl-2-oxo-6-vinyl-1,2-dihydro-1,5-naphthyridine-3-carbonitrile (208);

6-chloro-4-(4-(cyclohexyl(phenyl)methyl)piperazin-1-yl)-1-methyl-2-oxo-1,2-dihydro-1,5-naphthyridine-3-carbonitrile (209);

4-(4-(2-aminobenzyl)piperazin-1-yl)-6-bromo-1-methyl-2-oxo-1,2-dihydro-1,5-naphthyridine-3-carbonitrile (211);

N-(2-((4-(6-bromo-3-cyano-1-methyl-2-oxo-1,2-dihydro-1,5-naphthyridin-4-yl) piperazin-1-yl)methyl) phenyl) methanesulfonamide (212);

N-(2-((4-(6-bromo-3-cyano-1-methyl-2-oxo-1,2-dihydro-1,5-naphthyridin-4-yl) piperazin-1-yl)methyl) phenyl)benzamide (213);

1-(2-((4-(6-bromo-3-cyano-1-methyl-2-oxo-1,2-dihydro-1,5-naphthyridin-4-yl)piperazin-1-yl)methyl)phenyl)-3-phenylurea (214);

N-(2-((4-(6-bromo-3-cyano-1-methyl-2-oxo-1,2-dihydro-1,5-naphthyridin-4-yl)piperazin-1-yl)methyl) phenyl)acetamide (215);

6-chloro-4-(4-(indolin-7-ylmethyl)piperazin-1-yl)-1-methyl-2-oxo-1,2-dihydro-1,5-naphthyridine-3-carbonitrile (216);

8-(4-(bis(4-fluorophenyl)methyl)piperazin-1-yl)-5-methyl-6-oxo-5,6-dihydro-1,5-naphthyridine-2,7-dicarbonitrile (217);

4-(4-(bis(4-fluorophenyl)methyl)piperazin-1-yl)-6-chloro-1-methyl-2-oxo-1,2-dihydro-1,5-naphthyridine-3-carbonitrile (218);

6-chloro-4-(4-((2-hydroxyphenyl)(phenyl)methyl)piperazin-1-yl)-1-methyl-2-oxo-1,2-dihydro-1,5-naphthyridine-3-carbonitrile (219);

6-chloro-4-(4-((1-ethyl-1H-indol-4-yl)methyl) piperazin-1-yl)-1-methyl-2-oxo-1,2-dihydro-1,5-naphthyridine-3-carbonitrile (220);

6-chloro-1-methyl-4-(4-(naphthalen-1-ylmethyl)piperazin-1-yl)-2-oxo-1,2-dihydro-1,5-naphthyridine-3-carbonitrile (221);

6-chloro-4-(4-((4-fluoro-2-hydroxyphenyl)(4-fluorophenyl)methyl)piperazin-1-yl)-1-methyl-2-oxo-1,2-dihydro-1,5-naphthyridine-3-carbonitrile (222);

8-(4-benzhydrylpiperazin-1-yl)-5-methyl-7-nitro-6-oxo-5,6-dihydro-1,5-naphthyridine-2-carbonitrile (223);

3-bromo-4-(4-(1-(4-fluorophenyl)ethyl)piperazin-1-yl)-1,6-dimethyl-1,5-naphthyridin-2(1H)-one (224);

6-bromo-4-(4-((1-ethyl-1H-indol-4-yl)methyl)piperazin-1-yl)-1-methyl-2-oxo-1,2-dihydro-1,5-naphthyridine-3-carbonitrile (225);

4-(4-(bis(4-fluorophenyl)methyl)piperazin-1-yl)-1,6-dimethyl-2-oxo-1,2-dihydro-1,5-naphthyridine-3-carbonitrile (226);

4-(4-(bis(4-fluorophenyl)methyl)piperazin-1-yl)-1-methyl-3-(2,2,2-trifluoroacetyl)-1,5-naphthyridin-2(1H)-one (227);

4-(4-(bis(4-fluorophenyl)methyl)piperazin-1-yl)-1,6-dimethyl-3-(2,2,2-trifluoroacetyl)-1,5-naphthyridin-2(1H)-one (228);

4-(4-(bis(4-fluorophenyl)methyl)piperazin-1-yl)-6-bromo-2-oxo-1-(prop-2-yn-1-yl)-1,2-dihydro-1,5-naphthyridine-3-carbonitrile (229);

4-(4-(bis(4-fluorophenyl)methyl)piperazin-1-yl)-3-bromo-1-methyl-1,5-naphthyridin-2(1H)-one (230);

8-(4-(bis(4-fluorophenyl)methyl)piperazin-1-yl)-7-cyano-N,N,5-trimethyl-6-oxo-5,6-dihydro-1,5-naphthyridine-2-carboxamide (231);

4-(4-(bis(4-fluorophenyl)methyl) piperazin-1-yl)-1,6-dimethyl-3-(trifluoromethyl)-1,5-naphthyridin-2(1H)-one (232);

4-(4-(bis(4-fluorophenyl)methyl)piperazin-1-yl)-3-chloro-1,6-dimethyl-1,5-naphthyridin-2(1H)-one (233);

4-(4-(bis(4-fluorophenyl)methyl)piperazin-1-yl)-3-fluoro-1,6-dimethyl-1,5-naphthyridin-2(1H)-one (234);

4-(4-(bis(4-fluorophenyl)methyl)piperazin-1-yl)-6-bromo-1-methyl-2-oxo-1,2-dihydro-1,5-naphthyridine-3-carbonitrile, TFA (235);

3-bromo-4-(4-((1-ethyl-1H-indol-4-yl)methyl)piperazin-1-yl)-1-methyl-1,5-naphthyridin-2(1H)-one (236);

6-bromo-1-methyl-4-(4-(naphthalen-1-ylmethyl)piperazin-1-yl)-2-oxo-1,2-dihydro-1,5-naphthyridine-3-carbonitrile (237);

4-(4-([1,1'-biphenyl]-2-ylmethyl) piperazin-1-yl)-6-bromo-1-methyl-2-oxo-1,2-dihydro-1,5-naphthyridine-3-carbonitrile, TFA (238);

4-(4-(bis(4-fluorophenyl)methyl)piperazin-1-yl)-3-bromo-1,6-dimethyl-1,5-naphthyridin-2(1H)-one (239);

methyl 8-(4-(bis(4-fluorophenyl)methyl)piperazin-1-yl)-7-cyano-5-methyl-6-oxo-5,6-dihydro-1,5-naphthyridine-2-carboxylate (240);

8-(4-(bis(4-fluorophenyl)methyl)piperazin-1-yl)-7-cyano-5-methyl-6-oxo-5,6-dihydro-1,5-naphthyridine-2-carboxylic acid (241);

4-[4-(diphenylmethyl)piperazin-1-yl]-1-methyl-3-nitro-1,2-dihydro-1,5-naphthyridin-2-one (242);

4-[4-(diphenylmethyl)piperazin-1-yl]-1-ethyl-3-nitro-1,2-dihydro-1,5-naphthyridin-2-one (243);

4-[4-(diphenylmethyl)piperazin-1-yl]-1-(2-methoxyethyl)-3-nitro-1,2-dihydro-1,5-naphthyridin-2-one (244);

2-{4-[4-(diphenylmethyl)piperazin-1-yl]-3-nitro-2-oxo-1,2-dihydro-1,5-naphthyridin-1-yl}acetonitrile (245);

ethyl 2-{4-[4-(diphenylmethyl)piperazin-1-yl]-3-nitro-2-oxo-1,2-dihydro-1,5-naphthyridin-1-yl}acetate (246);

4-[4-(diphenylmethyl)piperazin-1-yl]-3-nitro-1-propyl-1,2-dihydro-1,5-naphthyridin-2-one (248);

4-{4-[cyclopropyl(4-fluorophenyl)methyl]piperazin-1-yl}-1,6-dimethyl-2-oxo-1,2-dihydro-1,5-naphthyridine-3-carbonitrile (250);

4-{4-[bis(4-fluoro-2-methoxyphenyl)methyl]piperazin-1-yl}-1,6-dimethyl-2-oxo-1,2-dihydro-1,5-naphthyridine-3-carbonitrile (251);

4-[4-(4-methoxybutan-2-yl)piperazin-1-yl]-1,6-dimethyl-2-oxo-1,2-dihydro-1,5-naphthyridine-3-carbonitrile (252);

4-[4-(3,4-dihydro-2H-1-benzopyran-4-yl)piperazin-1-yl]-1,6-dimethyl-2-oxo-1,2-dihydro-1,5-naphthyridine-3-carbonitrile (253);

4-{4-[(4-fluorophenyl)(2-methoxypyridin-3-yl)methyl]piperazin-1-yl}-1,6-dimethyl-2-oxo-1,2-dihydro-1,5-naphthyridine-3-carbonitrile (254);

4-{4-[(4-fluorophenyl)(3-methoxypyridin-2-yl)methyl]piperazin-1-yl}-1,6-dimethyl-2-oxo-1,2-dihydro-1,5-naphthyridine-3-carbonitrile (255);

4-{4-[(4-fluorophenyl)(pyridin-2-yl)methyl]piperazin-1-yl}-1,6-dimethyl-2-oxo-1,2-dihydro-1,5-naphthyridine-3-carbonitrile (256);

4-{4-[(2-bromo-6-hydroxyphenyl)methyl]piperazin-1-yl}-6-chloro-1-methyl-2-oxo-1,2-dihydro-1,5-naphthyridine-3-carbonitrile (258);

6-bromo-4-{4-[(2-hydroxy-6-methylphenyl)methyl]piperazin-1-yl}-1-methyl-2-oxo-1,2-dihydro-1,5-naphthyridine-3-carbonitrile (259);

8-{4-[2-(4-fluorophenyl)propan-2-yl]piperazin-1-yl}-5-methyl-7-nitro-6-oxo-5,6-dihydro-1,5-naphthyridine-2-carbonitrile (260);

4-{4-[(4-tert-butyl-2-hydroxyphenyl)methyl]piperazin-1-yl}-6-chloro-1-methyl-2-oxo-1,2-dihydro-1,5-naphthyridine-3-carbonitrile (261);

4-(4-{[2-hydroxy-5-(trifluoromethoxy)phenyl]methyl}piperazin-1-yl)-1,6-dimethyl-2-oxo-1,2-dihydro-1,5-naphthyridine-3-carbonitrile (262);

8-{4-[(4-bromo-2-hydroxyphenyl)methyl]piperazin-1-yl}-5-methyl-6-oxo-5,6-dihydro-1,5-naphthyridine-2,7-dicarbonitrile (263);

6-chloro-4-{4-[(2-hydroxy-6-methoxyphenyl)methyl]piperazin-1-yl}-1-methyl-2-oxo-1,2-dihydro-1,5-naphthyridine-3-carbonitrile (264);

8-(4-{[2-hydroxy-4-(trifluoromethoxy)phenyl]methyl}piperazin-1-yl)-5-methyl-6-oxo-5,6-dihydro-1,5-naphthyridine-2,7-dicarbonitrile (265);

6-bromo-4-{4-[(4-chloro-2-hydroxyphenyl)methyl]piperazin-1-yl}-1-methyl-2-oxo-1,2-dihydro-1,5-naphthyridine-3-carbonitrile (266);

6-chloro-4-{4-[(2-chloro-6-hydroxyphenyl)methyl]piperazin-1-yl}-1-methyl-2-oxo-1,2-dihydro-1,5-naphthyridine-3-carbonitrile (267);

4-{4-[(3-bromo-2-hydroxyphenyl)methyl]piperazin-1-yl}-6-chloro-1-methyl-2-oxo-1,2-dihydro-1,5-naphthyridine-3-carbonitrile (268);

8-{4-[(4-chloro-2-hydroxyphenyl) methyl]piperazin-1-yl}-5-methyl-6-oxo-5,6-dihydro-1,5-naphthyridine-2,7-dicarbonitrile (269);

6-bromo-4-(4-{[2-hydroxy-5-(trifluoromethoxy)phenyl]methyl}piperazin-1-yl)-1-methyl-2-oxo-1,2-dihydro-1,5-naphthyridine-3-carbonitrile (270);

6-bromo-4-{4-[(2-bromo-6-hydroxyphenyl)methyl]piperazin-1-yl}-1-methyl-2-oxo-1,2-dihydro-1,5-naphthyridine-3-carbonitrile (271);

6-chloro-4-{4-[(2-chlorophenyl)methyl]piperazin-1-yl}-1-methyl-2-oxo-1,2-dihydro-1,5-naphthyridine-3-carbonitrile (272);

6-chloro-4-{4-[(2-hydroxy-4-methylphenyl)methyl]piperazin-1-yl}-1-methyl-2-oxo-1,2-dihydro-1,5-naphthyridine-3-carbonitrile (273);

6-chloro-4-{4-[(3-fluoro-2-methoxyphenyl)methyl]piperazin-1-yl}-1-methyl-2-oxo-1,2-dihydro-1,5-naphthyridine-3-carbonitrile (274);

4-{4-[(5-bromo-2-hydroxyphenyl)methyl]piperazin-1-yl}-6-chloro-1-methyl-2-oxo-1,2-dihydro-1,5-naphthyridine-3-carbonitrile (275);

4-{4-[(4-bromo-2-hydroxyphenyl) methyl]piperazin-1-yl}-6-chloro-1-methyl-2-oxo-1,2-dihydro-1,5-naphthyridine-3-carbonitrile (276);

4-{4-[(5-bromo-2-hydroxyphenyl)methyl]piperazin-1-yl}-1,6-dimethyl-2-oxo-1,2-dihydro-1,5-naphthyridine-3-carbonitrile (277);

6-bromo-4-{4-[(3-chloro-2-hydroxyphenyl)methyl]piperazin-1-yl}-1-methyl-2-oxo-1,2-dihydro-1,5-naphthyridine-3-carbonitrile (278);

6-chloro-4-{4-[(3-fluoro-4-methoxyphenyl)methyl]piperazin-1-yl}-1-methyl-2-oxo-1,2-dihydro-1,5-naphthyridine-3-carbonitrile (279);

6-chloro-4-{4-[(2-fluoro-6-hydroxyphenyl)methyl]piperazin-1-yl}-1-methyl-2-oxo-1,2-dihydro-1,5-naphthyridine-3-carbonitrile (280);

6-chloro-4-{4-[(2-fluoro-3-methylphenyl)methyl]piperazin-1-yl}-1-methyl-2-oxo-1,2-dihydro-1,5-naphthyridine-3-carbonitrile (281);

6-bromo-4-{4-[(5-bromo-2-hydroxyphenyl)methyl]piperazin-1-yl}-1-methyl-2-oxo-1,2-dihydro-1,5-naphthyridine-3-carbonitrile (282);

6-chloro-4-{4-[(2-hydroxy-5-methylphenyl)methyl]piperazin-1-yl}-1-methyl-2-oxo-1,2-dihydro-1,5-naphthyridine-3-carbonitrile (283);

tert-butyl N-(2-{[4-(6-bromo-3-cyano-1-methyl-2-oxo-1,2-dihydro-1,5-naphthyridin-4-yl)piperazin-1-yl]methyl}phenyl)carbamate (284);

6-chloro-1-methyl-2-oxo-4-(4-{[2-(trifluoromethoxy)phenyl]methyl}piperazin-1-yl)-1,2-dihydro-1,5-naphthyridine-3-carbonitrile (285);

4-{4-[(3-bromo-2-hydroxyphenyl) methyl]piperazin-1-yl}-1,6-dimethyl-2-oxo-1,2-dihydro-1,5-naphthyridine-3-carbonitrile (286);

6-chloro-4-{4-[(2-chloro-4-fluorophenyl)methyl]piperazin-1-yl}-1-methyl-2-oxo-1,2-dihydro-1,5-naphthyridine-3-carbonitrile (287);

6-chloro-4-{4-[(4-chloro-2-hydroxyphenyl)methyl]piperazin-1-yl}-1-methyl-2-oxo-1,2-dihydro-1,5-naphthyridine-3-carbonitrile (288);

6-chloro-4-{4-[(3-fluoro-4-methylphenyl)methyl]piperazin-1-yl}-1-methyl-2-oxo-1,2-dihydro-1,5-naphthyridine-3-carbonitrile (289);

6-chloro-4-{4-[(3-fluoro-5-methylphenyl)methyl]piperazin-1-yl}-1-methyl-2-oxo-1,2-dihydro-1,5-naphthyridine-3-carbonitrile (290);

6-chloro-4-{4-[(3,5-difluorophenyl)methyl]piperazin-1-yl}-1-methyl-2-oxo-1,2-dihydro-1,5-naphthyridine-3-carbonitrile (291);

6-chloro-4-{4-[(2-hydroxy-6-methylphenyl)methyl]piperazin-1-yl}-1-methyl-2-oxo-1,2-dihydro-1,5-naphthyridine-3-carbonitrile (292);

6-chloro-4-{4-[(3-chloro-2-hydroxyphenyl)methyl]piperazin-1-yl}-1-methyl-2-oxo-1,2-dihydro-1,5-naphthyridine-3-carbonitrile (293);

6-bromo-4-{4-[(2-fluoro-6-hydroxyphenyl)methyl]piperazin-1-yl}-1-methyl-2-oxo-1,2-dihydro-1,5-naphthyridine-3-carbonitrile (294);

6-bromo-4-{4-[(2-hydroxy-4-methoxyphenyl)methyl]piperazin-1-yl}-1-methyl-2-oxo-1,2-dihydro-1,5-naphthyridine-3-carbonitrile (295);

4-{4-[(5-chloro-2-hydroxyphenyl)methyl]piperazin-1-yl}-1,6-dimethyl-2-oxo-1,2-dihydro-1,5-naphthyridine-3-carbonitrile (296);

6-bromo-4-{4-[(2-methoxyphenyl)methyl]piperazin-1-yl}-1-methyl-2-oxo-1,2-dihydro-1,5-naphthyridine-3-carbonitrile (297);

6-chloro-4-{4-[(3,5-difluoro-2-hydroxyphenyl)methyl]piperazin-1-yl}-1-methyl-2-oxo-1,2-dihydro-1,5-naphthyridine-3-carbonitrile (298);

6-bromo-4-{4-[(2,3-dihydro-1H-indol-7-yl)methyl]piperazin-1-yl}-1-methyl-2-oxo-1,2-dihydro-1,5-naphthyridine-3-carbonitrile (299);

6-bromo-4-{4-[(2-chlorophenyl)methyl]piperazin-1-yl}-1-methyl-2-oxo-1,2-dihydro-1,5-naphthyridine-3-carbonitrile (300);

6-chloro-4-{4-[(2-hydroxy-4-methoxyphenyl)methyl]piperazin-1-yl}-1-methyl-2-oxo-1,2-dihydro-1,5-naphthyridine-3-carbonitrile (301);

6-chloro-4-{4-[(3-chlorophenyl)methyl]piperazin-1-yl}-1-methyl-2-oxo-1,2-dihydro-1,5-naphthyridine-3-carbonitrile (302);

6-chloro-4-{4-[(1H-indol-7-yl)methyl]piperazin-1-yl}-1-methyl-2-oxo-1,2-dihydro-1,5-naphthyridine-3-carbonitrile (303);

6-bromo-4-{4-[(3-fluoro-2-hydroxyphenyl)methyl]piperazin-1-yl}-1-methyl-2-oxo-1,2-dihydro-1,5-naphthyridine-3-carbonitrile (304);

6-chloro-4-{4-[(2-hydroxy-5-methoxyphenyl)methyl]piperazin-1-yl}-1-methyl-2-oxo-1,2-dihydro-1,5-naphthyridine-3-carbonitrile (305);

6-chloro-4-{4-[(3-fluoro-2-hydroxyphenyl)methyl]piperazin-1-yl}-1-methyl-2-oxo-1,2-dihydro-1,5-naphthyridine-3-carbonitrile (306);

6-chloro-4-{4-[(3,5-dichloro-2-hydroxyphenyl)methyl]piperazin-1-yl}-1-methyl-2-oxo-1,2-dihydro-1,5-naphthyridine-3-carbonitrile (307);

6-chloro-4-{4-[(4-fluorophenyl)methyl]piperazin-1-yl}-1-methyl-2-oxo-1,2-dihydro-1,5-naphthyridine-3-carbonitrile (308);

6-bromo-4-{4-[(3-tert-butyl-2-hydroxyphenyl)methyl]piperazin-1-yl}-1-methyl-2-oxo-1,2-dihydro-1,5-naphthyridine-3-carbonitrile (309);

6-chloro-4-{4-[(2,4-dichlorophenyl) methyl]piperazin-1-yl}-1-methyl-2-oxo-1,2-dihydro-1,5-naphthyridine-3-carbonitrile (310);

6-chloro-4-(4-{[2-hydroxy-4-(trifluoromethyl)phenyl]methyl}piperazin-1-yl)-1-methyl-2-oxo-1,2-dihydro-1,5-naphthyridine-3-carbonitrile (311);

6-chloro-4-{4-[(5-fluoro-2-hydroxyphenyl)methyl]piperazin-1-yl}-1-methyl-2-oxo-1,2-dihydro-1,5-naphthyridine-3-carbonitrile (312);

6-chloro-4-(4-{[3-fluoro-5-(trifluoromethyl)phenyl]methyl}piperazin-1-yl)-1-methyl-2-oxo-1,2-dihydro-1,5-naphthyridine-3-carbonitrile (313);

6-bromo-4-{4-[(2-hydroxy-6-methoxyphenyl)methyl]piperazin-1-yl}-1-methyl-2-oxo-1,2-dihydro-1,5-naphthyridine-3-carbonitrile (314);

6-chloro-4-{4-[1-(4-fluorophenyl)-2-methylpropyl]piperazin-1-yl}-1-methyl-2-oxo-1,2-dihydro-1,5-naphthyridine-3-carbonitrile (315-316);

8-{4-[(2-hydroxyphenyl)methyl]piperazin-1-yl}-5-methyl-6-oxo-5,6-dihydro-1,5-naphthyridine-2,7-dicarbonitrile (317);

6-chloro-4-{4-[(2,5-difluorophenyl)methyl]piperazin-1-yl}-1-methyl-2-oxo-1,2-dihydro-1,5-naphthyridine-3-carbonitrile (318);

6-chloro-4-{4-[(3,4-difluorophenyl)methyl]piperazin-1-yl}-1-methyl-2-oxo-1,2-dihydro-1,5-naphthyridine-3-carbonitrile (319);

6-bromo-4-{4-[(3,5-difluoro-2-hydroxyphenyl)methyl]piperazin-1-yl}-1-methyl-2-oxo-1,2-dihydro-1,5-naphthyridine-3-carbonitrile (320);

6-chloro-4-{4-[(3-fluorophenyl)methyl]piperazin-1-yl}-1-methyl-2-oxo-1,2-dihydro-1,5-naphthyridine-3-carbonitrile (321);

6-chloro-4-{4-[(1H-indazol-7-yl)methyl]piperazin-1-yl}-1-methyl-2-oxo-1,2-dihydro-1,5-naphthyridine-3-carbonitrile (322);

6-chloro-4-{4-[(4-chloro-3-hydroxyphenyl)methyl]piperazin-1-yl}-1-methyl-2-oxo-1,2-dihydro-1,5-naphthyridine-3-carbonitrile (323);

6-chloro-4-{4-[(3-chloro-5-fluorophenyl)methyl]piperazin-1-yl}-1-methyl-2-oxo-1,2-dihydro-1,5-naphthyridine-3-carbonitrile (324);

8-[4-(diphenylmethyl)piperazin-1-yl]-5-methyl-6-oxo-5,6-dihydro-1,5-naphthyridine-2,7-dicarbonitrile (325);

6-chloro-4-{4-[(4-chloro-3-fluorophenyl)methyl]piperazin-1-yl}-1-methyl-2-oxo-1,2-dihydro-1,5-naphthyridine-3-carbonitrile (326);

6-chloro-4-{4-[(3-methoxyphenyl)methyl]piperazin-1-yl}-1-methyl-2-oxo-1,2-dihydro-1,5-naphthyridine-3-carbonitrile (327);

6-chloro-4-{4-[(3-hydroxy-4-methylphenyl)methyl]piperazin-1-yl}-1-methyl-2-oxo-1,2-dihydro-1,5-naphthyridine-3-carbonitrile (328);

4-{4-[(3-fluoro-2-hydroxyphenyl)methyl]piperazin-1-yl}-1,6-dimethyl-2-oxo-1,2-dihydro-1,5-naphthyridine-3-carbonitrile (329);

6-chloro-4-{4-[(2,3-difluorophenyl)methyl]piperazin-1-yl}-1-methyl-2-oxo-1,2-dihydro-1,5-naphthyridine-3-carbonitrile (330);

6-chloro-4-{4-[(2-methoxyphenyl)methyl]piperazin-1-yl}-1-methyl-2-oxo-1,2-dihydro-1,5-naphthyridine-3-carbonitrile (331);

8-{4-[(4-chloro-3-hydroxyphenyl)methyl]piperazin-1-yl}-5-methyl-6-oxo-5,6-dihydro-1,5-naphthyridine-2,7-dicarbonitrile (332);

6-bromo-4-{4-[(1H-indazol-7-yl)methyl]piperazin-1-yl}-1-methyl-2-oxo-1,2-dihydro-1,5-naphthyridine-3-carbonitrile (333);

4-{4-[(1-ethyl-1H-indol-4-yl)methyl]piperazin-1-yl}-1-methyl-2-oxo-1,2-dihydro-1,5-naphthyridine-3-carbonitrile (334);

6-chloro-4-{4-[(2-fluoro-6-methoxyphenyl)methyl]piperazin-1-yl}-1-methyl-2-oxo-1,2-dihydro-1,5-naphthyridine-3-carbonitrile (335);

6-chloro-4-{4-[(2-hydroxynaphthalen-1-yl)methyl]piperazin-1-yl}-1-methyl-2-oxo-1,2-dihydro-1,5-naphthyridine-3-carbonitrile (336);

4-{4-[(2-hydroxyphenyl)methyl]piperazin-1-yl}-1,6-dimethyl-2-oxo-1,2-dihydro-1,5-naphthyridine-3-carbonitrile (337);

6-chloro-4-{4-[(3-fluoro-5-hydroxyphenyl)methyl]piperazin-1-yl}-1-methyl-2-oxo-1,2-dihydro-1,5-naphthyridine-3-carbonitrile (338);

6-chloro-4-{4-[(2-fluorophenyl)methyl]piperazin-1-yl}-1-methyl-2-oxo-1,2-dihydro-1,5-naphthyridine-3-carbonitrile (339);

6-chloro-4-{4-[(5-cyano-2-fluorophenyl)methyl]piperazin-1-yl}-1-methyl-2-oxo-1,2-dihydro-1,5-naphthyridine-3-carbonitrile (340);

6-chloro-4-{4-[(4-methoxyphenyl) methyl]piperazin-1-yl}-1-methyl-2-oxo-1,2-dihydro-1,5-naphthyridine-3-carbonitrile (341);

8-{4-[1-(4-fluorophenyl)cyclopropyl]piperazin-1-yl}-5-methyl-7-nitro-6-oxo-5,6-dihydro-1,5-naphthyridine-2-carbonitrile (342);

4-(4-benzylpiperazin-1-yl)-6-chloro-1-methyl-2-oxo-1,2-dihydro-1,5-naphthyridine-3-carbonitrile (343);

6-bromo-4-{4-[(2-fluorophenyl)methyl]piperazin-1-yl}-1-methyl-2-oxo-1,2-dihydro-1,5-naphthyridine-3-carbonitrile (344);

6-chloro-4-{4-[(3-chloro-5-hydroxyphenyl)methyl]piperazin-1-yl}-1-methyl-2-oxo-1,2-dihydro-1,5-naphthyridine-3-carbonitrile (345);

6-chloro-1-methyl-4-{4-[(2-methylphenyl)methyl]piperazin-1-yl}-2-oxo-1,2-dihydro-1,5-naphthyridine-3-carbonitrile (346);

4-{4-[bis(4-fluorophenyl)methyl]piperazin-1-yl}-1-methyl-2-oxo-1,2-dihydro-1,5-naphthyridine-3-carbonitrile (347);

6-chloro-4-{4-[(4-fluoro-3-hydroxyphenyl)methyl]piperazin-1-yl}-1-methyl-2-oxo-1,2-dihydro-1,5-naphthyridine-3-carbonitrile (348);

4-{4-[(2-hydroxyphenyl)(phenyl)methyl]piperazin-1-yl}-1-methyl-2-oxo-1,2-dihydro-1,5-naphthyridine-3-carbonitrile (349);

6-chloro-4-{4-[(2,4-difluorophenyl)methyl]piperazin-1-yl}-1-methyl-2-oxo-1,2-dihydro-1,5-naphthyridine-3-carbonitrile (350);

6-chloro-4-{4-[(3-hydroxyphenyl)methyl]piperazin-1-yl}-1-methyl-2-oxo-1,2-dihydro-1,5-naphthyridine-3-carbonitrile (351);

4-{4-[(2-hydroxy-3-methoxyphenyl)methyl]piperazin-1-yl}-1,6-dimethyl-2-oxo-1,2-dihydro-1,5-naphthyridine-3-carbonitrile (352);

6-chloro-4-{4-[(3-hydroxy-4-methoxyphenyl)methyl]piperazin-1-yl}-1-methyl-2-oxo-1,2-dihydro-1,5-naphthyridine-3-carbonitrile (353);

6-chloro-4-{4-[(3-chloro-4-hydroxyphenyl)methyl]piperazin-1-yl}-1-methyl-2-oxo-1,2-dihydro-1,5-naphthyridine-3-carbonitrile (354);

6-chloro-4-(4-{[4-hydroxy-3-(trifluoromethyl)phenyl]methyl}piperazin-1-yl)-1-methyl-2-oxo-1,2-dihydro-1,5-naphthyridine-3-carbonitrile (355);

6-chloro-4-{4-[(4-hydroxy-3-methylphenyl)methyl]piperazin-1-yl}-1-methyl-2-oxo-1,2-dihydro-1,5-naphthyridine-3-carbonitrile (356);

6-chloro-4-{4-[(3-fluoro-4-hydroxyphenyl)methyl]piperazin-1-yl}-1-methyl-2-oxo-1,2-dihydro-1,5-naphthyridine-3-carbonitrile (357);

6-chloro-4-[4-(diphenylmethyl) piperazin-1-yl]-1-methyl-2-oxo-1,2-dihydro-1,5-naphthyridine-3-carbonitrile (358);

4-{4-[(1H-1,3-benzodiazol-7-yl)methyl]piperazin-1-yl}-6-chloro-1-methyl-2-oxo-1,2-dihydro-1,5-naphthyridine-3-carbonitrile (359);

4-{4-[(1H-1,3-benzodiazol-7-yl)methyl]piperazin-1-yl}-6-bromo-1-methyl-2-oxo-1,2-dihydro-1,5-naphthyridine-3-carbonitrile (360);

6-chloro-4-{4-[(4-hydroxyphenyl)methyl]piperazin-1-yl}-1-methyl-2-oxo-1,2-dihydro-1,5-naphthyridine-3-carbonitrile (362);

8-{4-[(3-fluoro-4-hydroxyphenyl) methyl]piperazin-1-yl}-5-methyl-6-oxo-5,6-dihydro-1,5-naphthyridine-2,7-dicarbonitrile (363);

6-chloro-4-{4-[(2-fluoro-5-methylphenyl)methyl]piperazin-1-yl}-1-methyl-2-oxo-1,2-dihydro-1,5-naphthyridine-3-carbonitrile (364);

6-chloro-4-{4-[(2-chloro-6-methoxyphenyl)methyl]piperazin-1-yl}-1-methyl-2-oxo-1,2-dihydro-1,5-naphthyridine-3-carbonitrile (365);

6-bromo-4-{4-[(3,5-dichloro-2-hydroxyphenyl)methyl]piperazin-1-yl}-1-methyl-2-oxo-1,2-dihydro-1,5-naphthyridine-3-carbonitrile (366);

6-bromo-4-{4-[(5-chloro-2-hydroxyphenyl)methyl]piperazin-1-yl}-1-methyl-2-oxo-1,2-dihydro-1,5-naphthyridine-3-carbonitrile (367);

6-bromo-4-{4-[(2-hydroxy-3-methoxyphenyl)methyl]piperazin-1-yl}-1-methyl-2-oxo-1,2-dihydro-1,5-naphthyridine-3-carbonitrile (368);

6-chloro-4-(4-{[2-hydroxy-5-(trifluoromethoxy)phenyl]methyl}piperazin-1-yl)-1-methyl-2-oxo-1,2-dihydro-1,5-naphthyridine-3-carbonitrile (369);

6-chloro-4-{4-[(5-chloro-2-hydroxyphenyl)methyl]piperazin-1-yl}-1-methyl-2-oxo-1,2-dihydro-1,5-naphthyridine-3-carbonitrile (370);

6-chloro-4-{4-[(2-hydroxy-3-methoxyphenyl)methyl]piperazin-1-yl}-1-methyl-2-oxo-1,2-dihydro-1,5-naphthyridine-3-carbonitrile (371);

6-bromo-4-{4-[(2-hydroxy-4-methylphenyl)methyl]piperazin-1-yl}-1-methyl-2-oxo-1,2-dihydro-1,5-naphthyridine-3-carbonitrile (372);

6-bromo-4-{4-[(1H-indol-7-yl)methyl]piperazin-1-yl}-1-methyl-2-oxo-1,2-dihydro-1,5-naphthyridine-3-carbonitrile (373);

6-bromo-1-methyl-2-oxo-4-{4-[(2-oxo-2,3-dihydro-1H-indol-7-yl)methyl]piperazin-1-yl}-1,2-dihydro-1,5-naphthyridine-3-carbonitrile (374);

6-chloro-4-(4-{[3-fluoro-4-(trifluoromethyl)phenyl]methyl}piperazin-1-yl)-1-methyl-2-oxo-1,2-dihydro-1,5-naphthyridine-3-carbonitrile (375);

6-chloro-1-methyl-2-oxo-4-{4-[(2-oxo-2,3-dihydro-1H-indol-7-yl)methyl]piperazin-1-yl}-1,2-dihydro-1,5-naphthyridine-3-carbonitrile (376);

6-chloro-4-{4-[1-(4-fluorophenyl)-3,3-dimethylbutyl]piperazin-1-yl}-1-methyl-2-oxo-1,2-dihydro-1,5-naphthyridine-3-carbonitrile (377-378);

6-chloro-4-{4-[(4-cyano-2-fluorophenyl)methyl]piperazin-1-yl}-1-methyl-2-oxo-1,2-dihydro-1,5-naphthyridine-3-carbonitrile (379);

6-bromo-4-{4-[(3-bromo-2-hydroxyphenyl)methyl]piperazin-1-yl}-1-methyl-2-oxo-1,2-dihydro-1,5-naphthyridine-3-carbonitrile (380);

6-chloro-4-(4-{[2-hydroxy-4-(trifluoromethoxy)phenyl]methyl}piperazin-1-yl)-1-methyl-2-oxo-1,2-dihydro-1,5-naphthyridine-3-carbonitrile (381);

6-chloro-4-{4-[cyclobutyl(4-fluorophenyl)methyl]piperazin-1-yl}-1-methyl-2-oxo-1,2-dihydro-1,5-naphthyridine-3-carbonitrile (382-383);

4-{4-[(3-tert-butyl-2-hydroxyphenyl)methyl]piperazin-1-yl}-6-chloro-1-methyl-2-oxo-1,2-dihydro-1,5-naphthyridine-3-carbonitrile (384);

6-chloro-1-methyl-4-{4-[(3-methylphenyl)methyl]piperazin-1-yl}-2-oxo-1,2-dihydro-1,5-naphthyridine-3-carbonitrile (385);

6-chloro-1-methyl-4-{4-[(4-methylphenyl)methyl]piperazin-1-yl}-2-oxo-1,2-dihydro-1,5-naphthyridine-3-carbonitrile (386);

6-chloro-4-{4-[1-(4-fluorophenyl)ethyl]piperazin-1-yl}-1-methyl-2-oxo-1,2-dihydro-1,5-naphthyridine-3-carbonitrile (387-388);

4-{4-[(3-chloro-2-hydroxyphenyl)methyl]piperazin-1-yl}-1,6-dimethyl-2-oxo-1,2-dihydro-1,5-naphthyridine-3-carbonitrile (389);

6-bromo-4-{4-[(2-chloro-6-hydroxyphenyl)methyl]piperazin-1-yl}-1-methyl-2-oxo-1,2-dihydro-1,5-naphthyridine-3-carbonitrile (390);

6-chloro-4-{4-[(2-hydroxy-3-methylphenyl)methyl]piperazin-1-yl}-1-methyl-2-oxo-1,2-dihydro-1,5-naphthyridine-3-carbonitrile (391);

8-{4-[(4-fluoro-2-methoxyphenyl)(4-fluorophenyl)methyl]piperazin-1-yl}-5-methyl-6-oxo-5,6-dihydro-1,5-naphthyridine-2-carbonitrile (392);

4-{4-[bis(4-chlorophenyl)methyl]piperazin-1-yl}-6-bromo-1-methyl-2-oxo-1,2-dihydro-1,5-naphthyridine-3-carbonitrile (393);

8-{4-[bis(4-chlorophenyl)methyl]piperazin-1-yl}-5-methyl-6-oxo-5,6-dihydro-1,5-naphthyridine-2,7-dicarbonitrile (394);

4-{4-[bis(4-chlorophenyl)methyl]piperazin-1-yl}-6-methoxy-1-methyl-2-oxo-1,2-dihydro-1,5-naphthyridine-3-carbonitrile (395);

4-{4-[(4-fluorophenyl)(2-methoxypyridin-3-yl)methyl]piperazin-1-yl}-6-methoxy-1-methyl-2-oxo-1,2-dihydro-1,5-naphthyridine-3-carbonitrile (396);

4-{4-[(4-fluorophenyl)(3-methoxypyridin-2-yl)methyl]piperazin-1-yl}-6-methoxy-1-methyl-2-oxo-1,2-dihydro-1,5-naphthyridine-3-carbonitrile (397);

4-{4-[1-(4-fluorophenyl)propyl]piperazin-1-yl}-1,6-dimethyl-2-oxo-1,2-dihydro-1,5-naphthyridine-3-carbonitrile (398);

8-{4-[(S)-(4-chlorophenyl)(phenyl)methyl]piperazin-1-yl}-5-methyl-7-nitro-6-oxo-5,6-dihydro-1,5-naphthyridine-2-carbonitrile (399);

8-{4-[(4-fluorophenyl)(pyridin-2-yl)methyl]piperazin-1-yl}-5-methyl-6-oxo-5,6-dihydro-1,5-naphthyridine-2,7-dicarbonitrile (400);

4-{4-[(4-fluoro-2-methoxyphenyl)(pyrimidin-2-yl)methyl]piperazin-1-yl}-6-methoxy-1-methyl-2-oxo-1,2-dihydro-1,5-naphthyridine-3-carbonitrile (401);

4-{4-[bis(4-fluoro-2-methoxyphenyl)methyl]piperazin-1-yl}-6-methoxy-1-methyl-2-oxo-1,2-dihydro-1,5-naphthyridine-3-carbonitrile (402);

4-{4-[(4-fluorophenyl)(pyridin-2-yl)methyl]piperazin-1-yl}-6-methoxy-1-methyl-2-oxo-1,2-dihydro-1,5-naphthyridine-3-carbonitrile (403);

5-methyl-8-{4-[(naphthalen-1-yl)methyl]piperazin-1-yl}-6-oxo-5,6-dihydro-1,5-naphthyridine-2,7-dicarbonitrile (404);

8-{4-[(4-fluoro-2-methoxyphenyl)(4-fluorophenyl)methyl]piperazin-1-yl}-5-methyl-6-oxo-5,6-dihydro-1,5-naphthyridine-2,7-dicarbonitrile (405-407);

5-methyl-8-{4-[(4-methylphenyl)(phenyl)methyl]piperazin-1-yl}-6-oxo-5,6-dihydro-1,5-naphthyridine-2,7-dicarbonitrile (408);

8-{4-[bis(4-fluoro-2-methoxyphenyl)methyl]piperazin-1-yl}-5-methyl-6-oxo-5,6-dihydro-1,5-naphthyridine-2,7-dicarbonitrile (409);

8-{4-[(4-fluorophenyl)(3-methoxypyridin-2-yl)methyl]piperazin-1-yl}-5-methyl-6-oxo-5,6-dihydro-1,5-naphthyridine-2,7-dicarbonitrile (410);

8-{4-[(4-fluorophenyl)(phenyl)methyl]piperazin-1-yl}-5-methyl-6-oxo-5,6-dihydro-1,5-naphthyridine-2,7-dicarbonitrile (411);

4-{4-[(4-fluoro-2-methoxyphenyl)(4-fluorophenyl)methyl]piperazin-1-yl}-6-methoxy-1-methyl-2-oxo-1,2-dihydro-1,5-naphthyridine-3-carbonitrile (412);

4-{4-[(4-fluoro-2-methoxyphenyl)(4-fluorophenyl)methyl]piperazin-1-yl}-6-methoxy-1-methyl-2-oxo-1,2-dihydro-1,5-naphthyridine-3-carbonitrile (413);

8-{4-[(S)-(4-chlorophenyl)(phenyl)methyl]piperazin-1-yl}-5-methyl-6-oxo-5,6-dihydro-1,5-naphthyridine-2,7-dicarbonitrile (414);

5-methyl-8-{4-[(naphthalen-1-yl)methyl]piperazin-1-yl}-7-nitro-6-oxo-5,6-dihydro-1,5-naphthyridine-2-carbonitrile (415);

8-{4-[(4-fluorophenyl)(2-methoxy-4-methylphenyl)methyl]piperazin-1-yl}-5-methyl-7-nitro-6-oxo-5,6-dihydro-1,5-naphthyridine-2-carbonitrile (416);

6-chloro-4-{4-[(4-chlorophenyl)methyl]piperazin-1-yl}-1-methyl-2-oxo-1,2-dihydro-1,5-naphthyridine-3-carbonitrile (417);

8-{4-[(2-hydroxyphenyl)(phenyl)methyl]piperazin-1-yl}-5-methyl-6-oxo-5,6-dihydro-1,5-naphthyridine-2,7-dicarbonitrile (418);

6-chloro-4-{4-[(2-chloro-6-methylphenyl)methyl]piperazin-1-yl}-1-methyl-2-oxo-1,2-dihydro-1,5-naphthyridine-3-carbonitrile (419);

6-chloro-4-{4-[(2-chloro-6-fluorophenyl)methyl]piperazin-1-yl}-1-methyl-2-oxo-1,2-dihydro-1,5-naphthyridine-3-carbonitrile (420);

6-chloro-4-{4-[1-(4-fluorophenyl)cyclopropyl]piperazin-1-yl}-1-methyl-2-oxo-1,2-dihydro-1,5-naphthyridine-3-carbonitrile (421);

6-chloro-4-{4-[(2,6-difluorophenyl) methyl]piperazin-1-yl}-1-methyl-2-oxo-1,2-dihydro-1,5-naphthyridine-3-carbonitrile (422);

6-chloro-4-{4-[(2-fluoro-4-methylphenyl)methyl]piperazin-1-yl}-1-methyl-2-oxo-1,2-dihydro-1,5-naphthyridine-3-carbonitrile (423);

6-chloro-4-{4-[(4-cyano-2-methoxyphenyl)methyl]piperazin-1-yl}-1-methyl-2-oxo-1,2-dihydro-1,5-naphthyridine-3-carbonitrile (424);

6-chloro-4-{4-[2-(4-fluorophenyl)propan-2-yl]piperazin-1-yl}-1-methyl-2-oxo-1,2-dihydro-1,5-naphthyridine-3-carbonitrile (425);

4-(4-(bis(4-fluorophenyl)methyl)piperazin-1-yl)-1-methyl-1,5-naphthyridin-2(1H)-one (426);

4-{4-[bis(4-fluorophenyl)methyl]piperazin-1-yl}-1,6-dimethyl-1,2-dihydro-1,5-naphthyridin-2-one (427);

6-bromo-4-{4-[(S)-(4-chlorophenyl)(phenyl)methyl]piperazin-1-yl}-1-methyl-2-oxo-1,2-dihydro-1,5-naphthyridine-3-carbonitrile (428);

6-bromo-4-{4-[(4-chlorophenyl)(phenyl)methyl]piperazin-1-yl}-1-methyl-2-oxo-1,2-dihydro-1,5-naphthyridine-3-carbonitrile (429);

6-bromo-4-{4-[(4-fluorophenyl)(phenyl)methyl]piperazin-1-yl}-1-methyl-2-oxo-1,2-dihydro-1,5-naphthyridine-3-carbonitrile (430);

6-bromo-1-methyl-4-{4-[(4-methylphenyl)(phenyl)methyl]piperazin-1-yl}-2-oxo-1,2-dihydro-1,5-naphthyridine-3-carbonitrile (431); or 8-{4-[bis(4-fluorophenyl)methyl]piperazin-1-yl}-5-methyl-6-oxo-5,6-dihydro-1,5-naphthyridine-2-carbonitrile (432).

9. A pharmaceutical composition comprising a compound according to claim 1 or a pharmaceutically-acceptable salt thereof; and a pharmaceutically acceptable carrier.

10. A method of inhibiting activity of at least one of diacylglycerol kinase selected from diacylglycerol kinase alpha (DGKα) and diacylglycerol kinase zeta (DGKζ) for treating a disease comprising the administration to a subject having said disease a therapeutically-effective amount of at least one compound according to claim 1, wherein said disease is cancer or viral infections.

11. The method according to claim 10, wherein said cancer is selected from cancer of the colon, pancreatic cancer, breast cancer, prostate cancer, lung cancer, ovarian cancer, cervical cancer, renal cancer, cancer of the head and neck, lymphoma, leukemia and melanoma.

* * * * *

UNITED STATES PATENT AND TRADEMARK OFFICE
CERTIFICATE OF CORRECTION

PATENT NO. : 11,866,430 B2
APPLICATION NO. : 17/254914
DATED : January 9, 2024
INVENTOR(S) : Chupak et al.

It is certified that error appears in the above-identified patent and that said Letters Patent is hereby corrected as shown below:

In the Specification

Column 1, Lines 6-8, delete "This application claims the benefit of U.S. Provisional Application Ser. No. 62/690,444, filed Jun. 27, 2018, which is incorporated herein in its entirety." and insert -- This application is a 371 application of International Application No. PCT/US2019/039131 filed on June 26, 2019, which claims the benefit of U.S. Provisional Application Serial No. 62/690,444, filed June 27, 2018, the content of each is hereby fully incorporated by reference in its entirety for all purposes. --.

In the Claims

Claim 8, Column 486, Line 60 (Approx.), delete "(21):" and insert -- (21); --.

Claim 8, Column 487, Line 3, delete "(28-30):" and insert -- (28-30); --.

Claim 8, Column 491, Line 37, delete "(200):" and insert -- (200); --.

Signed and Sealed this
Fourteenth Day of October, 2025

John A. Squires
*Director of the United States Patent and Trademark Office*